United States Patent
Haketa et al.

(10) Patent No.: US 10,840,456 B2
(45) Date of Patent: Nov. 17, 2020

(54) COMPOUND, MATERIAL FOR ORGANIC ELECTROLUMINESCENCE DEVICES, ORGANIC ELECTROLUMINESCENCE DEVICE, AND ELECTRONIC DEVICE

(71) Applicant: IDEMITSU KOSAN CO., LTD., Chiyoda-ku (JP)

(72) Inventors: Tasuku Haketa, Chiba (JP); Hirokatsu Ito, Ichihara (JP); Yu Kudo, Chiba (JP)

(73) Assignee: IDEMITSU KOSAN CO., LTD., Chiyoda-ku (JP)

( * ) Notice: Subject to any disclaimer, the term of this patent is extended or adjusted under 35 U.S.C. 154(b) by 252 days.

(21) Appl. No.: 15/850,166

(22) Filed: Dec. 21, 2017

(65) Prior Publication Data

US 2018/0182974 A1     Jun. 28, 2018

(30) Foreign Application Priority Data

Dec. 28, 2016 (JP) ................. 2016-256118

(51) Int. Cl.
   *H01L 51/50* (2006.01)
   *H01L 51/00* (2006.01)
   (Continued)

(52) U.S. Cl.
   CPC ........ *H01L 51/0061* (2013.01); *C07D 405/12* (2013.01); *C07D 471/06* (2013.01);
   (Continued)

(58) Field of Classification Search
   None
   See application file for complete search history.

(56) References Cited

FOREIGN PATENT DOCUMENTS

| KR | 2016-68423 | * | 6/2016 | ............. C09K 11/06 |
| KR | 10-2016-0111778 | | 9/2016 | |

(Continued)

*Primary Examiner* — Gregory D Clark
(74) *Attorney, Agent, or Firm* — Oblon, McClelland, Maier & Neustadt, L.L.P.

(57) ABSTRACT

A compound represented by formula (1):

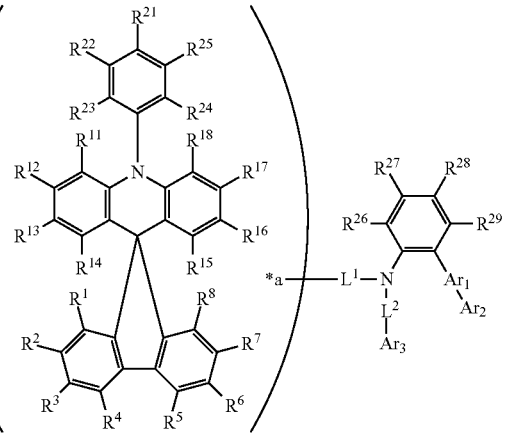

(1)

wherein each symbol is as defined in the specification, provides a high performance organic electroluminescence device which comprises a cathode, an anode and an organic layer between the cathode and the anode, wherein the organic layer comprises a light emitting layer and at least one layer of the organic layer comprises the compound.

26 Claims, 1 Drawing Sheet

(51) Int. Cl.
*C07D 471/06* (2006.01)
*C07D 405/12* (2006.01)
*H01L 51/52* (2006.01)

(52) U.S. Cl.
CPC ........ *H01L 51/0072* (2013.01); *H01L 51/006* (2013.01); *H01L 51/0054* (2013.01); *H01L 51/0073* (2013.01); *H01L 51/0074* (2013.01); *H01L 51/5012* (2013.01); *H01L 51/5016* (2013.01); *H01L 51/5056* (2013.01); *H01L 51/5064* (2013.01); *H01L 51/5206* (2013.01); *H01L 51/5221* (2013.01)

(56) References Cited

FOREIGN PATENT DOCUMENTS

| KR | 2017136391 | * 12/2017 | ............ H01L 51/50 |
| WO | WO 2006/080640 A1 | 8/2006 | |
| WO | WO 2016/027989 A1 | 2/2016 | |
| WO | WO 2016/204453 A1 | 12/2016 | |

* cited by examiner

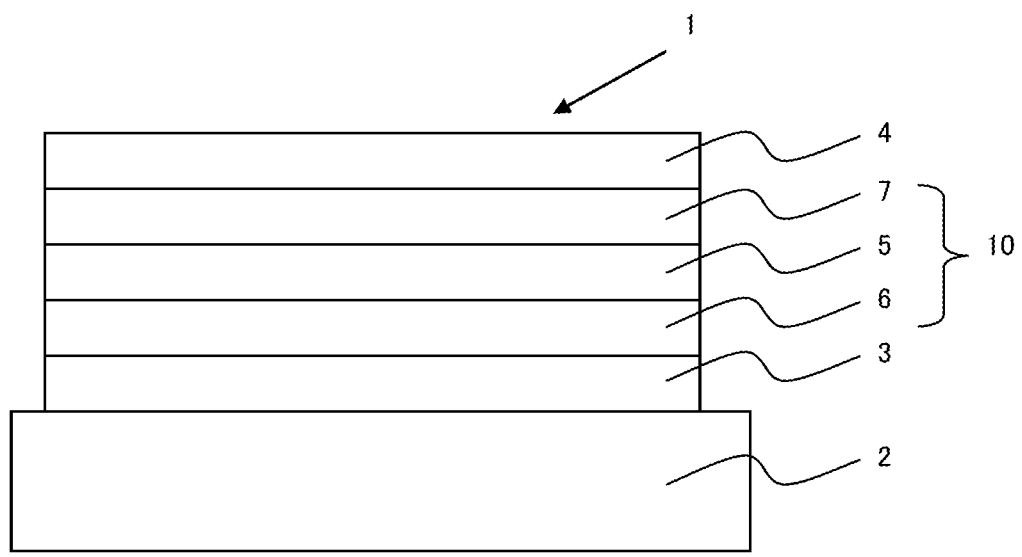

COMPOUND, MATERIAL FOR ORGANIC ELECTROLUMINESCENCE DEVICES, ORGANIC ELECTROLUMINESCENCE DEVICE, AND ELECTRONIC DEVICE

CROSS-REFERENCE TO RELATED APPLICATION

This application is based upon and claims the benefit of priority from the prior Japanese Patent Application No. 2016-256118, filed on Dec. 28, 2016, the entire contents of which are incorporated herein by reference.

TECHNICAL FIELD

The present invention relates to compounds, materials for organic electroluminescence devices comprising the compounds, organic electroluminescence devices comprising the materials, and electronic devices.

BACKGROUND ART

An organic electroluminescence device (organic EL device) comprises an organic layer, such as a hole injecting layer, a hole transporting layer, a light emitting layer, an electron transporting layer, and an electron injecting layer. It is therefore important for improving the performance of organic EL device to develop a compound functionally suitable for each organic layer.

To improve the performance of organic EL device, it has been known to form a hole transporting layer into a two-layered structure, in which the hole transporting layer closer to a light emitting layer has a function to block electrons or a function to prevent the diffusion of exciting energy from the light emitting layer. As another method for improving the performance of organic EL device, it has been known to form an electron transporting layer into a two-layered structure, in which the electron transporting layer closer to a light emitting layer has a function, such as a hole blocking ability and a triplet blocking ability.

Patent Literature 1 describes that the compound of the following formula is usable as a material for organic EL device.

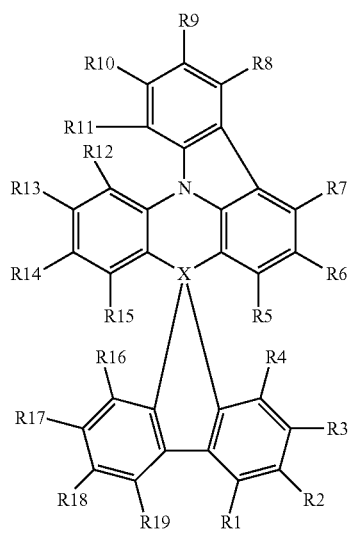

Patent Literature 2 describes that the compound of the following formula is usable in a hole transporting layer of organic EL device.

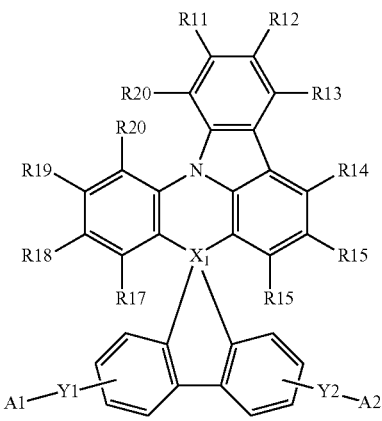

The specific compounds include the compounds of formulae 2-2 and 2-14.

Formula 2-2

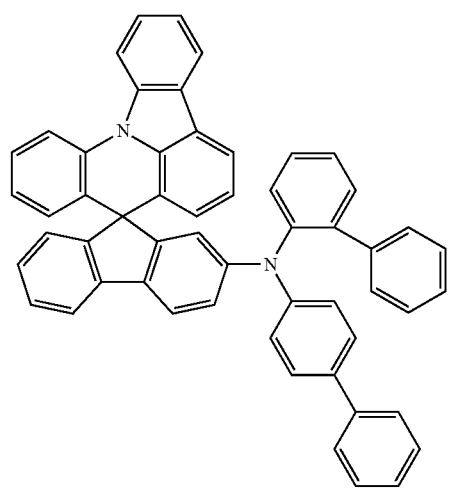

Formula 2-14

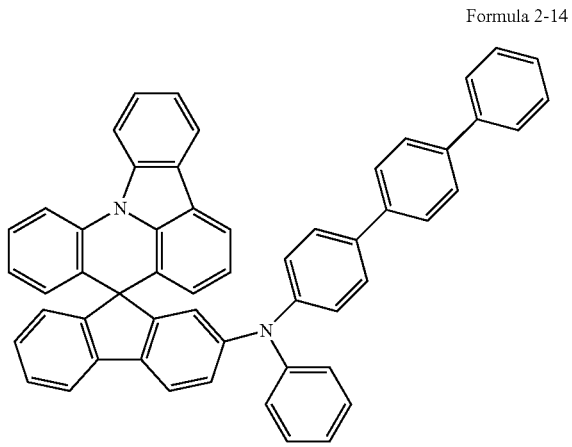

Patent Literature 3 describes that the compound of the following formula is usable as a material for organic EL device.

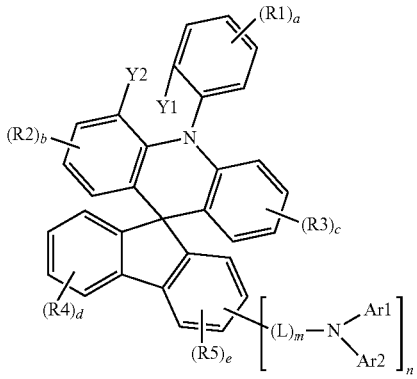

As described above, many compounds have been proposed as materials for organic EL devices. However, a compound which further improves the performance of organic EL devices has been still demanded to develop.

CITATION LIST

Patent Literature

Patent Literature 1: WO 2006/080640A1

Patent Literature 2: WO 2016/027989A1

Patent Literature 3: KR 20160111778A

SUMMARY OF INVENTION

Technical Problem

The present invention has been made to solve the above problems and an object thereof is to provide compounds which realize organic EL devices exhibiting good organic EL performance, organic EL devices which comprise the compounds and exhibit good organic EL performance, and electronic devices comprising the organic EL devices.

Solution to Problem

As the result of extensive research, the inventors have found that the above object is achieved by a compound represented by formula (1) and an organic EL device comprising the compound represented by formula (1).

In an aspect, the present invention provides a compound represented by formula (1):

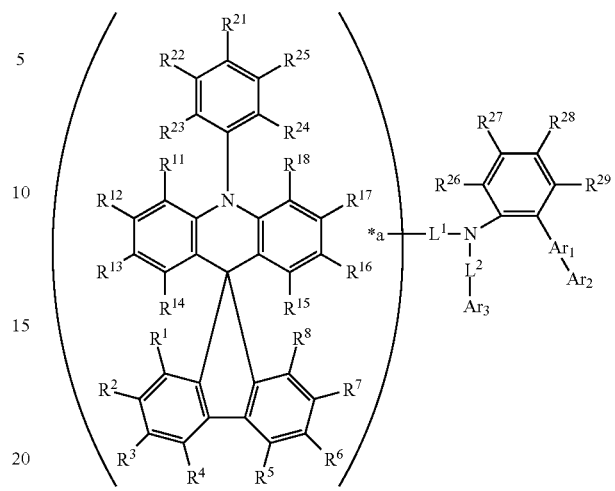

wherein:
one selected from $R^1$ to $R^8$, $R^{11}$ to $R^{18}$, and $R^{21}$ to $R^{25}$ is a single bond bonded to *a;
each of $R^1$ to $R^8$, $R^{11}$ to $R^{18}$, and $R^{21}$ to $R^{25}$ which is not the single bond bonded to *a is independently a hydrogen atom or a substituent;
provided that $R^{11}$ and $R^{23}$ each being not the single bond bonded to *a, or $R^{18}$ and $R^{24}$ each being not the single bond bonded to *a may be bonded to each other to form a single bond;
each of $R^{26}$ to $R^{29}$ is a hydrogen atom or a substituent;
adjacent two selected from $R^{26}$ to $R^{29}$ may be bonded to each other to form a ring structure;
each of $L^1$ and $L^2$ is independently a single bond or a substituted or unsubstituted arylene group having 6 to 30 ring carbon atoms;
$Ar_1$ is a substituted or unsubstituted arylene group having 6 to 30 ring carbon atoms; and
each of $Ar_2$ and $Ar_2$ is independently a substituted or unsubstituted aryl group having 6 to 30 ring carbon atoms or a substituted or unsubstituted heteroaryl group having 5 to 30 ring atoms.

In another aspect, the present invention provides a material for organic EL devices comprising the compound represented by formula (1).

In still another aspect, the present invention provides an organic electroluminescence device comprising a cathode, an anode and an organic layer between the cathode and the anode, wherein the organic layer comprises a light emitting layer and at least one layer of the organic layer comprises the compound represented by formula (1).

In still another aspect, the present invention provides an electronic device comprising the organic electroluminescence device.

Advantageous Effects of Invention

The compounds of the invention provide organic EL devices having good organic EL performance.

BRIEF DESCRIPTION OF DRAWINGS

FIG. 1 is a schematic view showing the structure of an organic EL device in an aspect of the invention.

DESCRIPTION OF EMBODIMENTS

The term of "XX to YY carbon atoms" referred to by "a substituted or unsubstituted group ZZ having XX to YY carbon atoms" used herein is the number of carbon atoms of the unsubstituted group ZZ and does not include any carbon atom in the substituent of the substituted group ZZ.

The term of "XX to YY atoms" referred to by "a substituted or unsubstituted group ZZ having XX to YY atoms" used herein is the number of atoms of the unsubstituted group ZZ and does not include any atom in the substituent of the substituted group ZZ.

The term of "unsubstituted group ZZ" referred to by "substituted or unsubstituted group ZZ" used herein means that no hydrogen atom in the group ZZ is substituted by a substituent.

The definition of "hydrogen atom" used herein includes isotopes different in the neutron numbers, i.e., light hydrogen (protium), heavy hydrogen (deuterium), and tritium.

The number of "ring carbon atoms" referred to herein means the number of the carbon atoms included in the atoms which are members forming the ring itself of a compound in which a series of atoms is bonded to form a ring (for example, a monocyclic compound, a fused ring compound, a cross-linked compound, a carbocyclic compound, and a heterocyclic compound). If the ring has a substituent, the carbon atom in the substituent is not included in the ring carbon atom. The same applies to the number of "ring carbon atom" described below, unless otherwise noted. For example, a benzene ring has 6 ring carbon atoms, a naphthalene ring has 10 ring carbon atoms, a pyridine ring has 5 ring carbon atoms, and a furan ring has 4 ring carbon atoms. If a benzene ring or a naphthalene ring has, for example, an alkyl substituent, the carbon atom in the alkyl substituent is not counted as the ring carbon atom of the benzene or naphthalene ring. In case of a fluorene ring to which a fluorene substituent is bonded (inclusive of a spirofluorene ring), the carbon atom in the fluorene substituent is not counted as the ring carbon atom of the fluorene ring.

The number of "ring atom" referred to herein means the number of the atoms which are members forming the ring itself (for example, a monocyclic ring, a fused ring, and a ring assembly) of a compound in which a series of atoms is bonded to form the ring (for example, a monocyclic compound, a fused ring compound, a cross-linked compound, a carbocyclic compound, and a heterocyclic compound). The atom not forming the ring (for example, hydrogen atom(s) for saturating the valence of the atom which forms the ring) and the atom in a substituent, if the ring is substituted, are not counted as the ring atom. The same applies to the number of "ring atoms" described below, unless otherwise noted. For example, a pyridine ring has 6 ring atoms, a quinazoline ring has 10 ring atoms, and a furan ring has 5 ring atoms. The hydrogen atom on the ring carbon atom of a pyridine ring or a quinazoline ring and the atom in a substituent are not counted as the ring atom. In case of a fluorene ring to which a fluorene substituent is bonded (inclusive of a spirofluorene ring), the atom in the fluorene substituent is not counted as the ring atom of the fluorene ring.

The compound in an aspect of the invention is represented by formula (1) (hereinafter also referred to as "compound (1)"):

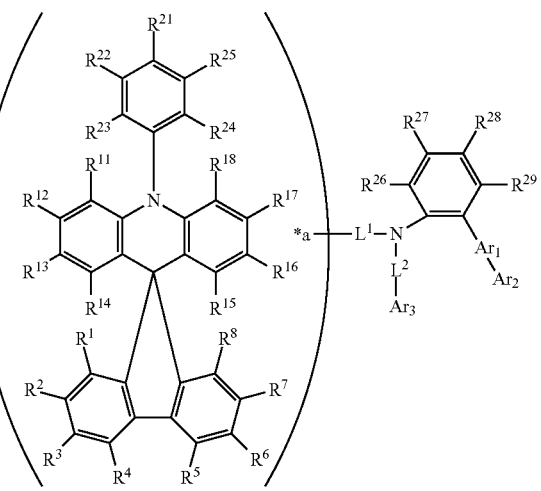

(1)

wherein:
one selected from $R^1$ to $R^8$, $R^{11}$ to $R^{18}$, and $R^{21}$ to $R^{25}$ is a single bond bonded to *a;

each of $R^1$ to $R^8$, $R^{11}$ to $R^{18}$, and $R^{21}$ to $R^{25}$ which is not a single bond bonded to *a is independently a hydrogen atom or a substituent;

provided that $R^{11}$ and $R^{23}$ each being not a single bond bonded to *a, or $R^{18}$ and $R^{24}$ each being not a single bond bonded to *a may be bonded to each other to form a single bond;

each of $R^{26}$ to $R^{29}$ is a hydrogen atom or a substituent;

adjacent two selected from $R^{26}$ to $R^{29}$ may be bonded to each other to form a ring structure;

each of $L^1$ and $L^2$ is independently a single bond or a substituted or unsubstituted arylene group having 6 to 30 ring carbon atoms;

$Ar_1$ is a substituted or unsubstituted arylene group having 6 to 30 ring carbon atoms; and each of $Ar_2$ and $Ar_3$ is independently a substituted or unsubstituted aryl group having 6 to 30 ring carbon atoms or a substituted or unsubstituted heteroaryl group having 5 to 30 ring atoms.

In formula (1), one selected from $R^1$ to $R^8$, $R^{11}$ to $R^{18}$, and $R^{21}$ to $R^{25}$, preferably one selected from $R^2$ to $R^7$, $R^{12}$, $R^{13}$, $R^{16}$, and $R^{17}$, more preferably one selected from $R^2$ to $R^7$, and still more preferably one selected from $R^2$, $R^4$, $R^5$, and $R^7$ is a single bond bonded to *a.

Each of $R^1$ to $R^8$, $R^1$ to $R^{18}$, and $R^{21}$ to $R^{25}$ which is not a single bond bonded to *a is independently a hydrogen atom or a substituent, and preferably a hydrogen atom.

One of a pair of $R^{11}$ and $R^{23}$ and a pair of $R^{18}$ and $R^{24}$ may be bonded to each other to form a single bond. Namely, $R^{11}$ and $R^{23}$ each being not a single bond bonded to *a, or $R^{18}$ and $R^{24}$ each being not a single bond bonded to *a may be bonded to each other to form a single bond.

In an embodiment of the invention, one of a pair of $R^{11}$ and $R^{23}$ and a pair of $R^{18}$ and $R^{24}$ form such a single bond.

For example, when $R^{11}$ and $R^{23}$ form such a single bond, one selected from $R^1$ to $R^8$, $R^{12}$ to $R^{18}$, $R^{21}$, $R^{22}$, $R^{24}$, and $R^{25}$, preferably one selected from $R^2$ to $R^7$, $R^{13}$, $R^{16}$, and $R^{17}$, more preferably one selected from $R^2$ to $R^7$ and $R^{17}$, and still more preferably one selected from $R^2$, $R^4$, $R^5$, and $R^7$ is a single bond bonded to *a.

In another embodiment of the invention, both of a pair of $R^{11}$ and $R^{23}$ and a pair of $R^{18}$ and $R^{24}$ fail to form such a single bond.

In a preferred embodiment of the invention, the compound (1) is represented by formula (1a) or (1b):

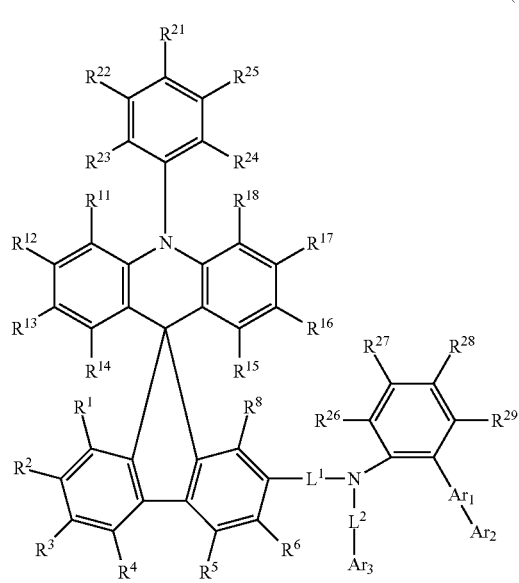

(1a)

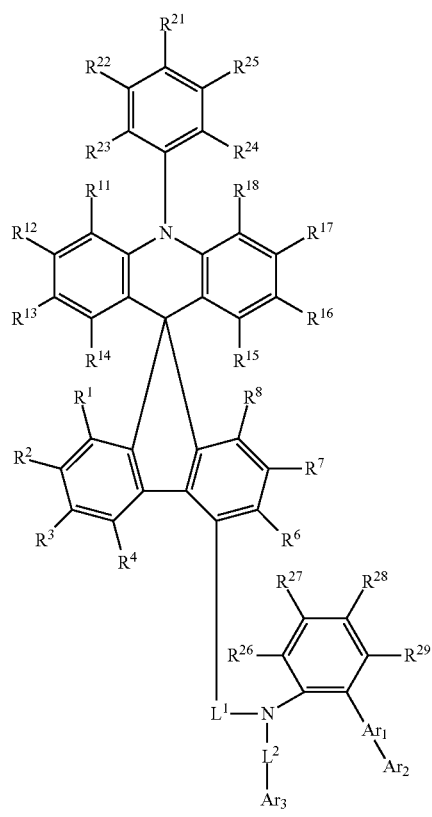

(1b)

wherein each symbol is as defined in formula (1).

When $R^{11}$ and $R^{23}$ are bonded to each other to form a ring structure, the compound (1) is represented by formula (2):

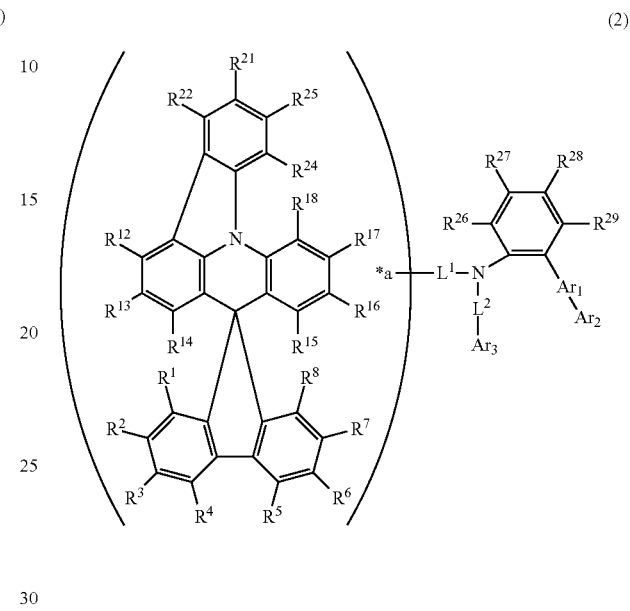

(2)

wherein each of $R^{18}$ and $R^{24}$ is independently a hydrogen atom or a substituent and the other symbols are as defined in formula (1).

Formula (2) is preferably represented by any of formulae (2a) to (2d):

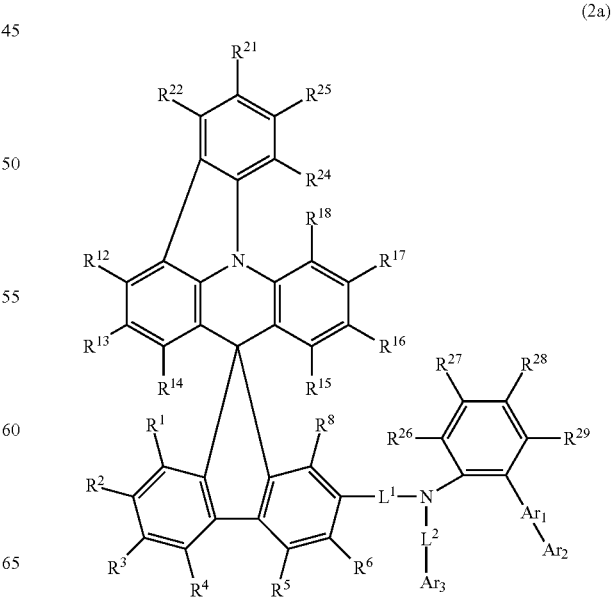

(2a)

-continued (2b)
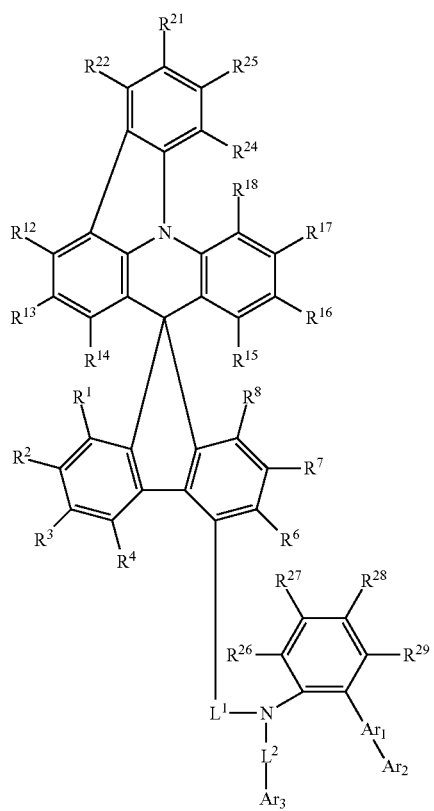

wherein each symbol is as defined in formula (2), (2c)
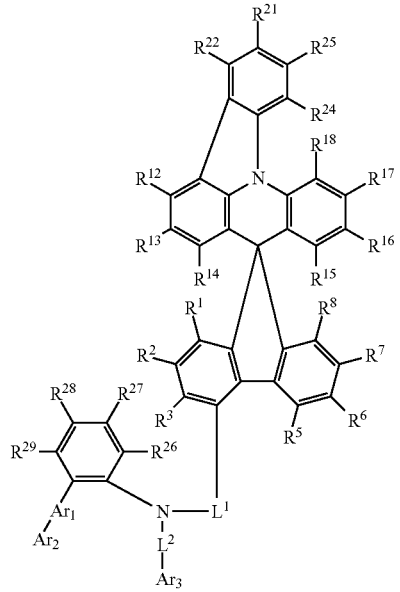

-continued (2d)
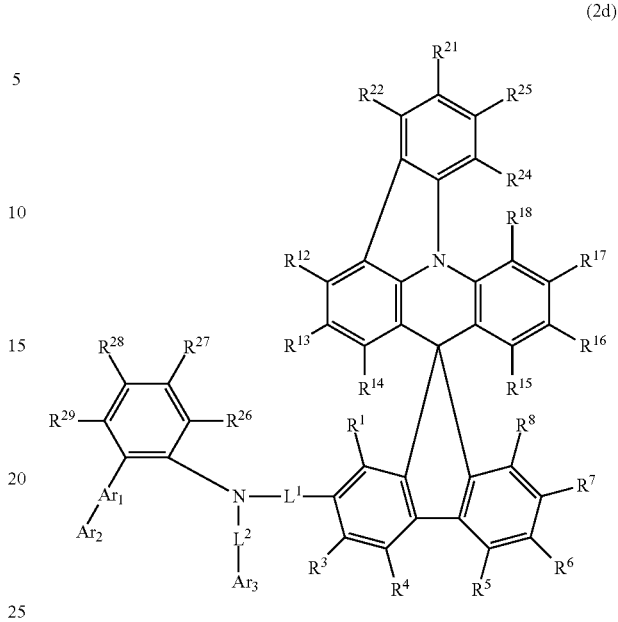

wherein each symbol is as defined in formula (2).

When each of $R^{11}$, $R^{23}$, $R^{18}$, and $R^{24}$ is independently a hydrogen atom or a substituent, i.e., when $R^{11}$ and $R^{23}$ do not form a single bond and $R^{18}$ and $R^{24}$ do not form a single bond, the compound (1) is represented by formula (3):

(3)
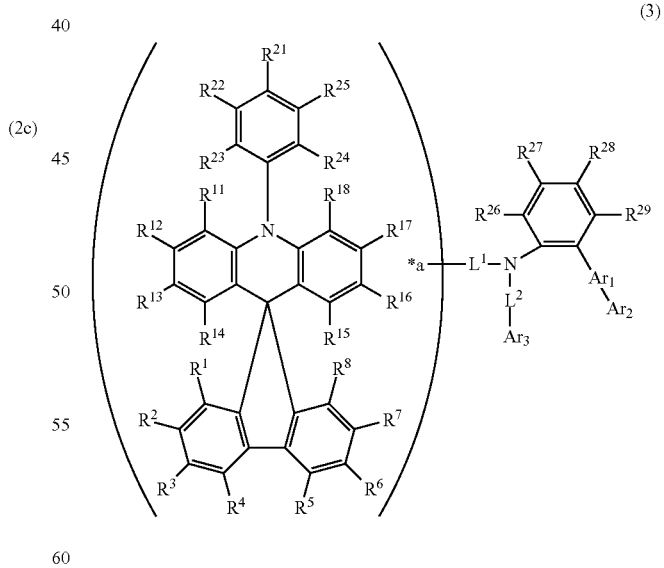

wherein each of $R^{11}$, $R^{23}$, $R^{18}$, and $R^{24}$ is a hydrogen atom or a substituent. $R^{11}$ and $R^{23}$ do not form a single bond, $R^{18}$ and $R^{24}$ do not form a single bond, and the other symbols are as defined in formula (1).

Formula (3) is preferably represented by formula (3a) or (3b):

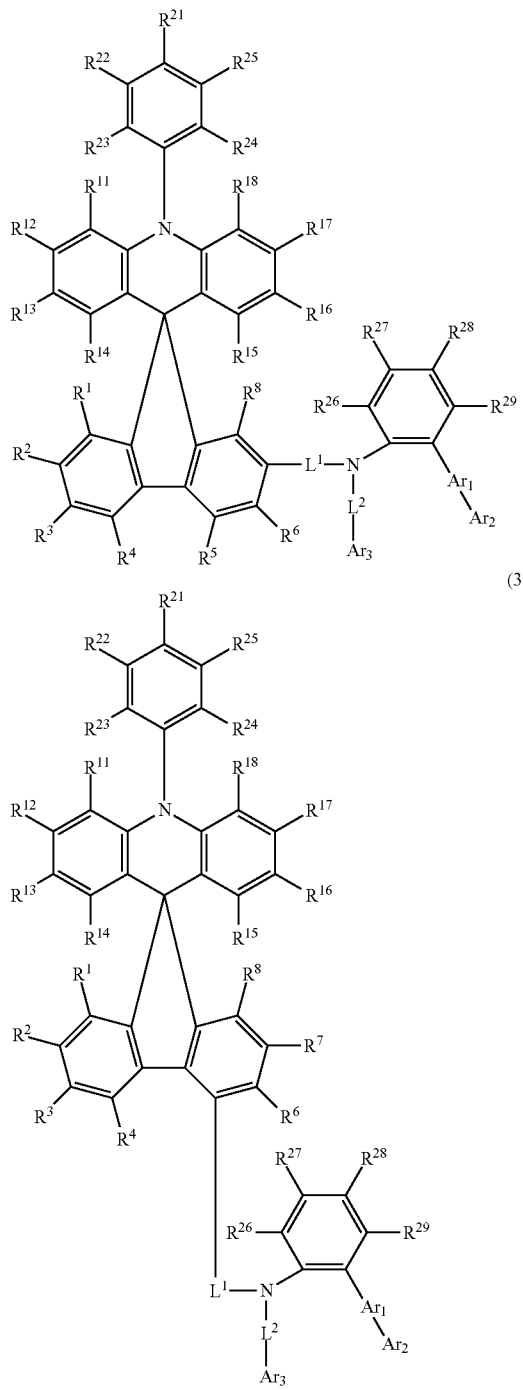

wherein each symbol is as defined in formula (3).

The meanings of the symbols in formulae (1), (1a), (1b), (2), (2a) to (2d), (3), (3a), and (3b) are explained below.

Each of $R^1$ to $R^8$, $R^{12}$ to $R^{17}$, $R^{21}$, $R^{22}$, and $R^{25}$ which is not a single bond bonded to *a is independently a hydrogen atom or a substituent, preferably a hydrogen atom.

Each of $R^{11}$, $R^{18}$, $R^{23}$, and $R^{24}$ which is not a single bond bonded to *a and do not form the single bond mentioned above is independently a hydrogen atom or a substituent, preferably a hydrogen atom. Each of $R^{26}$ to $R^{29}$ is independently a hydrogen atom or a substituent, preferably a hydrogen atom.

The details of the substituent referred to simply by "substituent" and the optional substituent referred to by "substituted or unsubstituted" will be described below.

In a preferred embodiment of the invention, $R^2$, $R^4$, $R^5$, or $R^7$ is a single bond bonded to *a.

In a preferred embodiment of the invention, the compound (1) is represented by formula (2A) or (3A):

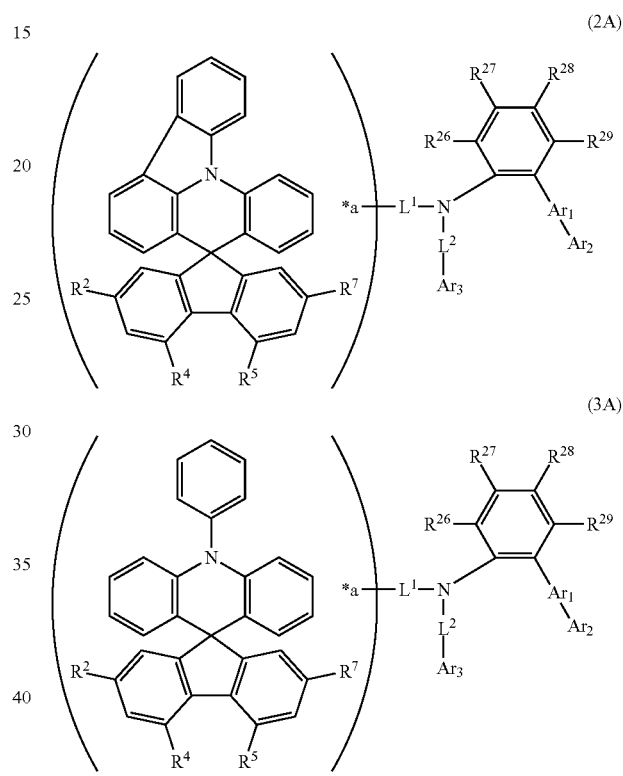

wherein one selected from $R^2$, $R^4$, $R^5$, and $R^7$ is a single bond bonded to *a, the others of $R^2$, $R^4$, $R^5$, and $R^7$ are each hydrogen atom, and the other symbols are as defined in formula (1).

In a more preferred embodiment of the invention, the compound (1) is represented by formula (2B) or (3B):

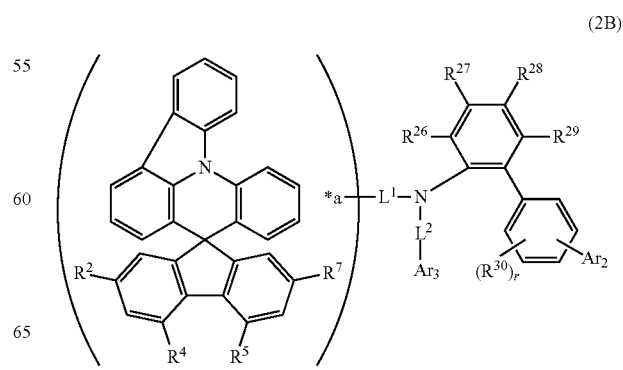

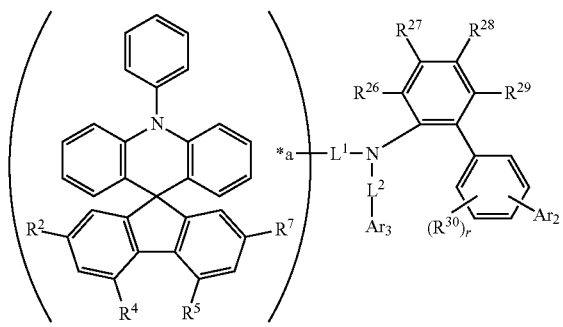

(3B)

wherein:

one selected from $R^2$, $R^4$, $R^5$, and $R^7$ is a single bond bonded to *a and the others of $R^2$, $R^4$, $R^5$, and $R^7$ are each hydrogen atom;

each $R^{30}$ is independently a hydrogen atom, a substituted or unsubstituted alkyl group having 1 to 30 carbon atoms, a substituted or unsubstituted cycloalkyl group having 3 to 30 ring carbon atoms, a substituted or unsubstituted aryl group having 6 to 30 ring carbon atoms, a substituted or unsubstituted heteroaryl group having 5 to 30 ring atoms, an alkoxy group having a substituted or unsubstituted alkyl group having 1 to 30 carbon atoms, a substituted or unsubstituted haloalkyl group having 1 to 30 carbon atoms, a haloalkoxy group having a substituted or unsubstituted haloalkyl group having 1 to 30 carbon atoms, a halogen atom, a cyano group, or a nitro group;

r is an integer of 0 to 4; and the other symbols are as defined in formula (1).

r is preferably an integer of 0 to 2, more preferably an integer of 0 to 1, and still more preferably 0. Preferably, each $R^{30}$ is independently a hydrogen atom, a substituted or unsubstituted alkyl group having 1 to 30 carbon atoms, a substituted or unsubstituted aryl group having 6 to 30 ring carbon atoms, or a substituted or unsubstituted heteroaryl group having 5 to 30 ring atoms.

The alkyl group of the substituted or unsubstituted alkyl group having 1 to 30, preferably 1 to 18, and more preferably 1 to 8 carbon atoms for $R^{30}$ is, for example, selected from a methyl group, an ethyl group, a n-propyl group, an isopropyl group, a n-butyl group, an isobutyl group, a s-butyl group, a t-butyl group, a pentyl group (inclusive of isomeric groups), a hexyl group (inclusive of isomeric groups), a heptyl group (inclusive of isomeric groups), an octyl group (inclusive of isomeric groups), a nonyl group (inclusive of isomeric groups), a decyl group (inclusive of isomeric groups), an undecyl group (inclusive of isomeric groups), and a dodecyl group (inclusive of isomeric groups); preferably selected from a methyl group, an ethyl group, a n-propyl group, an isopropyl group, a n-butyl group, an isobutyl group, a s-butyl group, a t-butyl group, and a pentyl group (inclusive of isomeric groups); more preferably selected from a methyl group, an ethyl group, a n-propyl group, an isopropyl group, a n-butyl group, an isobutyl group, a s-butyl group, and a t-butyl group; and still more preferably selected from a methyl group and a t-butyl group.

The aryl group of the substituted or unsubstituted aryl group having 6 to 30, preferably 6 to 25, and more preferably 6 to 18 ring carbon atoms for $R^{30}$ is, for example, selected from a phenyl group, a biphenylyl group, a terphenylyl group, a biphenylenyl group, a naphthyl group, an acenaphthylenyl group, an anthryl group, a benzanthryl group, an aceanthryl group, a phenanthryl group, a benzophenanthryl group, a phenalenyl group, a fluorenyl group, a pentacenyl group, a picenyl group, a pentaphenyl group, a pyrenyl group, a chrysenyl group, a benzochrysenyl group, a s-indacenyl group, an as-indacenyl group, a fluoranthenyl group, a perylenyl group, a triphenylenyl group, a fluorenyl group, and a 9,9-spirobifluorenyl group; preferably selected from a phenyl group, a biphenylyl group, a terphenylyl group, and a naphthyl group; more preferably selected from a phenyl group, a biphenylyl group, and a naphthyl group; and still more preferably a phenyl group.

The substituted or unsubstituted heteroaryl group having 5 to 30, preferably 5 to 25, and more preferably 5 to 18 ring atoms for $R^{30}$ comprises 1 to 5, preferably 1 to 3, more preferably 1 to 2 ring heteroatoms, for example, a nitrogen atom, a sulfur atom, and an oxygen atom. The heteroaryl group is, for example, selected from a pyrrolyl group, a furyl group, a thienyl group, a pyridyl group, a pyridazinyl group, a pyrimidinyl group, a pyrazinyl group, a triazinyl group, an imidazolyl group, an oxazolyl group, a thiazolyl group, a pyrazolyl group, an isoxazolyl group, an isothiazolyl group, an oxadiazolyl group, a thiadiazolyl group, a triazolyl group, an indolyl group, an isoindolyl group, an indolizinyl group, a quinolizinyl group, a quinolyl group, an isoquinolyl group, a cinnolyl group, a phthalazinyl group, a quinazolinyl group, a quinoxalinyl group, a benzimidazolyl group, a benzoxazolyl group, a benzothiazolyl group, an indazolyl group, a benzisoxazolyl group, a benzisothiazolyl group, a phenanthridinyl group, an acridinyl group, a phenanthrolinyl group, a phenazinyl group, a phenothiazinyl group, a phenoxazinyl group, a xanthenyl group, a benzofuranyl group, a dibenzofuranyl group, a naphthobenzofuranyl group, a benzothiophenyl group (a benzothienyl group), a dibenzothiophenyl group (a dibenzothienyl group), a naphthobenzothiophenyl group (a naphthobenzothienyl group), a N-carbazolyl group, and a C-carbazolyl group; preferably selected from a furyl group, a thienyl group, a pyridyl group, a pyridazinyl group, a pyrimidinyl group, a pyrazinyl group, a triazinyl group, a benzofuranyl group, a benzothiophenyl group, a dibenzofuranyl group, a naphthobenzofuranyl group, a dibenzothiophenyl group, a naphthobenzothiophenyl group, a carbazolyl group, and a benzocarbazolyl group; and more preferably selected from a thienyl group, a benzothiophenyl group, a dibenzofuranyl group, a naphthobenzofuranyl group, a dibenzothiophenyl group, a naphthobenzothiophenyl group, a N-carbazolyl group, a C-carbazolyl group, and a benzocarbazolyl group. Preferred examples of the substituted heteroaryl group include a N-phenylcarbazolyl group, a N-biphenylylcarbazolyl group, a N-phenylphenylcarbazolyl group, a N-naphthylcarbazolyl group, a phenyldibenzofuranyl group, and a phenyldibenzothiophenyl group (a phenyldibenzothienyl group).

Examples of the substituted or unsubstituted cycloalkyl group having 3 to 30 ring carbon atoms for $R^{30}$ include a cyclopropyl group, a cyclobutyl group, a cyclopentyl group, a cyclohexyl group, and a cycloheptyl group.

The details of the alkyl group having 1 to 30 carbon atoms in the alkoxy group for $R^{30}$ are the same as those of the alkyl group having 1 to 30 carbon atoms mentioned above. The alkoxy group is preferably a t-butoxy group, a propoxy group, an ethoxy group, or a methoxy group, more preferably an ethoxy group or a methoxy group, and still more preferably a methoxy group.

The substituted or unsubstituted haloalkyl group having 1 to 30 carbon atoms for $R^{30}$ is a group derived from the alkyl group having 1 to 30 carbon atoms mentioned above by replacing at least one, preferably 1 to 7 hydrogen atoms or all the hydrogen atoms with a halogen atom, such as a fluorine atom, a chlorine atom, a bromine atom, and an iodine atom, preferably a fluorine atom. Preferred example thereof is a fluoroalkyl group having 1 to 30, preferably 1 to 18, and more preferably 1 to 8 carbon atoms, with a heptafluoropropyl group (inclusive of isomeric groups), a pentafluoroethyl group, a 2,2,2-trifluoroethyl group, and a trifluoromethyl group being more preferred, a pentafluoroethyl group, a 2,2,2-trifluoroethyl group, and a trifluoromethyl group being still more preferred, and a trifluoromethyl group being particularly preferred.

The details of the haloalkyl group having 1 to 30 carbon atoms in the haloalkoxy group for $R^{30}$ are the same as those of the haloalkyl group having 1 to 30 carbon atoms mentioned above. Preferred example thereof is a fluoroalkoxy group having 1 to 30, preferably 1 to 18, and more preferably 1 to 8 carbon atoms, with a heptafluoropropoxy group (inclusive of isomeric groups), a pentafluoroethoxy group, a 2,2,2-trifluoroethoxy group, and a trifluoromethoxy group being more preferred, a pentafluoroethoxy group, a 2,2,2-trifluoroethoxy group, and a trifluoromethoxy group being still more preferred, and a trifluoromethoxy group being particularly preferred.

$Ar_1$ is a substituted or unsubstituted arylene group having 6 to 30, preferably 6 to 25, and more preferably 6 to 18 ring carbon atoms. The arylene group is, for example, selected from a phenylene group, a biphenylene group, a terphenylene group, a biphenylenylene group, a naphthylene group, an acenaphthylene group, an anthrylene group, a benzanthrylene group, an aceanthrylene group, a phenanthrylene group, a benzophenanthrylene group, a phenalenylene group, a pentacenylene group, a picenylene group, a pentaphenylene group, a pyrenylene group, a chrysenylene group, a benzochrysenylene group, a s-indacenylene group, an as-indacenylene group, a fluoranthenylene group, a perylenylene group, a triphenylenylene group, a fluorenylene group, and a 9,9'-spirobifluorenylene group; preferably selected from a phenylene group, a biphenylene group, a terphenylene group, a naphthylene group, a phenanthrylene group, a triphenylenylene group, a fluorenylene group, and a 9,9'-spirobifluorenylene group; more preferably selected from an o-phenylene group, a m-phenylene group, a p-phenylene group, a biphenyl-4,4'-diyl group, a biphenyl-4,3'-diyl group, a 1,4-naphthylene group, and a 2,6-naphthylene group; still more preferably selected from an o-phenylene group, a m-phenylene group, and a p-phenylene group; and particularly preferably a p-phenylene group.

Each of $Ar_2$ and $Ar_8$ is a substituted or unsubstituted, preferably unsubstituted aryl group having 6 to 30 ring carbon atoms or a substituted or unsubstituted, preferably unsubstituted heteroaryl group having 5 to 30 ring atoms, and preferably a substituted or unsubstituted, preferably unsubstituted aryl group having 6 to 30 ring carbon atoms.

The substituted or unsubstituted aryl group having 6 to 30, preferably 6 to 25, and more preferably 6 to 18 ring carbon atoms for $Ar_2$ and $Ar_3$ is selected from a substituted or unsubstituted non-fused aryl group (inclusive of ring assembly) having 6 to 18, preferably 6 to 12, and more preferably 6 ring carbon atoms and a substituted or unsubstituted fused aryl group having 10 to 30, preferably 10 to 25, and more preferably 10 to 18 ring carbon atoms. The non-fused aryl group and the fused aryl group are, for example, selected from a phenyl group, a biphenylyl group, a terphenylyl group, a biphenylenyl group, a naphthyl group, an acenaphthylenyl group, an anthryl group, a benzanthryl group, an aceanthryl group, a phenanthryl group, a benzophenanthryl group, a phenalenyl group, a pentacenyl group, a picenyl group, a pentaphenyl group, a pyrenyl group, a chrysenyl group, a benzochrysenyl group, a s-indacenyl group, an as-indacenyl group, a fluoranthenyl group, a perylenyl group, a triphenylenyl group, a fluorenyl group, and a 9,9'-spirobifluorenyl group; preferably selected from a phenyl group, a biphenylyl group, a terphenylyl group, a naphthyl group, a phenanthryl group, a triphenylenyl group, a fluorenyl group, and a 9,9'-spirobifluorenyl group; and more preferably selected from a phenyl group, an o-biphenylyl group, a m-biphenylyl group, a p-biphenylyl group, a 1,1':4',1"-terphenyl-4-yl group, a 1,1':4',1"-terphenyl-2-yl group, a 1-naphthyl group, 2-naphthyl group, a 2-phenanthryl group, a 9-phenanthryl group, a 2-triphenylenyl group, a 2-fluorenyl group, a 4-fluorenyl group, a 9,9'-spirobifluoren-2-yl group, and a 9,9'-spirobifluoren-4-yl group.

The substituted aryl group having 6 to 30, preferably 6 to 25, and more preferably 6 to 18 ring carbon atoms for $Ar_2$ and $Ar_3$ is preferably a 9,9-dimethylfluorenyl group or a 9,9-diphenylfluorenyl group, and more preferably a 9,9-dimethylfluoren-2-yl group, a 9,9-dimethylfluoren-4-yl group, a 9,9-diphenylfluoren-2-yl group, or a 9,9-diphenylfluoren-4-yl group.

In an embodiment of the invention, the substituted or unsubstituted aryl group for $Ar_2$ and $Ar_3$ is preferably a substituted or unsubstituted aryl group having 6 to 10 ring carbon atoms, and in another embodiment of the invention, preferably a substituted or unsubstituted aryl group having 11 to 30 ring carbon atoms.

Examples of the aryl group having 6 to 10 ring carbon atoms include a phenyl group and a naphthyl group, with a phenyl group, a 1-naphthyl group, and a 2-naphthyl group being preferred.

Examples of the aryl group having 11 to 30 ring carbon atoms include a biphenylyl group, a terphenylyl group, a phenanthryl group, a triphenylenyl group, a fluorenyl group, a 9,9'-spirobifluorenyl group, a 9,9-dimethylfluorenyl group, and a 9,9-diphenylfluorenyl group, with an o-biphenylyl group, a m-biphenylyl group, a p-biphenylyl group, a 1,1':4',1"-terphenyl-4-yl group, a 1,1':4',1"-terphenyl-2-yl group, a 2-phenanthryl group, a 9-phenanthryl group, a 2-triphenylenyl group, a 2-fluorenyl group, a 4-fluorenyl group, a 9,9'-spirobifluoren-2-yl group, a 9,9'-spirobifluoren-4-yl group, a 9,9-dimethylfluoren-2-yl group, a 9,9-dimethylfluoren-4-yl group, a 9,9-diphenylfluoren-2-yl group, and a 9,9-diphenylfluoren-4-yl group being preferred.

The substituted or unsubstituted heteroaryl group having 5 to 30, preferably 5 to 25, and more preferably 5 to 18 ring atoms for $Ar_2$ and $Ar_a$ comprises 1 to 5, preferably 1 to 3, more preferably 1 to 2 ring heteroatoms, for example, a nitrogen atom, a sulfur atom, and an oxygen atom.

The substituted or unsubstituted heteroaryl group having 5 to 30 ring atoms is selected from a substituted or unsubstituted non-fused heteroaryl group (inclusive of ring assembly) having 5 to 30, preferably 5 to 25, and more preferably 5 to 18 ring atoms and a substituted or unsubstituted fused heteroaryl group having 9 to 30, preferably 9 to 25, and more preferably 9 to 18 ring atoms. The non-fused heteroaryl group is a mono-valent residue obtained by removing one hydrogen atom on a carbon atom or a nitrogen atom of a monocyclic ring or an assembly of rings each of which is, for example, selected from pyrrole, imidazole, pyrazole, triazole, furan, thiophene, thiazole, isothiazole, oxazole, isoxazole, oxadiazole, thiadiazole, pyridine, pyrazine, pyridazine, pyrimidine, triazine, bipyrrole, terpyrrole, bithiophene, terthiophene, bipyridine, and terpyridine. Preferred examples of the non-fused heteroaryl group include an imidazolyl group, a triazolyl group, a furanyl group, a thienyl group, an isothiazolyl group, an oxazolyl group, an isoxazolyl group, a pyridinyl group, a pyrimidinyl group, and a triazinyl group.

The fused heteroaryl group is a mono-valent residue obtained by removing one hydrogen atom on a carbon atom or a nitrogen atom of a fused ring which is, for example, selected from indole, isoindole, benzofuran, isobenzofuran, benzothiophene, indolizine, quinolizine, quinoline, isoquinoline, cinnoline, phthalazine, quinazoline, quinoxaline, benzimidazole, benzoxazole, benzothiazole, indazole, benzisoxazole, benzisothiazole, benzofuran, dibenzofuran, naphthobenzofuran, benzothiophene, dibenzothiophene, naphthobenzothiophene, carbazole, benzo carbazole, phenanthridine, acridine, phenanthroline, phenazine, phenothiazine, phenoxazine, xanthene, dibenzazepine, tribenzazepine, dihydrodibenzazepine, di(benzimidazo)benzo[1,3,5]azepine, (benzimidazo)benzimidazole, and (benzimidazo)phenanthridine. Preferred examples of the fused heteroaryl group include a dibenzofuranyl group, a dibenzothiophenyl group (dibenzothienyl group), a quinazolinyl group, a benzimidazolyl group, a naphthobenzofuranyl group, a naphthobenzothiophenyl group (naphthobenzothienyl group), a N-carbazolyl group, a C-carbazolyl group, a N-benzocarbazolyl group, and a C-benzocarbazolyl group, with a 2-dibenzofuranyl group, a 4-dibenzofuranyl group, a 2-dibenzothiophenyl group, a 4-dibenzothiophenyl group, a N-carbazolyl group, a C-carbazolyl group, a N-benzocarbazolyl group, and a C-benzocarbazolyl group being more preferred.

In an embodiment of the invention, each of $Ar_2$ and $Ar_3$ is selected from a substituted or unsubstituted, preferably unsubstituted aryl group having 6 to 30, preferably 6 to 25, and more preferably 6 to 18 ring carbon atoms and a substituted or unsubstituted, preferably unsubstituted fused heteroaryl group having 9 to 30, preferably 9 to 25, and more preferably 9 to 18 ring atoms.

In another embodiment of the invention, each of $Ar_2$ and $Ar_3$ is selected from a substituted or unsubstituted, preferably unsubstituted non-fused aryl group (inclusive of ring assembly) having 6 to 18, preferably 6 to 12, and more preferably 6 ring carbon atoms and a substituted or unsubstituted, preferably unsubstituted fused heteroaryl group having 9 to 30, preferably 9 to 25, and more preferably 9 to 18 ring atoms.

In still another embodiment of the invention, each of $Ar_2$ and $Ar_3$ is selected from a substituted or unsubstituted, preferably unsubstituted fused aryl group having 10 to 30, preferably 10 to 25, and more preferably 10 to 18 ring carbon atoms and a substituted or unsubstituted, preferably unsubstituted fused heteroaryl group having 9 to 30, preferably 9 to 25, and more preferably 9 to 18 ring atoms.

The optional substituent of the substituted or unsubstituted aryl group having 6 to 30 ring carbon atoms and the substituted or unsubstituted heteroaryl group having 5 to 30 ring atoms for $Ar_2$ and $Ar_9$ is selected from those described below.

The optional substituent is preferably an alkyl group having 1 to 30, preferably 1 to 18, and more preferably 1 to 8 carbon atoms, an aryl group having 6 to 30, preferably 6 to 25, and more preferably 6 to 18 ring carbon atoms, or a heteroaryl group having 5 to 30, preferably 5 to 25, and more preferably 5 to 18 ring atoms.

The alkyl group as the optional substituent is preferably a methyl group, an ethyl group, a n-propyl group, an isopropyl group, a n-butyl group, an isobutyl group, a s-butyl group, a t-butyl group, a pentyl group (inclusive of isomeric groups), or a hexyl group (inclusive of isomeric groups).

The aryl group as the optional substituent is preferably a phenyl group, a biphenylyl group, a terphenylyl group, a naphthyl group, a phenanthryl group, a triphenylenyl group, a 9,9-dimethylfluorenyl group, a 9,9-diphenylfluorenyl group, or a 9,9'-spirobifluorenyl group and more preferably a phenyl group, an o-biphenylyl group, a m-biphenylyl group, a p-biphenylyl group, a 1,1':4',1''-terphenyl-4-yl group, a 1,1':4',1''-terphenyl-2-yl group, a 1-naphthyl group, 2-naphthyl group, a 2-phenanthryl group, a 9-phenanthryl group, a 2-triphenylenyl group, a 2-fluorenyl group, a 4-fluorenyl group, a 9,9'-spirobifluoren-2-yl group, and a 9,9'-spirobifluoren-4-yl group, a 9,9-dimethylfluoren-2-yl group, a 9,9-dimethylfluoren-4-yl group, a 9,9-diphenylfluoren-2-yl group, or a 9,9-diphenylfluoren-4-yl group. The heteroaryl group as the optional substituent is preferably a dibenzofuranyl group or a dibenzothiophenyl group (a dibenzothienyl group) and more preferably a 2-dibenzofuranyl group, a 4-dibenzofuranyl group, a 2-dibenzothiophenyl group, or a 4-dibenzothiophenyl group.

The arylene group of the substituted or unsubstituted arylene group having 6 to 30, preferably 6 to 25, and more preferably 6 to 18 ring carbon atoms for $L^1$ and $L^2$ is, for example, selected from a phenylene group, a biphenylene group, a terphenylene group, a biphenylenylene group, a naphthylene group, an acenaphthylene group, an anthrylene group, a benzanthrylene group, an aceanthrylene group, a phenanthrylene group, a benzophenanthrylene group, a phenalenylene group, a pentacenylene group, a picenylene group, a pentaphenylene group, a pyrenylene group, a chrysenylene group, a benzochrysenylene group, a s-indacenylene group, an as-indacenylene group, a fluoranthenylene group, a perylenylene group, a triphenylenylene group, a fluorenylene group, and a 9,9'-spirobifluorenylene group; preferably selected from a phenylene group, a biphenylene group, a terphenylene group, a naphthylene group, a phenanthrylene group, a triphenylenylene group, a fluorenylene group, and a 9,9'-spirobifluorenylene group; more preferably selected from an o-phenylene group, a m-phenylene group, a p-phenylene group, a biphenyl-4,4'-diyl group, a biphenyl-4,3'-diyl group, a 1,4-naphthylene group, and a 2,6-naphthylene group; still more preferably selected from an o-phenylene group, a m-phenylene group, and a p-phenylene group; and particularly preferably a p-phenylene group.

$L^1$ is preferably a single bond and $L^2$ is preferably a substituted or unsubstituted arylene group having 6 to 30 ring carbon atoms.

$L^1$ and $L^2$ may be the same or different.

The substituent referred to herein simply by "substituent" (i.e., $R^1$ to $R^8$, $R^{11}$ to $R^{18}$, $R^{21}$ to $R^{25}$, $R^{26}$ to $R^{29}$, etc.) and the optional substituent referred to herein by "substituted or unsubstituted" is, unless otherwise noted, selected from an alkyl group having 1 to 30, preferably 1 to 18, and more preferably 1 to 8 carbon atoms; a cycloalkyl group having 3 to 30, preferably 3 to 10, more preferably 3 to 8, and still more preferably 5 or 6 ring carbon atoms; an aryl group having 6 to 30, preferably 6 to 25, more preferably 6 to 18 ring carbon atoms; an aralkyl group having 7 to 31, preferably 7 to 26, and more preferably 7 to 20 carbon atoms which includes an aryl group having 6 to 30, preferably 6 to 25, and more preferably 6 to 18 ring carbon atoms: an alkoxy group having an alkyl group having 1 to 30, preferably 1 to 18, and more preferably 1 to 8 carbon atoms; an aryloxy group having an aryl group having 6 to 30, preferably 6 to 25, and more preferably 6 to 18 ring carbon atoms; a mono-, di- or tri-substituted silyl group having a substituent selected from an alkyl group having 1 to 30, preferably 1 to 18, and more preferably 1 to 8 carbon atoms and an aryl group having 6 to 30, preferably 6 to 25, and more preferably 6 to 18 ring carbon atoms; a haloalkyl group having 1 to 30, preferably 1 to 18, and more preferably 1 to 8 carbon atoms; a haloalkoxy group having a haloalkyl group having 1 to 30, preferably 1 to 18, and more preferably 1 to 8 carbon atoms; a heteroaryl group having 5 to 30, preferably 5 to 25, and more preferably 5 to 18 ring atoms; a halogen atom; a cyano group; and a nitro group.

Each of the substituent and the optional substituent is preferably selected from the alkyl group, the aryl group, and the heteroaryl group.

Examples of the alkyl group having 1 to 30 carbon atoms include a methyl group, an ethyl group, a n-propyl group, an isopropyl group, a n-butyl group, an isobutyl group, a s-butyl group, a t-butyl group, a pentyl group (inclusive of isomeric groups), a hexyl group (inclusive of isomeric groups), a heptyl group (inclusive of isomeric groups), an octyl group (inclusive of isomeric groups), a nonyl group (inclusive of isomeric groups), a decyl group (inclusive of isomeric groups), an undecyl group (inclusive of isomeric groups), and a dodecyl group (inclusive of isomeric groups). Preferred are a methyl group, an ethyl group, a n-propyl group, an isopropyl group, a n-butyl group, an isobutyl group, a s-butyl group, a t-butyl group, and a pentyl group (inclusive of isomeric groups), with a methyl group, an ethyl group, a n-propyl group, an isopropyl group, a n-butyl group, an isobutyl group, a s-butyl group, and a t-butyl group being more preferred, and a methyl group, an ethyl group, and a t-butyl group being still more preferred.

Examples of the cycloalkyl group having 3 to 30 ring carbon atoms include a cyclopropyl group, a cyclobutyl group, a cyclopentyl group, a cyclohexyl group, and a cycloheptyl group.

Examples of the aryl group having 6 to 30 ring carbon atoms include a phenyl group, a biphenylyl group, a terphenylyl group, a biphenylenyl group, a naphthyl group, an acenaphthylenyl group, an anthryl group, a benzanthryl group, an aceanthryl group, a phenanthryl group, a benzophenanthryl group, a phenalenyl group, a fluorenyl group, a 9,9-dimethylfluorenyl group, a 9,9-diphenylfluorenyl group, a pentacenyl group, a picenyl group, a pentaphenyl group, a pyrenyl group, a chrysenyl group, a benzochrysenyl group, a s-indacenyl group, an as-indacenyl group, a fluoranthenyl group, a triphenyl group, and a perylenyl group. Preferred are a phenyl group, a biphenylyl group, a terphenylyl group, a naphthyl group, a 9,9-dimethylfluorenyl group, a 9,9-diphenylfluorenyl group, a phenanthryl group, and a triphenyl group.

The details of the aryl group having 6 to 30 ring carbon atoms of the aralkyl group having 7 to 31 carbon atoms are the same as those of the aryl group having 6 to 30 ring carbon atoms mentioned above. The alkyl portion of the aralkyl group is selected from the alkyl group mentioned above so as to allow the aralkyl group to have 7 to 31 carbon atoms. Preferred examples of the aralkyl group having 7 to 31 carbon atoms are a benzyl group, a phenethyl group, and a phenylpropyl group, with a benzyl group being preferred.

The details of the alkyl group having 1 to 30 carbon atoms and the aryl group having 6 to 30 ring carbon atoms for the mono- or di-substituted amino group are the same as those of the alkyl group having 1 to 30 carbon atoms mentioned above and the aryl group having 6 to 30 ring carbon atoms mentioned above. Examples of the mono- or di-substituted amino group include a dialkylamino group, a diarylamino group, and an alkylarylamino group.

The details of the alkyl group having 1 to 30 carbon atoms for the alkoxy group are the same as those of the alkyl group having 1 to 30 carbon atoms mentioned above. Examples of the alkoxy group include a t-butoxy group, a propoxy group, an ethoxy group, and a methoxy group, with an ethoxy group and a methoxy group being more preferred, and a methoxy group being still more preferred.

The details of the aryl group having 6 to 30 ring carbon atoms for the aryloxy group are the same as those of the aryl group having 6 to 30 ring carbon atoms mentioned above. Preferred examples of the aryloxy group include a terphenyloxy group, a biphenyloxy group, and a phenoxy group, with a biphenyloxy group and a phenoxy group being more preferred, and a phenoxy group being still more preferred.

The details of the alkyl group having 1 to 30 carbon atoms and the aryl group having 6 to 30 ring carbon atoms for the mono-, di- or tri-substituted silyl group are the same as those of the alkyl group having 1 to 30 carbon atoms mentioned above and the aryl group having 6 to 30 ring carbon atoms mentioned above. Preferred is a tri-substituted silyl group, for example, a trimethylsilyl group, a triethylsilyl group, a t-butyldimethylsilyl group, a propyldimethylsilyl group, an isopropyldimethylsilyl group, a triphenylsilyl group, a phenyldimethylsilyl group, a t-butyldiphenylsilyl group, and a tritolylsilyl group.

The haloalkyl group having 1 to 30 carbon atoms is a group derived from the alkyl group having 1 to 30 carbon atoms mentioned above by replacing at least one, preferably 1 to 7 hydrogen atoms or all the hydrogen atoms with a halogen atom, such as a fluorine atom, a chlorine atom, a bromine atom, and an iodine atom, preferably a fluorine atom. Preferred example thereof is a fluoroalkyl group having 1 to 30, preferably 1 to 18, and more preferably 1 to 8 carbon atoms, with a heptafluoropropyl group (inclusive of isomeric groups), a pentafluoroethyl group, a 2,2,2-trifluoroethyl group, and a trifluoromethyl group being more preferred, a pentafluoroethyl group, a 2,2,2-trifluoroethyl group, and a trifluoromethyl group being still more preferred, and a trifluoromethyl group being particularly preferred.

The details of the haloalkyl group having 1 to 30 carbon atoms for the haloalkoxy group are the same as those of the haloalkyl group having 1 to 30 carbon atoms mentioned above. Preferred example thereof is a fluoroalkoxy group having 1 to 30, preferably 1 to 18, and more preferably 1 to 8 carbon atoms, with a heptafluoropropoxy group (inclusive of isomeric groups), a pentafluoroethoxy group, a 2,2,2-trifluoroethoxy group, and trifluoromethoxy group being more preferred, a pentafluoroethoxy group, a 2,2,2-trifluoroethoxy group, and trifluoromethoxy group being still more preferred, and a trifluoromethoxy group being particularly preferred.

The heteroaryl group having 5 to 30 ring atoms comprises 1 to 5, preferably 1 to 3, more preferably 1 to 2 ring heteroatoms, for example, a nitrogen atom, a sulfur atom, and an oxygen atom.

Examples of the heteroaryl group include a pyrrolyl group, a furyl group, a thienyl group, a pyridyl group, a pyridazinyl group, a pyrimidinyl group, a pyrazinyl group, a triazinyl group, an imidazolyl group, an oxazolyl group, a thiazolyl group, a pyrazolyl group, an isoxazolyl group, an isothiazolyl group, an oxadiazolyl group, a thiadiazolyl group, a triazolyl group, an indolyl group, an isoindolyl group, a benzofuranyl group, an isobenzofuranyl group, a benzothiophenyl group (a benzothienyl group), an indolizinyl group, a quinolizinyl group, a quinolyl group, an isoquinolyl group, a cinnolyl group, a phthalazinyl group, a quinazolinyl group, a quinoxalinyl group, a benzimidazolyl group, a benzoxazolyl group, a benzothiazolyl group, an indazolyl group, a benzisoxazolyl group, a benzisothiazolyl group, a dibenzofuranyl group, a naphthobenzofuranyl group, a dibenzothiophenyl group (a dibenzothienyl group), a naphthobenzothiophenyl group (a naphthobenzothienyl group), a N-carbazolyl group, a C-carbazolyl group (a N-phenylcarbazolyl group), a benzo-N-carbazolyl group, a benzo-C-carbazolyl group, a phenanthridinyl group, an acridinyl group, a phenanthrolinyl group, a phenazinyl group, a phenothiazinyl group, a phenoxazinyl group, and a xanthenyl group. Preferred are a benzofuranyl group, a benzothiophenyl group, a dibenzofuranyl group, a dibenzothiophenyl group, a N-phenylcarbazolyl group, and a N-carbazolyl group.

The halogen atom is a fluorine atom, a chlorine atom, a bromine atom, or an iodine atom, with a fluorine atom being preferred.

The method of producing the compound (1) is not particularly limited. A person skilled in the art could easily produce the compound (1) by using or modifying known synthesis reactions with reference to the examples described below.

The spiro carbon atom in formula (1) can be an asymmetric carbon atom. When the spiro carbon atoms is asymmetric, the compound (1) of the invention may be any of a single optical isomer, a racemic mixture, and a mixture of two optical isomers in an arbitrary ratio.

Examples of the compound (1) of the invention are shown below, although not limited thereto.

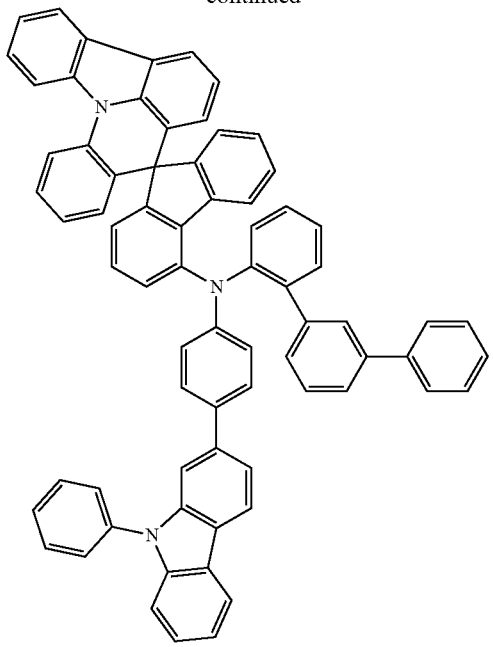

-continued

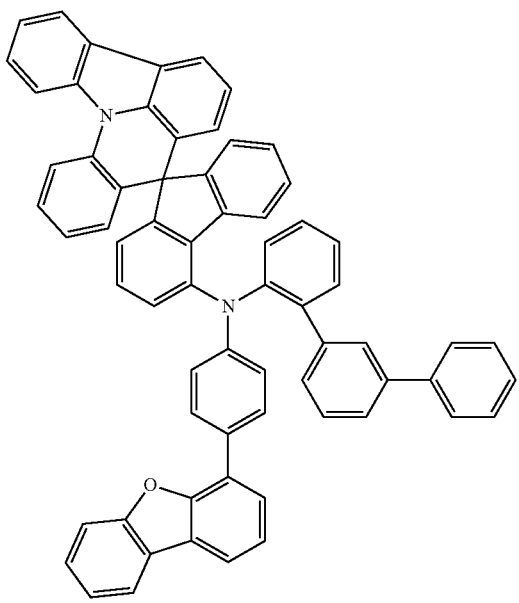

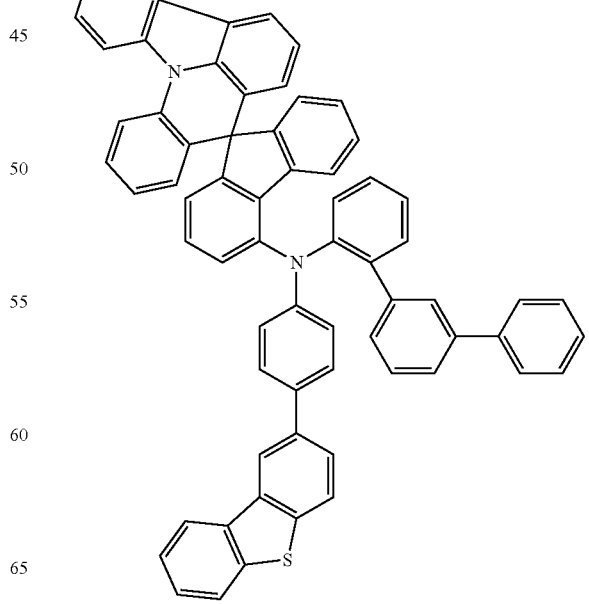

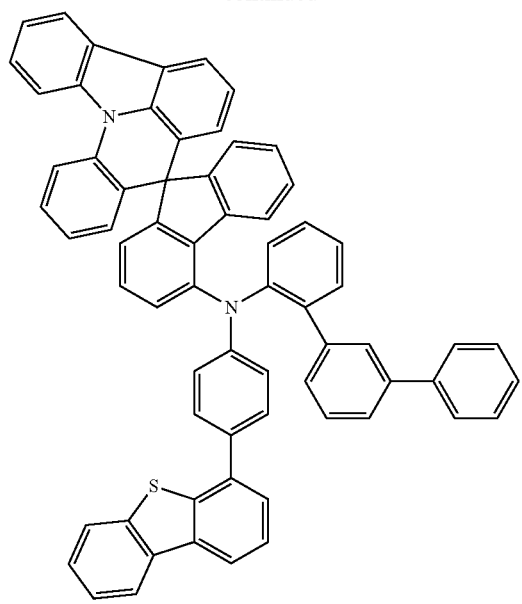
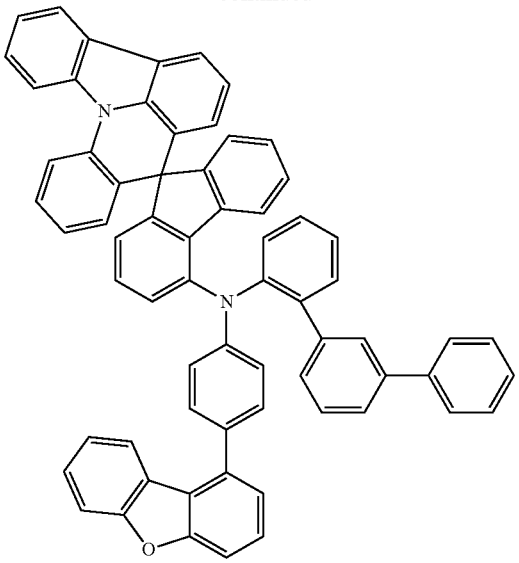
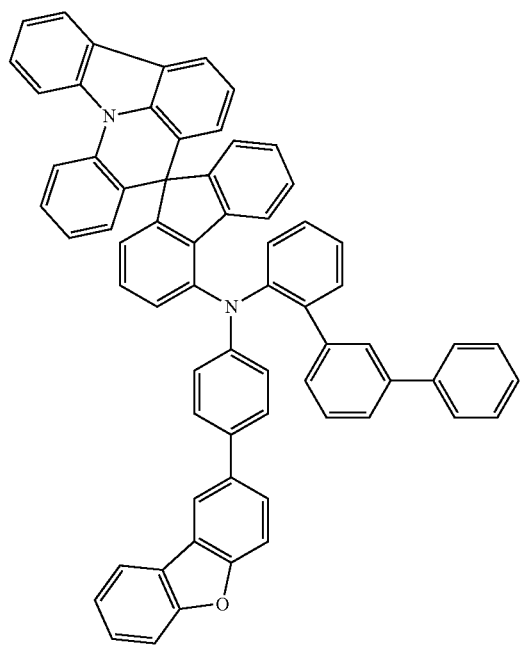
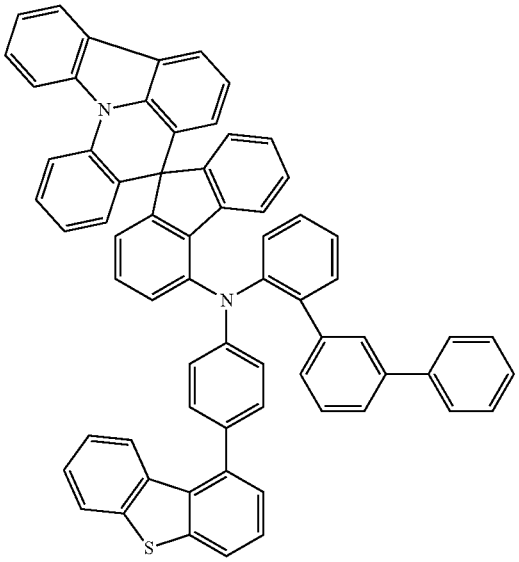

25
-continued
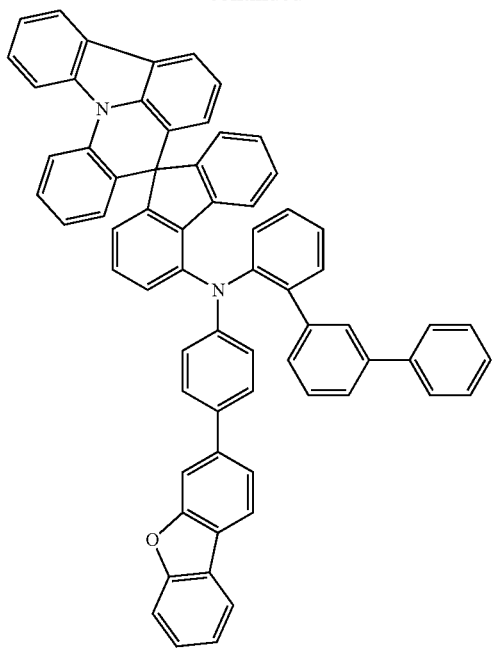
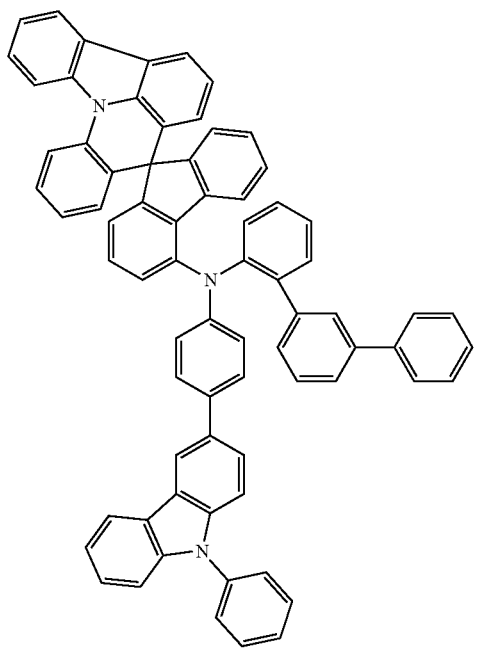
26
-continued
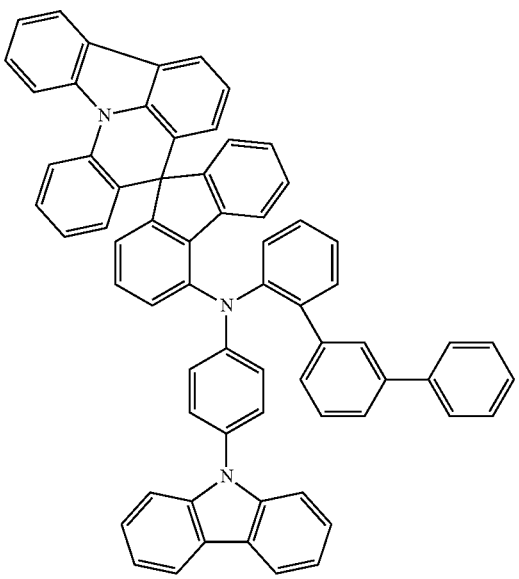
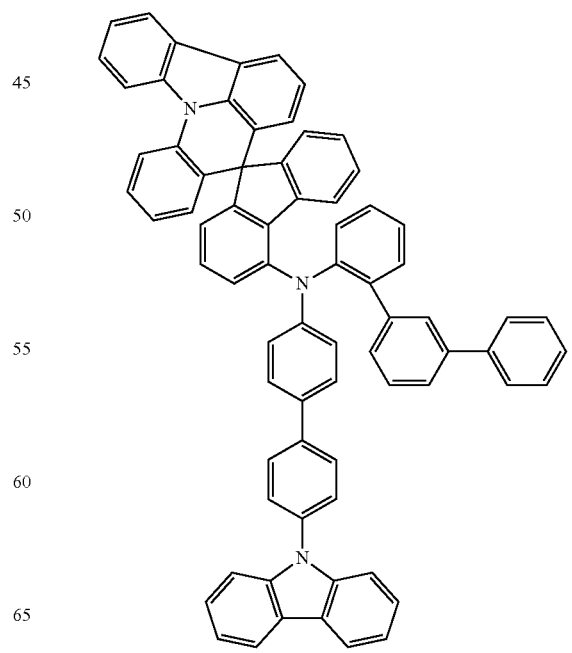

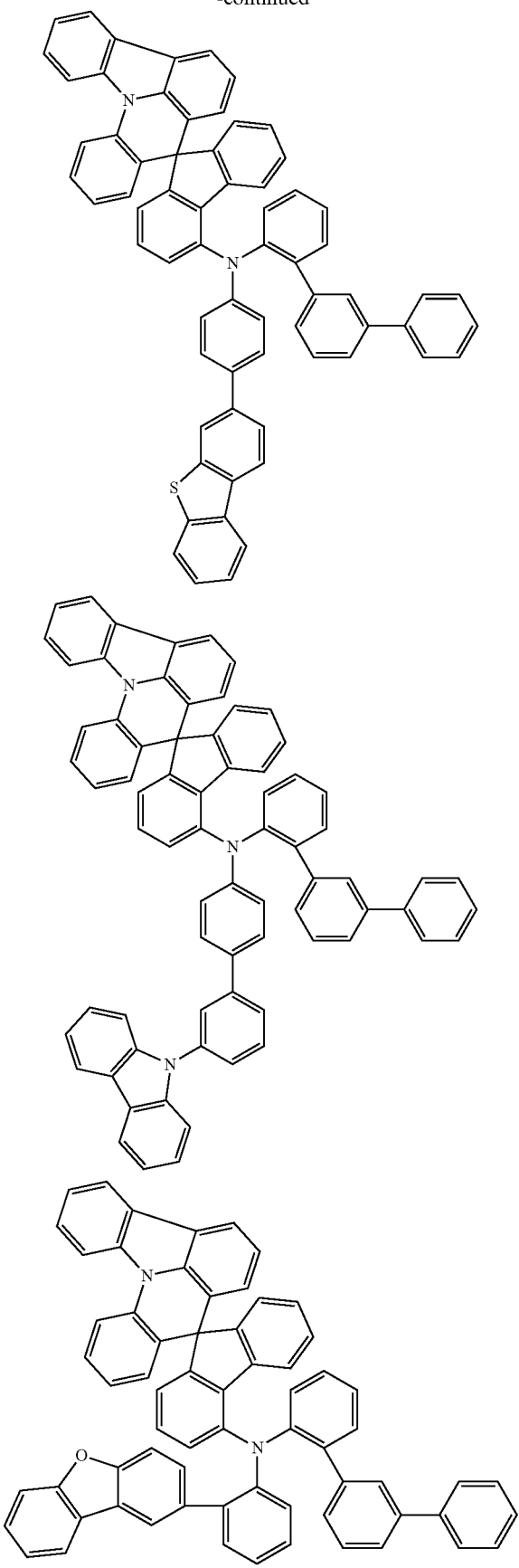
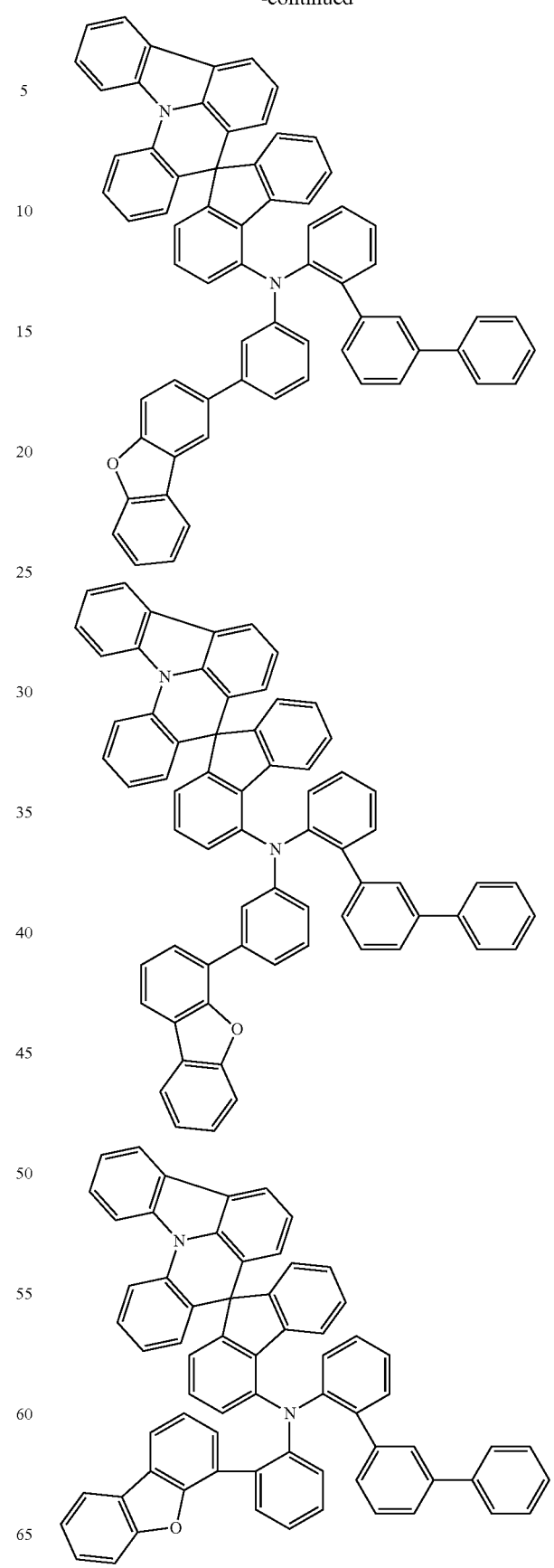

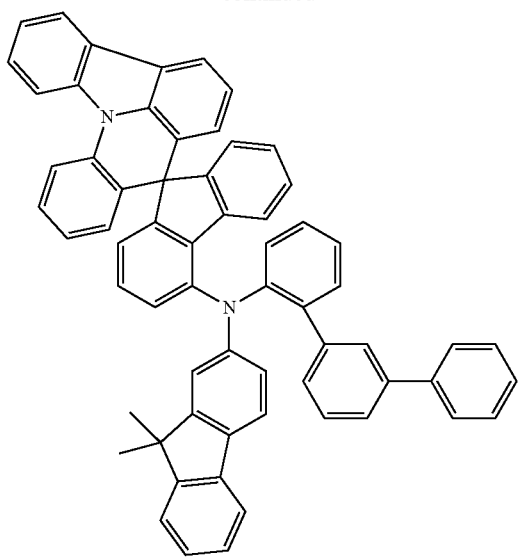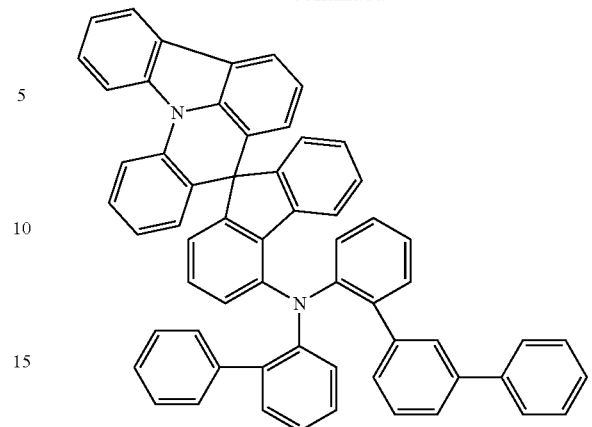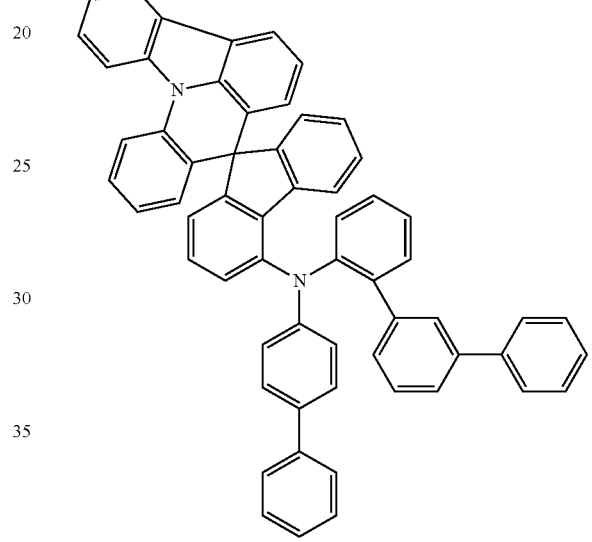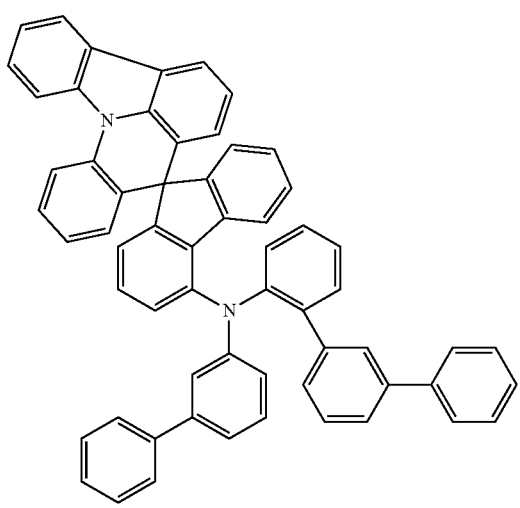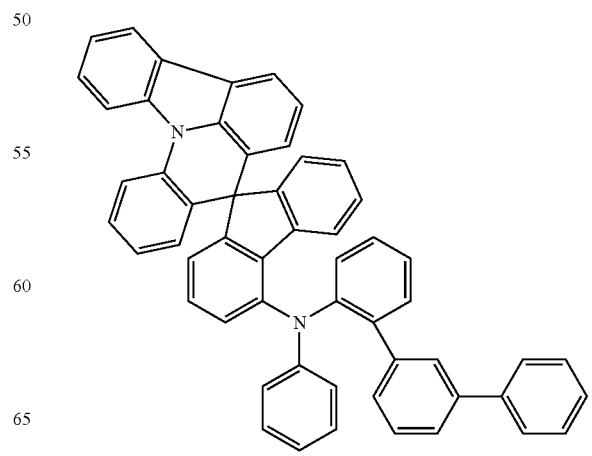

31
-continued
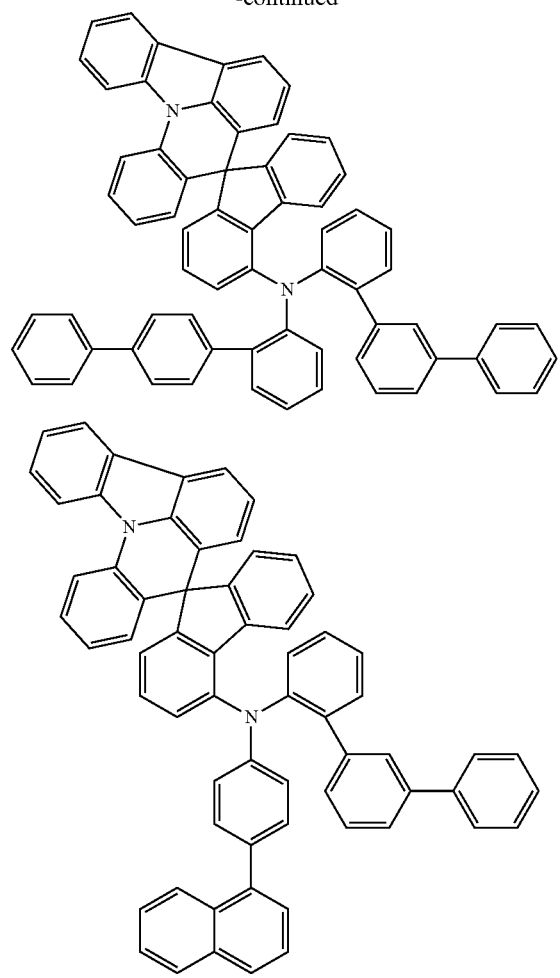
32
-continued
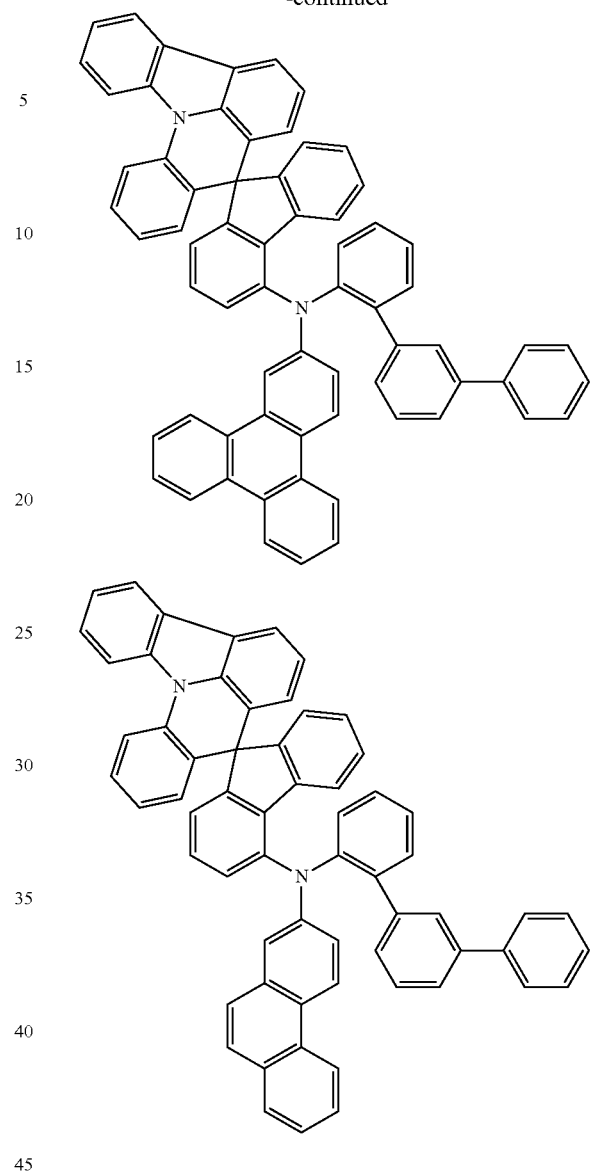
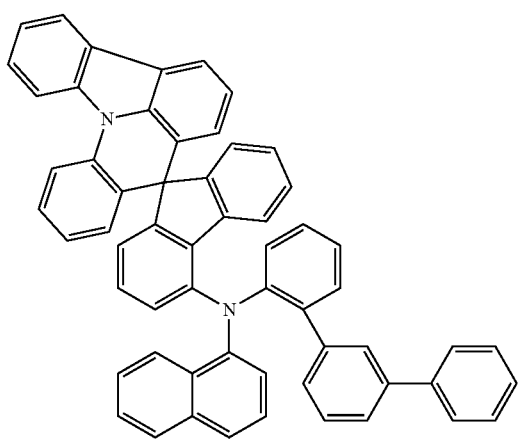
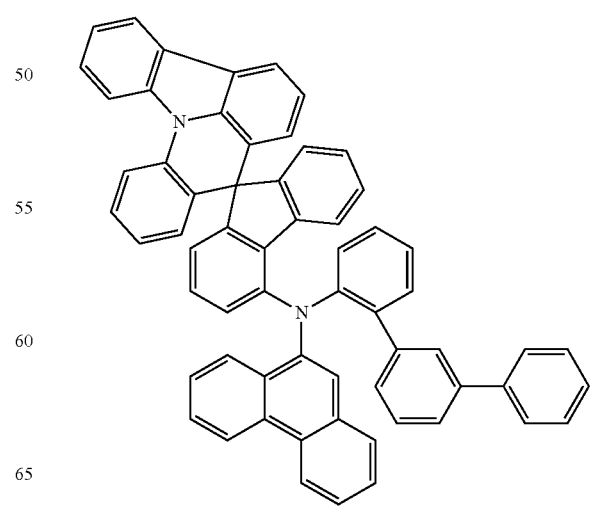

33
-continued
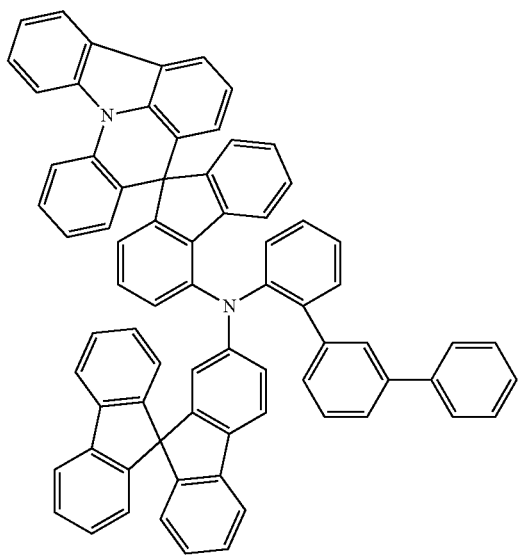
34
-continued
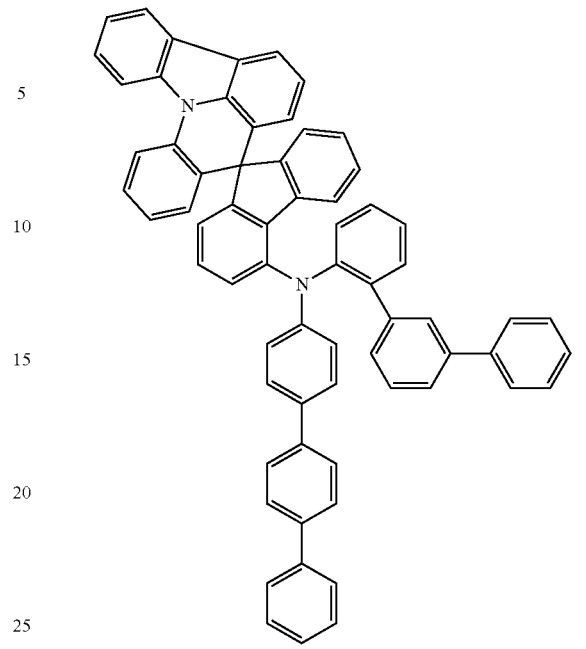
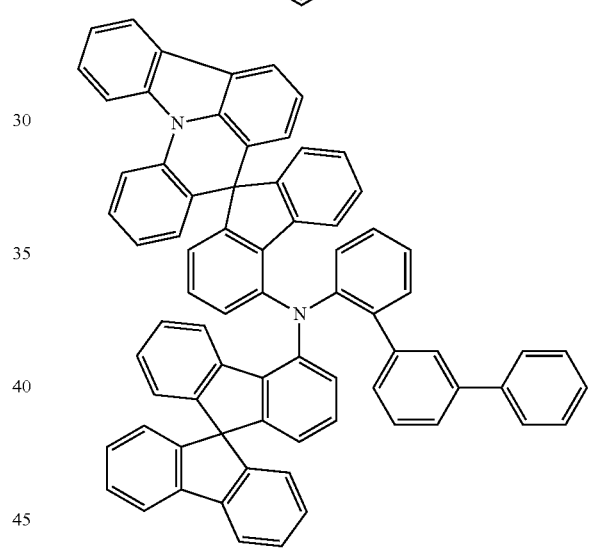
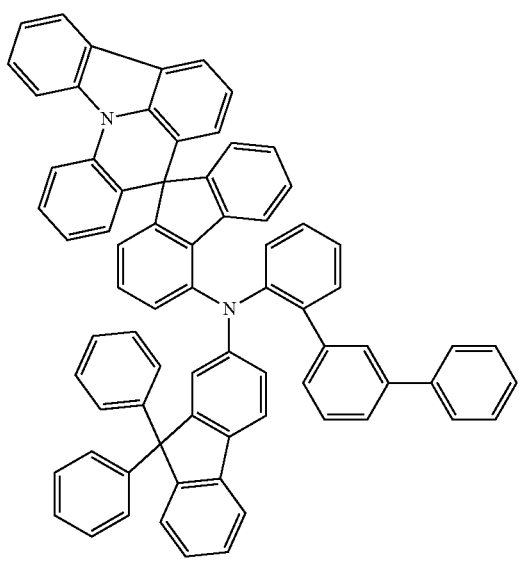
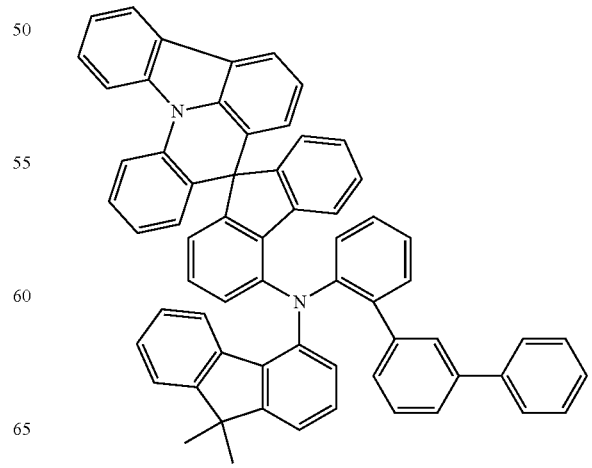

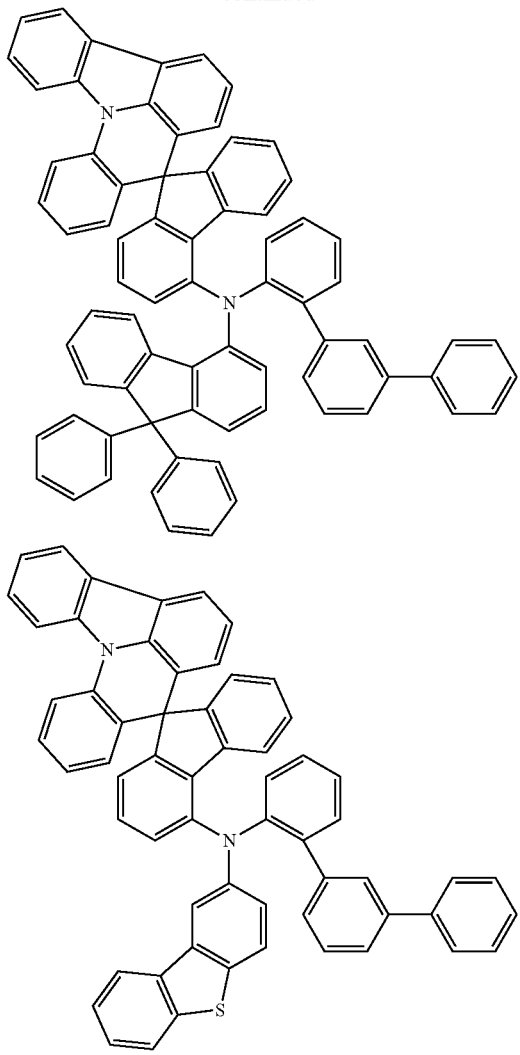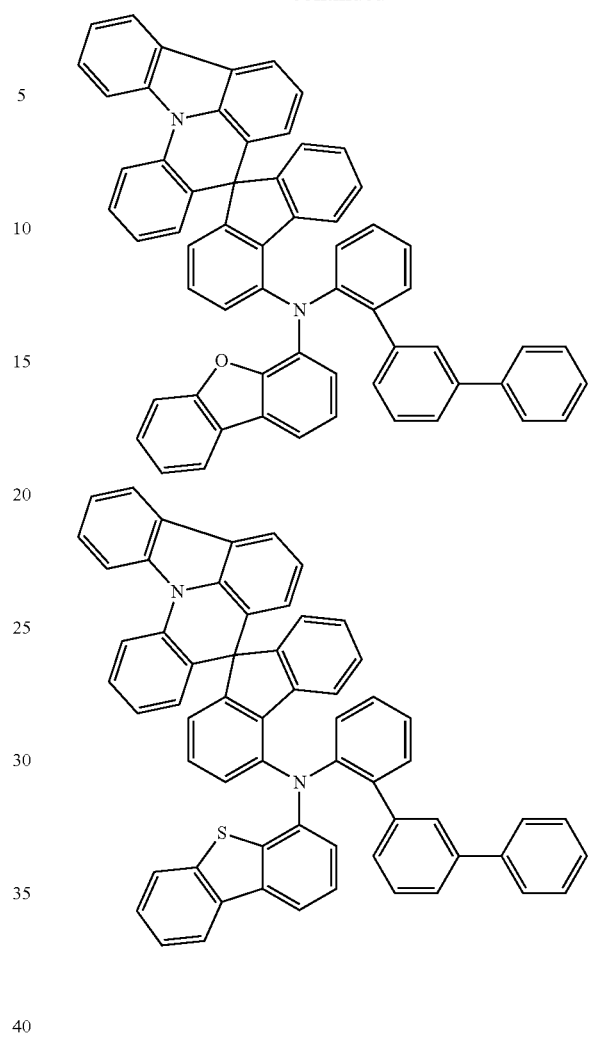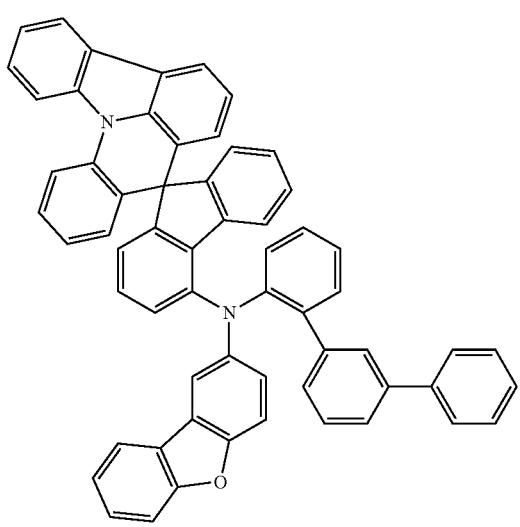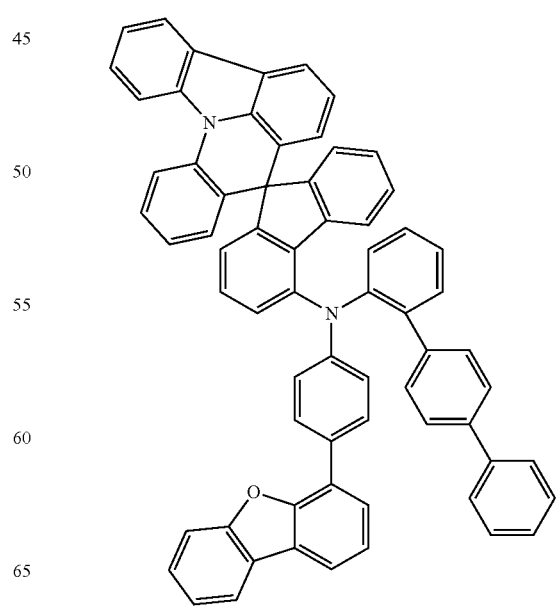

37
-continued
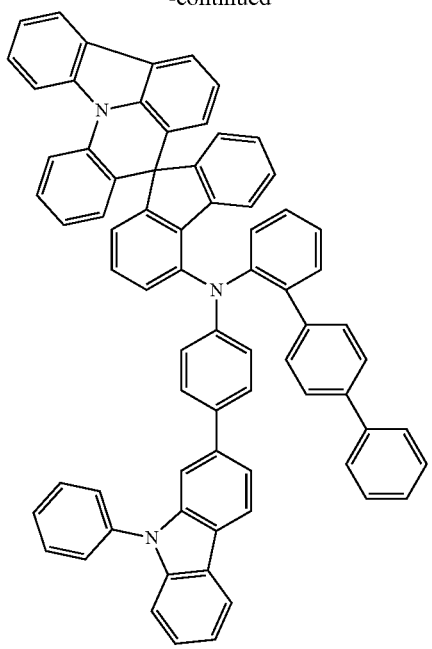
38
-continued
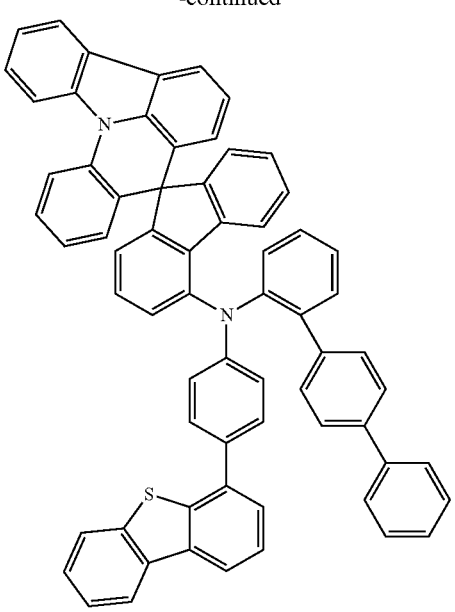
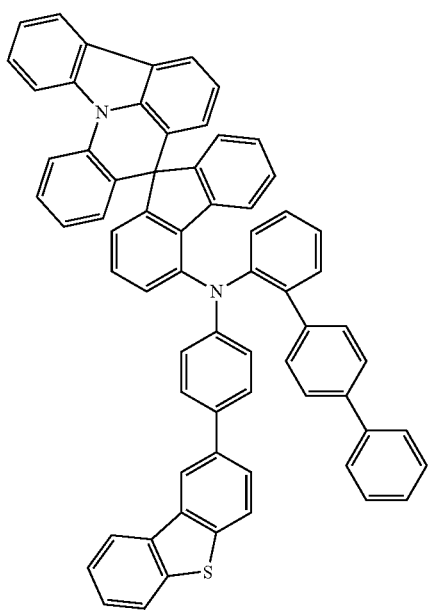
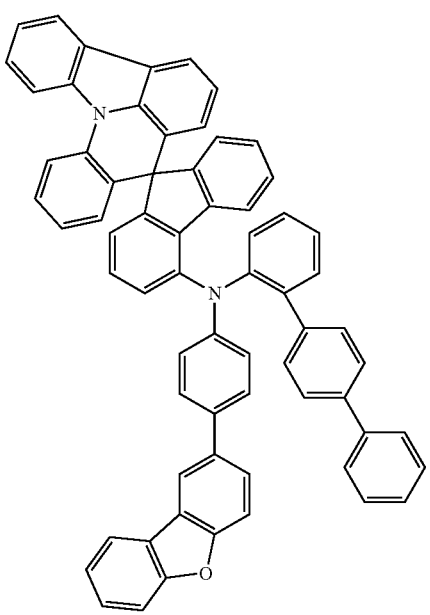

39
-continued
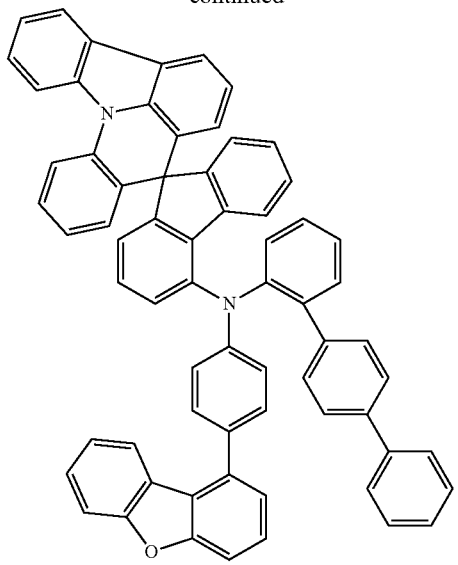
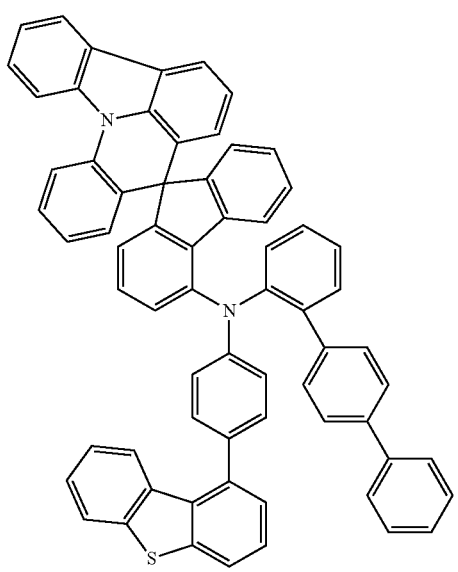
40
-continued
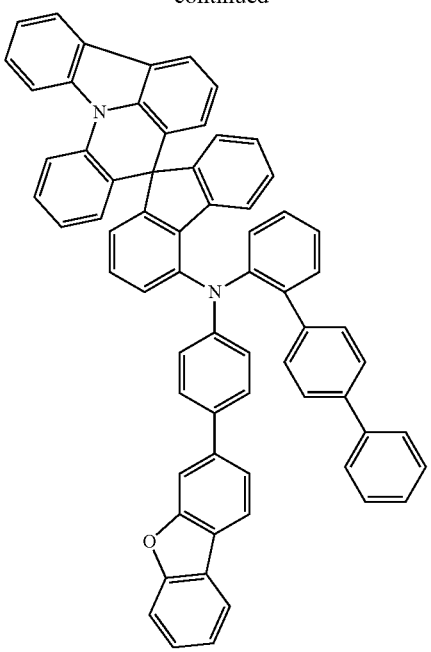
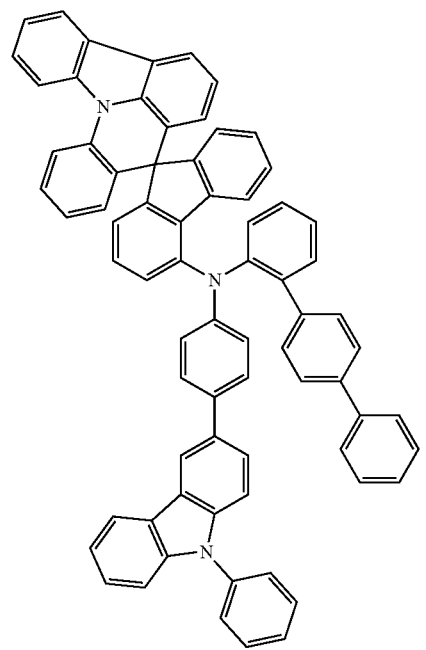

41
-continued
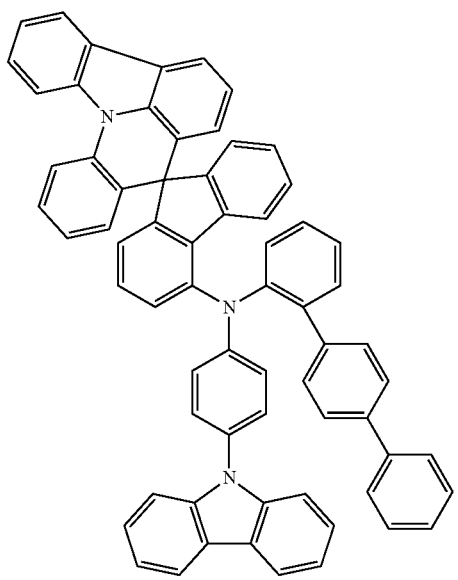
42
-continued
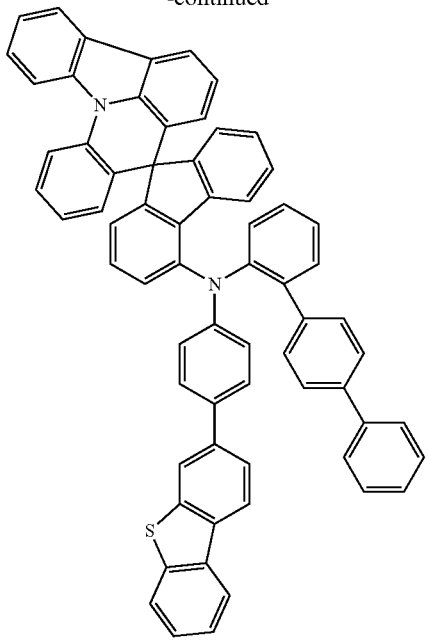
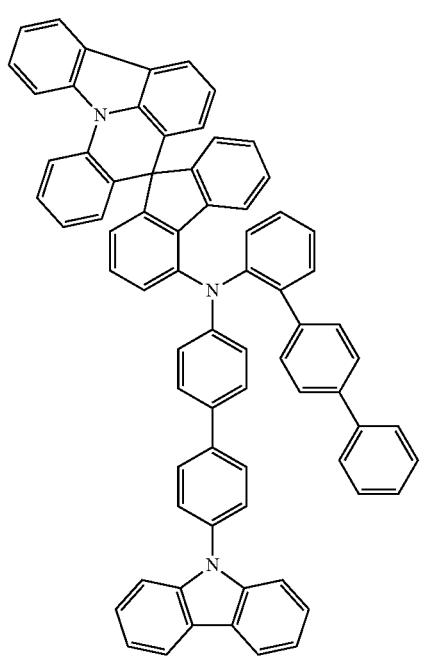
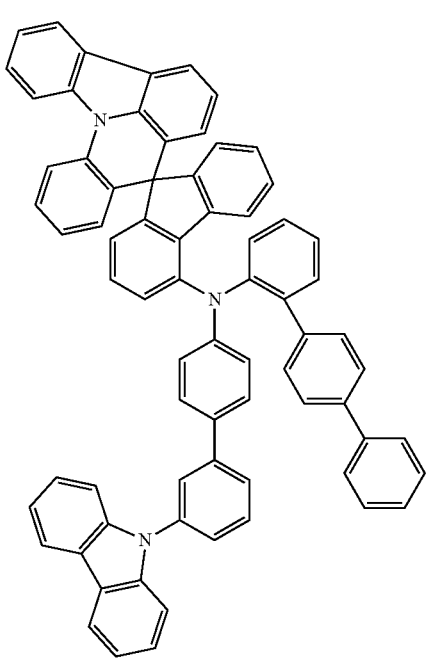

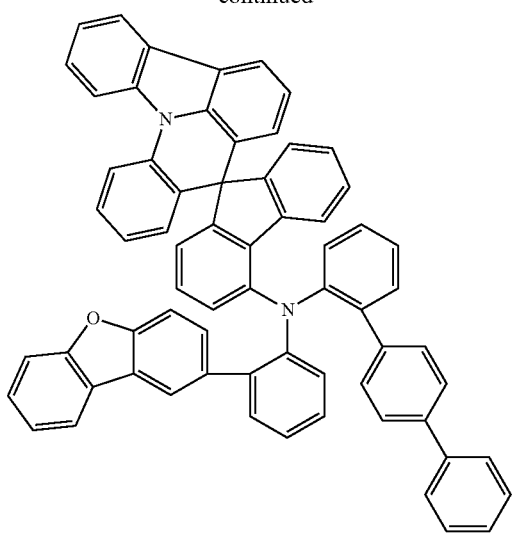
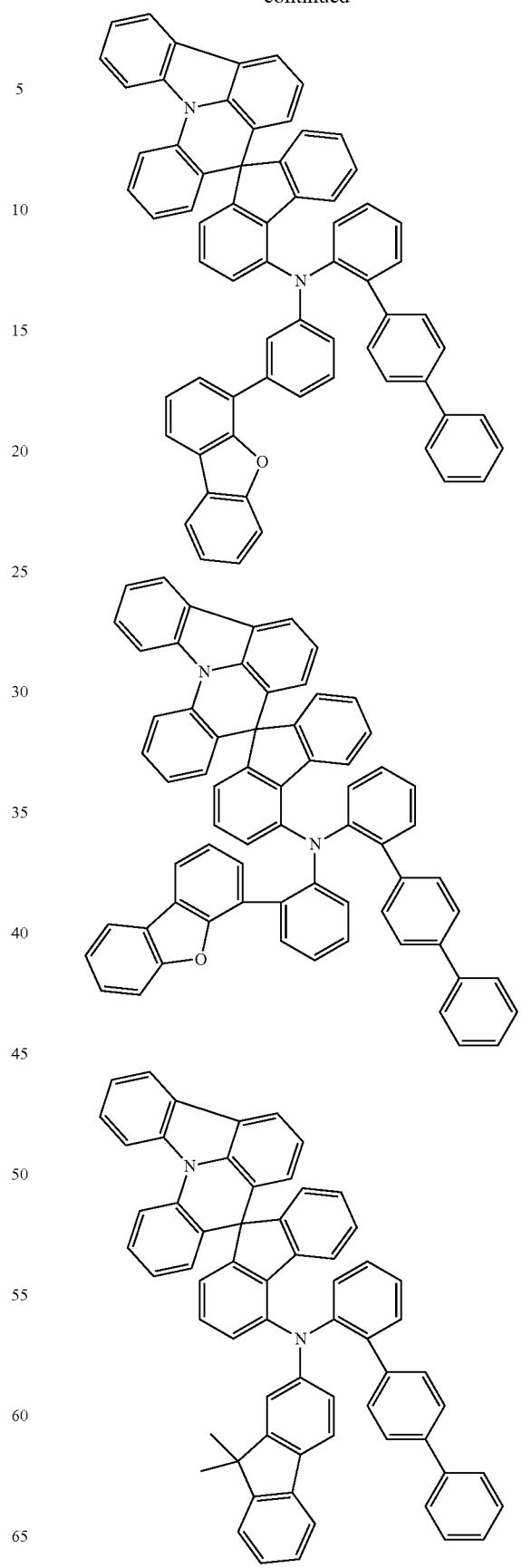
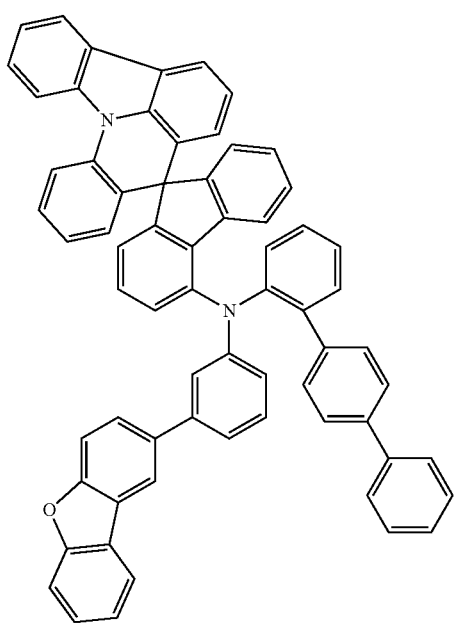

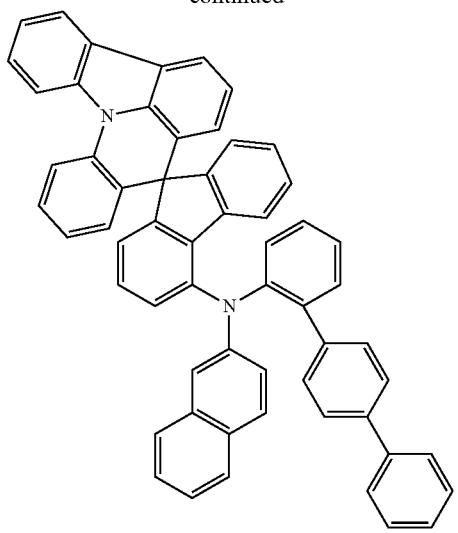
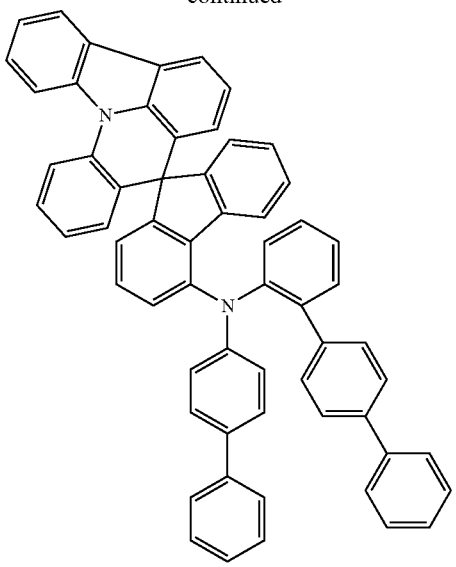
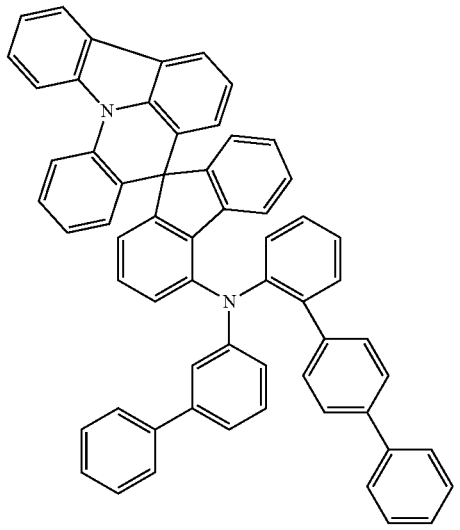
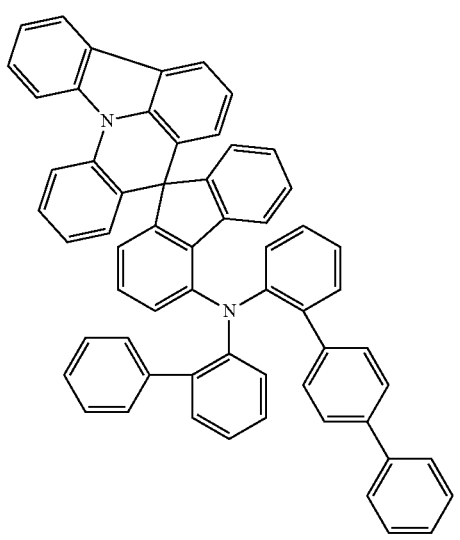
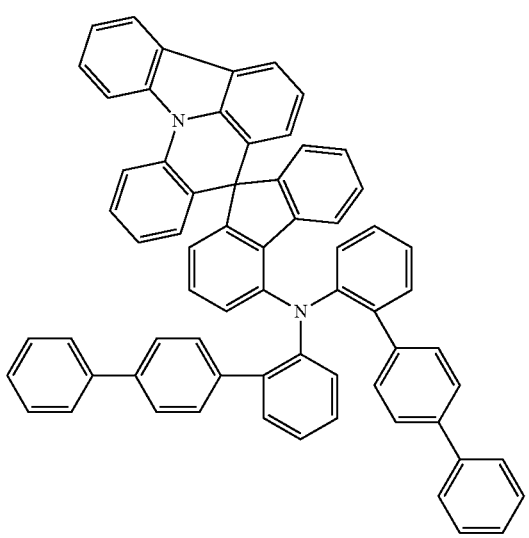

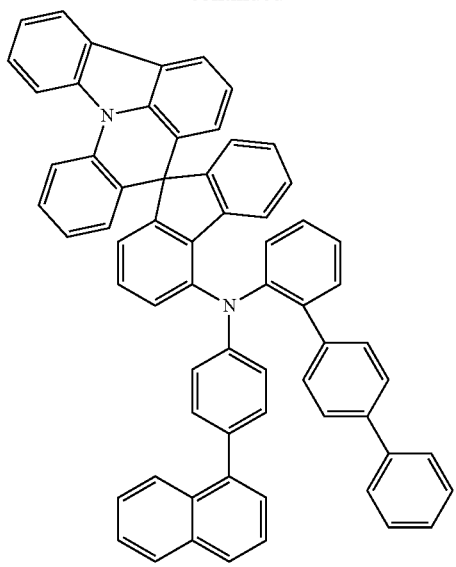
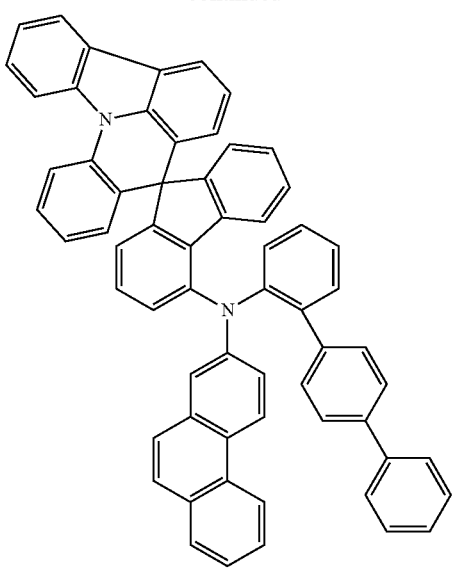
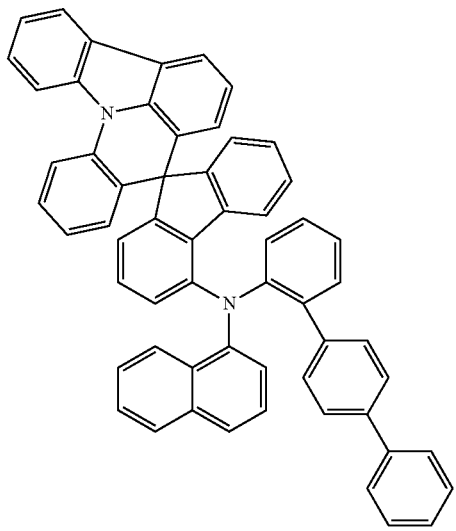
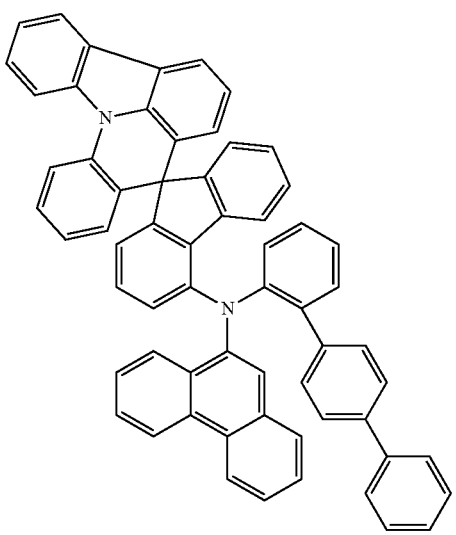
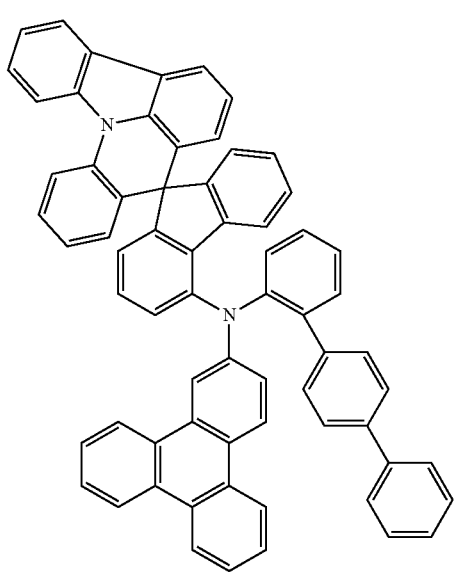
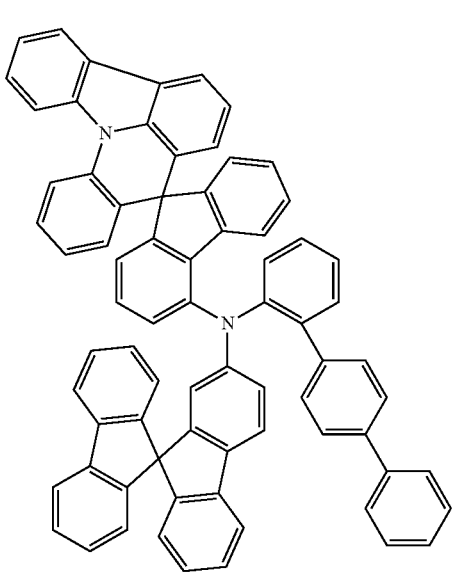

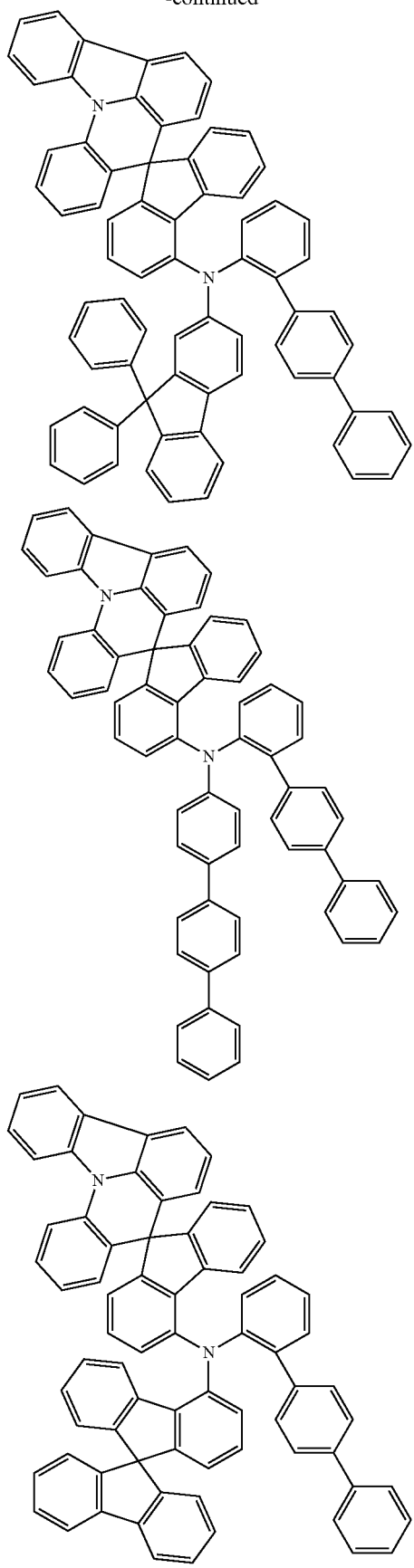
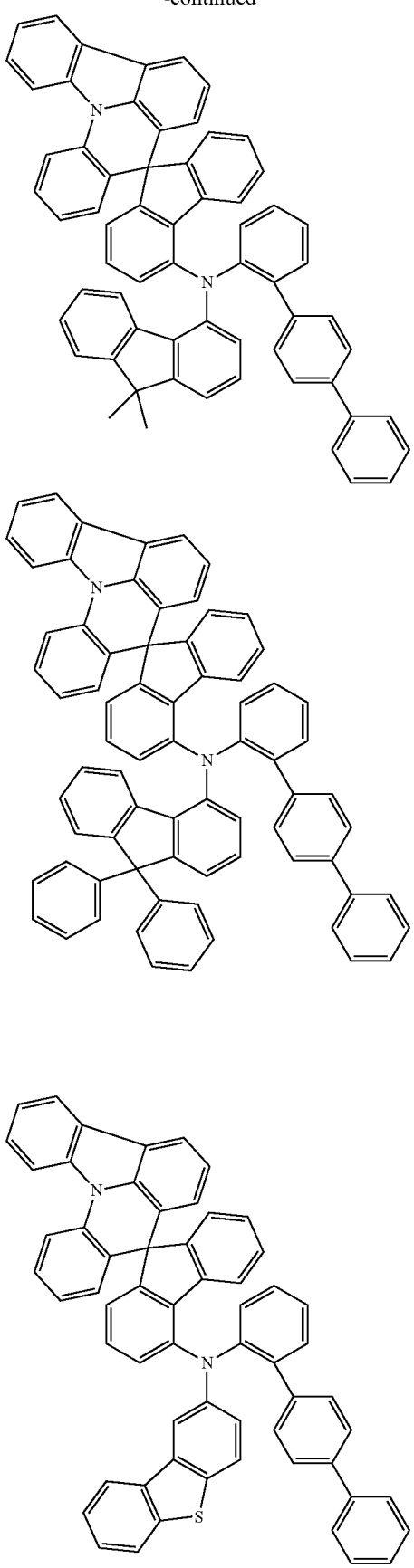

51
-continued
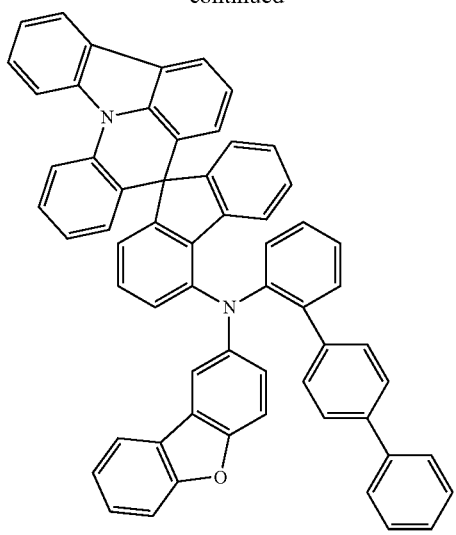
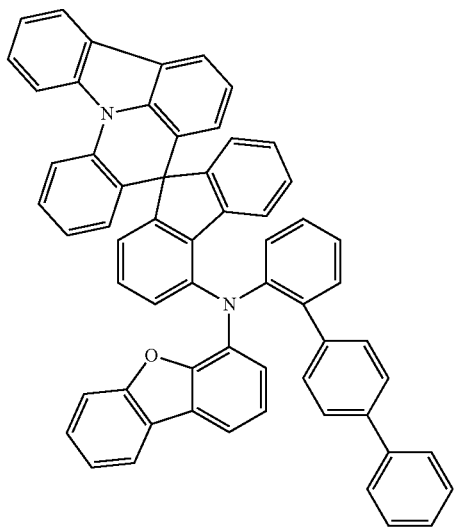
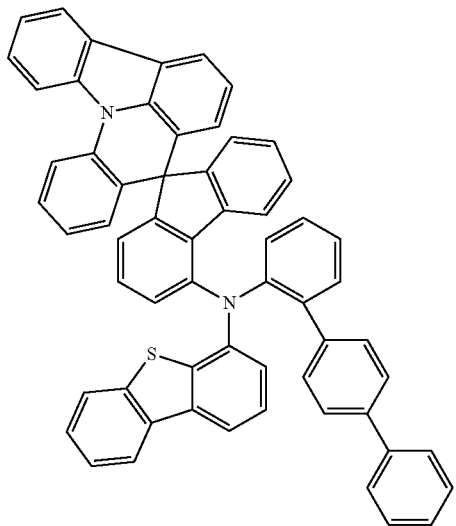
52
-continued
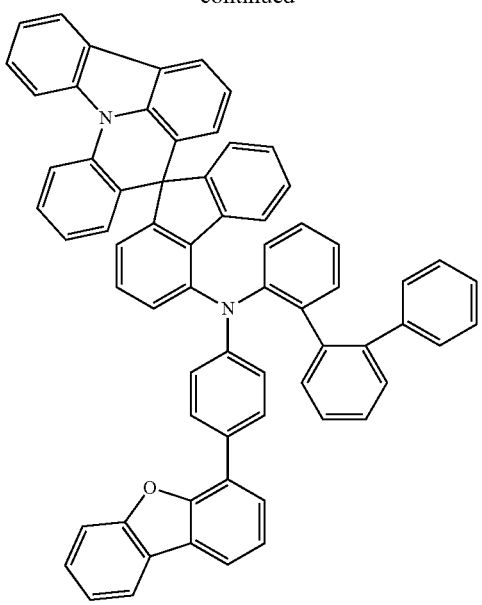
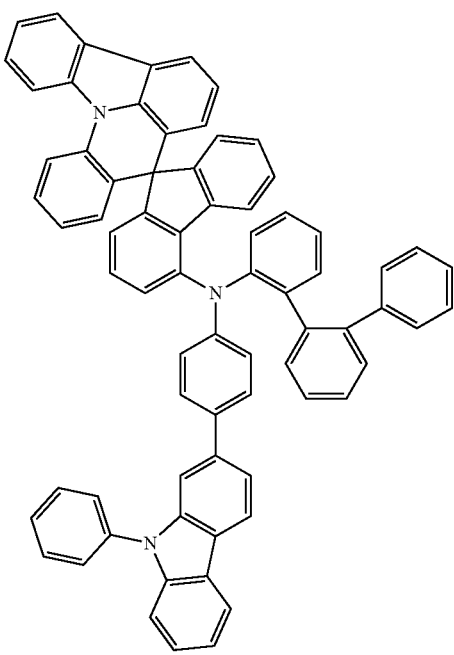

53
-continued
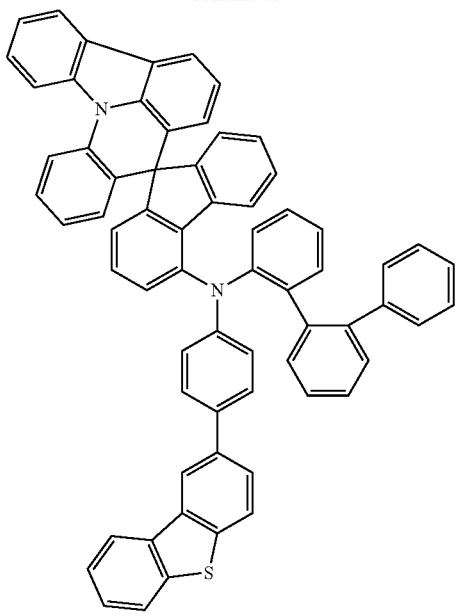
54
-continued
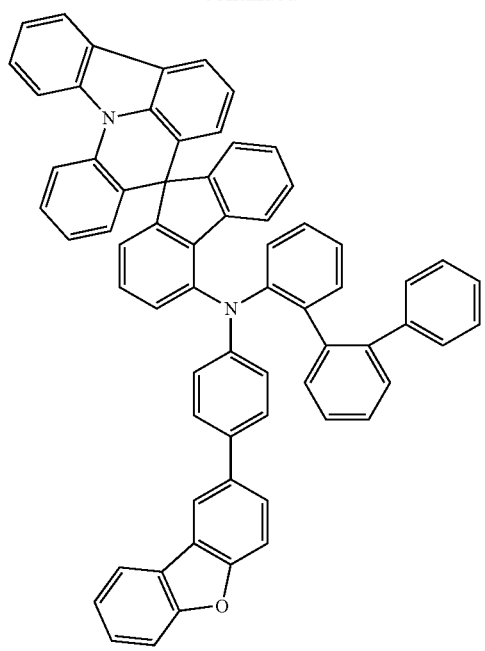
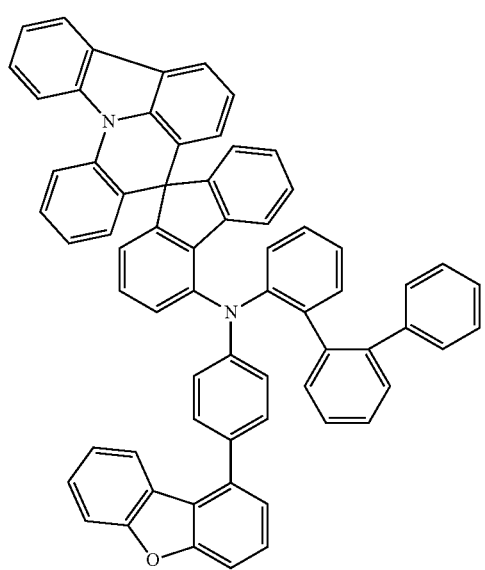

55
-continued
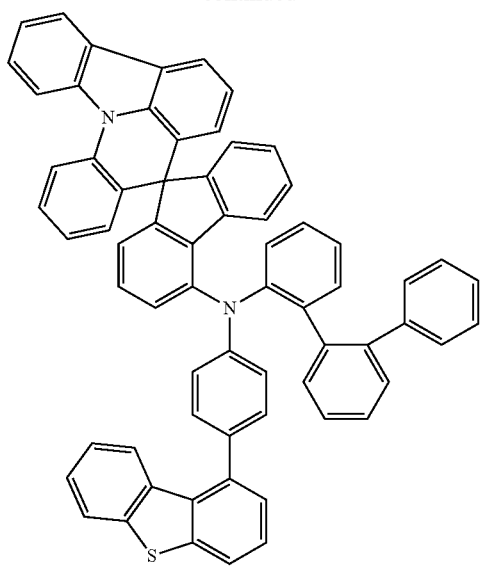
56
-continued
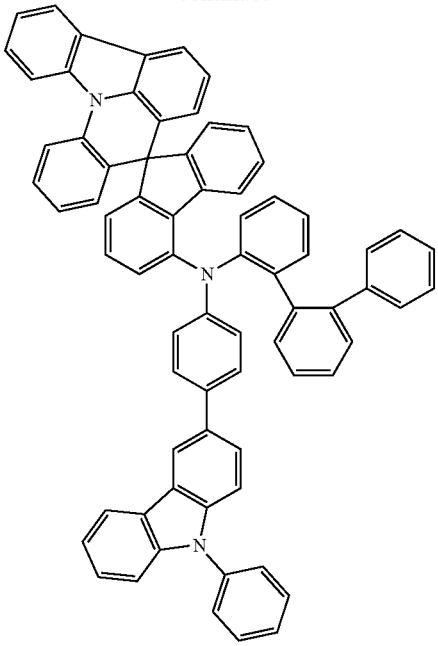
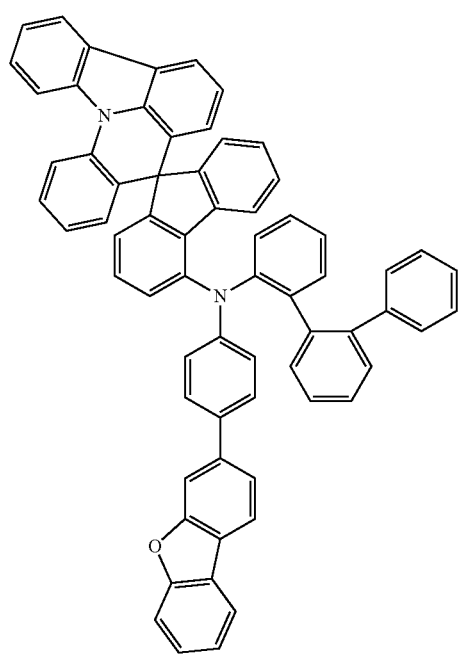
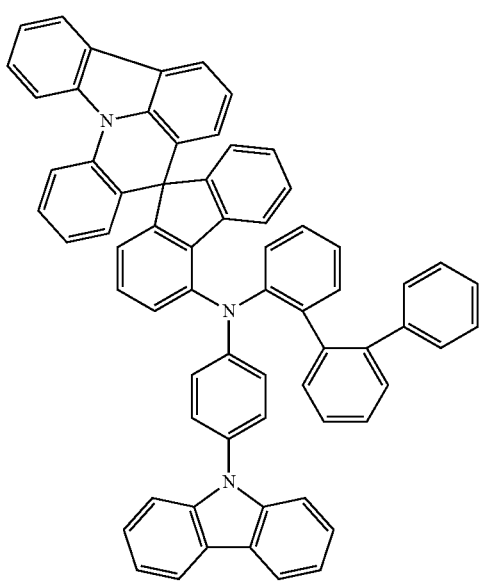

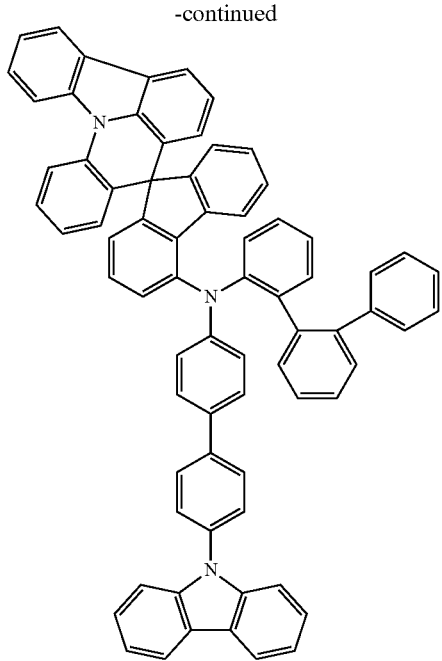
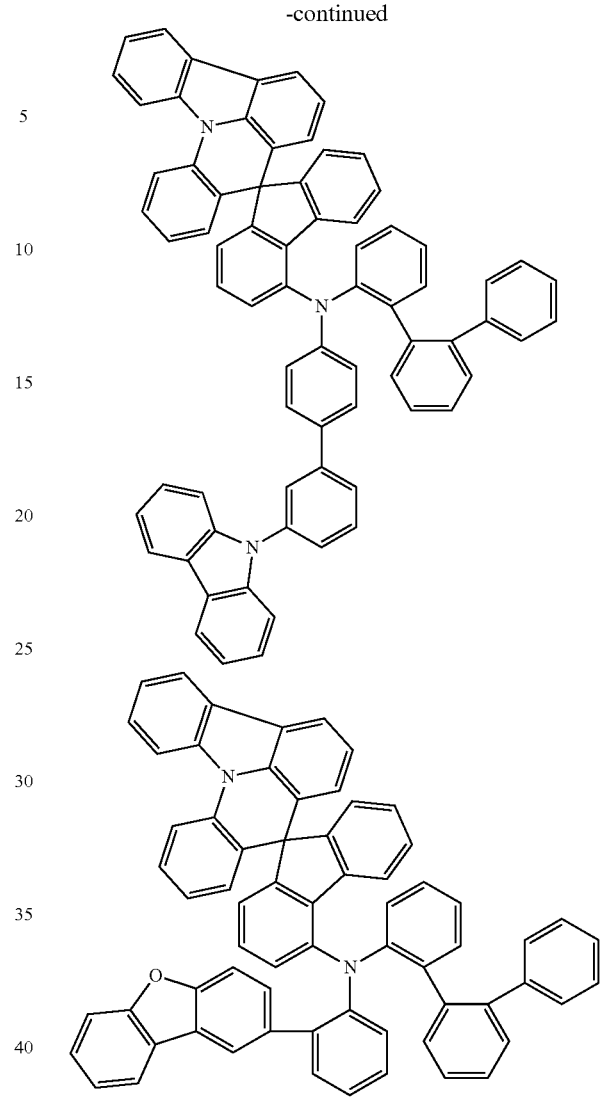
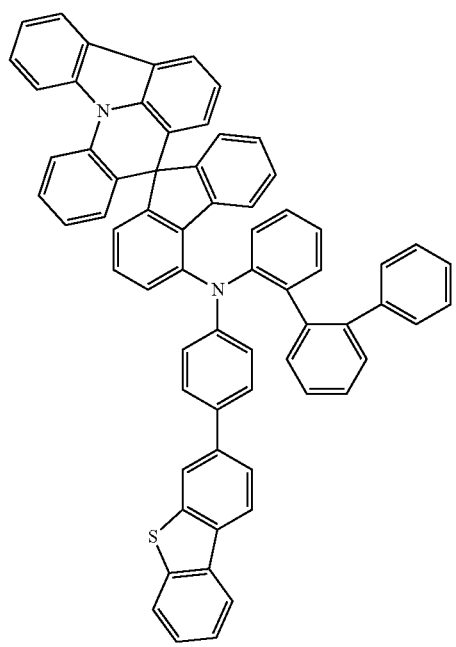
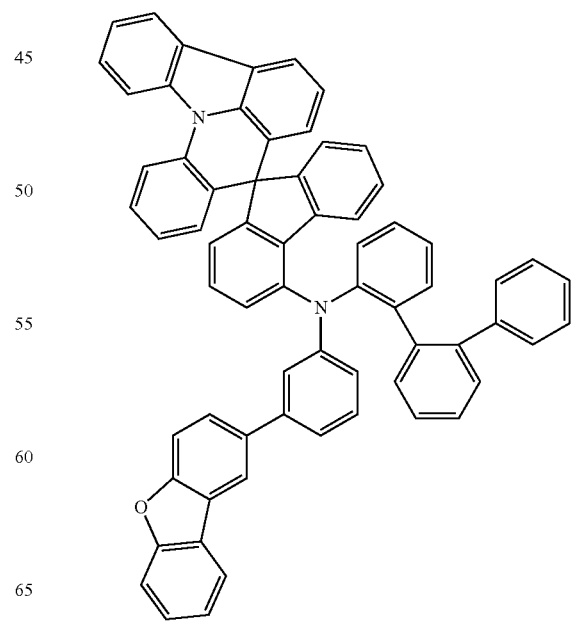

59
-continued
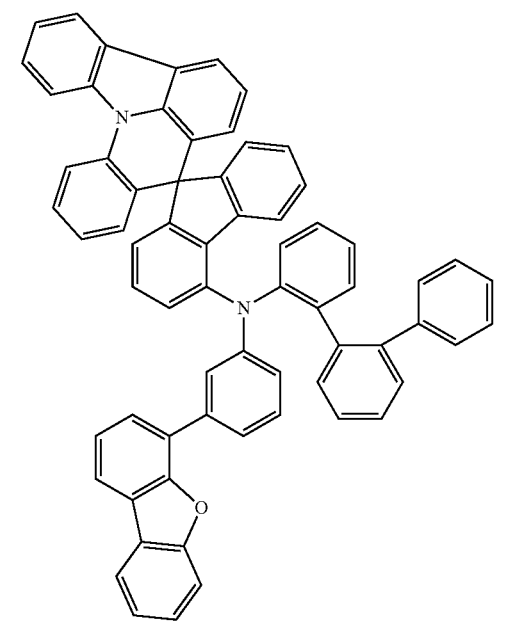
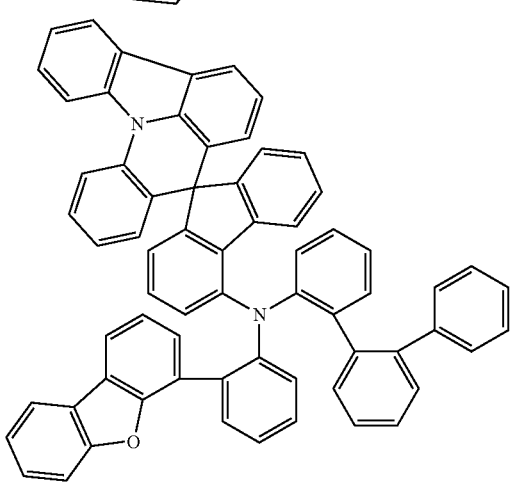
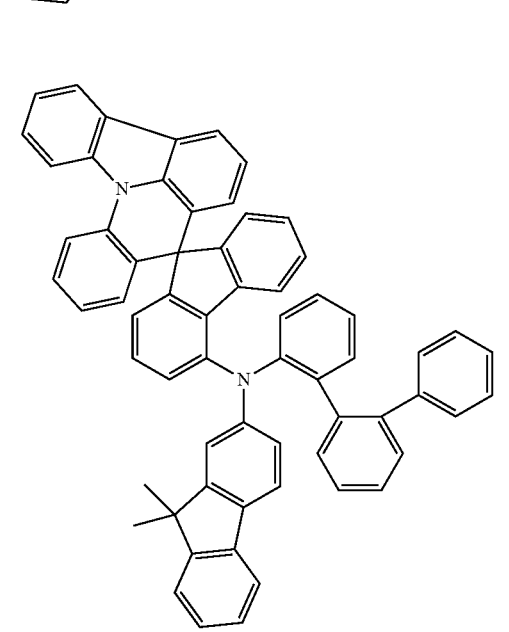
60
-continued
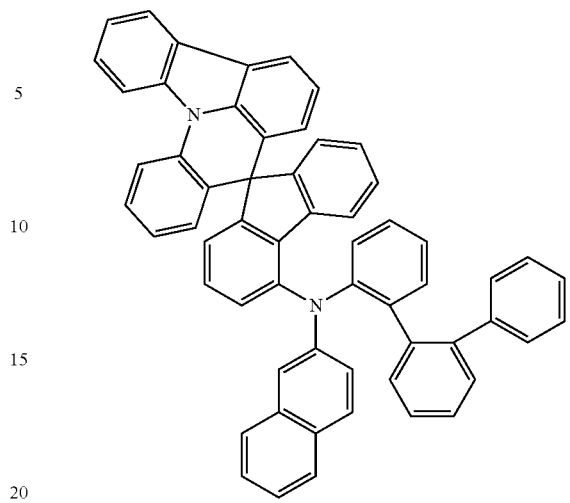
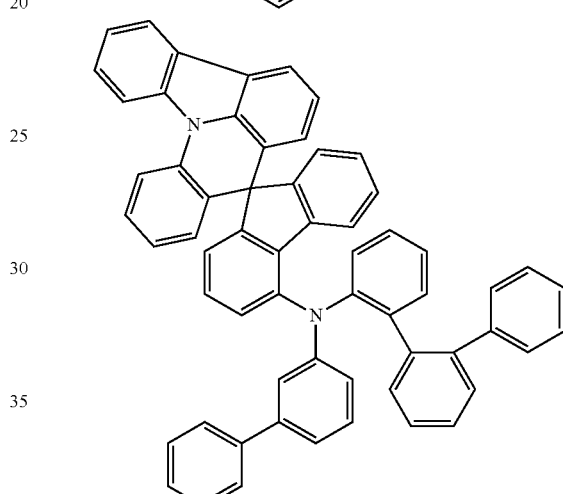
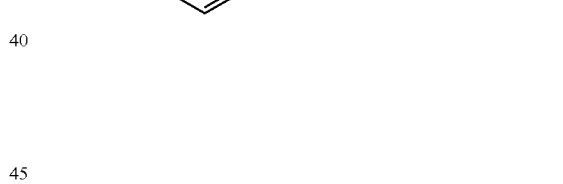
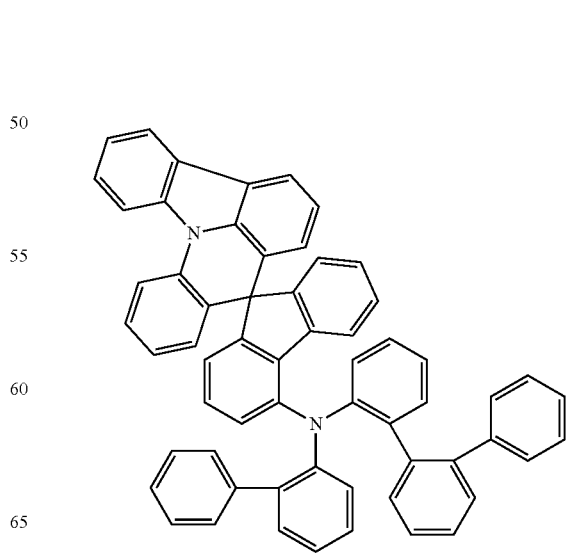

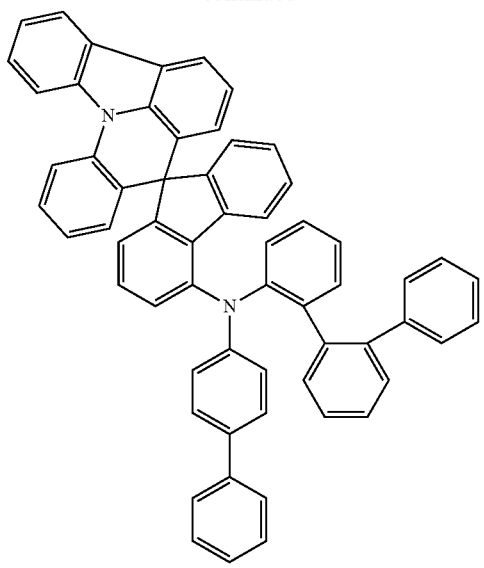
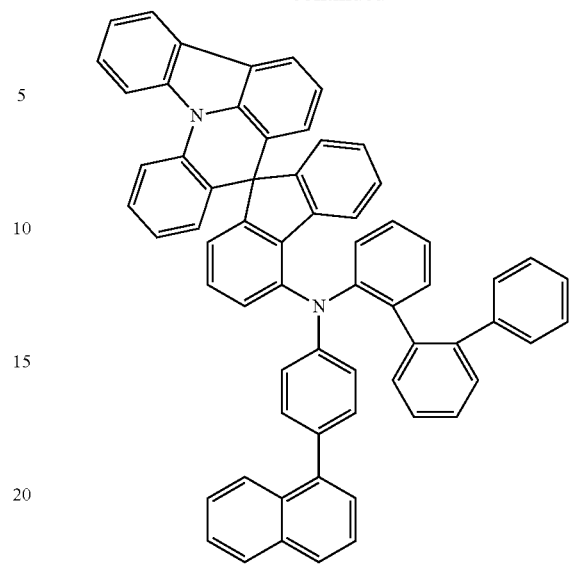
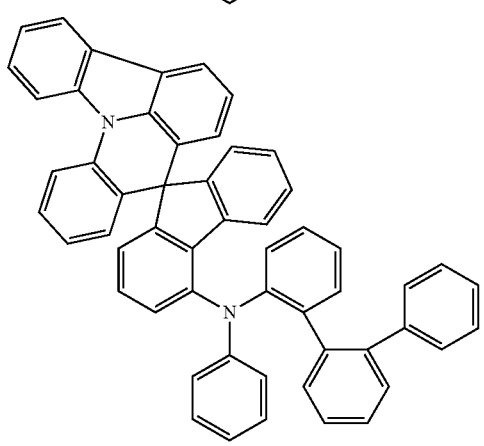
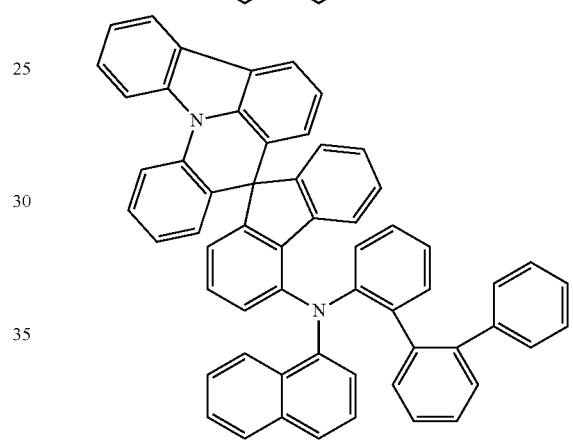
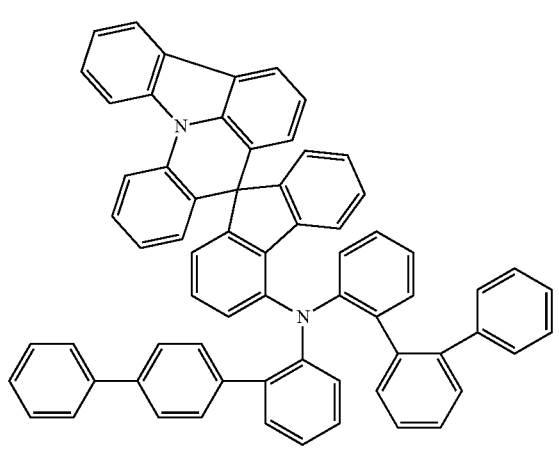
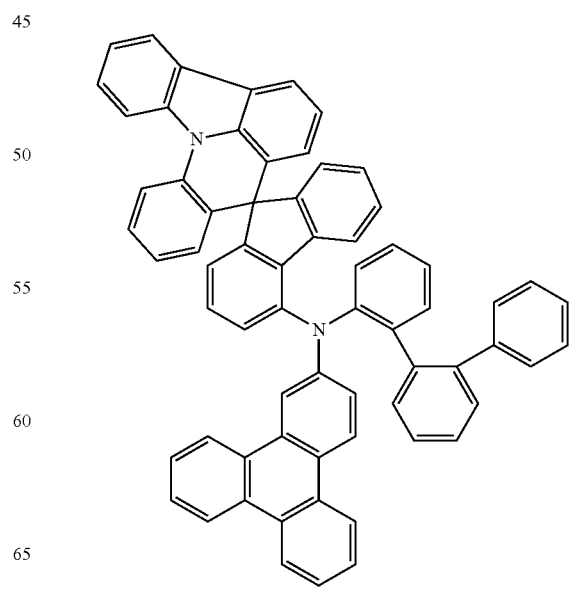

-continued
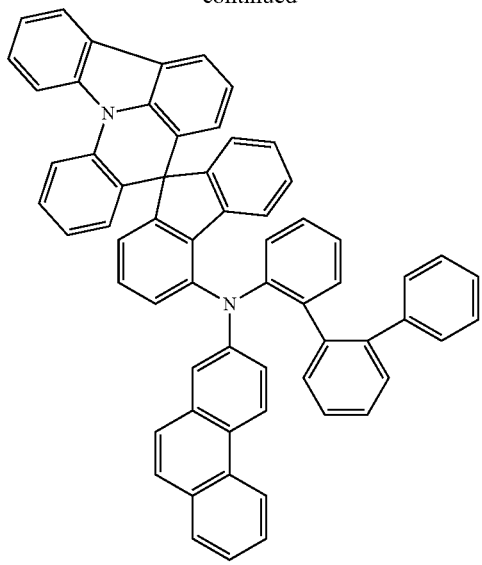
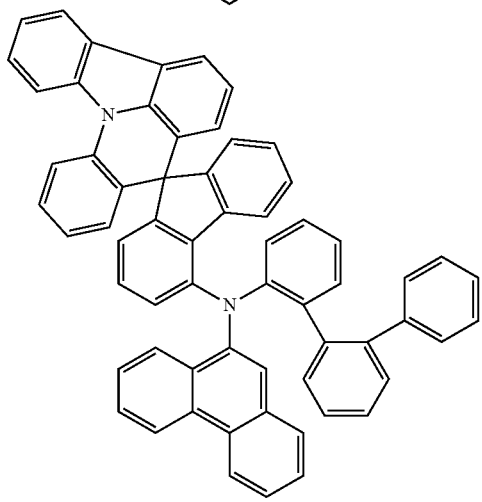
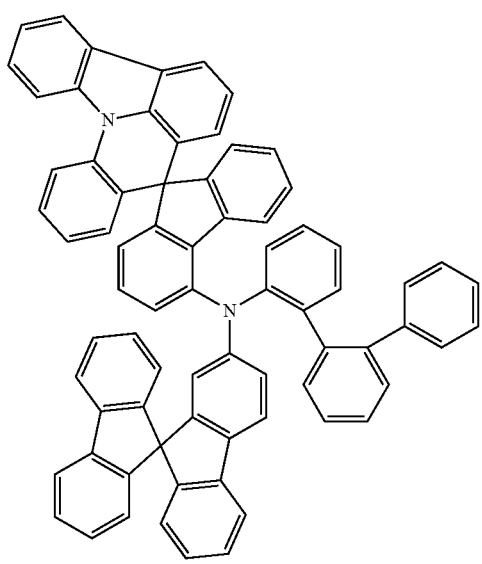
-continued
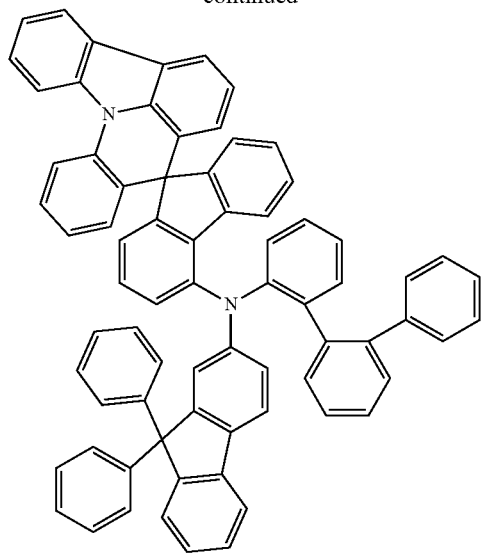
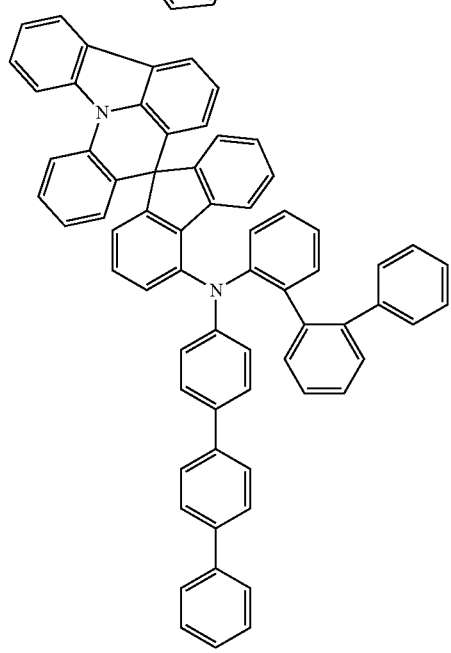
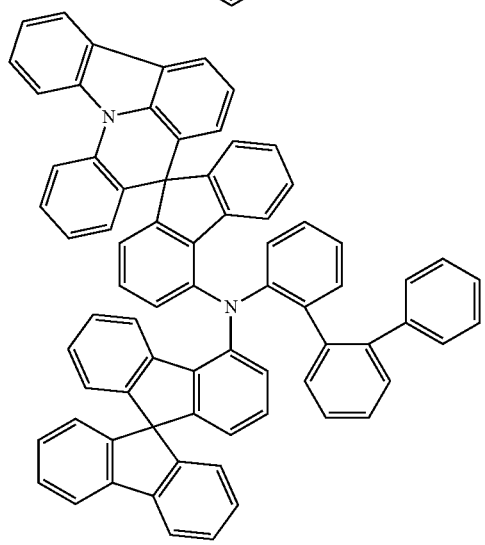

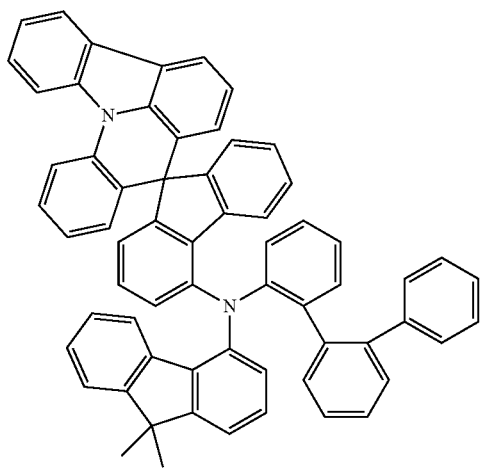
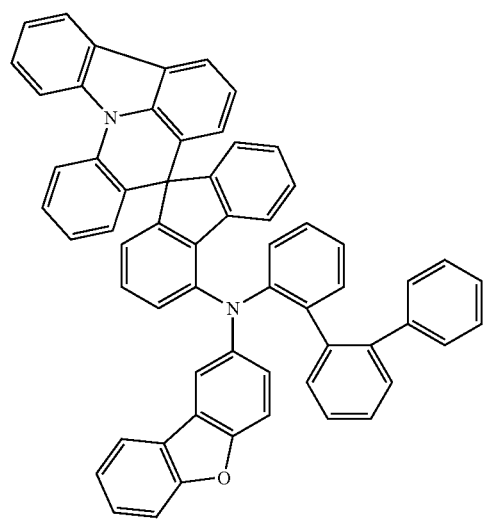
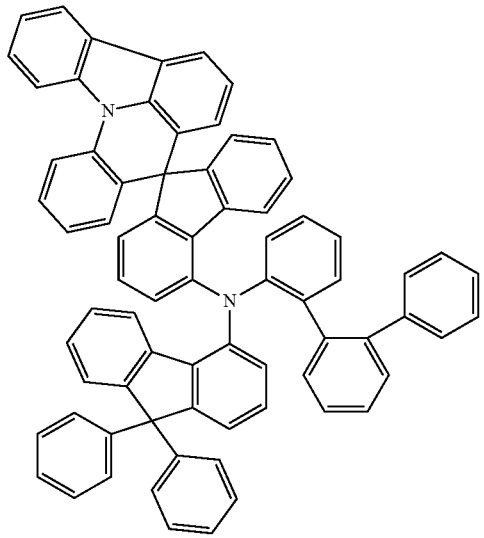
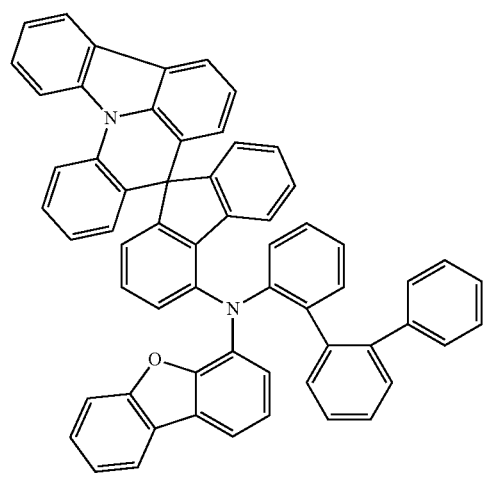
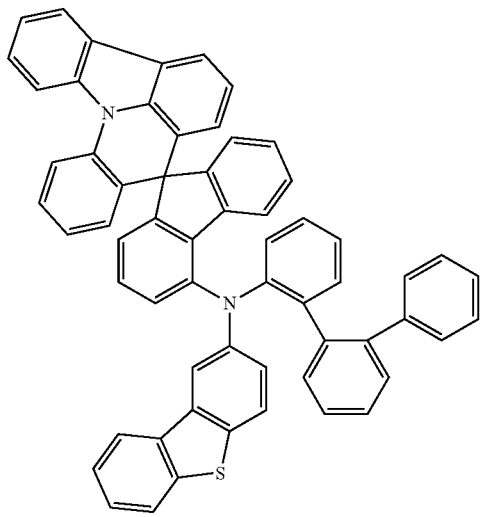
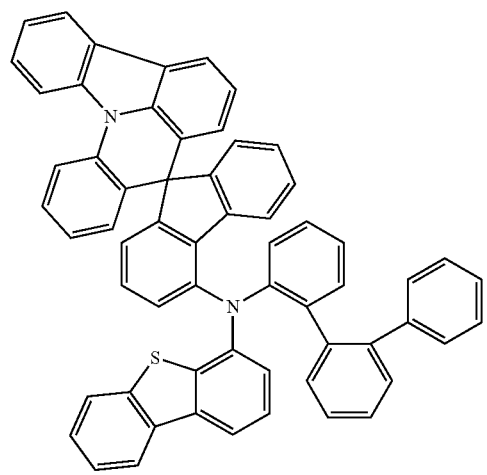

-continued
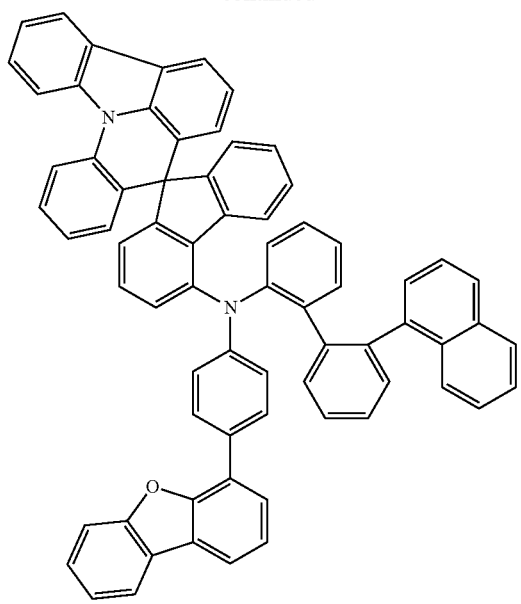
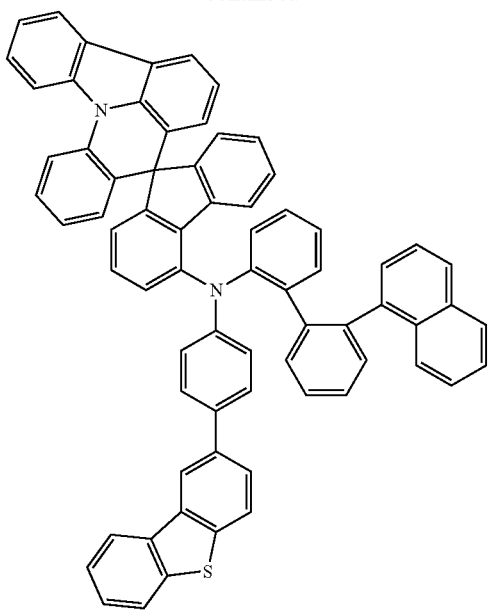
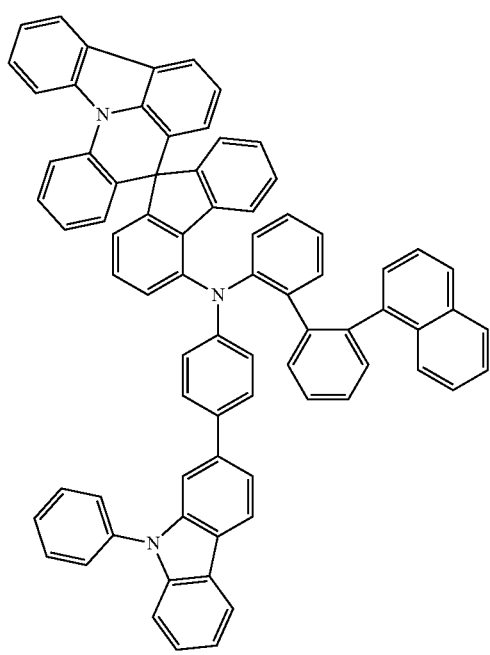
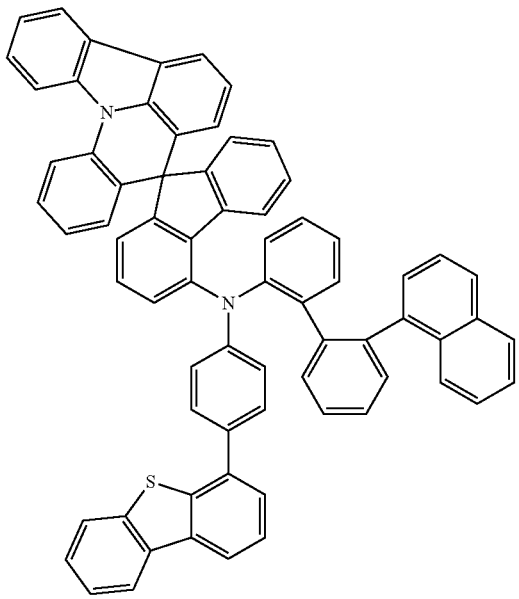

-continued
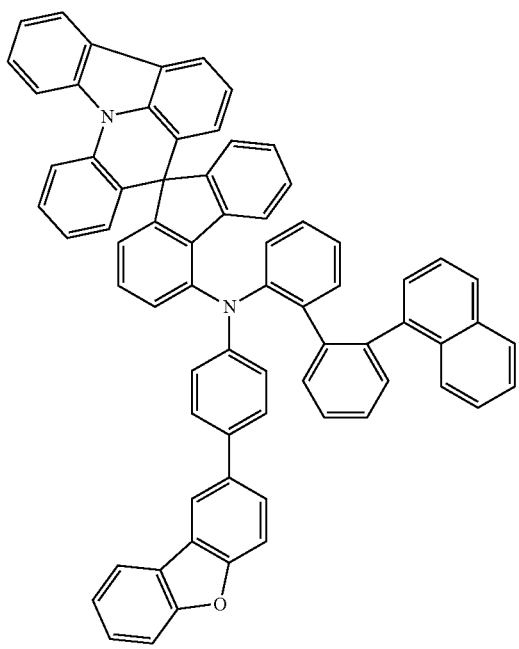
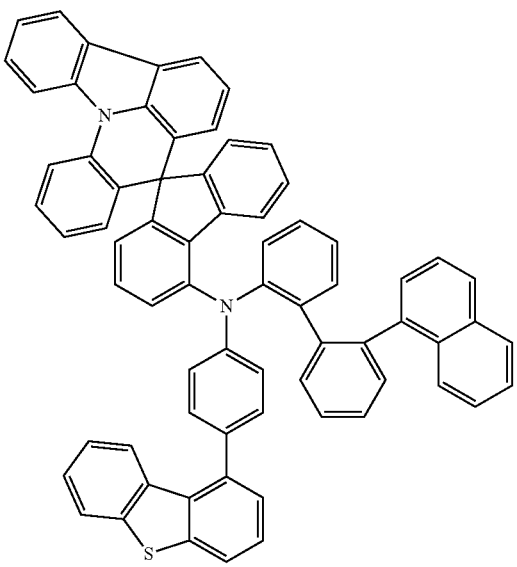
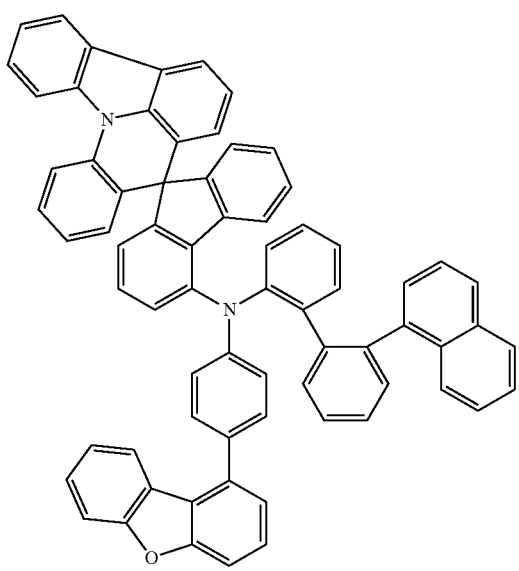
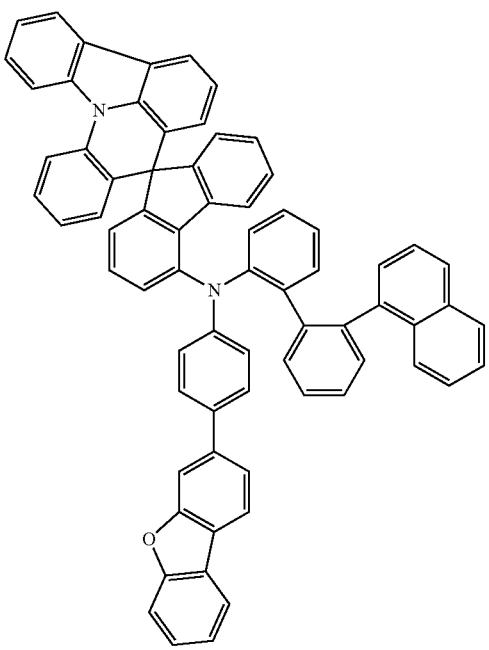

71
-continued
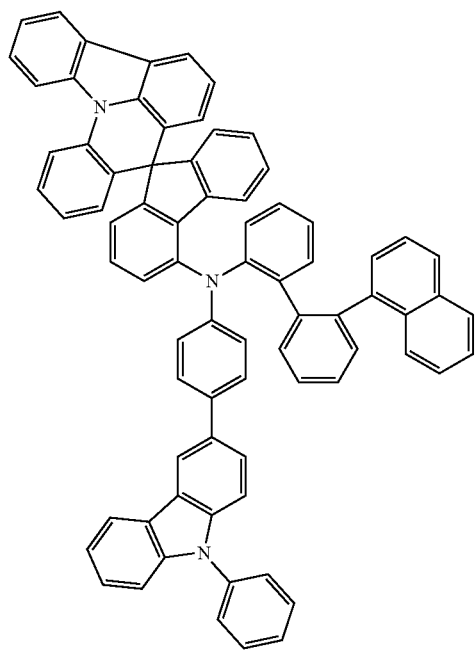
72
-continued
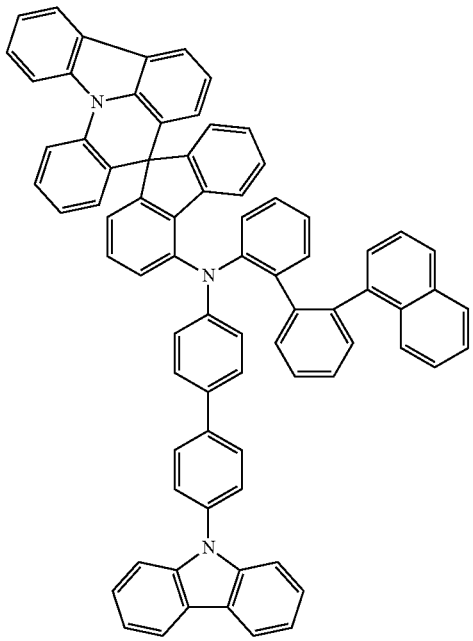
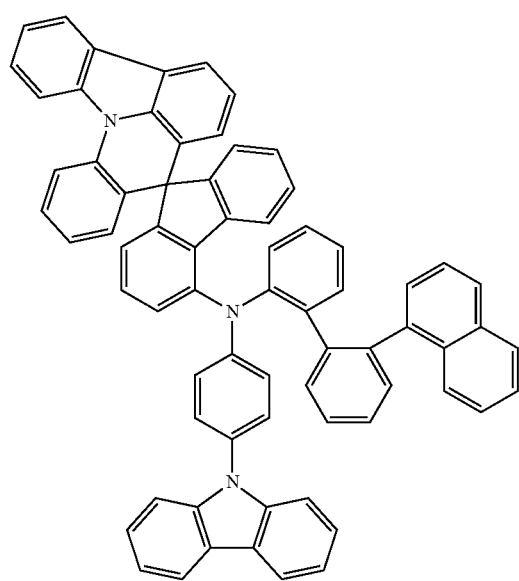
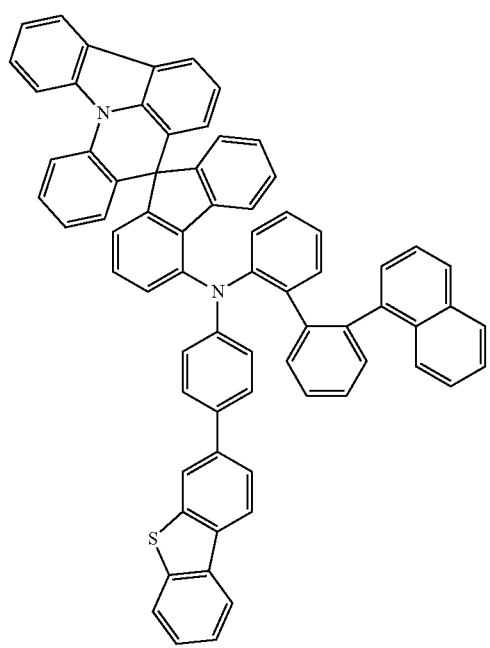

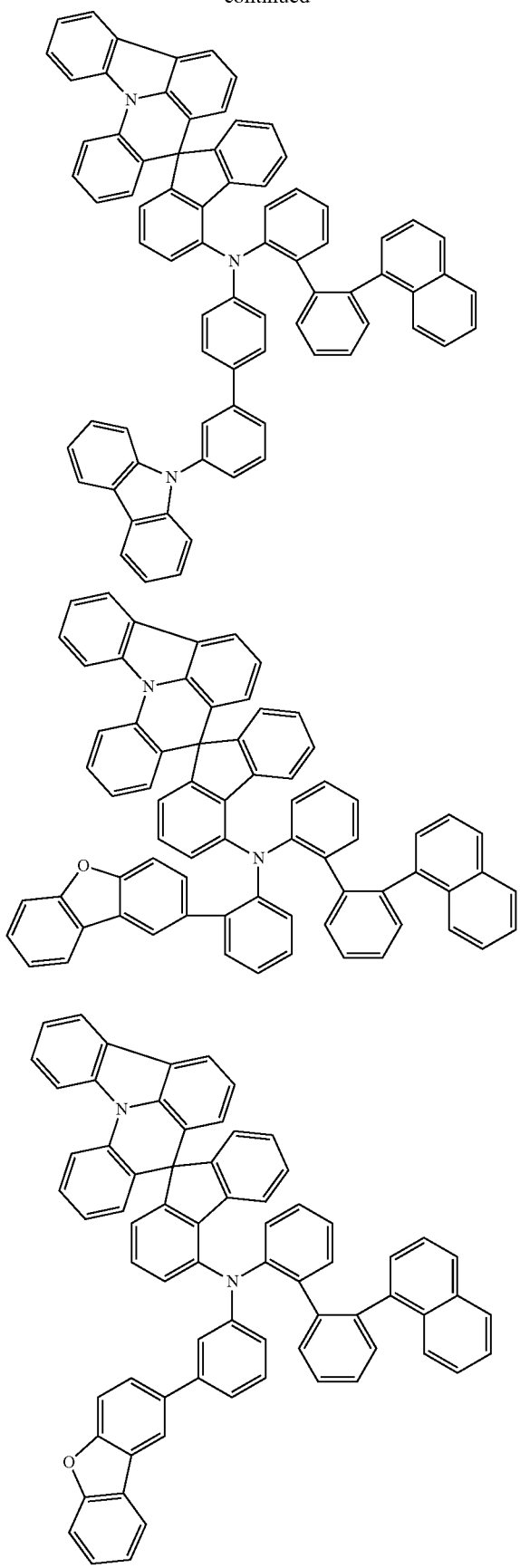
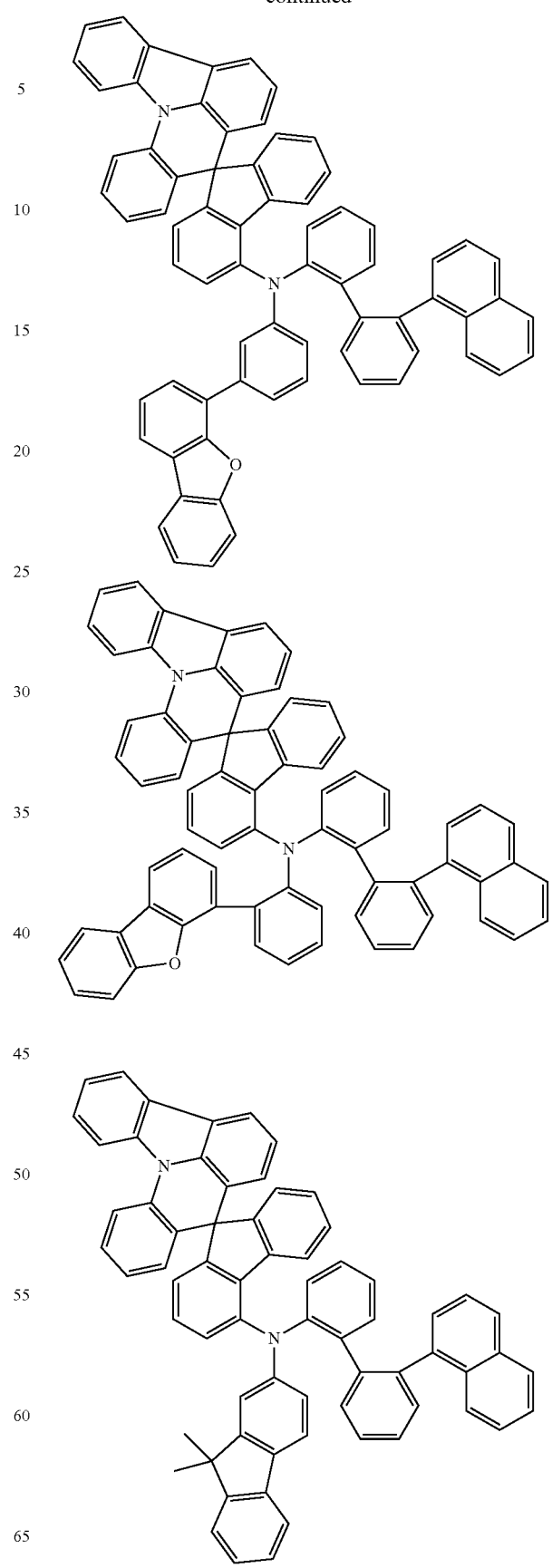

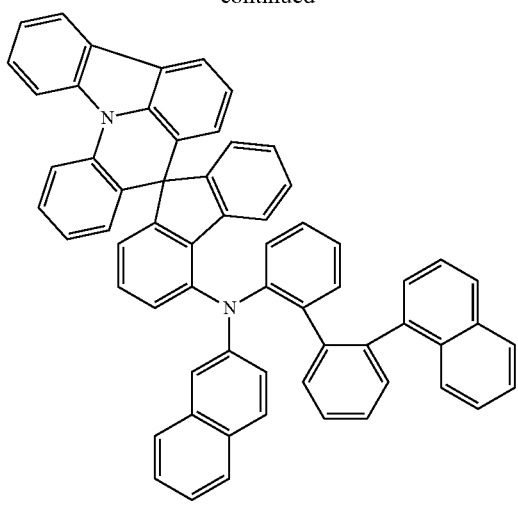
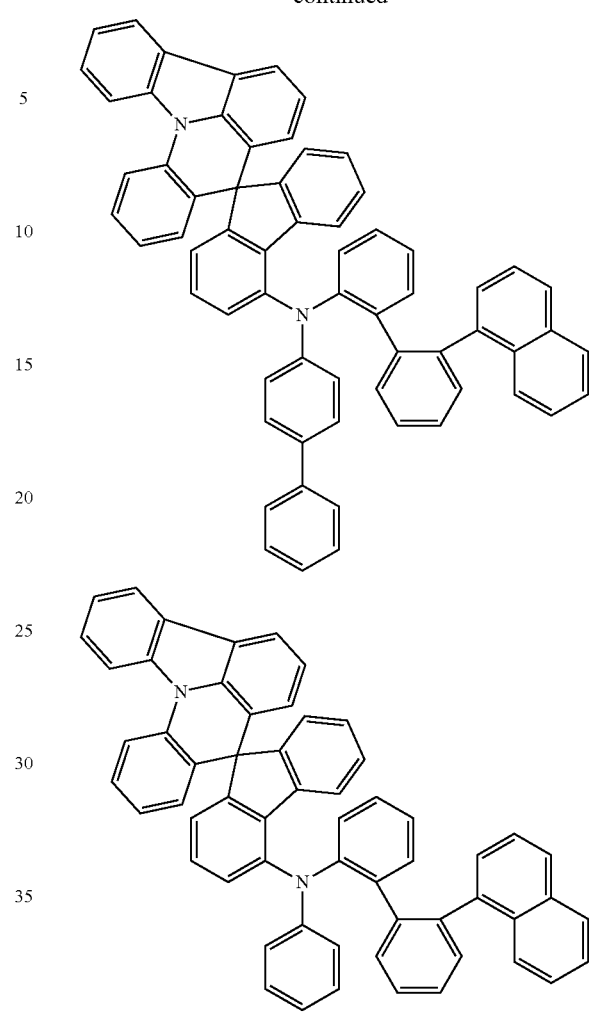
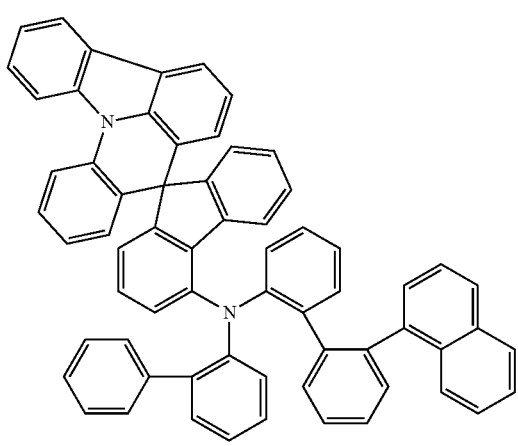
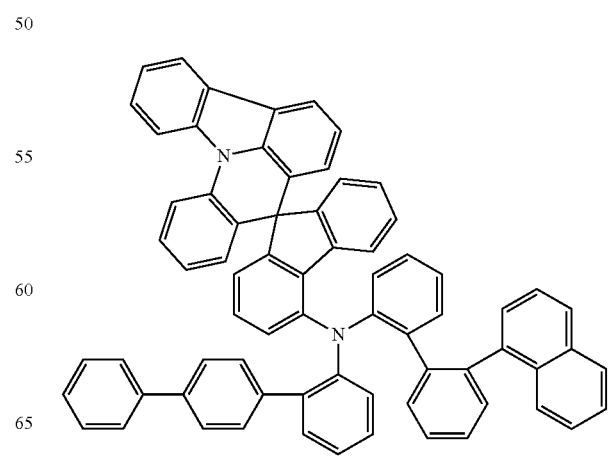

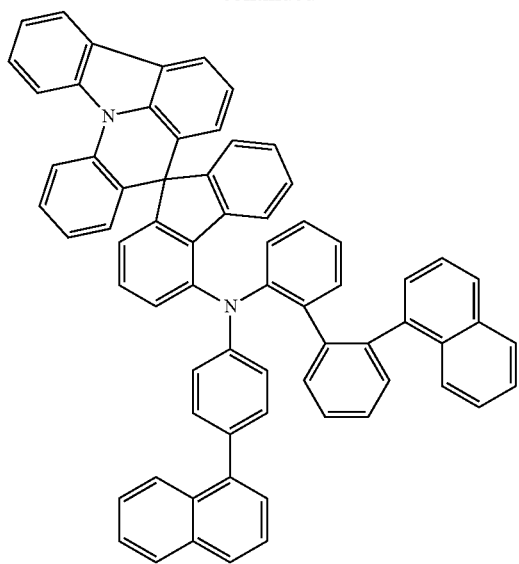
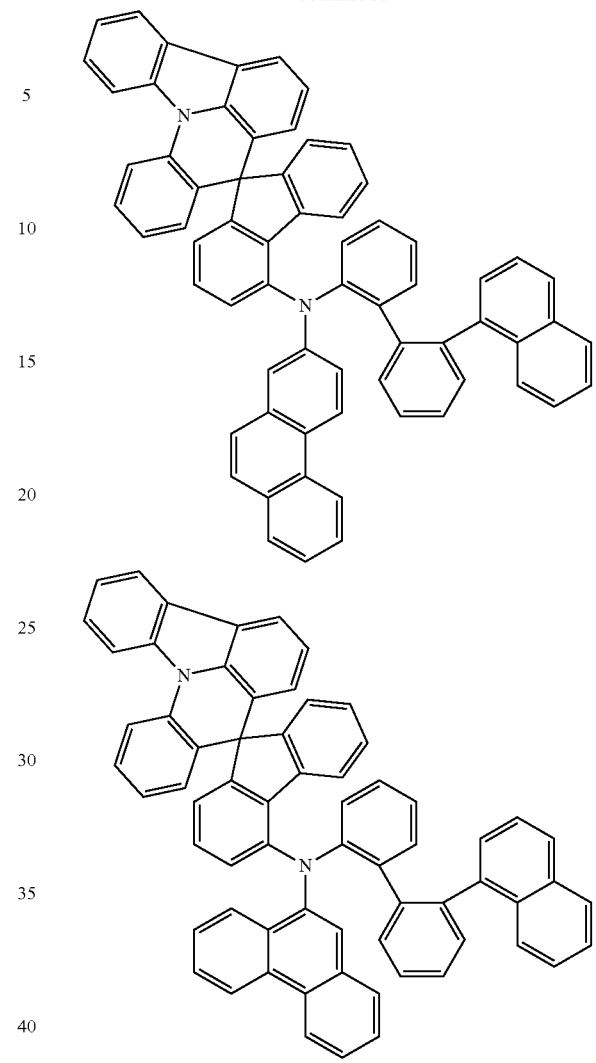
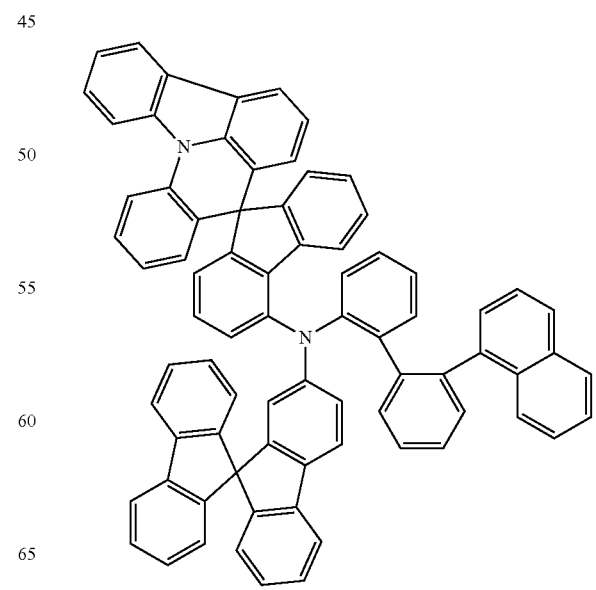

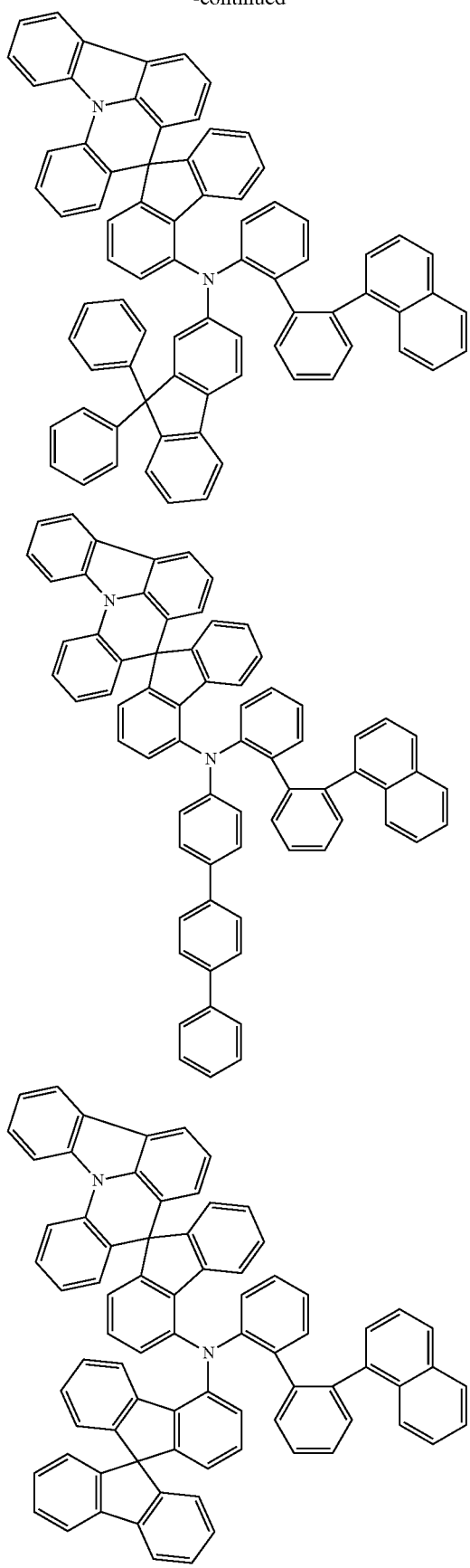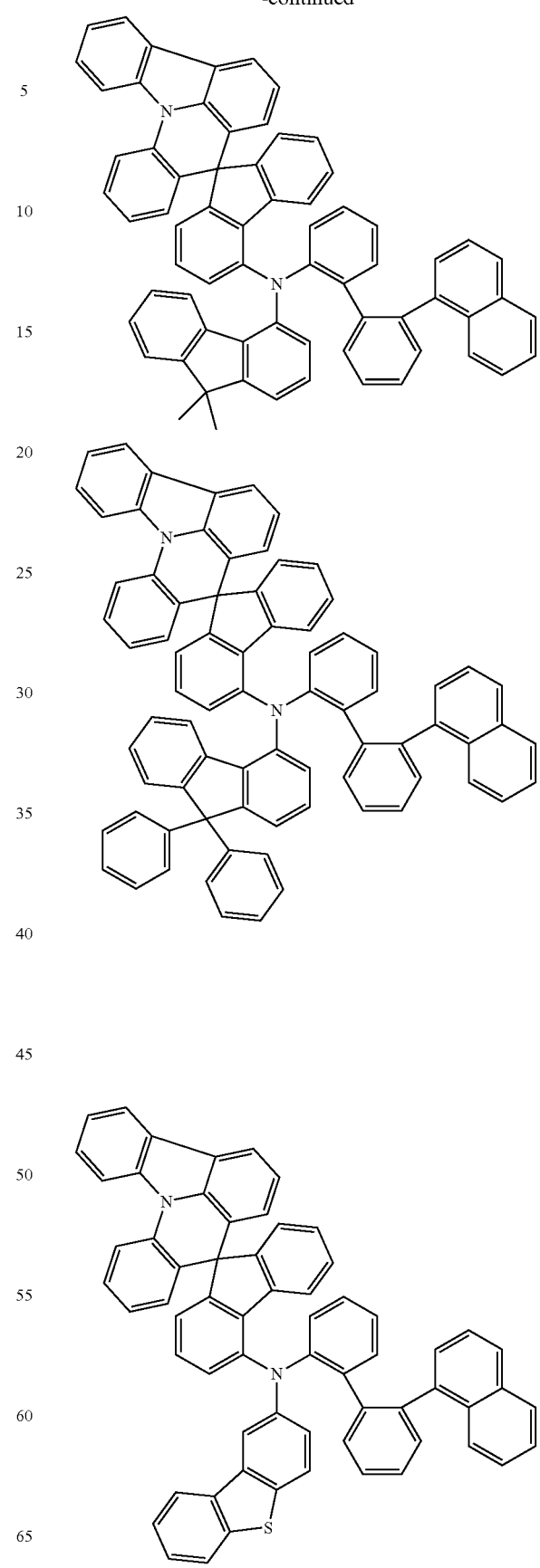

81
-continued
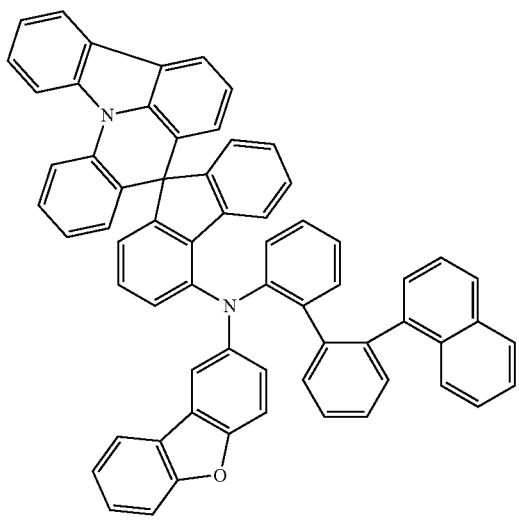
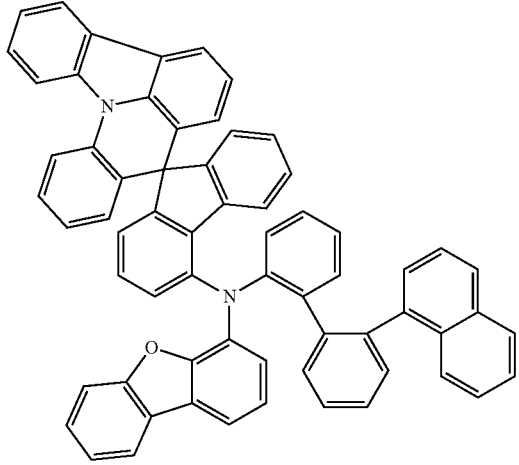
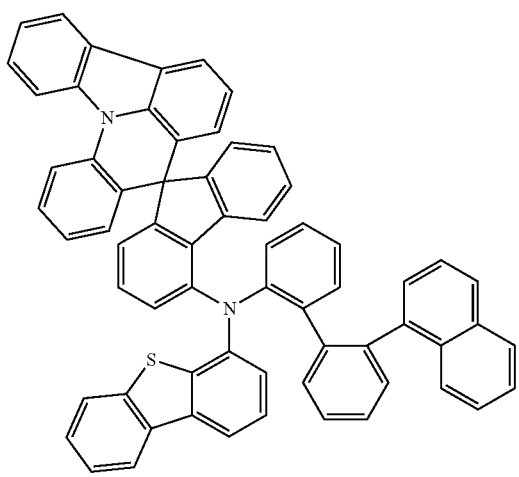
82
-continued
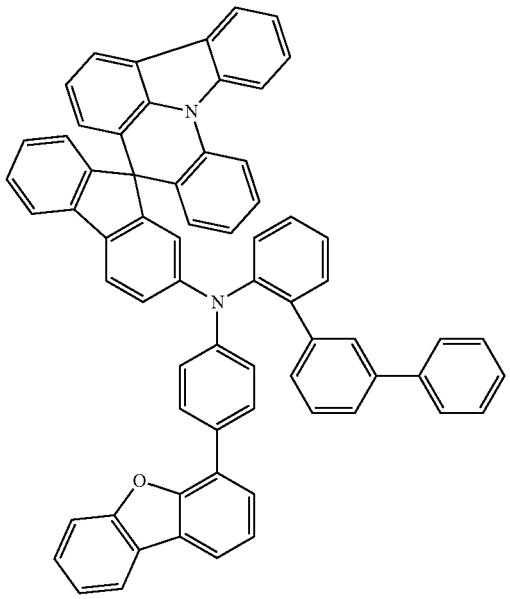
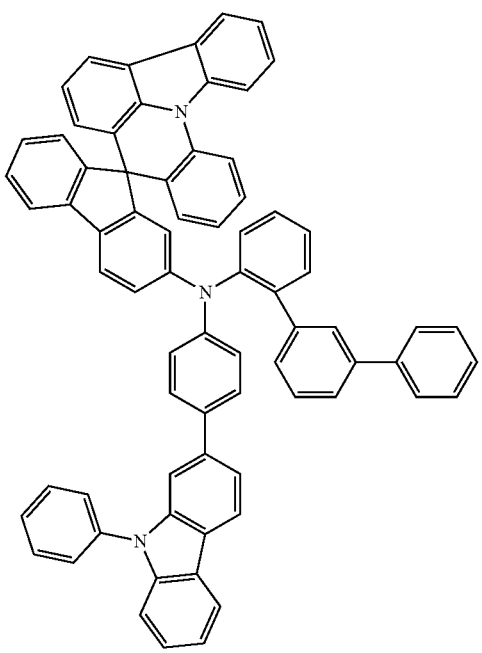

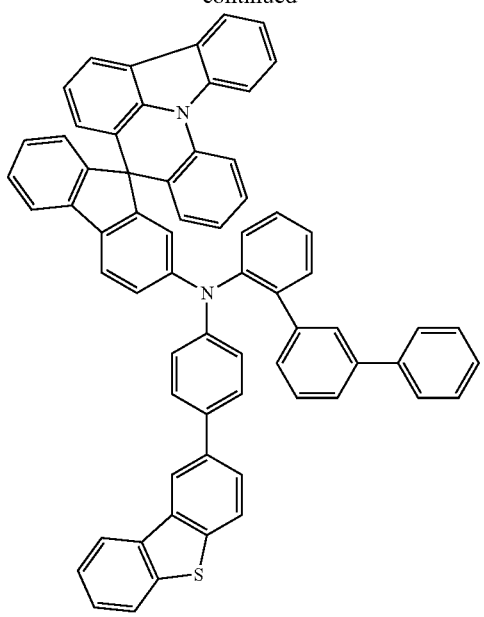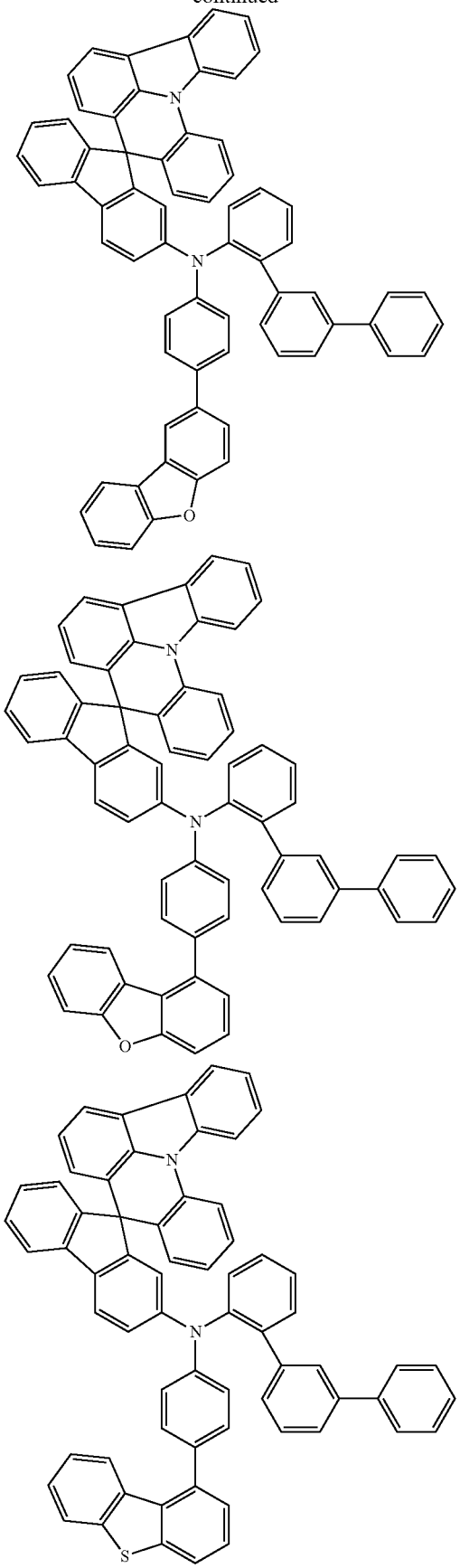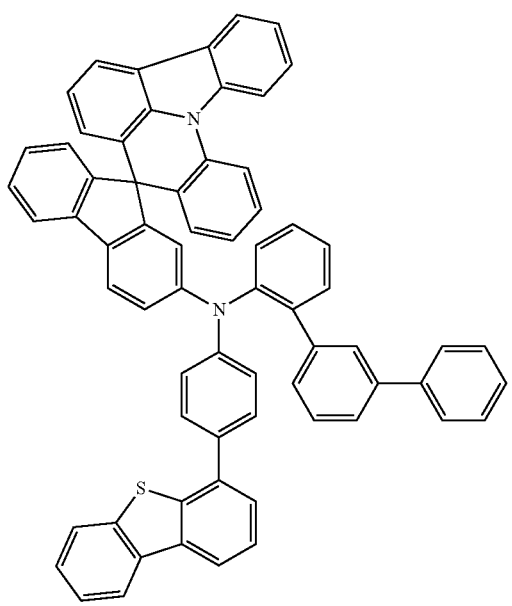

85
-continued
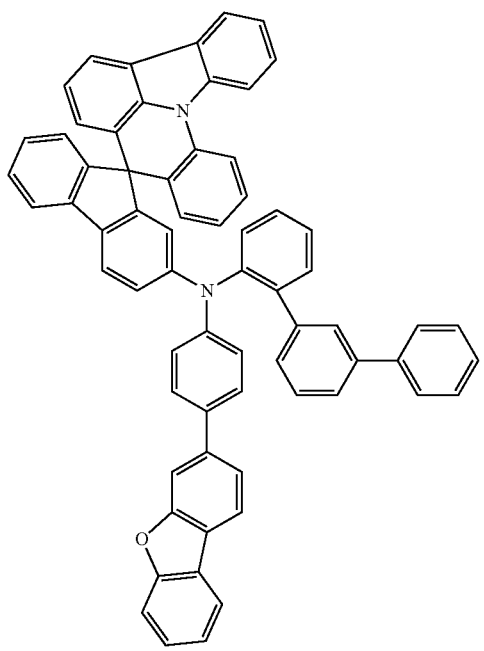
86
-continued
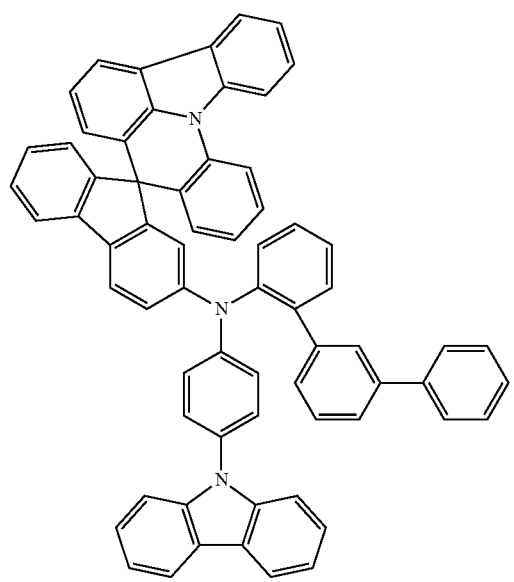
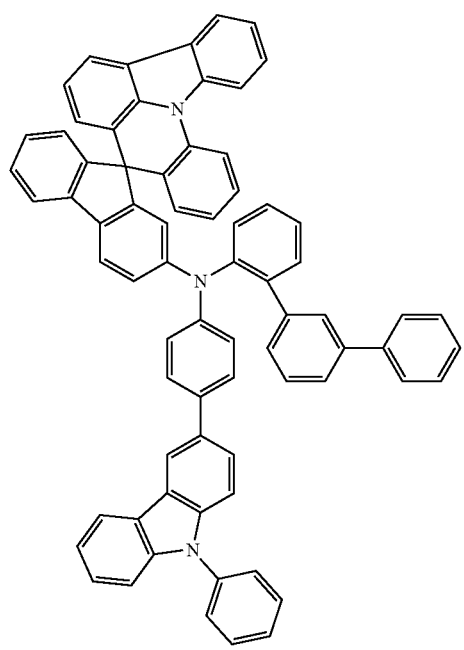
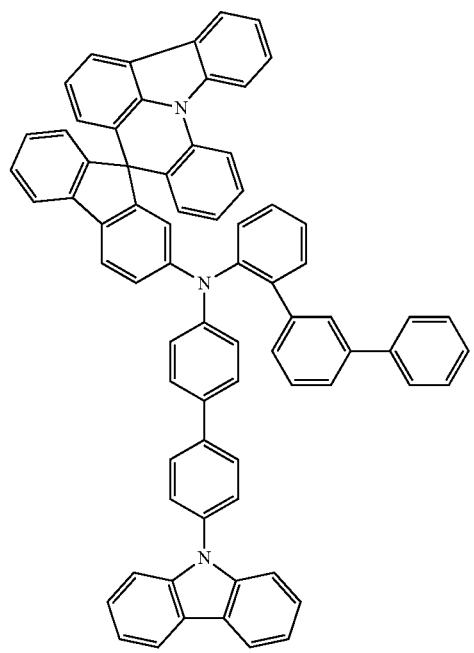

87
-continued
88
-continued
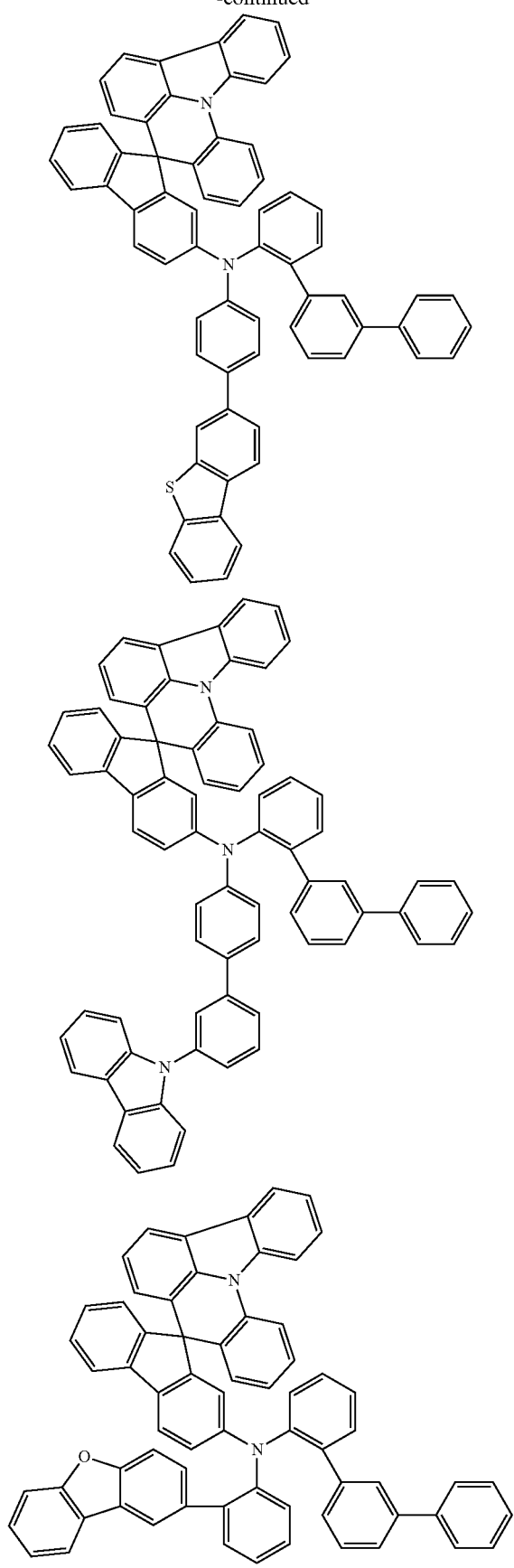
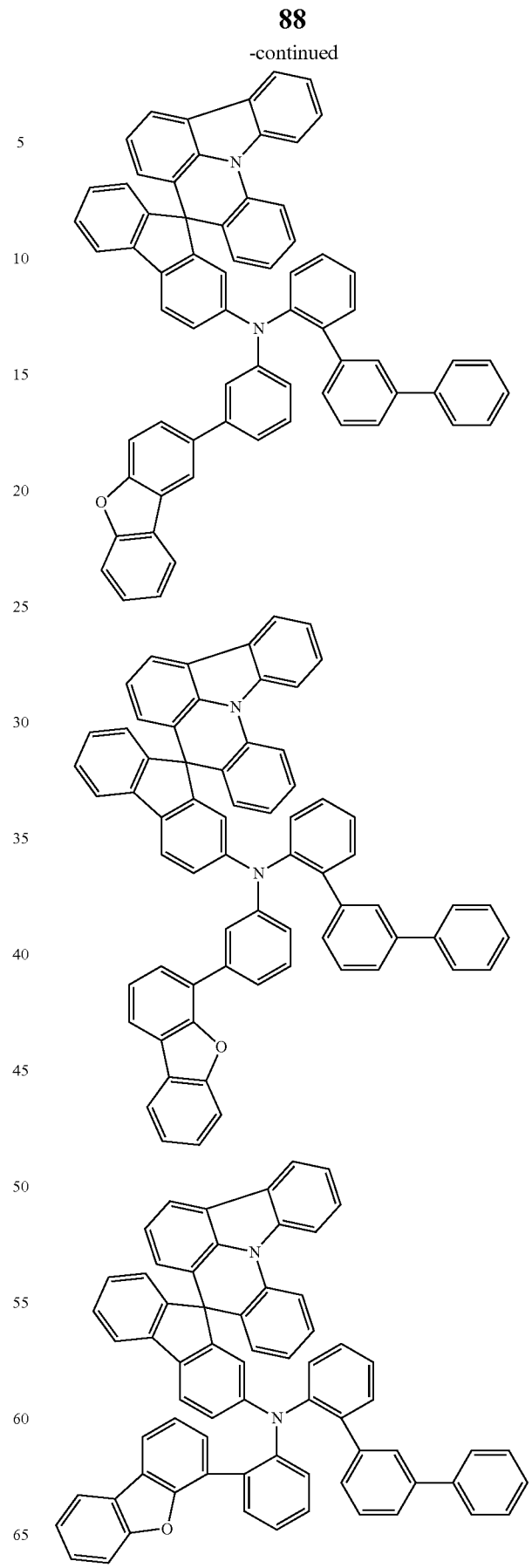

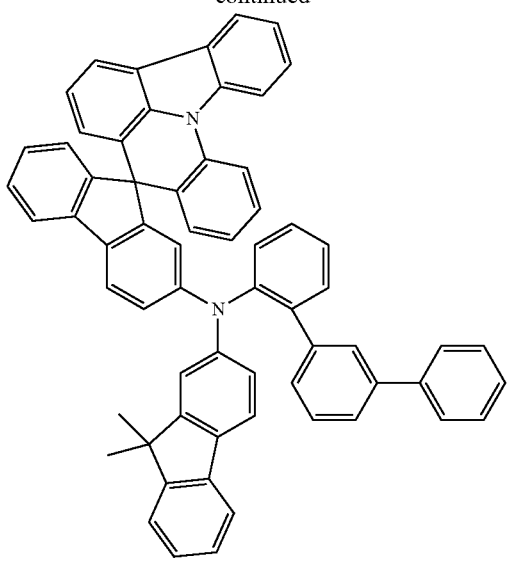
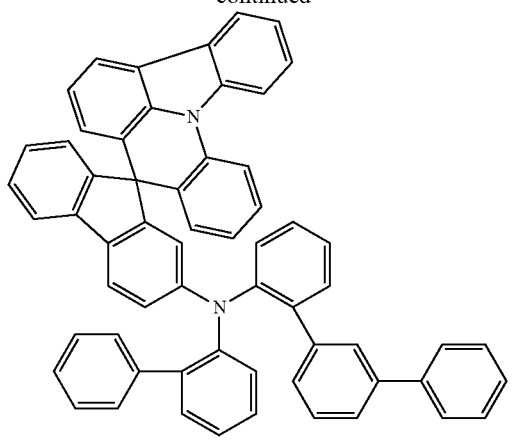
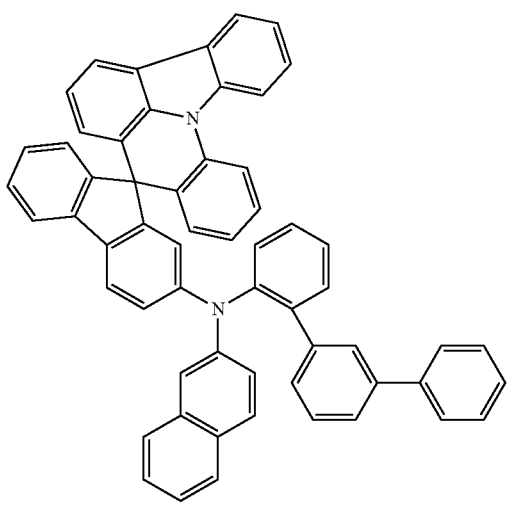
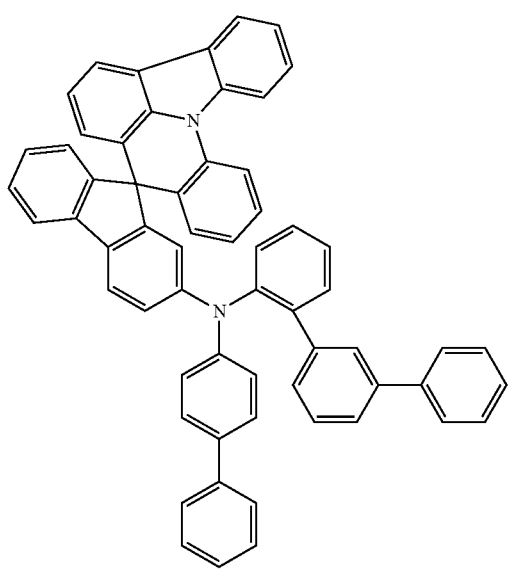
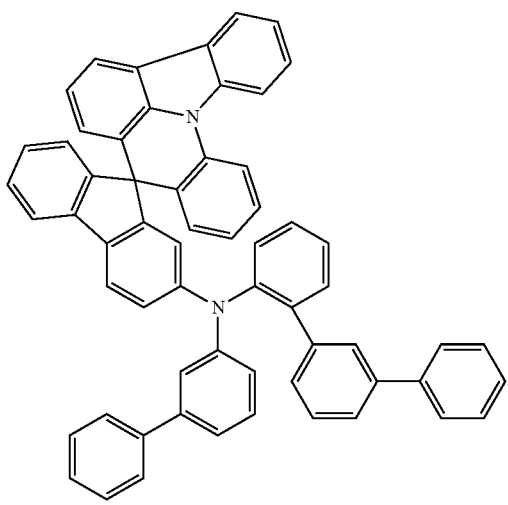
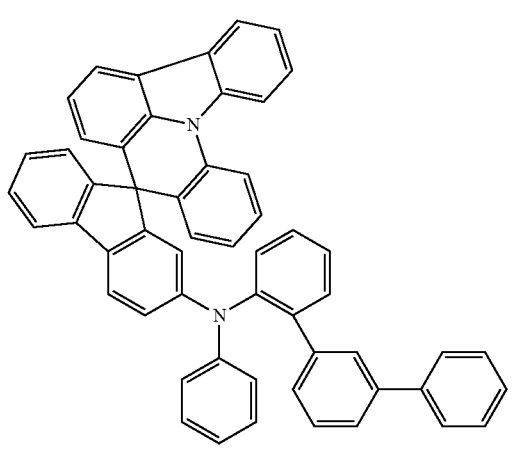

-continued
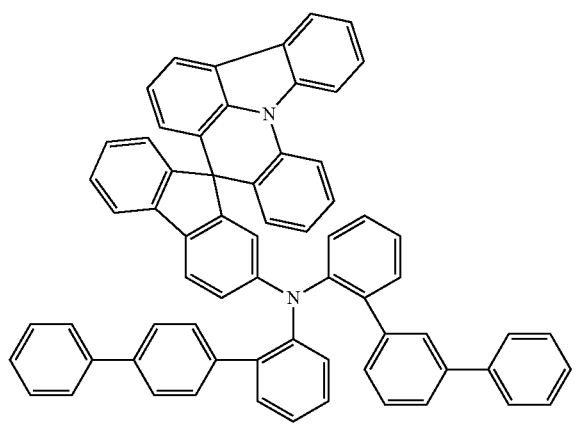

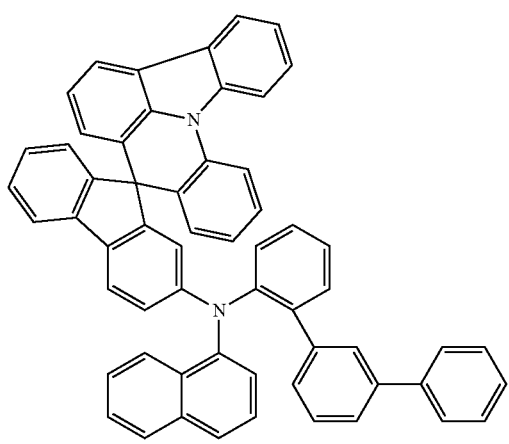
-continued
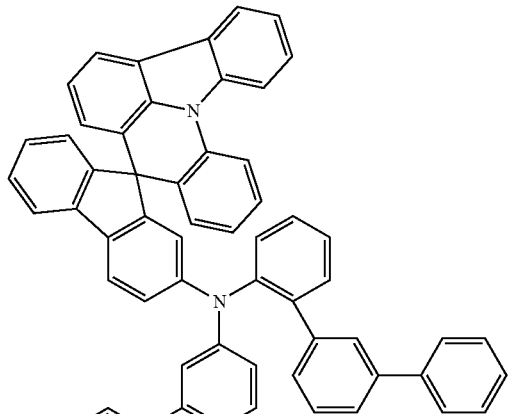
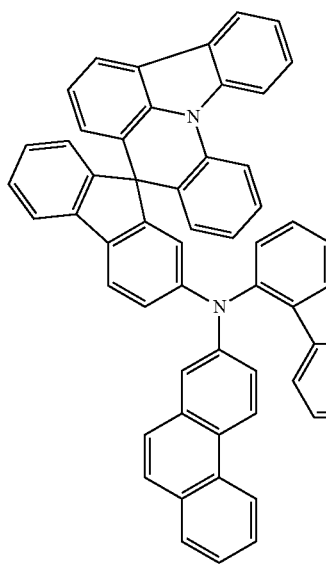
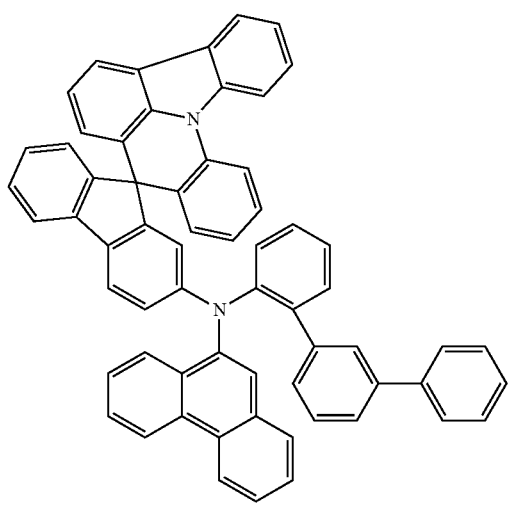

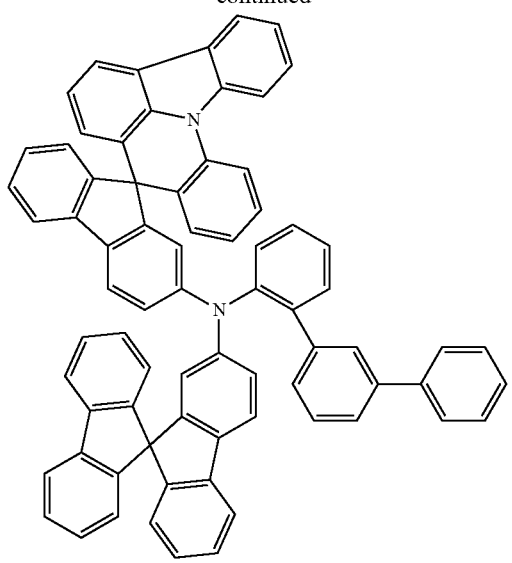
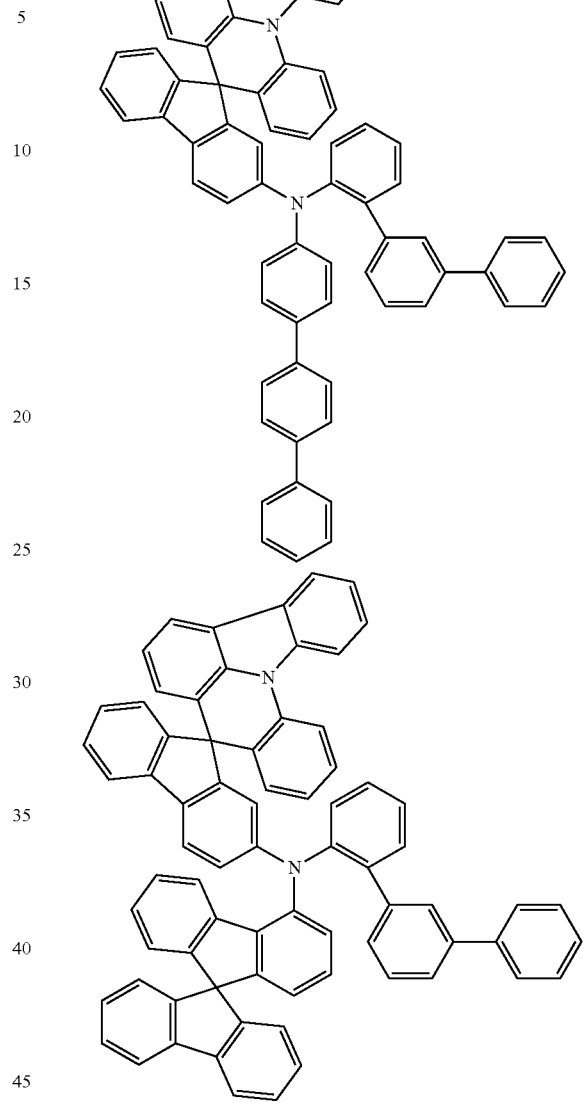
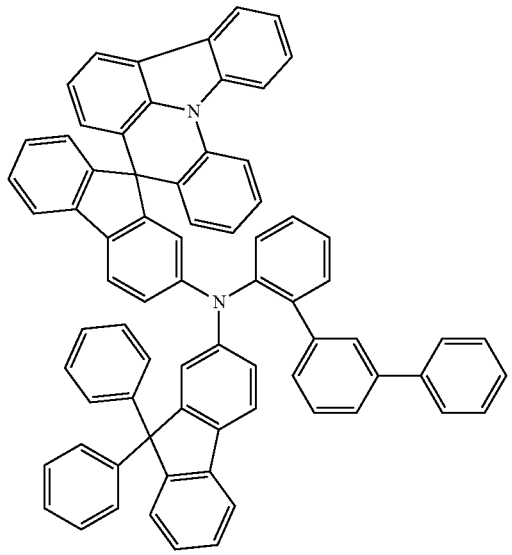
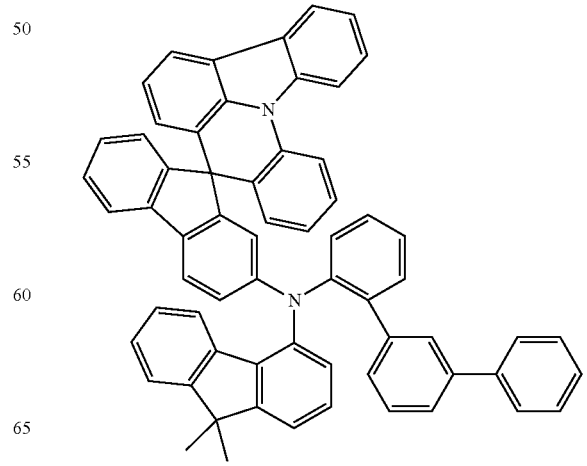

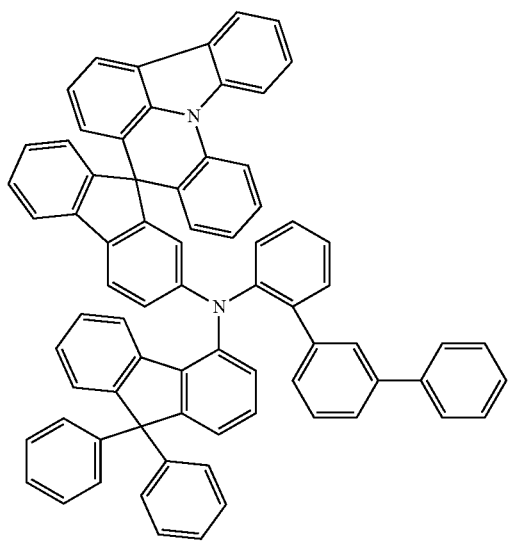
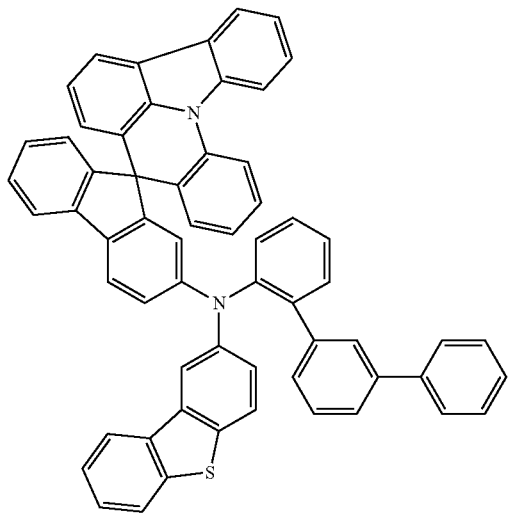
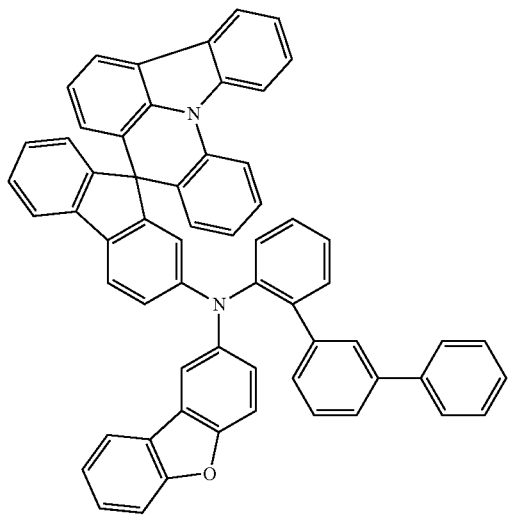
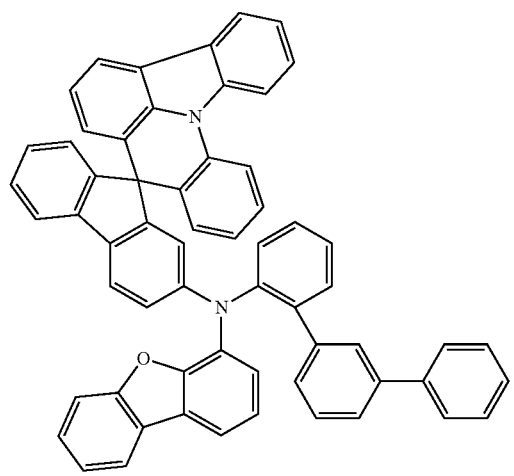
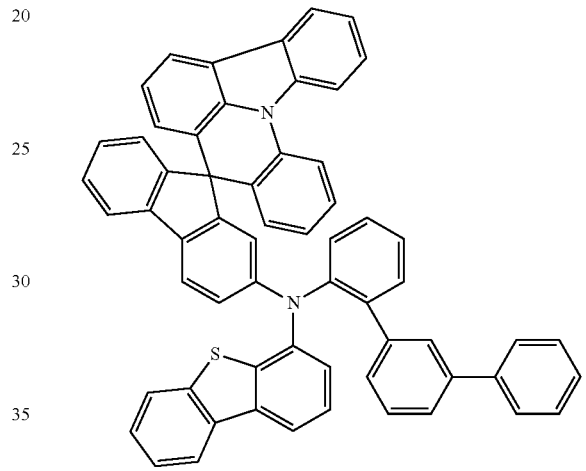
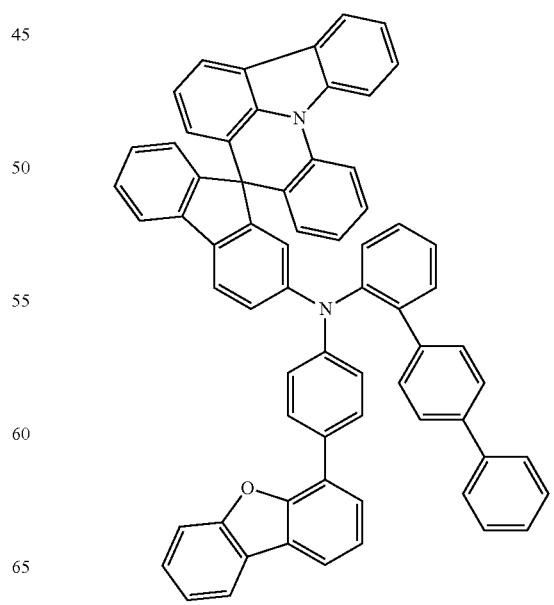

97
-continued
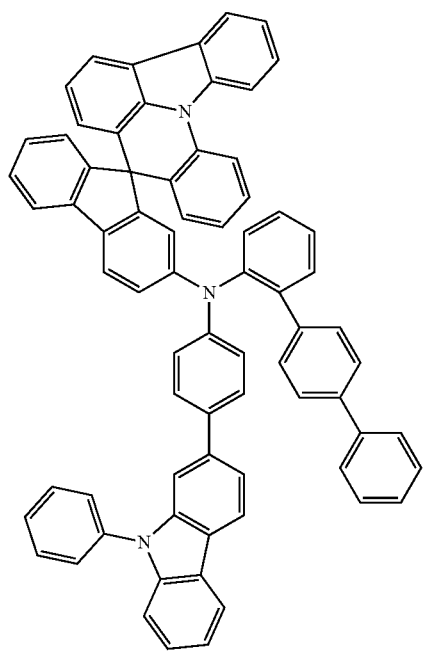
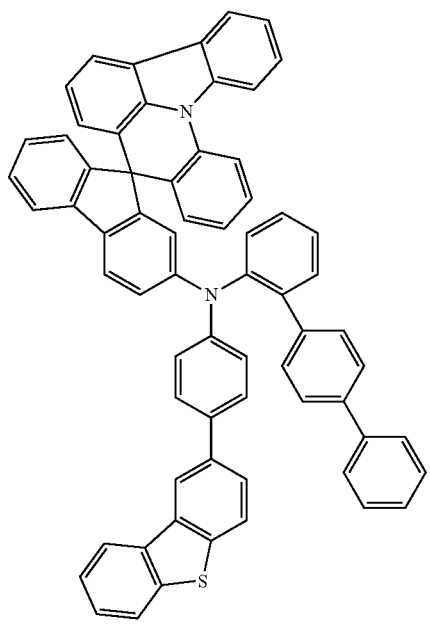
98
-continued
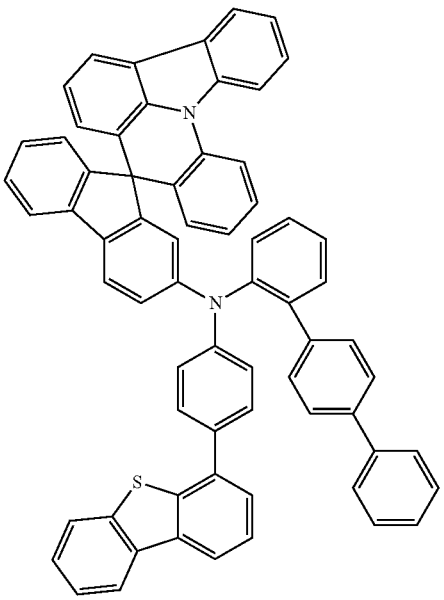
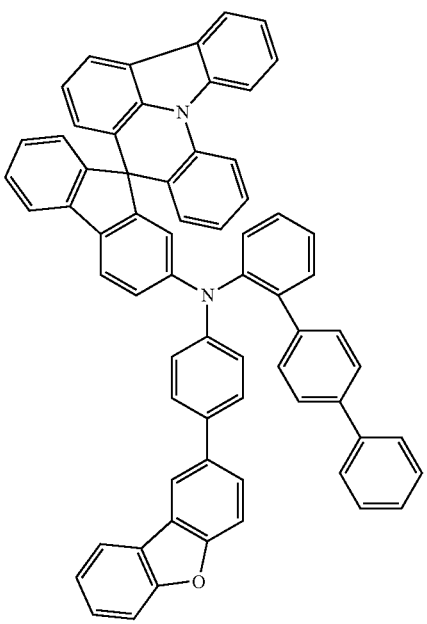

99
-continued
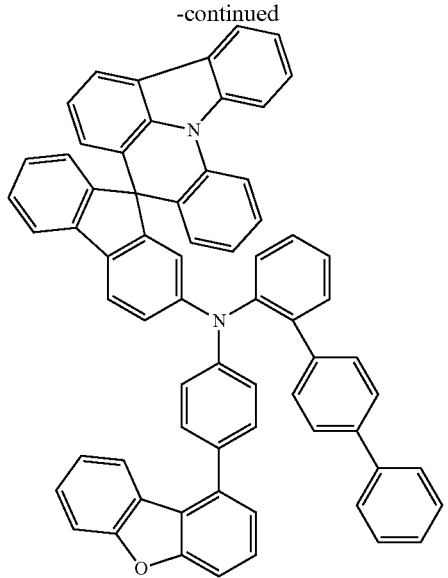
100
-continued
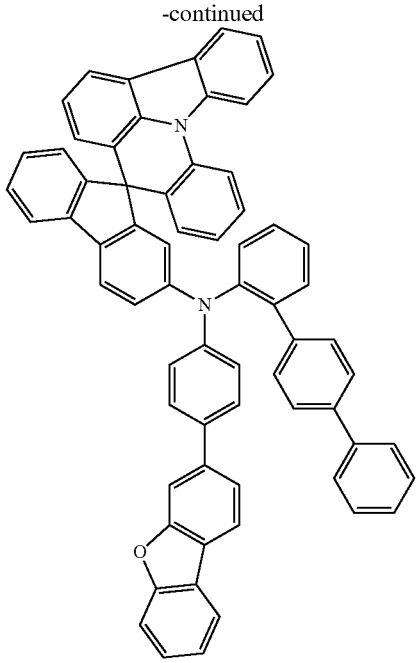
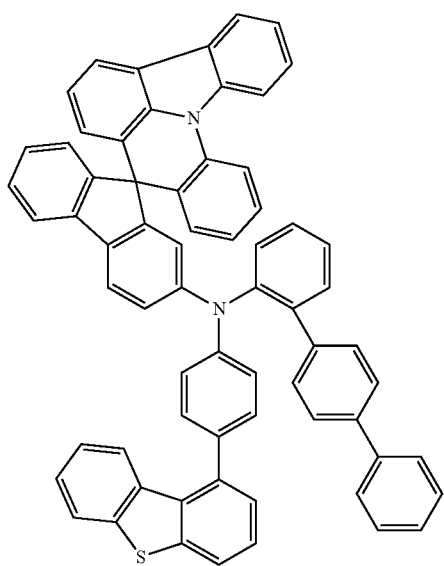
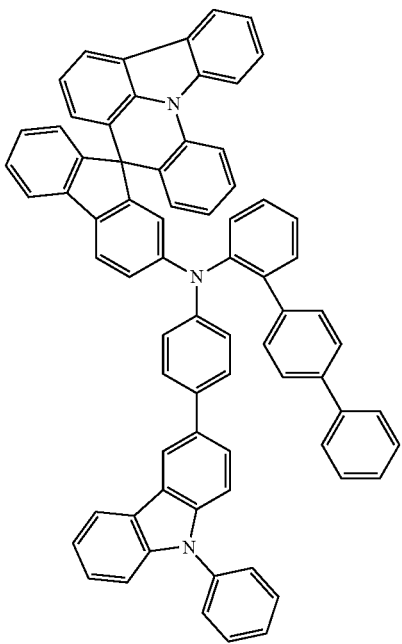

101
-continued
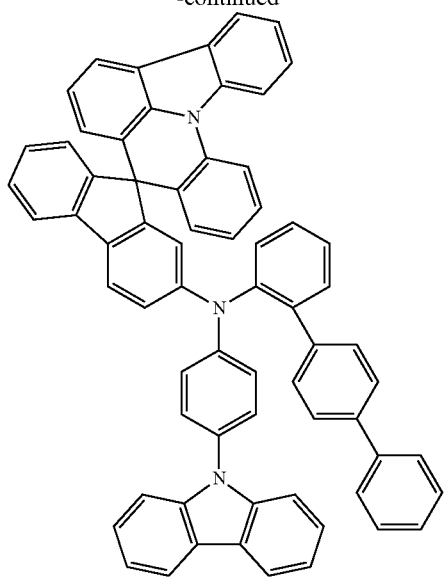
102
-continued
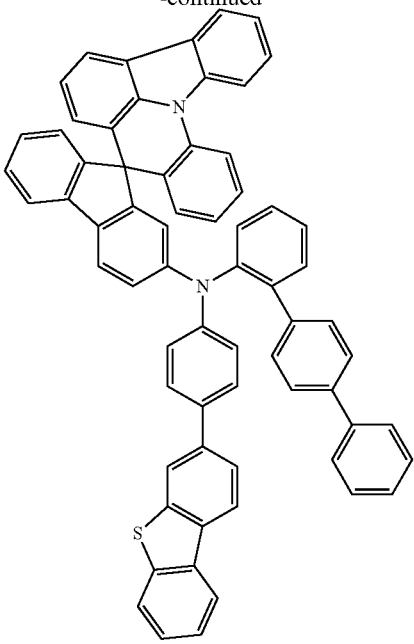
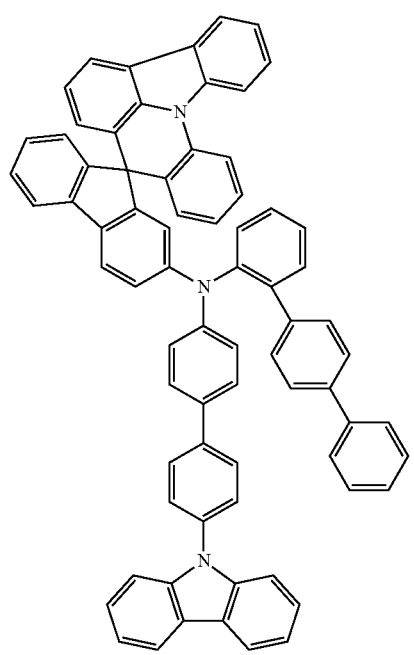
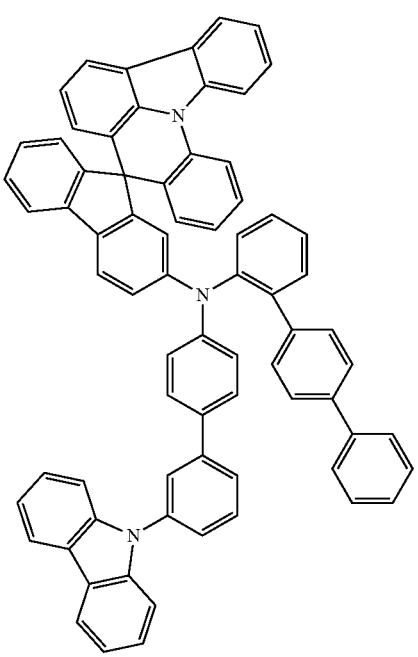

103
-continued
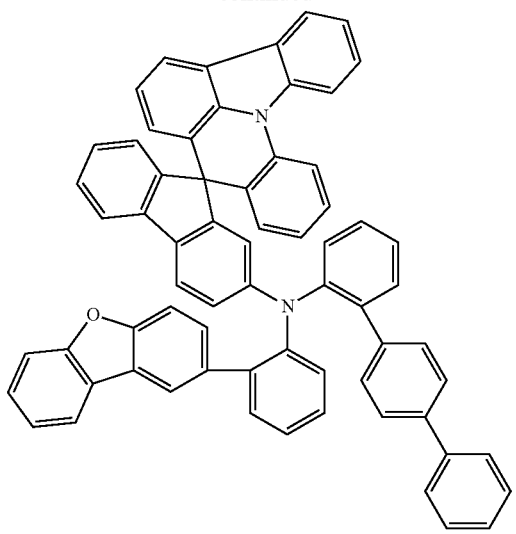
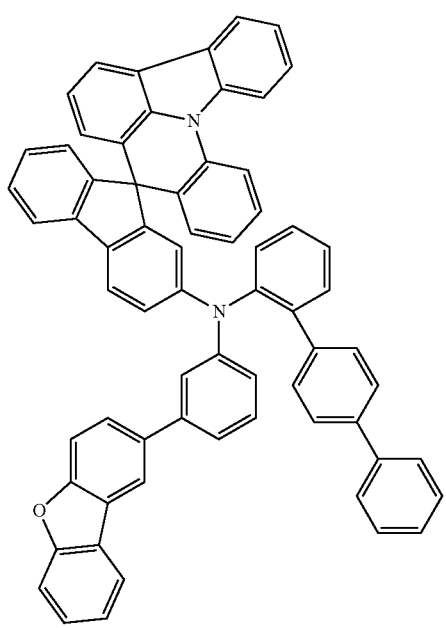
104
-continued
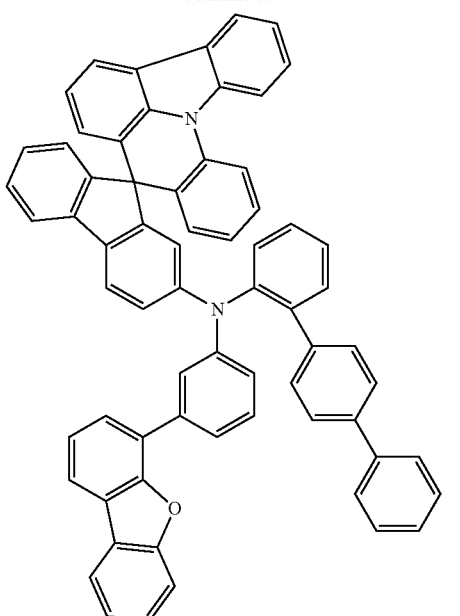
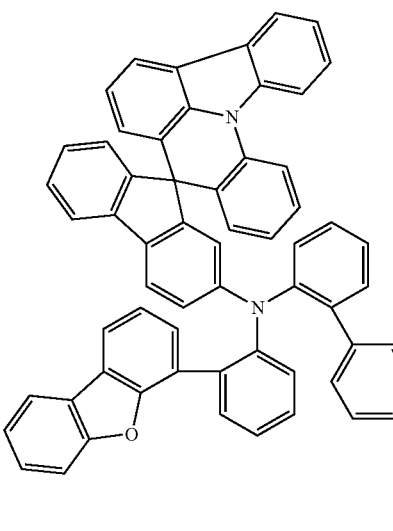
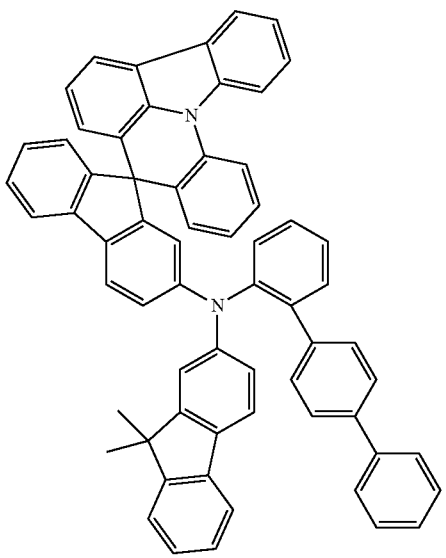

105
-continued
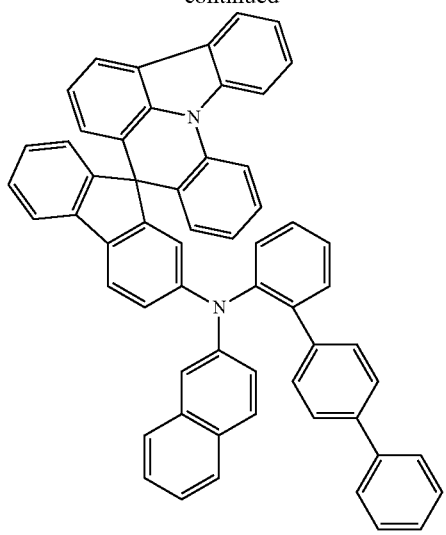
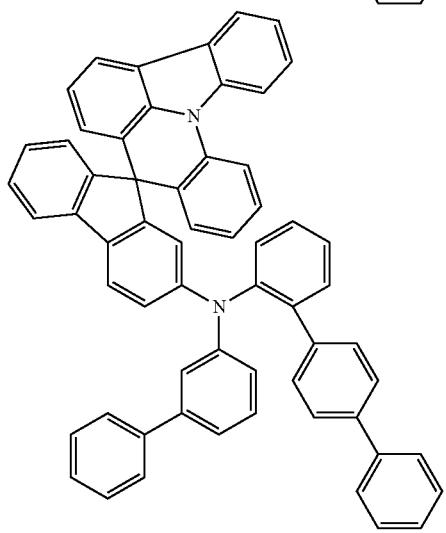
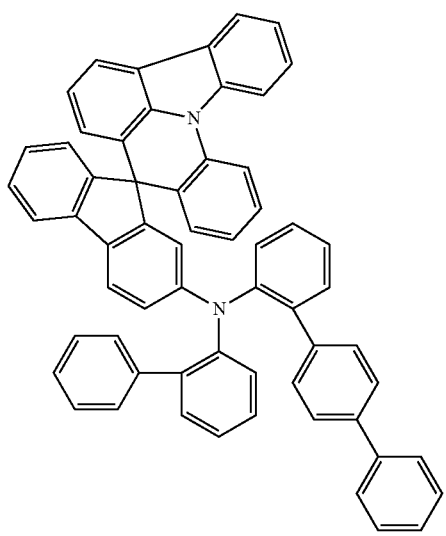
106
-continued
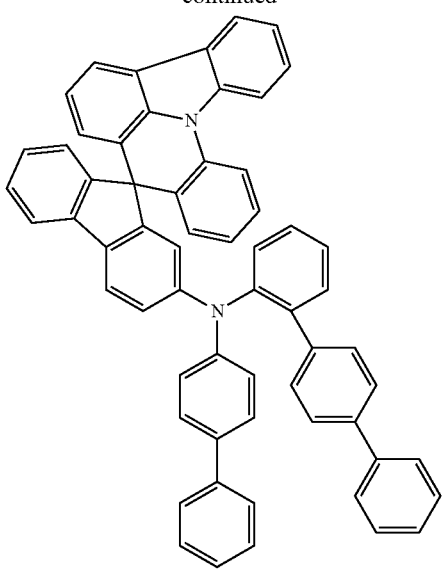
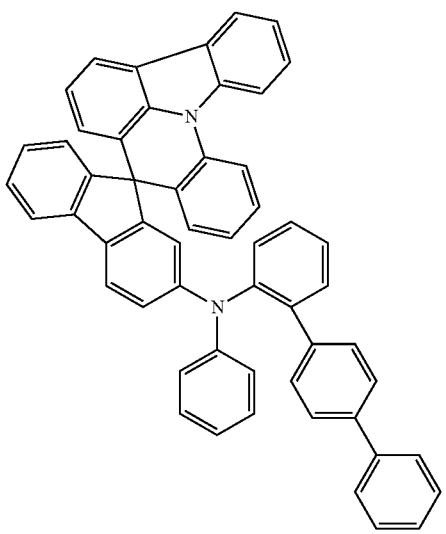
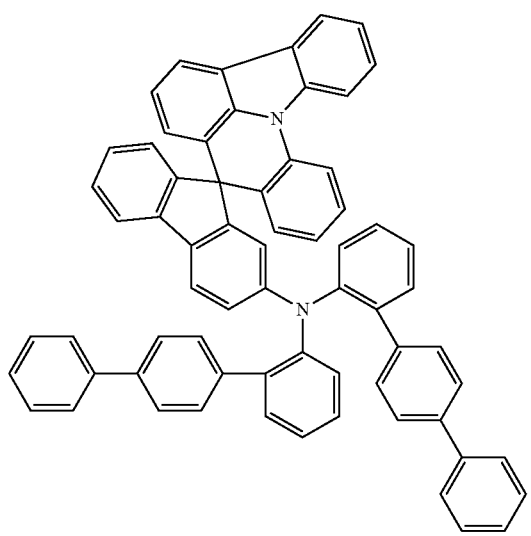

107
-continued
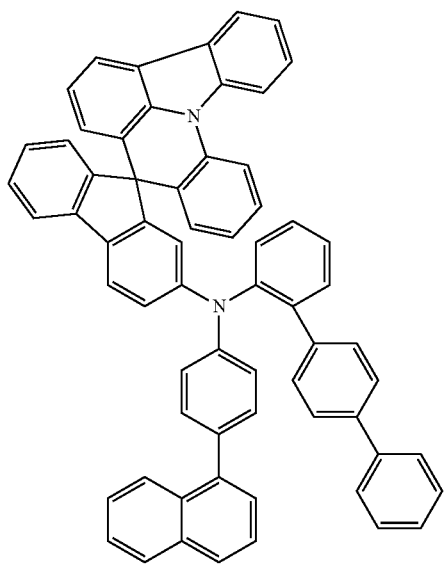
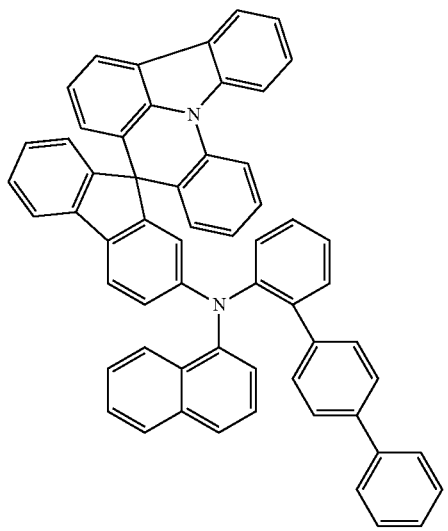
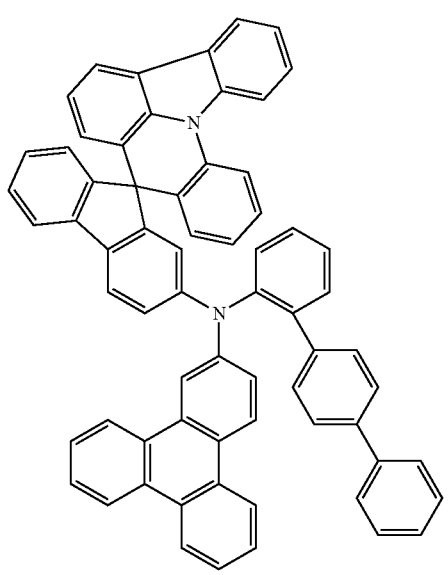
108
-continued
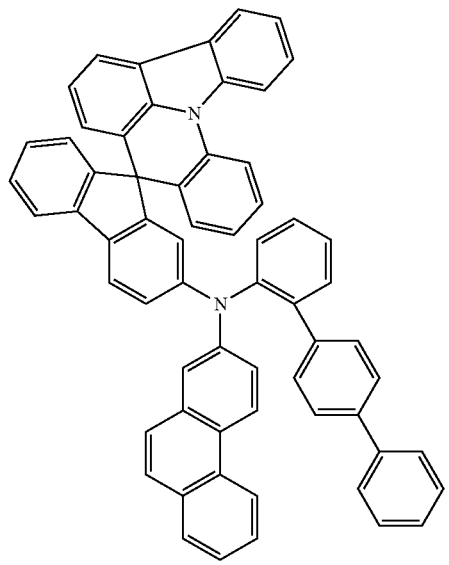
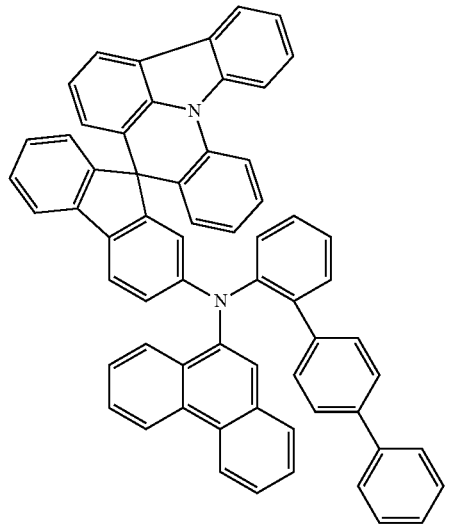
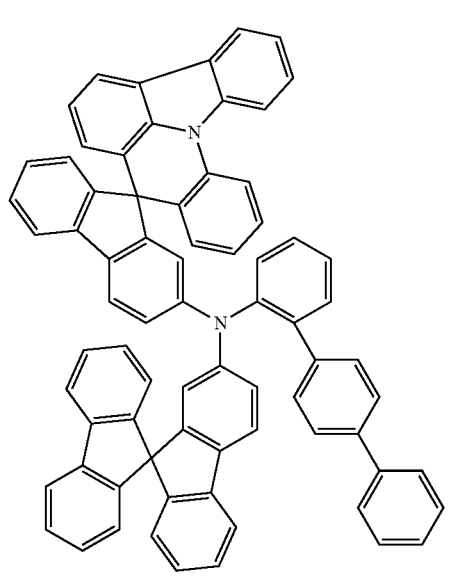

109
-continued
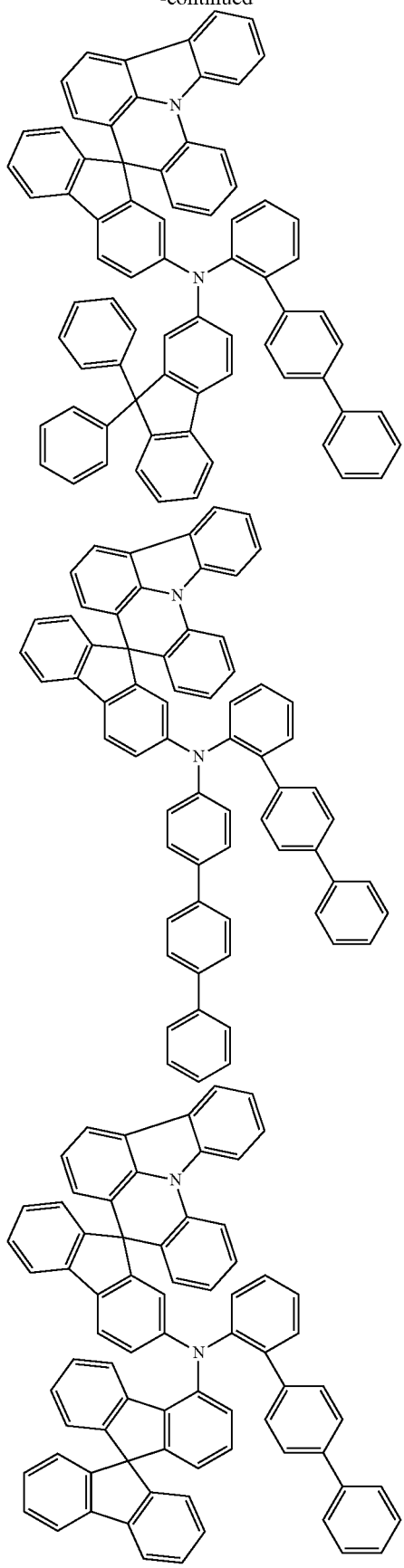
110
-continued
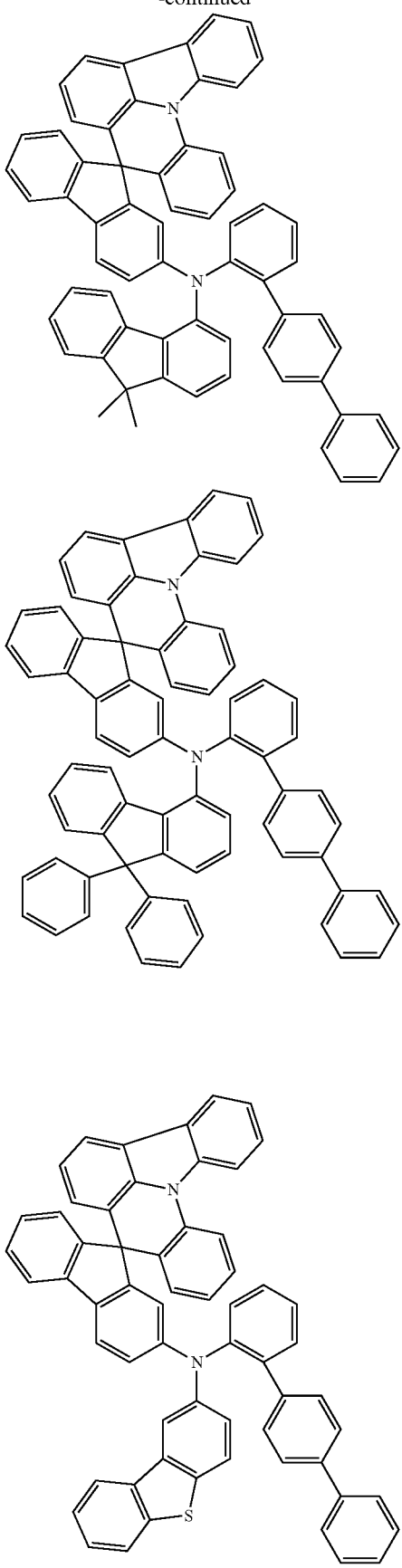

111
-continued
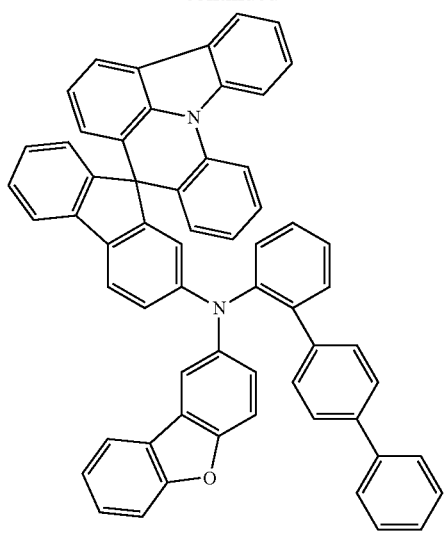
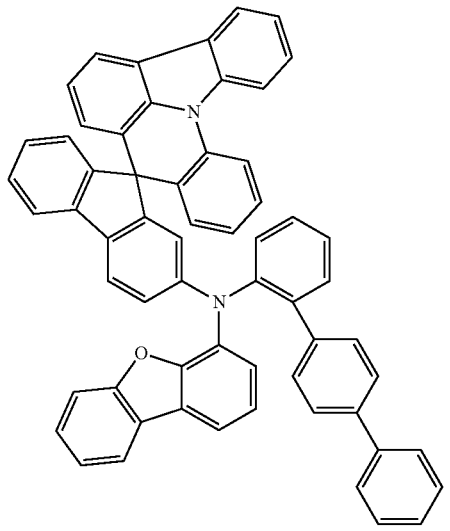
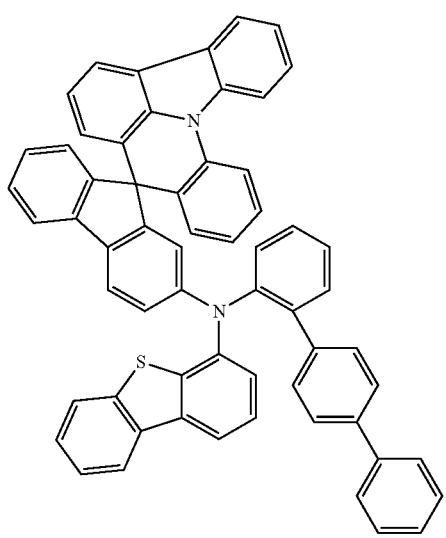
112
-continued
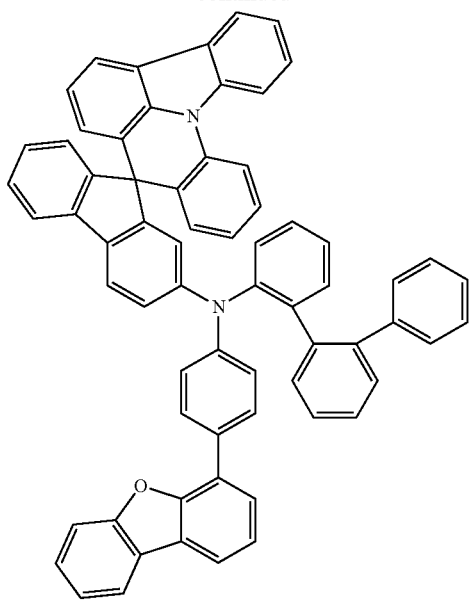
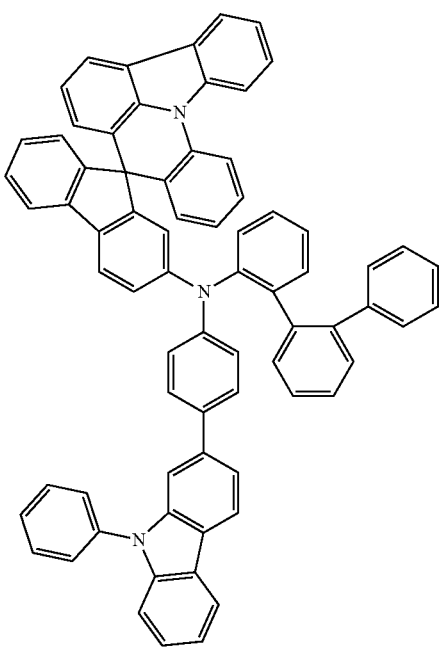

113
-continued
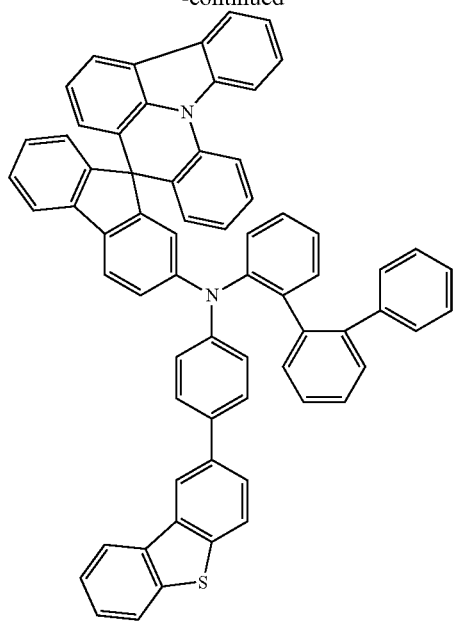
114
-continued
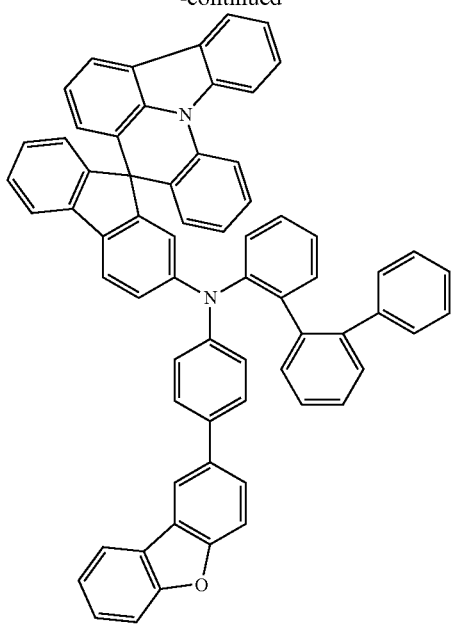
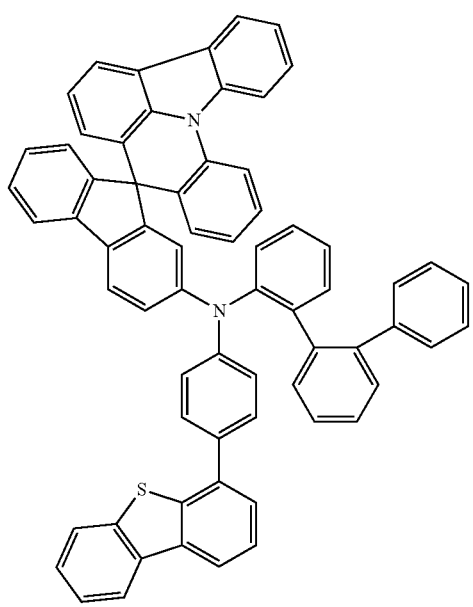
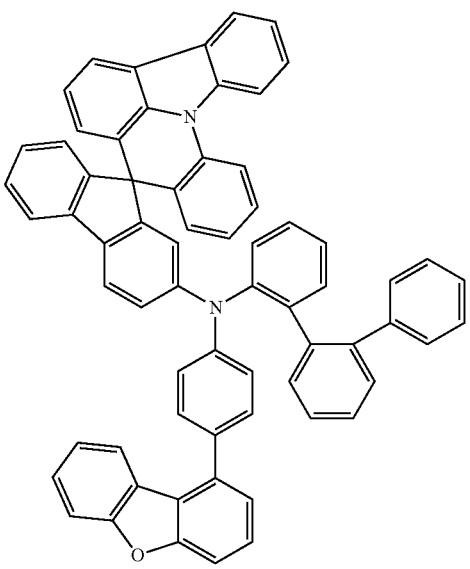

115
-continued
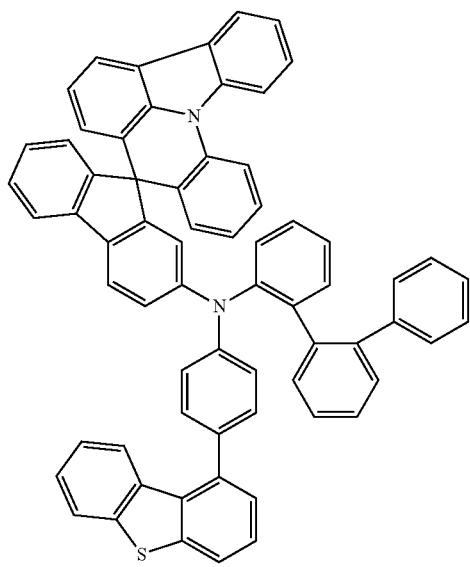
116
-continued
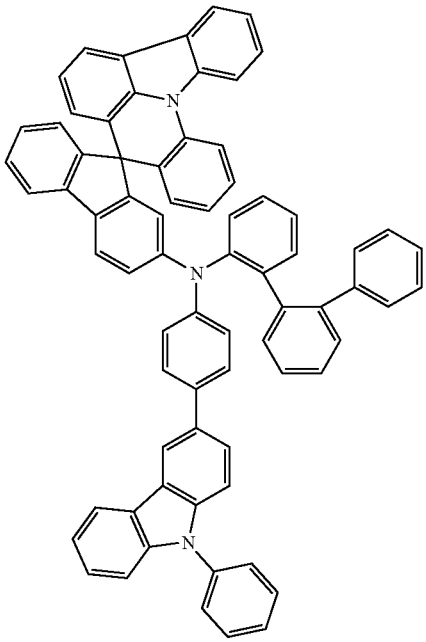
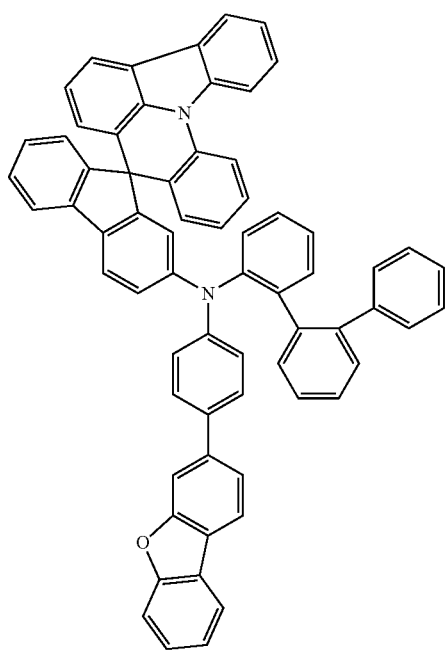
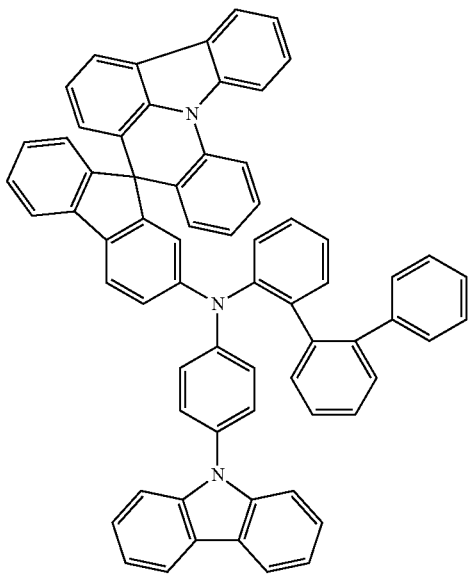

117
-continued
118
-continued
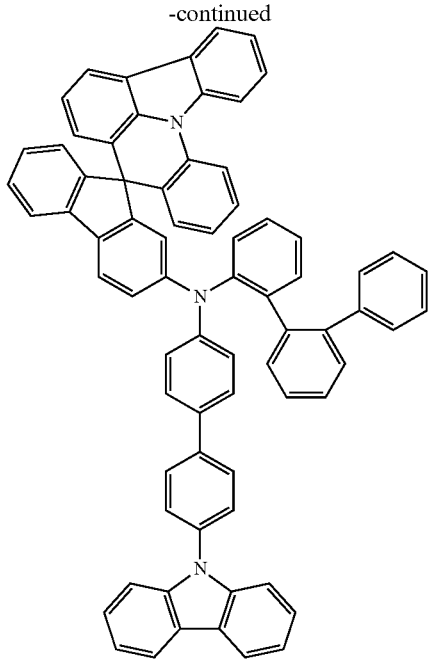
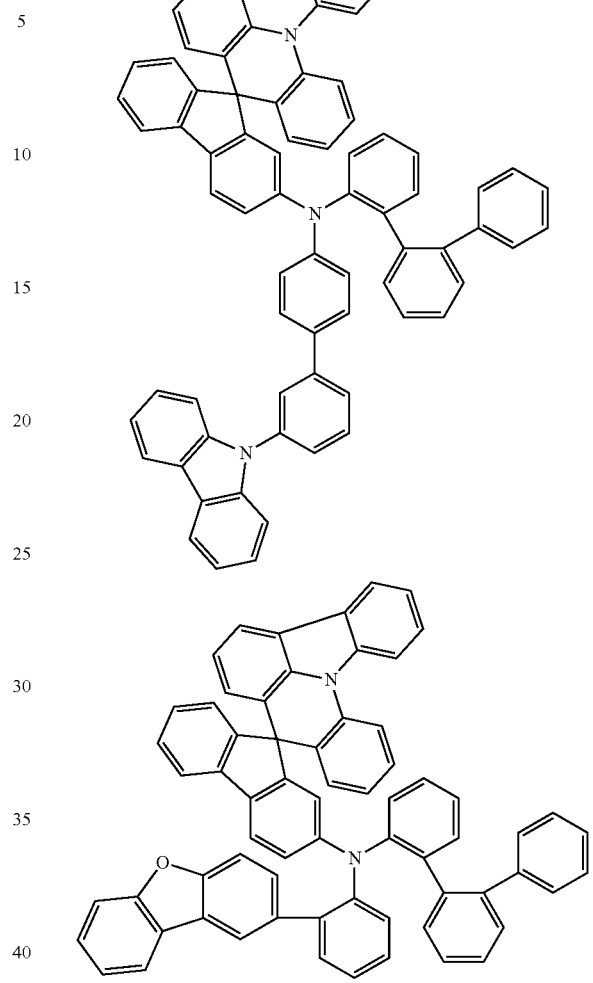
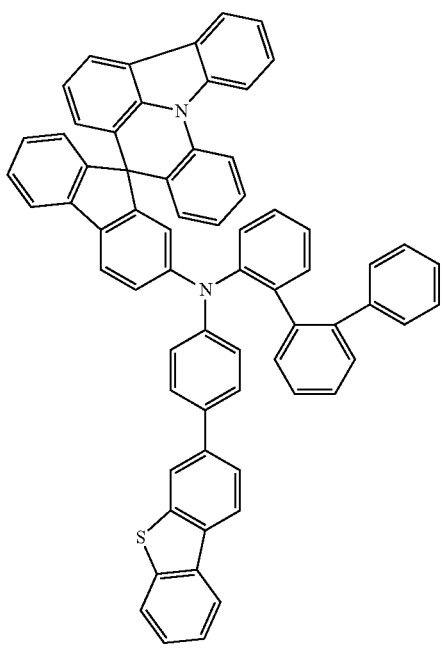
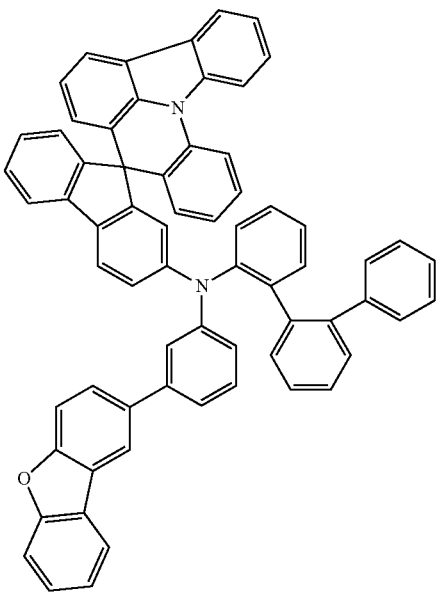

119
-continued
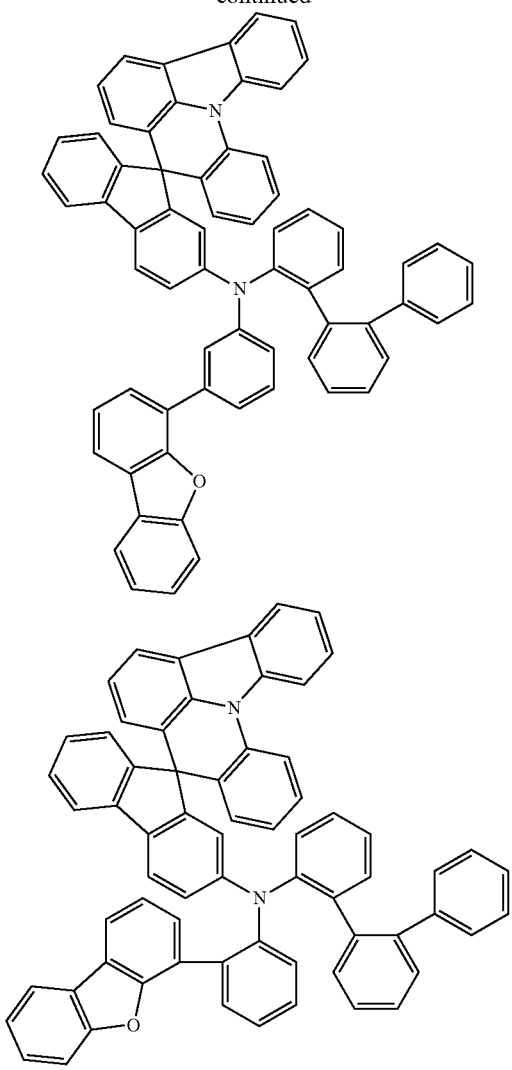
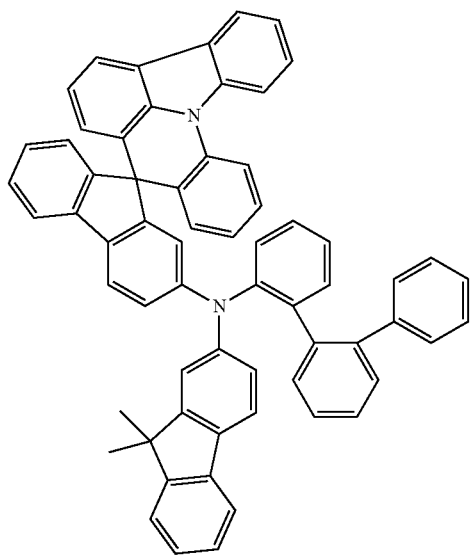
120
-continued
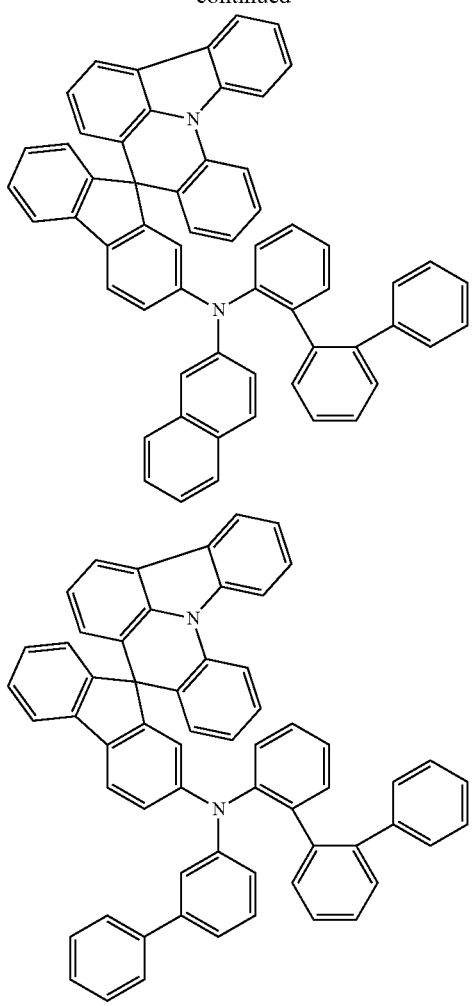
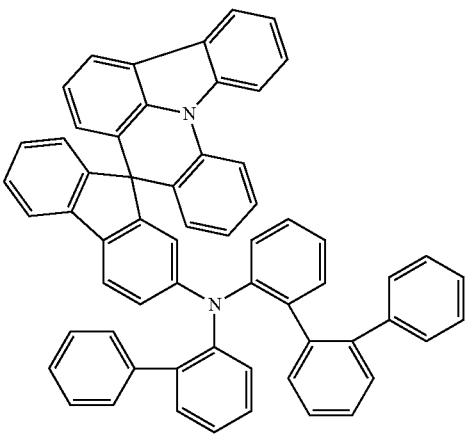

121
-continued
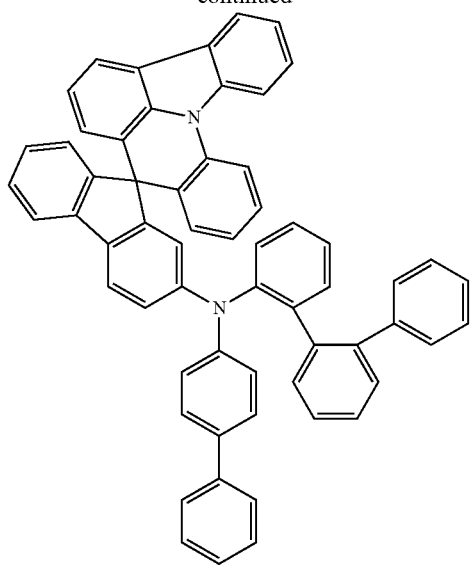
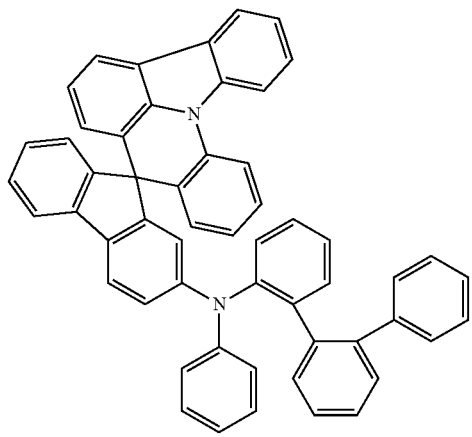
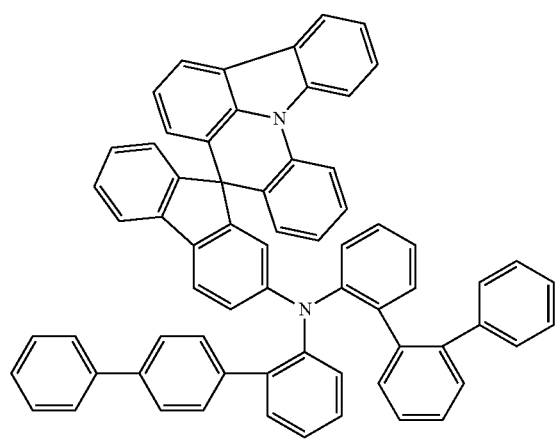
122
-continued
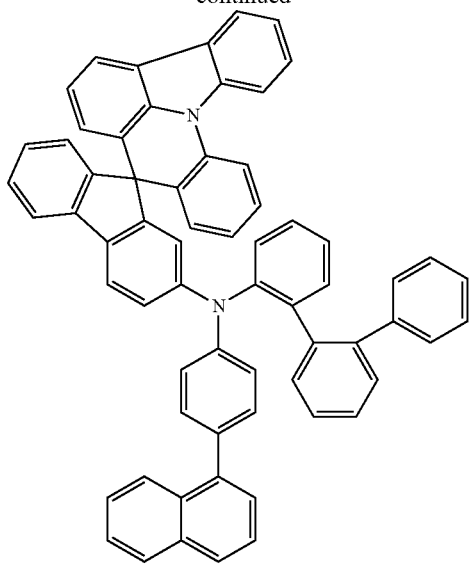
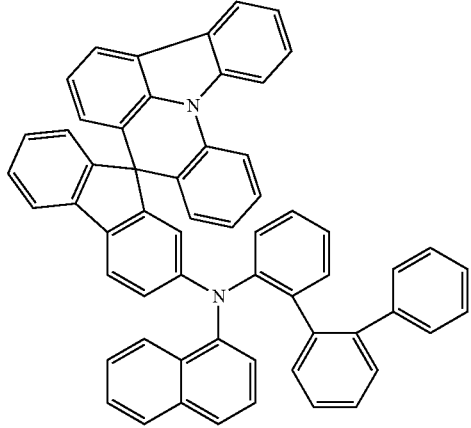
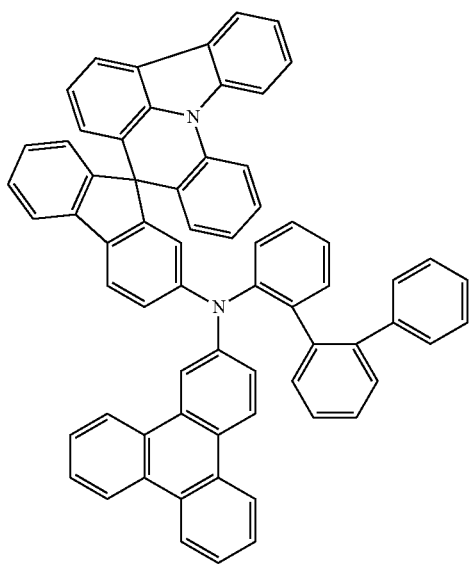

123
-continued
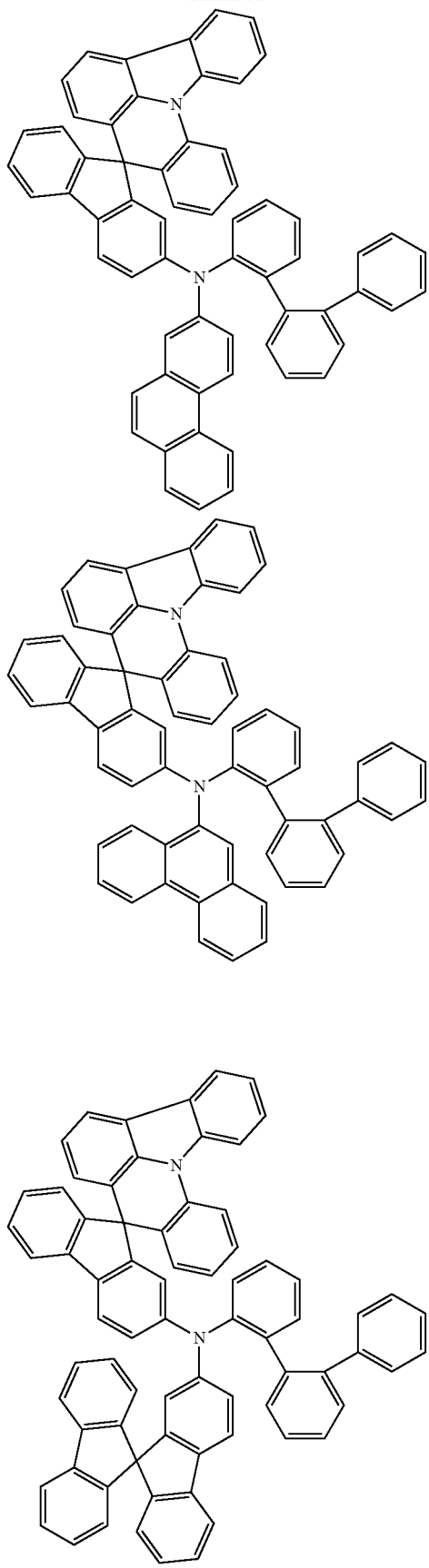
124
-continued
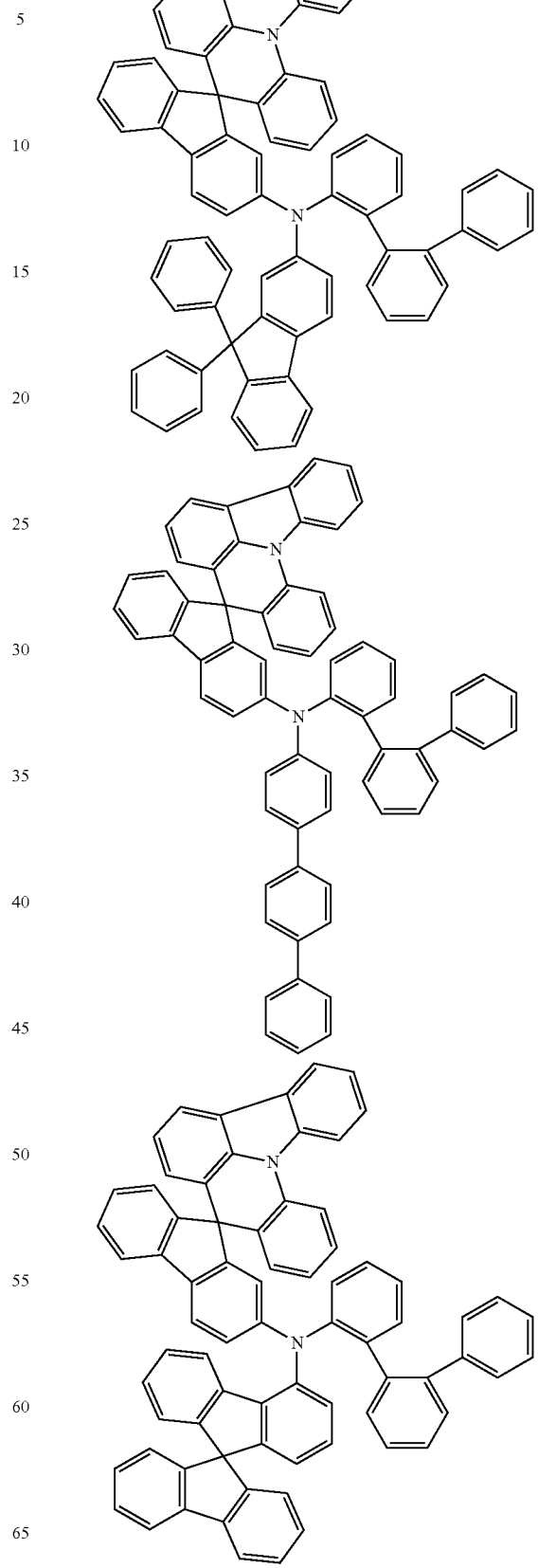

125
-continued
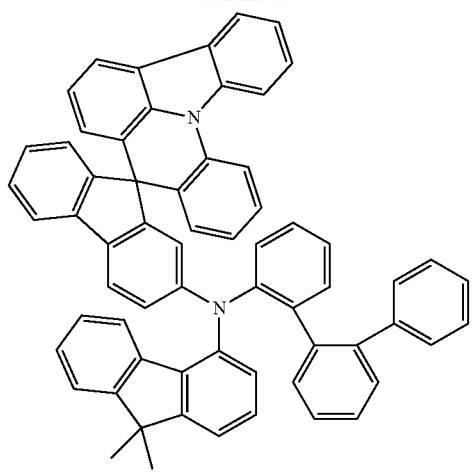
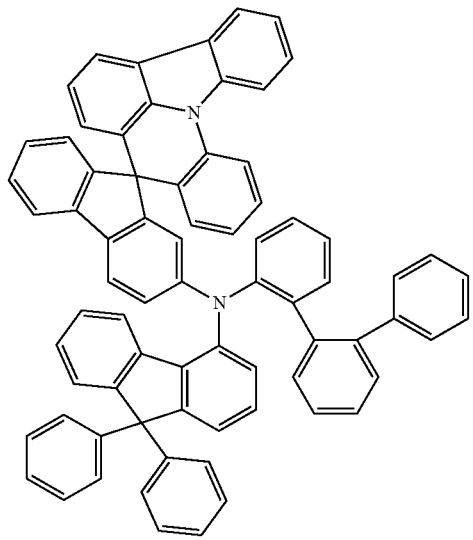
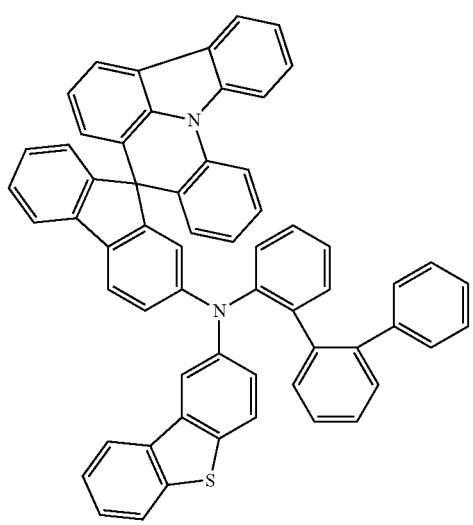
126
-continued
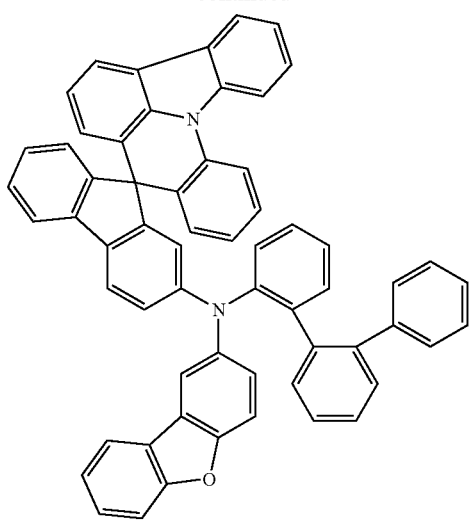
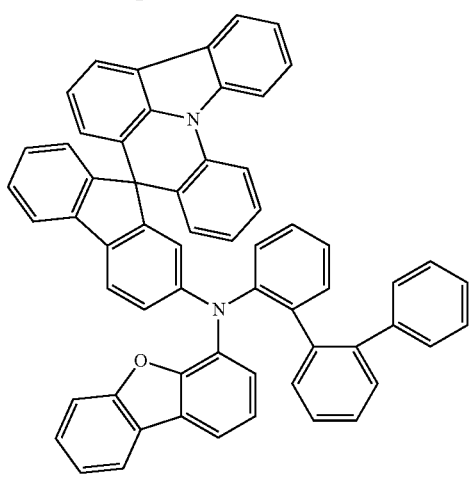
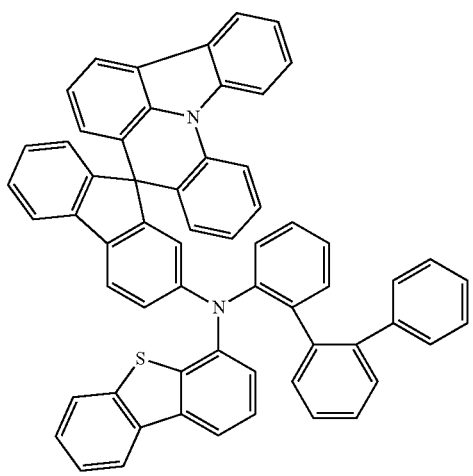

127
-continued
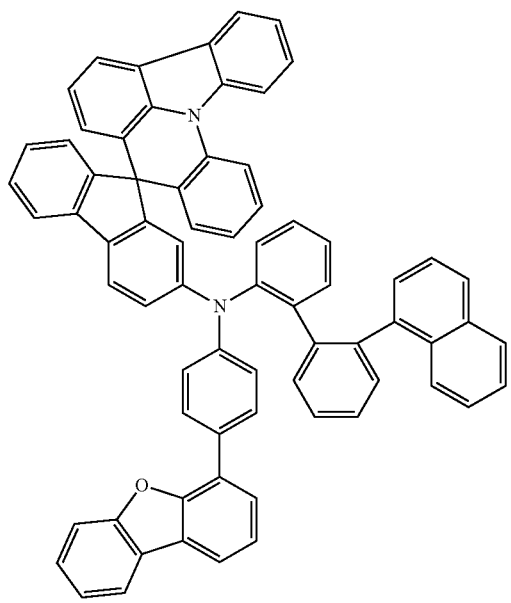
128
-continued
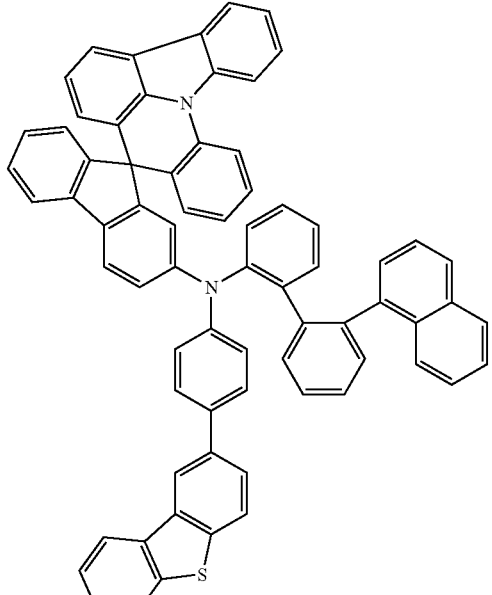
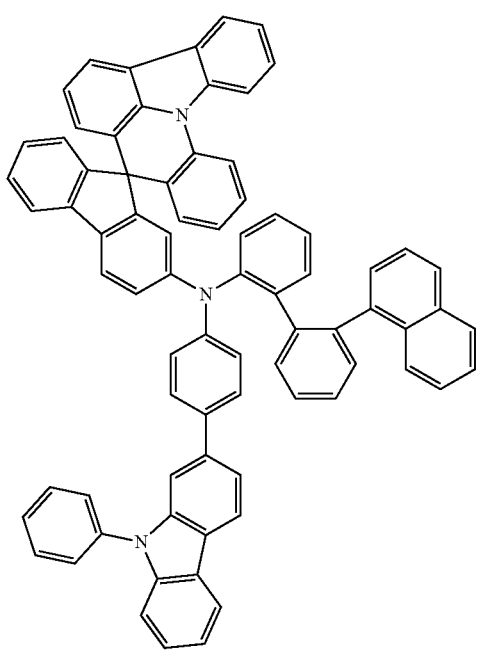
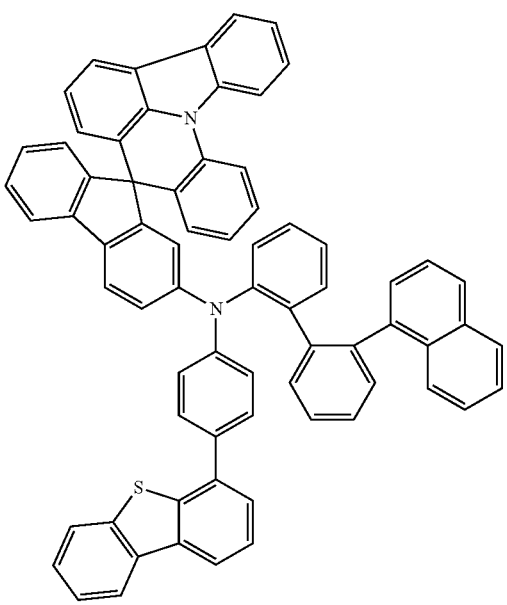

129
-continued
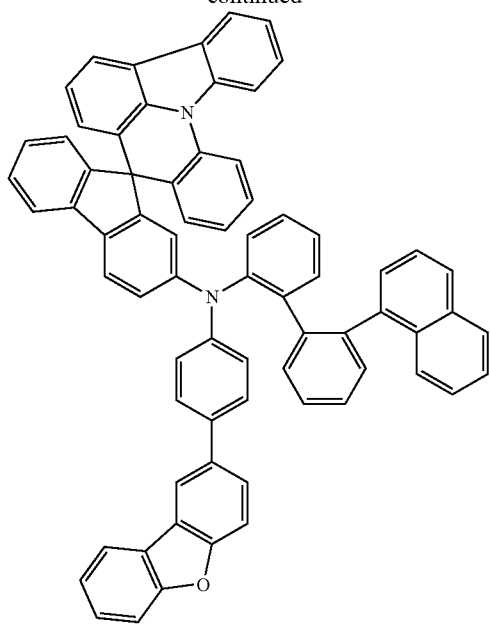
130
-continued
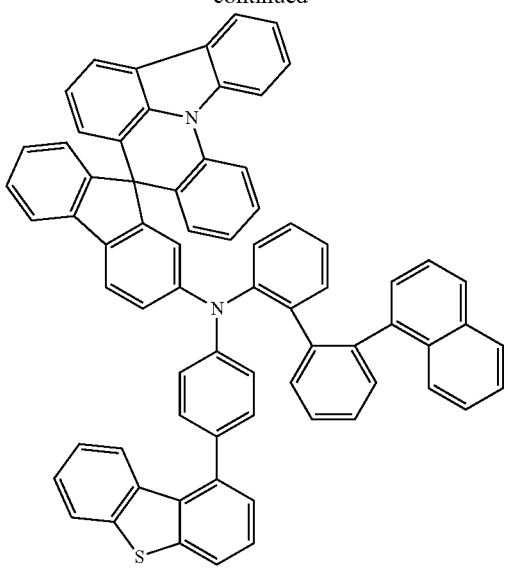
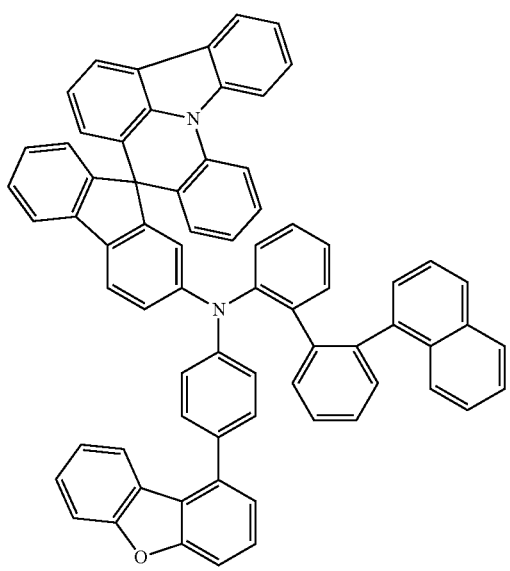
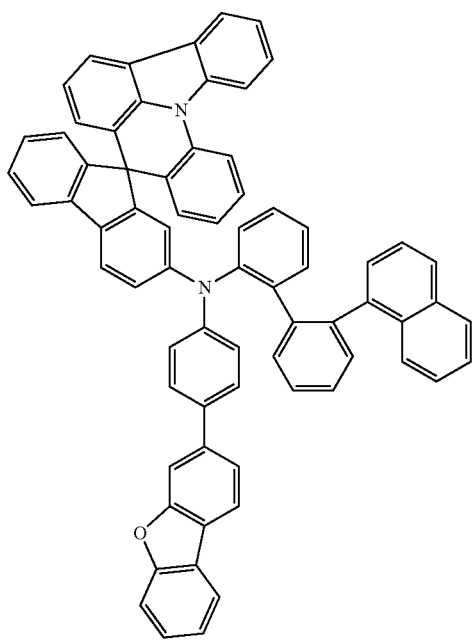

131
-continued
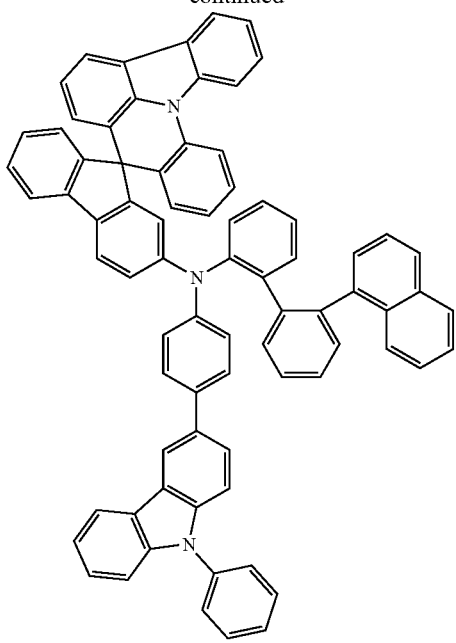
132
-continued
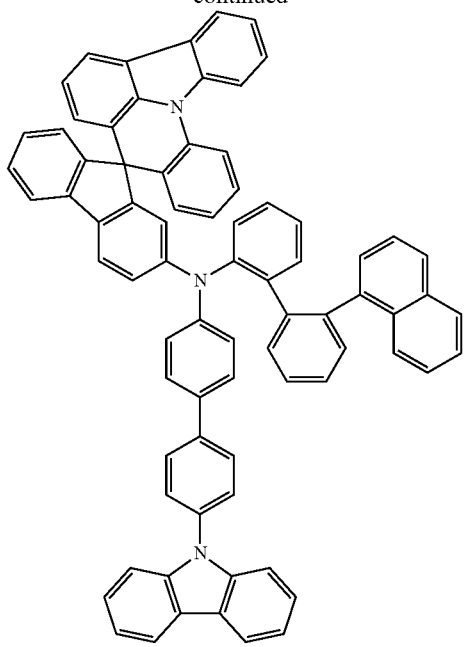
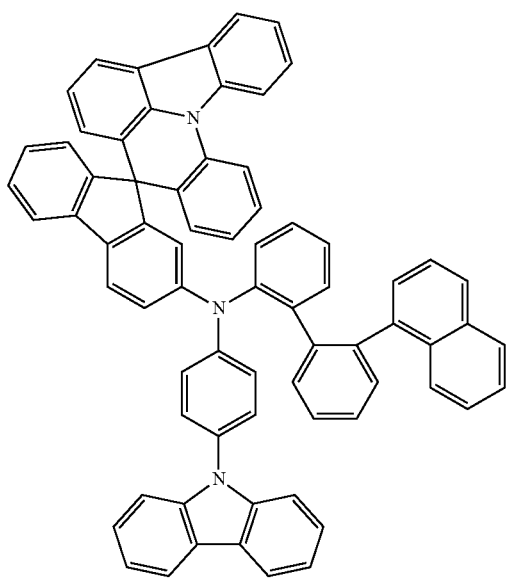
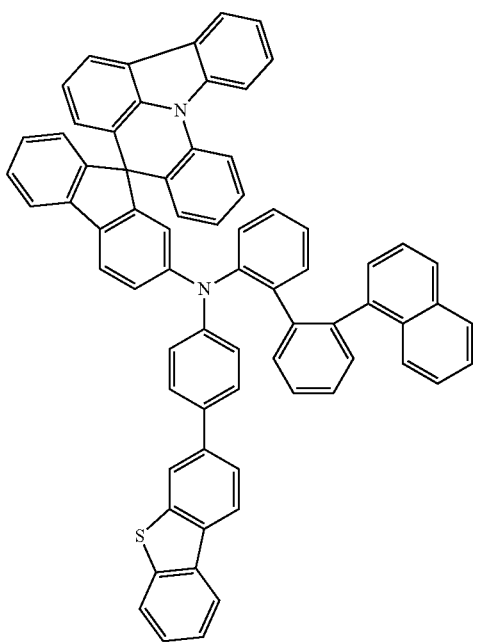

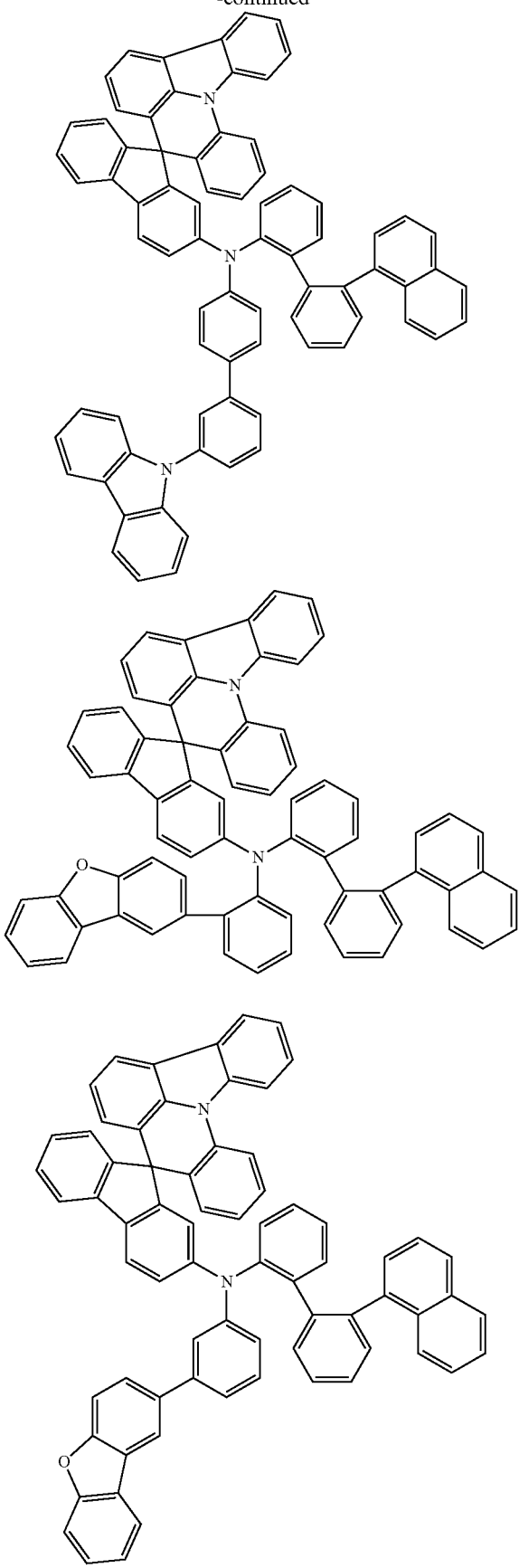
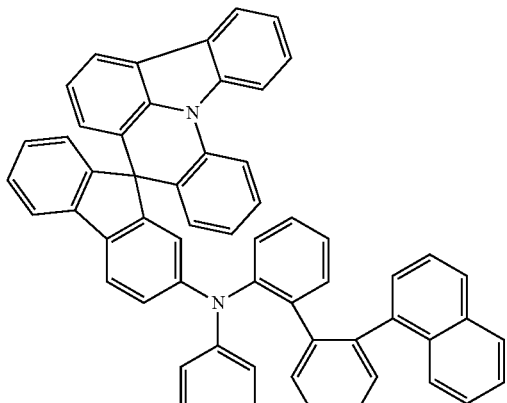
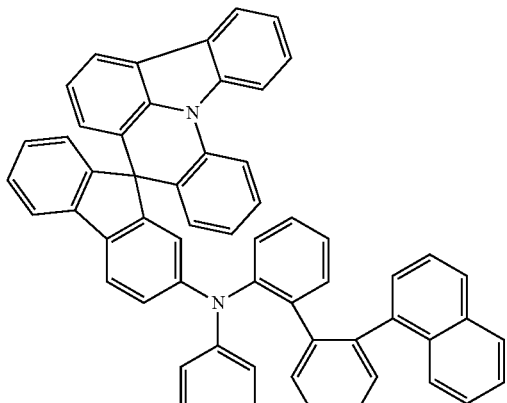

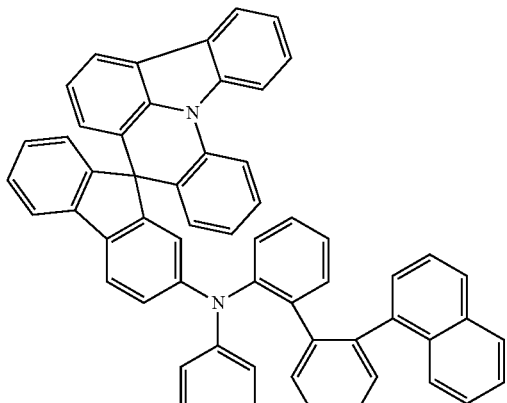

135
-continued

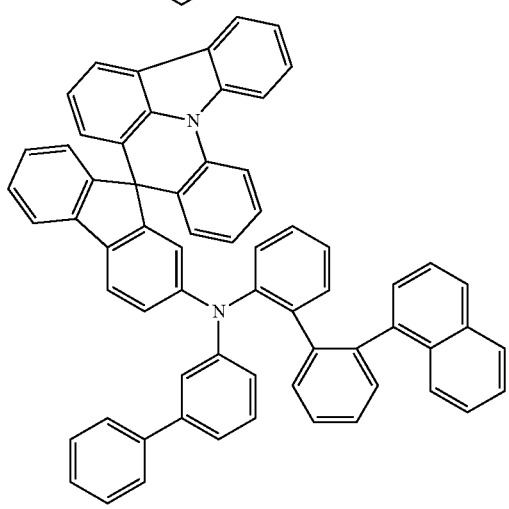
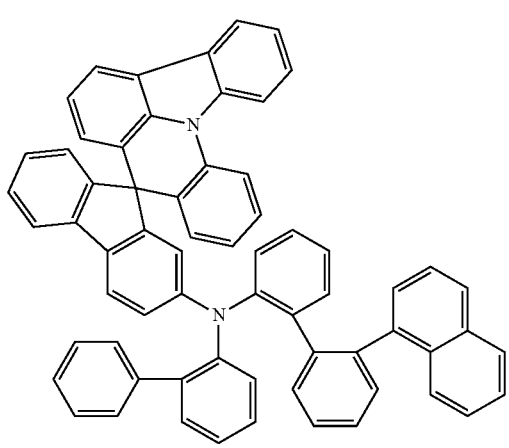
136
-continued
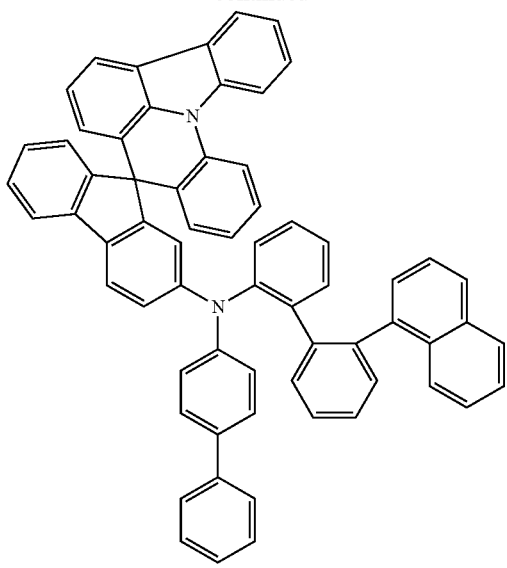
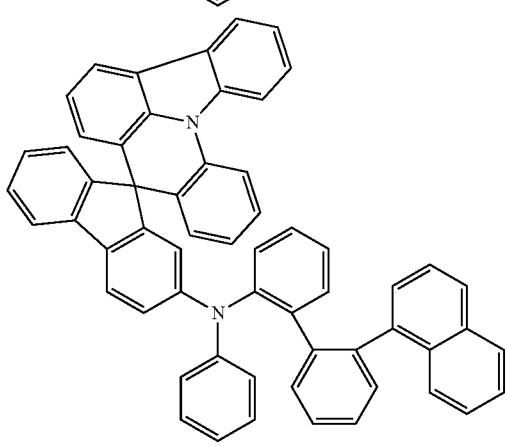
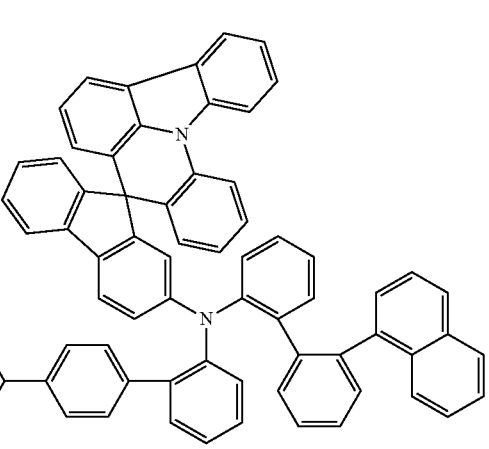

137
-continued
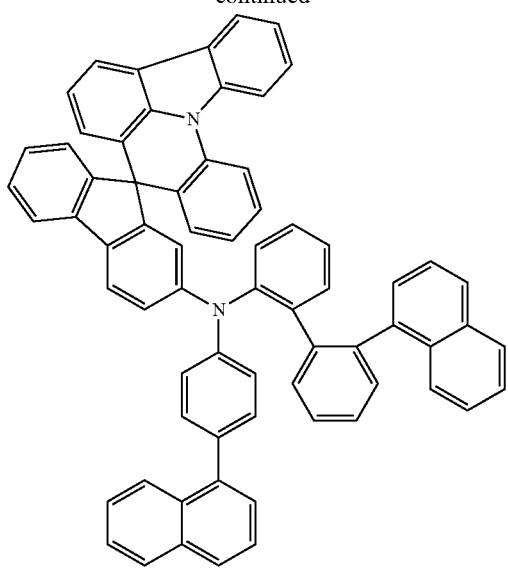
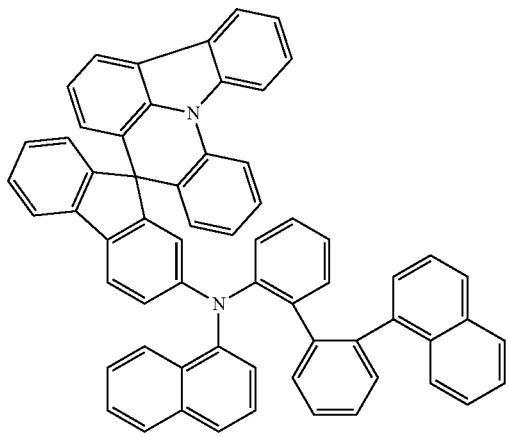
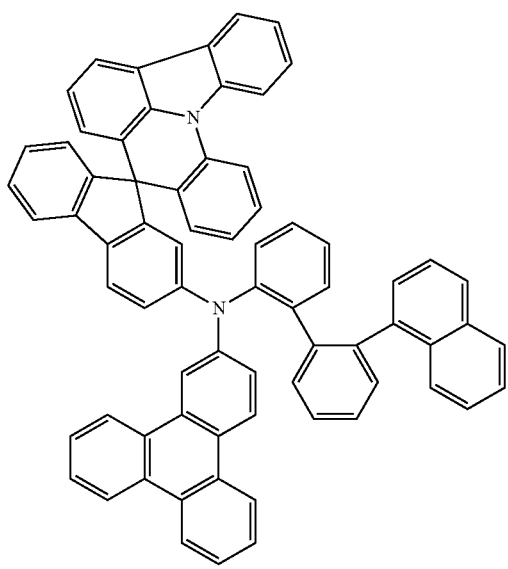
138
-continued
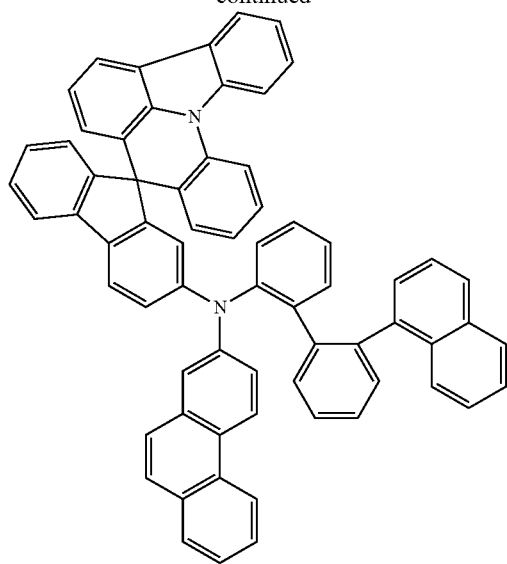
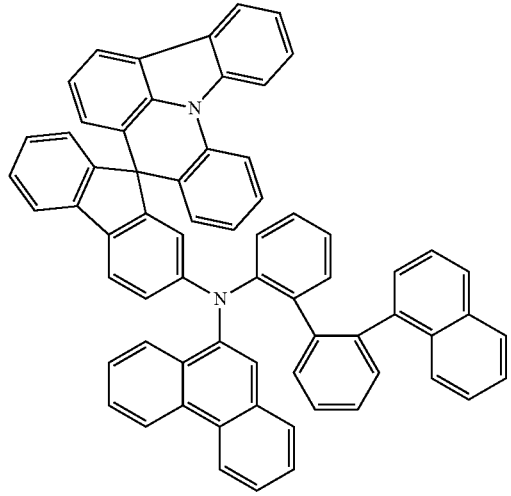
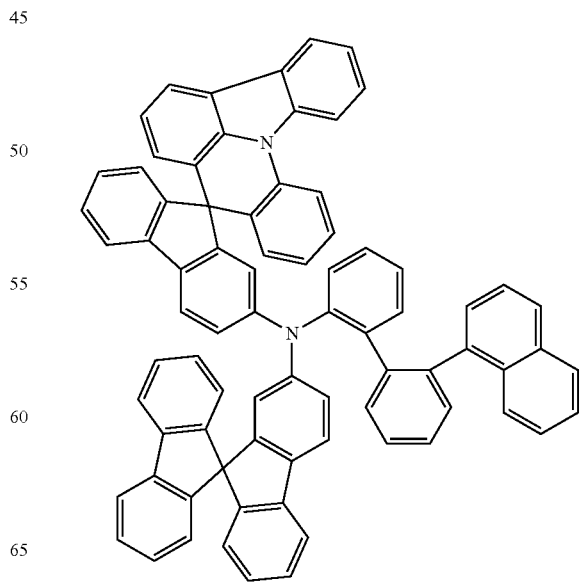

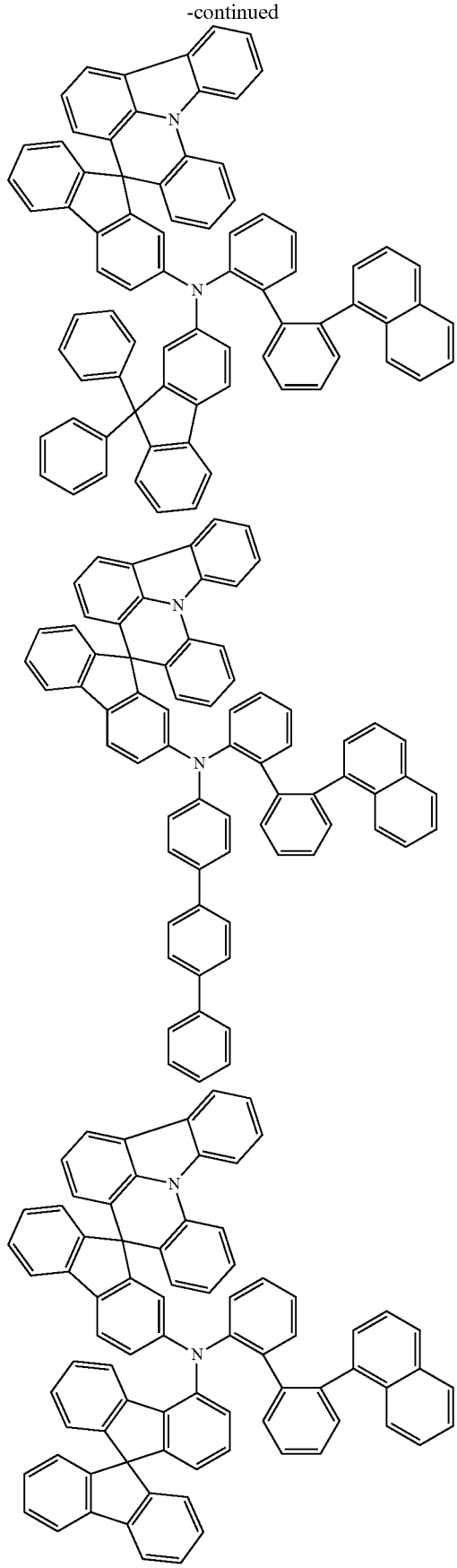
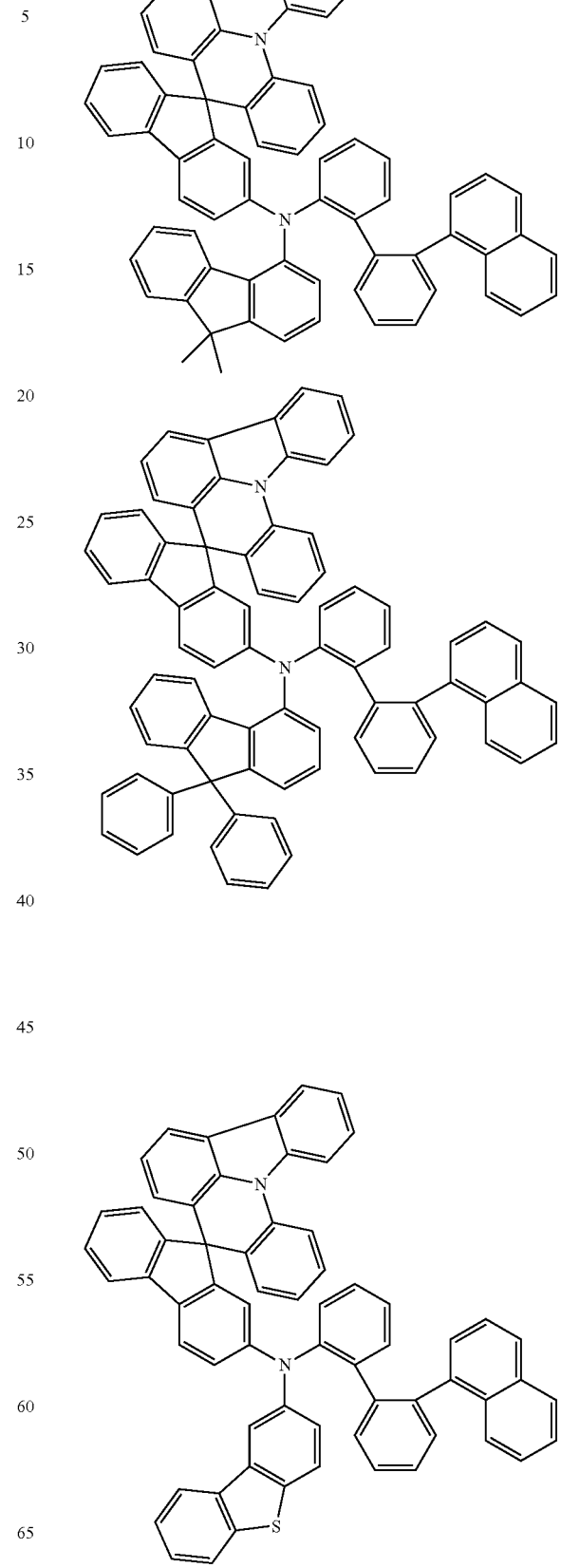

141
-continued
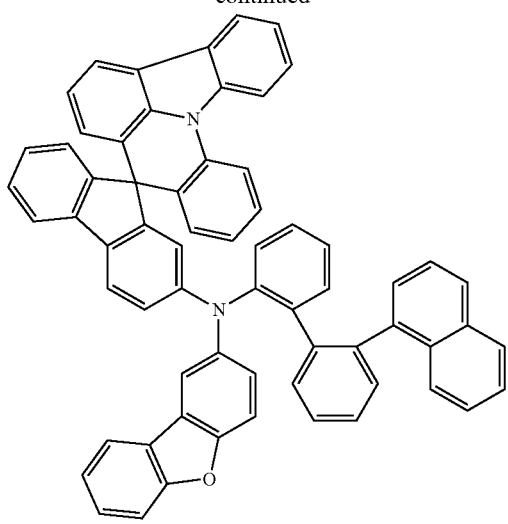
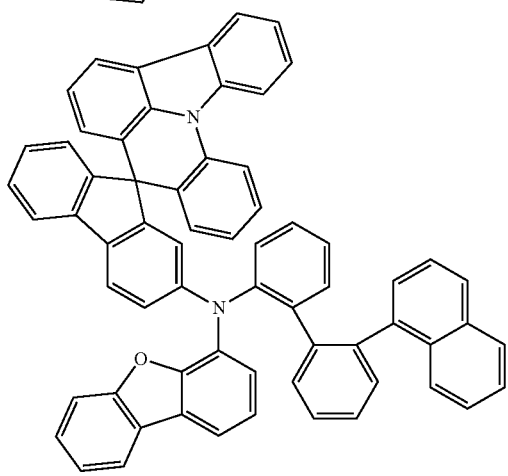
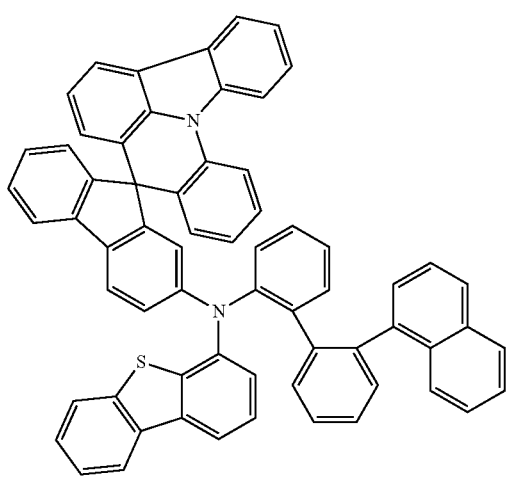
142
-continued
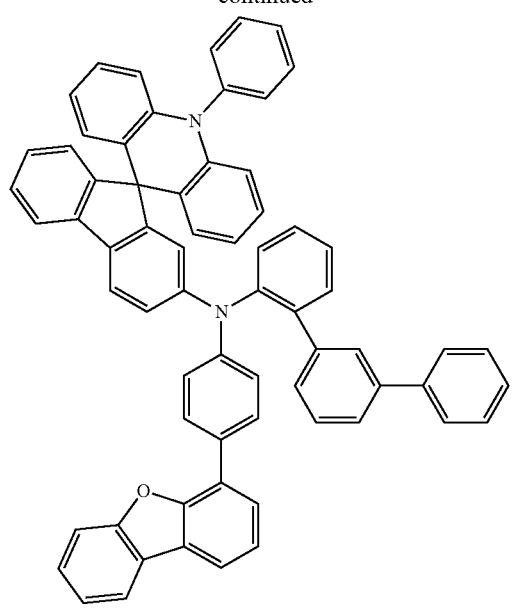
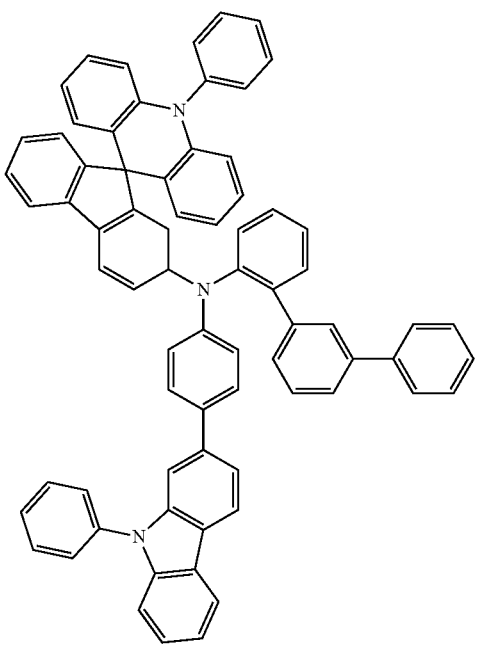

143
-continued
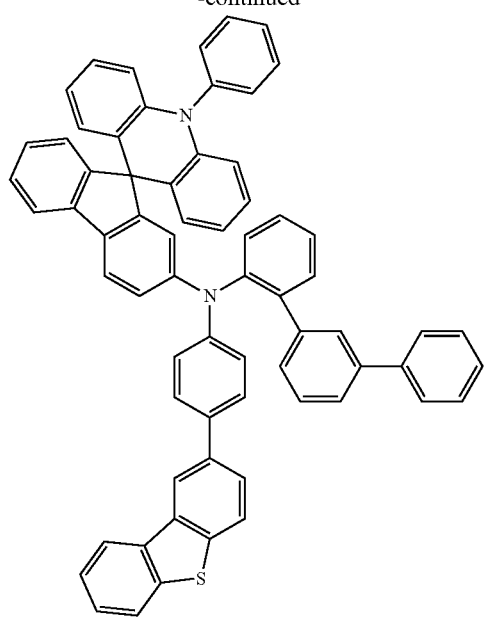
144
-continued
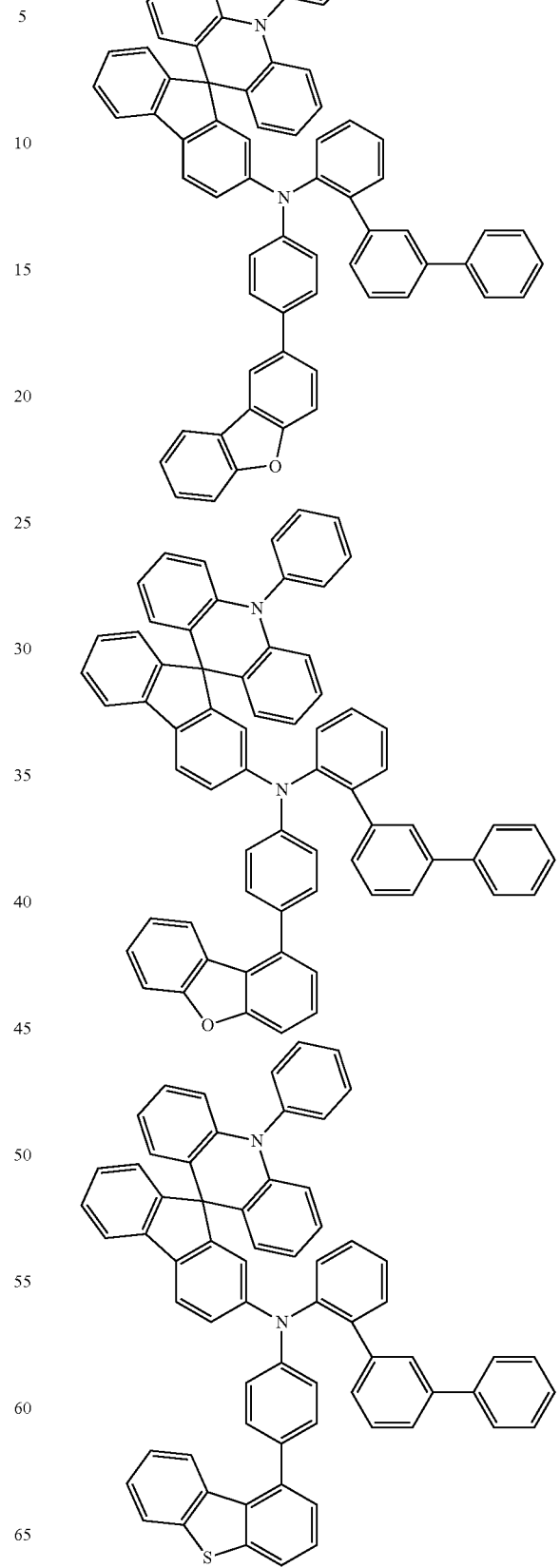
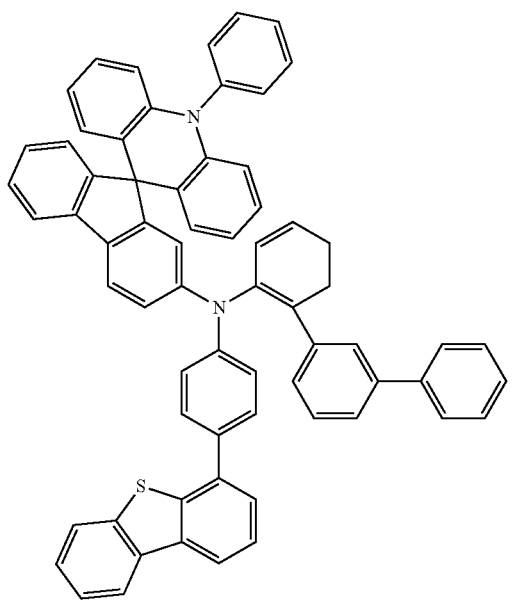

145
-continued
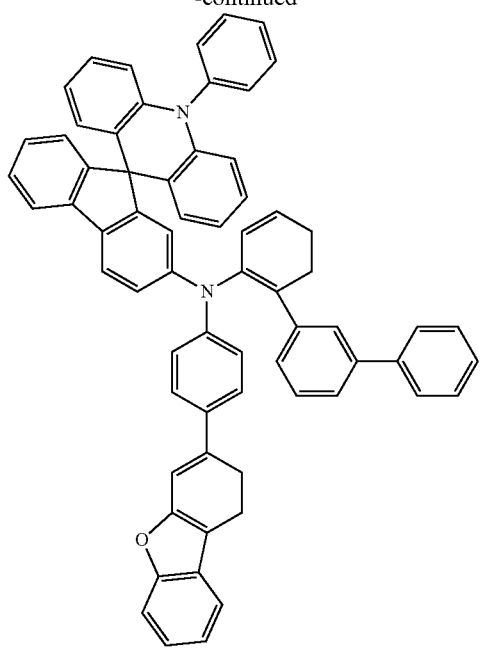
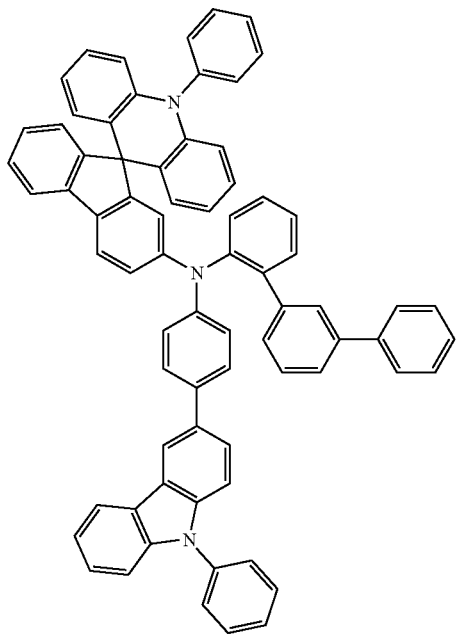
146
-continued
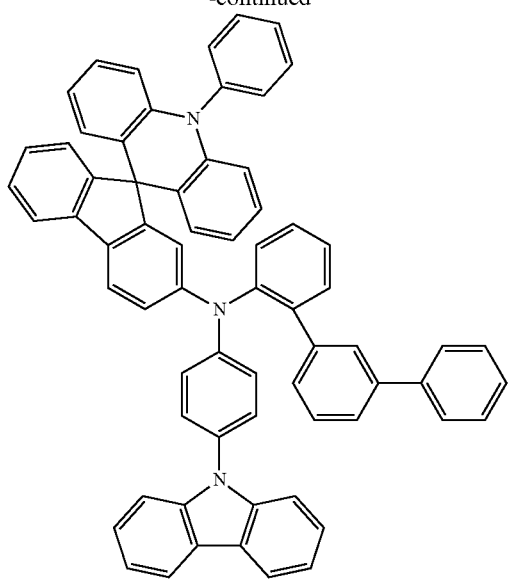
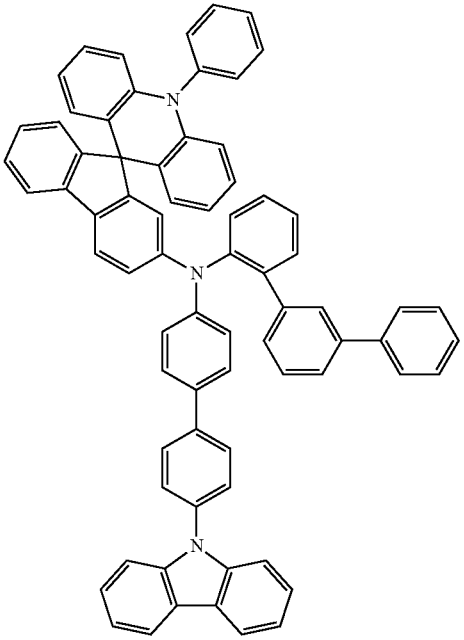

147
-continued
148
-continued
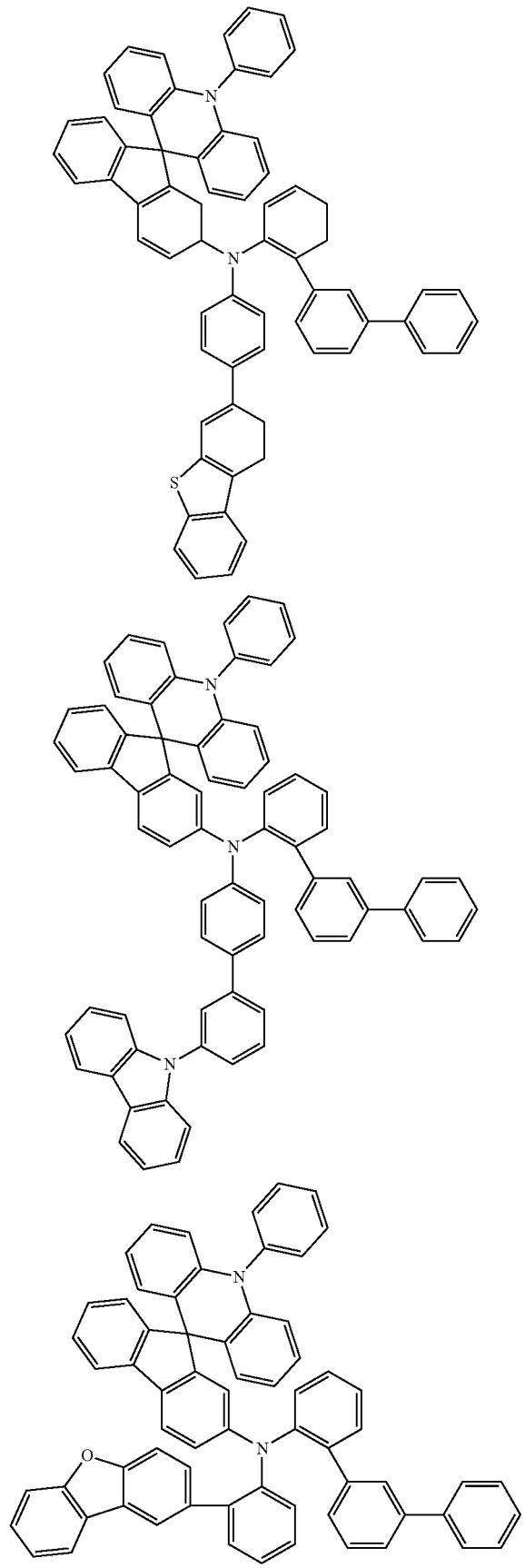
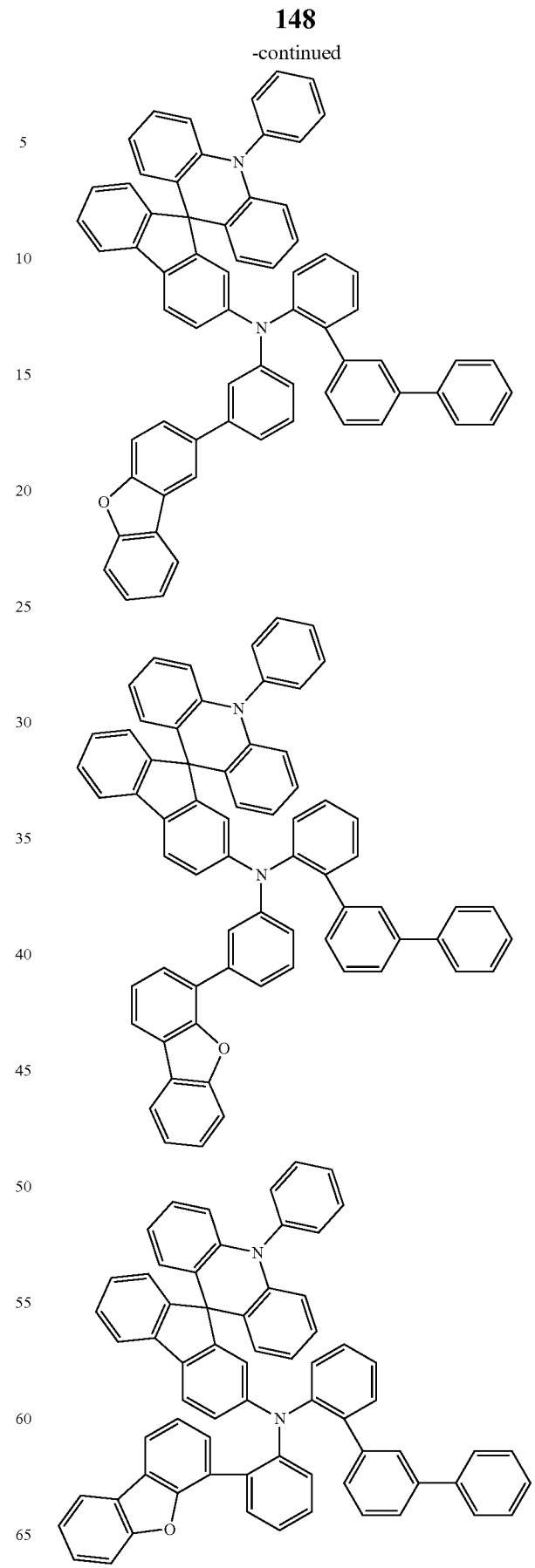

149
-continued
150
-continued
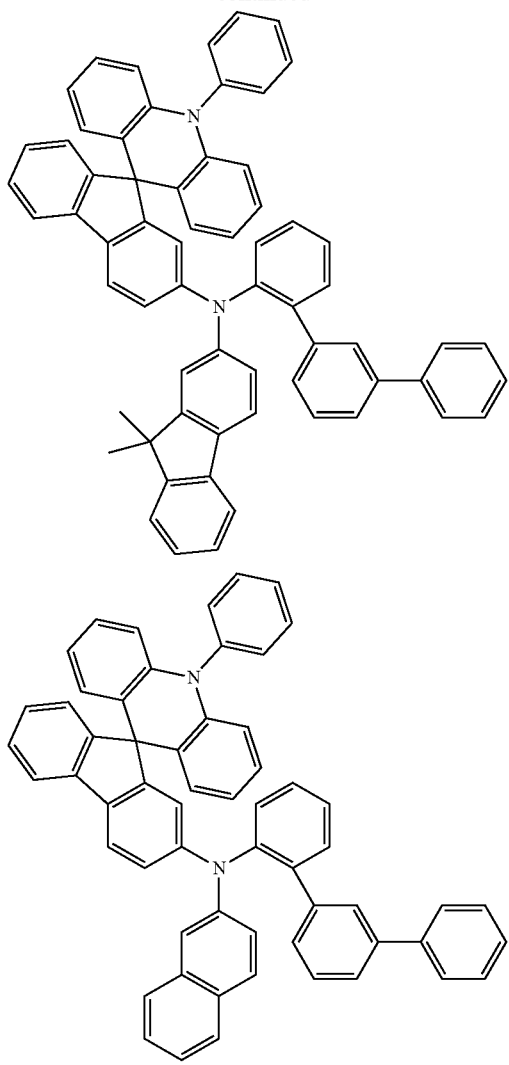
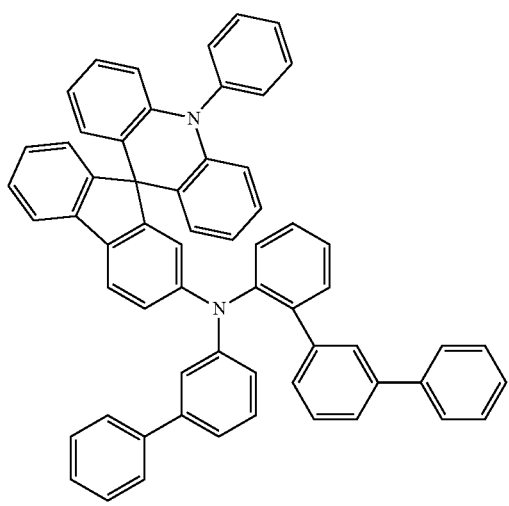
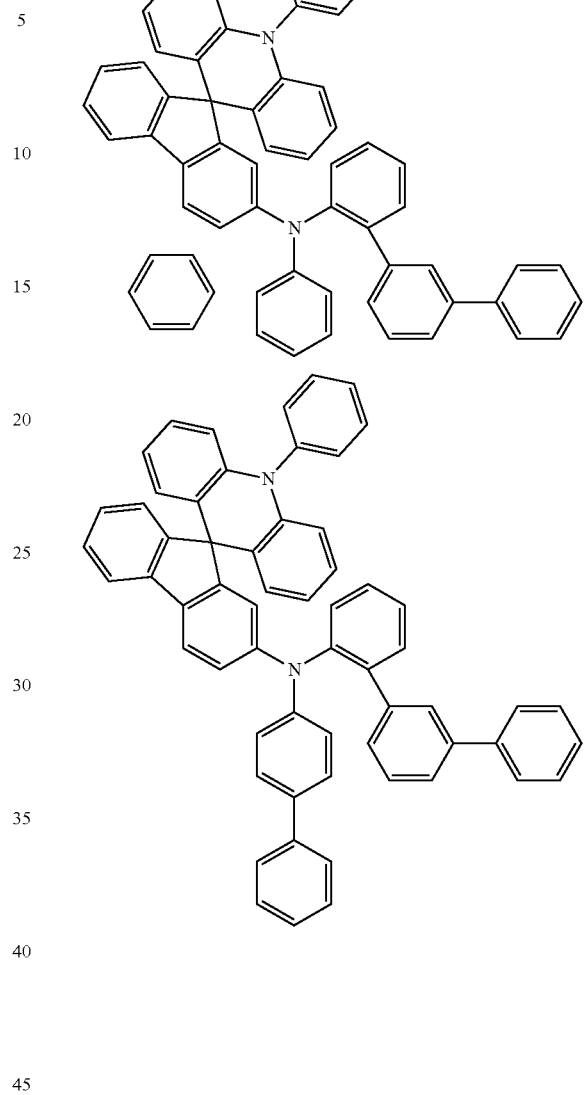
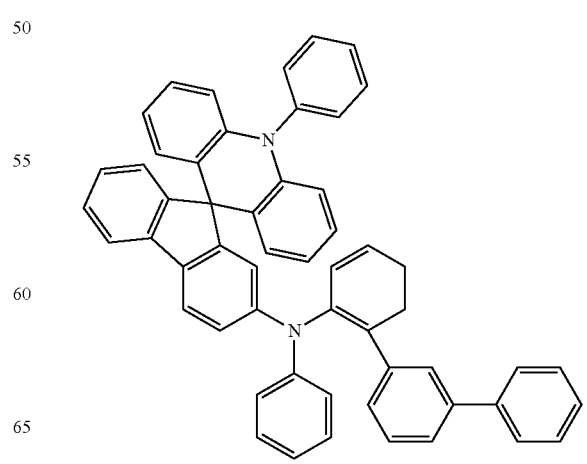

151
-continued
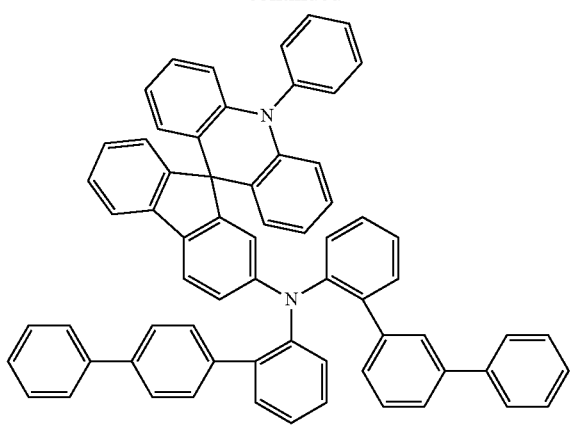
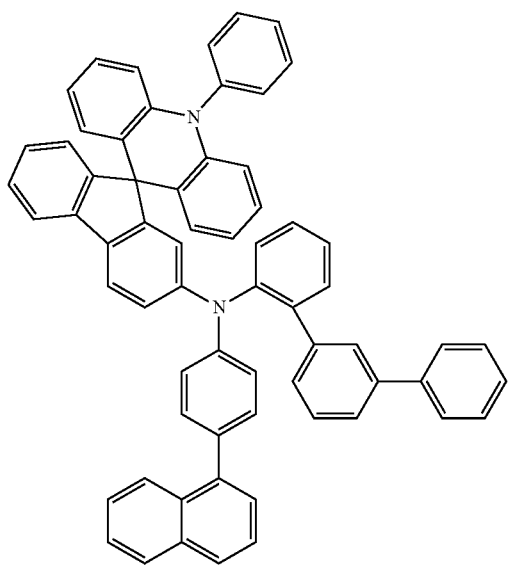
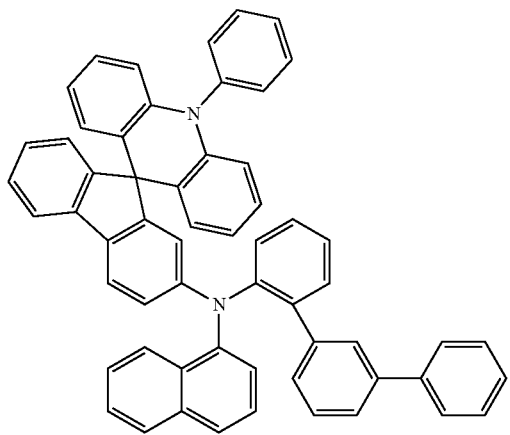
152
-continued
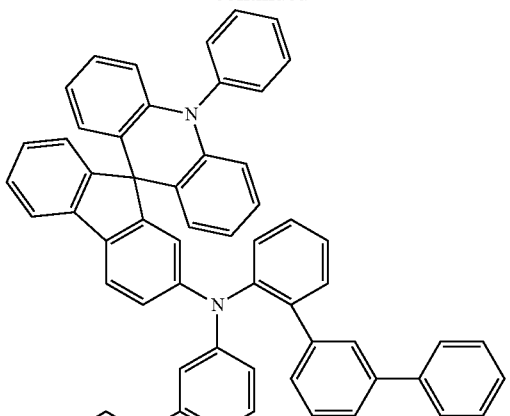
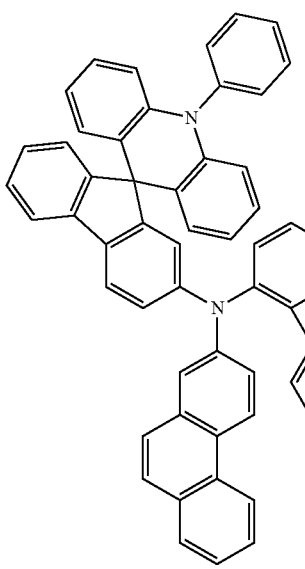
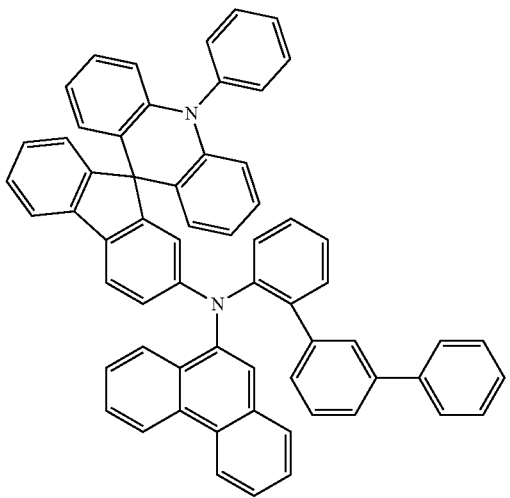

153
-continued
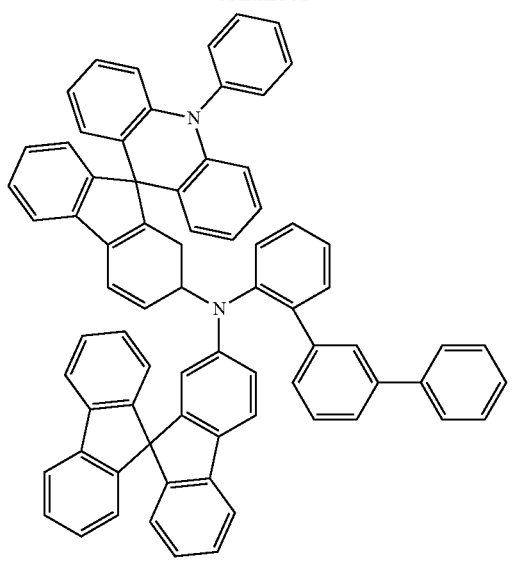
154
-continued
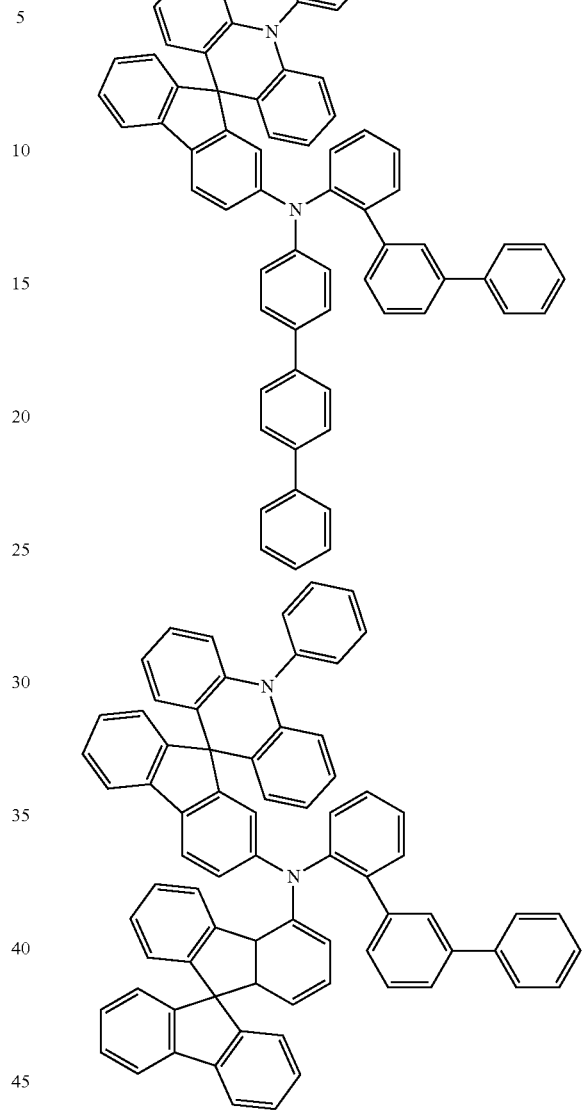
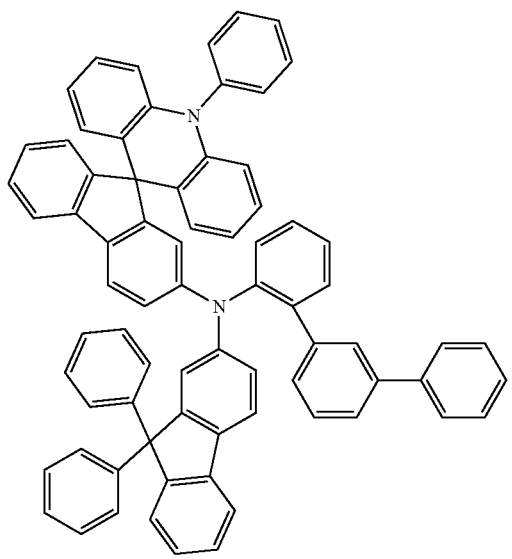
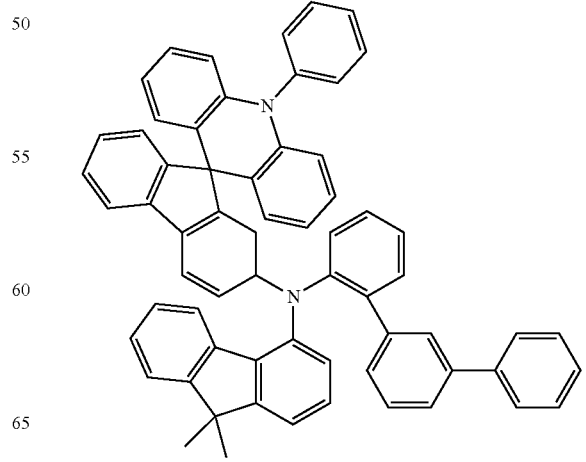

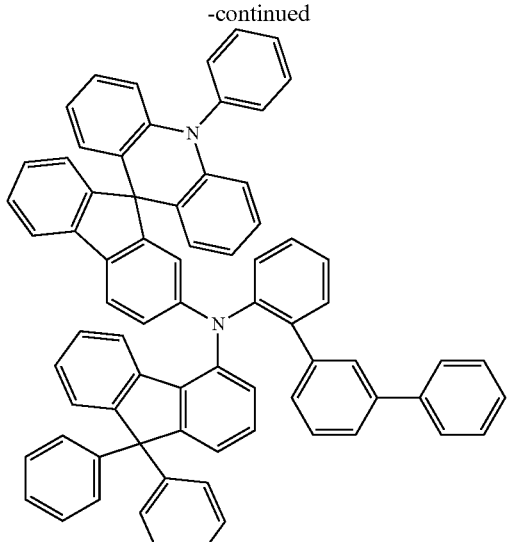
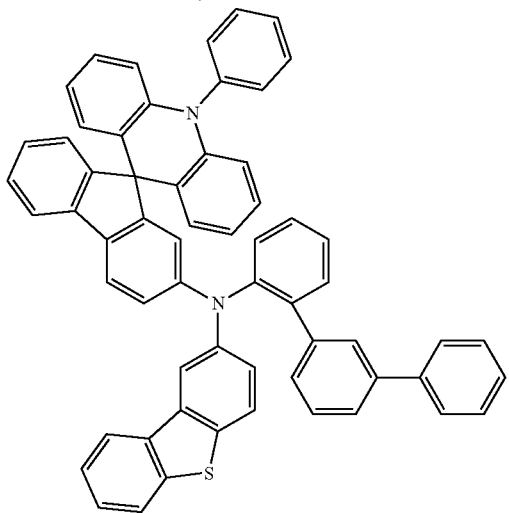
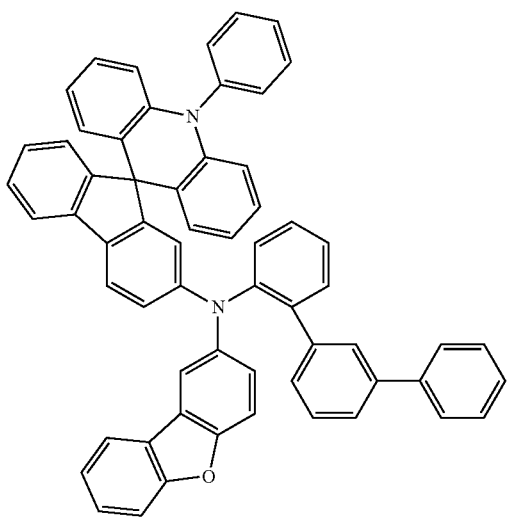
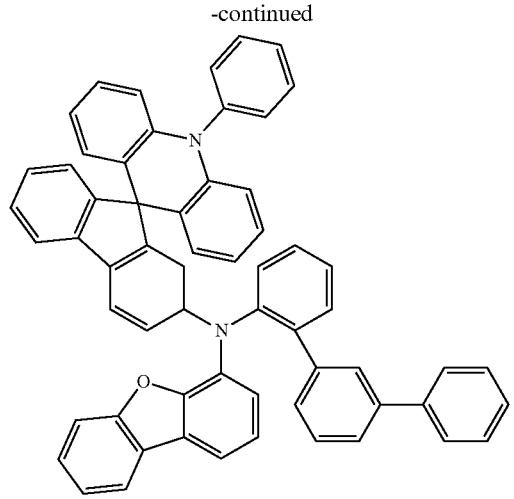
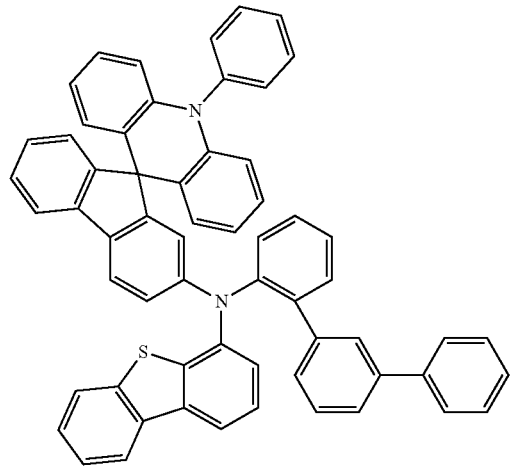
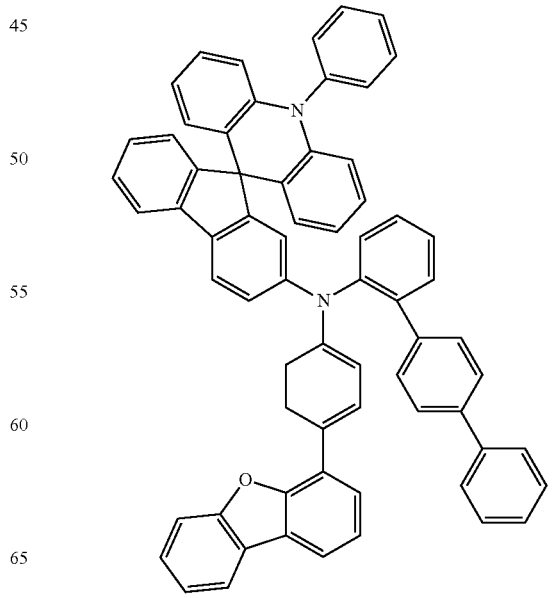

157
-continued
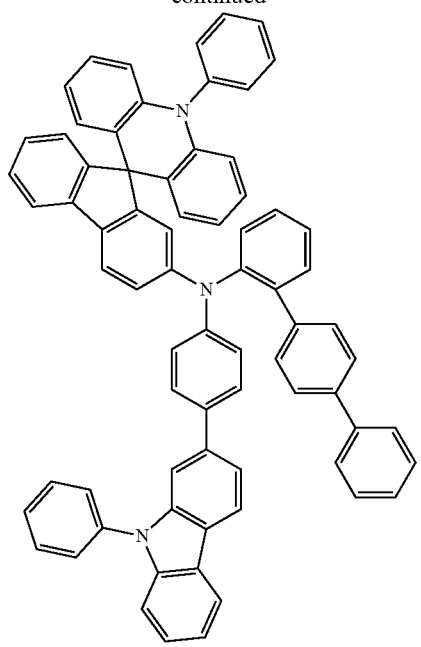
158
-continued
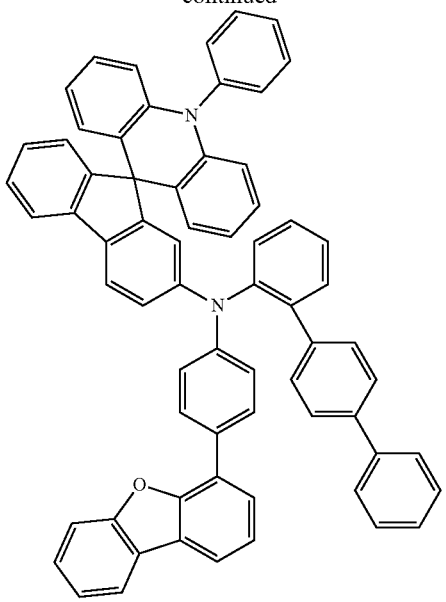
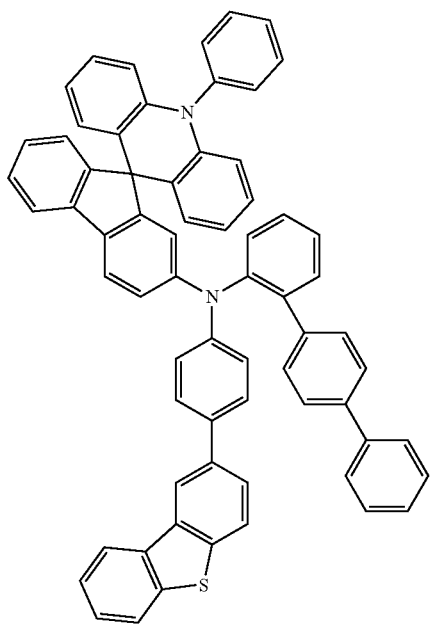
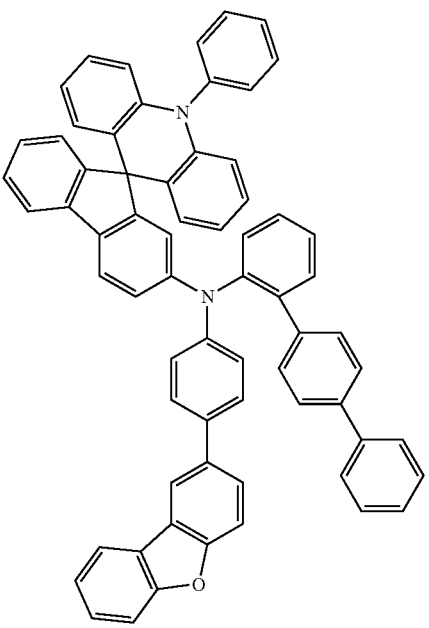

159
-continued
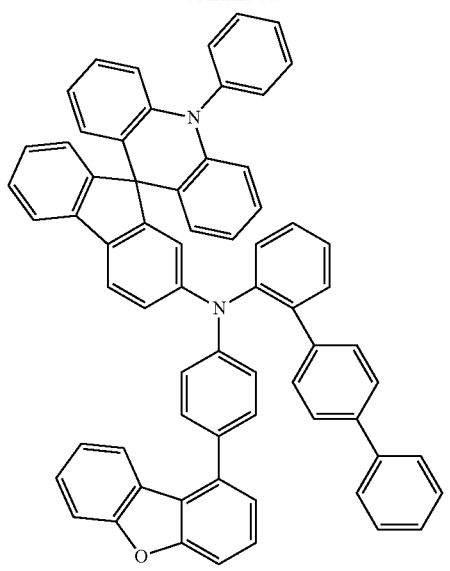
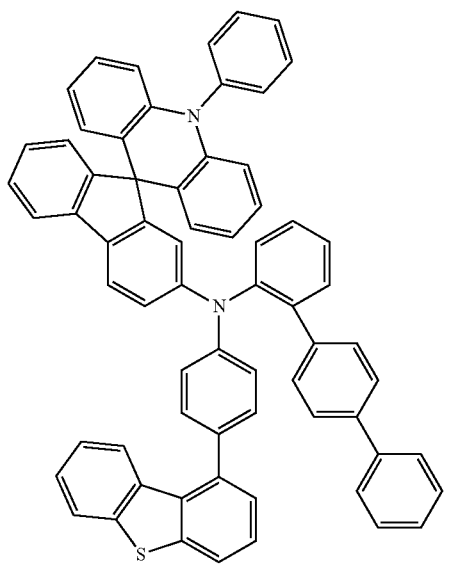
160
-continued
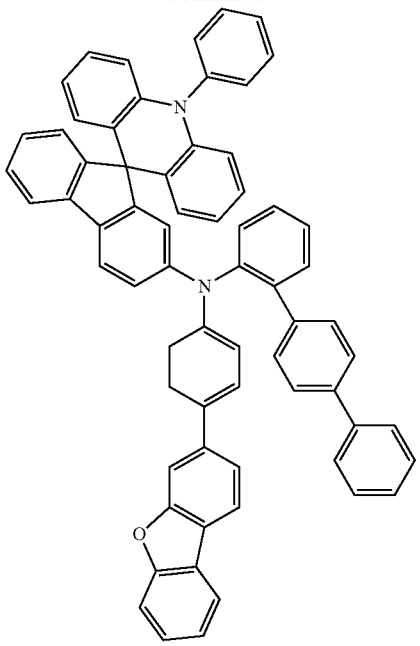
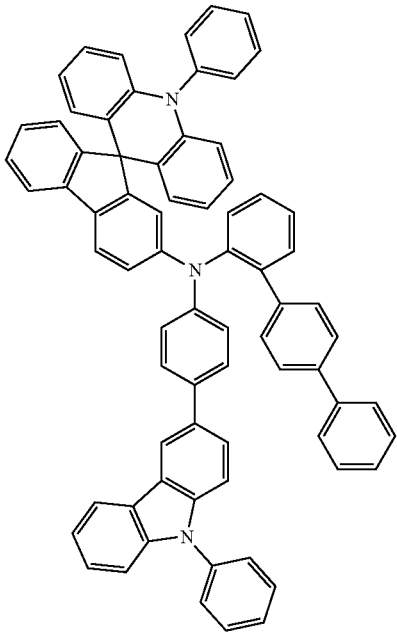

161
-continued
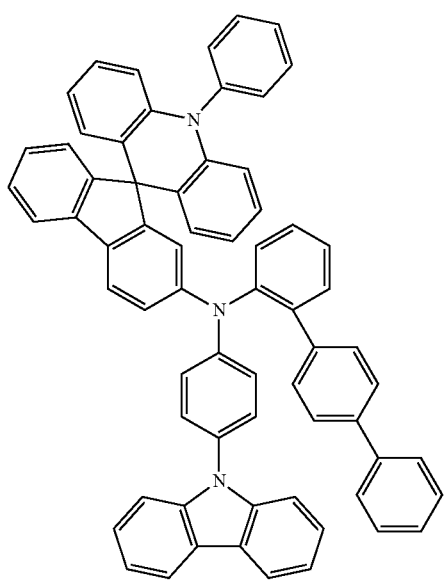
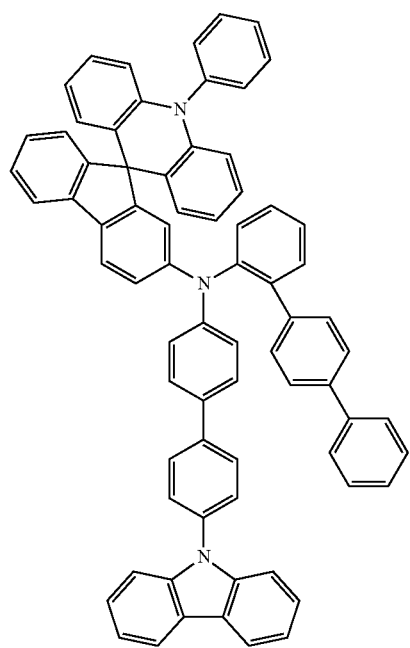
162
-continued
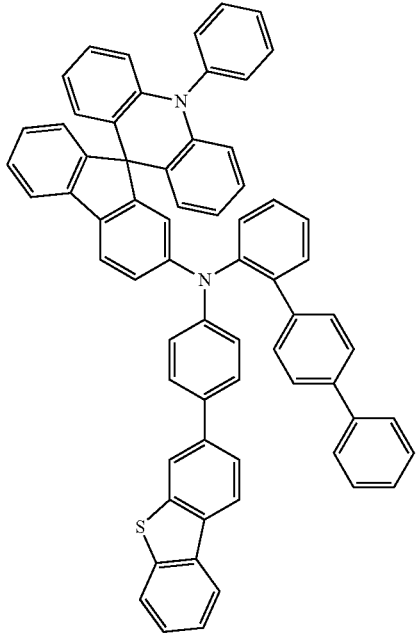
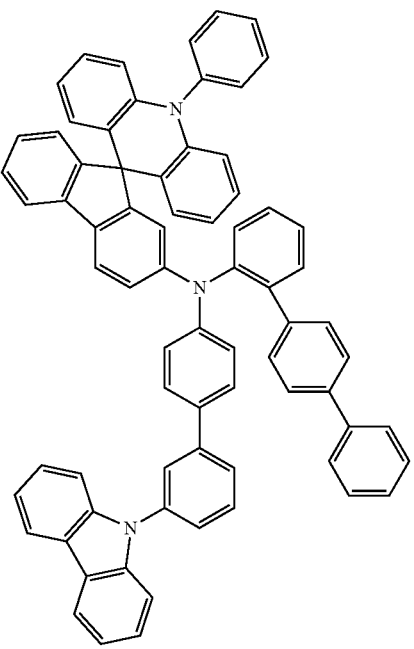

163
-continued
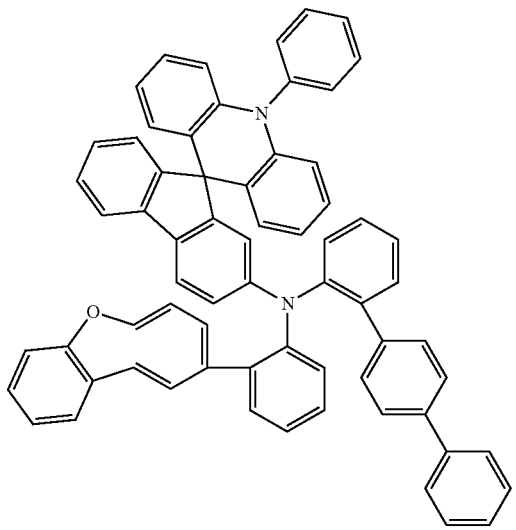
164
-continued
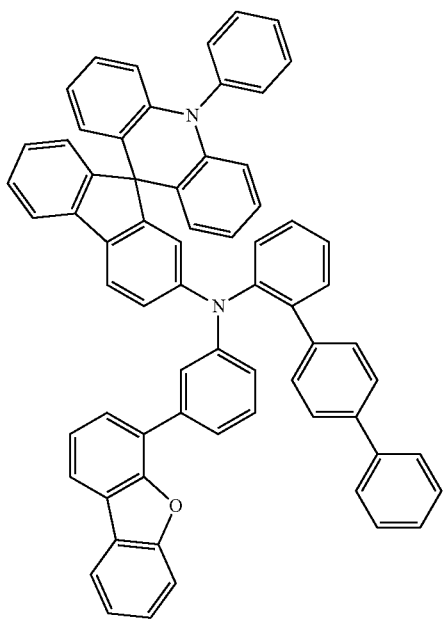
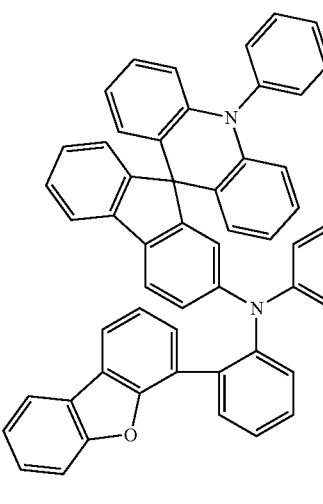
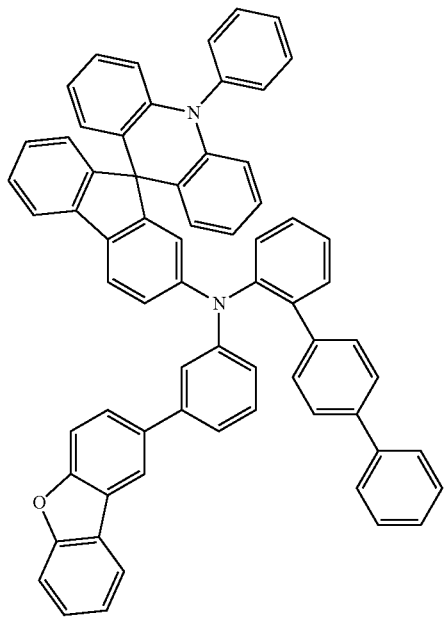
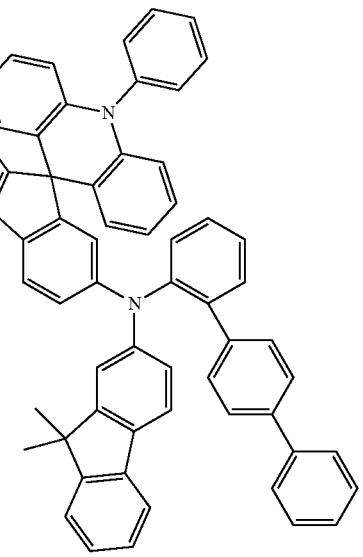

165
-continued
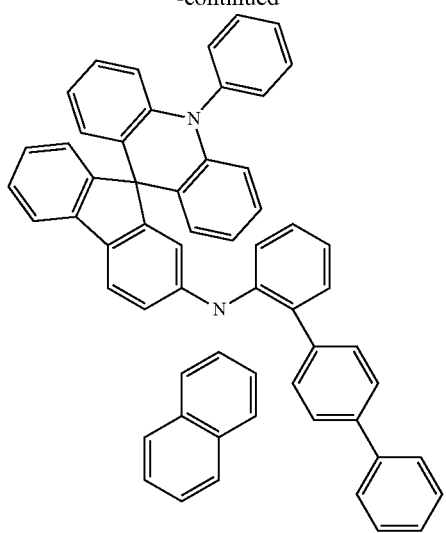
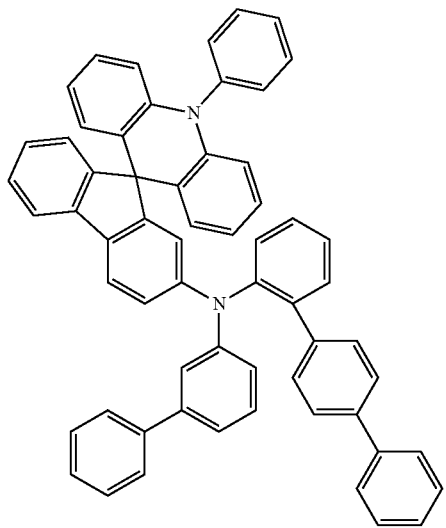
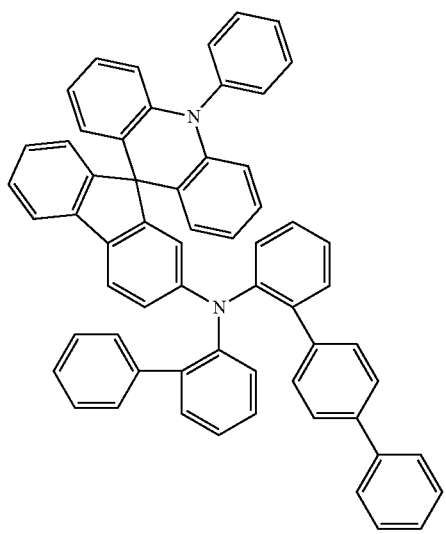
166
-continued
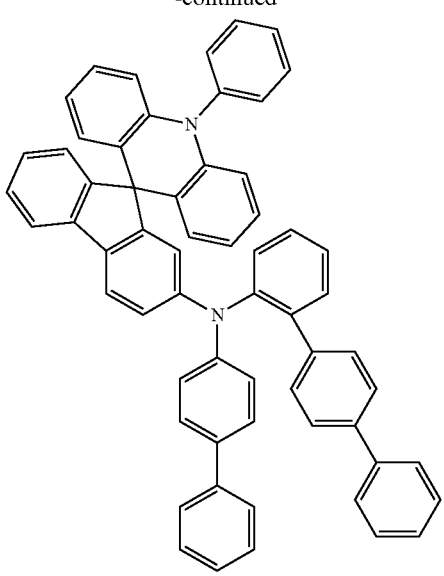
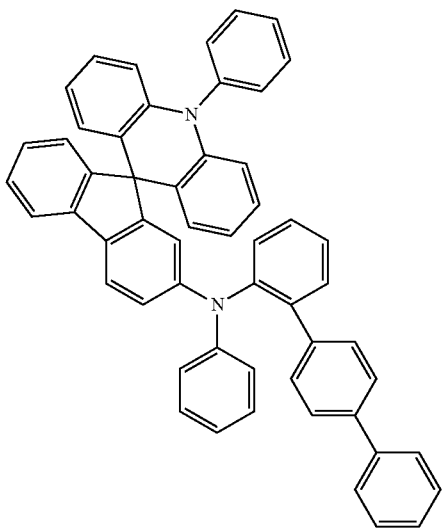
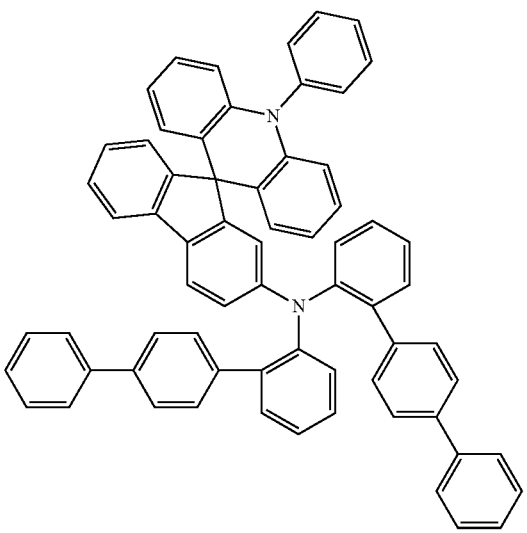

167
-continued
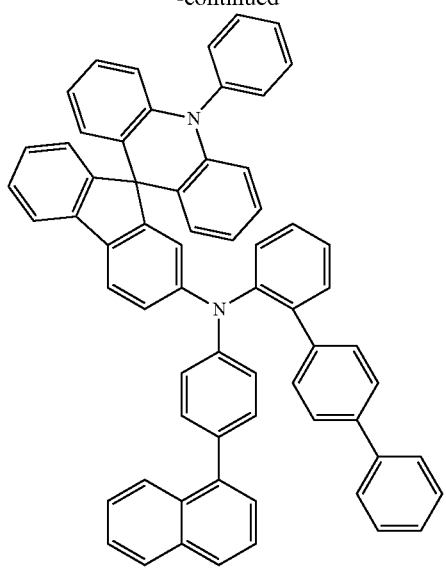
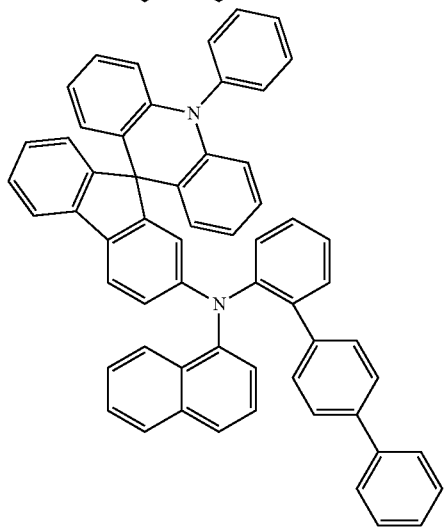
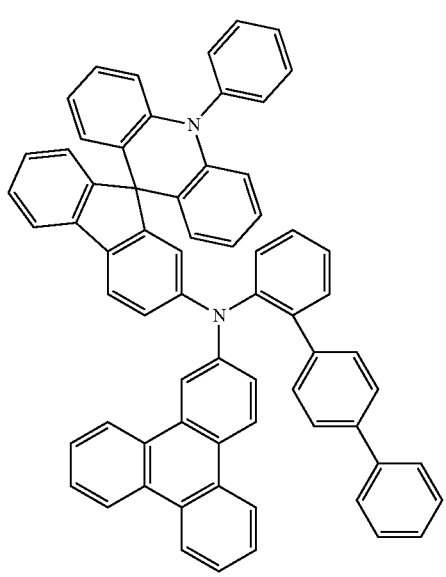
168
-continued
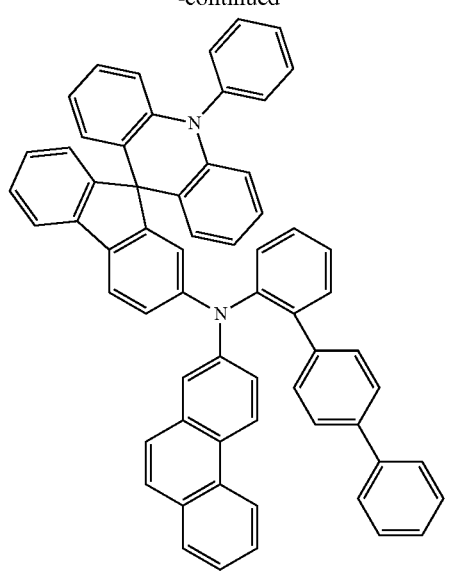
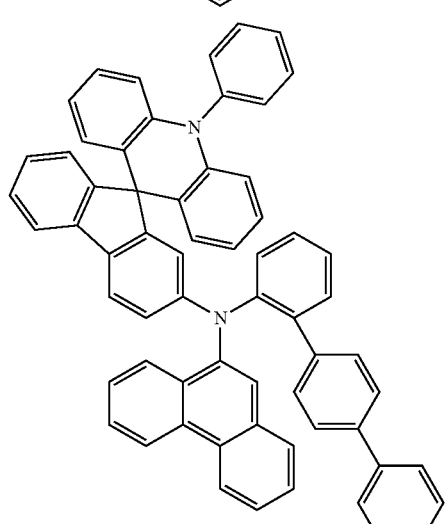
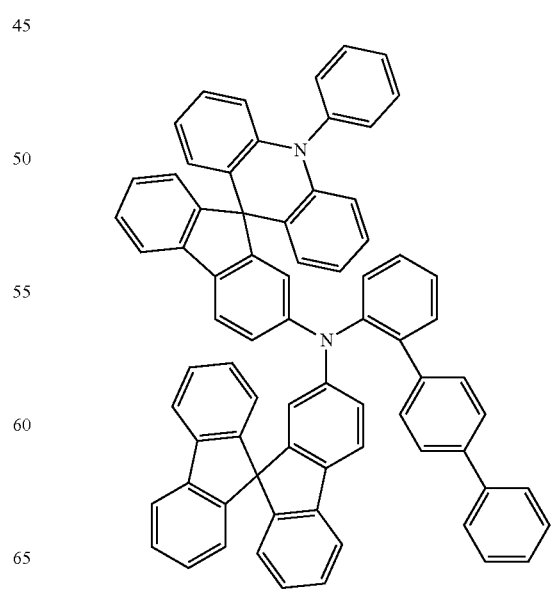

169
-continued
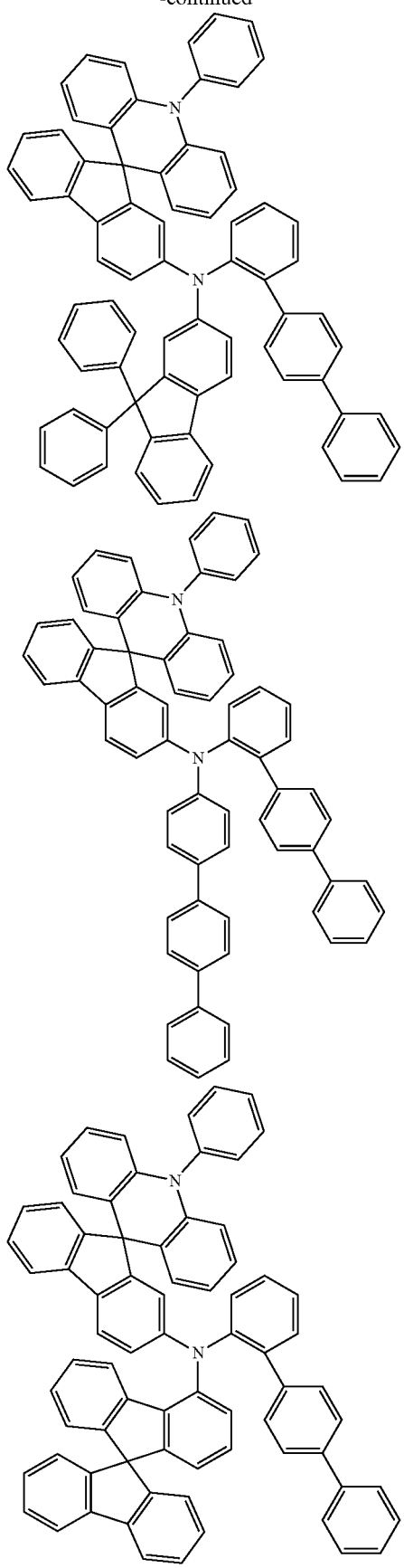
170
-continued
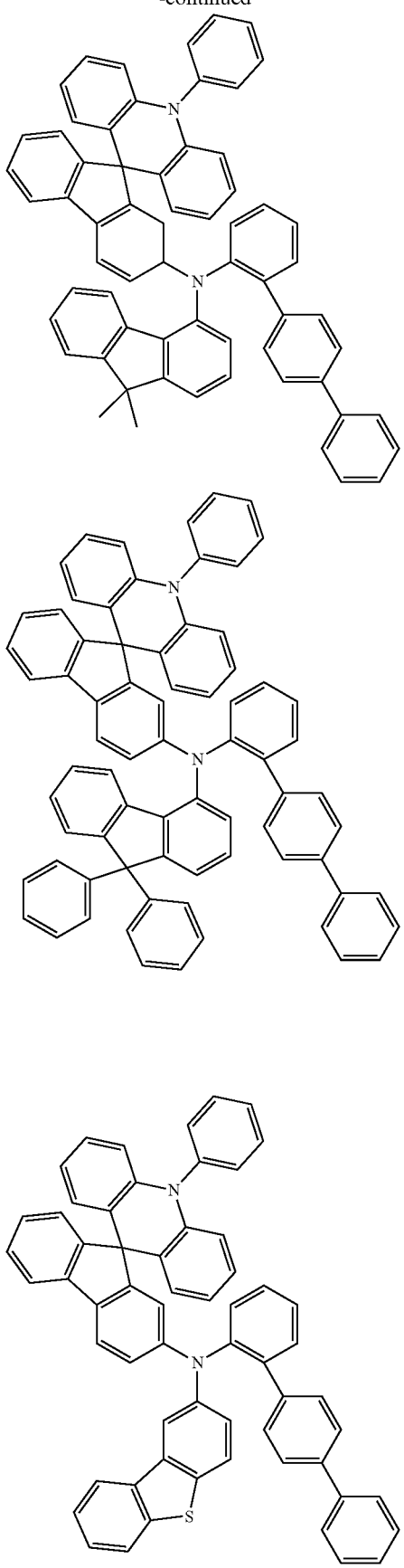

171
-continued
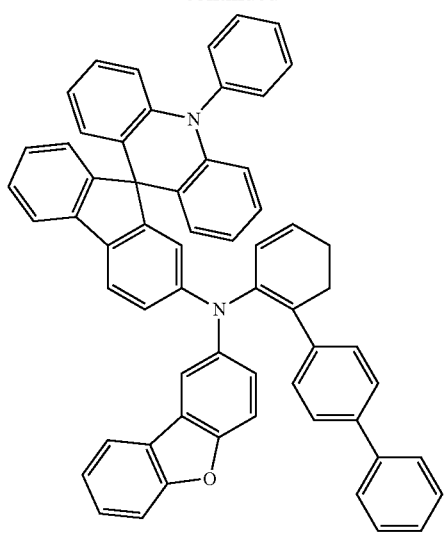
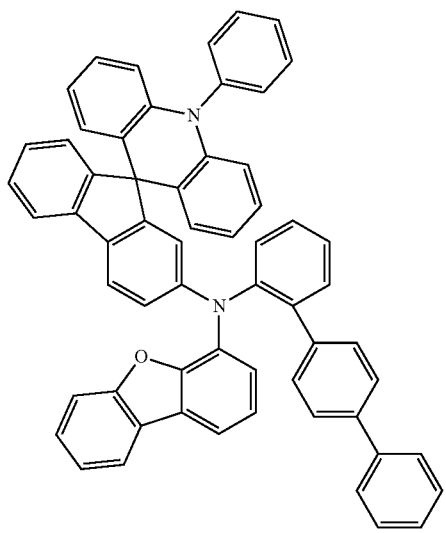
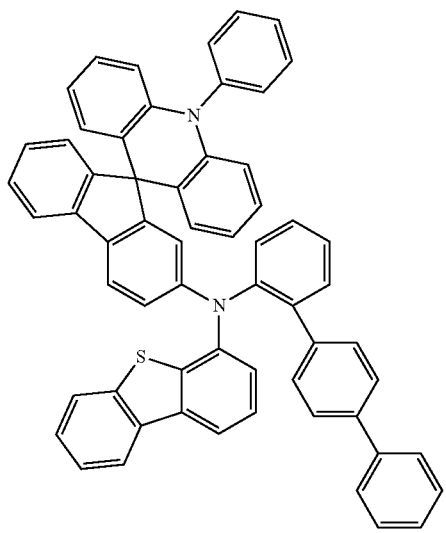
172
-continued
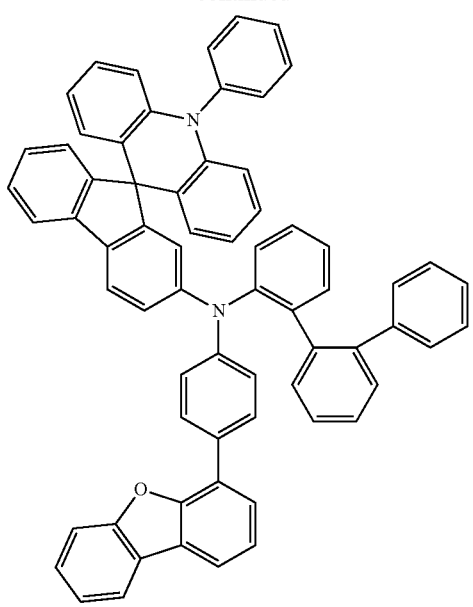
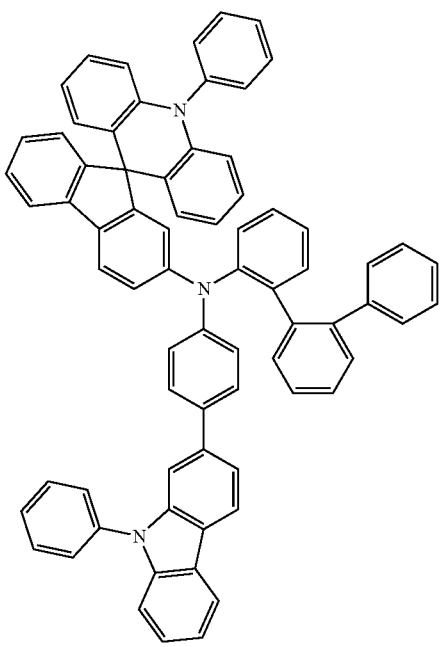

173
-continued
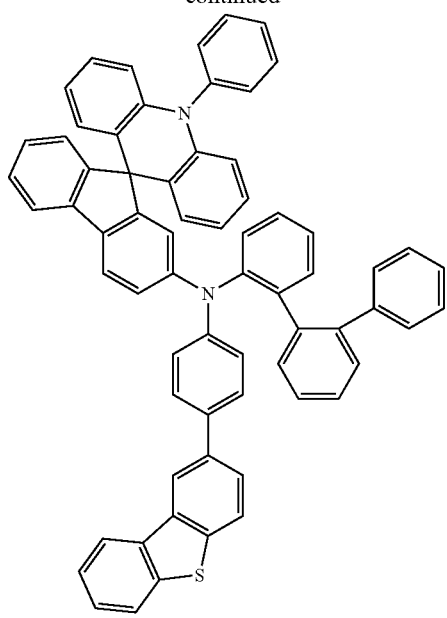
174
-continued
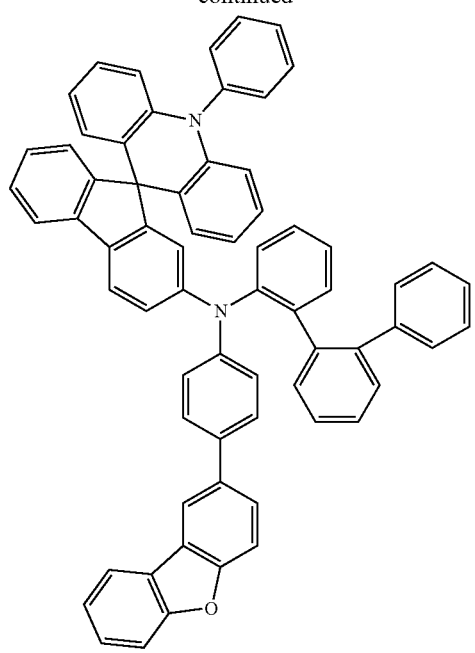
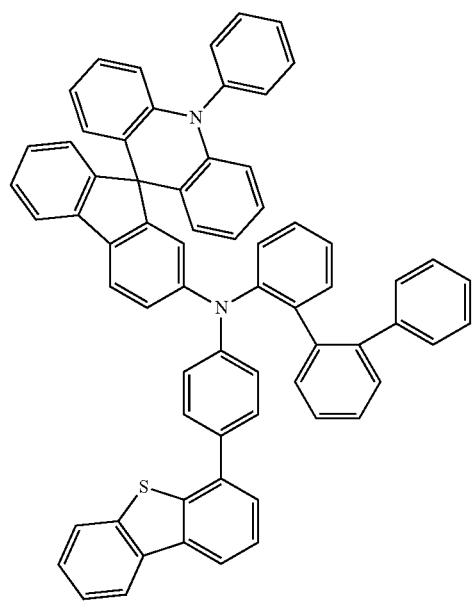
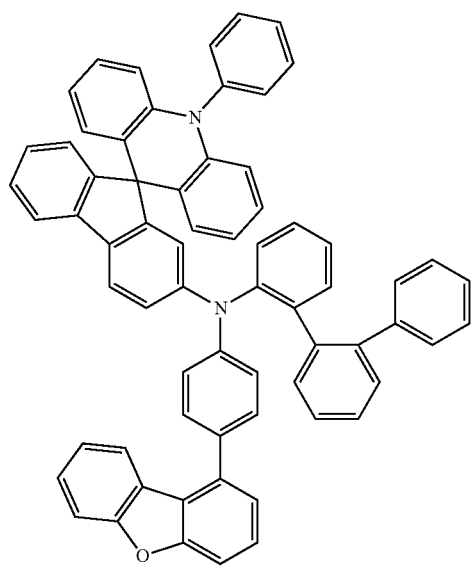

175
-continued
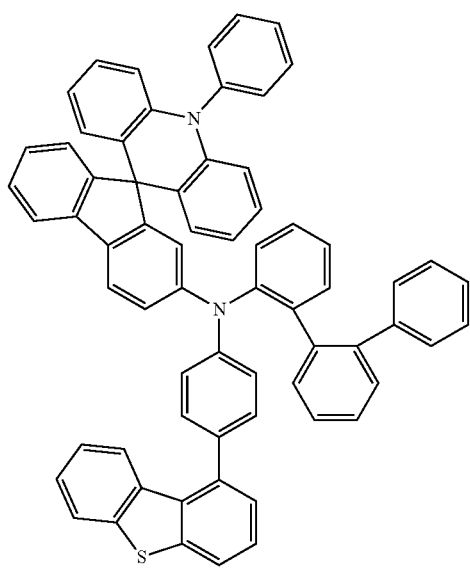
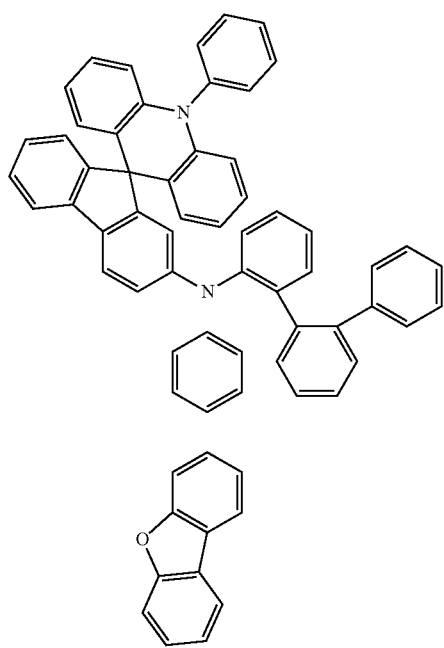
176
-continued
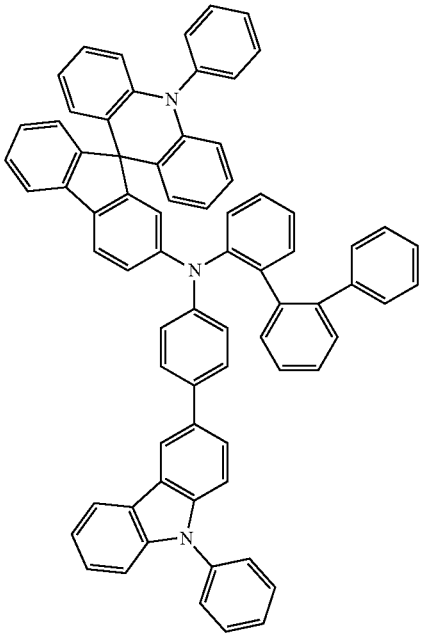
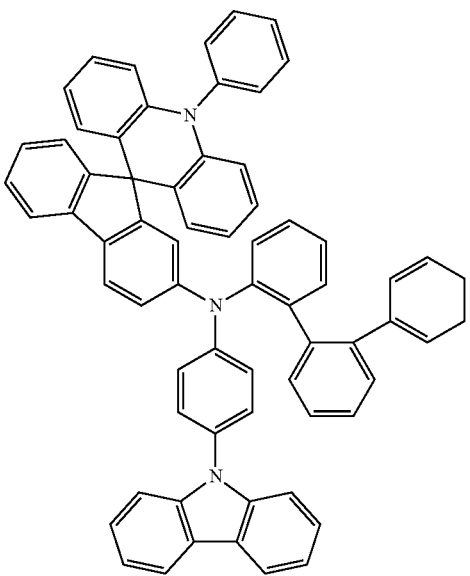

177
-continued
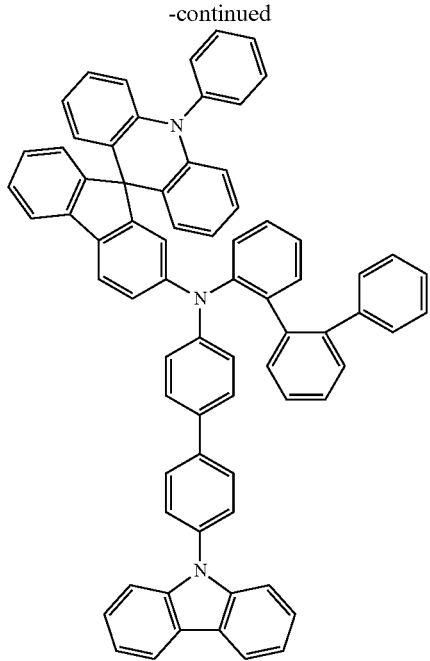
178
-continued
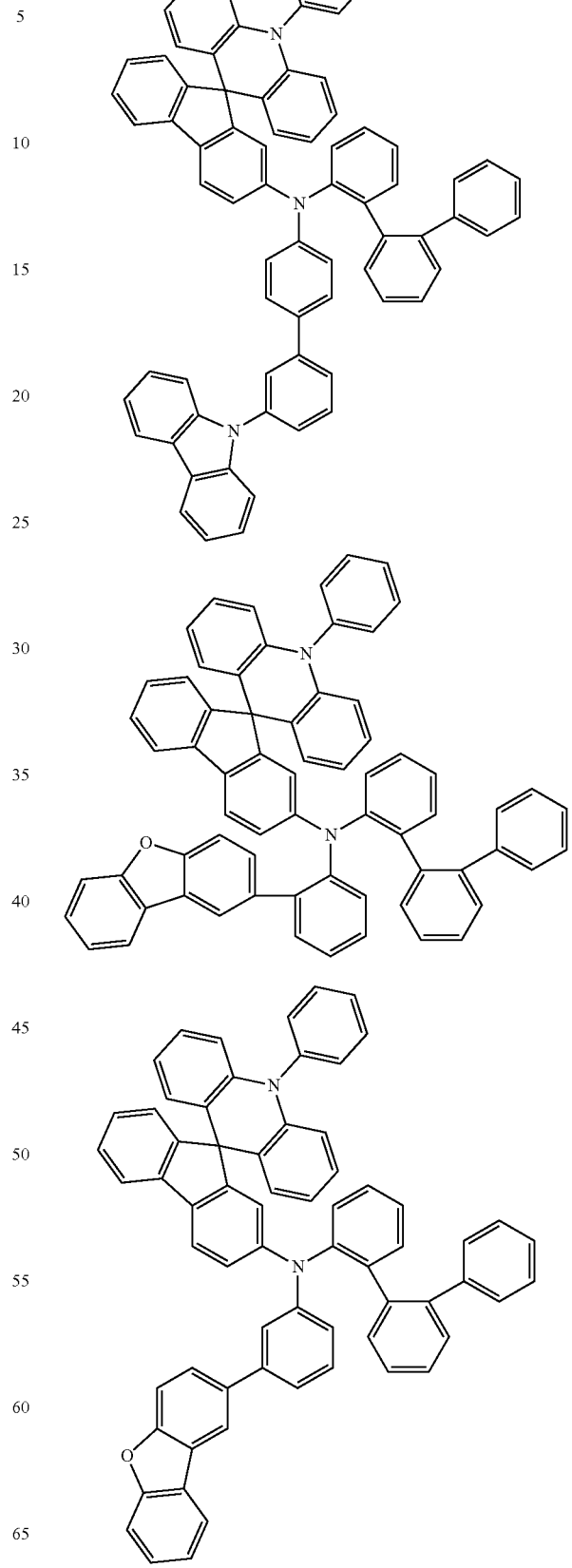
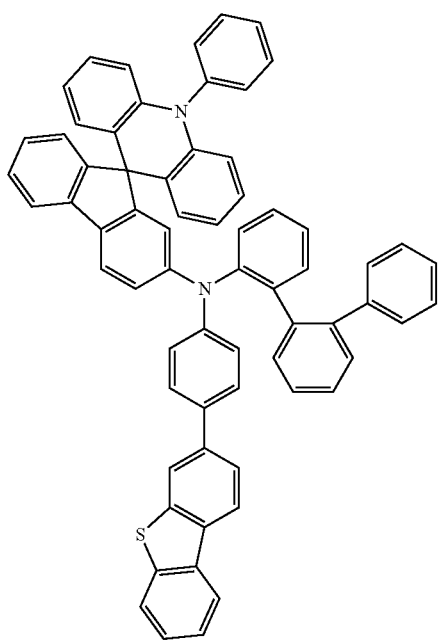

179
-continued
180
-continued
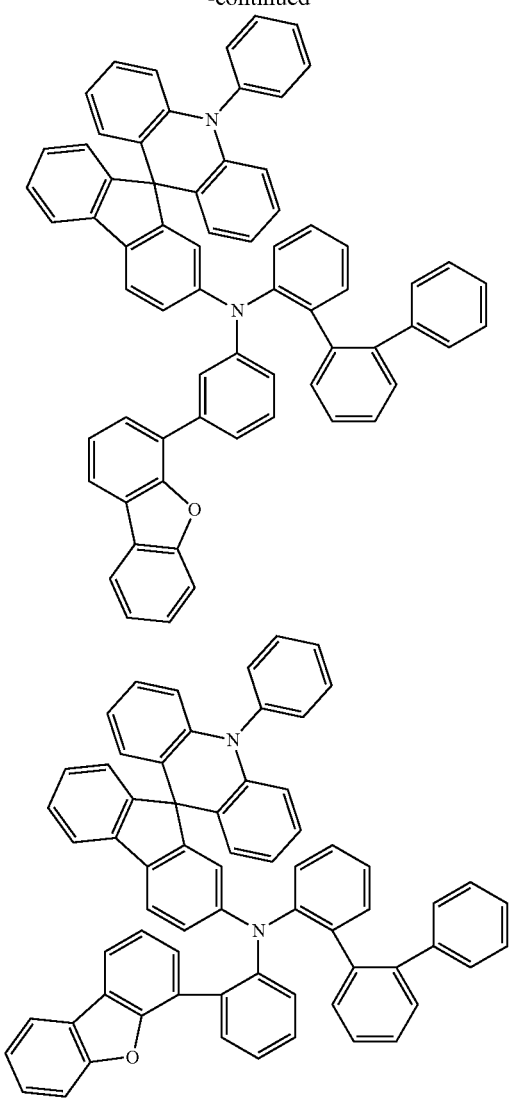
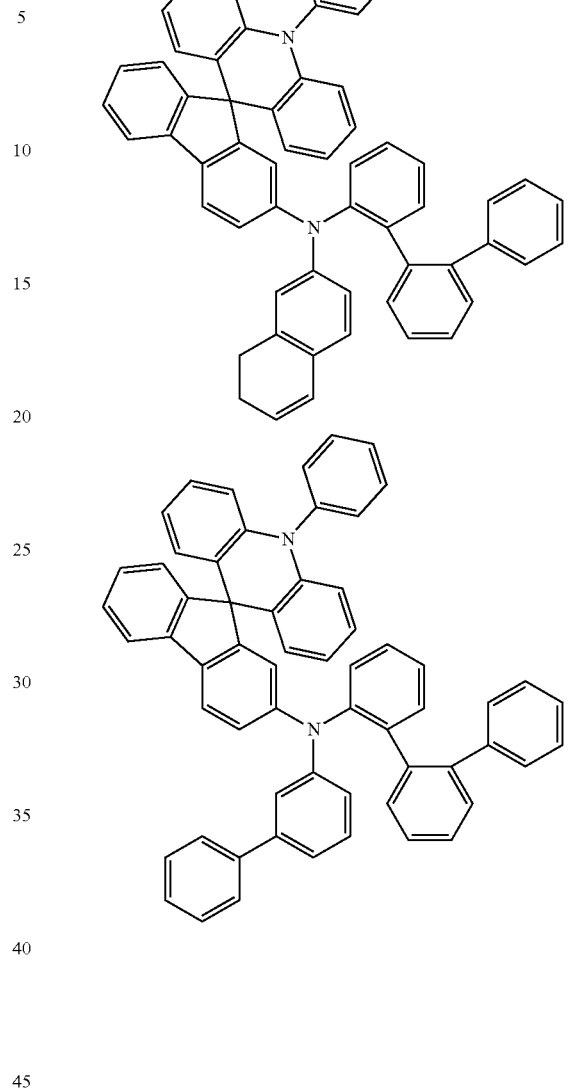
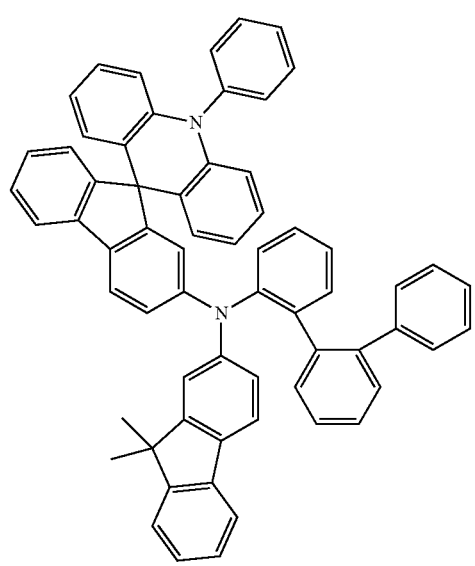
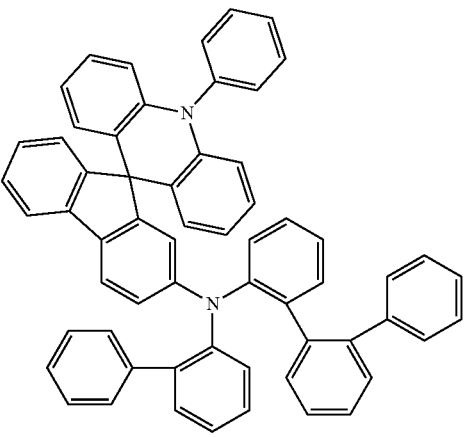

181
-continued
182
-continued
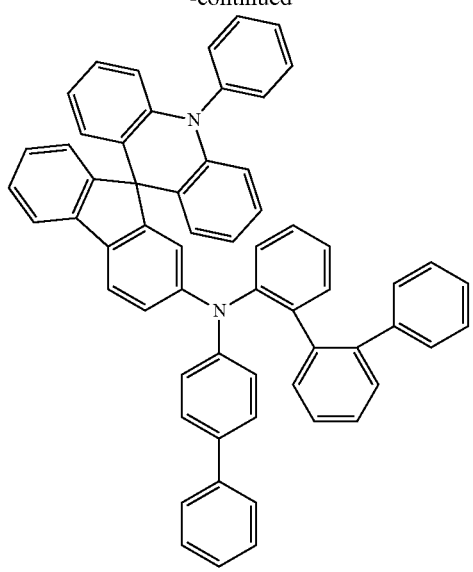
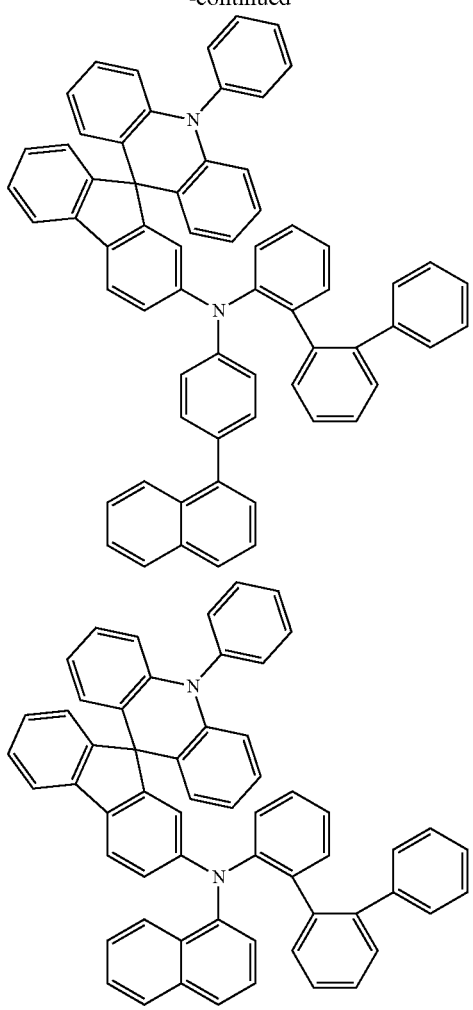
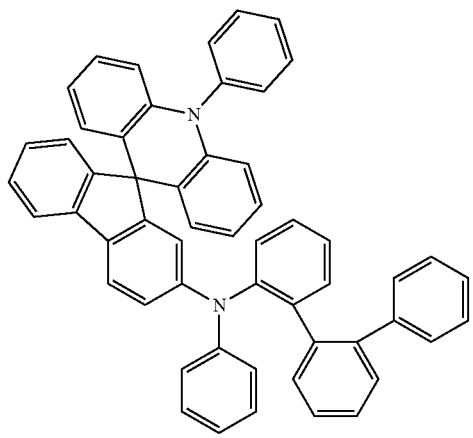
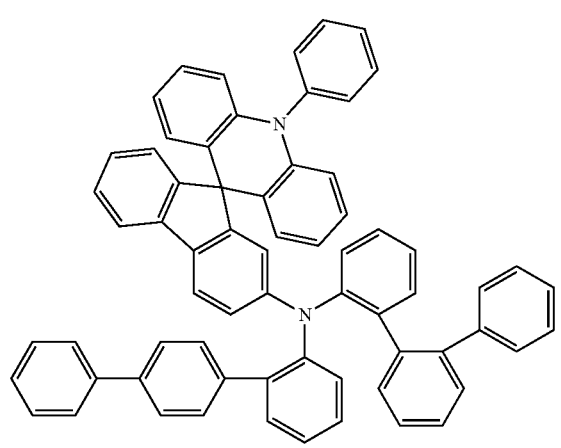
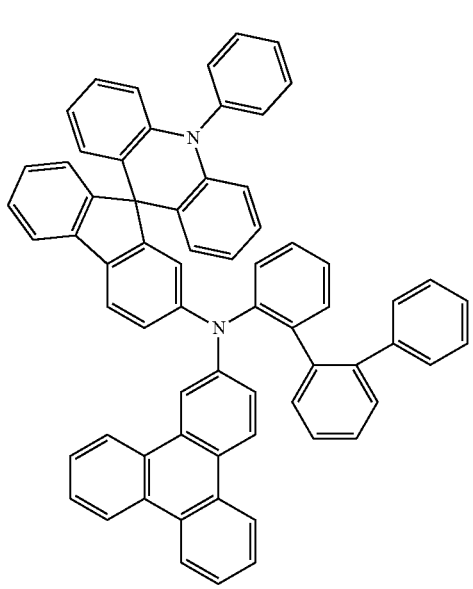

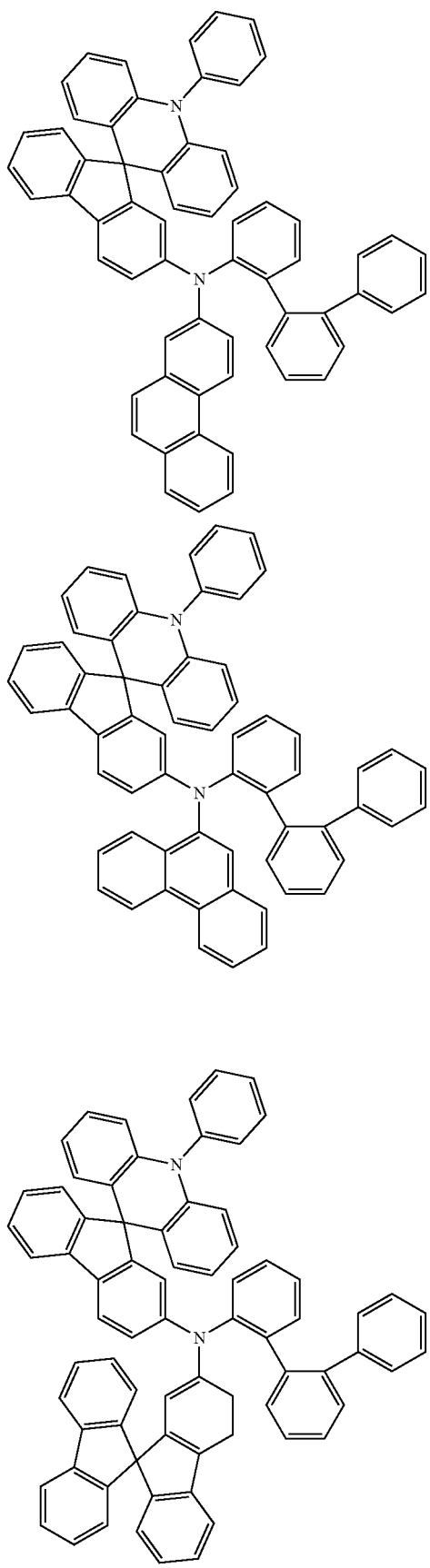
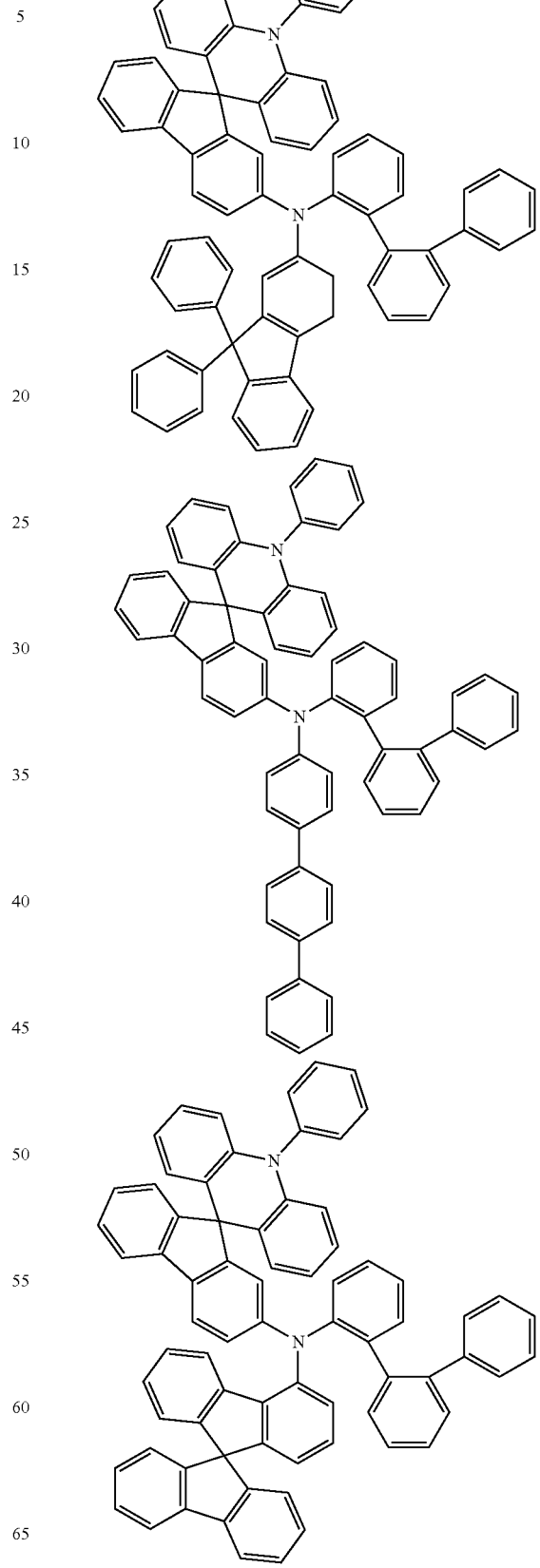

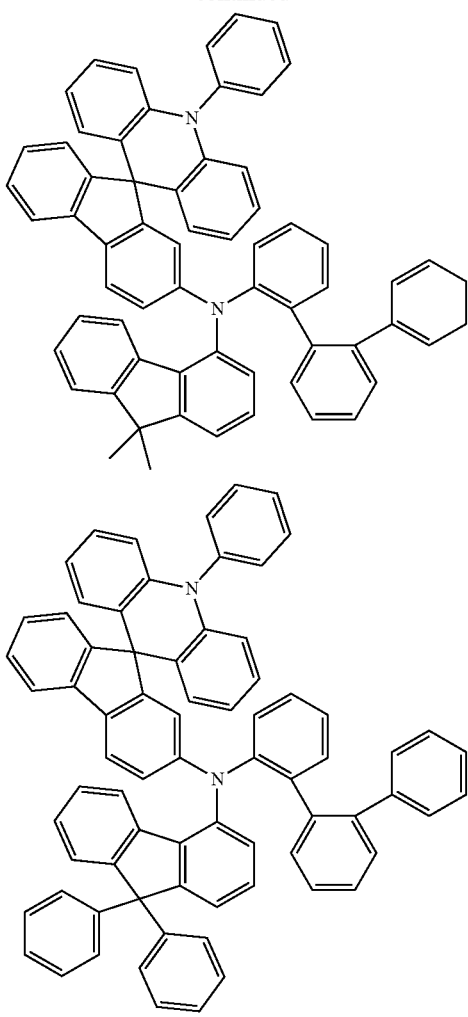
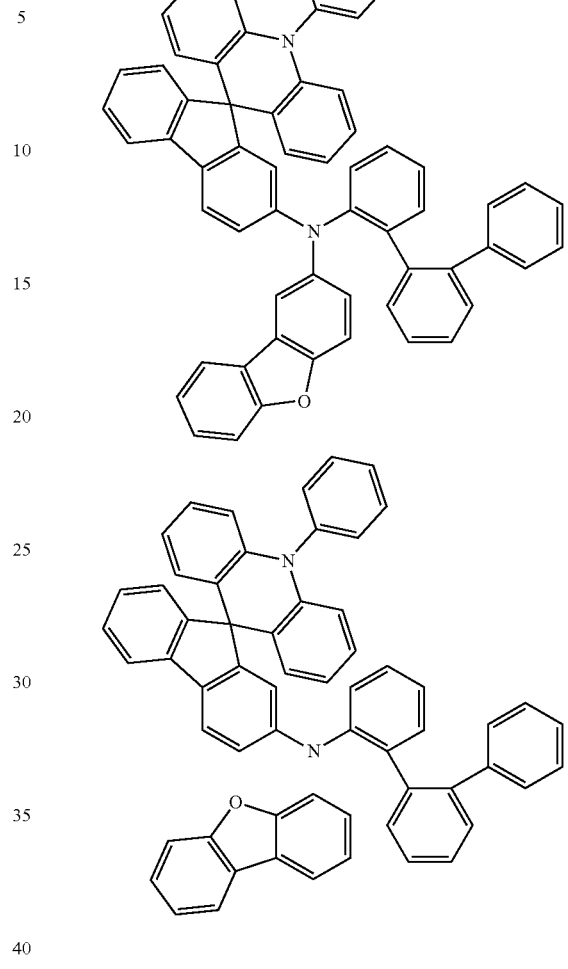
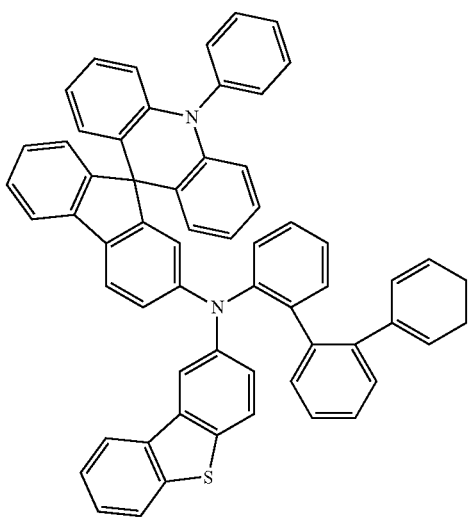
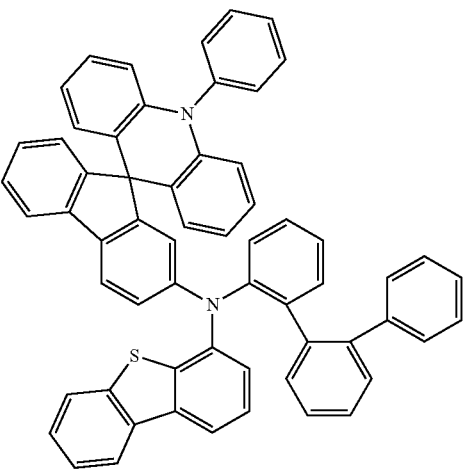

187
-continued
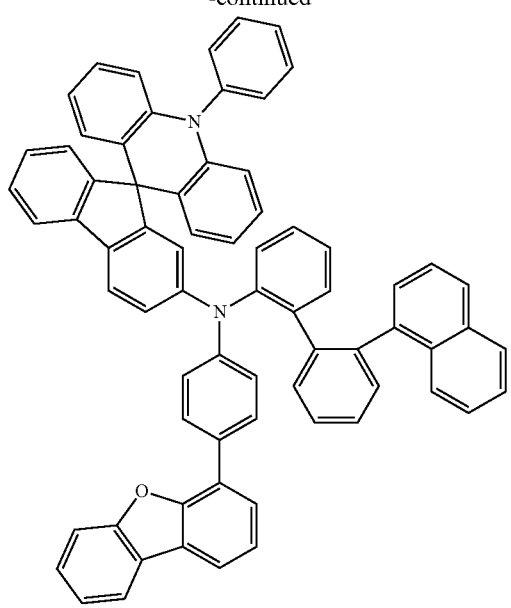
188
-continued
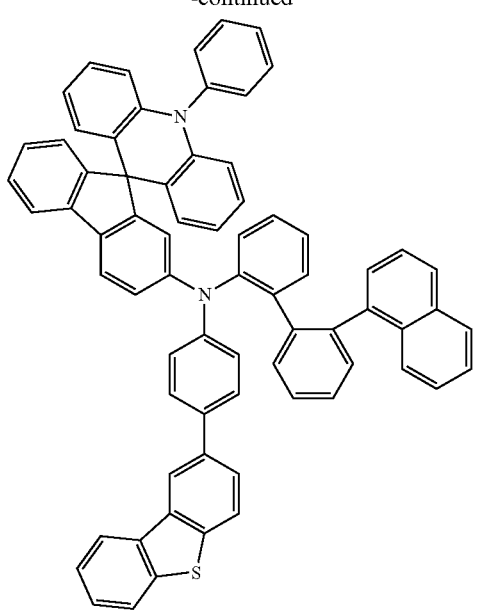
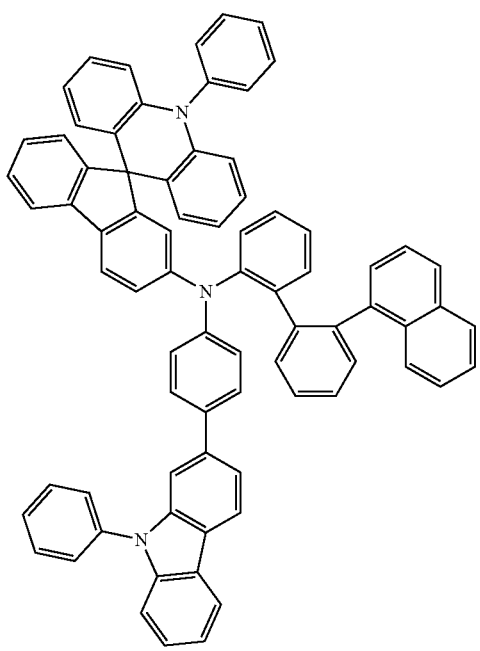
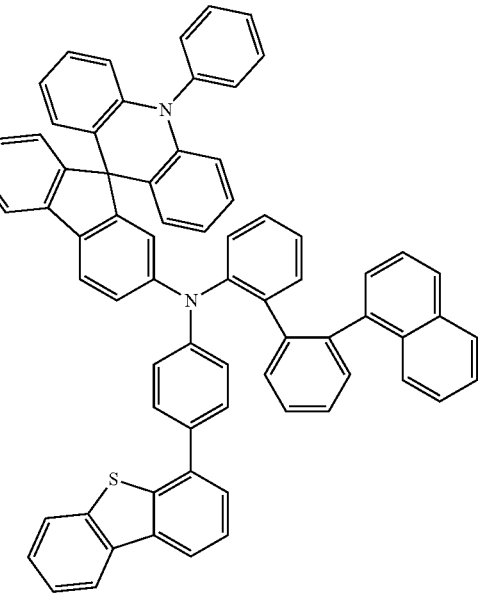

189
-continued
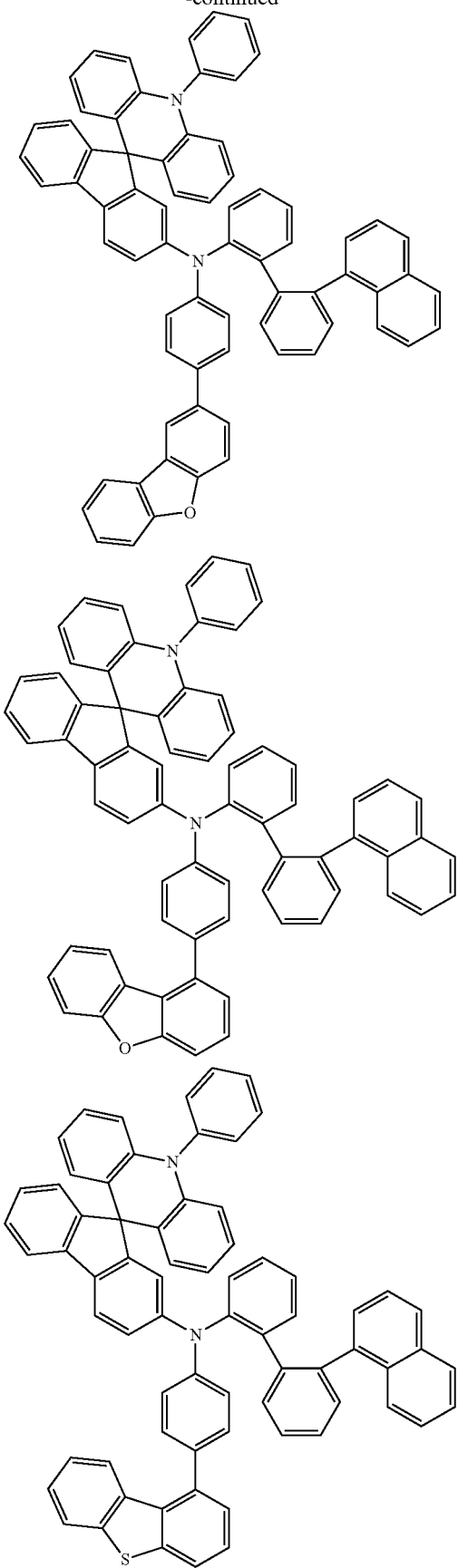
190
-continued
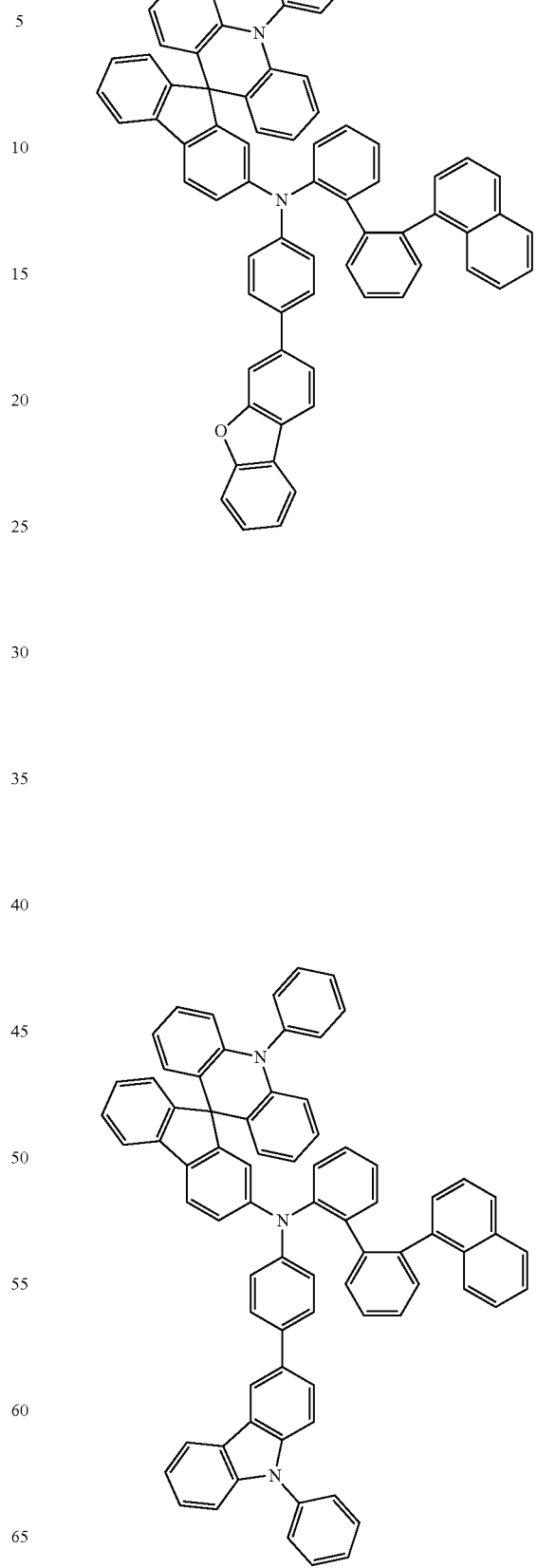

191
-continued
192
-continued
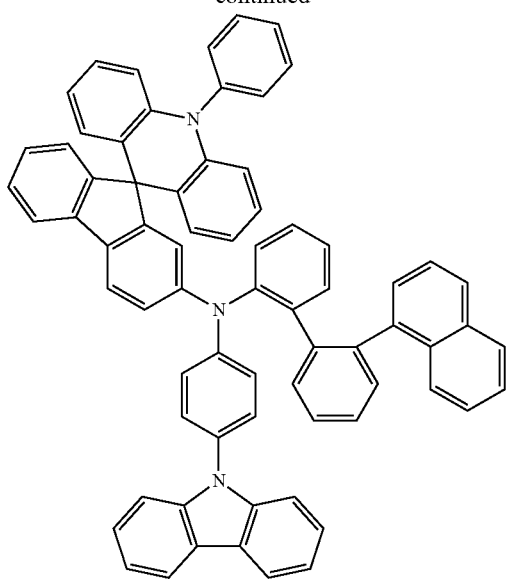
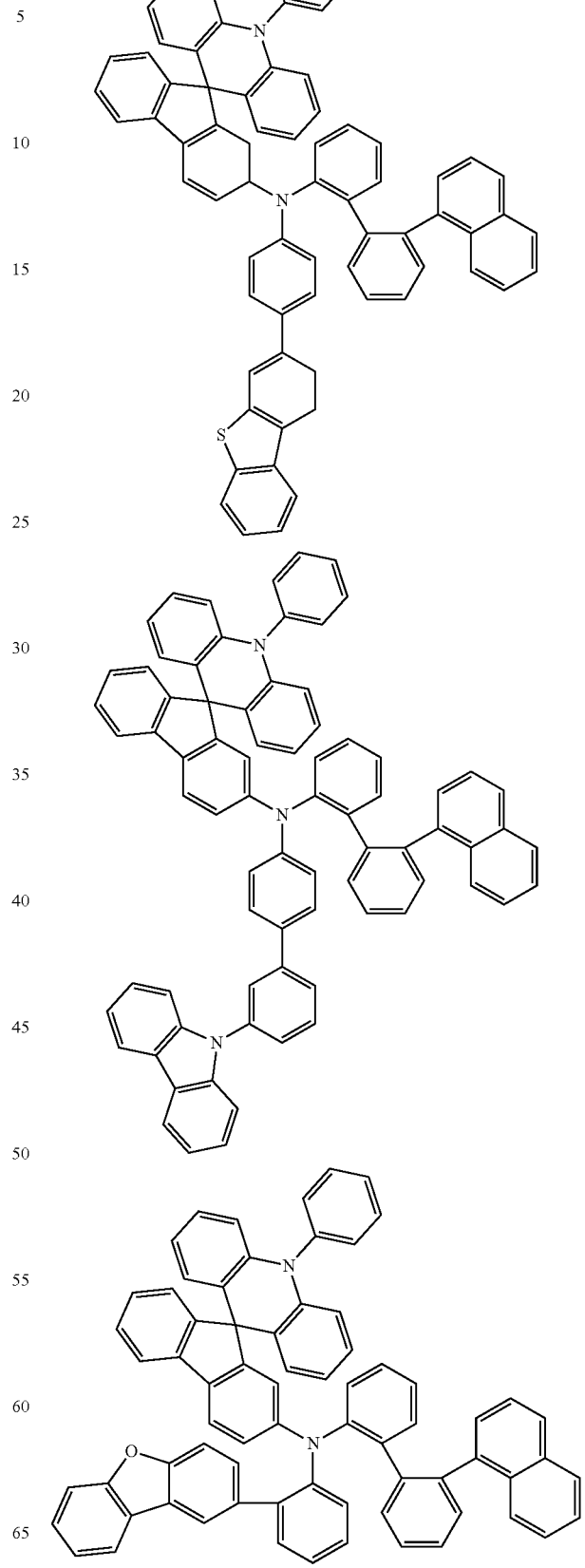

193
-continued
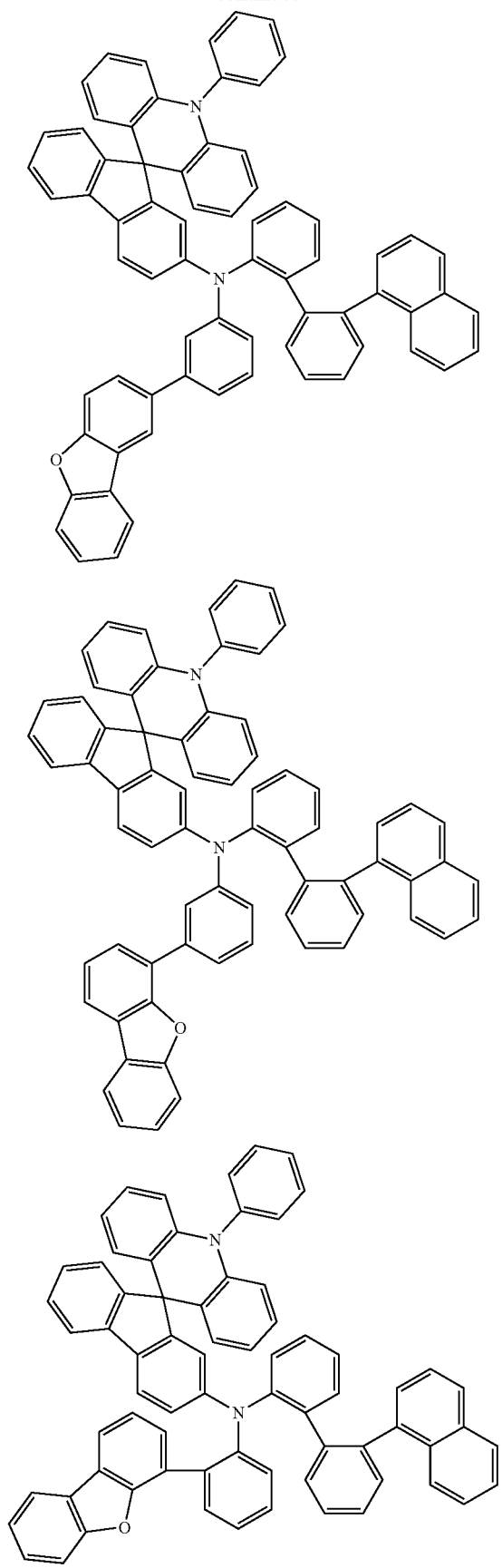
194
-continued
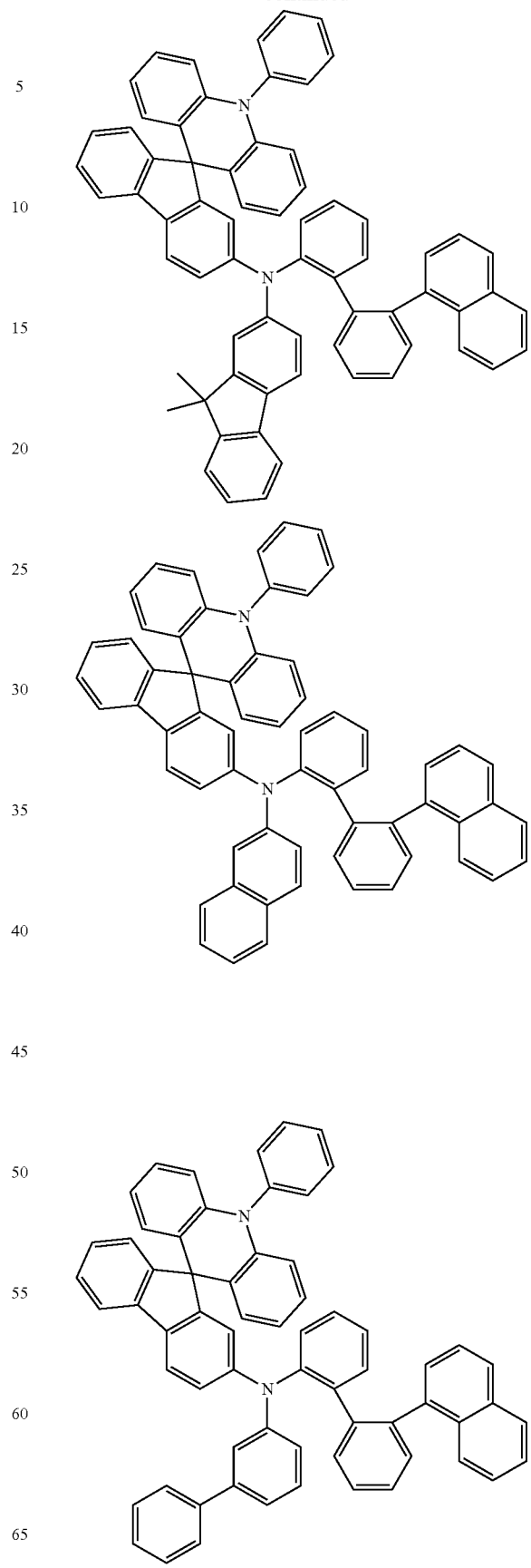

195
-continued
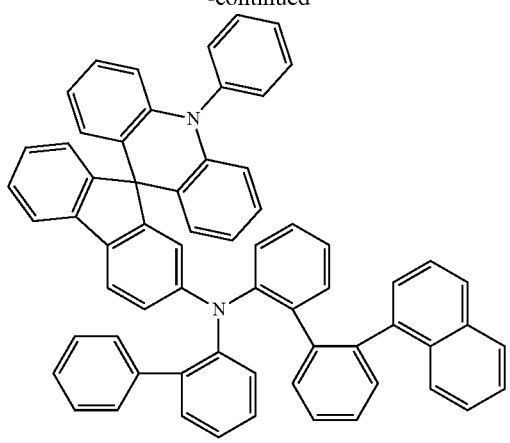
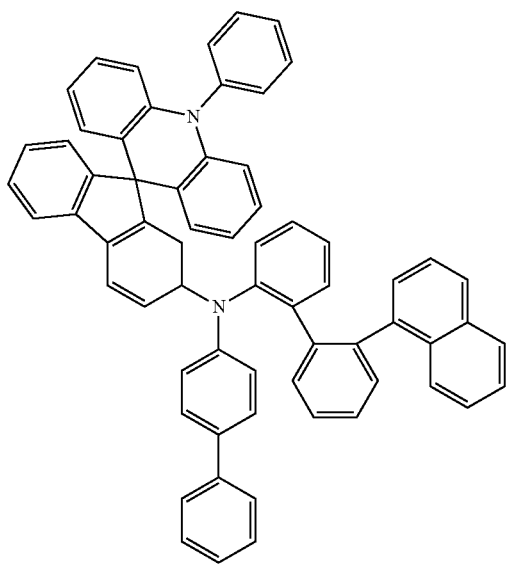
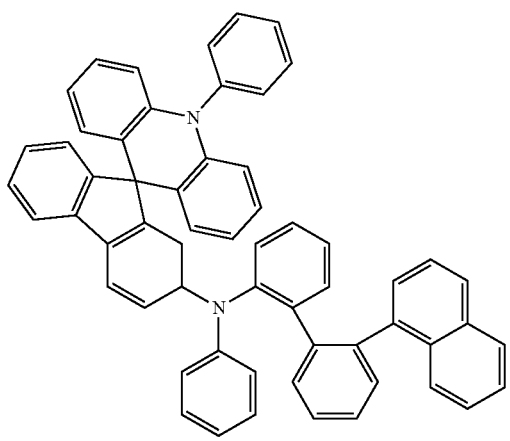
196
-continued
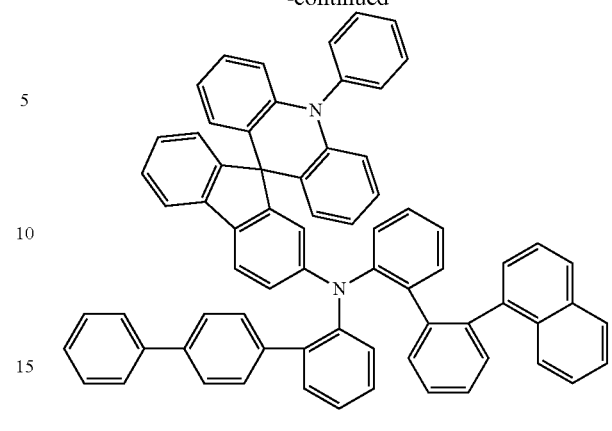
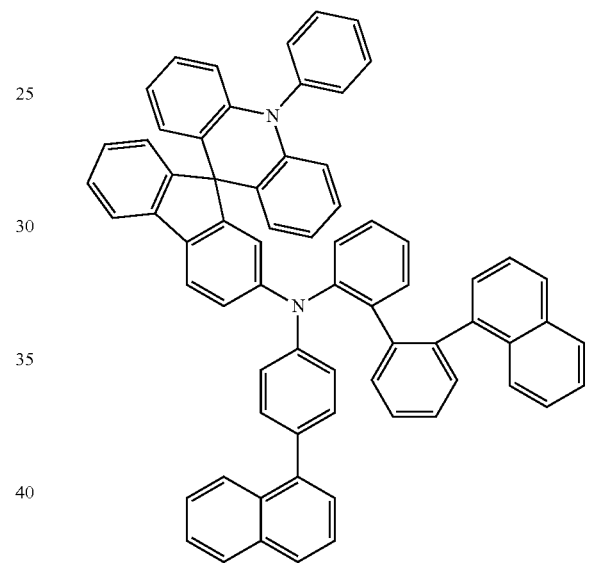
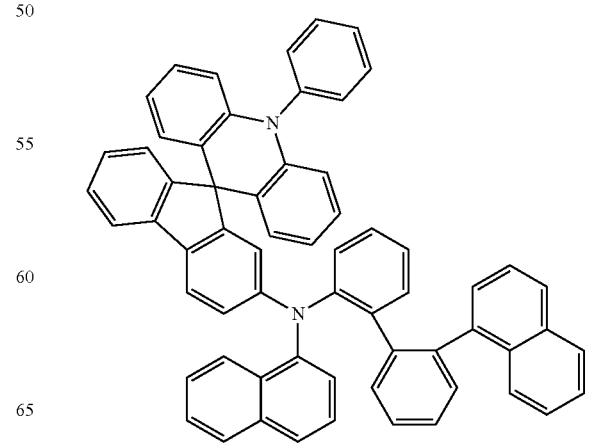

197
-continued
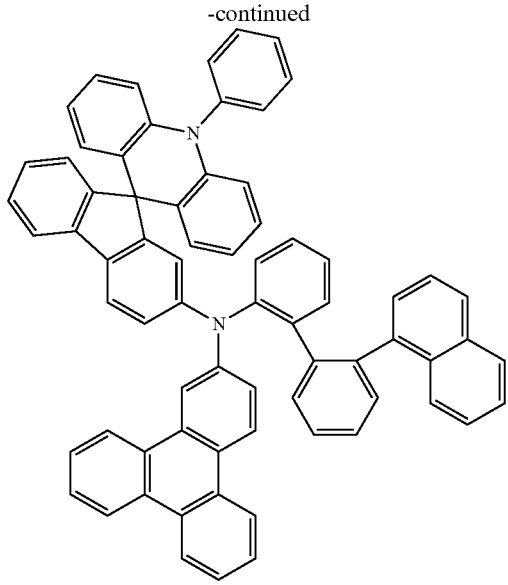
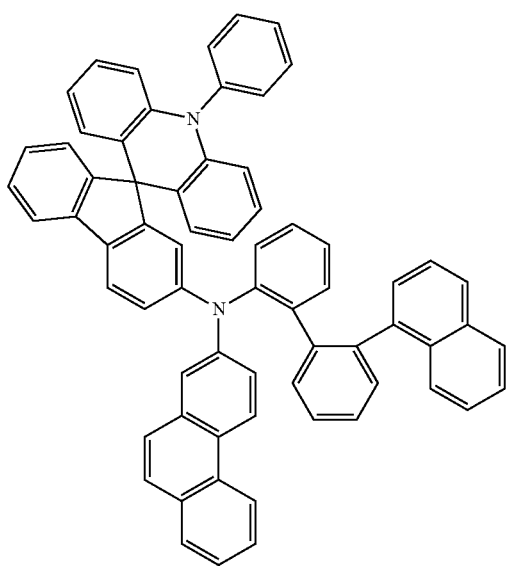
198
-continued
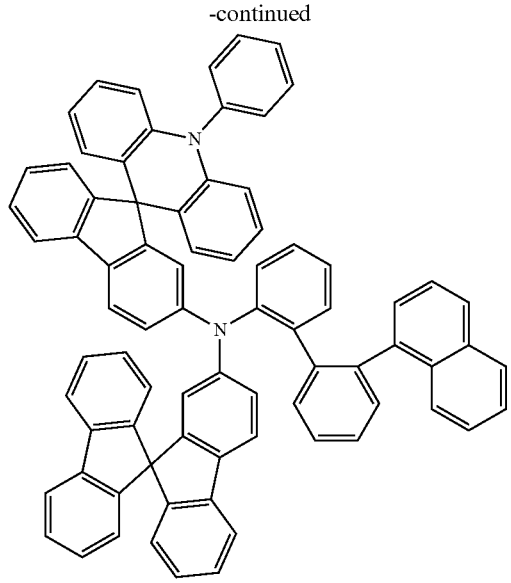
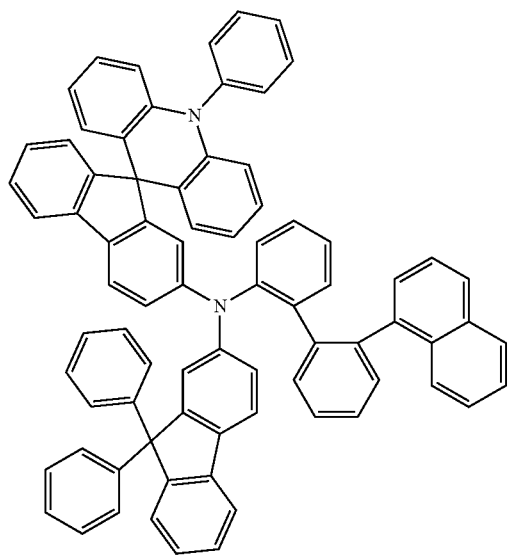

199
-continued
200
-continued
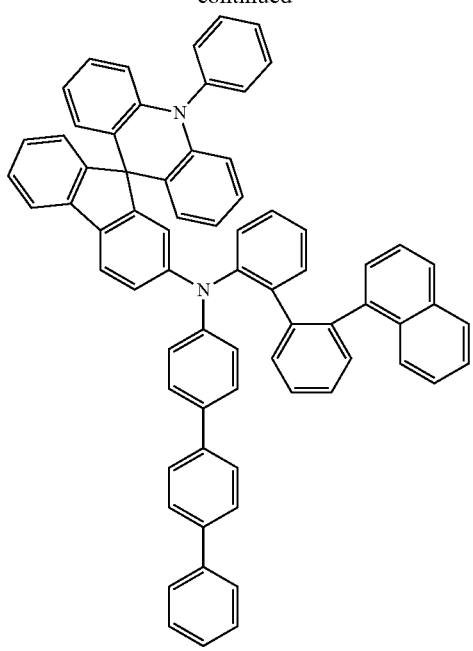
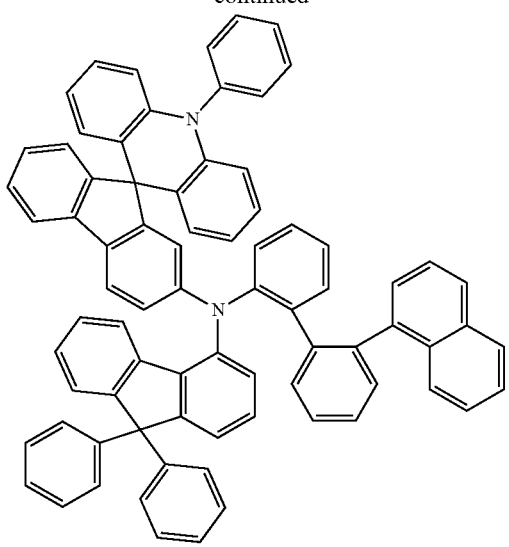
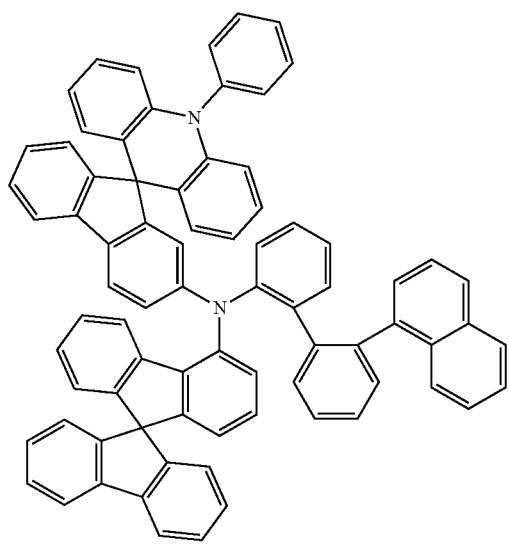
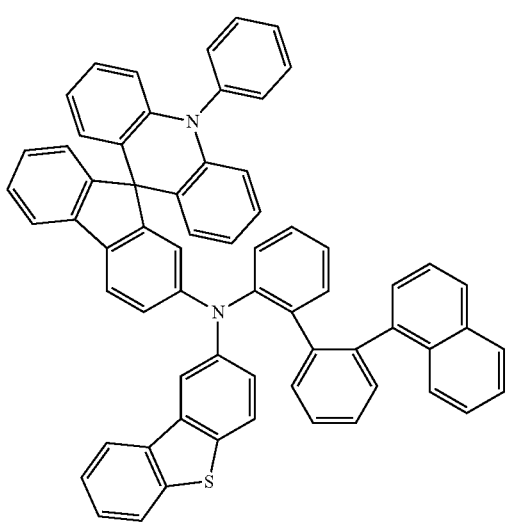
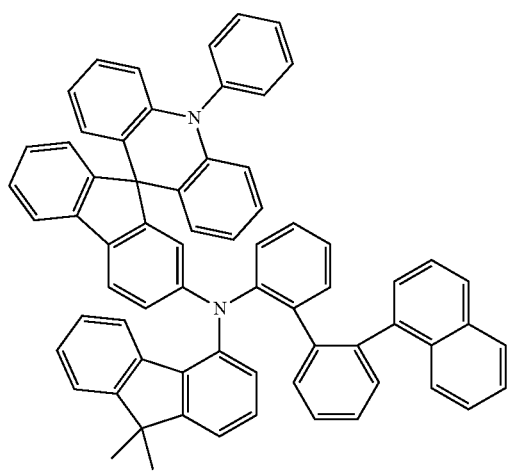

201
-continued
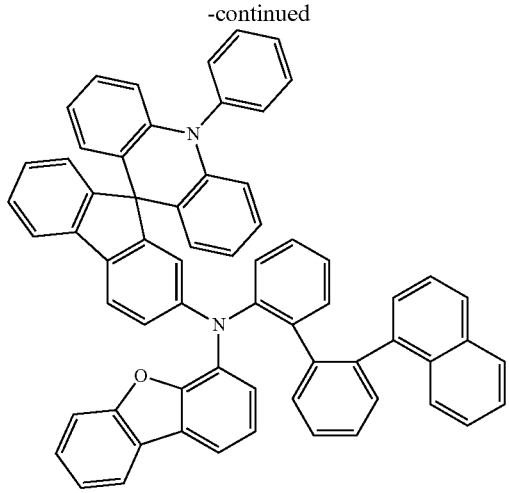
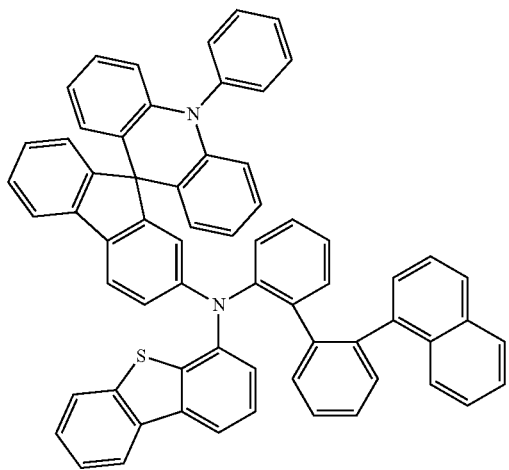
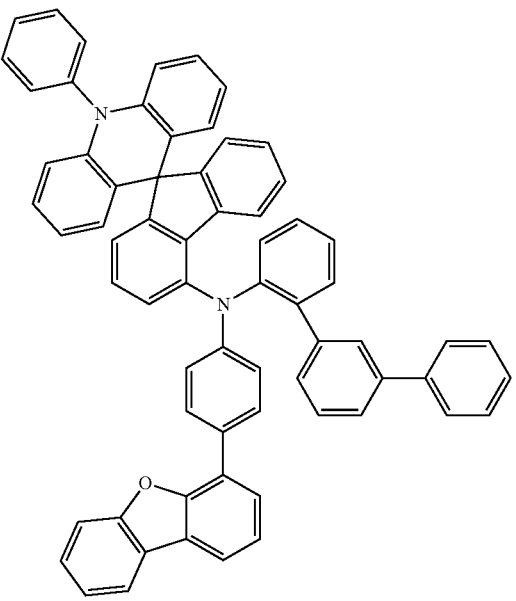
202
-continued
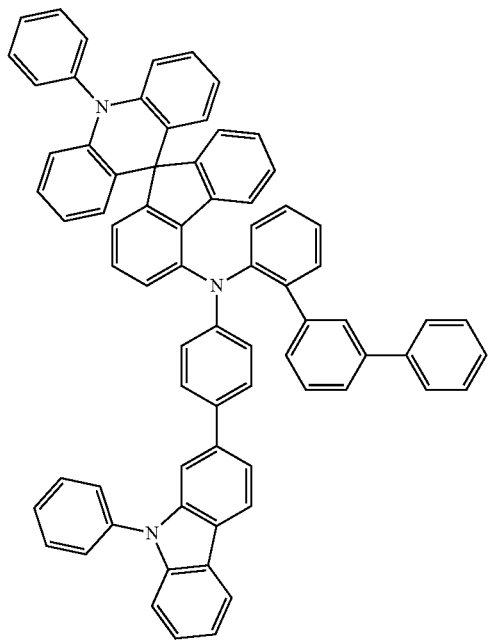
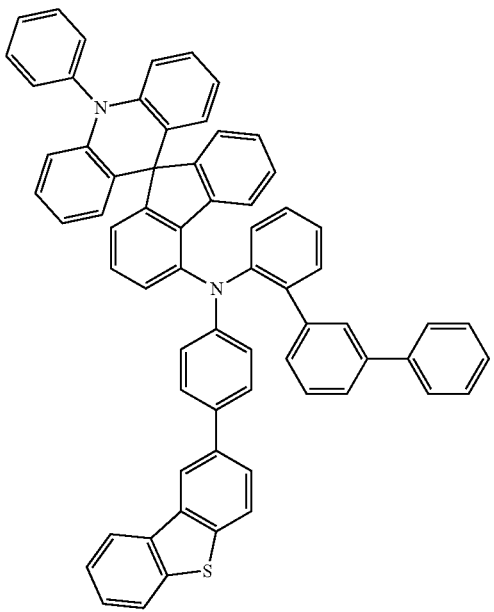

203
-continued
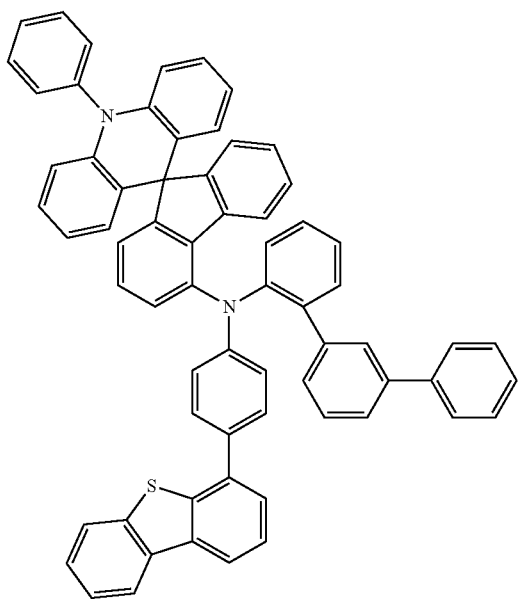
204
-continued
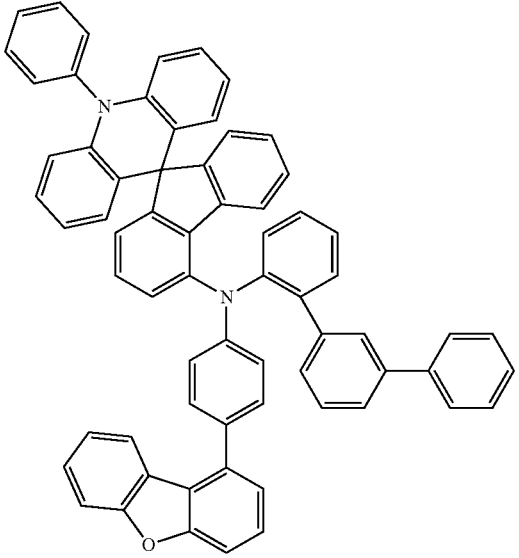
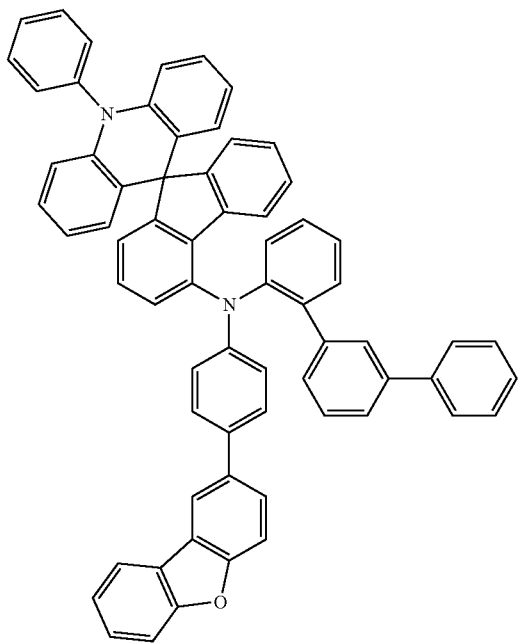
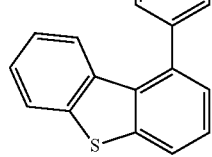

205
-continued
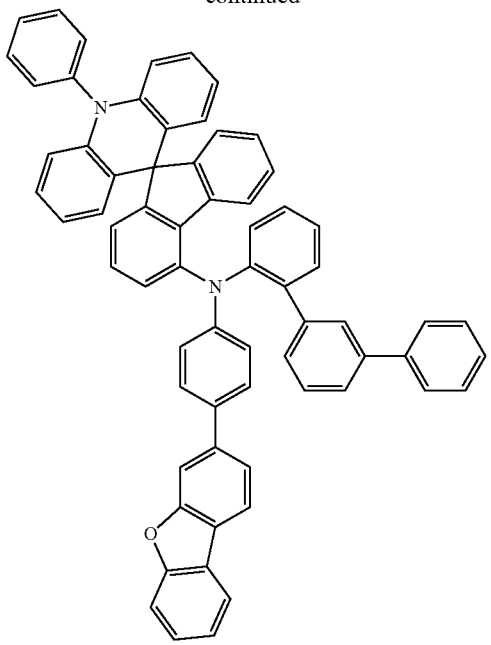
206
-continued
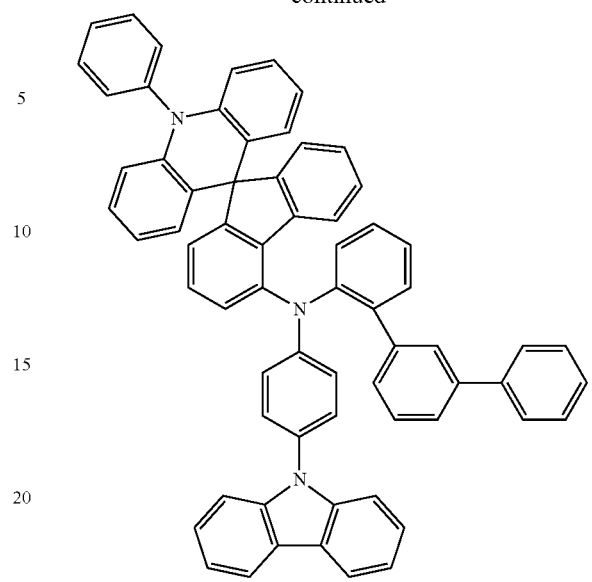
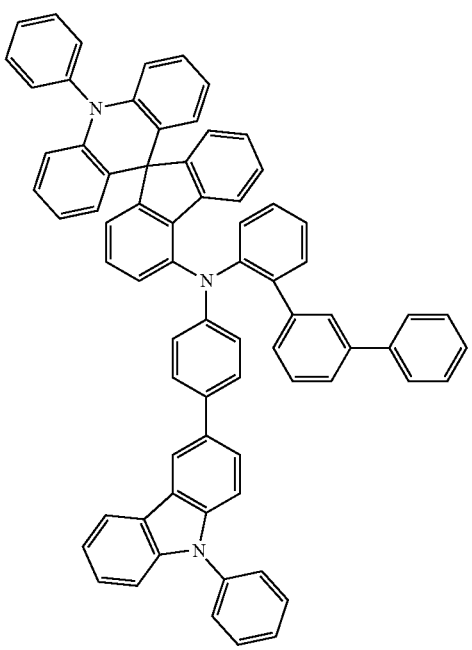
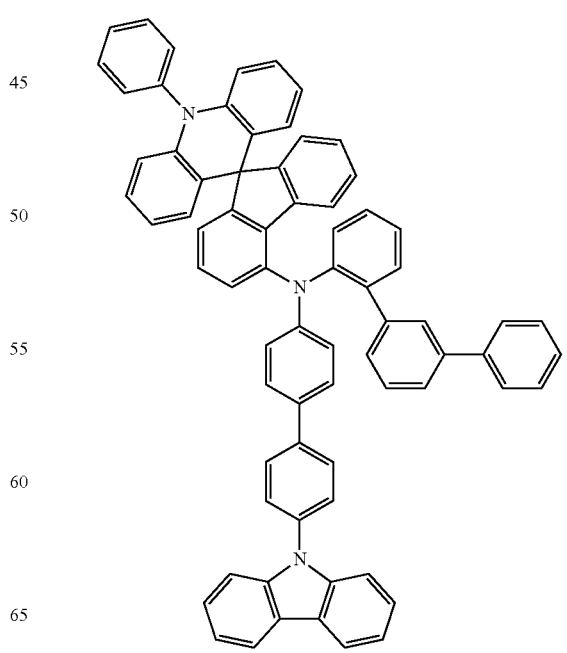

207
-continued
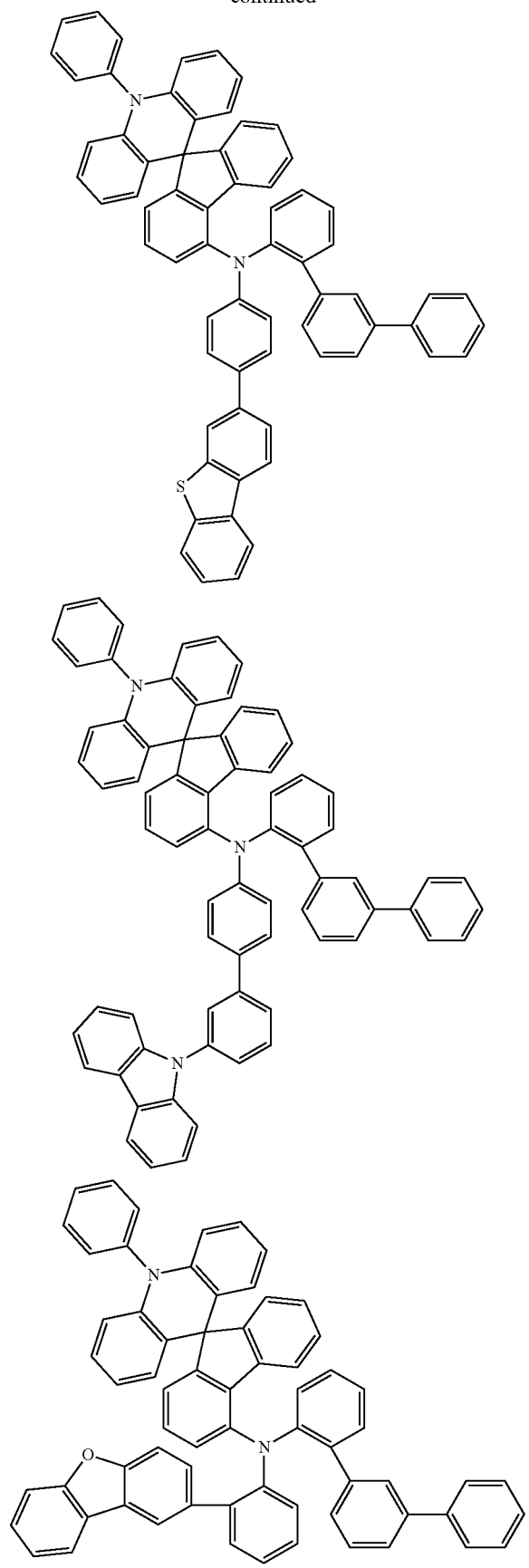
208
-continued
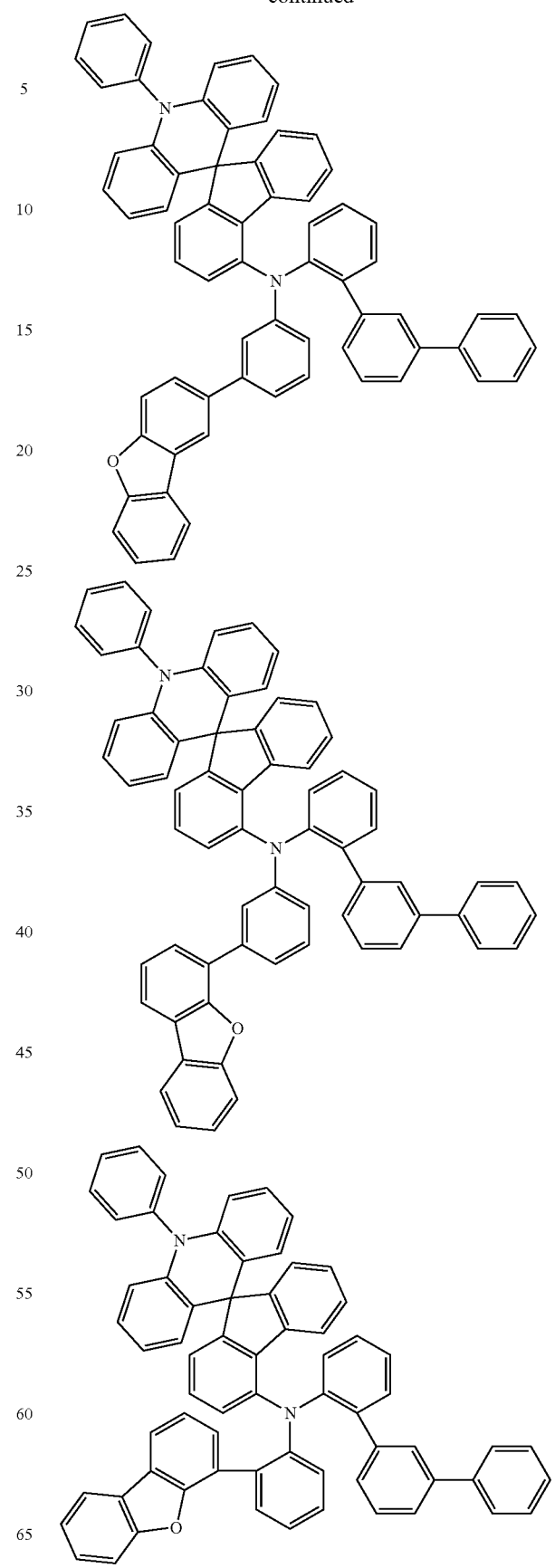

209
-continued
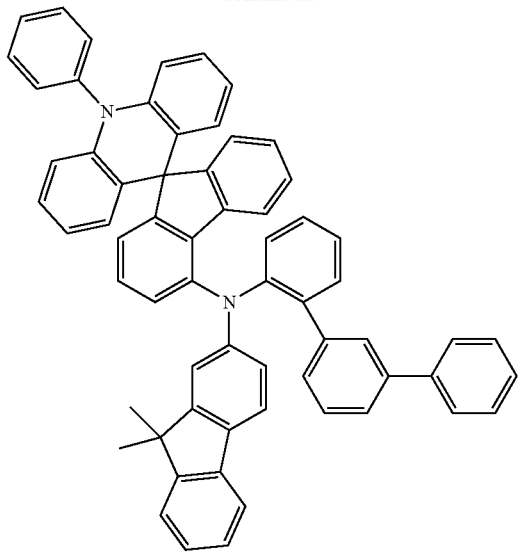
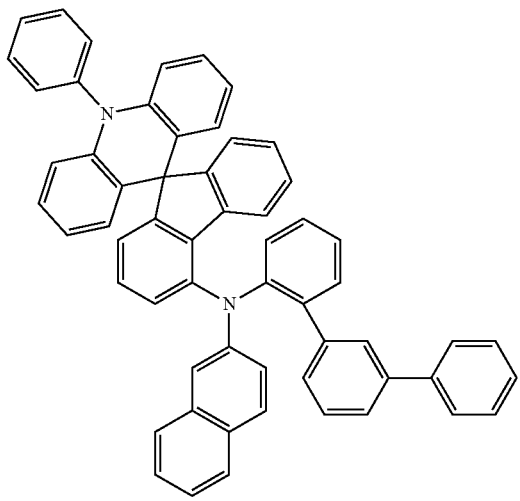
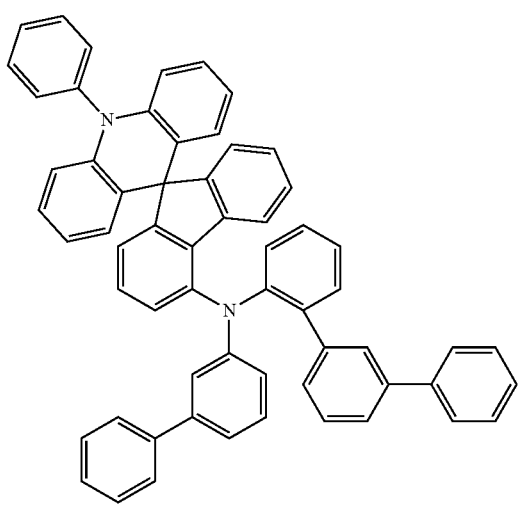
210
-continued
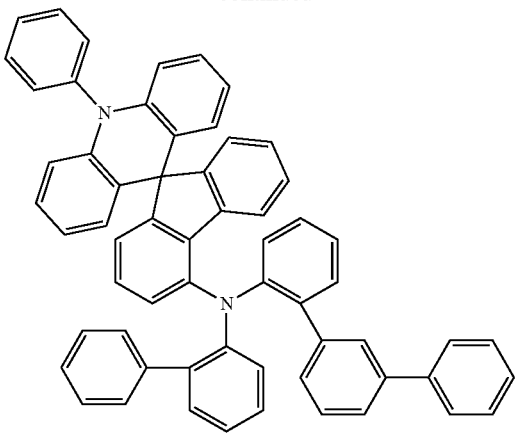
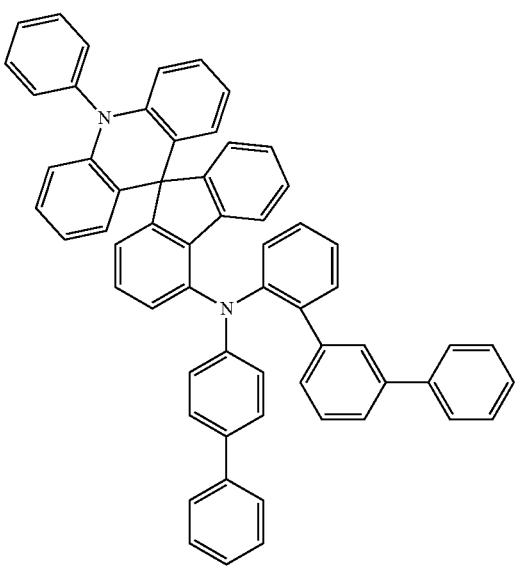
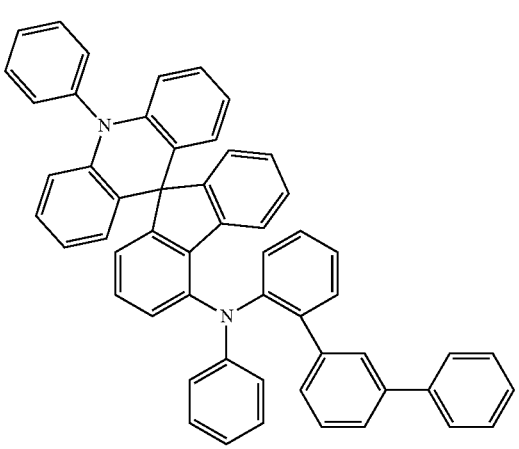

211
-continued
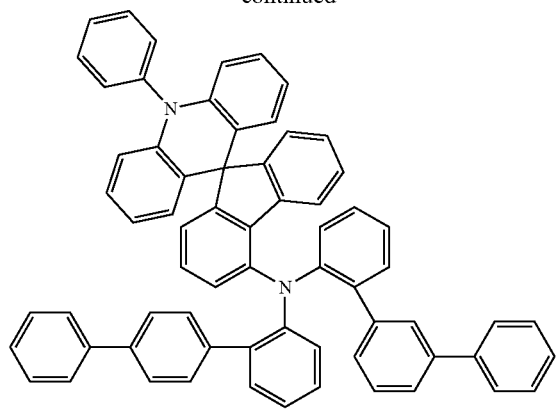
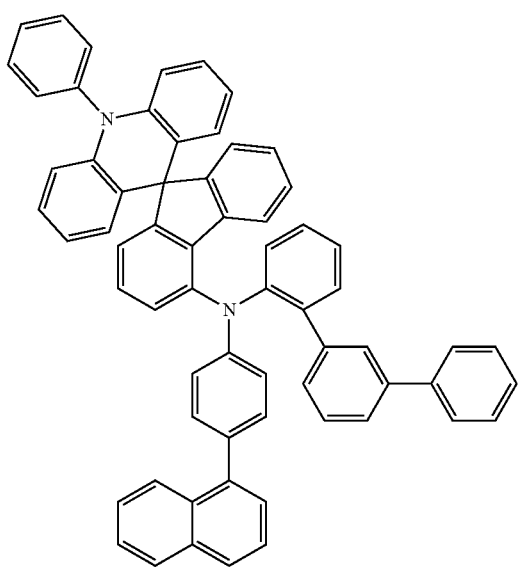
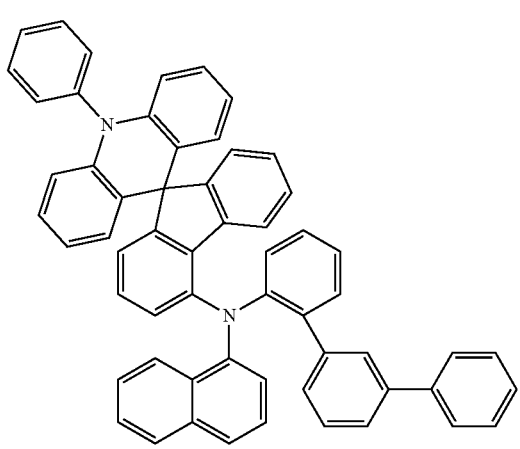
212
-continued
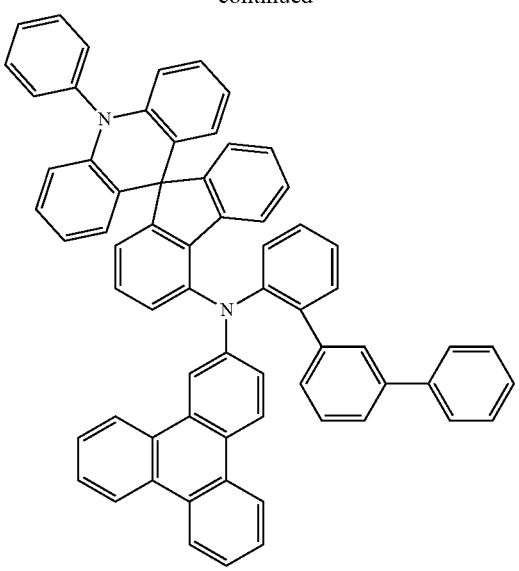
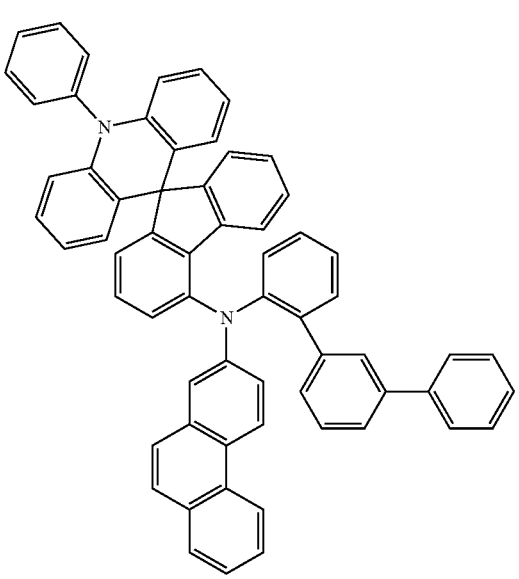
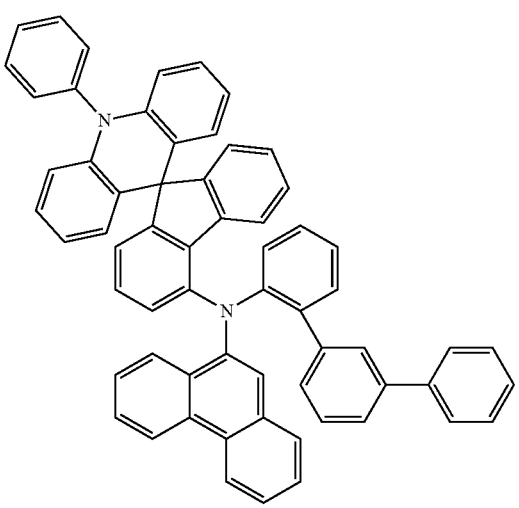

213
-continued
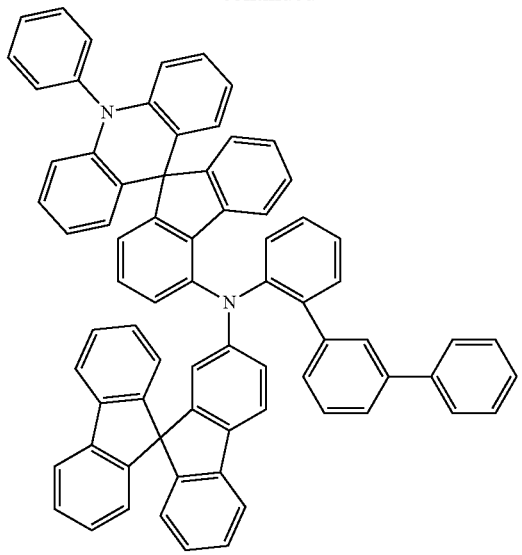
214
-continued
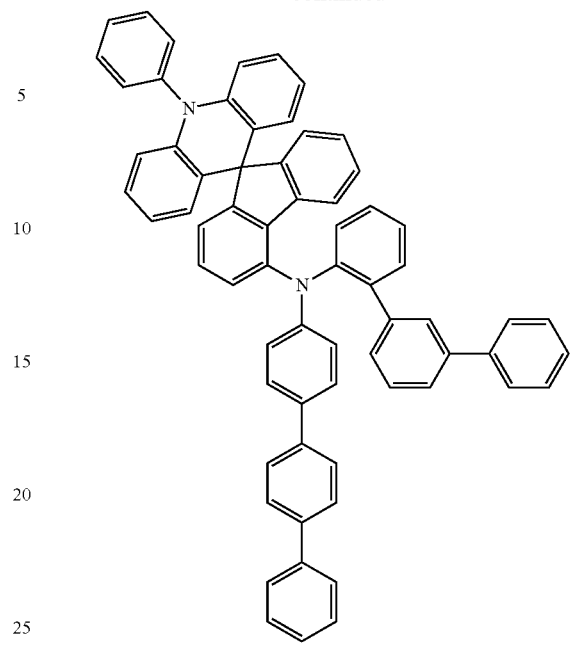
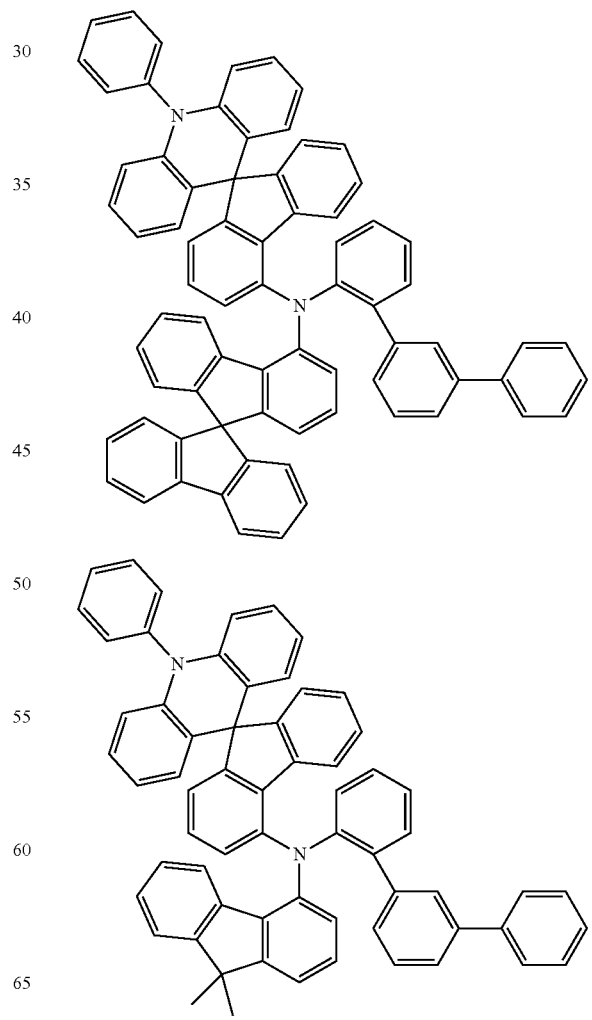
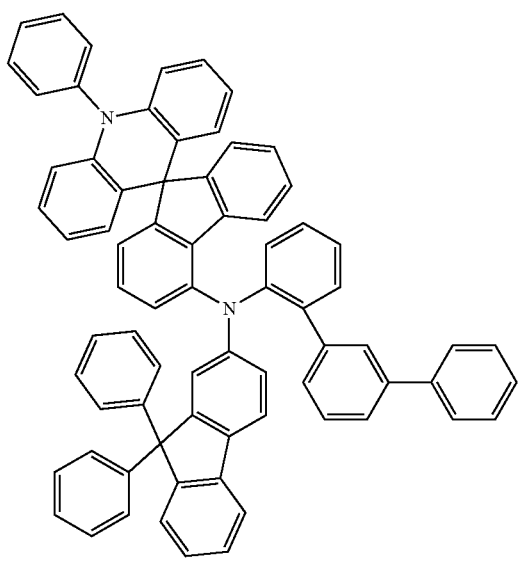

215
-continued
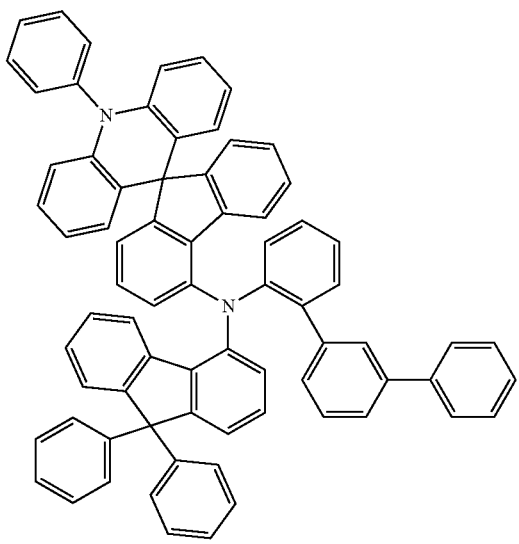
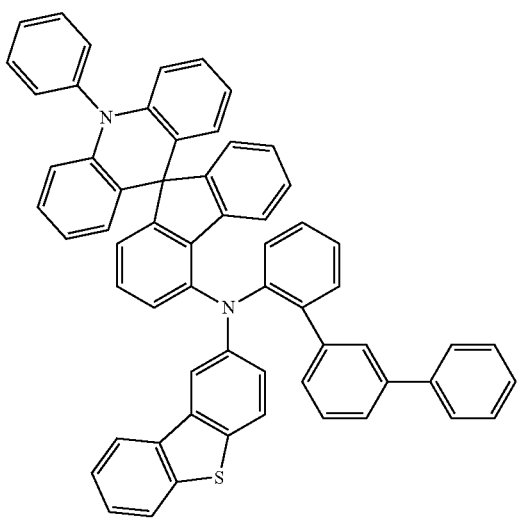
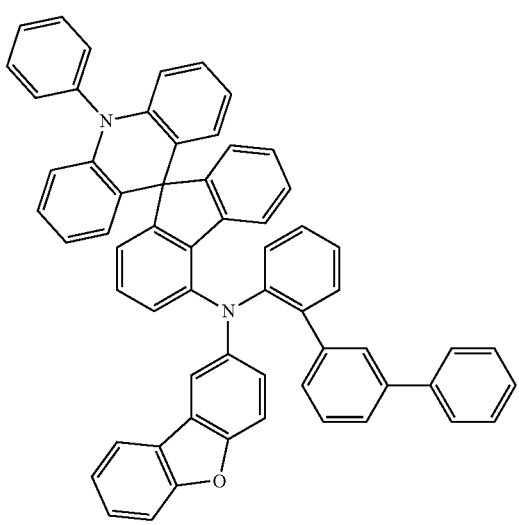
216
-continued
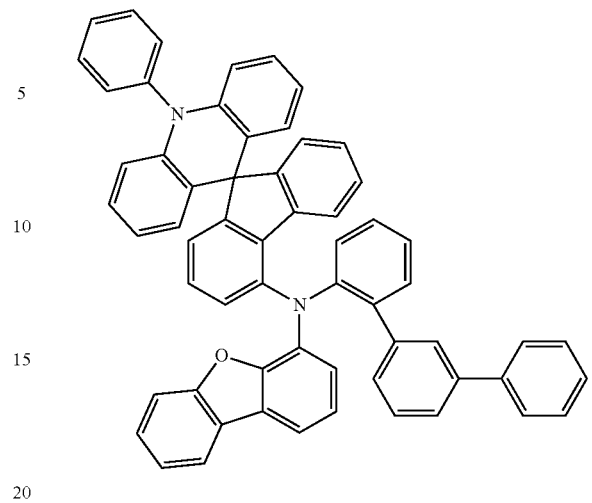
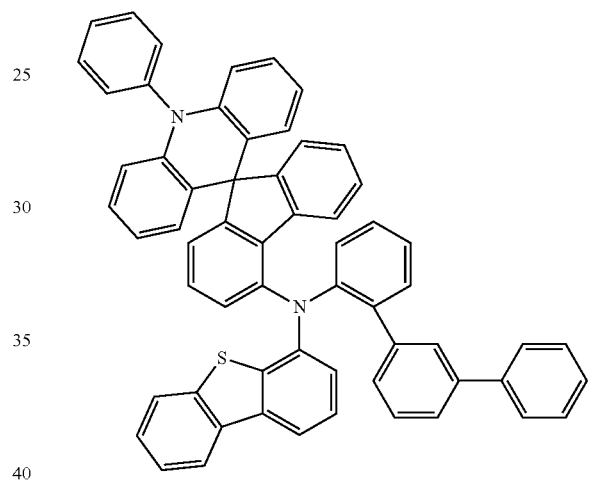
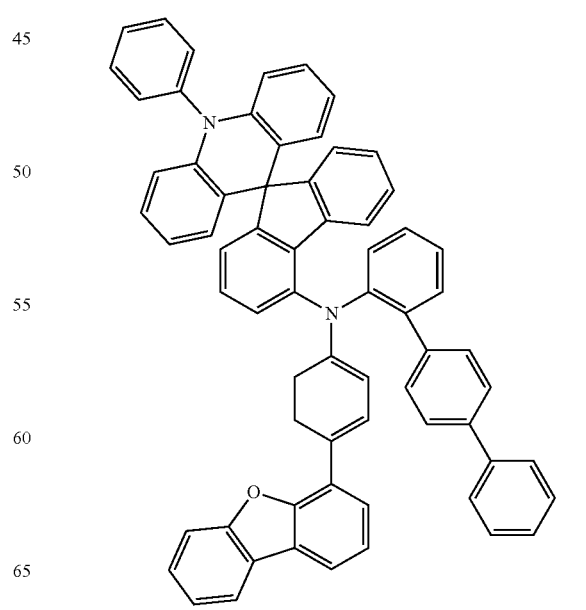

217
-continued
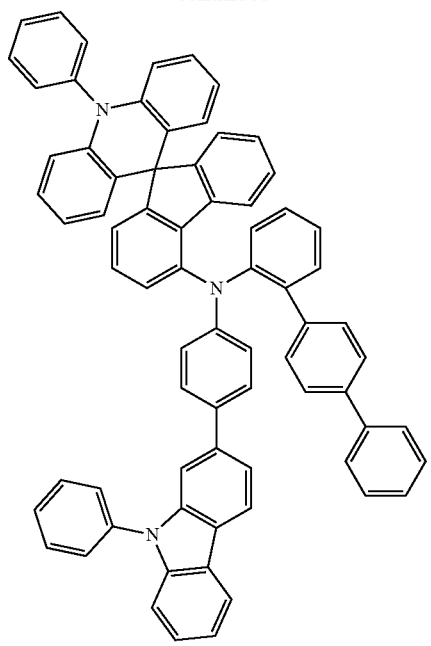
218
-continued
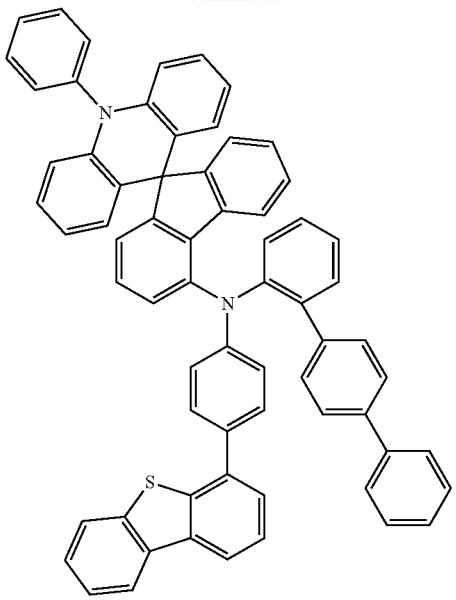
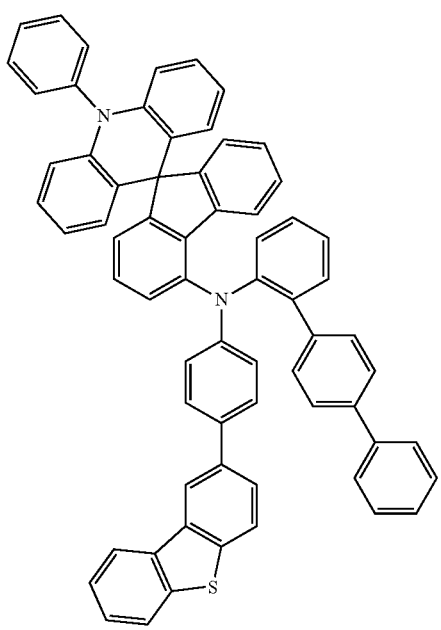
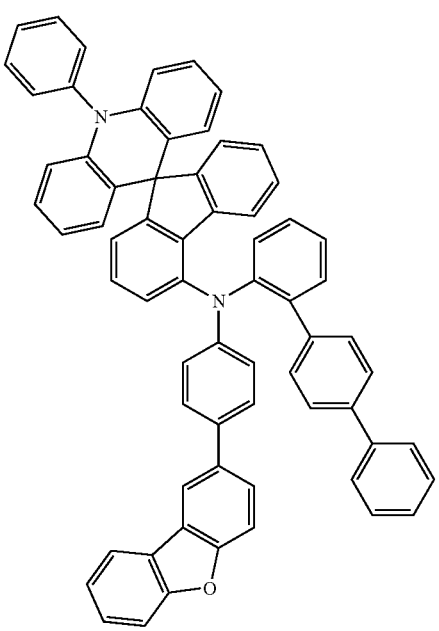

219
-continued
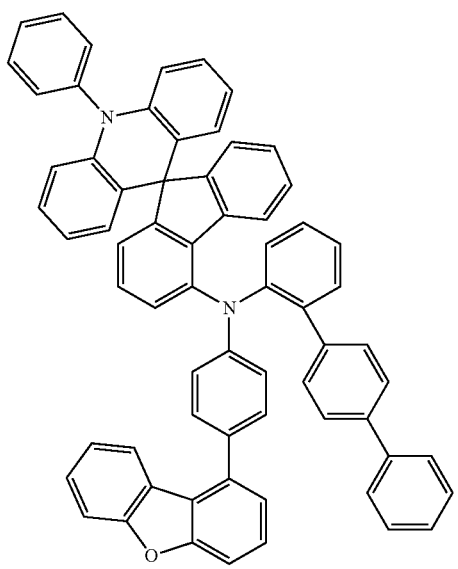
220
-continued
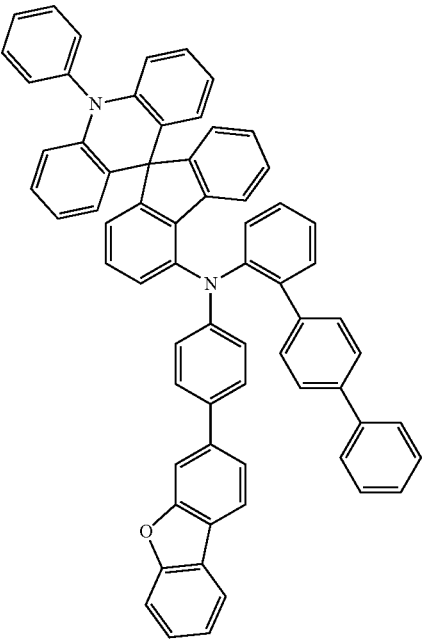
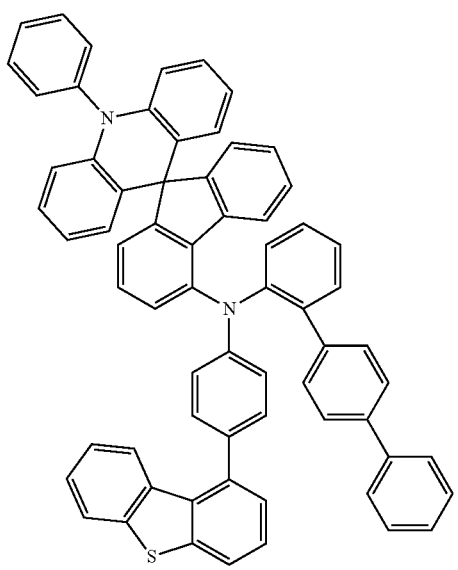
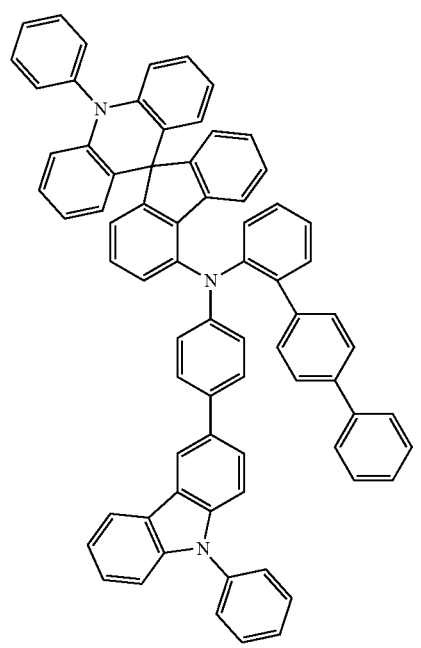

221
-continued
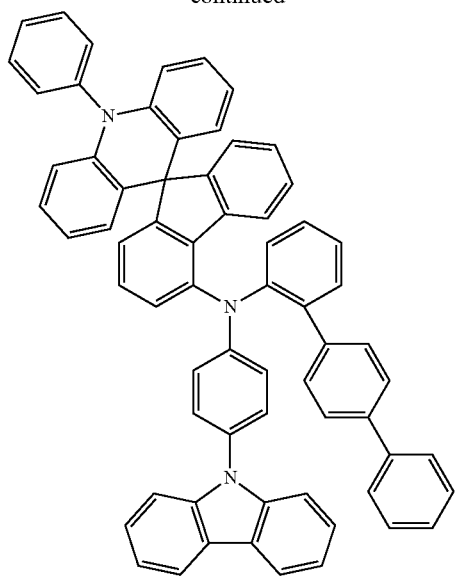
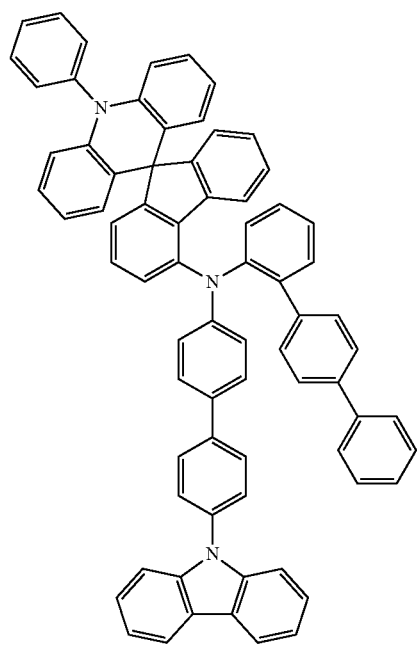
222
-continued
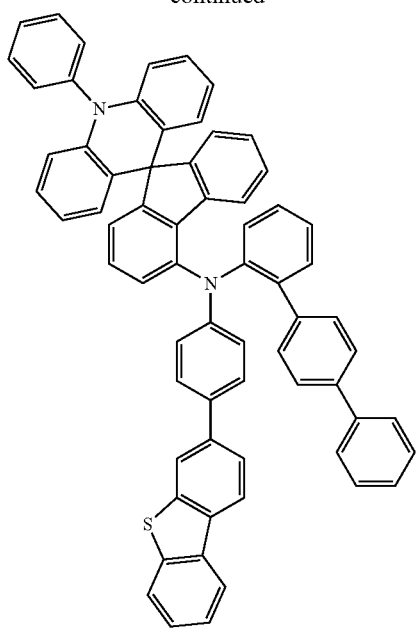
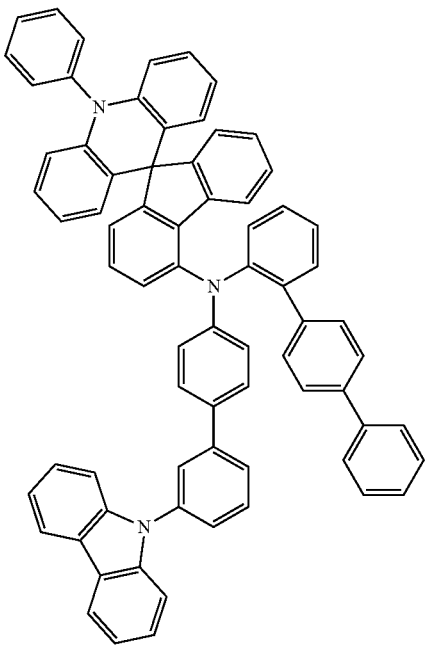

223
-continued
224
-continued
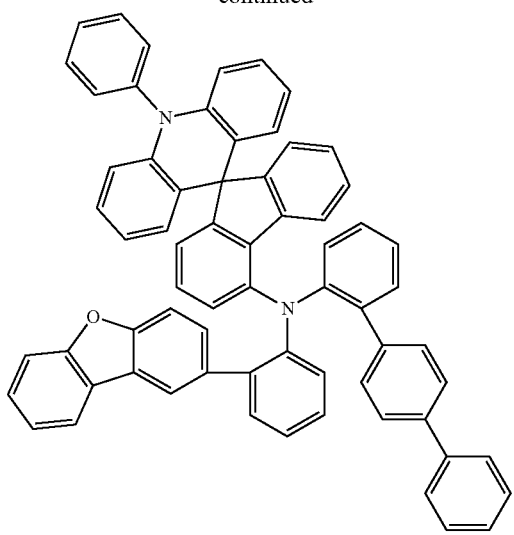
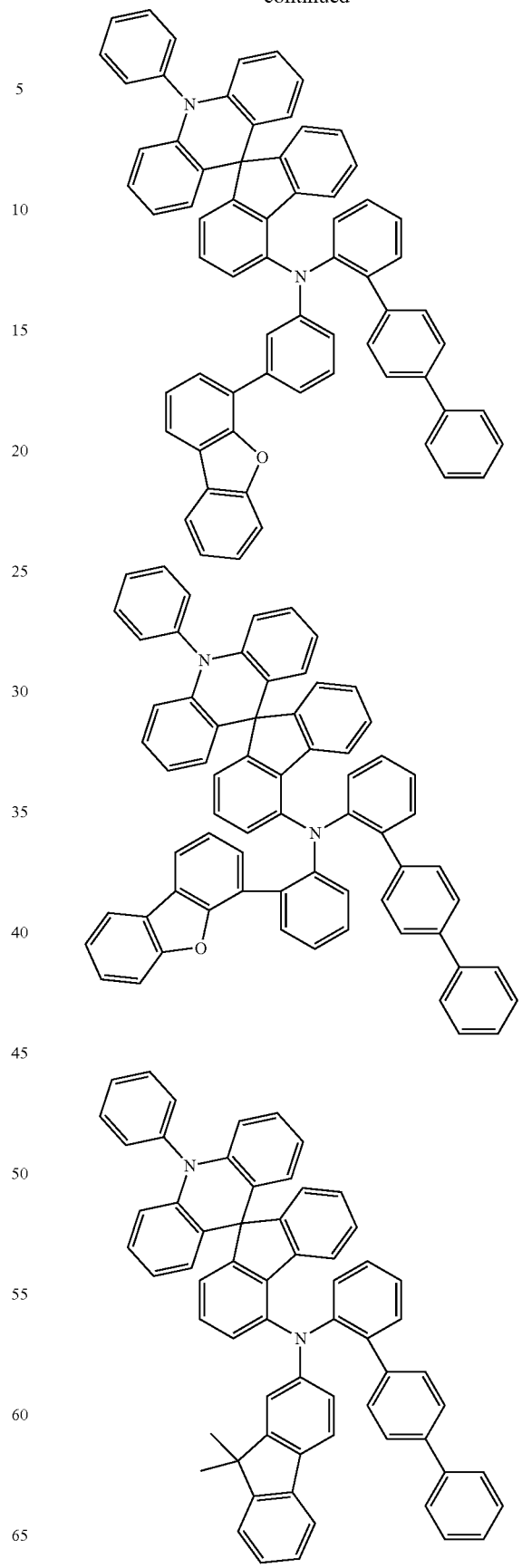
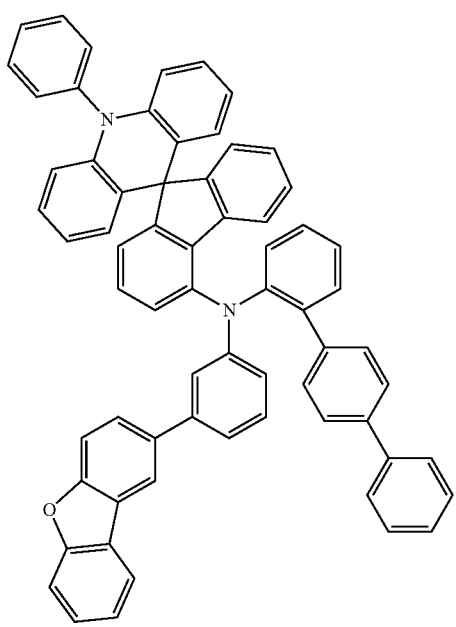

225
-continued
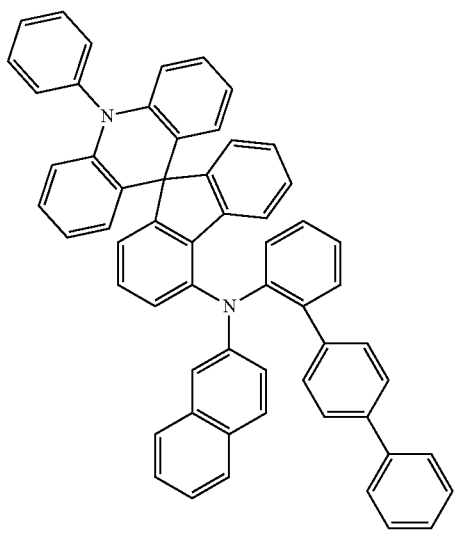
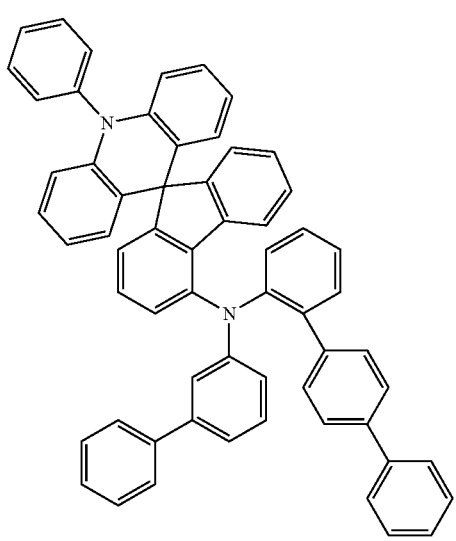
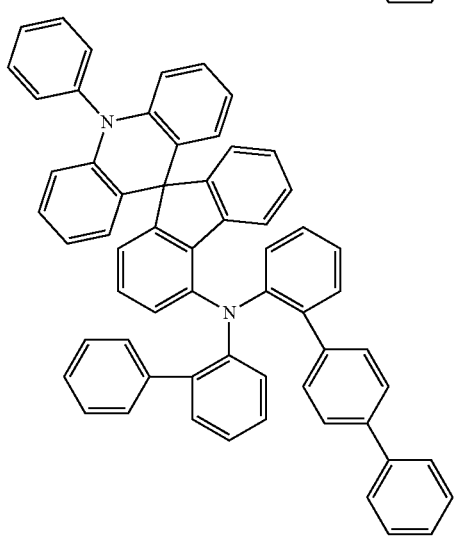
226
-continued
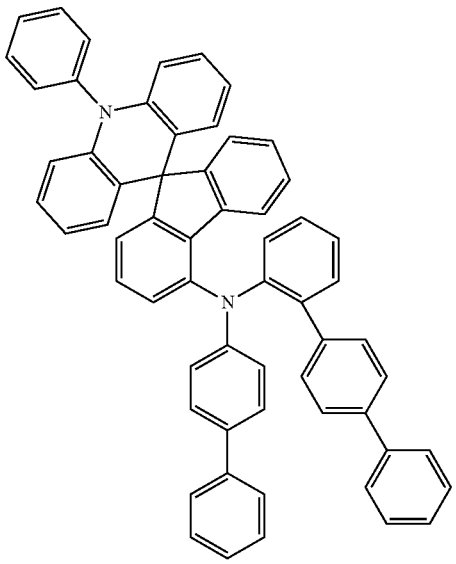
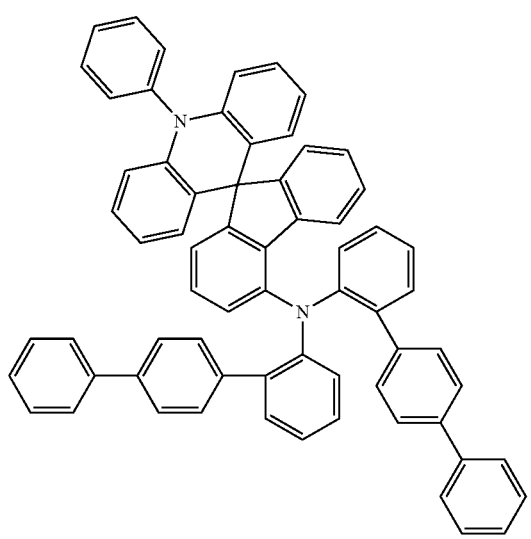

227
-continued
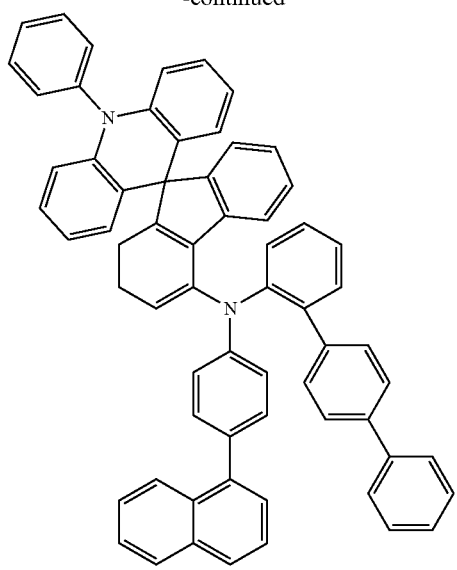
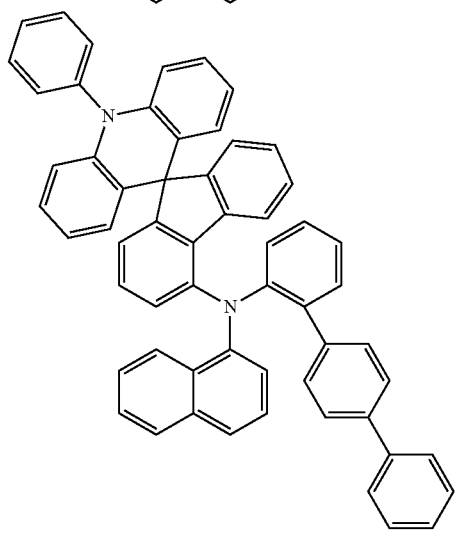
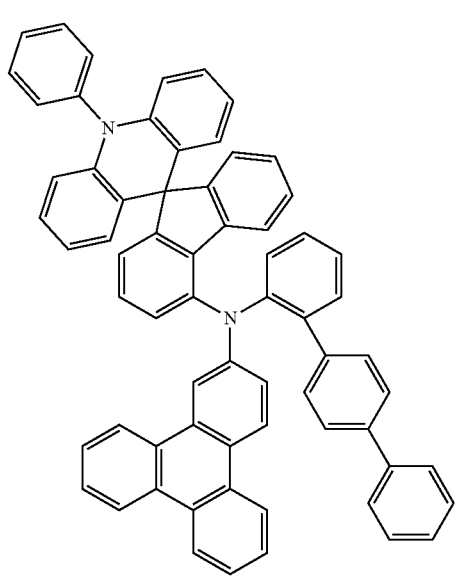
228
-continued
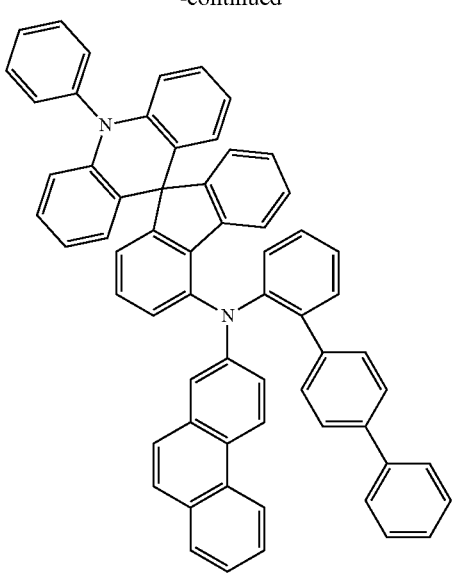
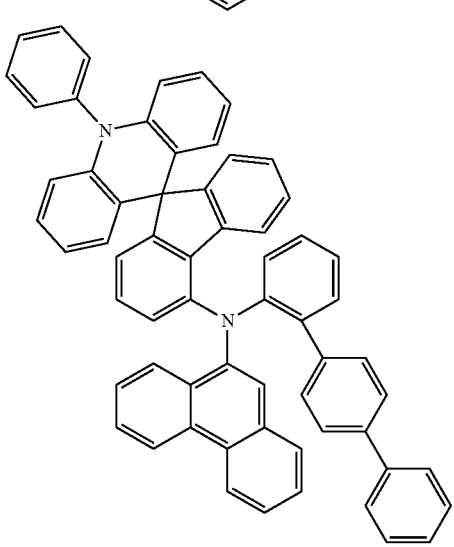
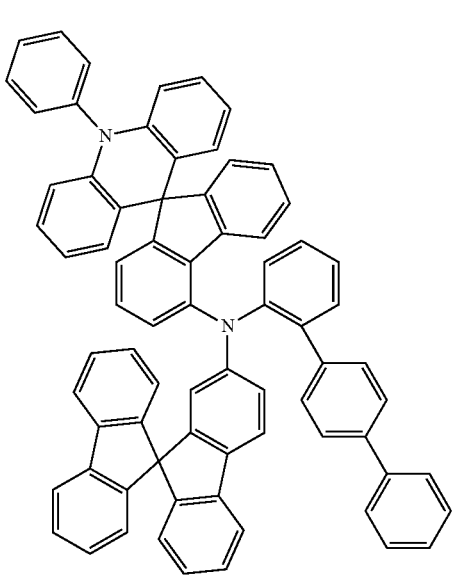

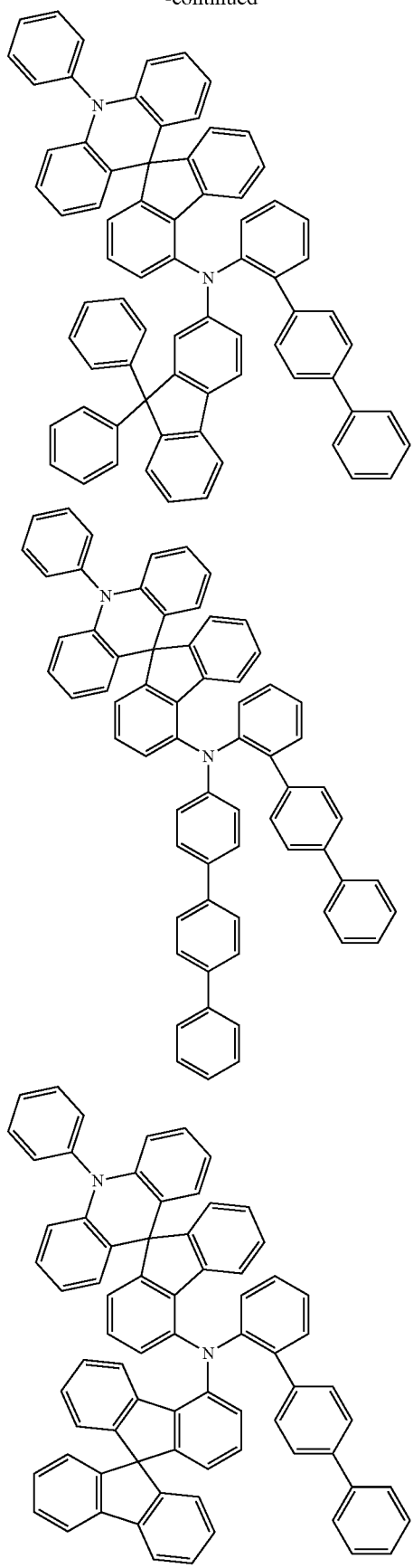
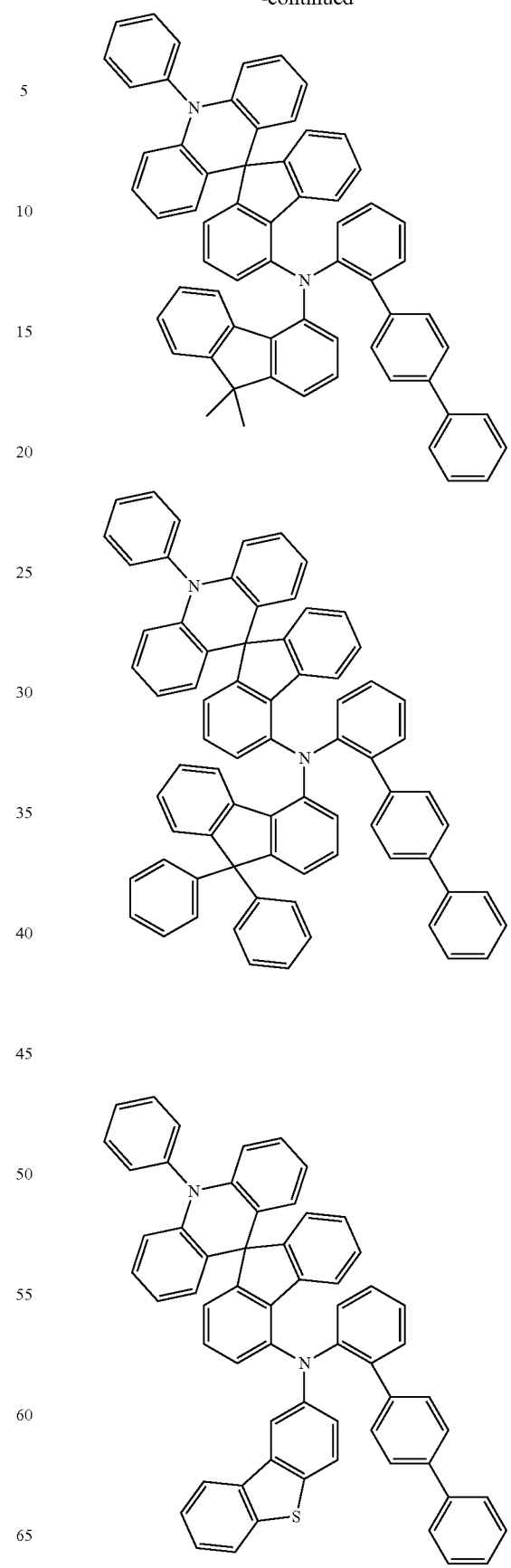

231
-continued
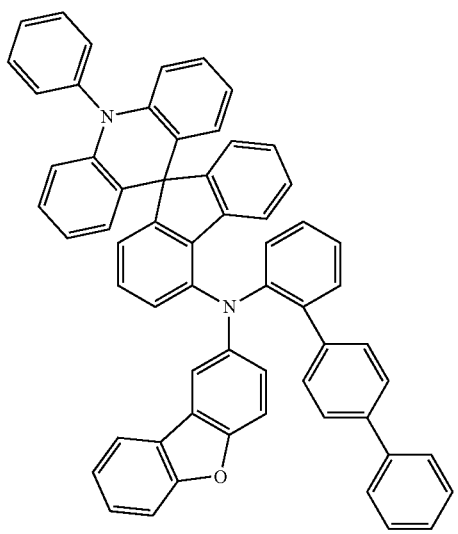
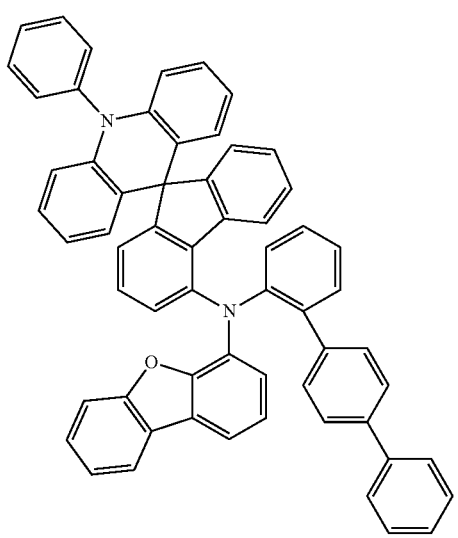
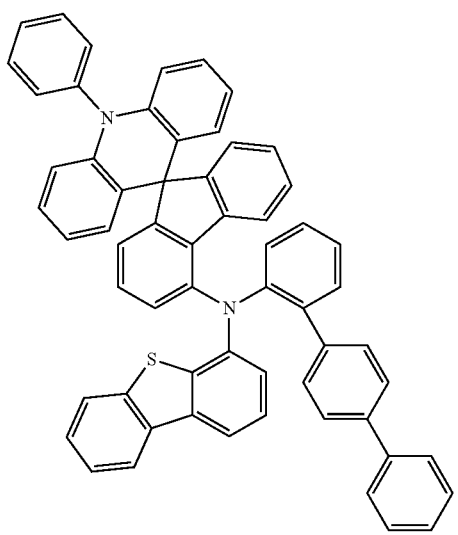
232
-continued
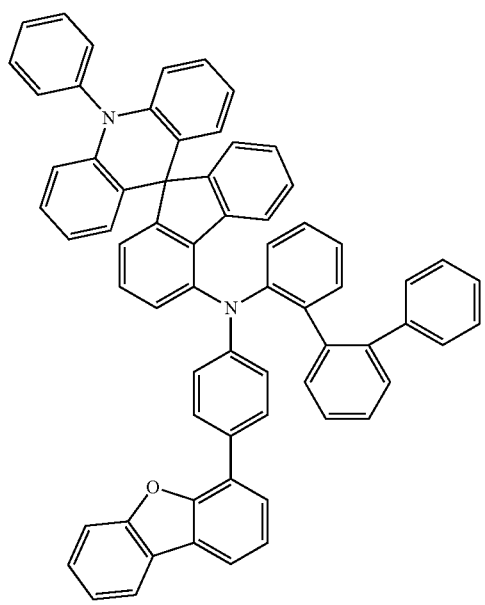
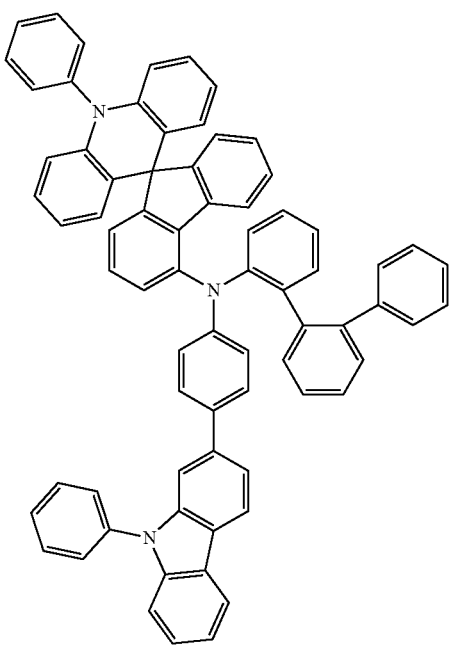

233
-continued
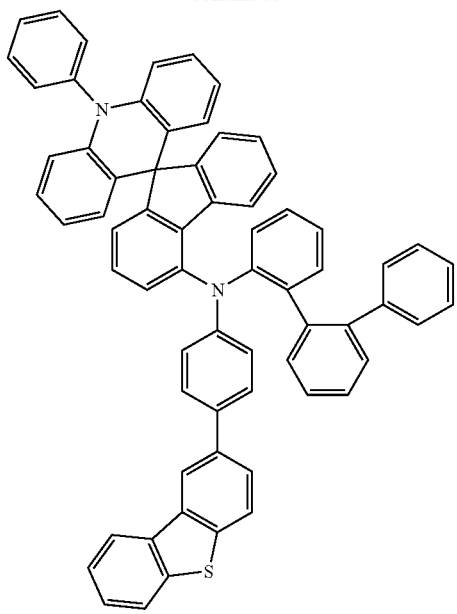
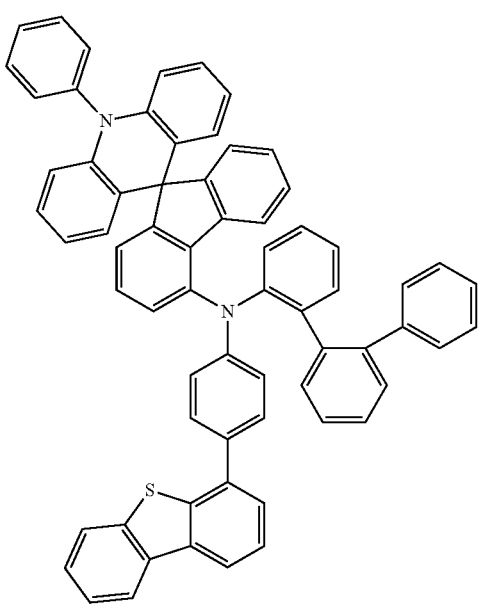
234
-continued
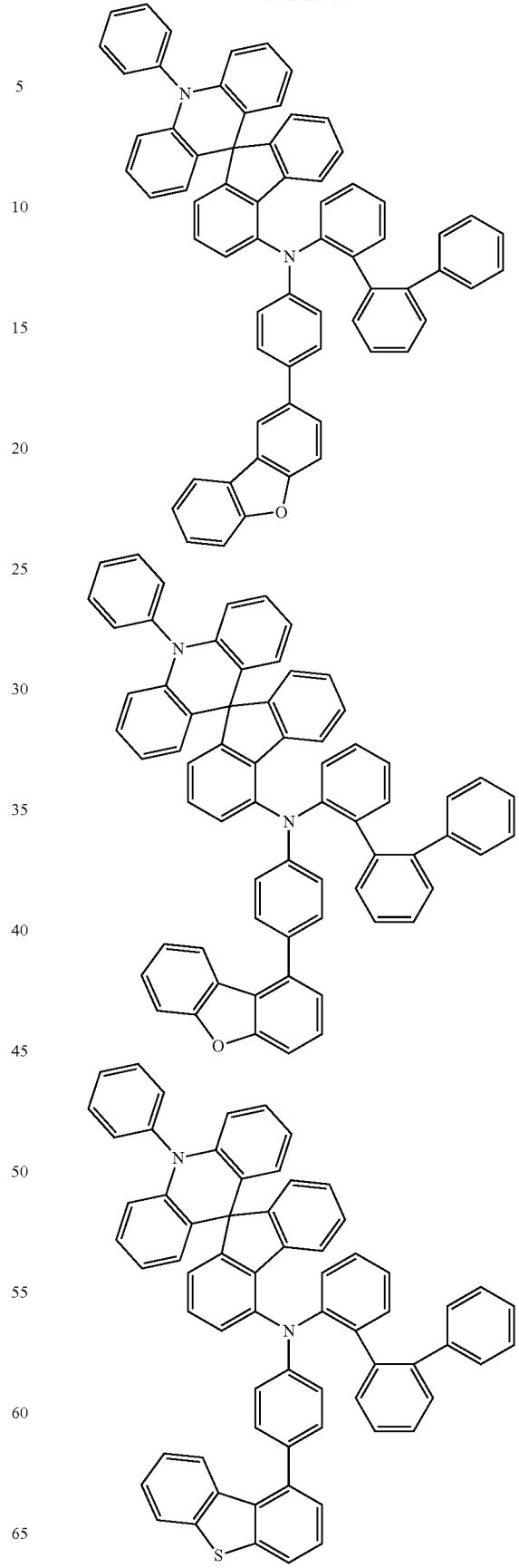

235
-continued
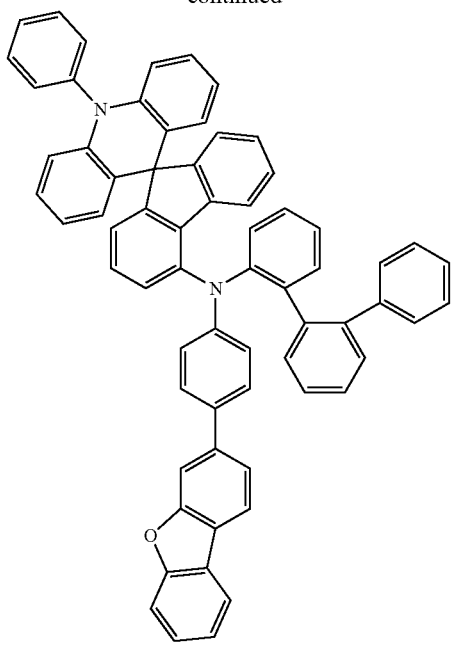
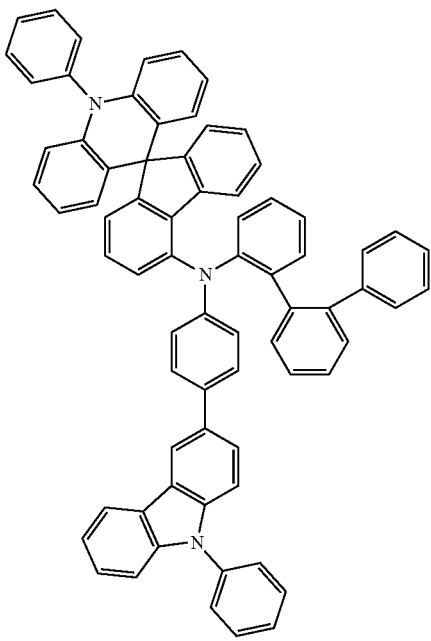
236
-continued
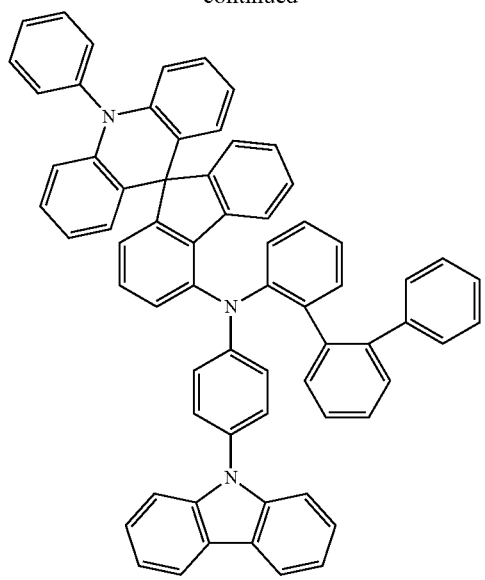
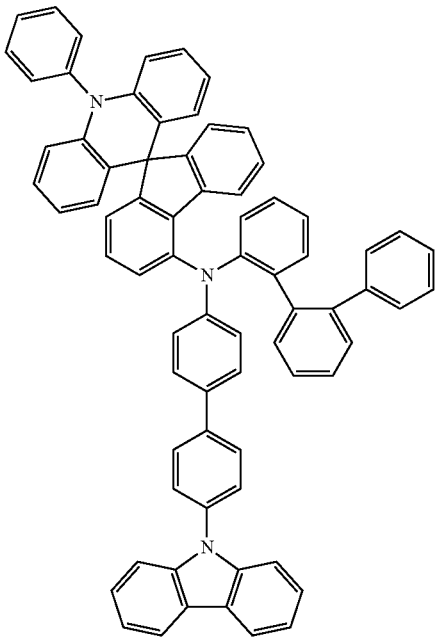

237
-continued
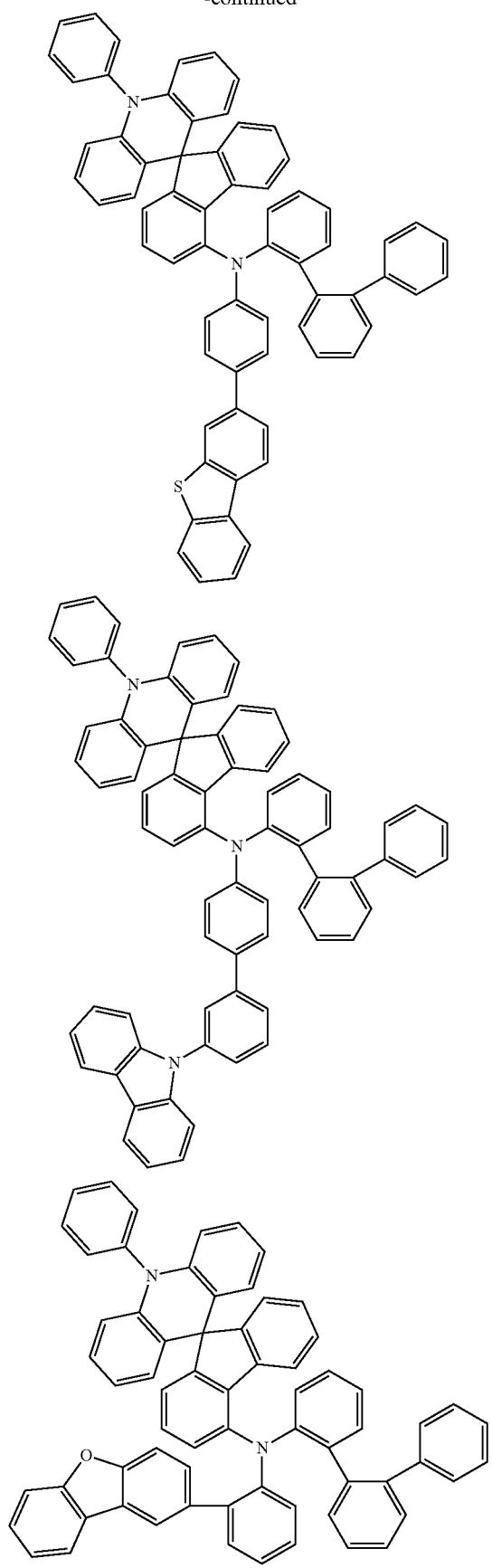
238
-continued
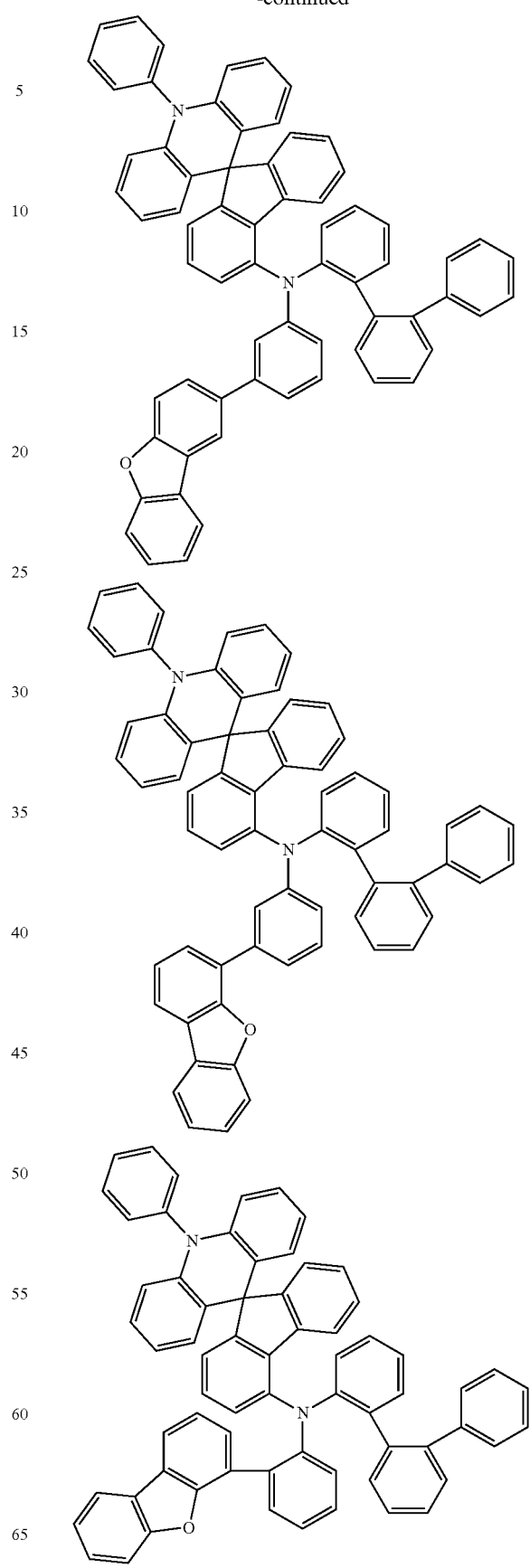

239
-continued
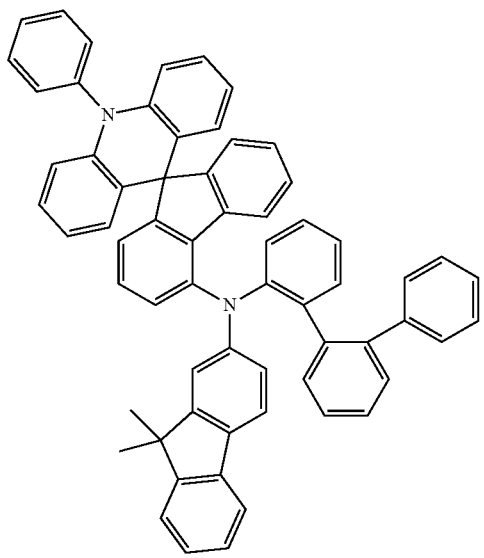
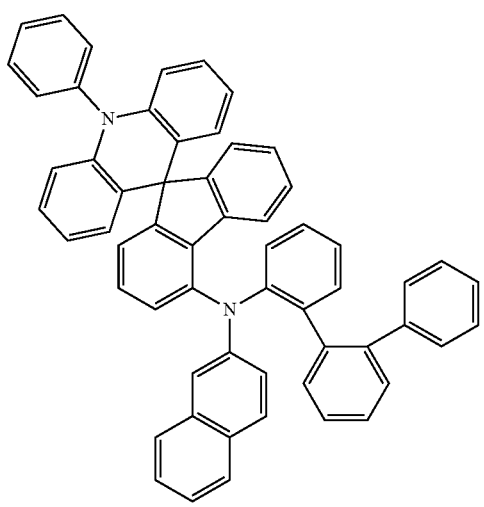
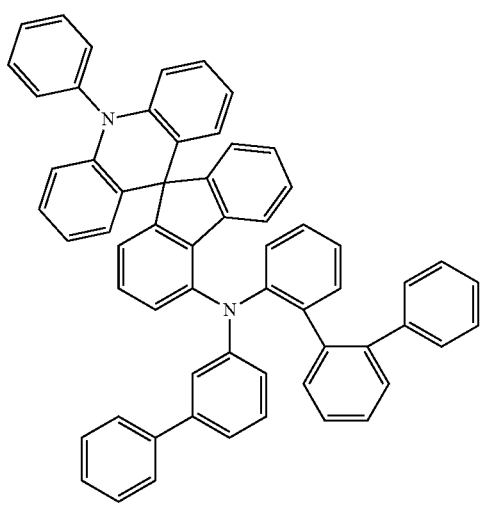
240
-continued
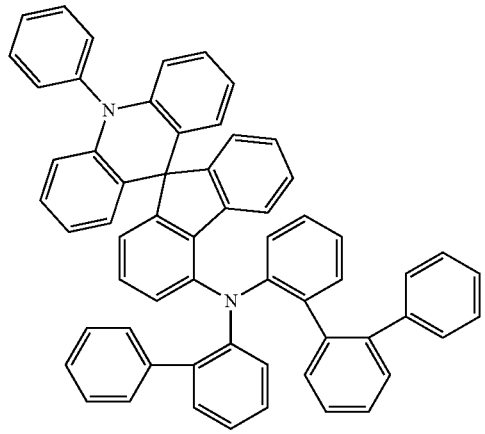
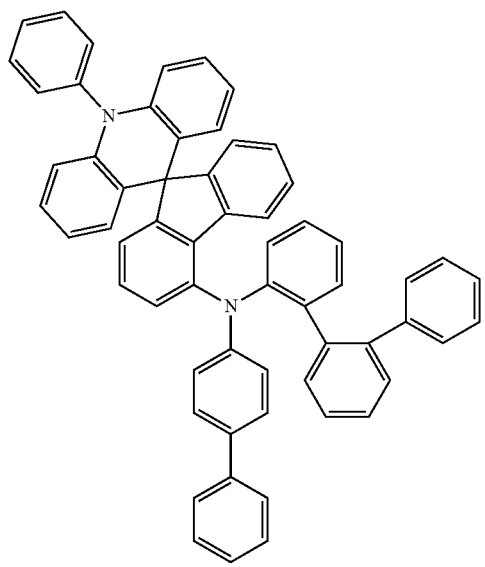

241
-continued
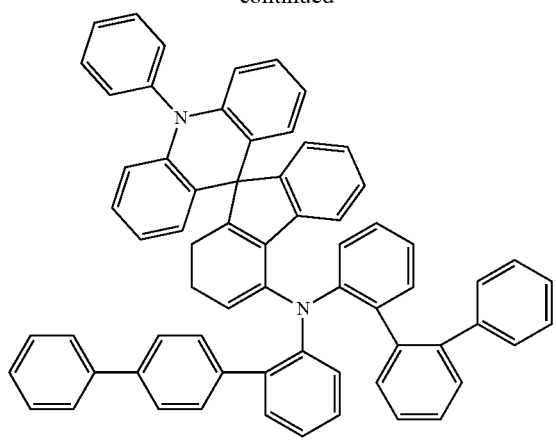
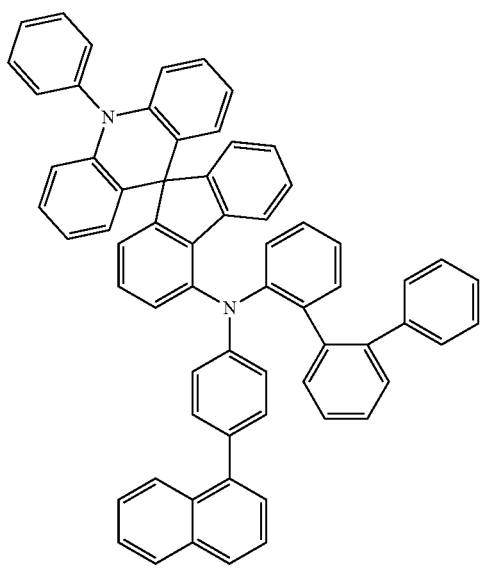
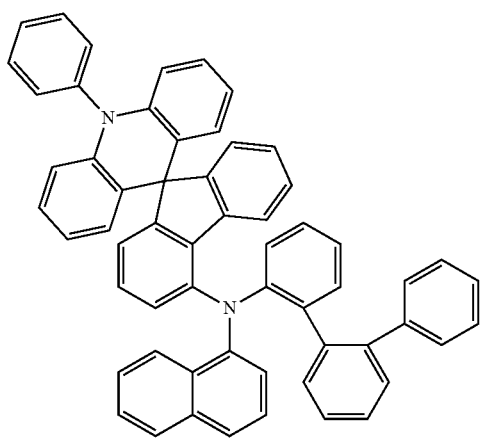
242
-continued
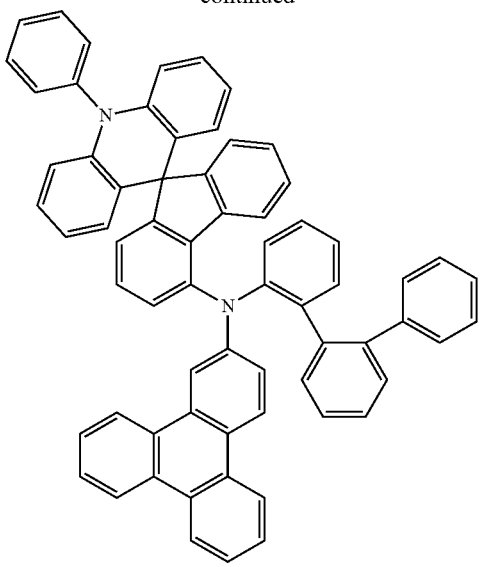
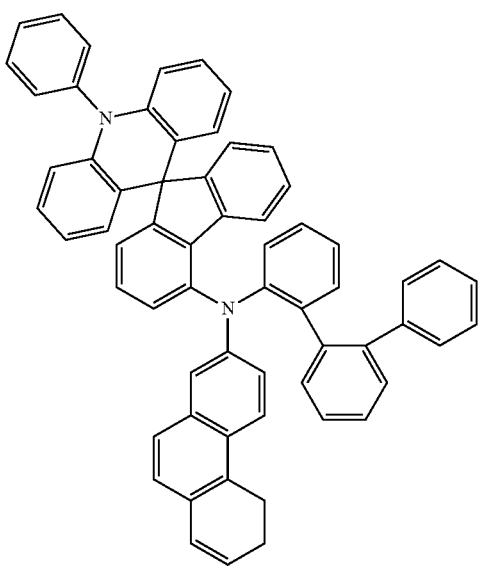
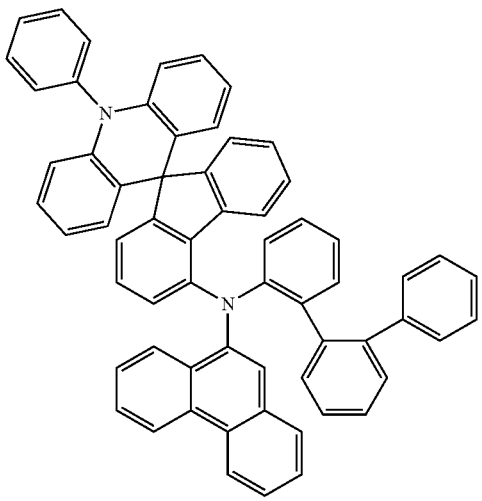

243
-continued
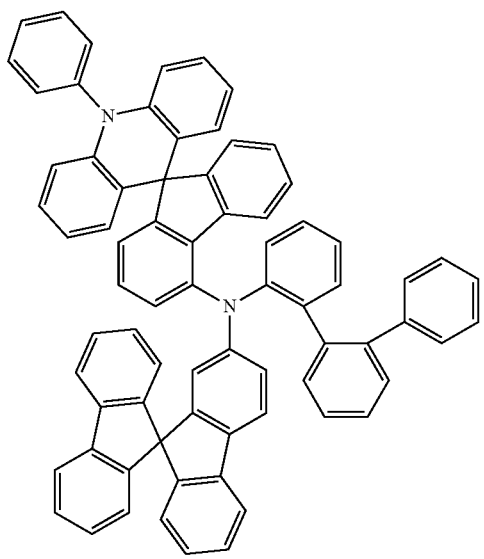
244
-continued
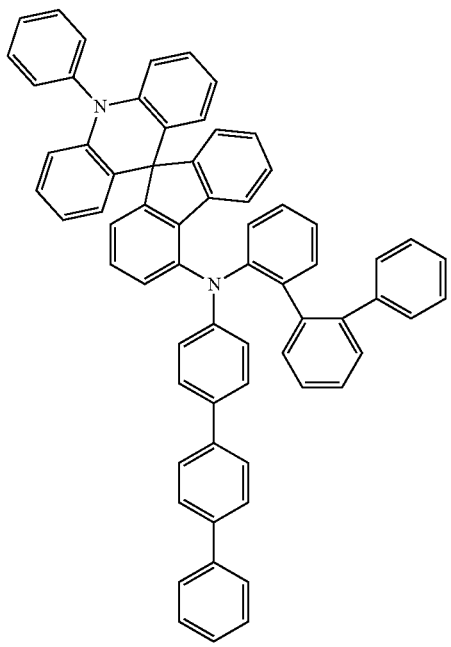
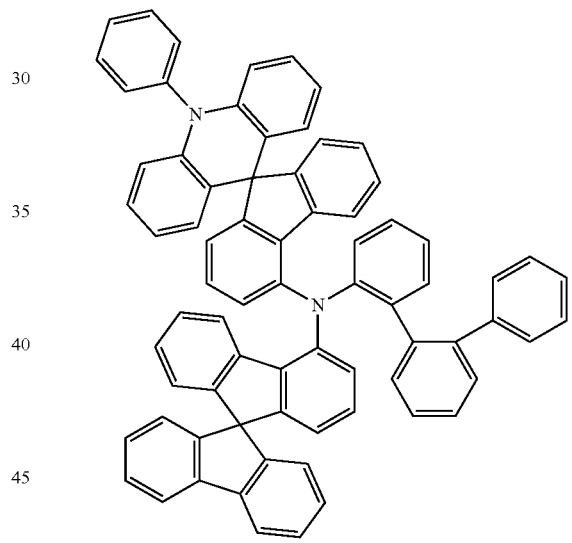
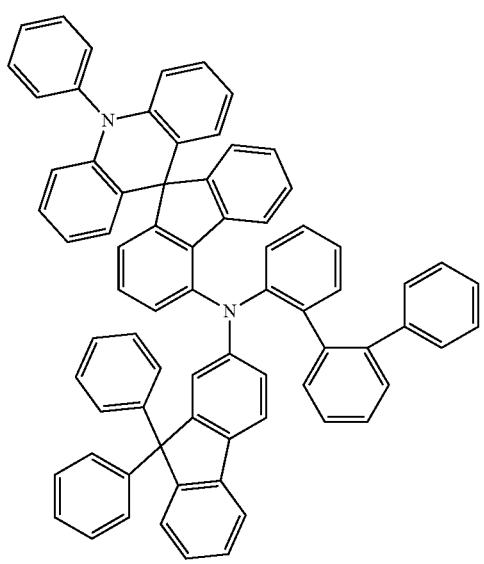
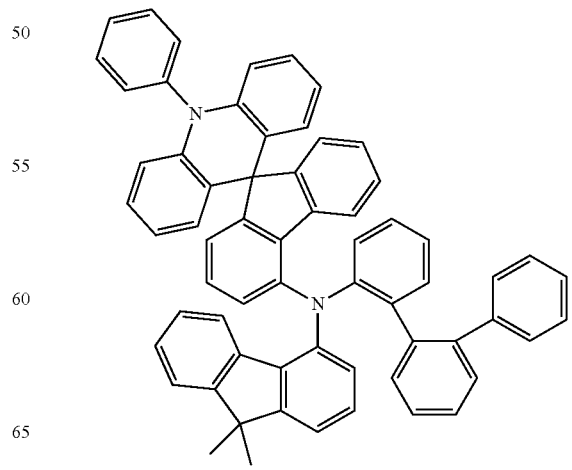

245
-continued
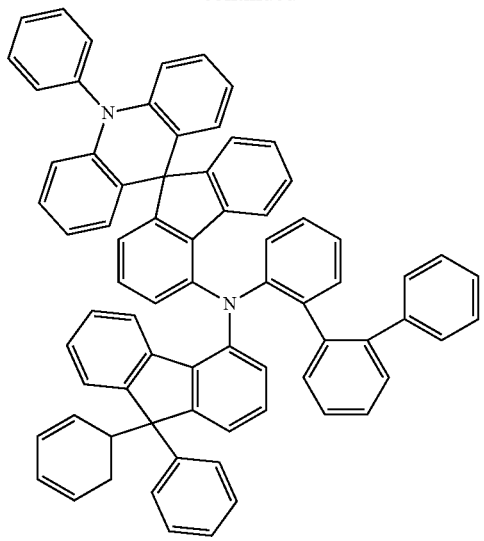
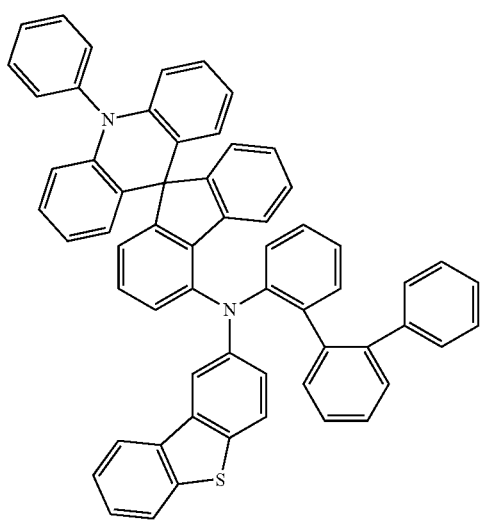
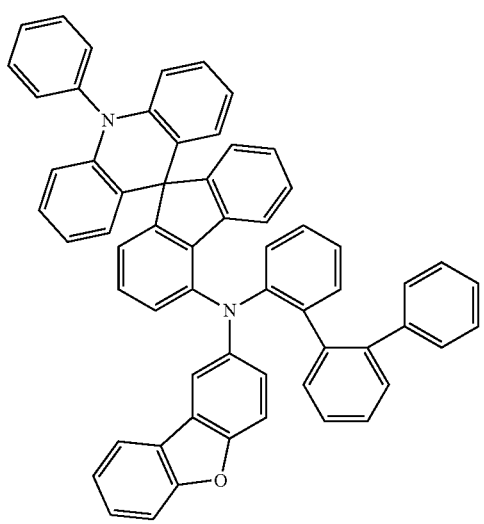
246
-continued
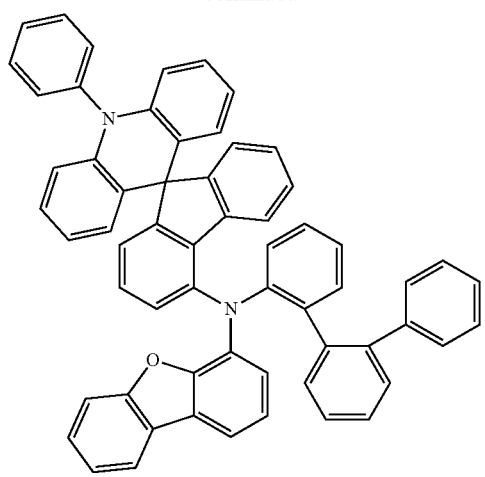
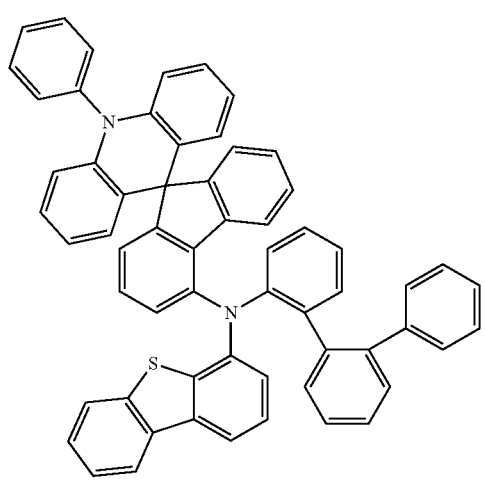
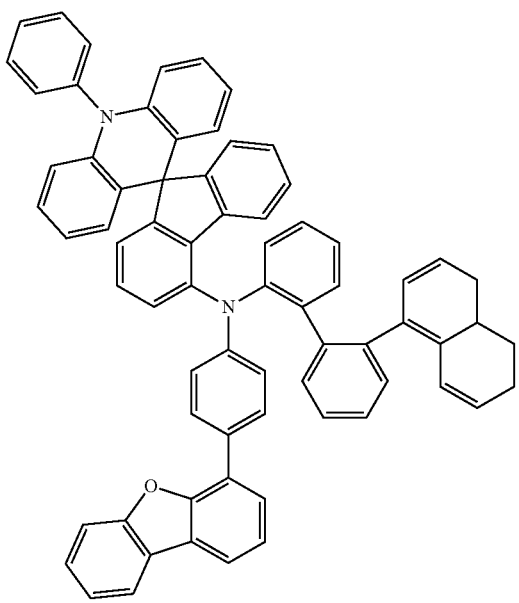

247
-continued
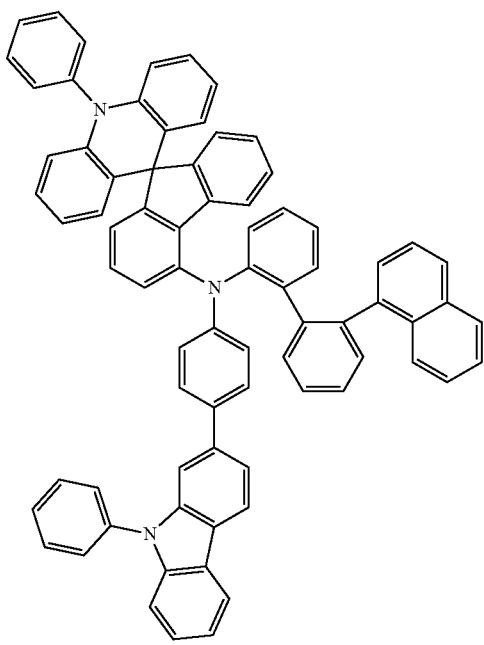
248
-continued
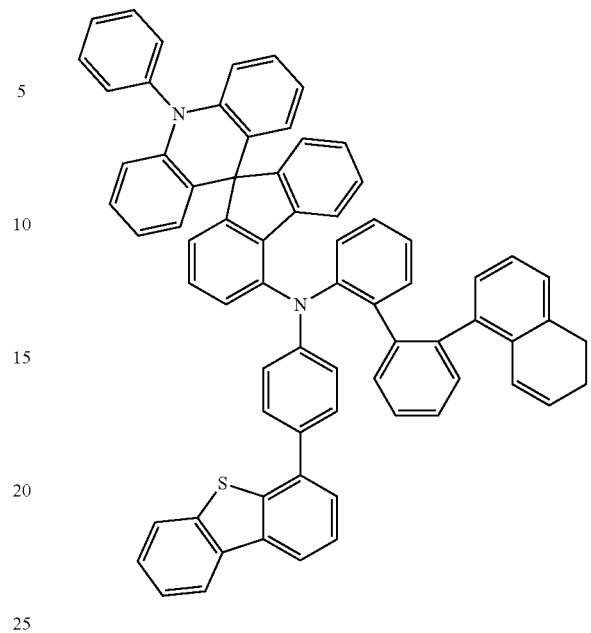
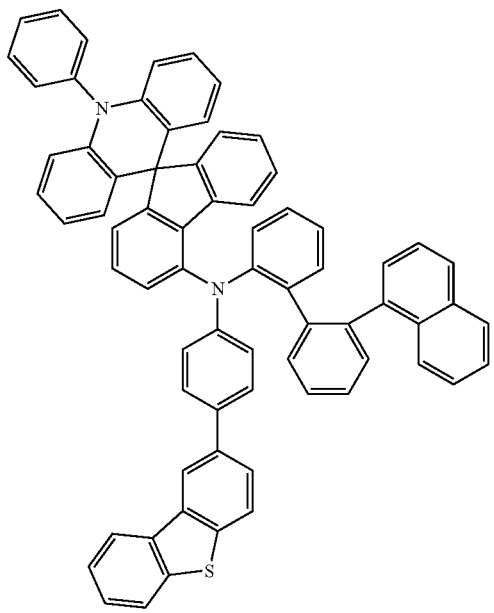
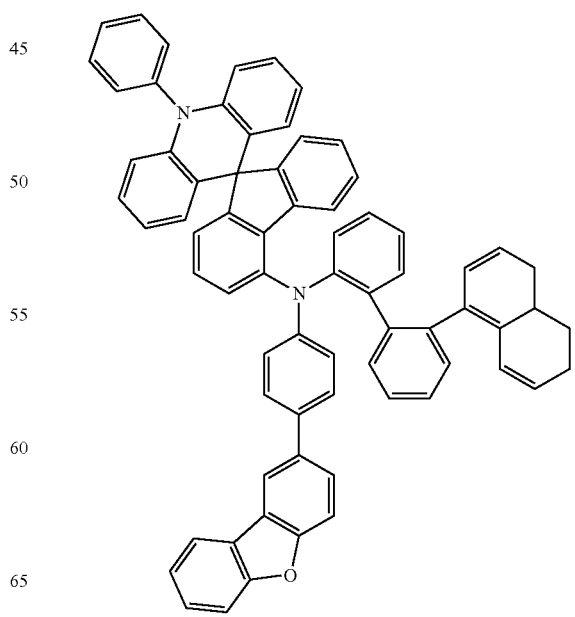

249
-continued
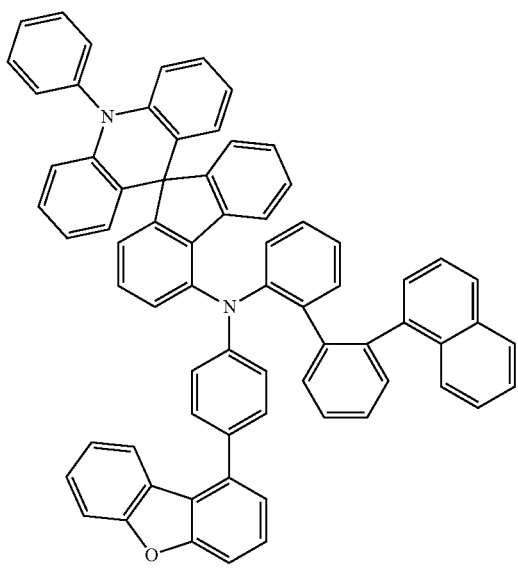
250
-continued
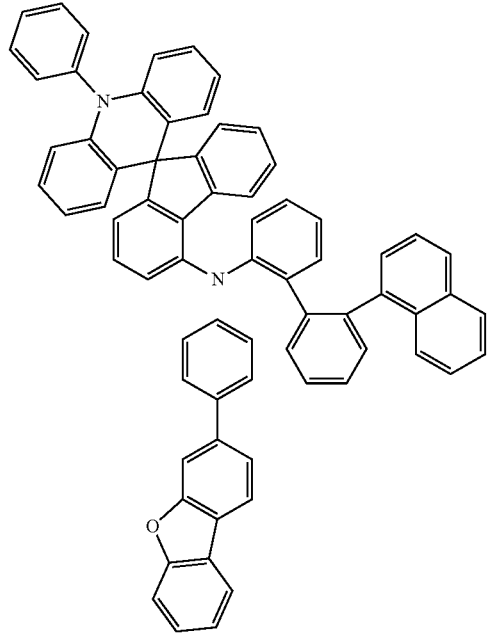
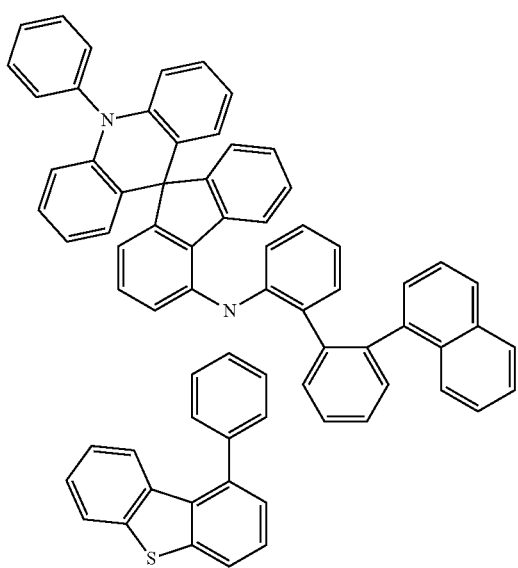
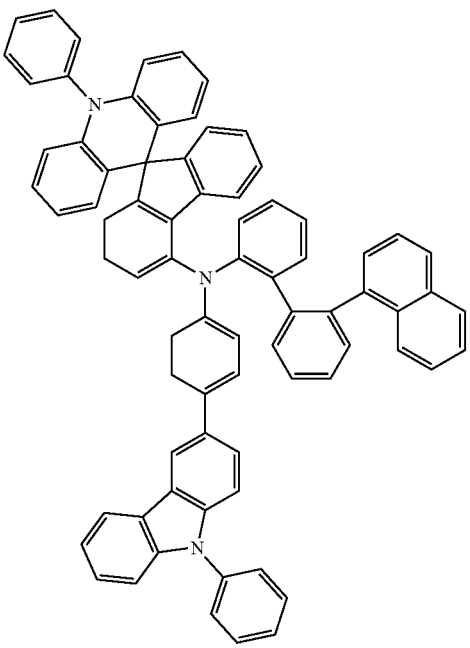

251
-continued
252
-continued
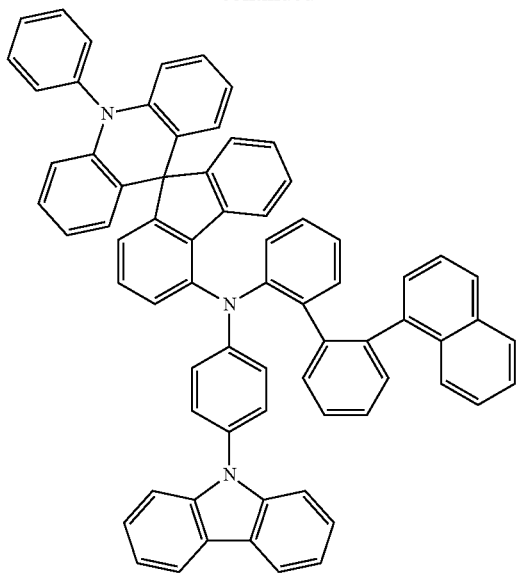
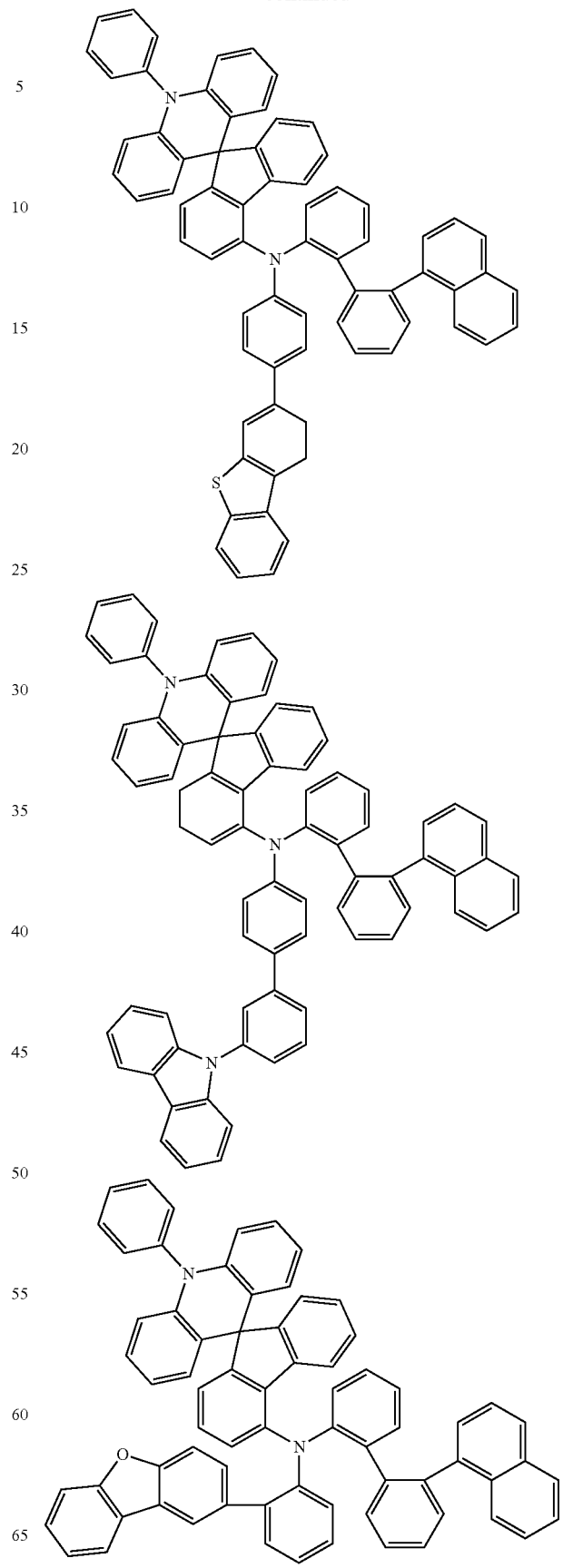

253
-continued
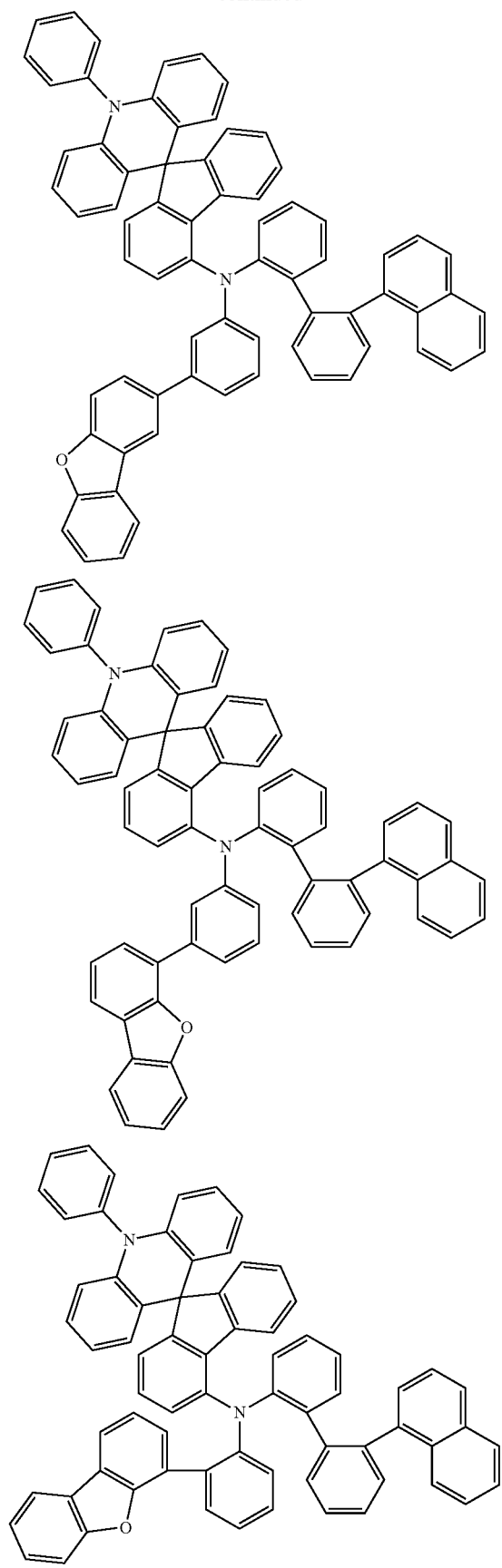
254
-continued
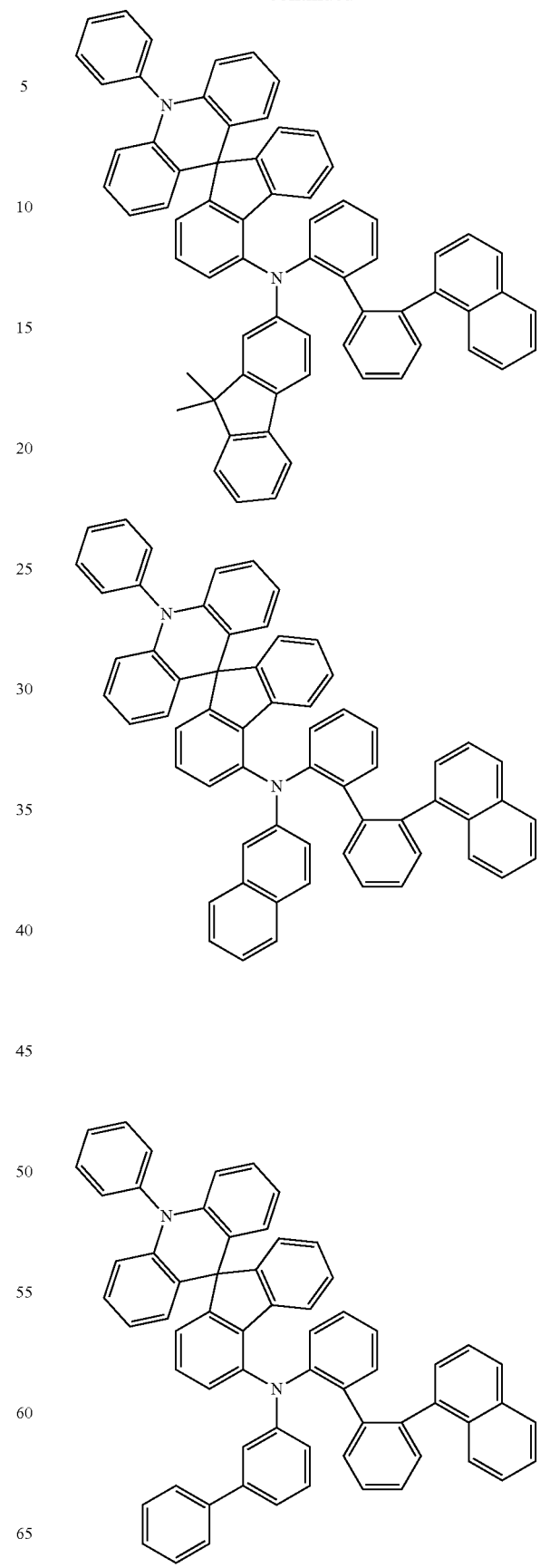

255
-continued
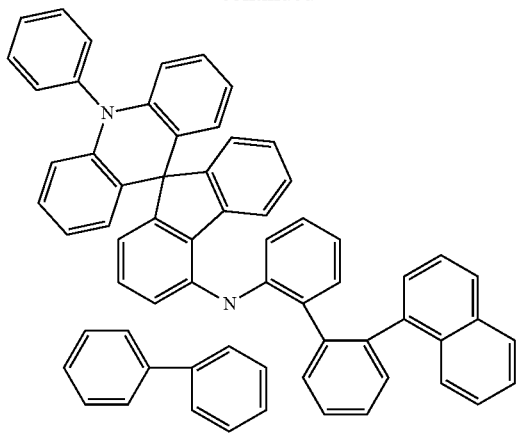
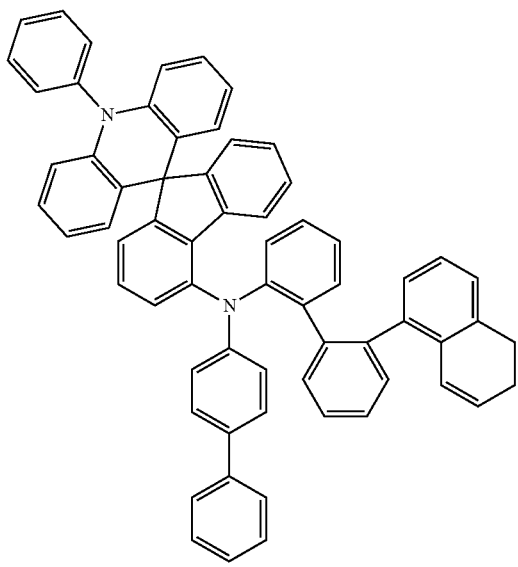
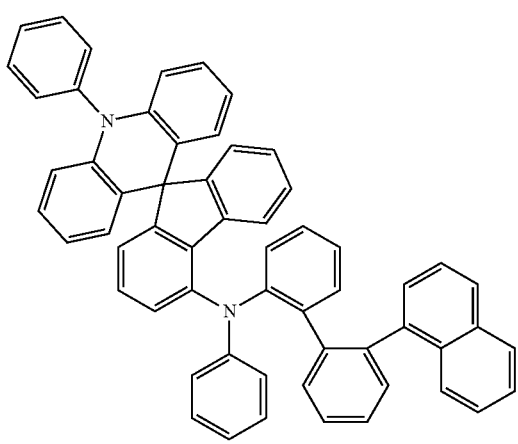
256
-continued
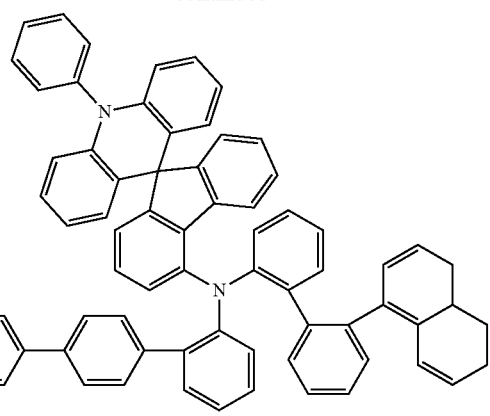
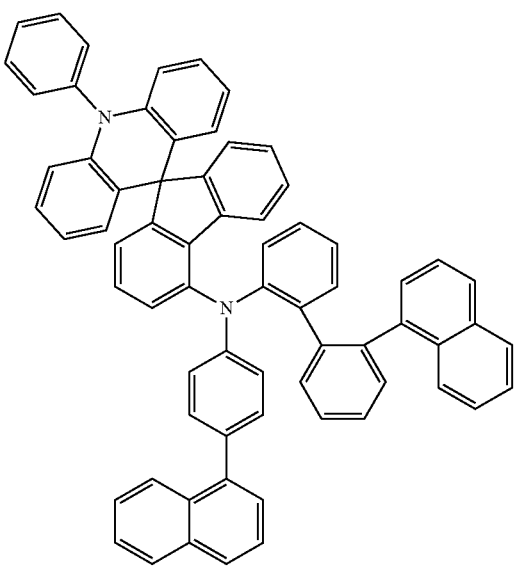
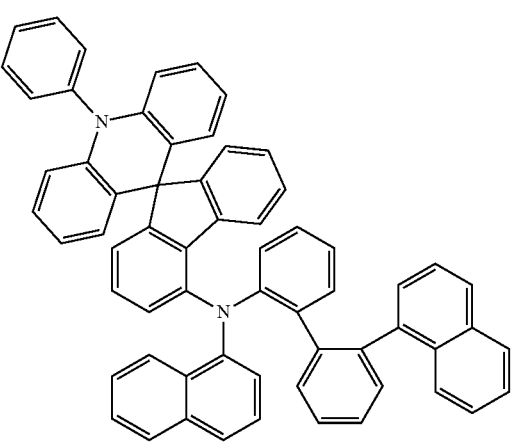

257
-continued
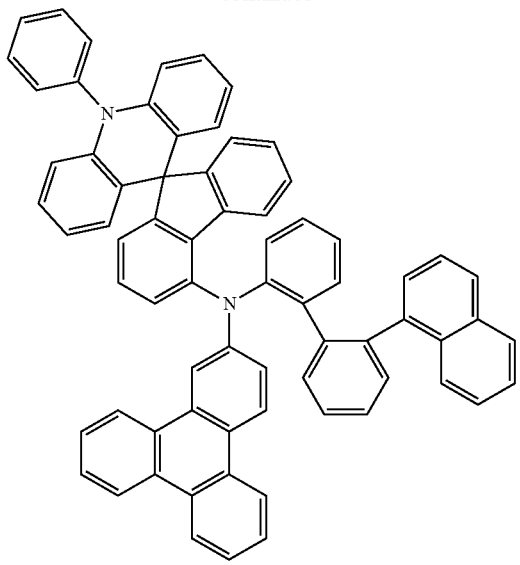
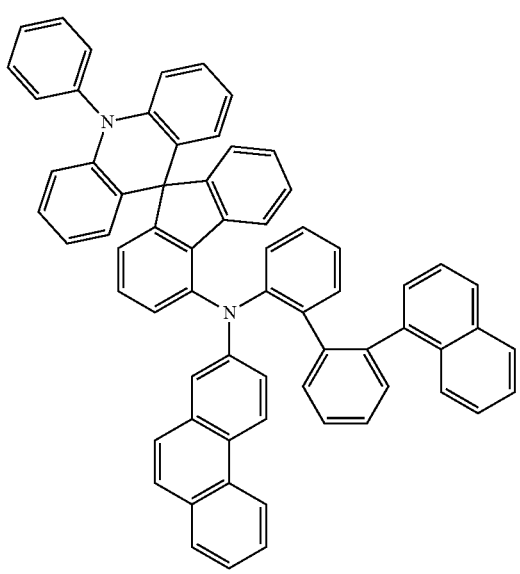
258
-continued
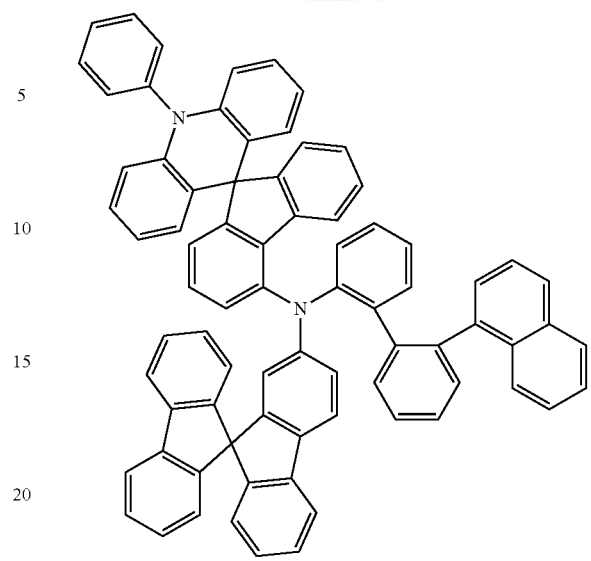
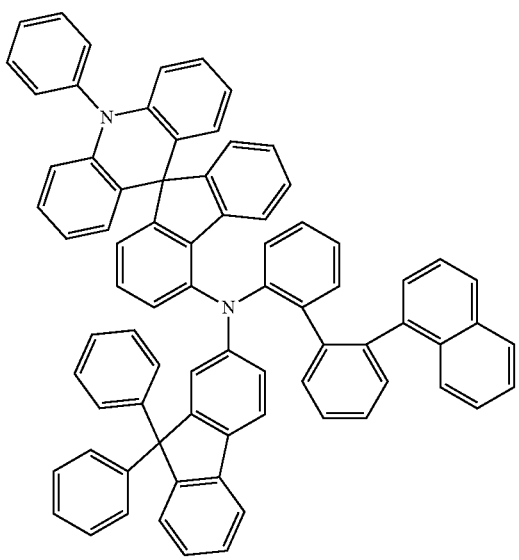

259
-continued
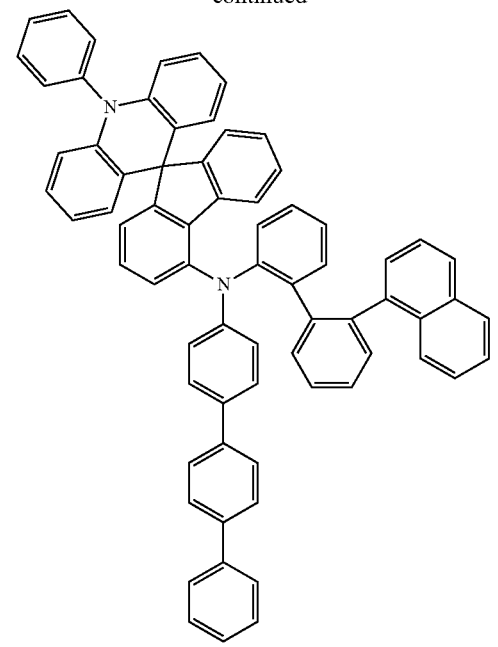
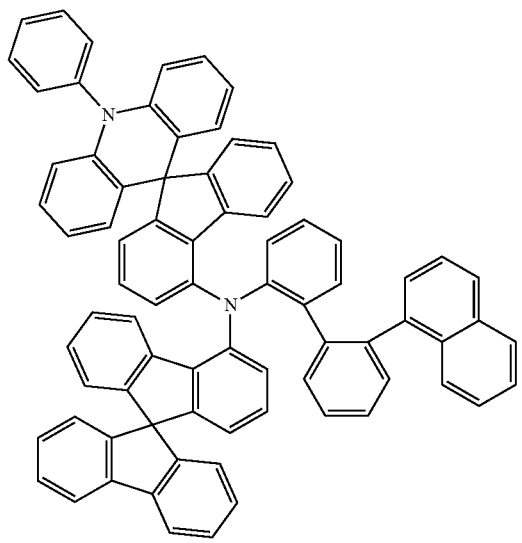
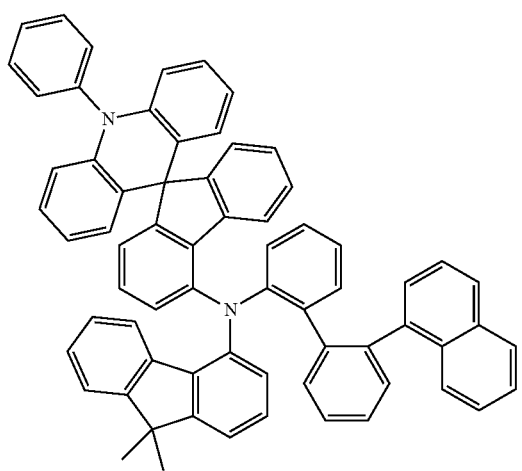
260
-continued
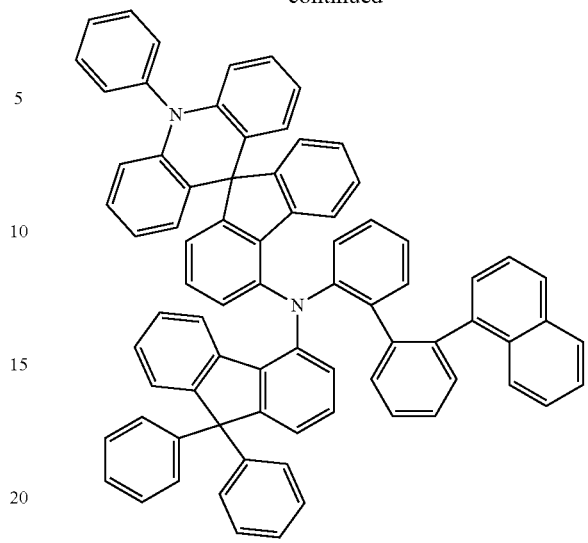
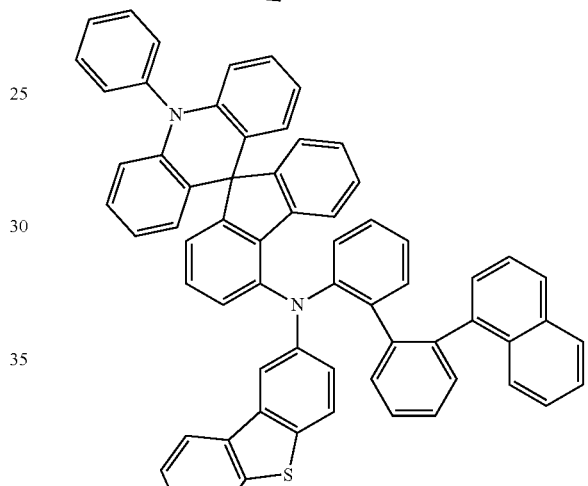
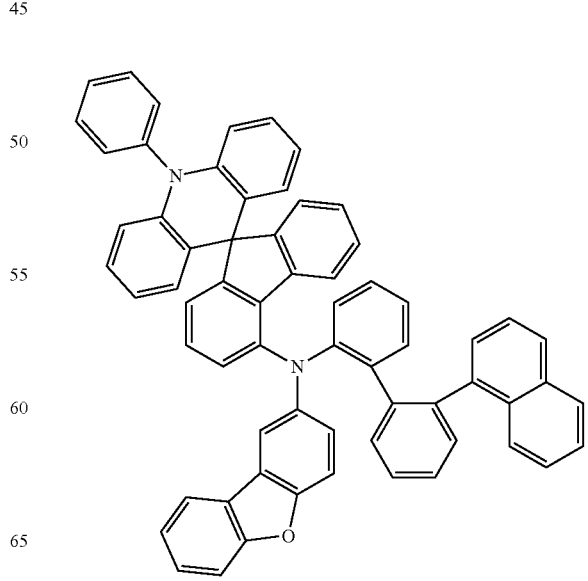

261
-continued
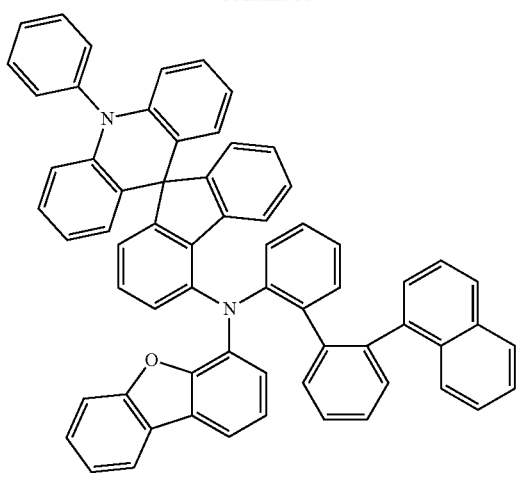
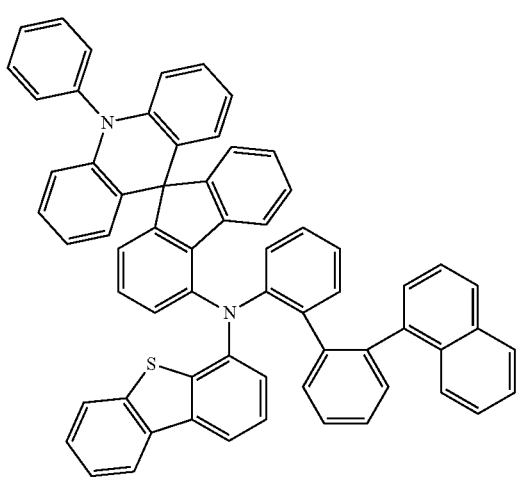
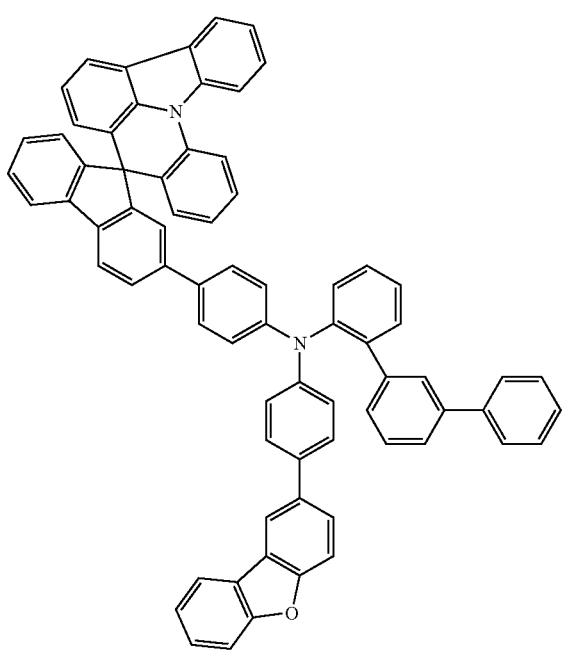
262
-continued
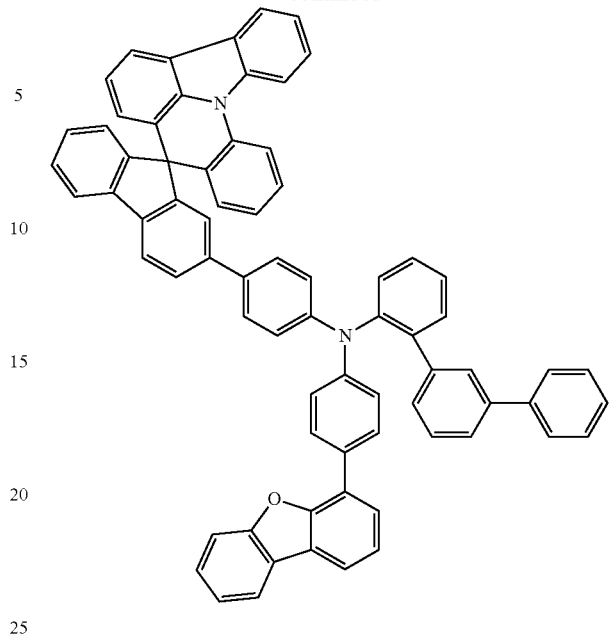
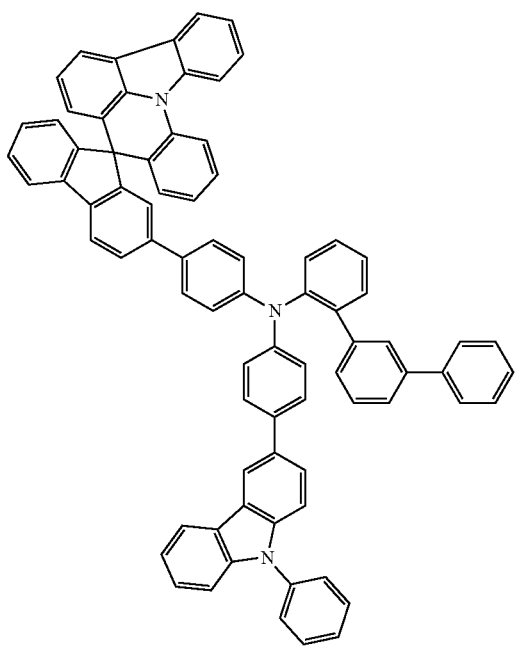

263
-continued
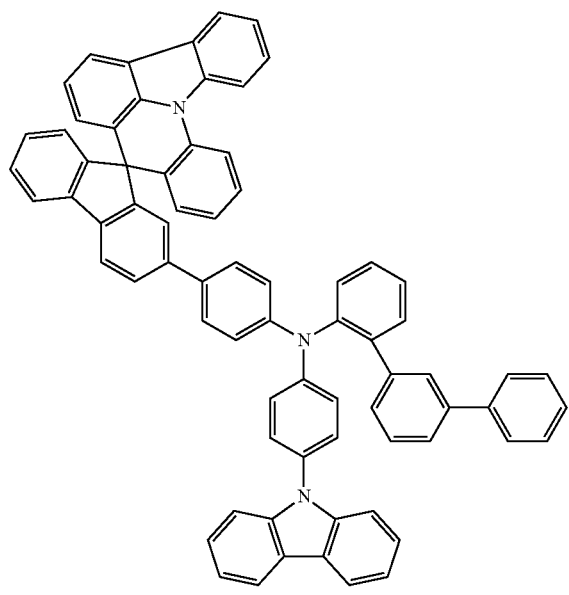
264
-continued
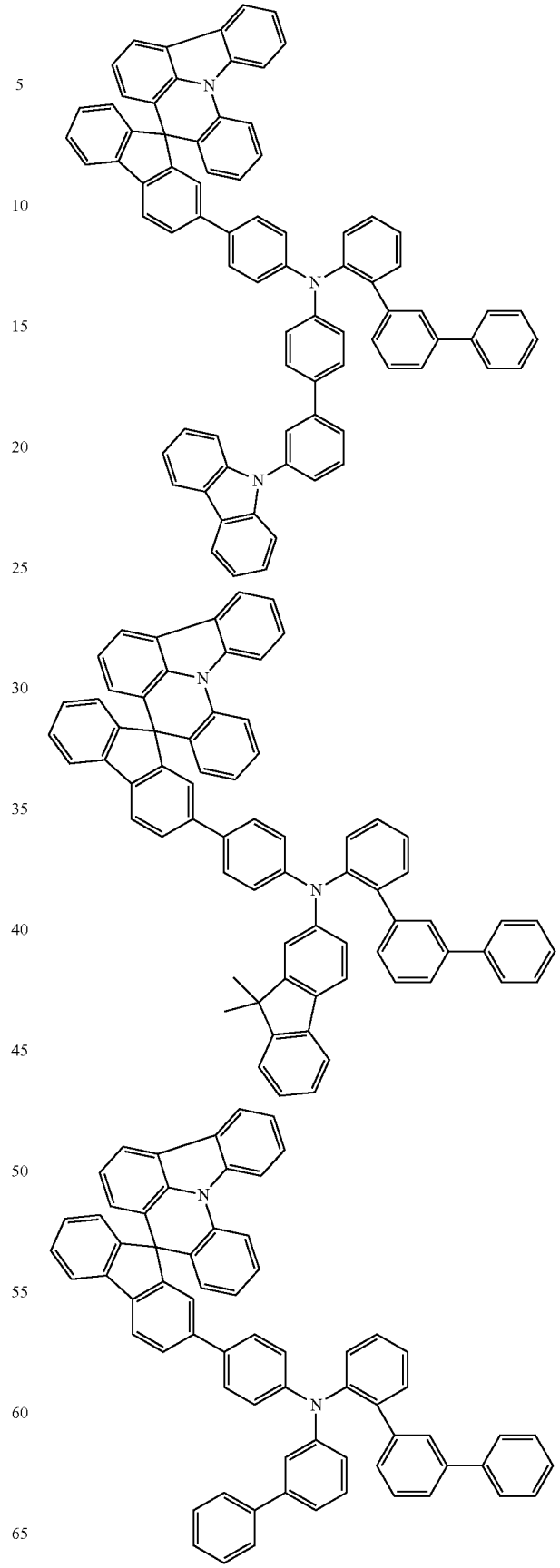
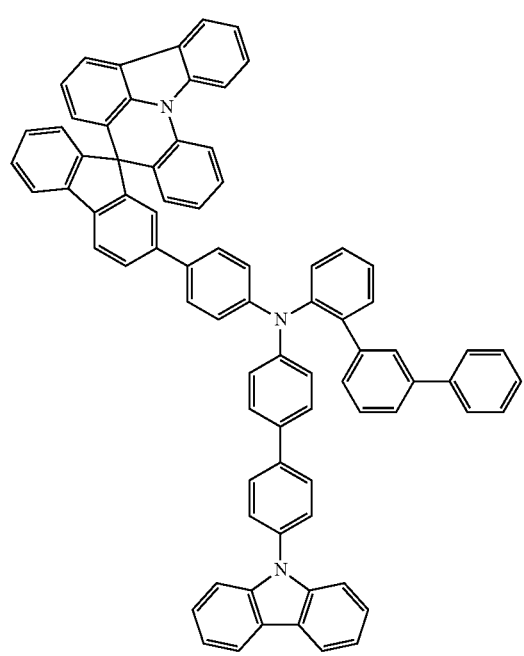

265
-continued
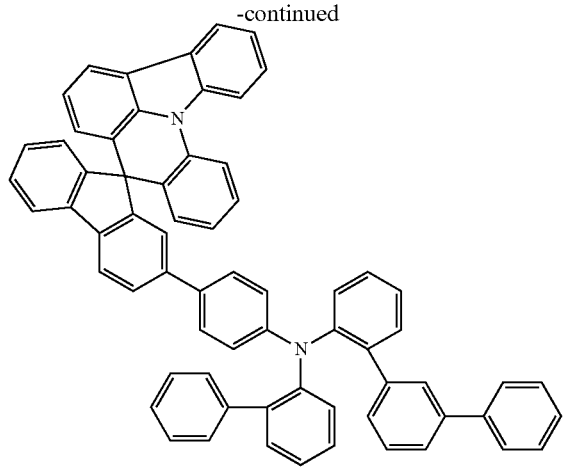
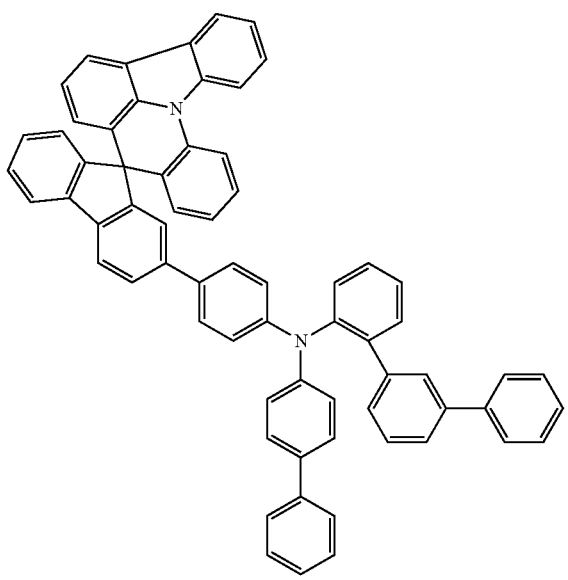
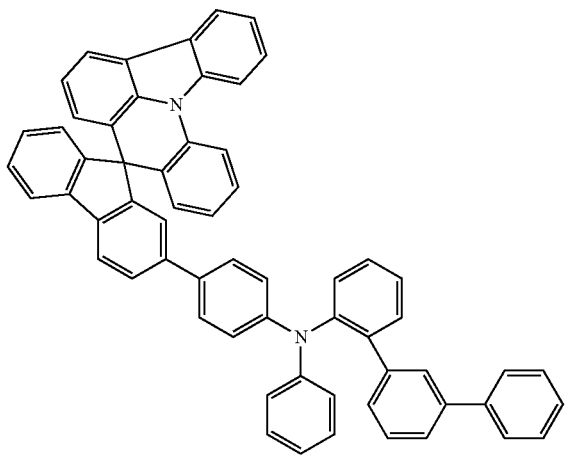
266
-continued
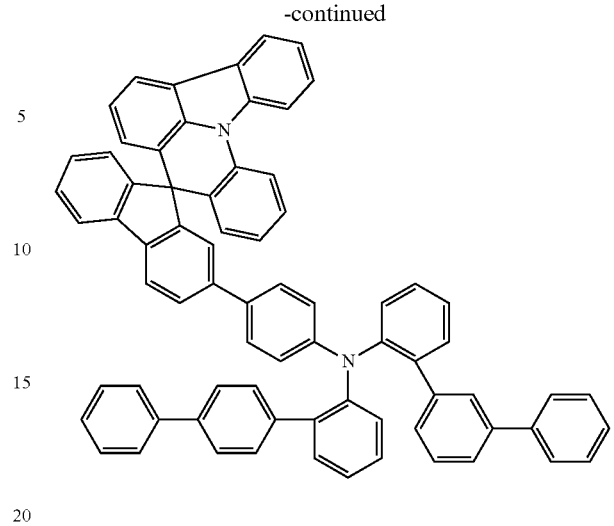
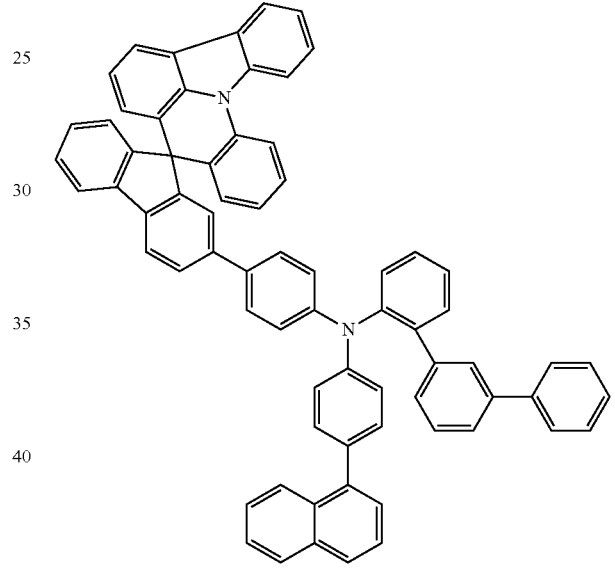
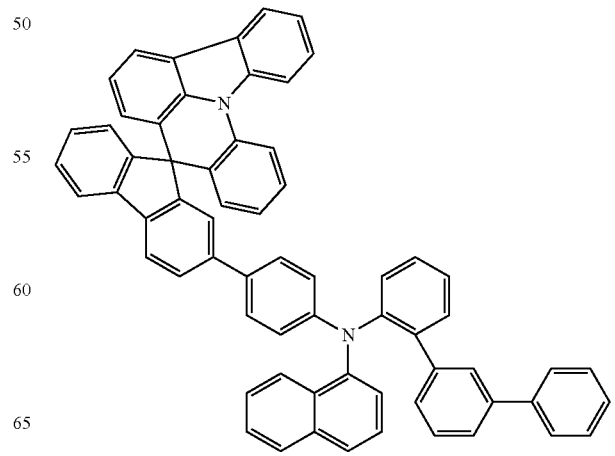

267
-continued
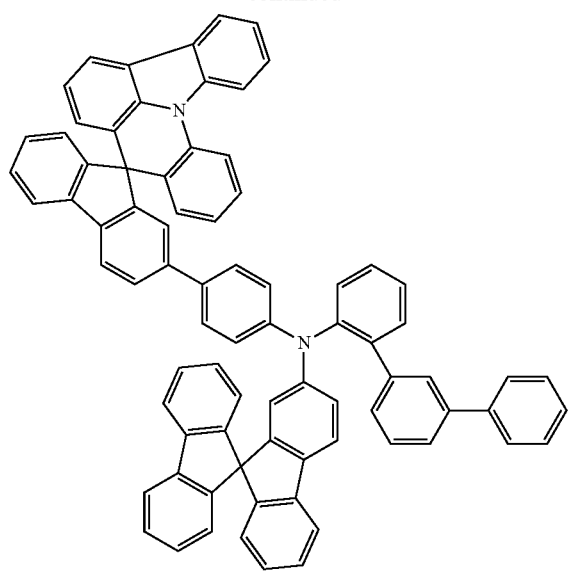
268
-continued
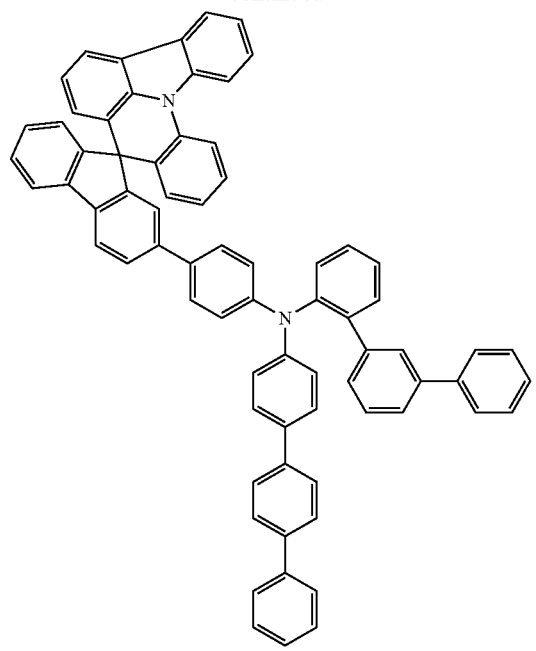
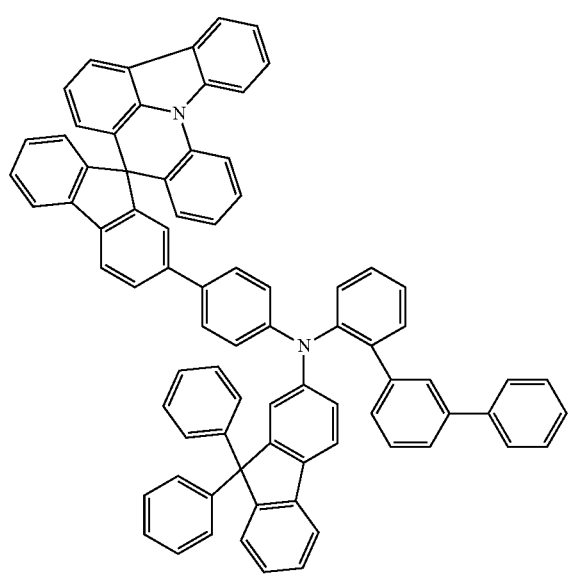
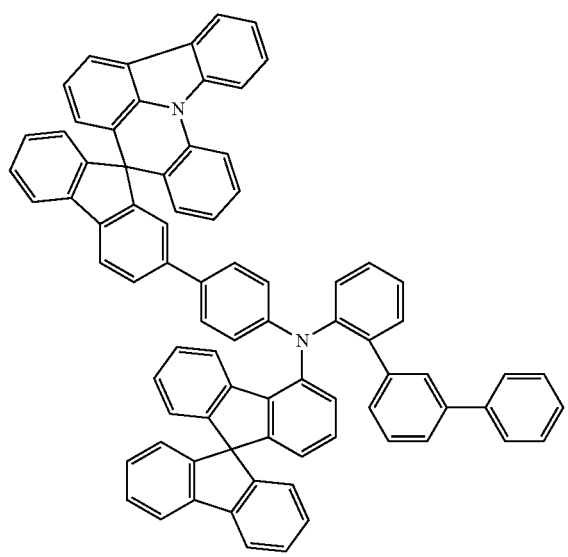

269
-continued
270
-continued
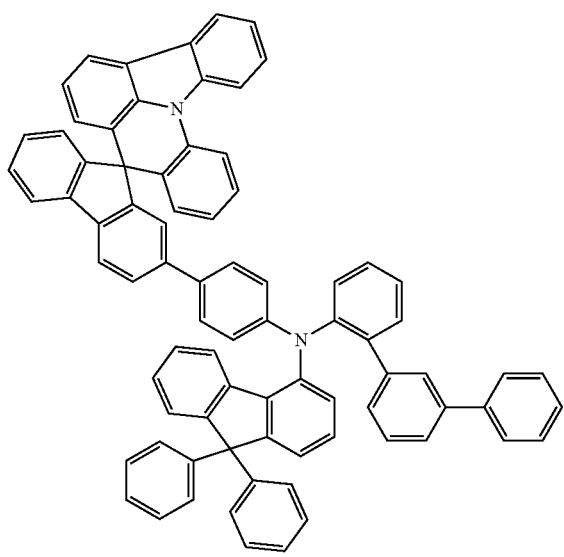
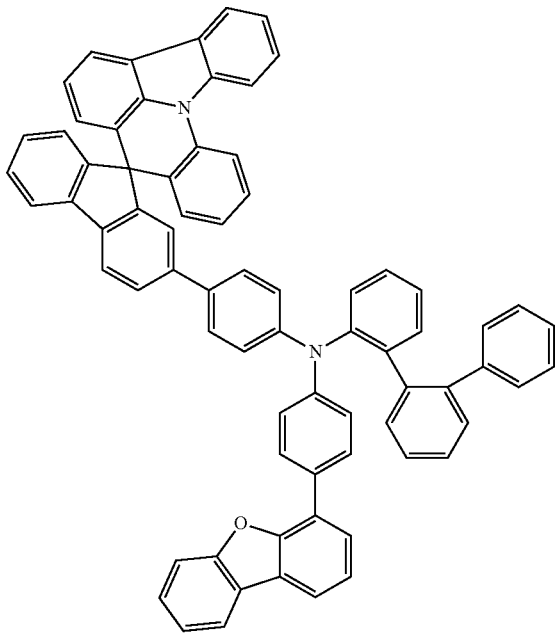
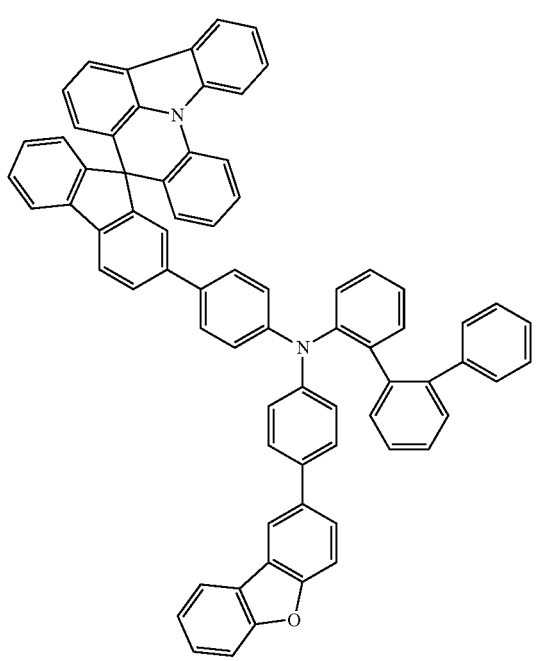
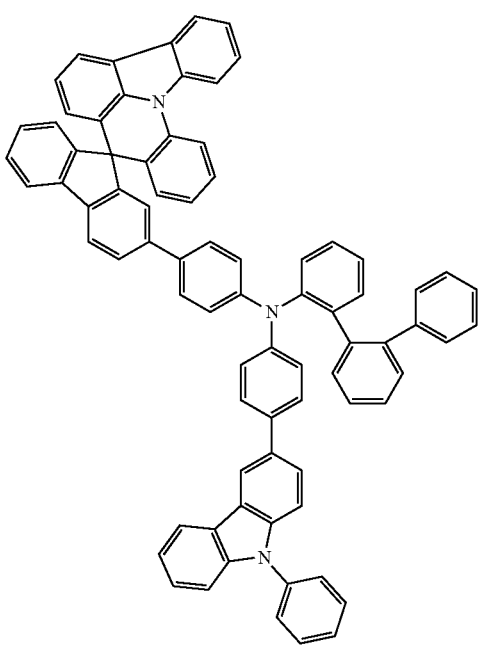

271
-continued
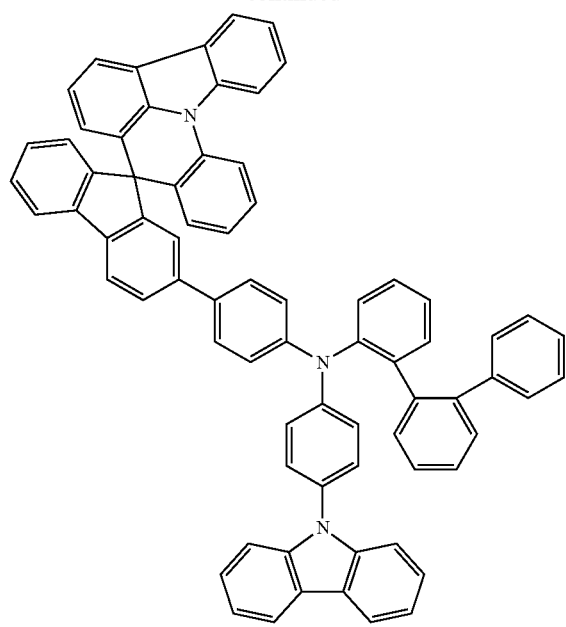
272
-continued
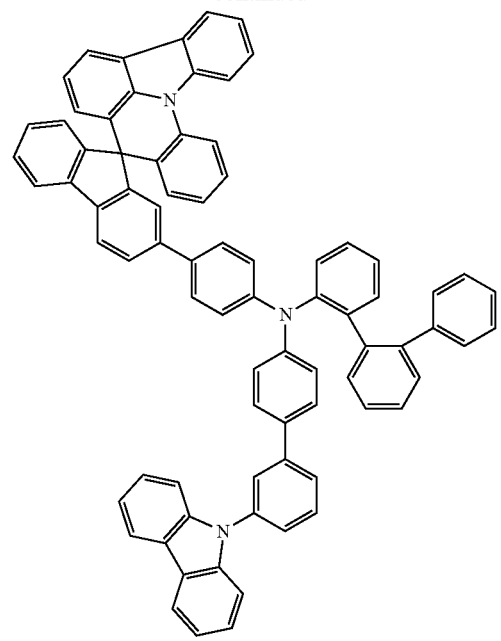
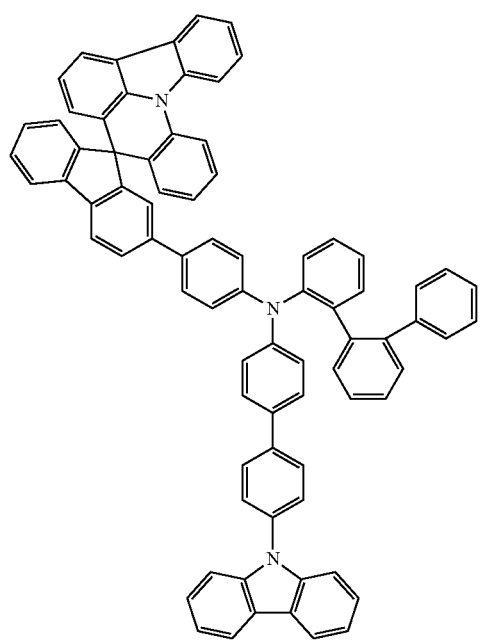
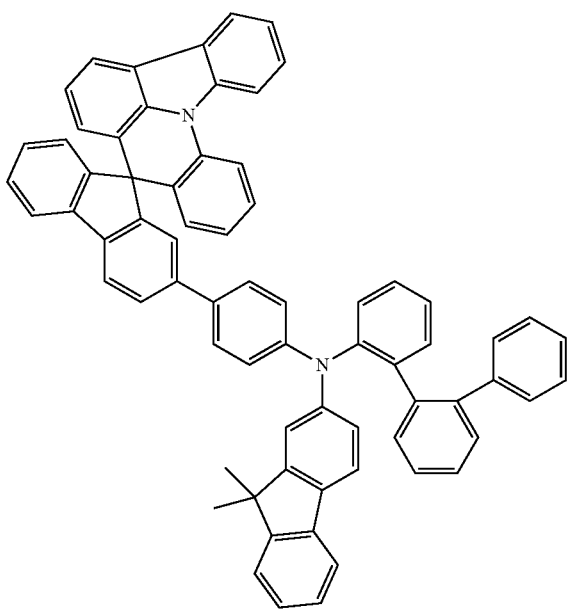

273
-continued
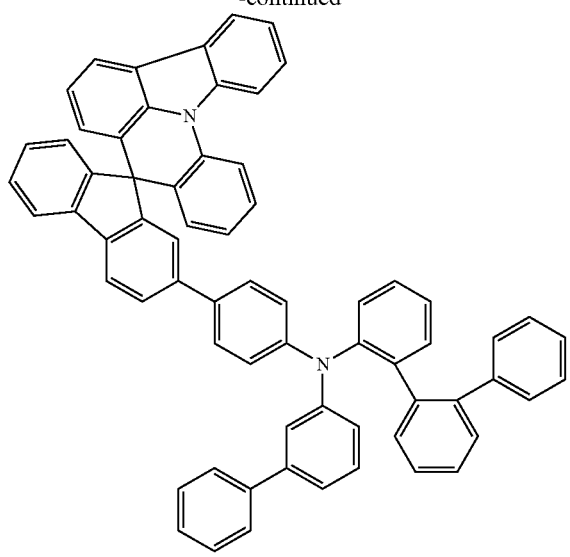
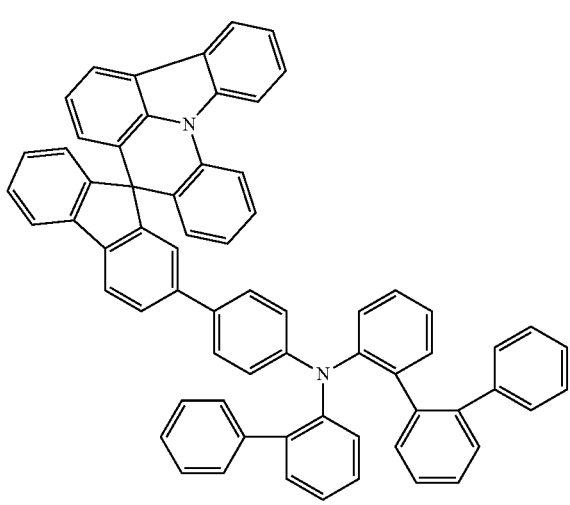
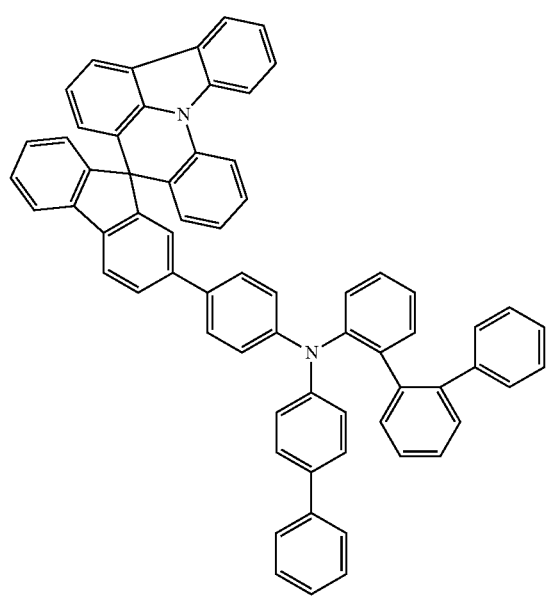
274
-continued
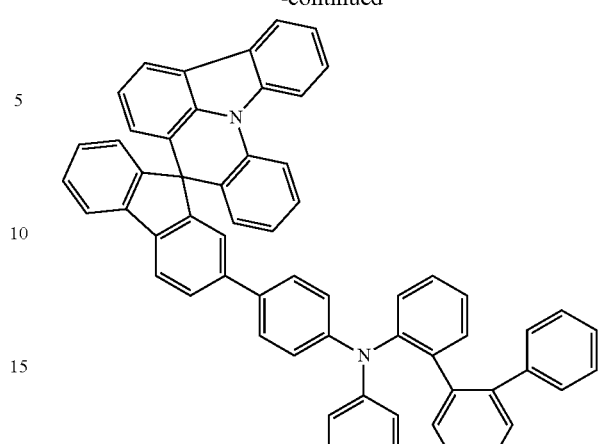
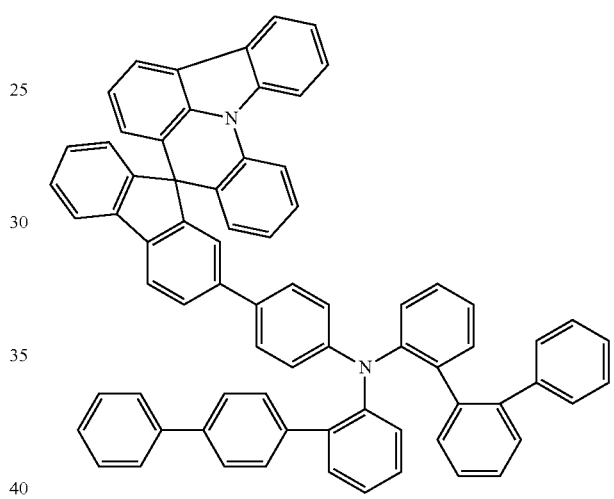
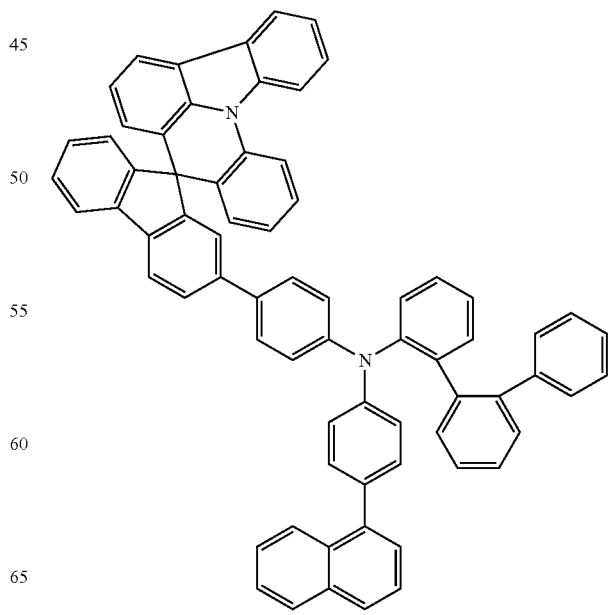

275
-continued
276
-continued
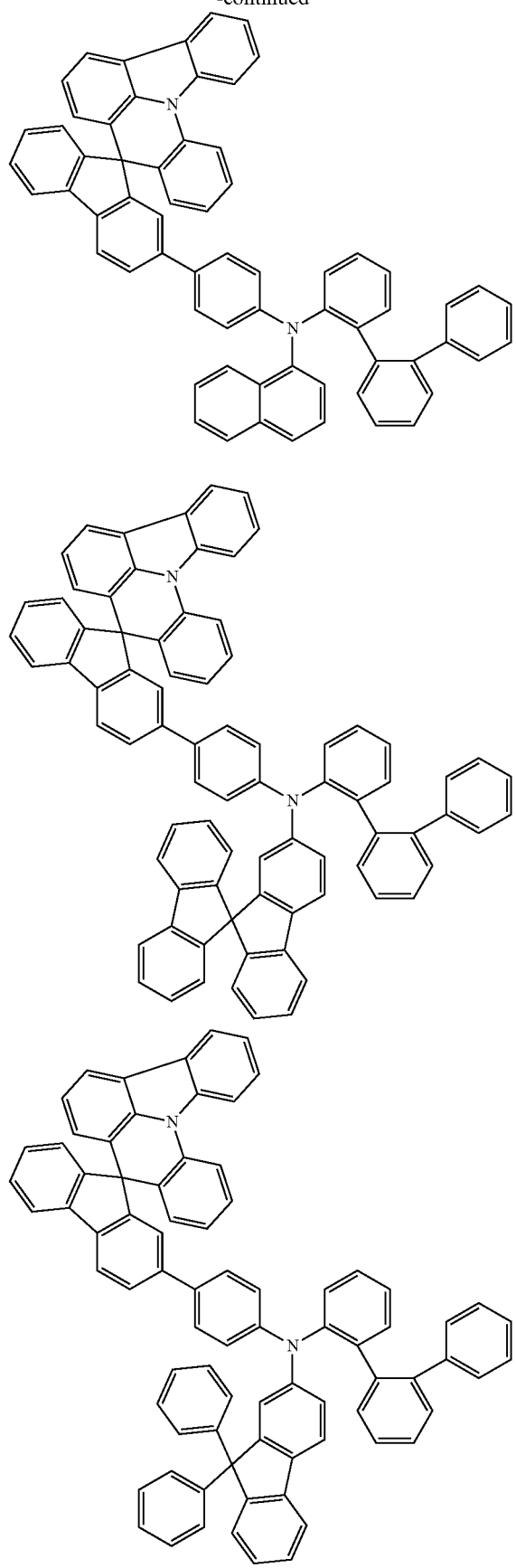
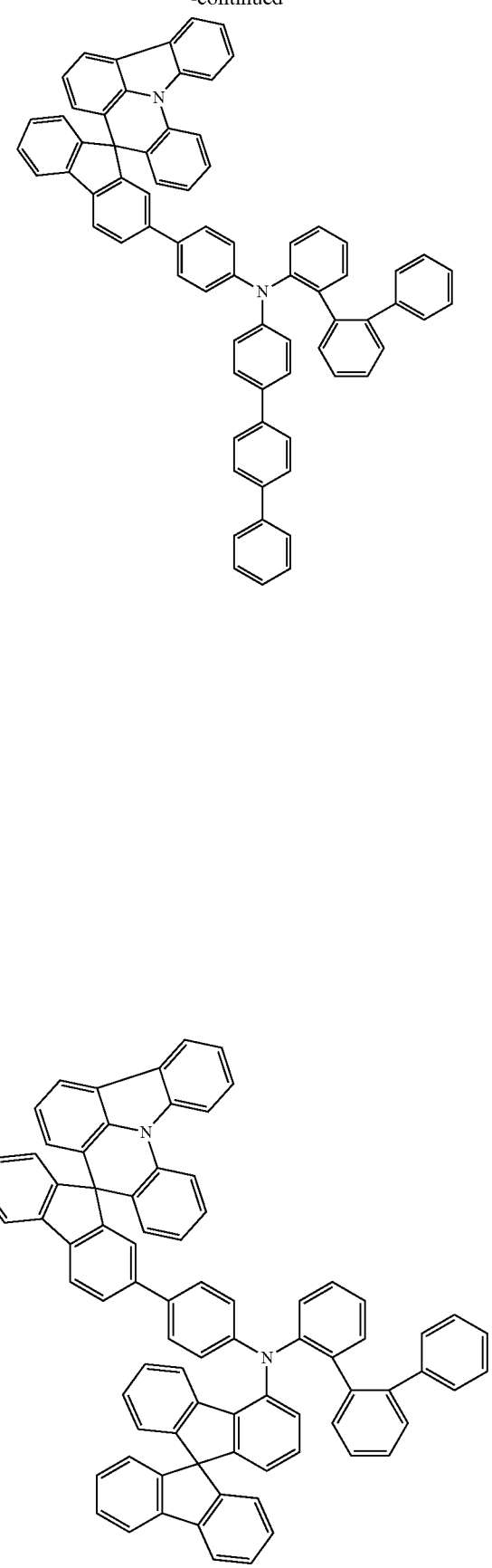

277
-continued
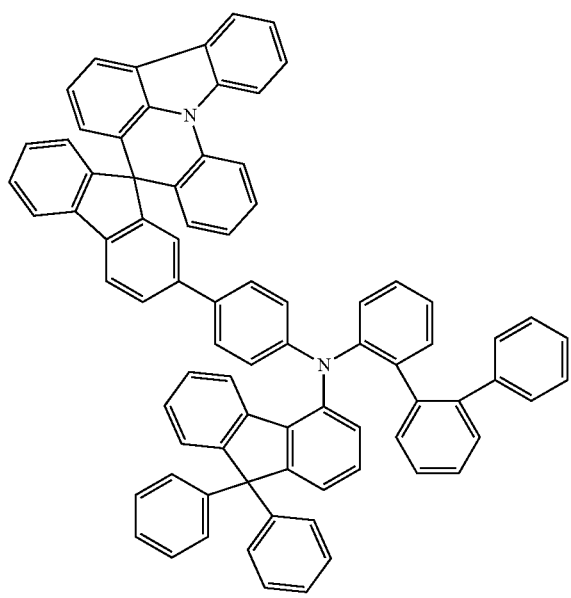
278
-continued
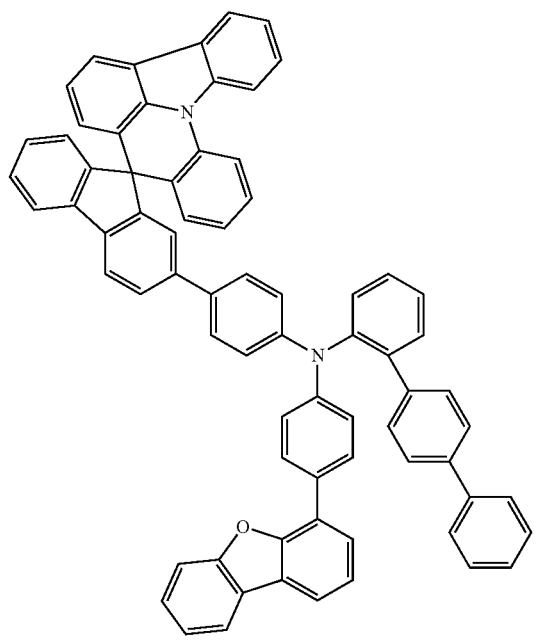
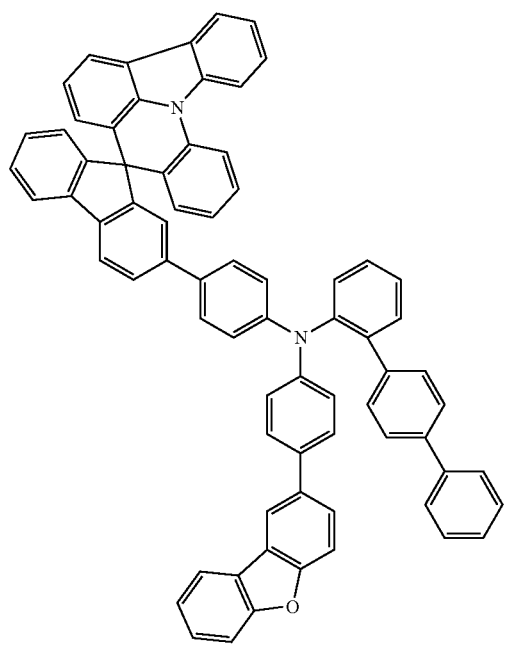
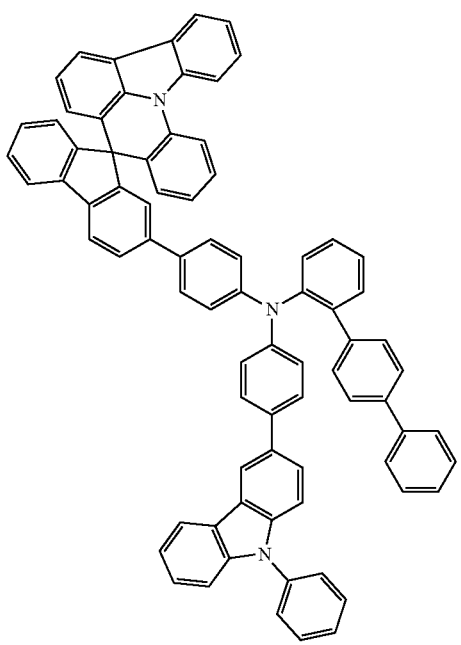

279
-continued
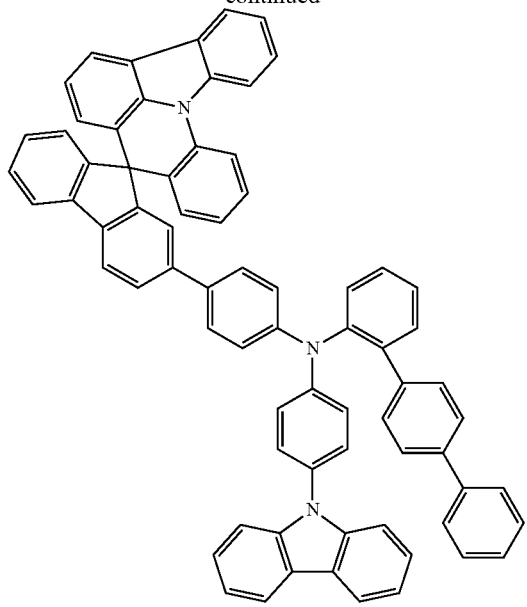
280
-continued
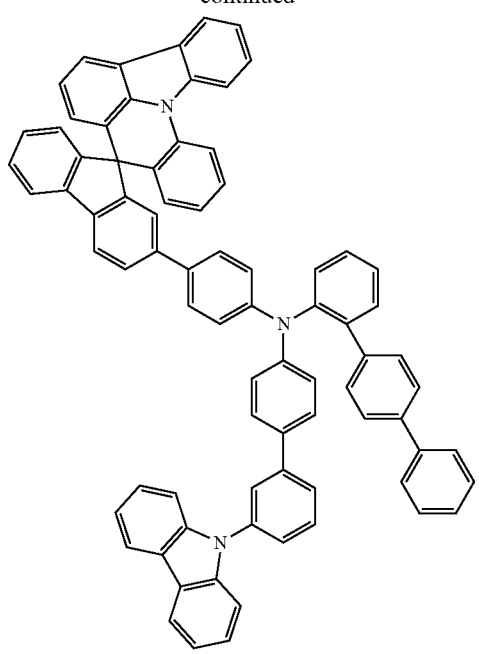
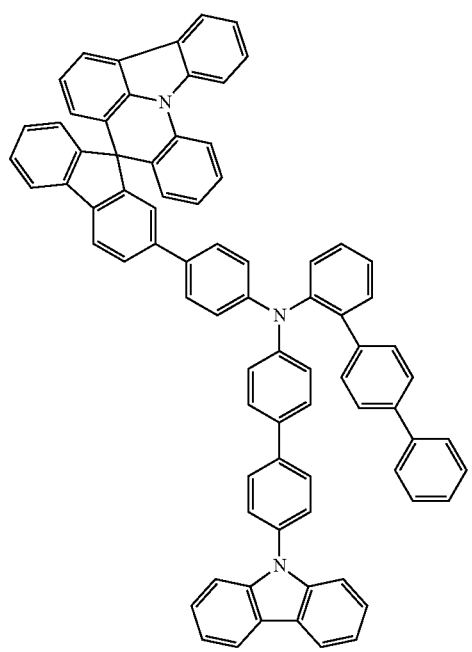
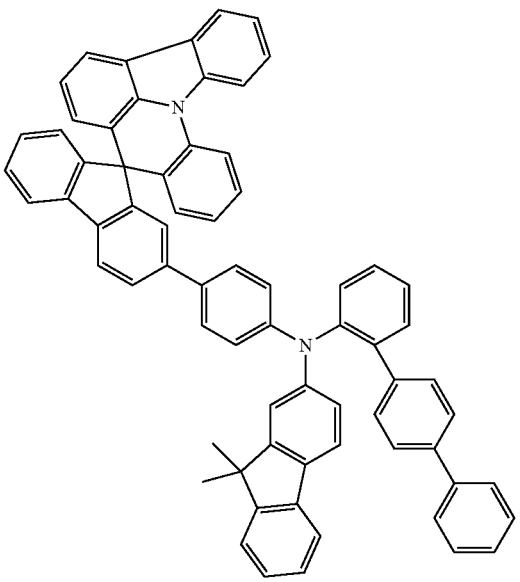

281
-continued
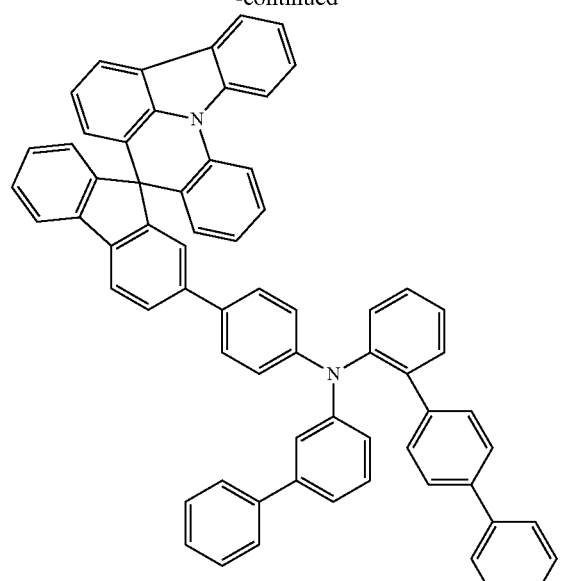
282
-continued
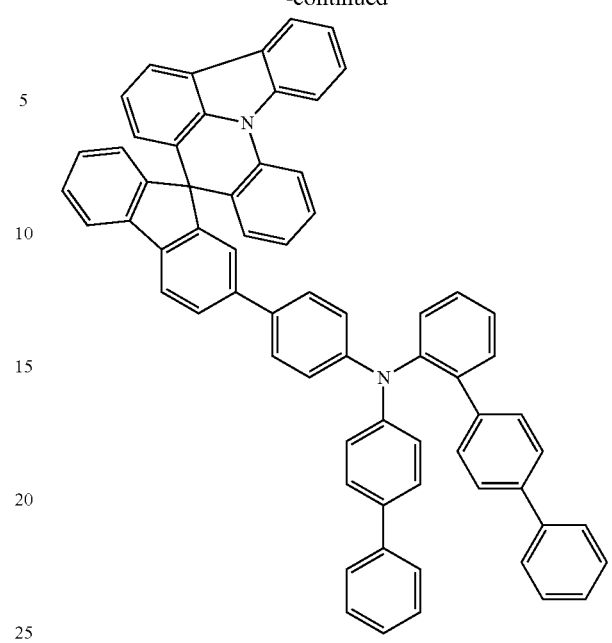
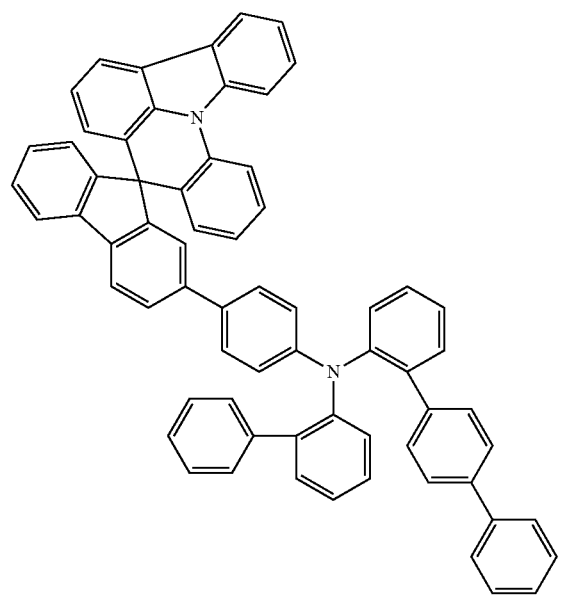
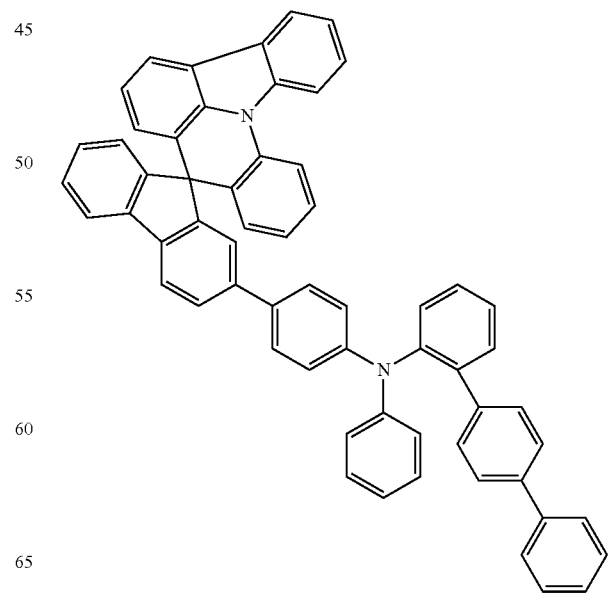

283
-continued
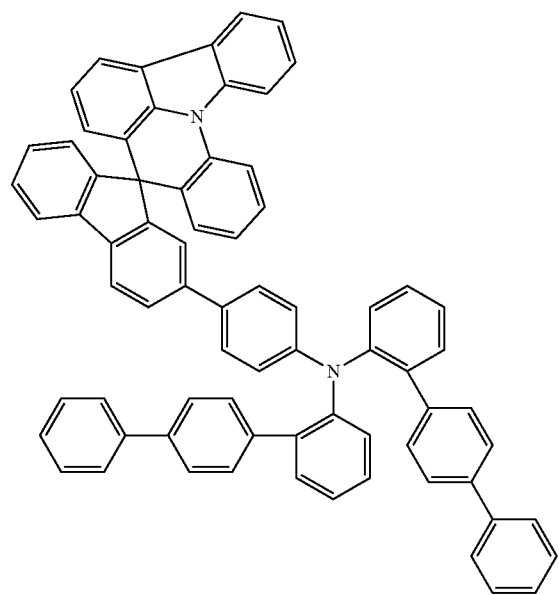
284
-continued
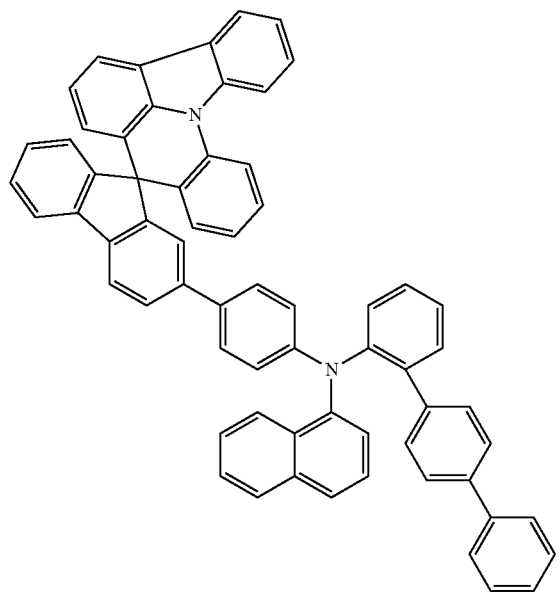
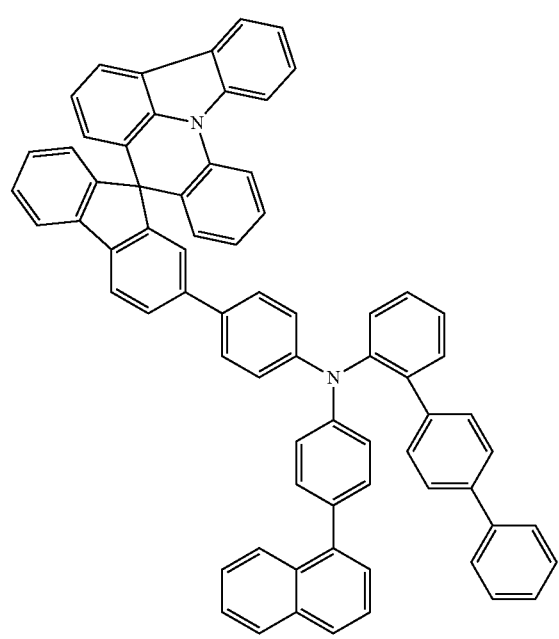
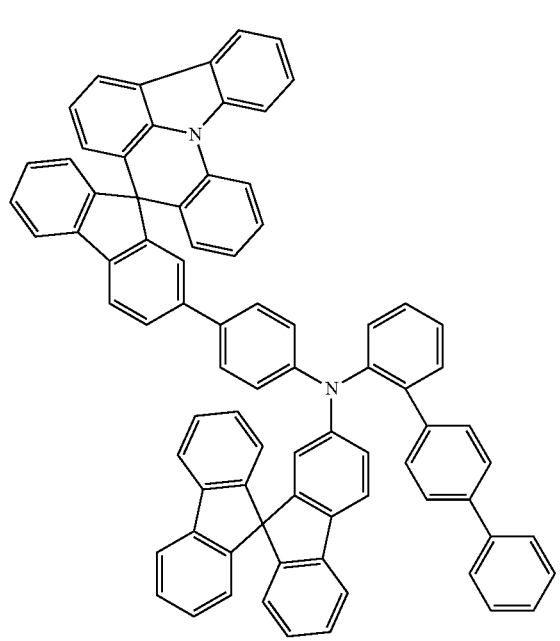

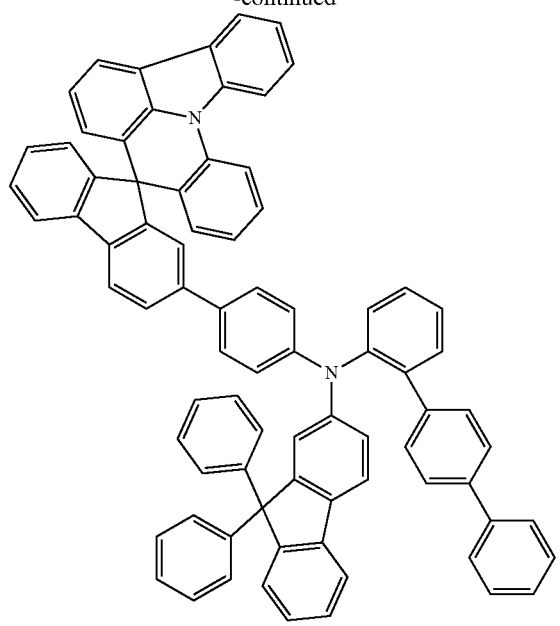
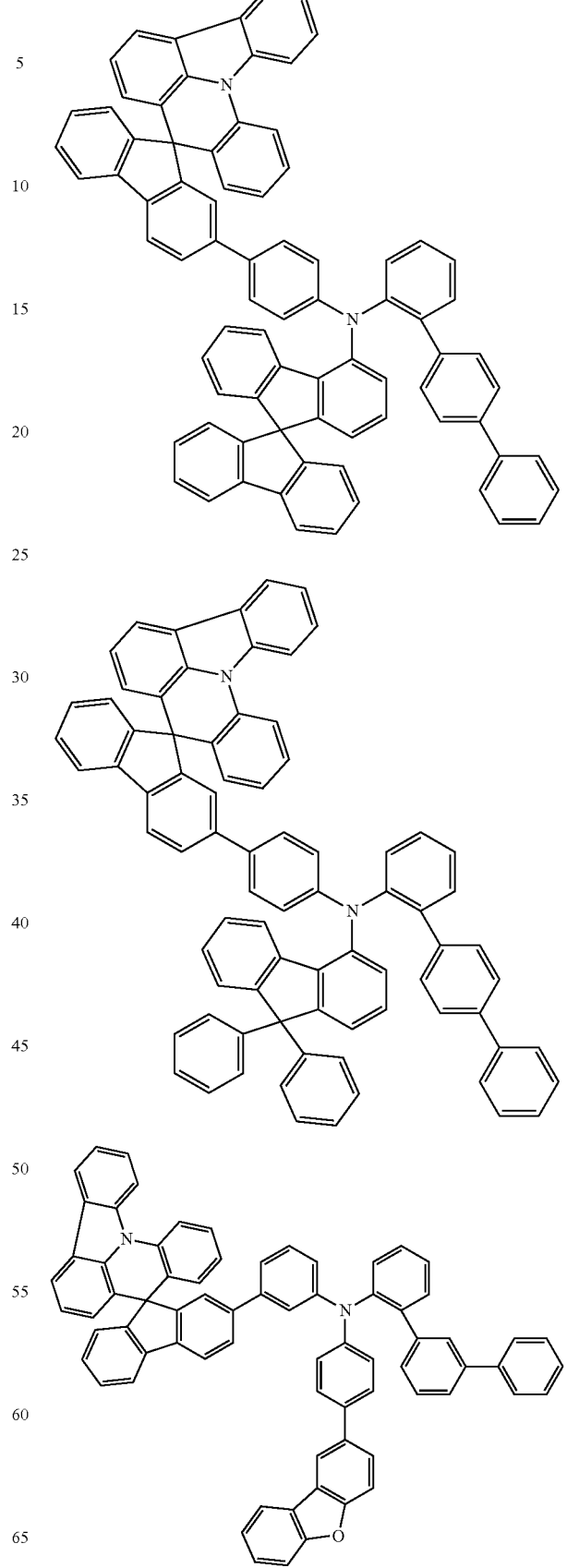

287
-continued
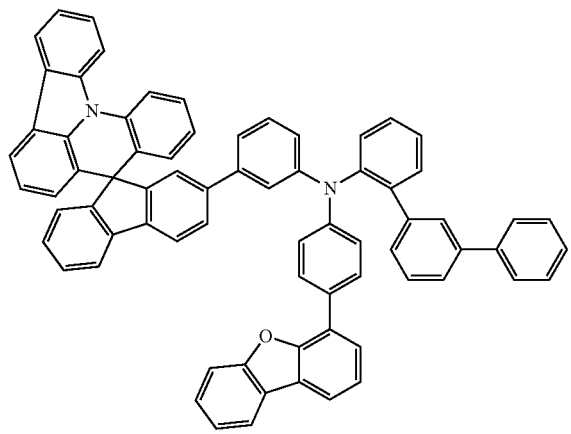
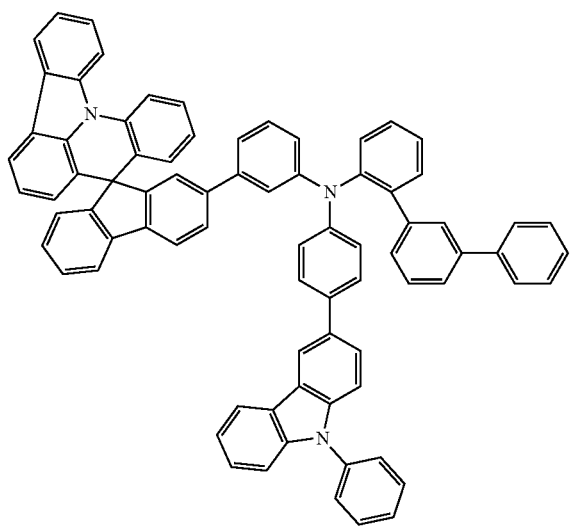
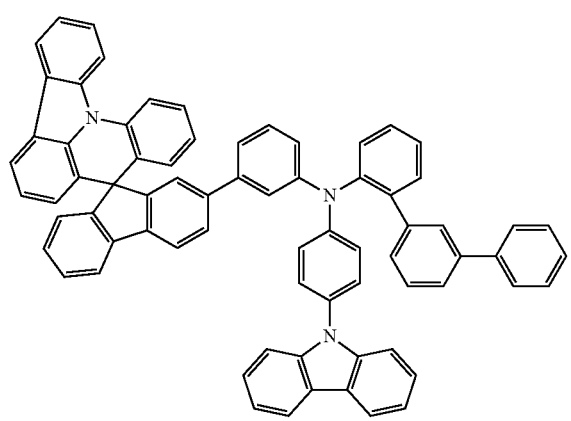
288
-continued
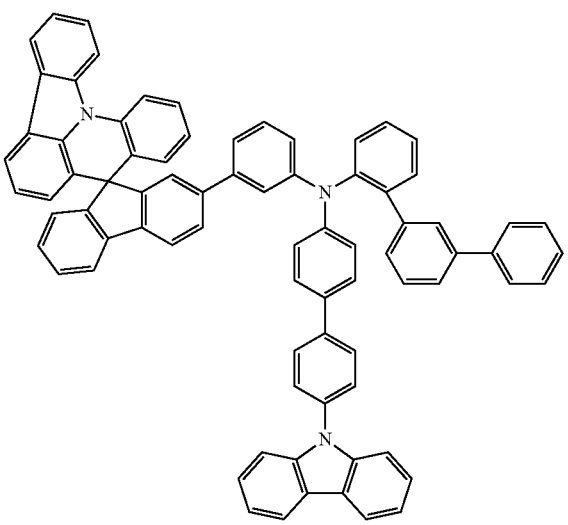
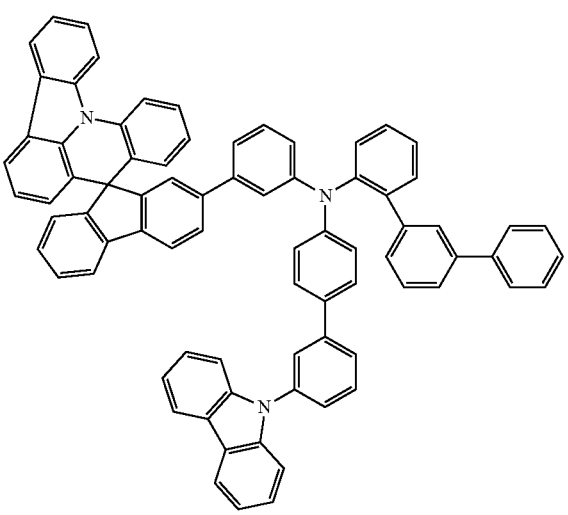
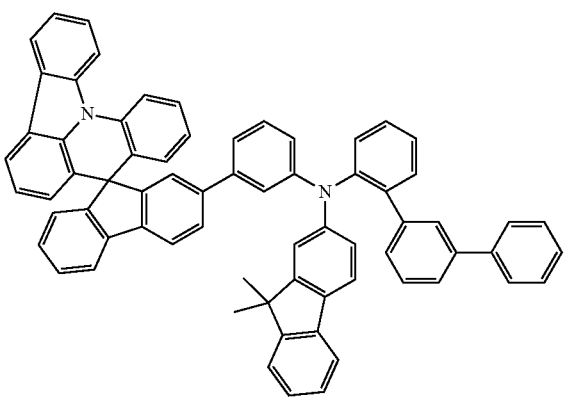

289
-continued
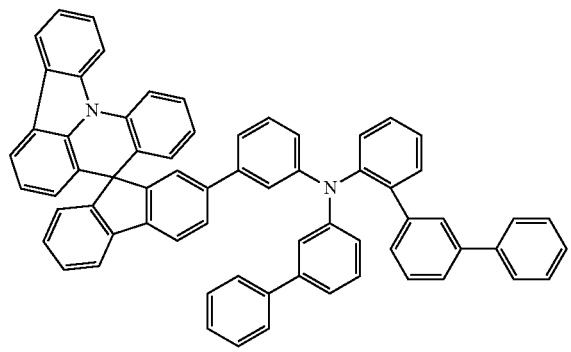
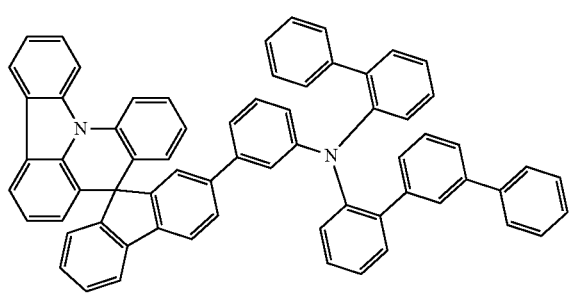
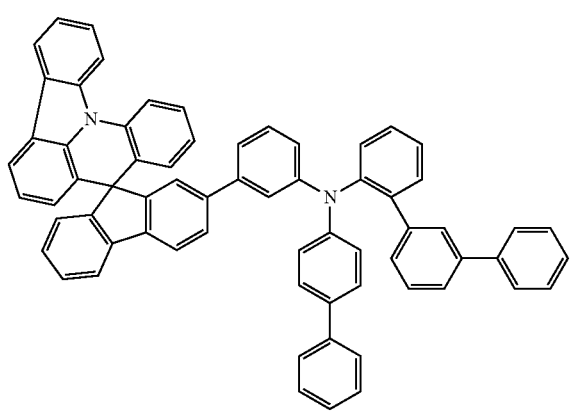
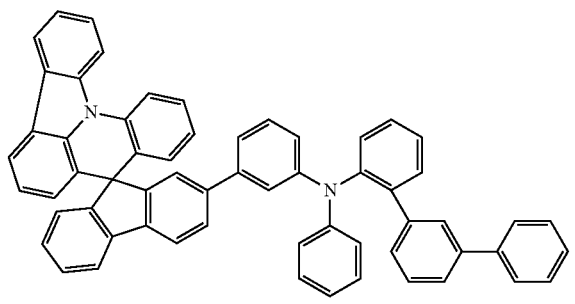
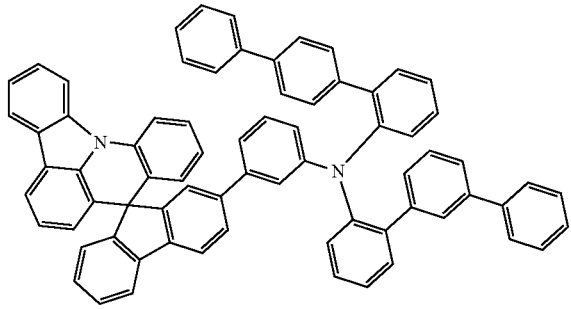
290
-continued
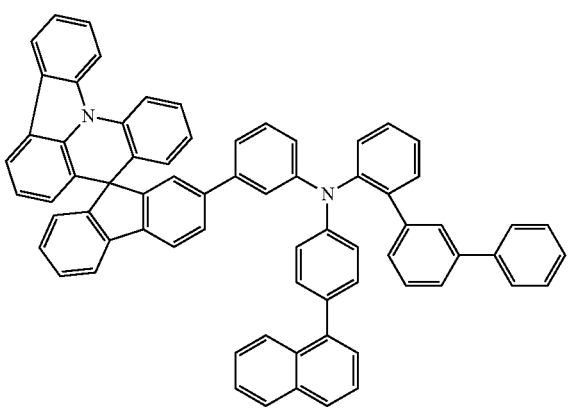
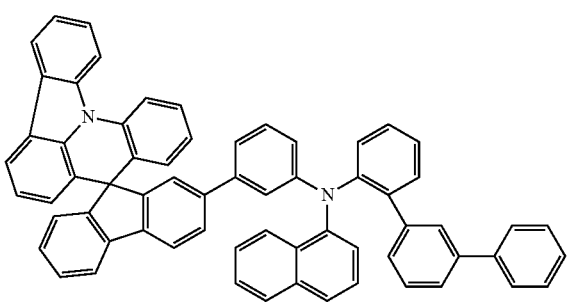
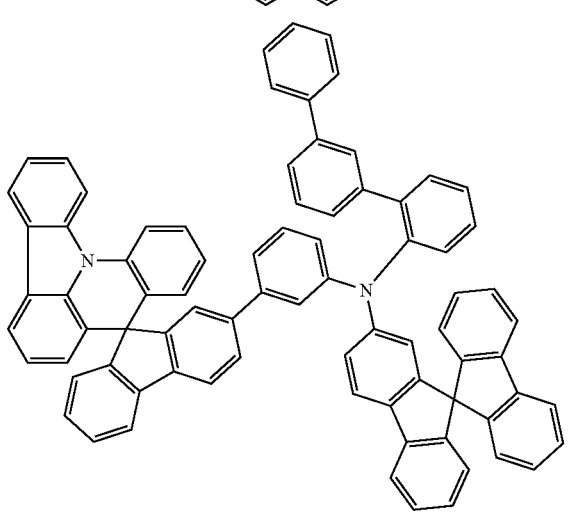
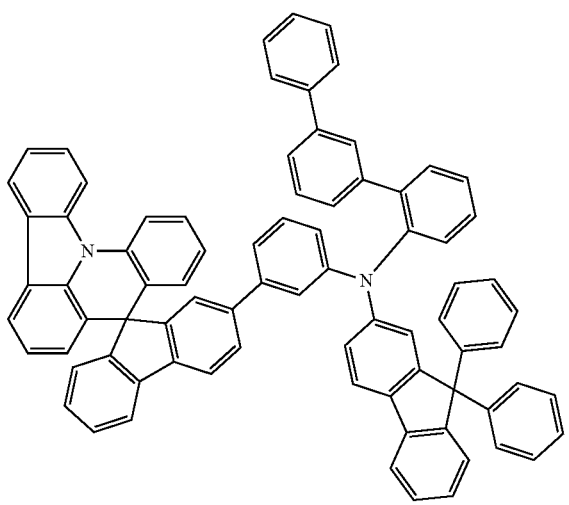

291
-continued
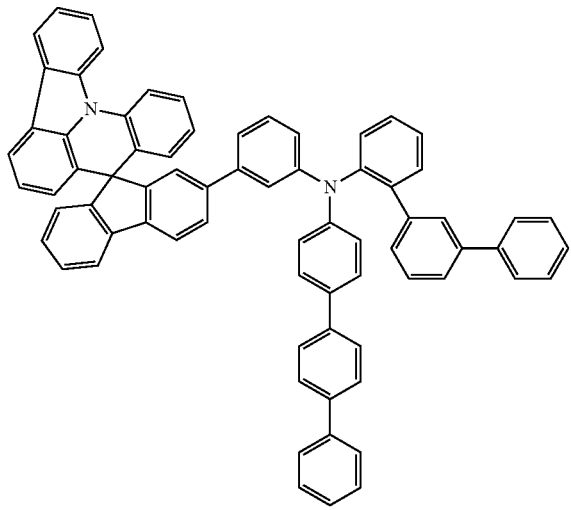
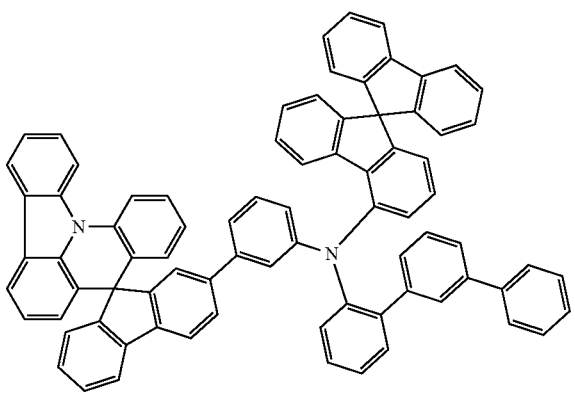
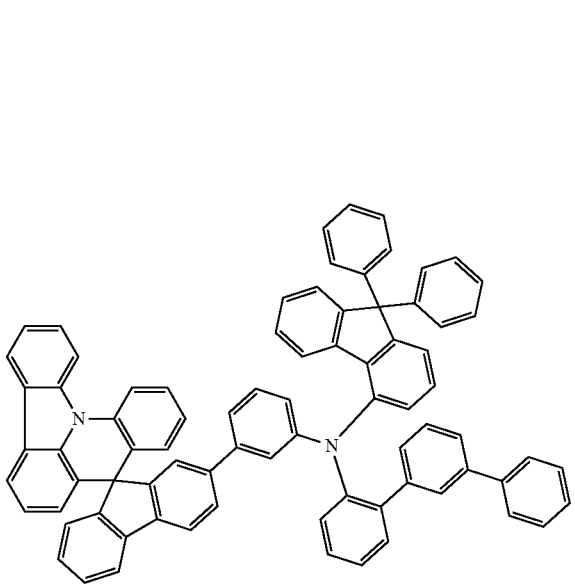
292
-continued
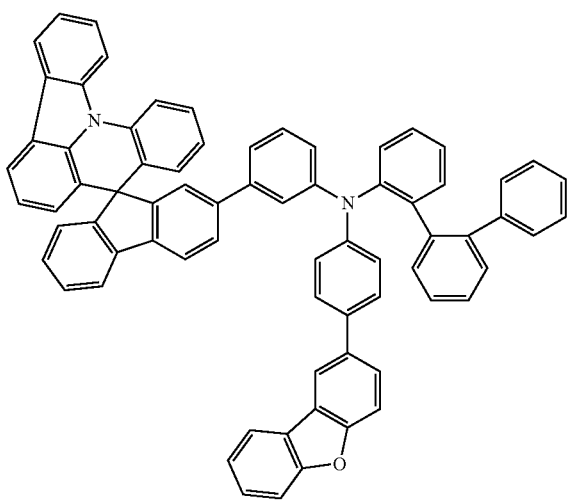
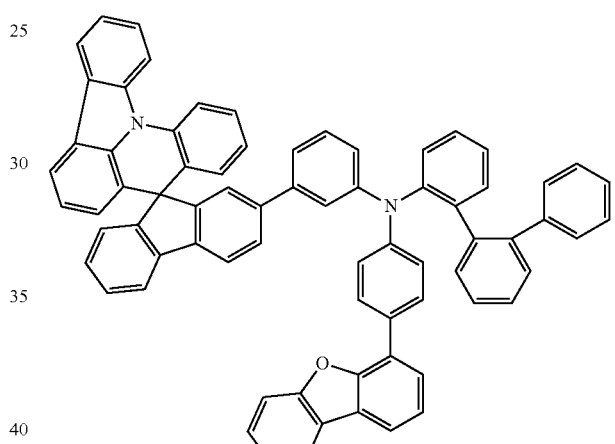
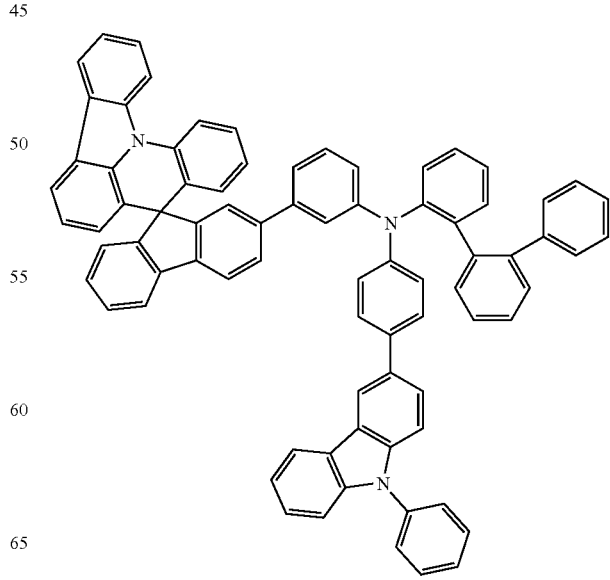

293
-continued
294
-continued
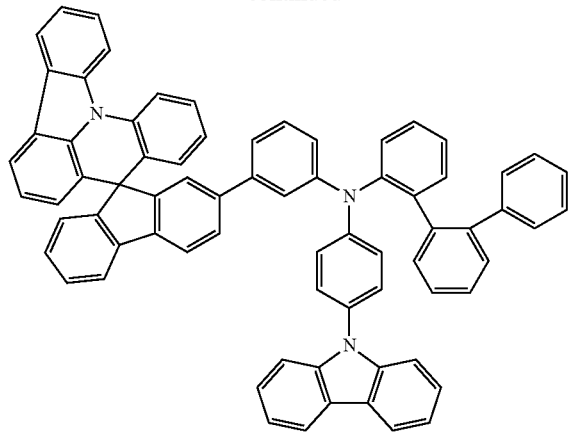
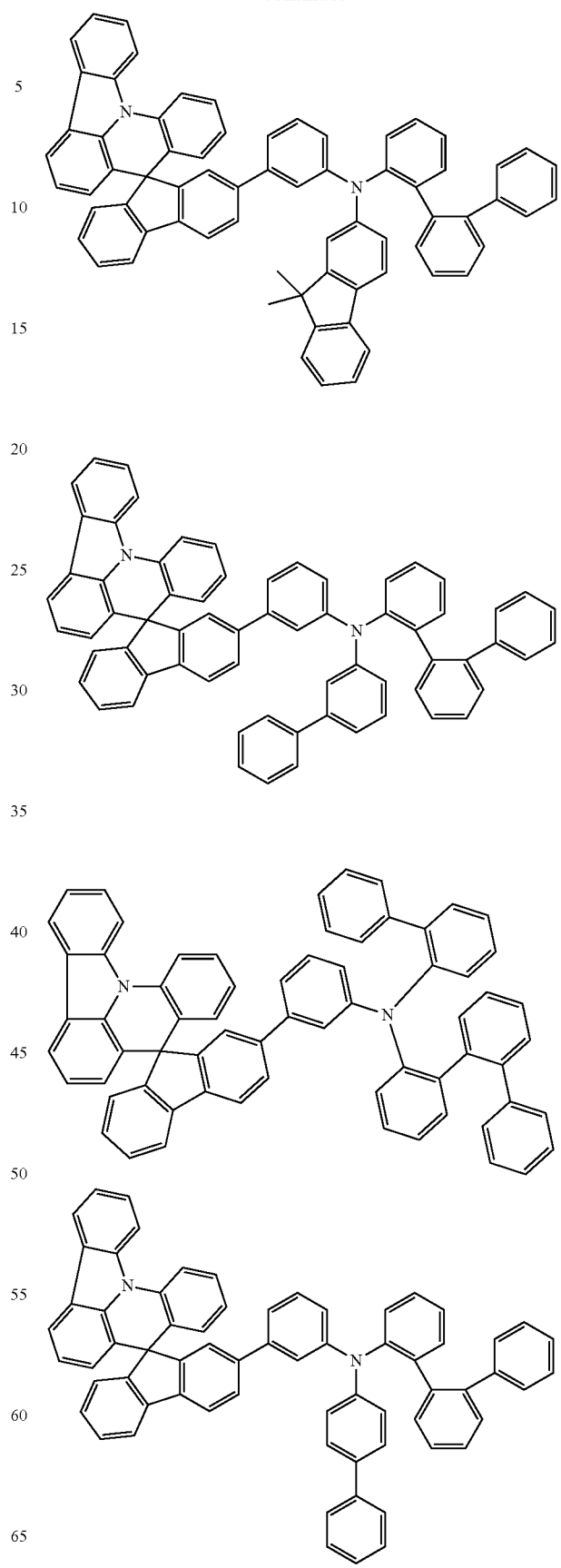

295
-continued
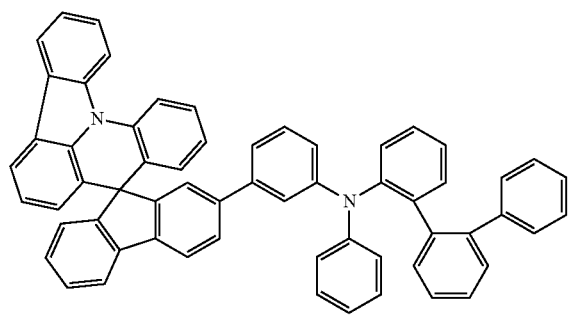
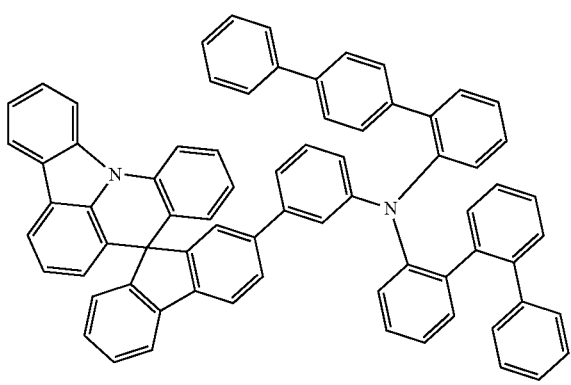
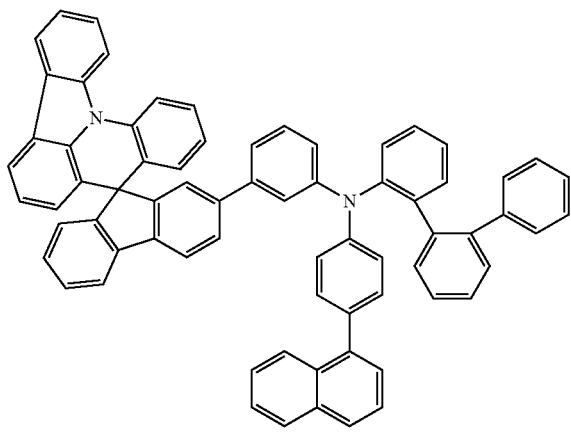
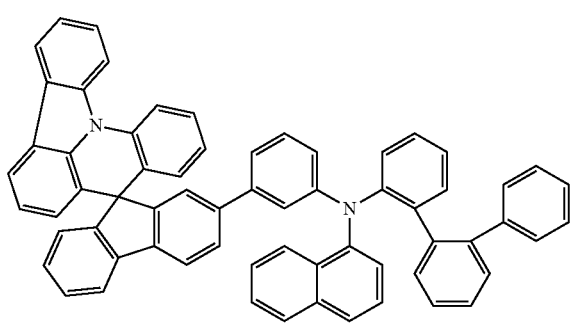
296
-continued
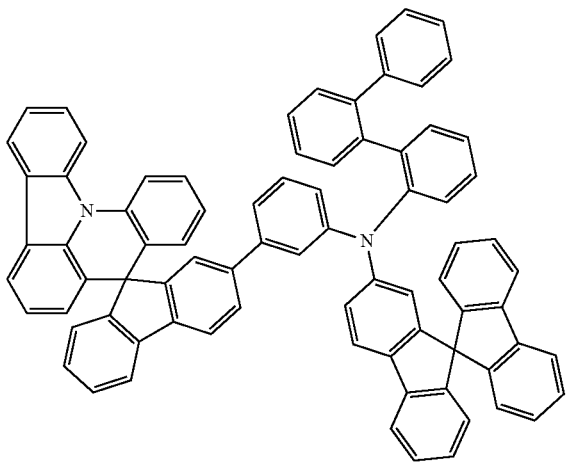
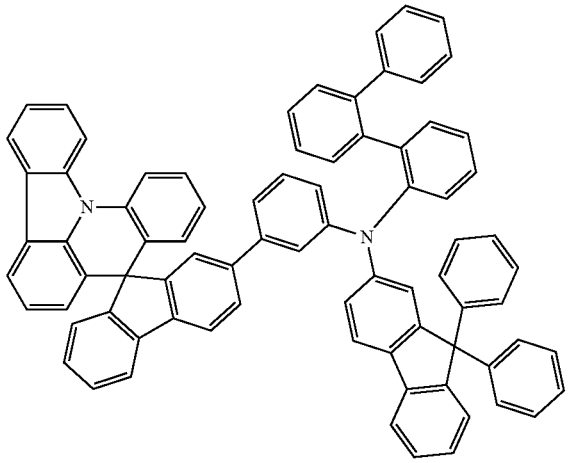
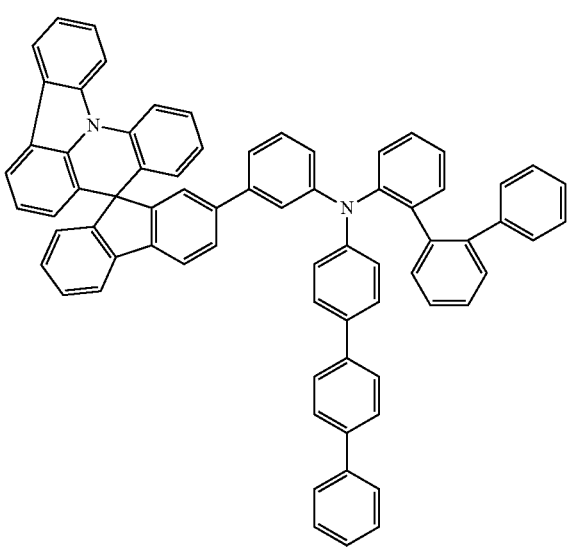

297
-continued
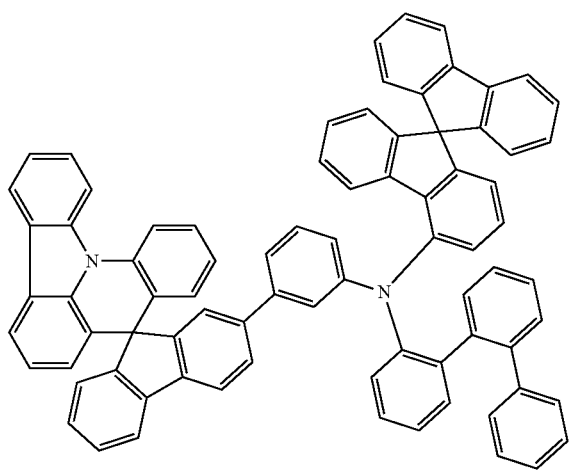
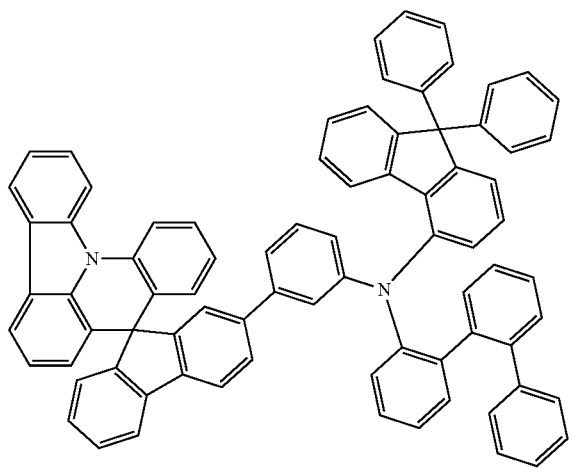
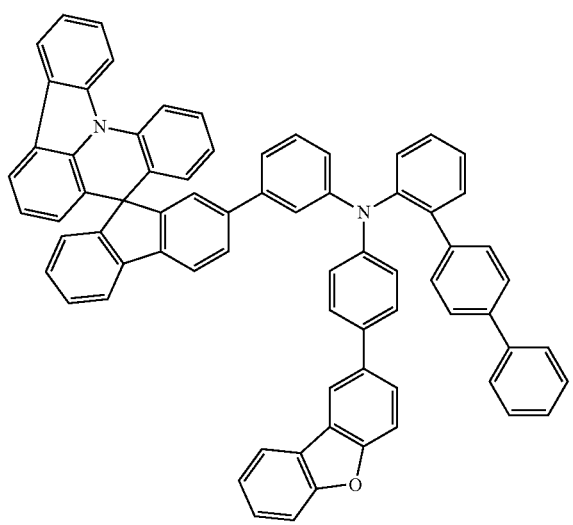
298
-continued
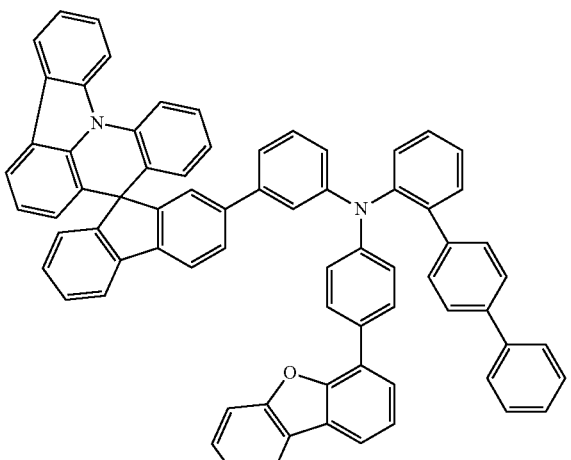
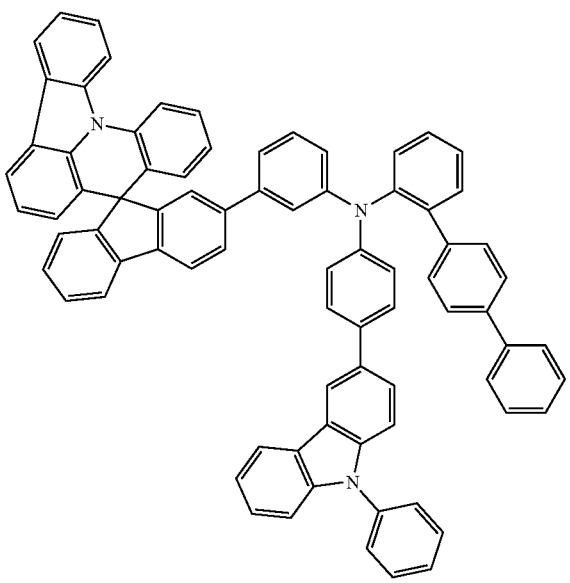
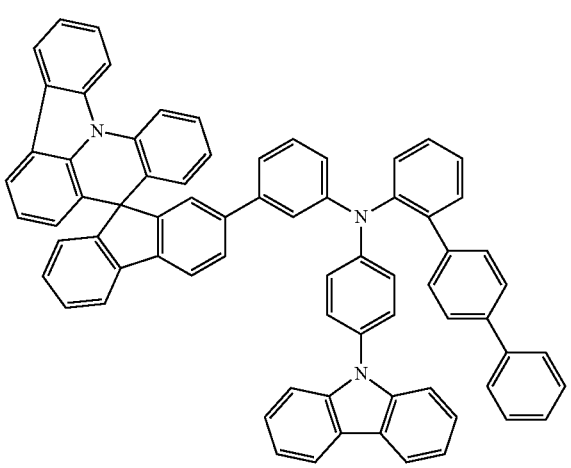

299
-continued
300
-continued
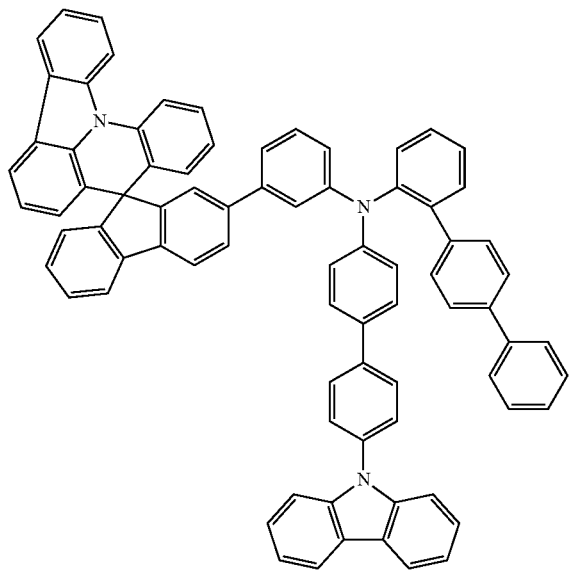
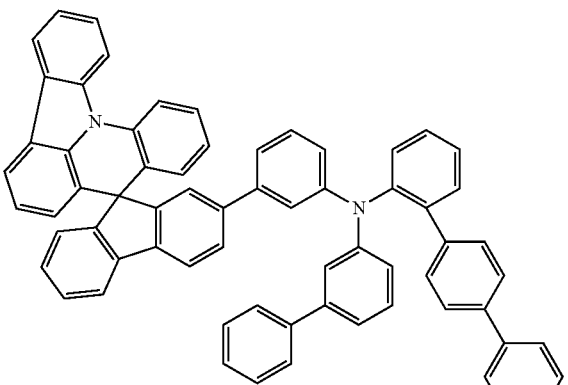
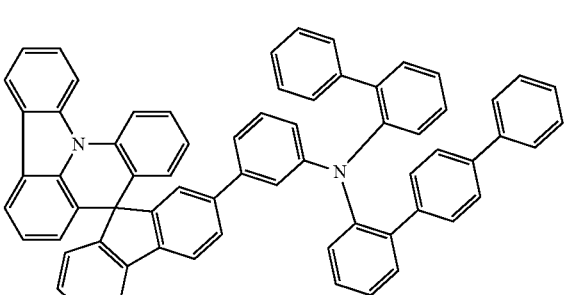
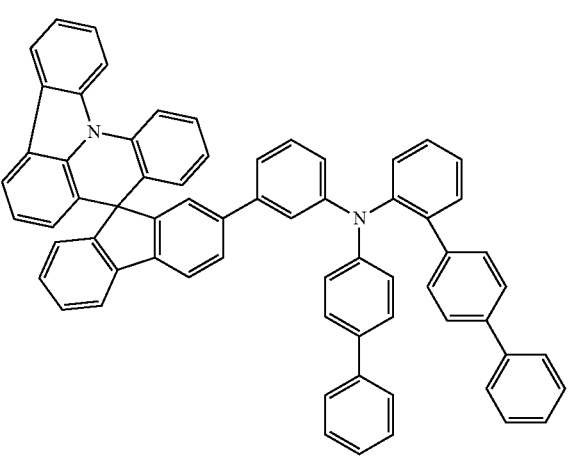
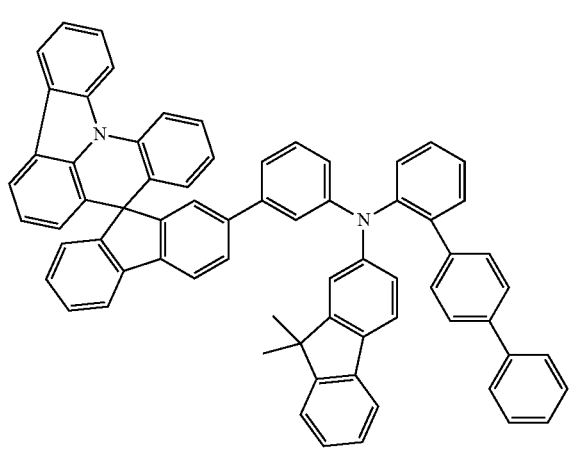
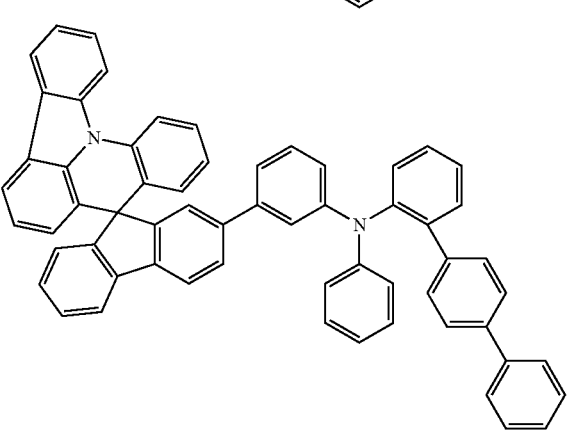

301
-continued
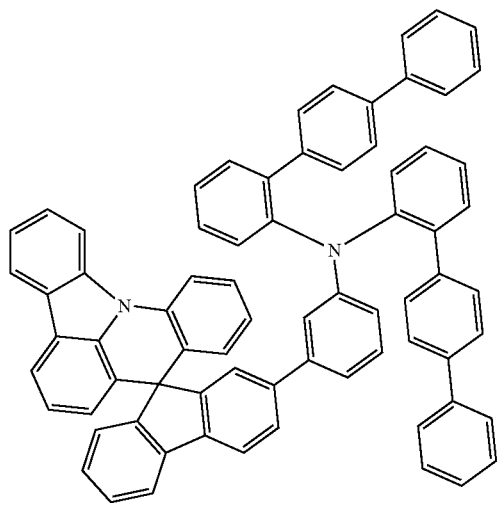
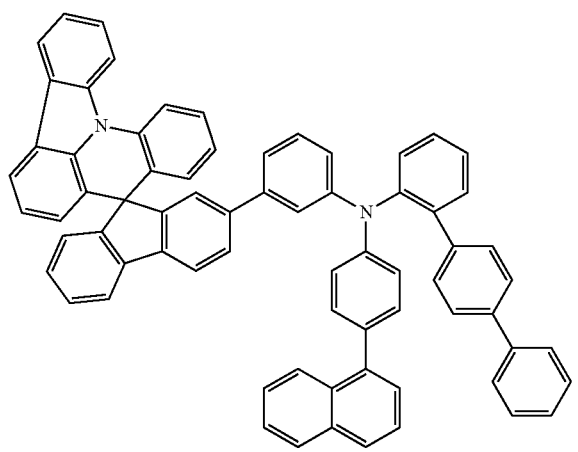
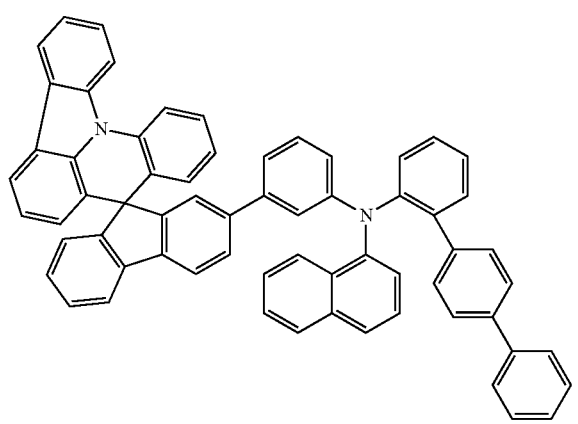
302
-continued
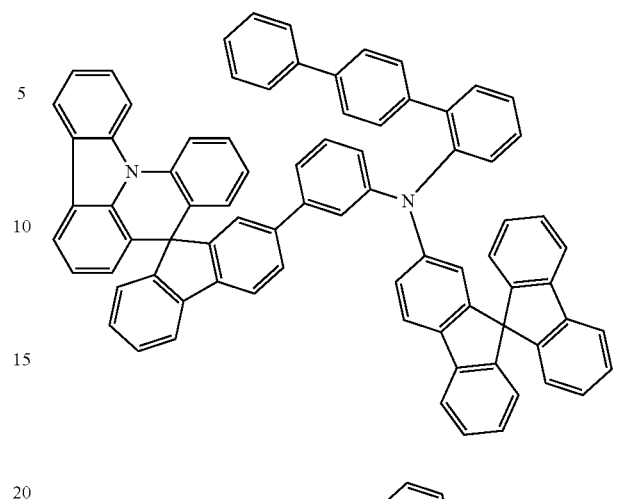
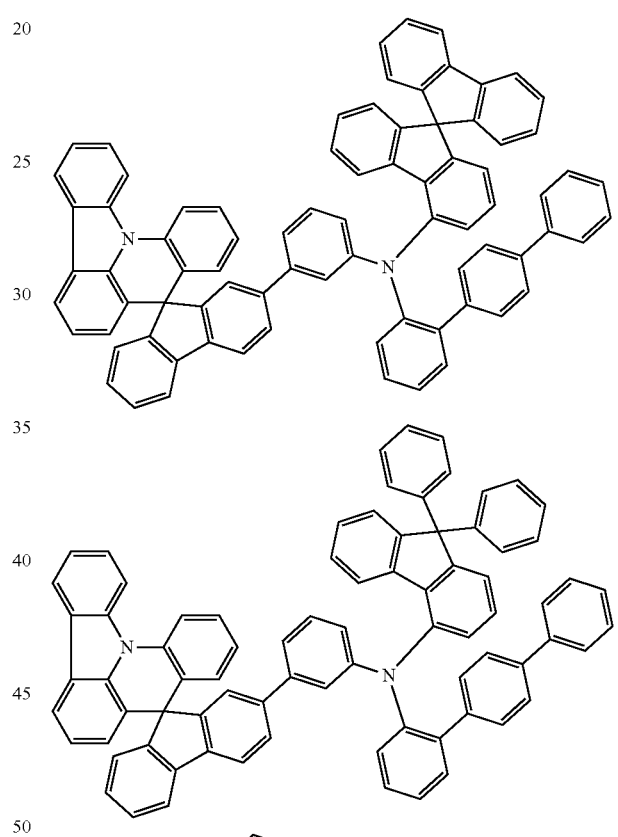

303
-continued
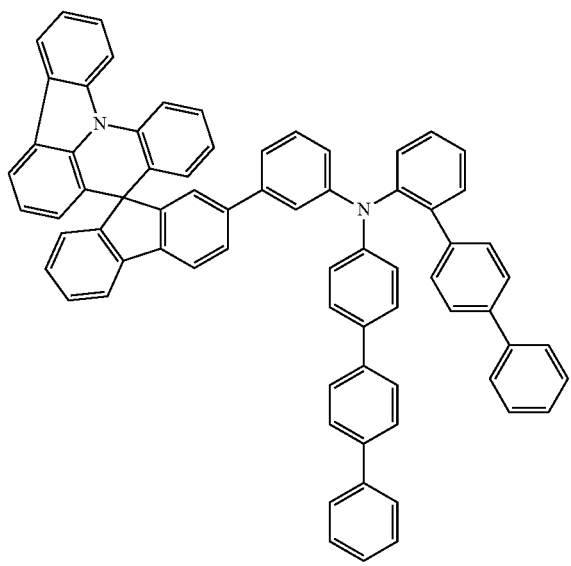
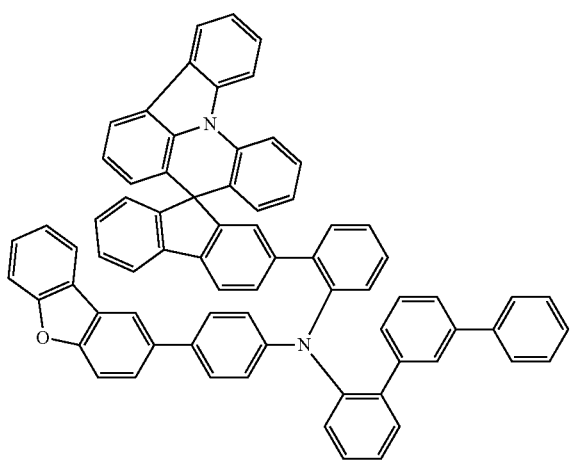
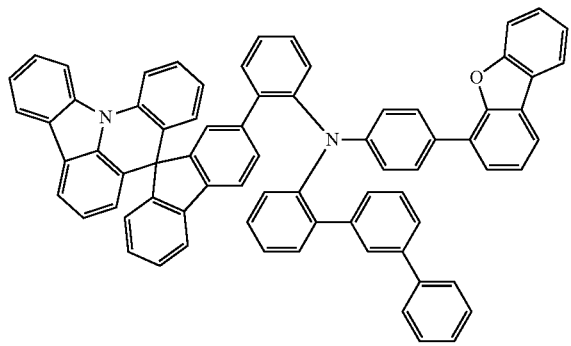
304
-continued
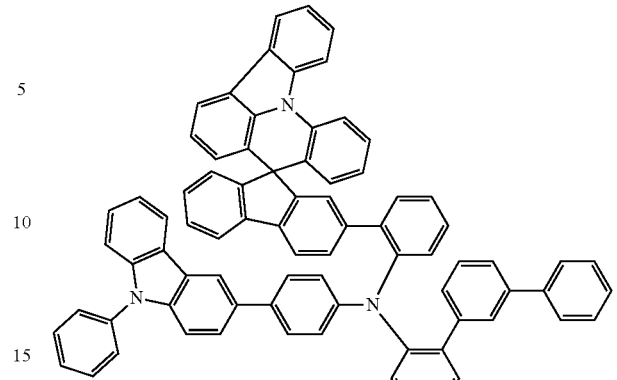
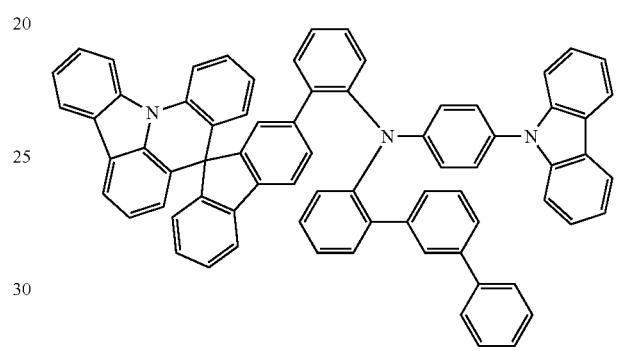
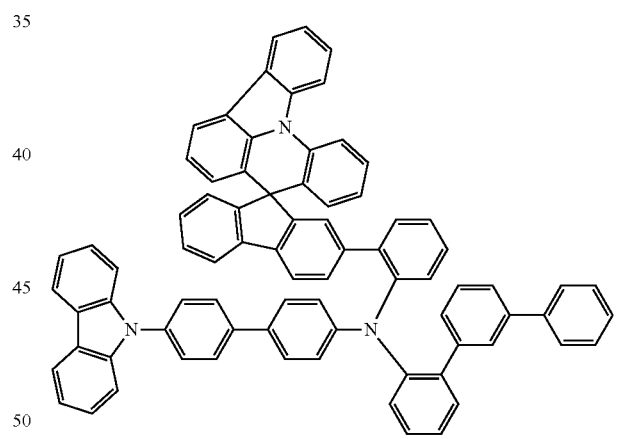
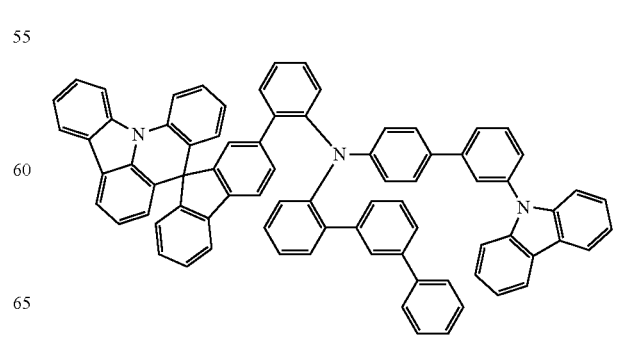

305
-continued
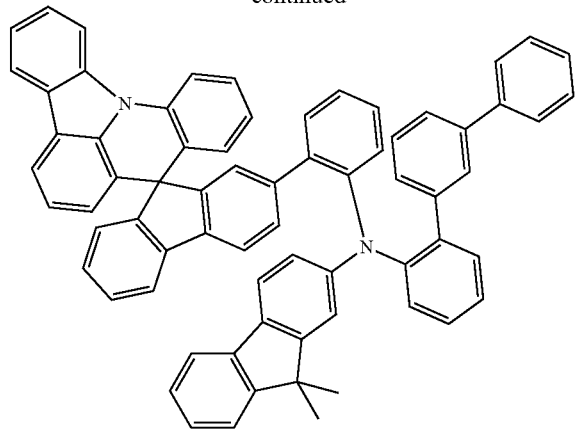
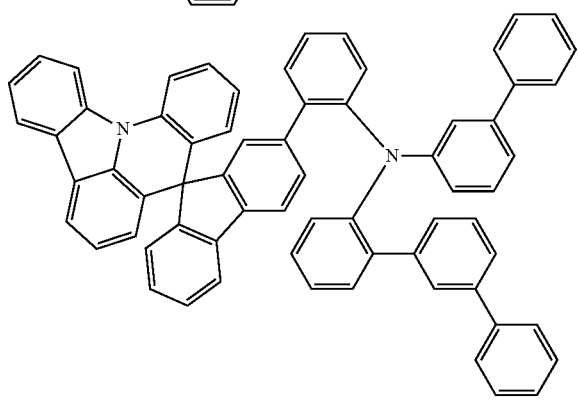
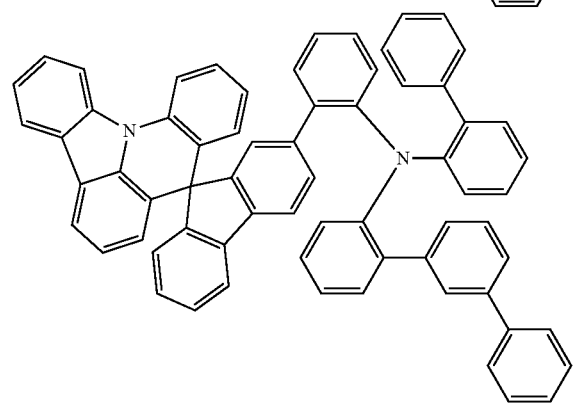
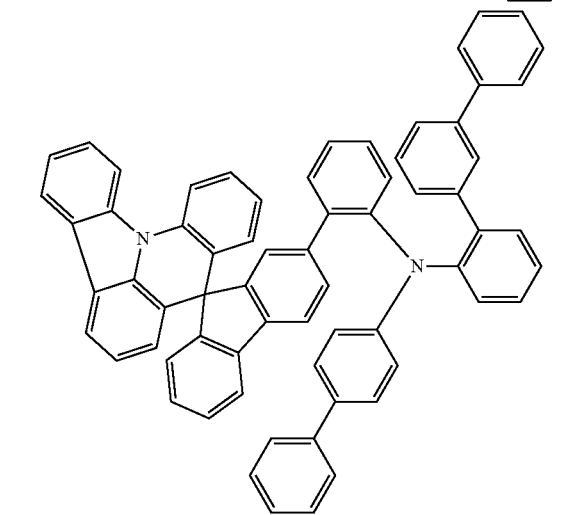
306
-continued
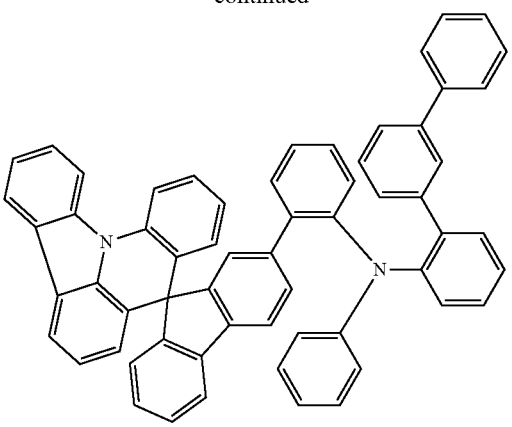
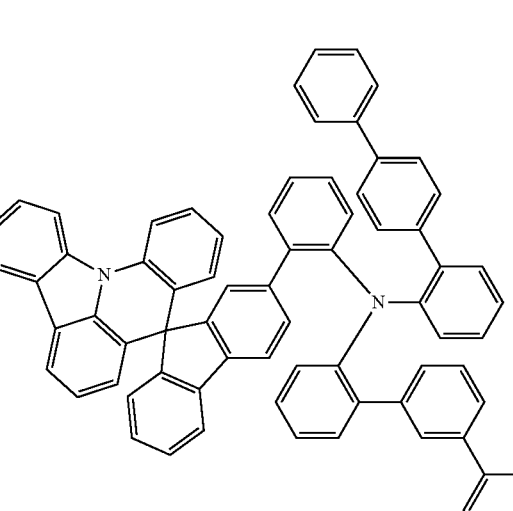
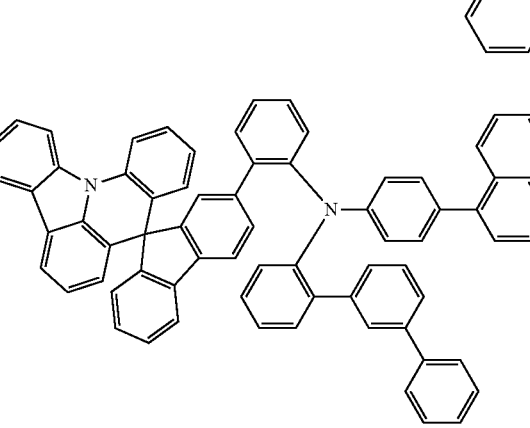
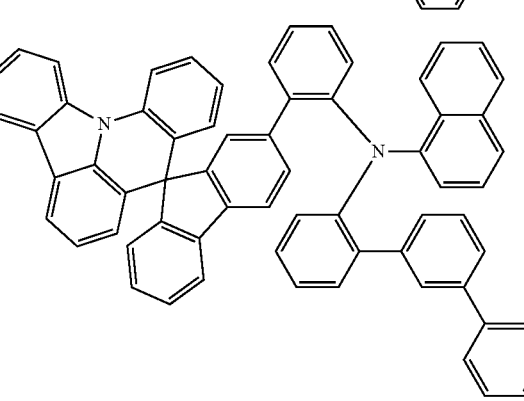

307
-continued
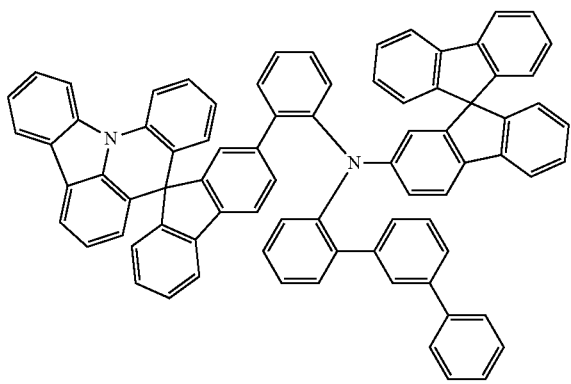
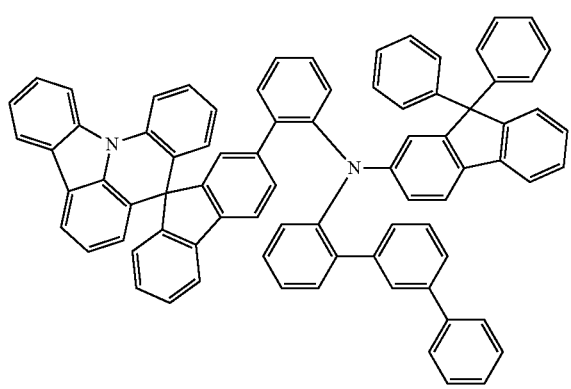
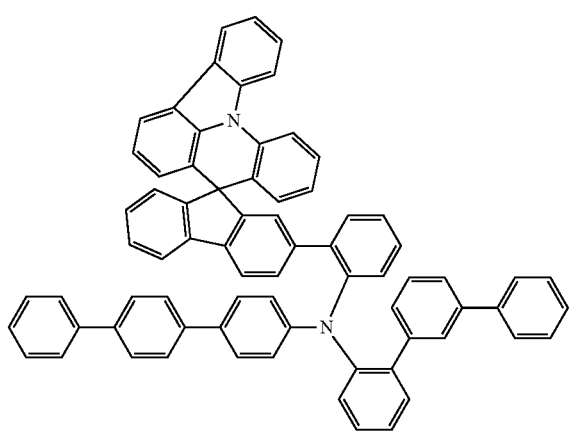
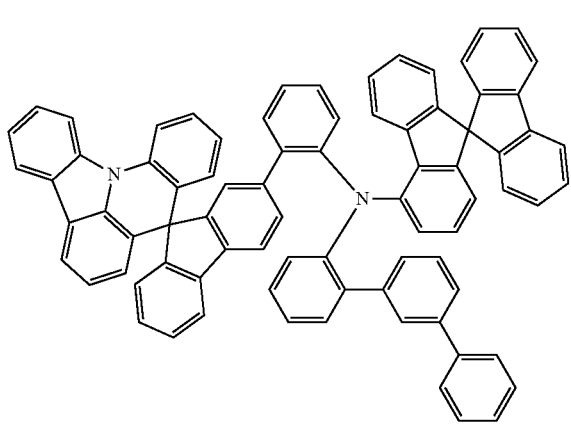
308
-continued
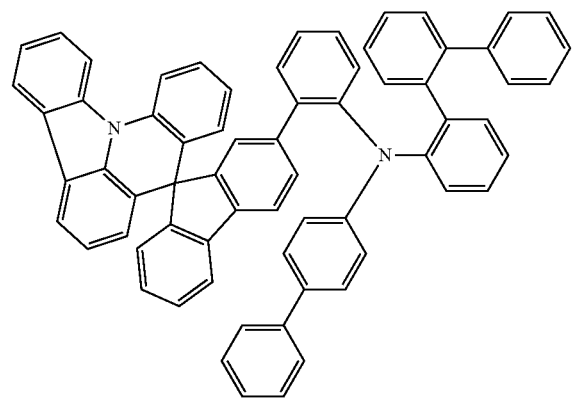
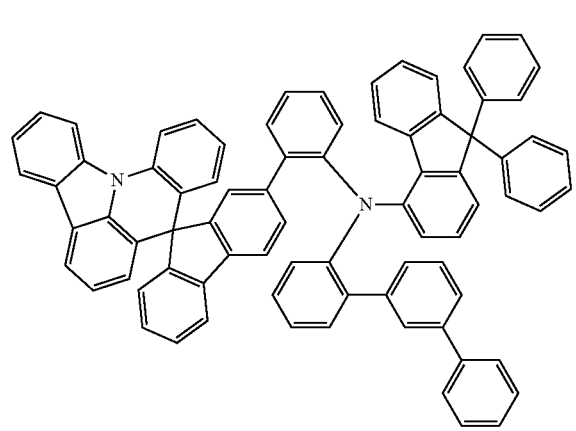
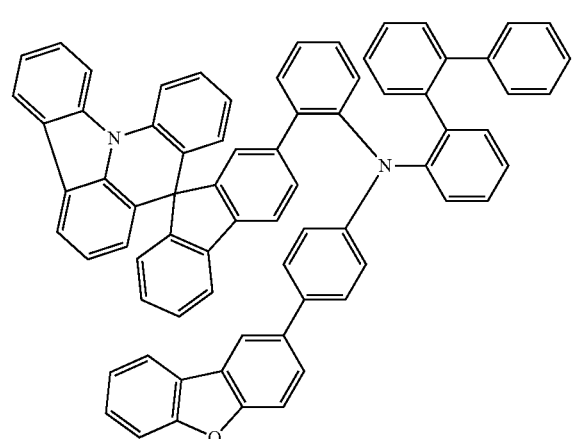
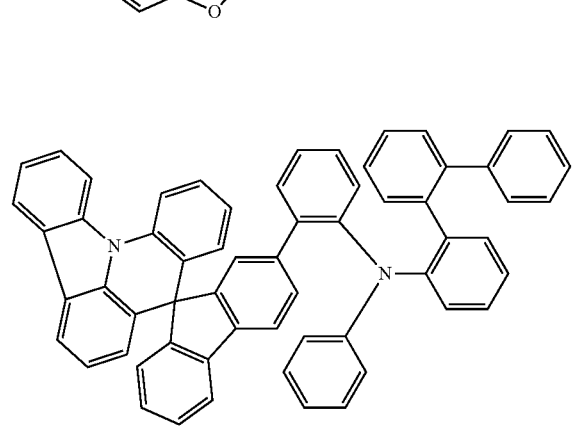

309
-continued
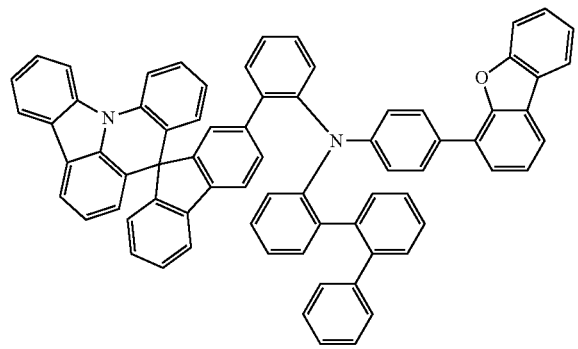
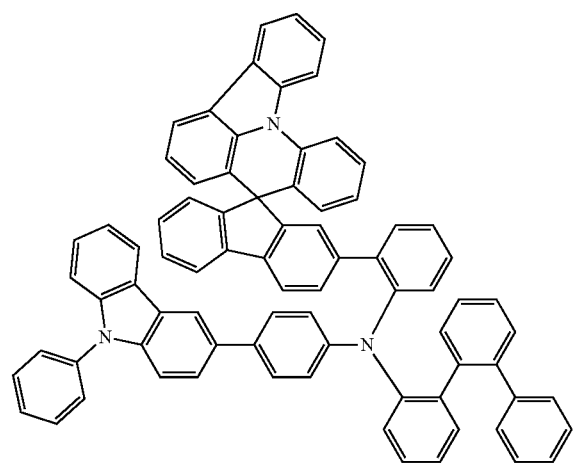
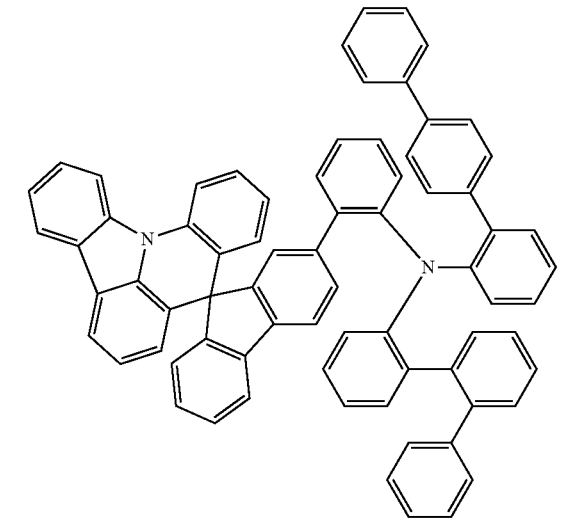
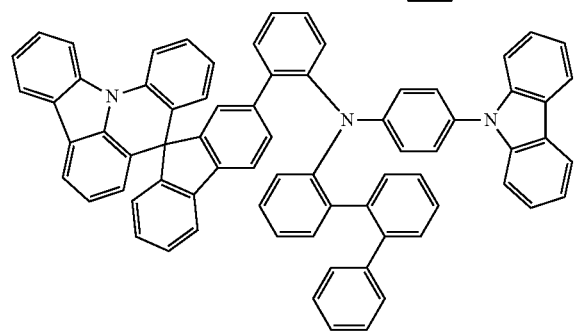
310
-continued
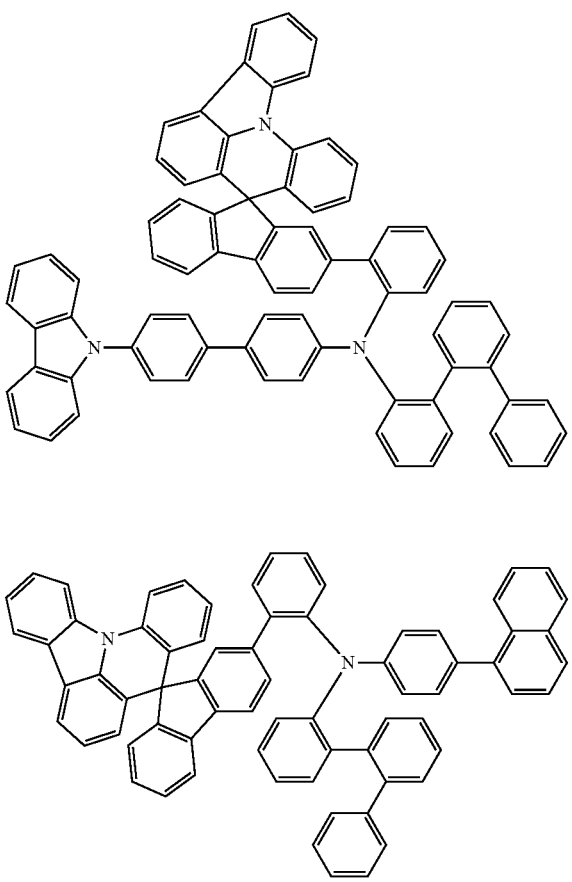
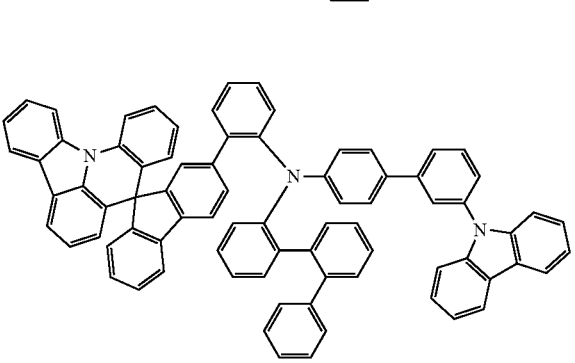
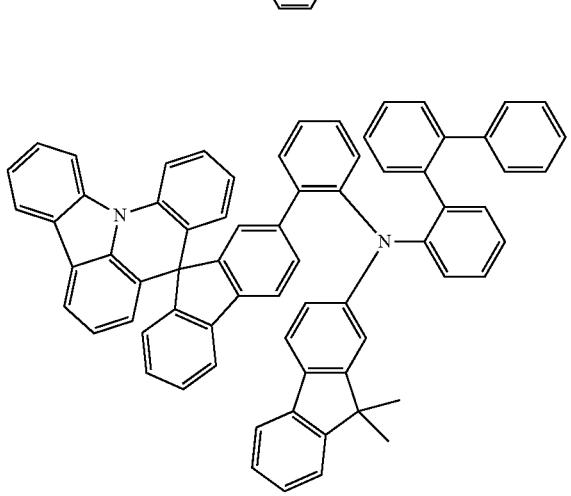

311
-continued
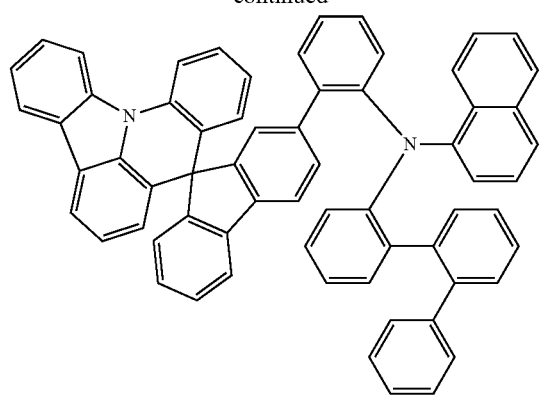
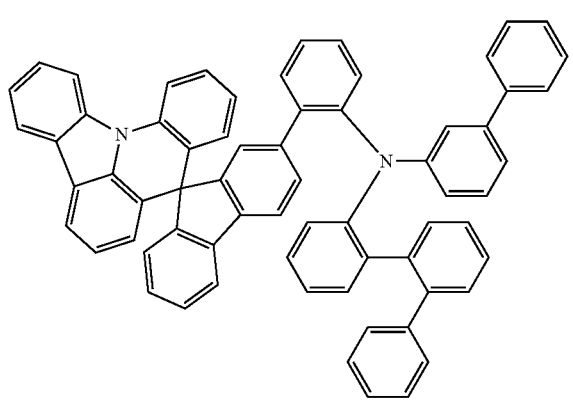
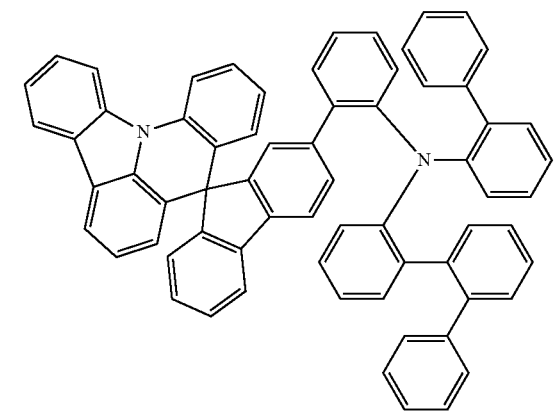
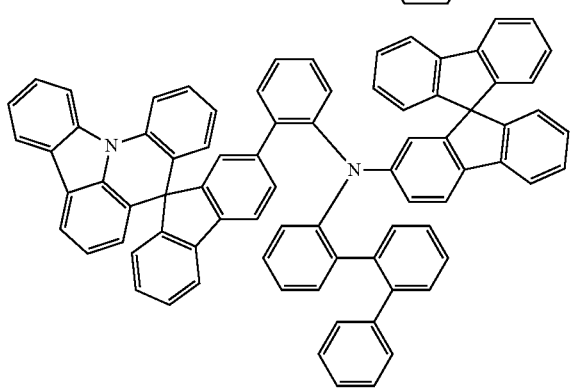
312
-continued
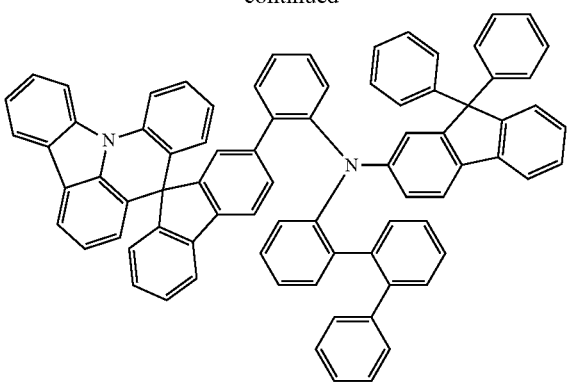
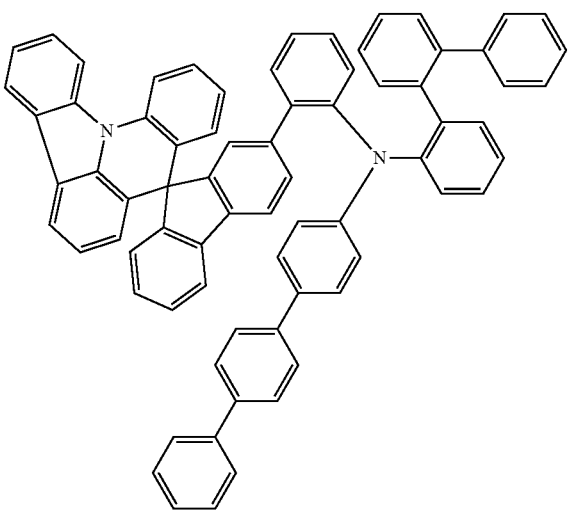
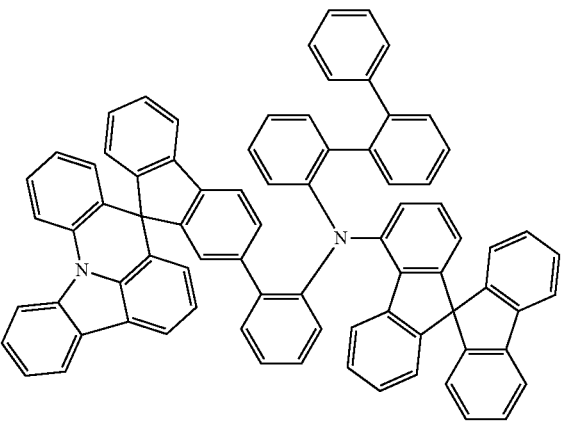
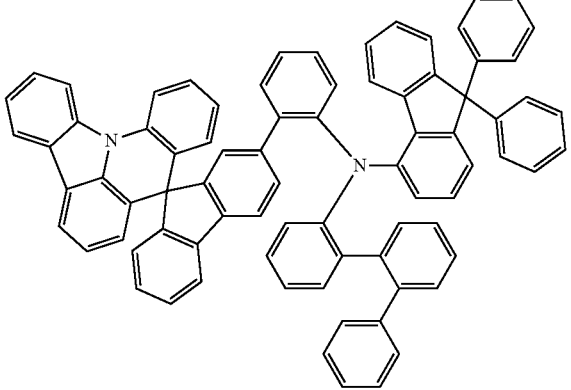

313
-continued
314
-continued
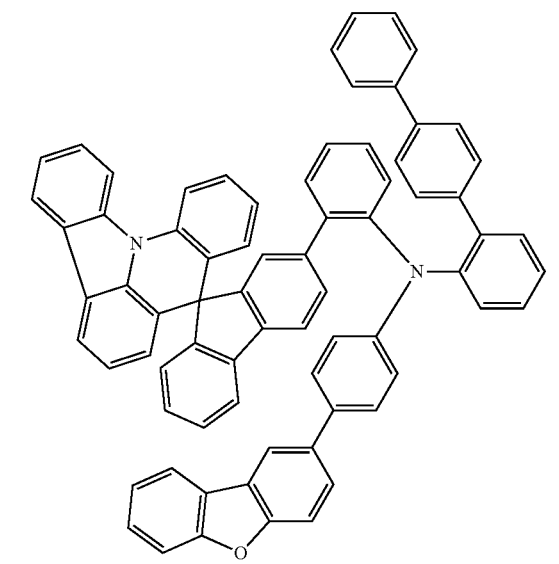
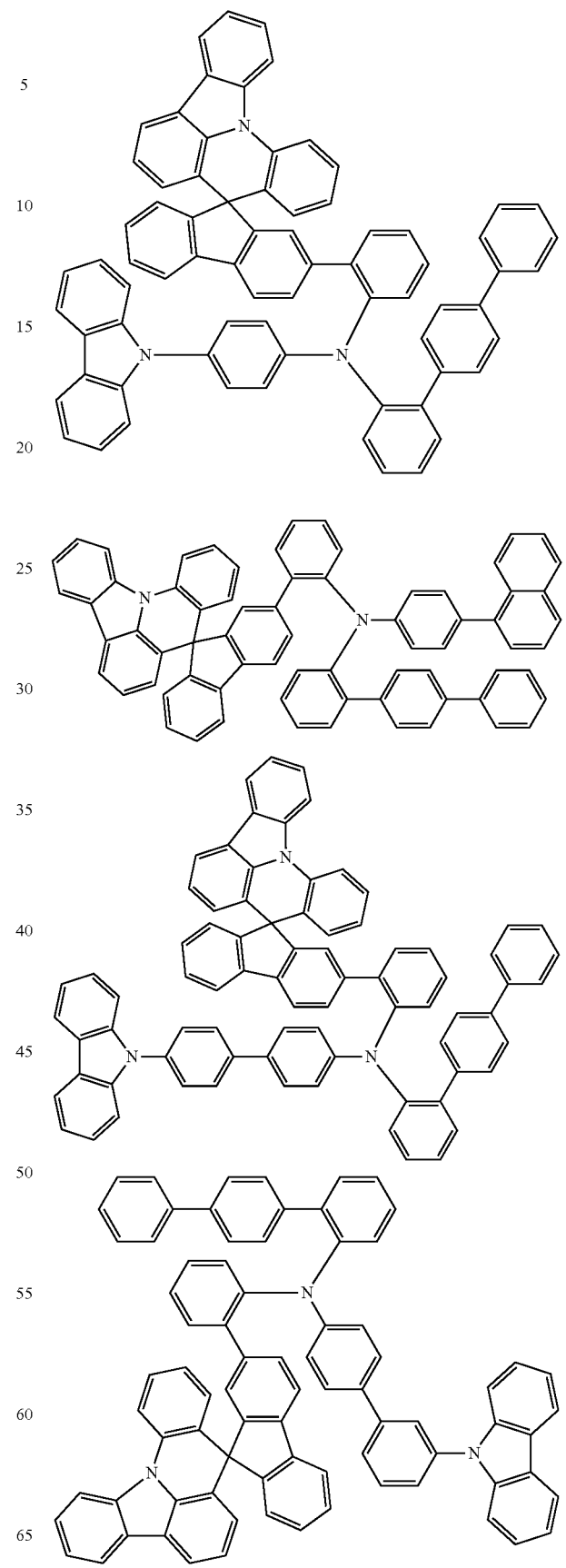

315
-continued
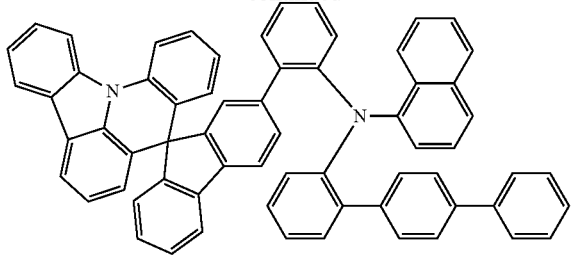
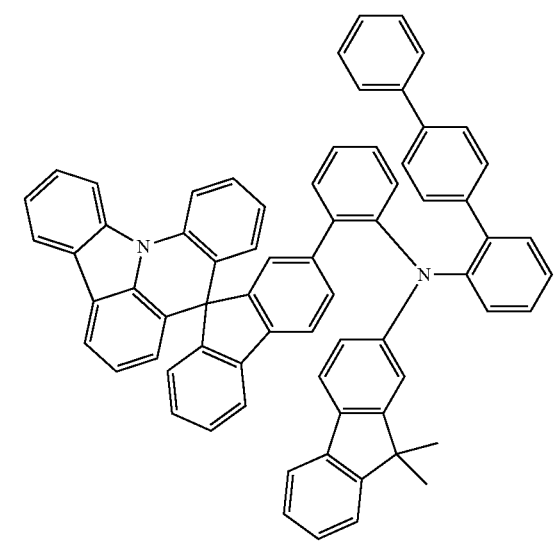
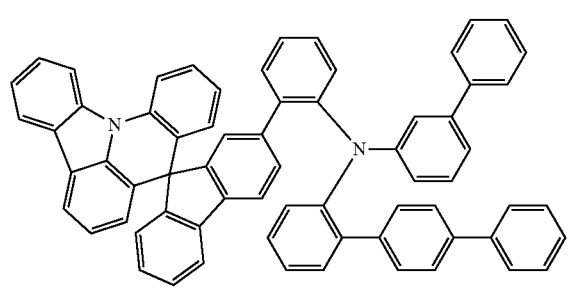
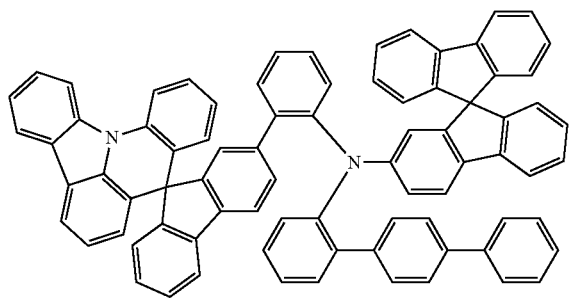
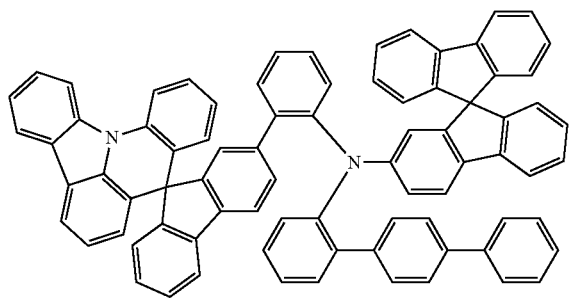
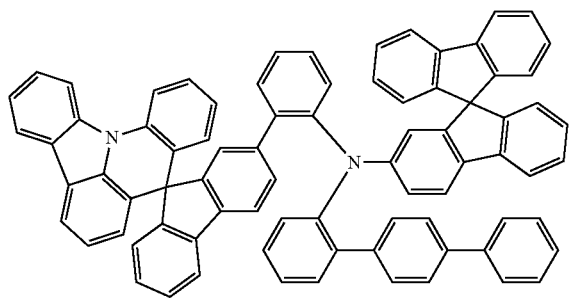
316
-continued
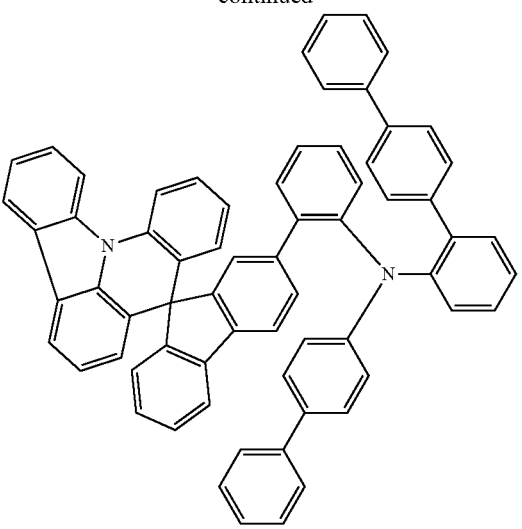
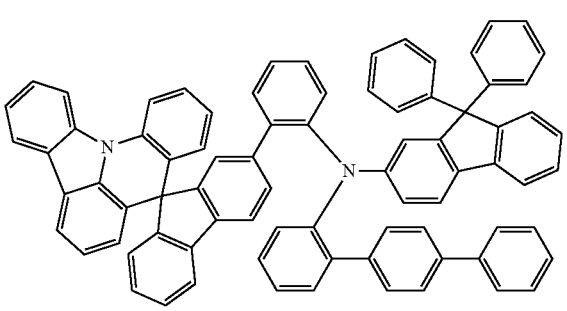
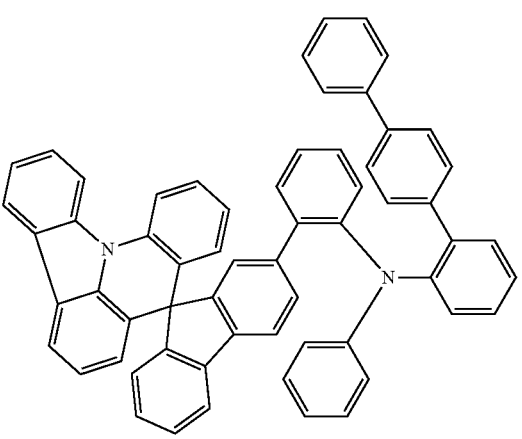
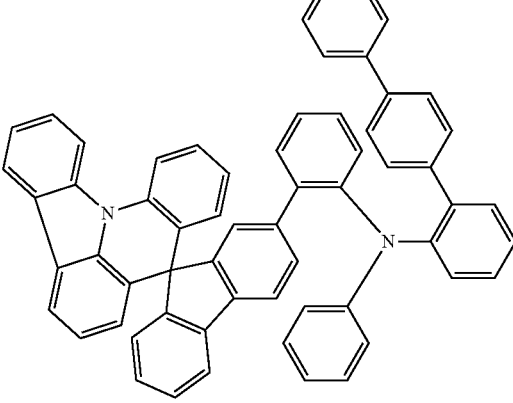
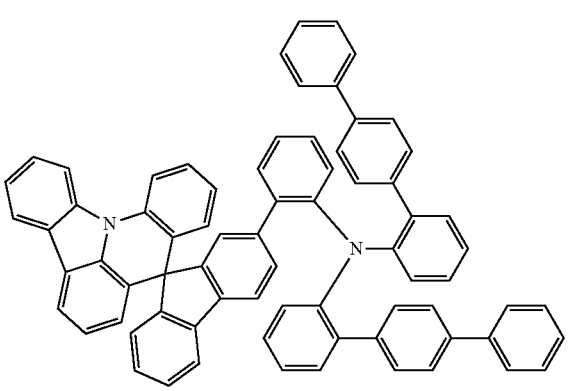

317
-continued
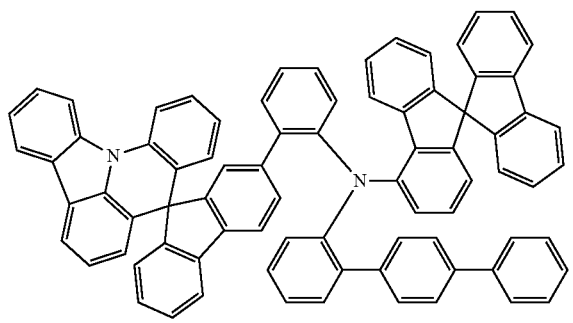
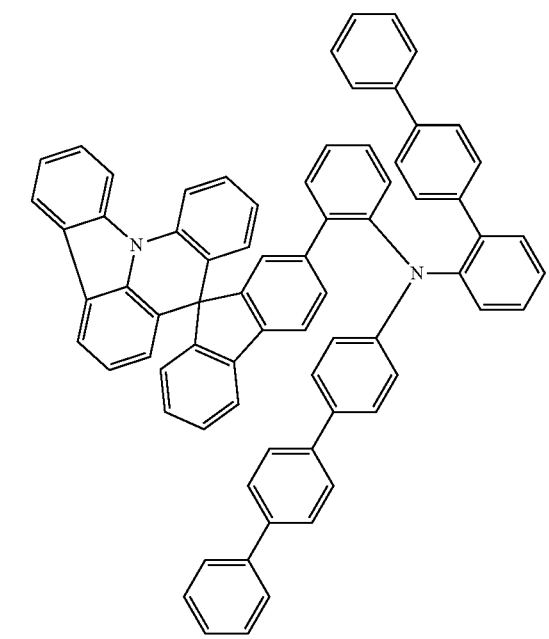
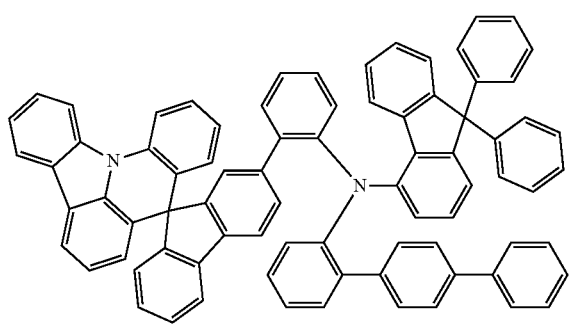
318
-continued
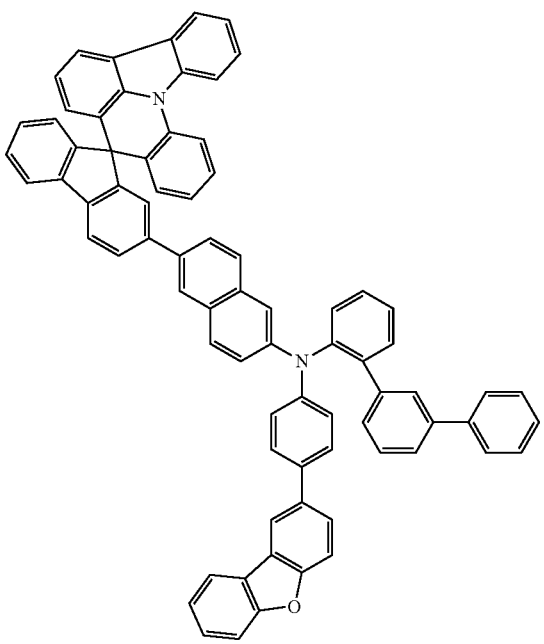
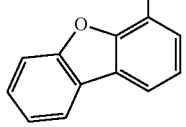

319
-continued
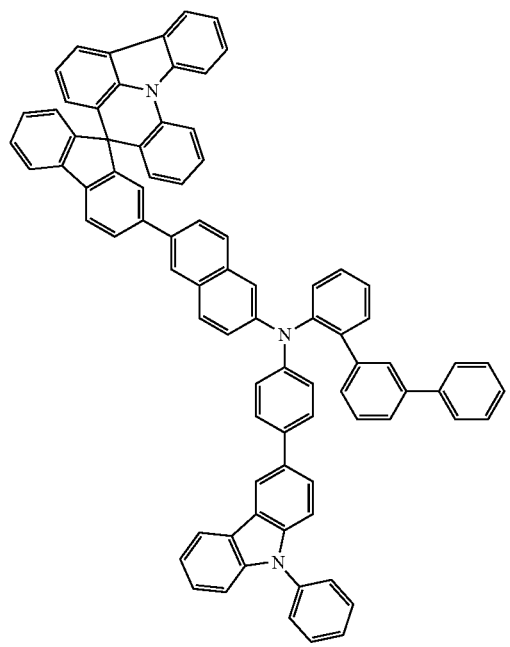
320
-continued
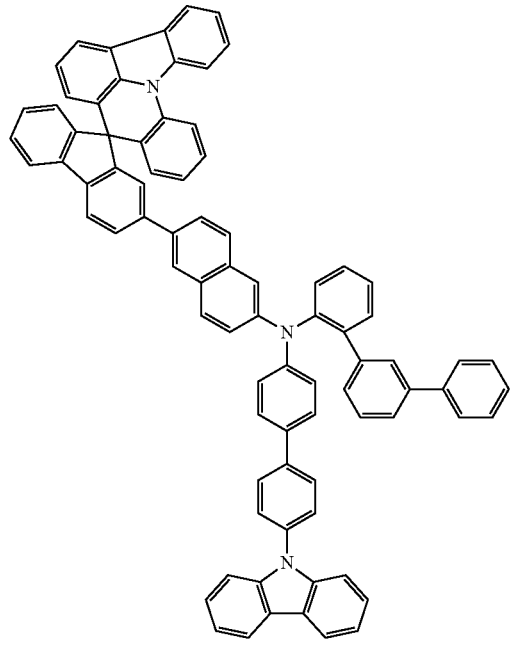
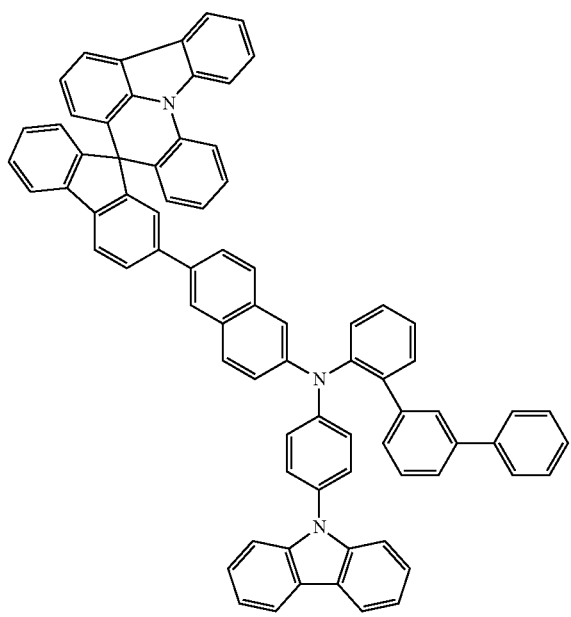
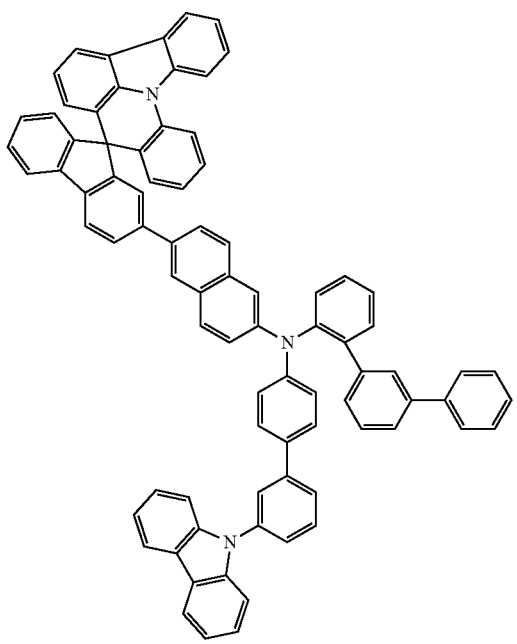

321
-continued
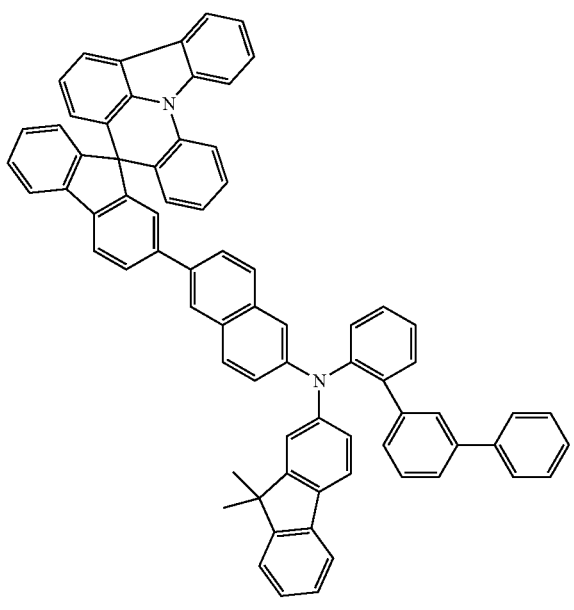
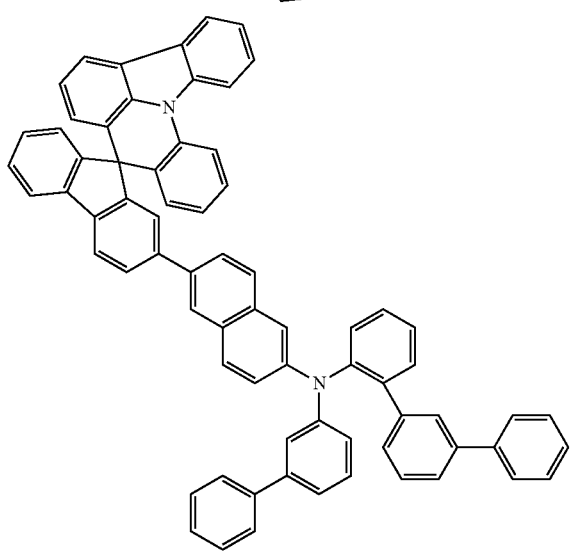
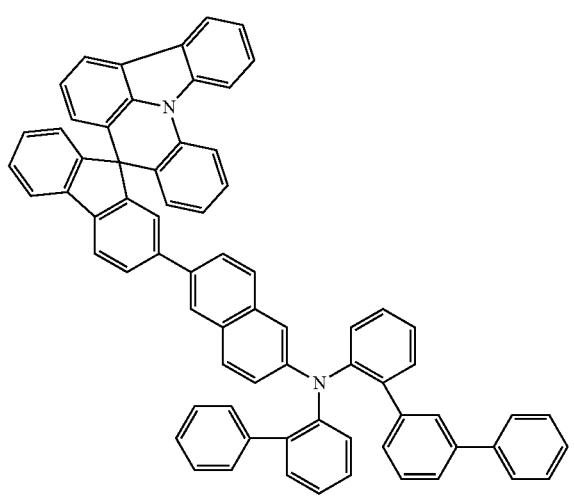
322
-continued
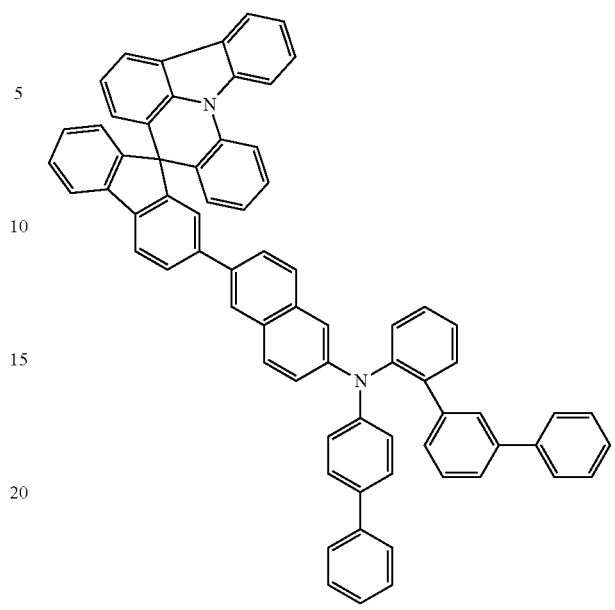
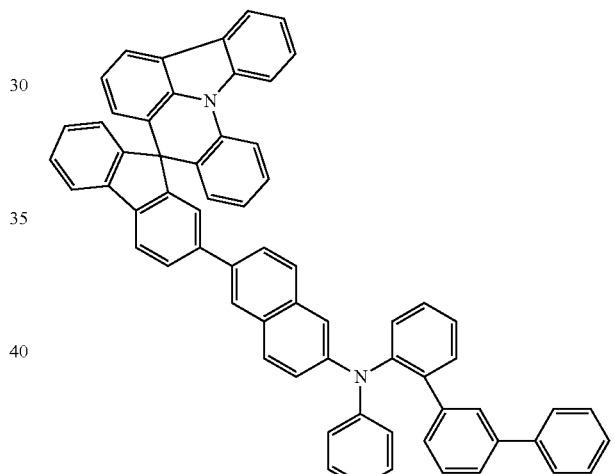
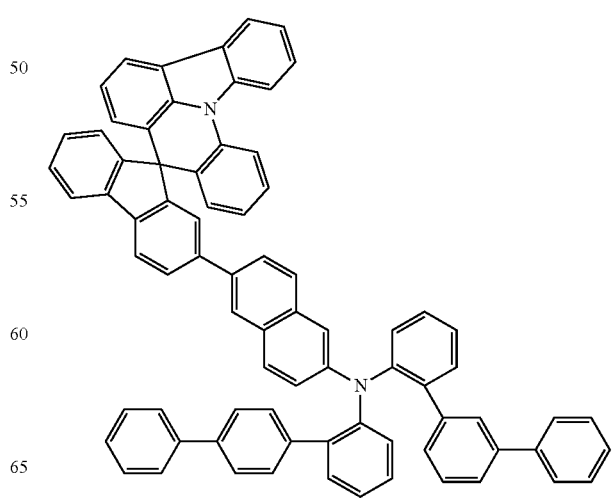

323
-continued
324
-continued
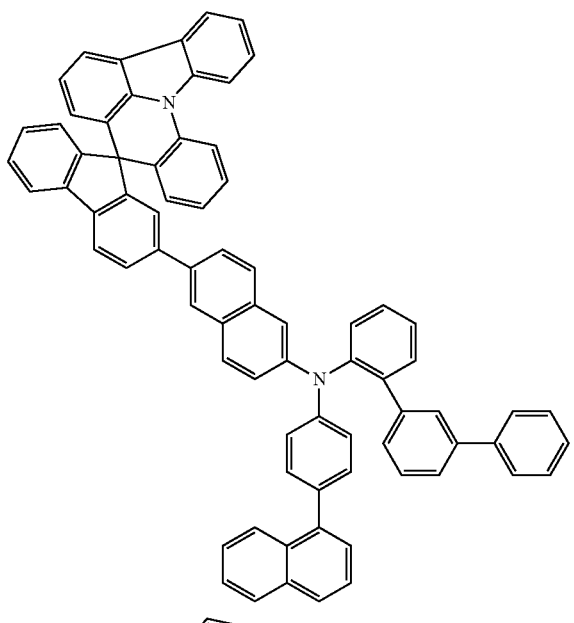
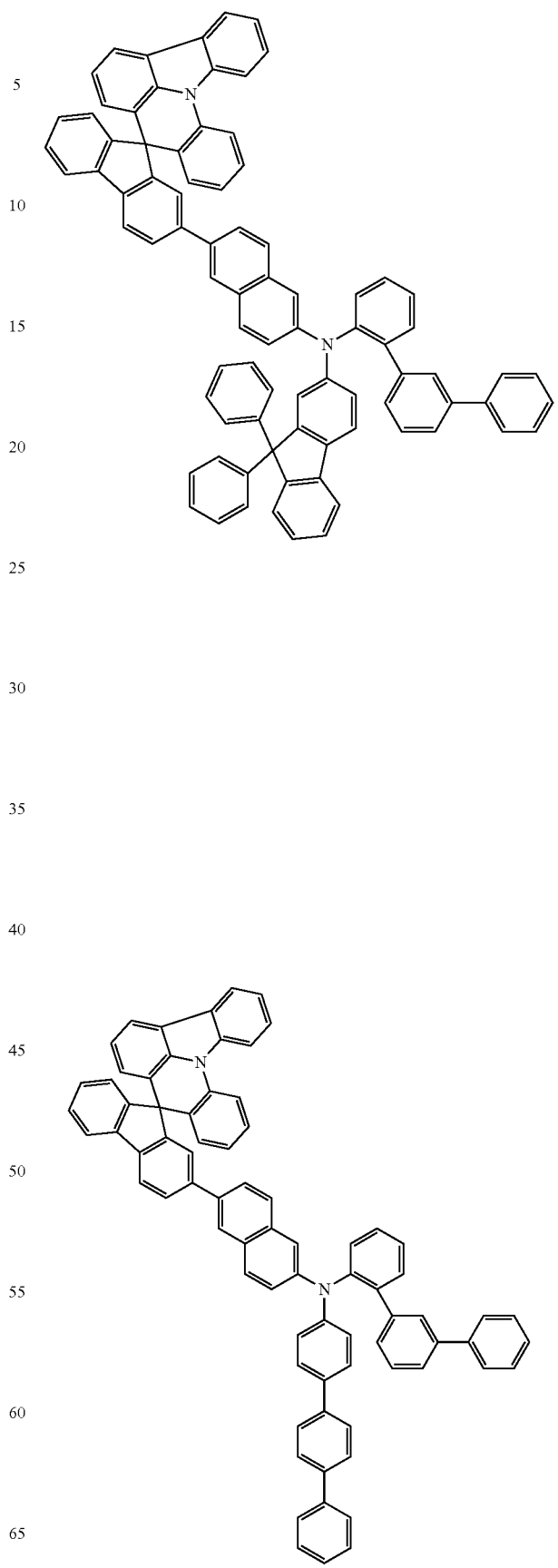

325
-continued
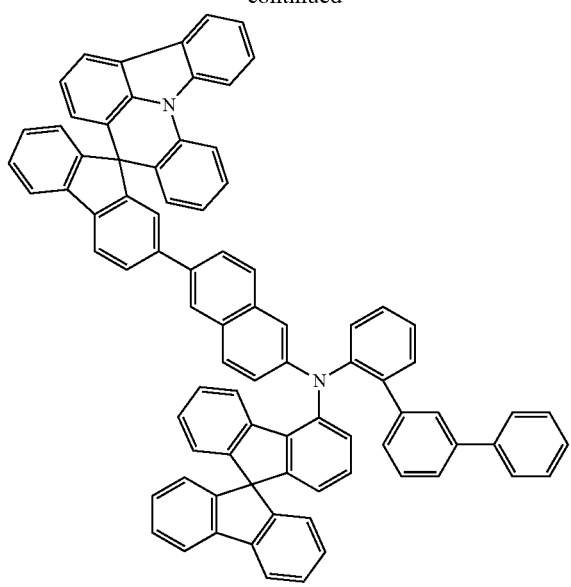
326
-continued
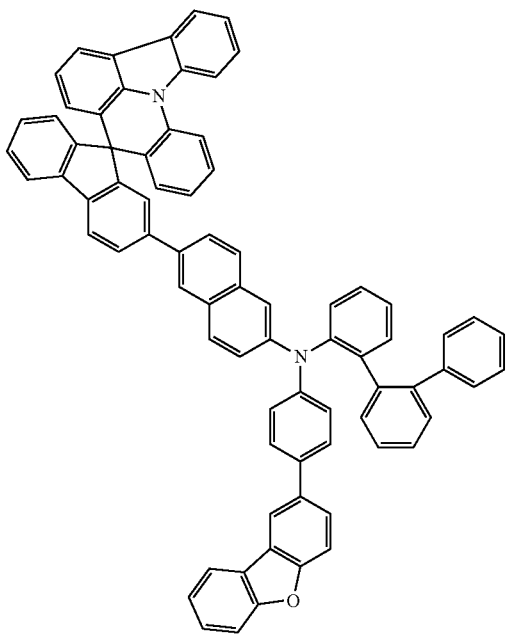
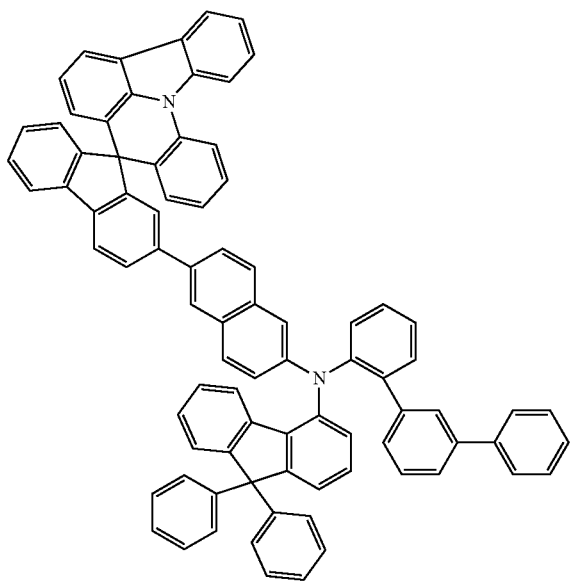
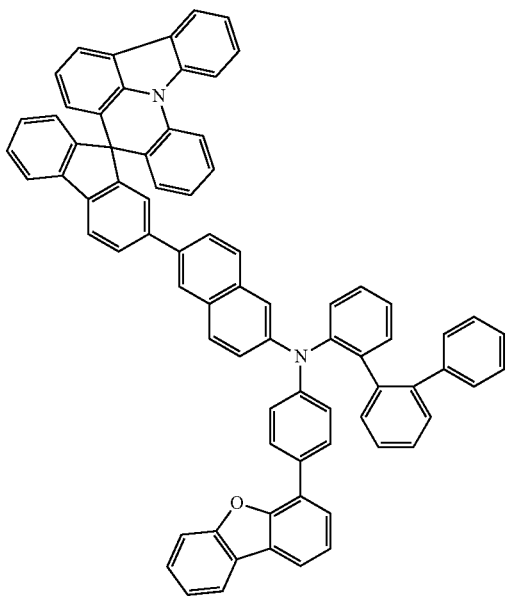

327
-continued
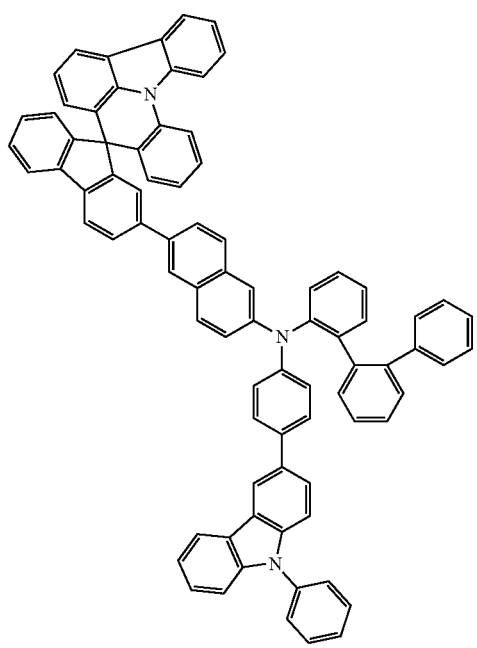
328
-continued
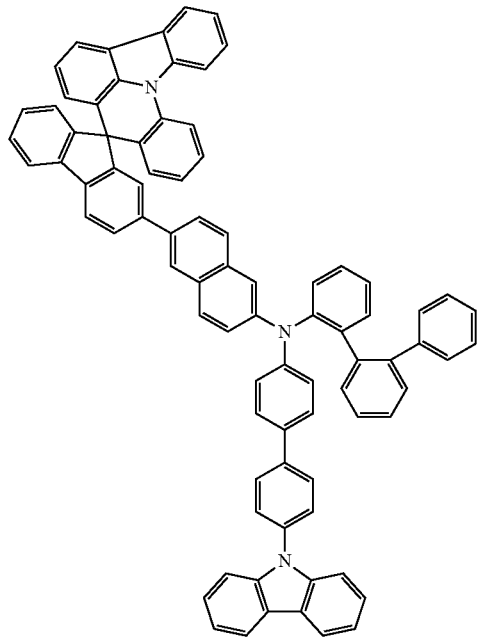
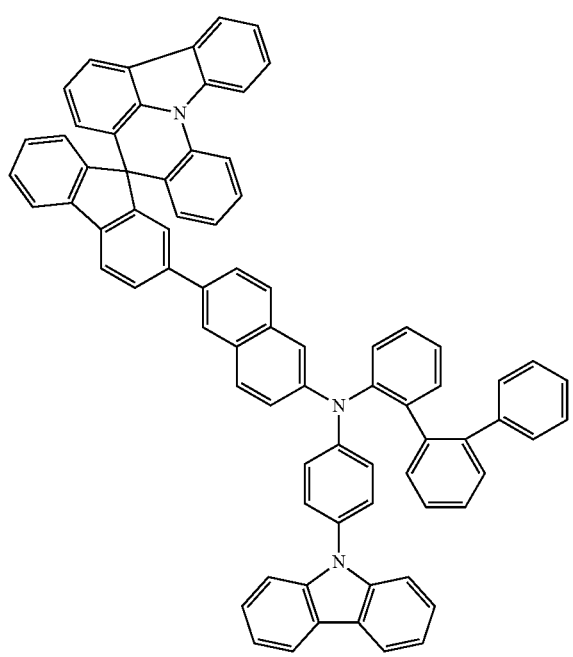
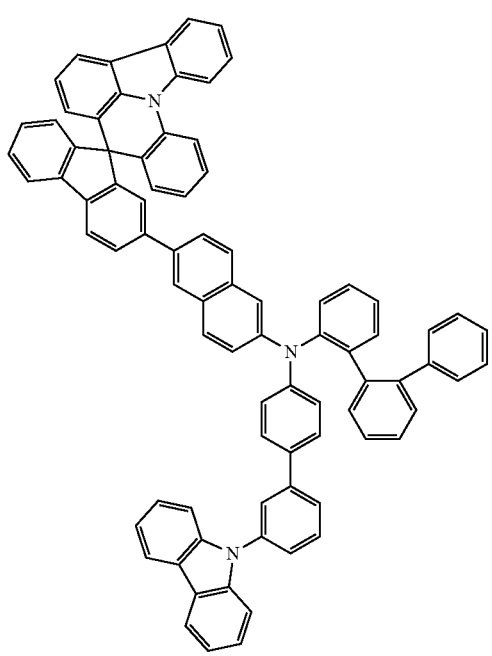

329
-continued
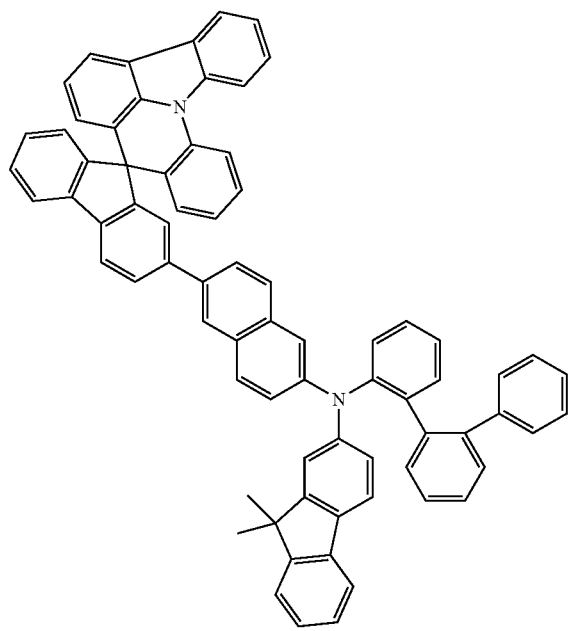
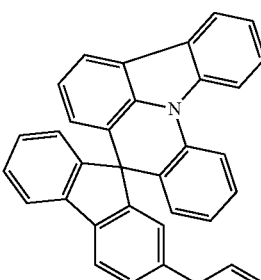
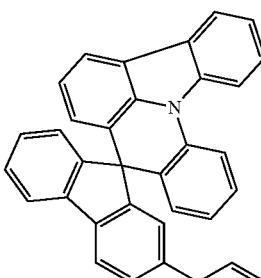
330
-continued
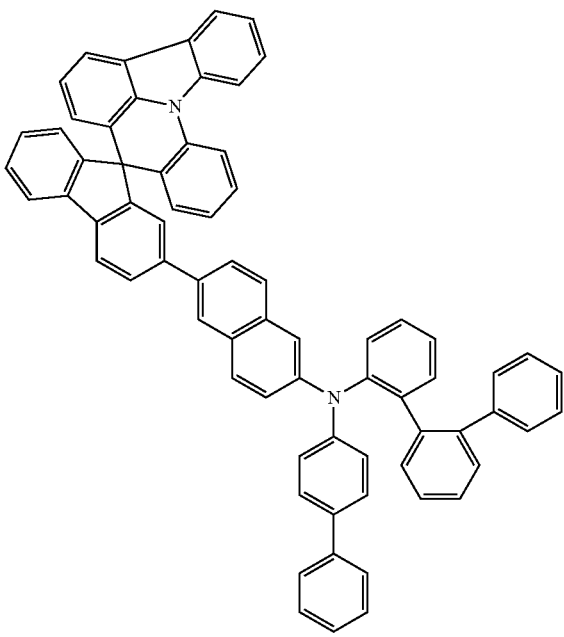
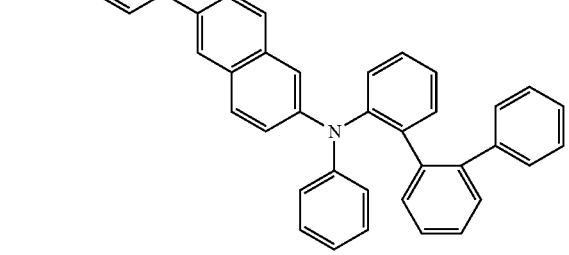
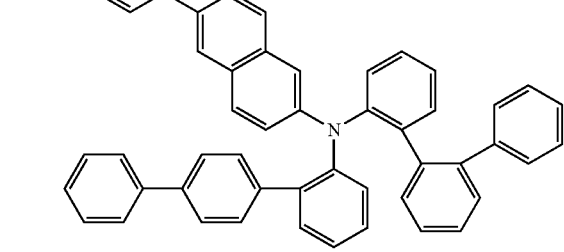

331
-continued
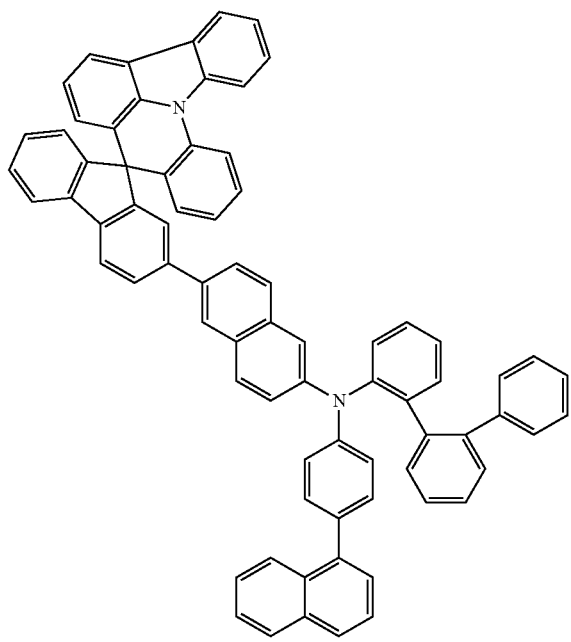
332
-continued
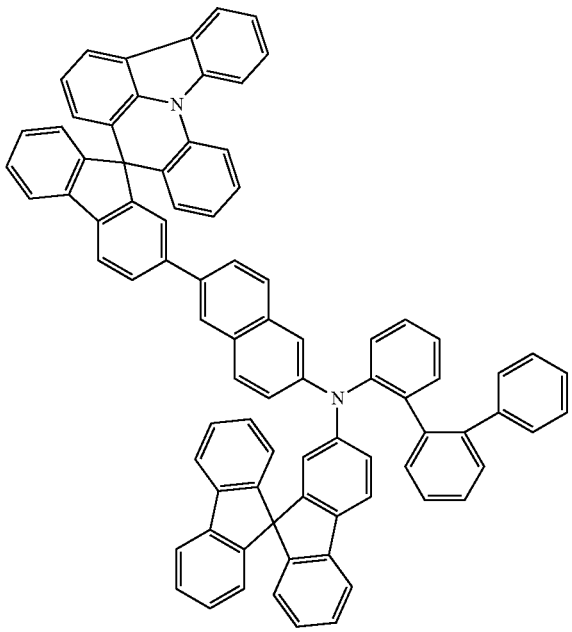
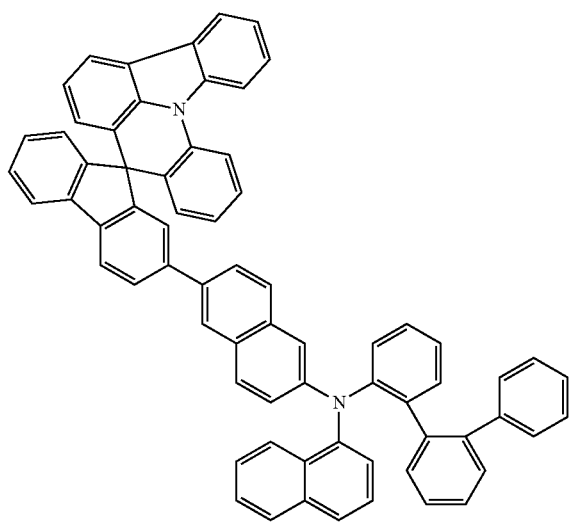
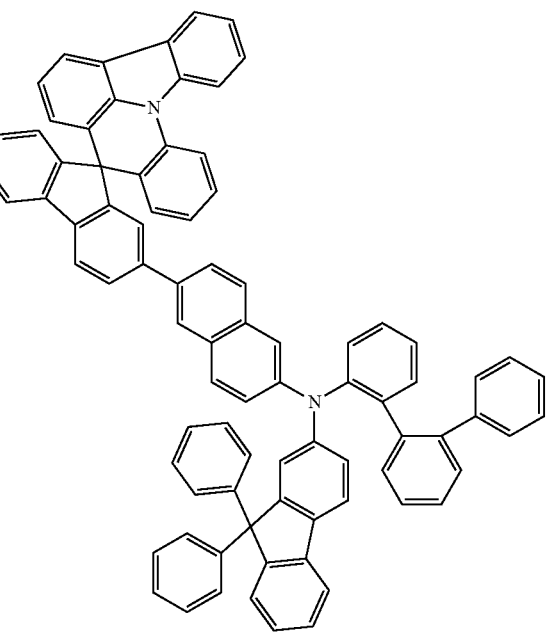

333
-continued
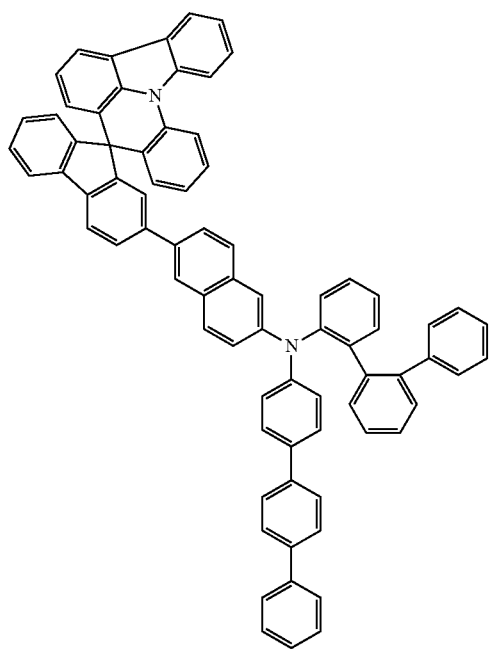
334
-continued
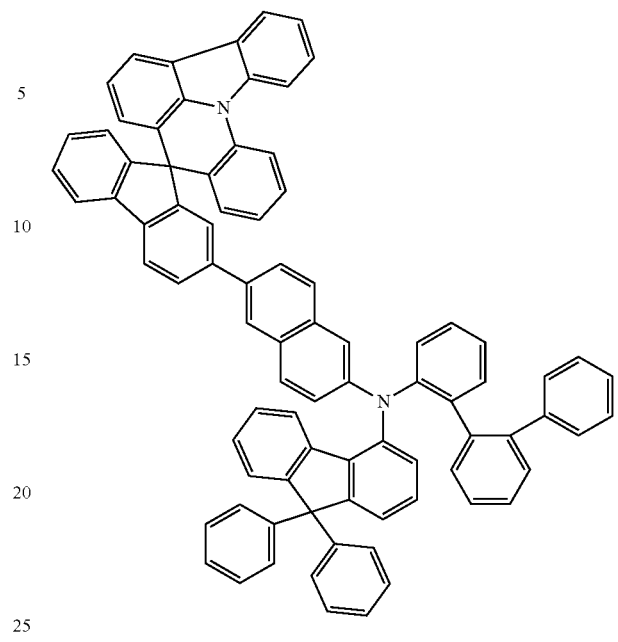
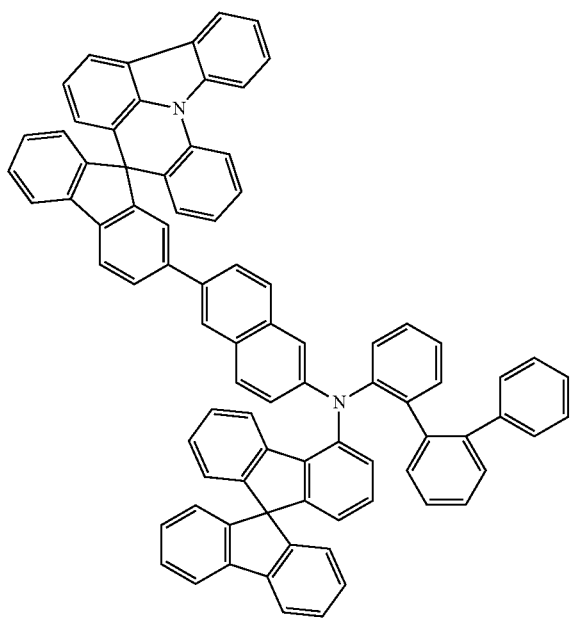
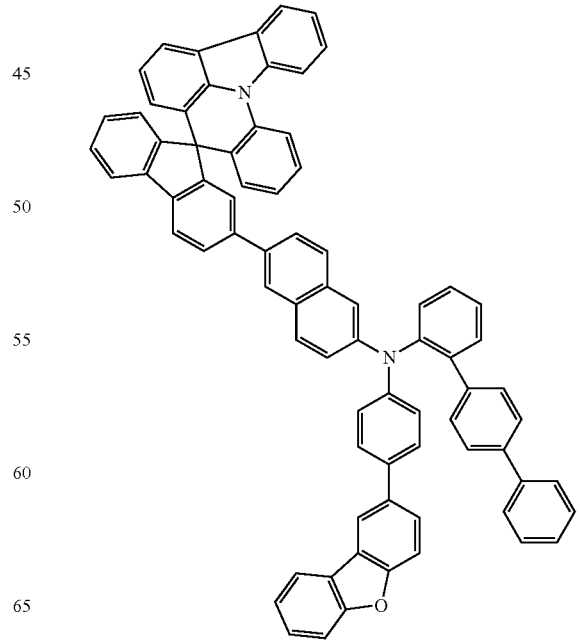

335
-continued
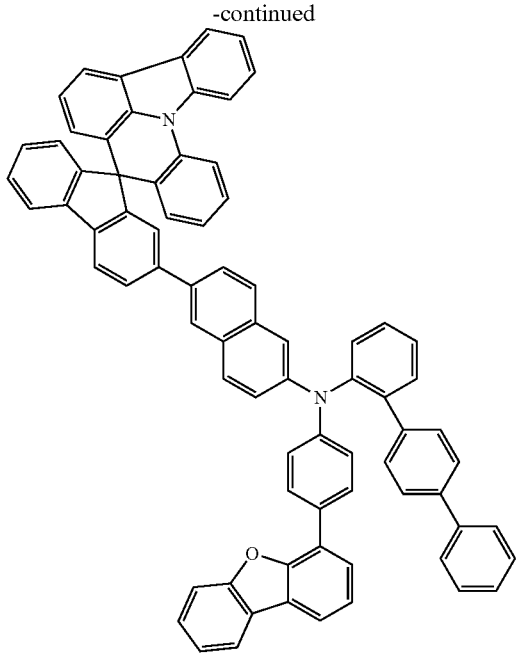
336
-continued
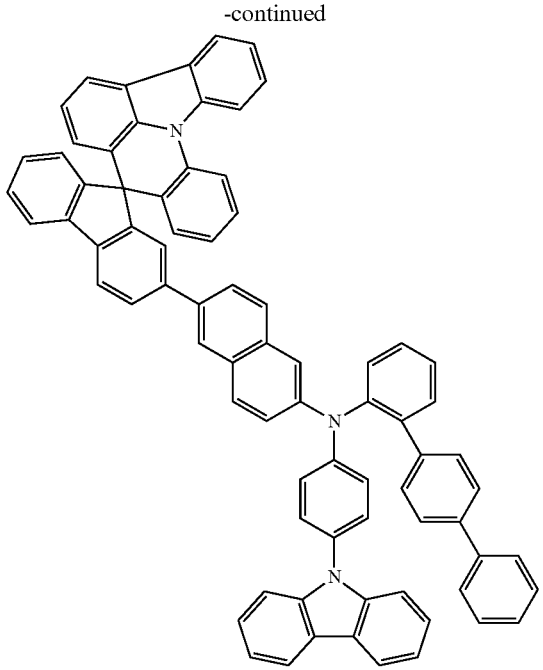
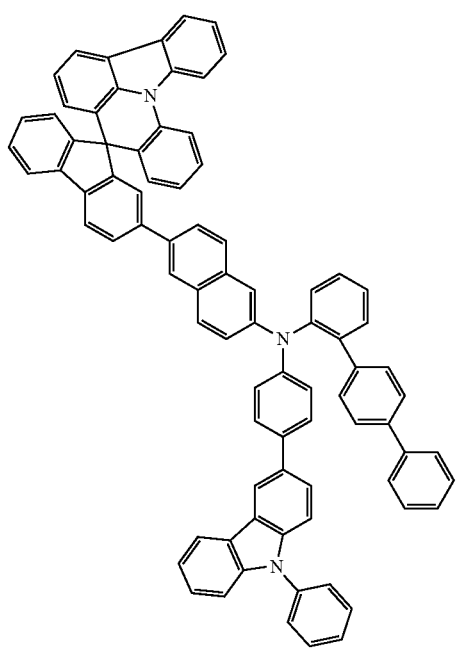
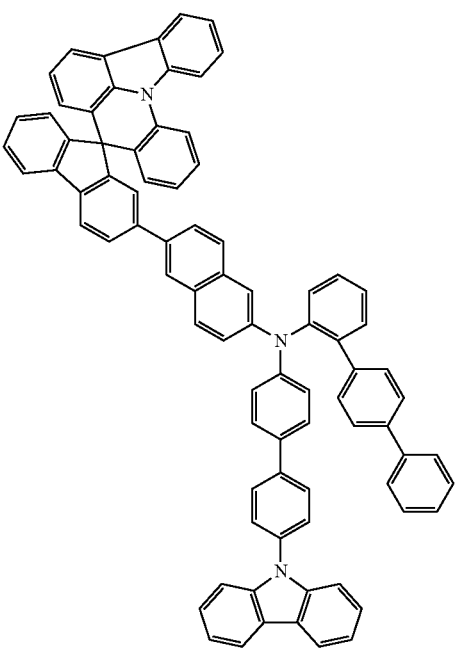

337
-continued
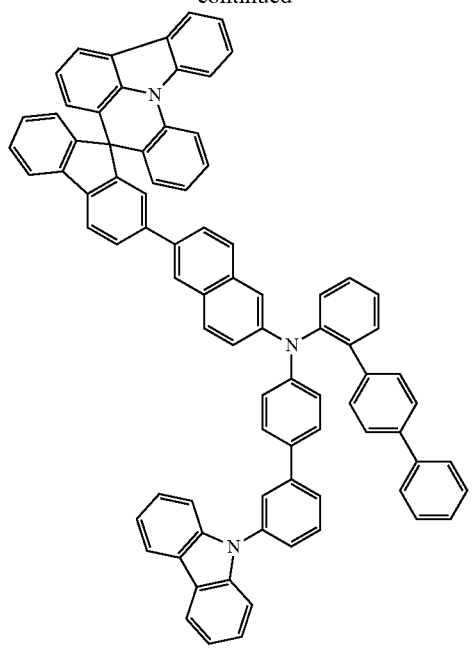
338
-continued
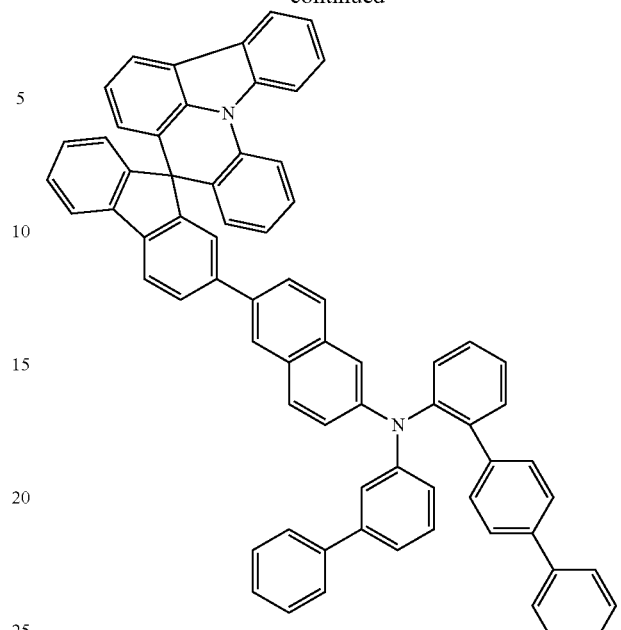
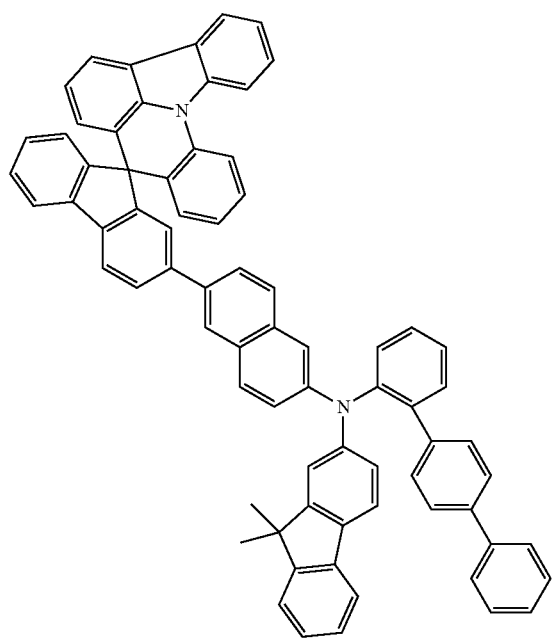
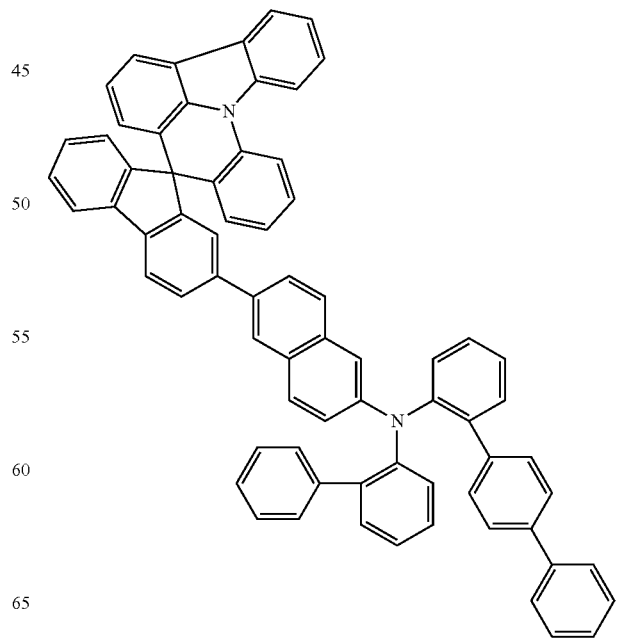

339
-continued
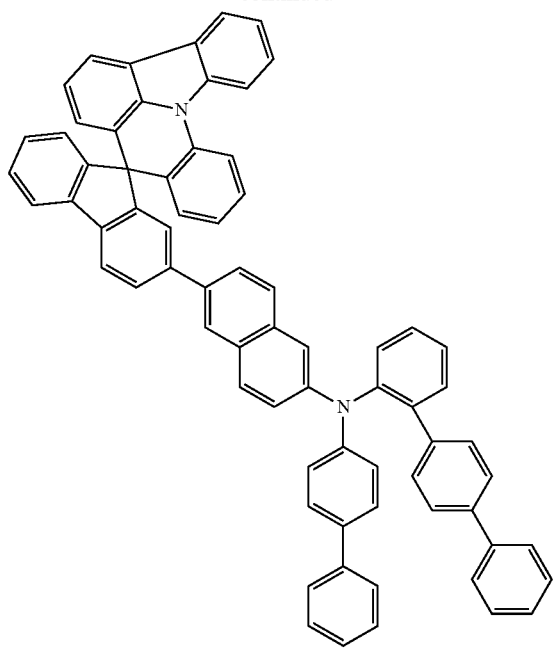
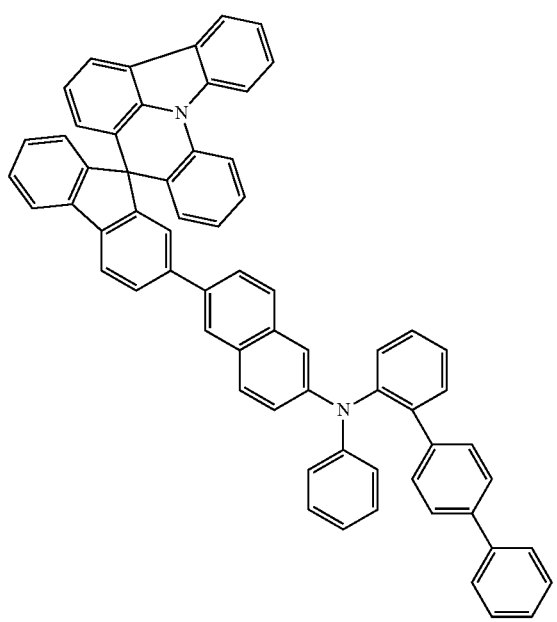
340
-continued
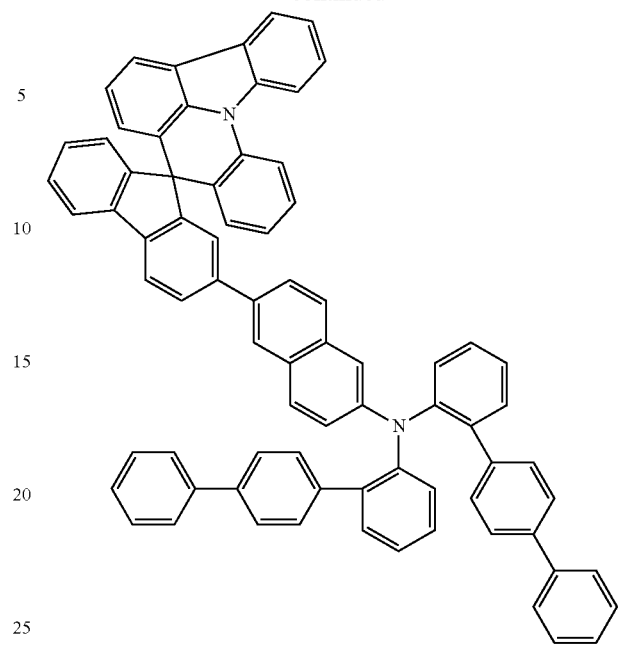
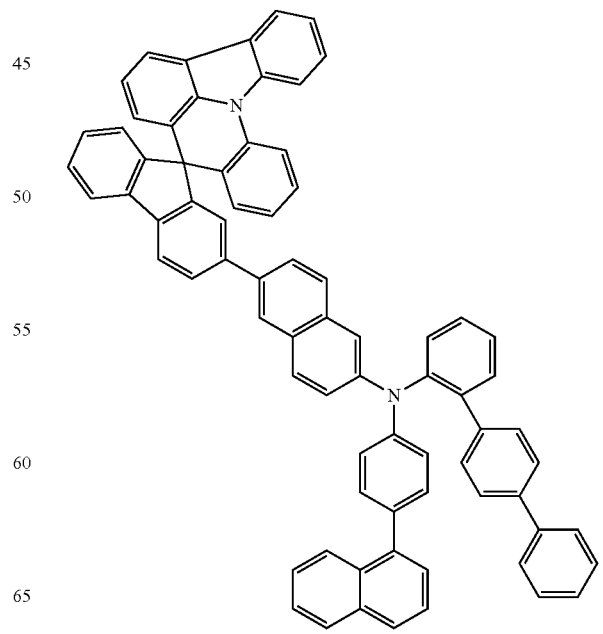

341
-continued
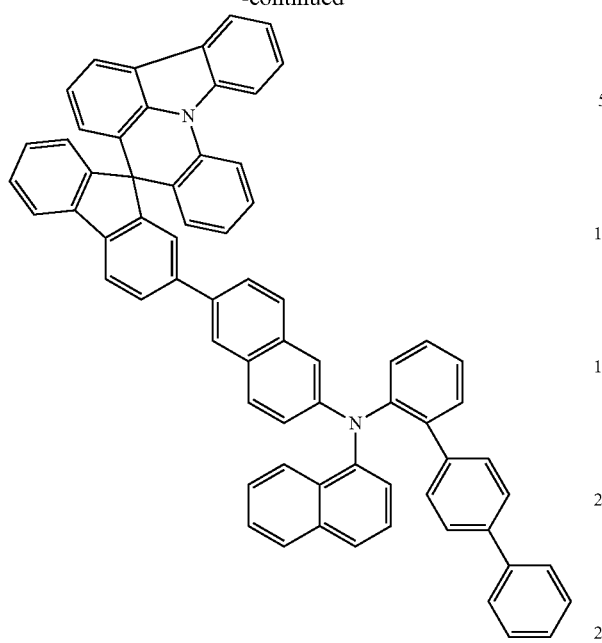
342
-continued
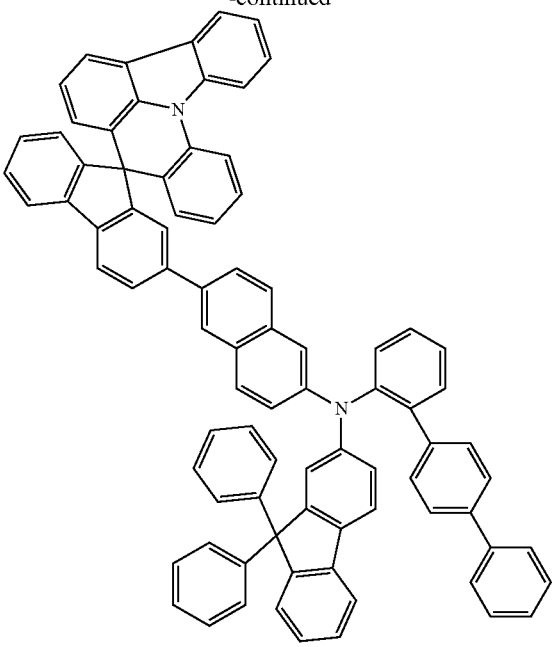
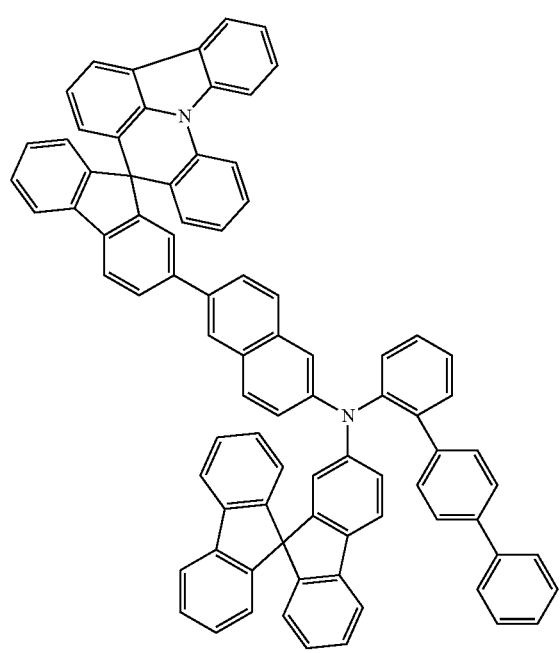
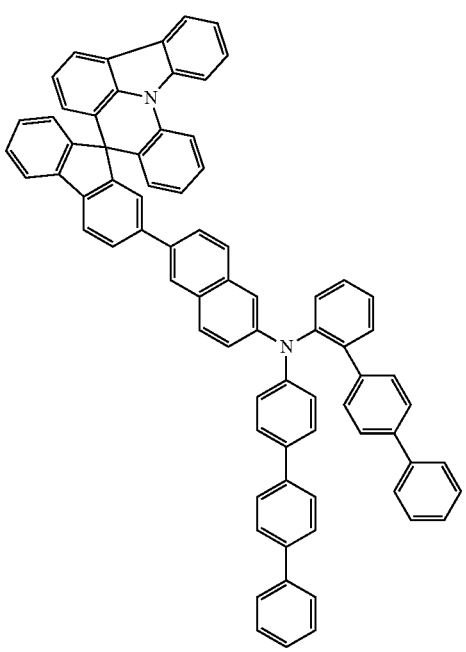

343
-continued
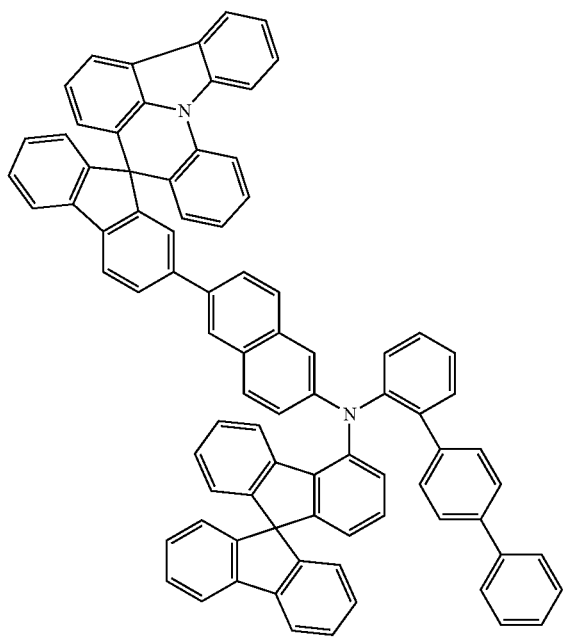
344
-continued
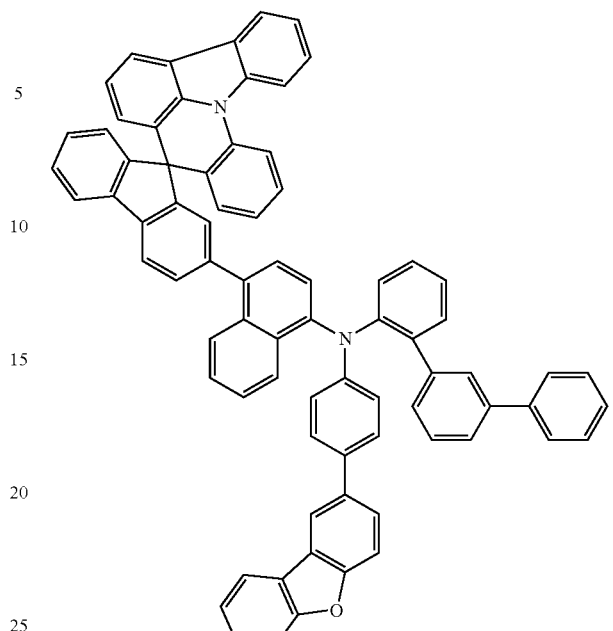
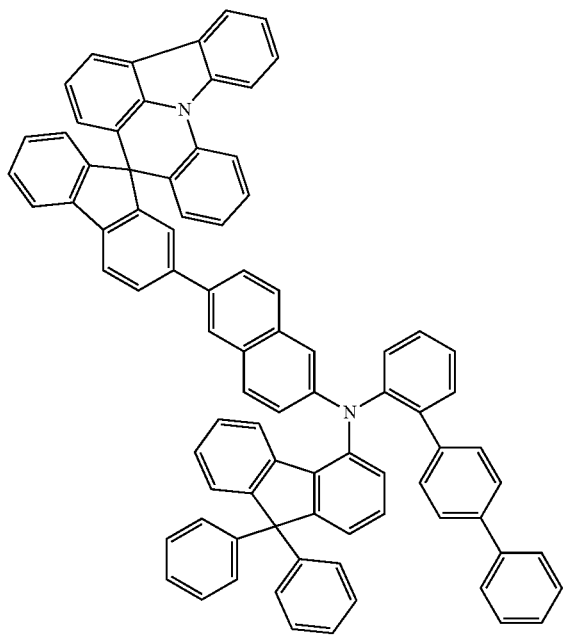
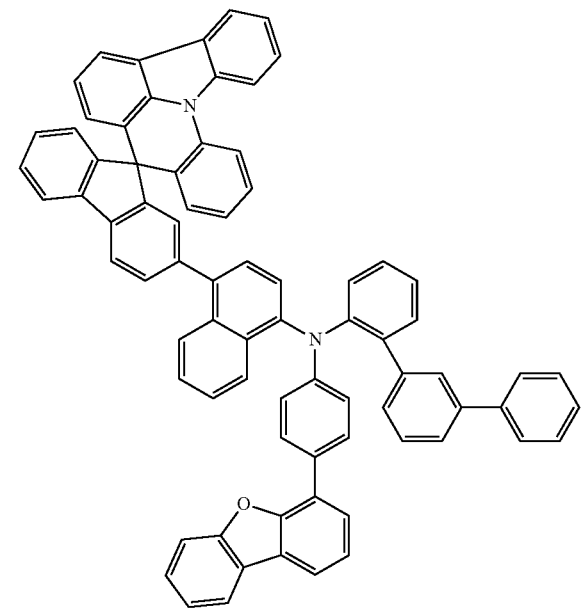

345
-continued
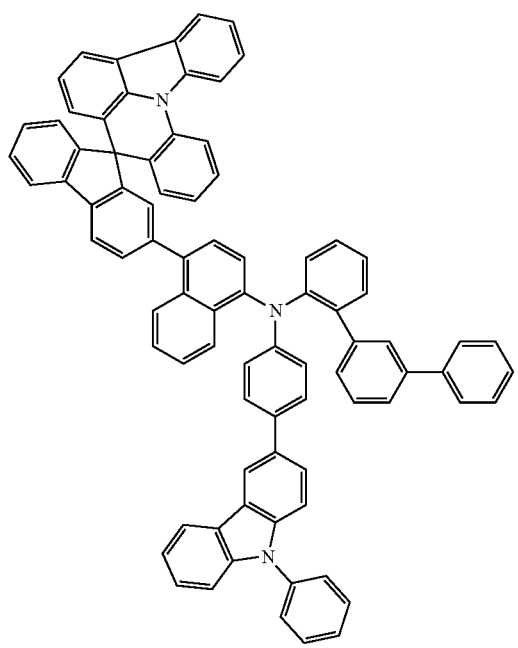
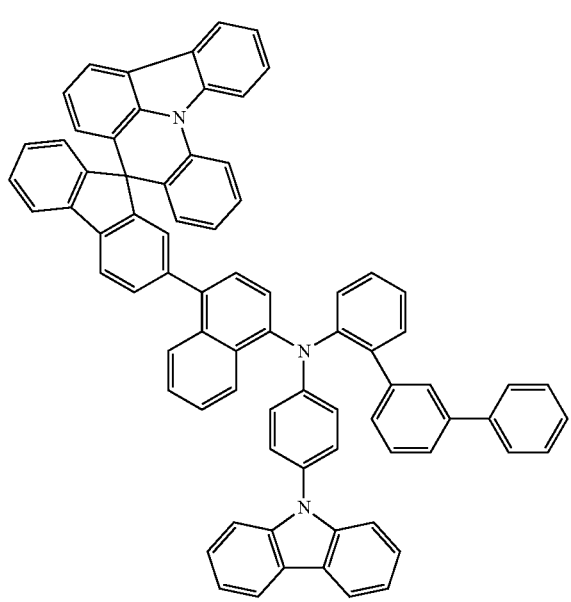
346
-continued
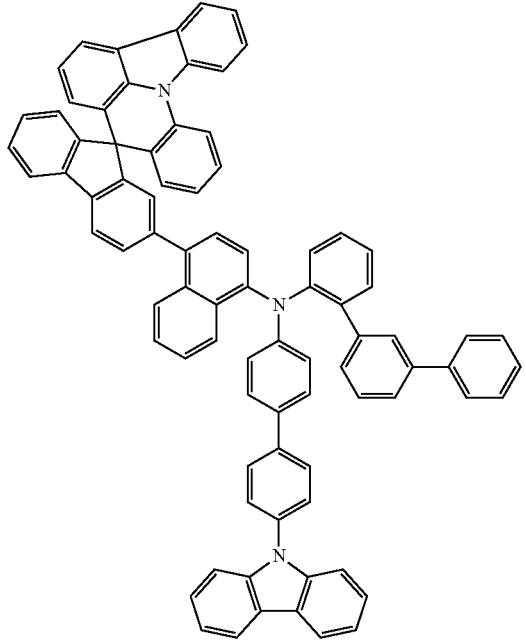
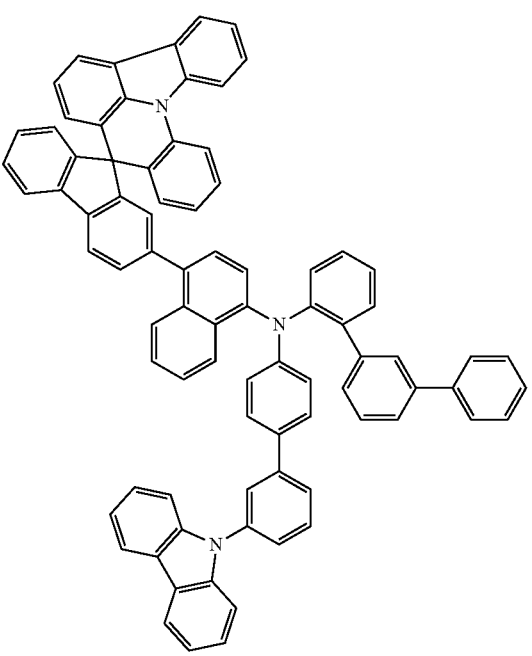

347
-continued
348
-continued
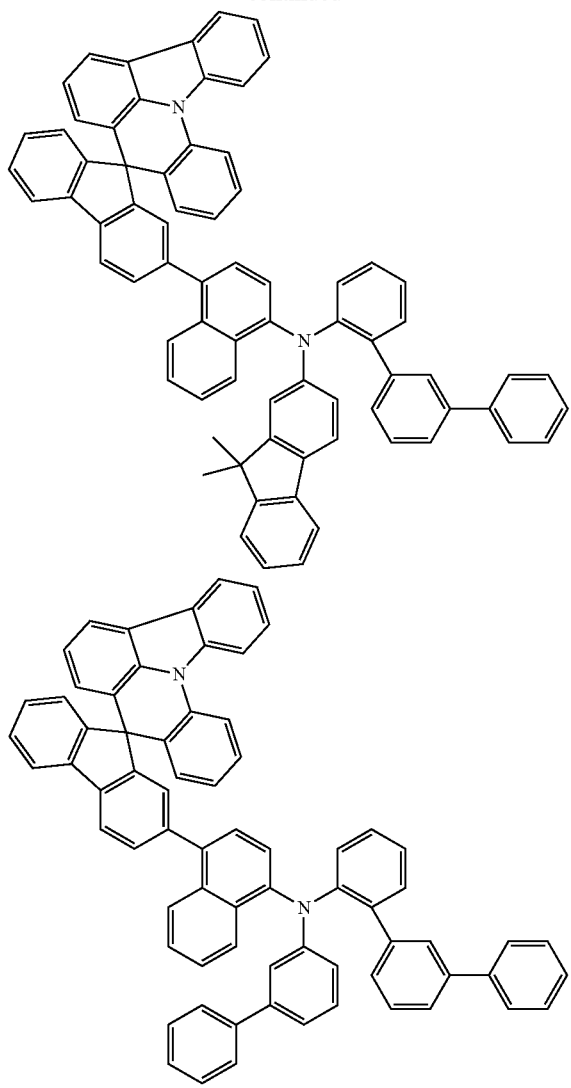
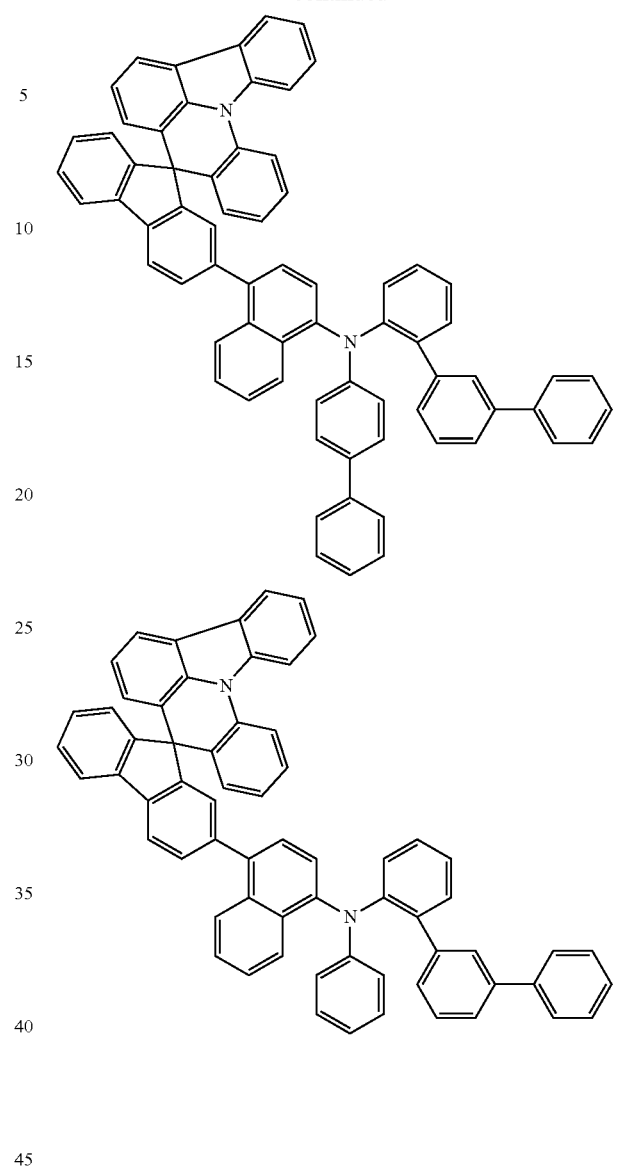
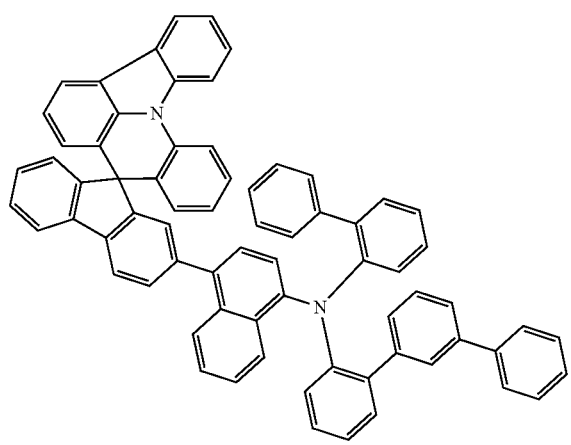
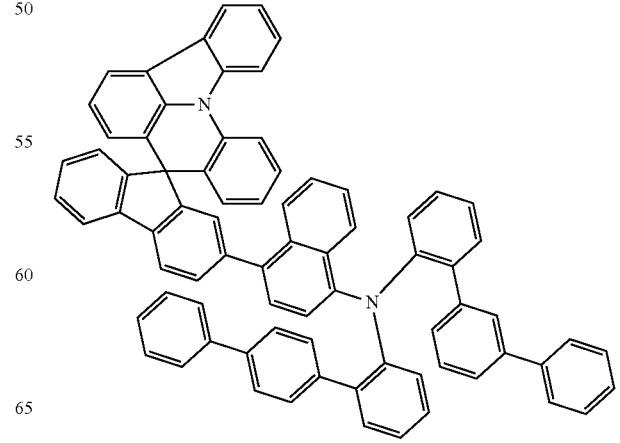

349
-continued
350
-continued
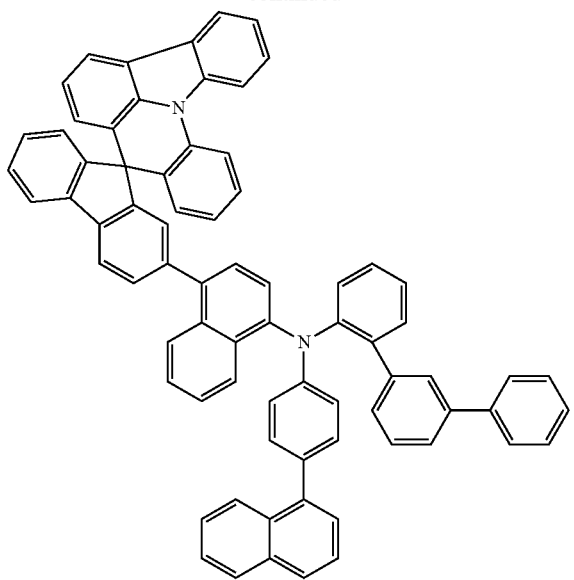
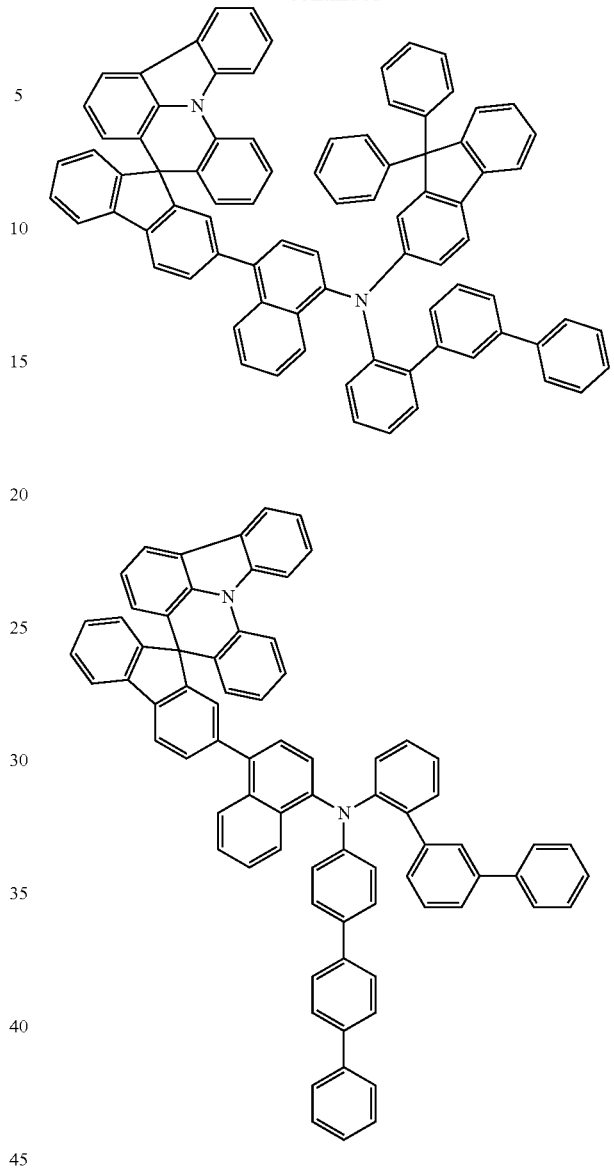
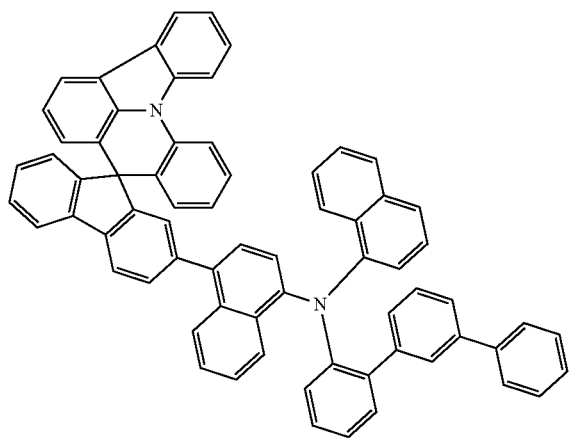
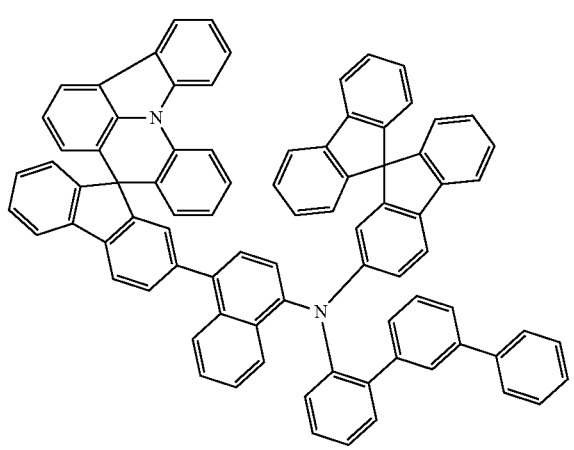
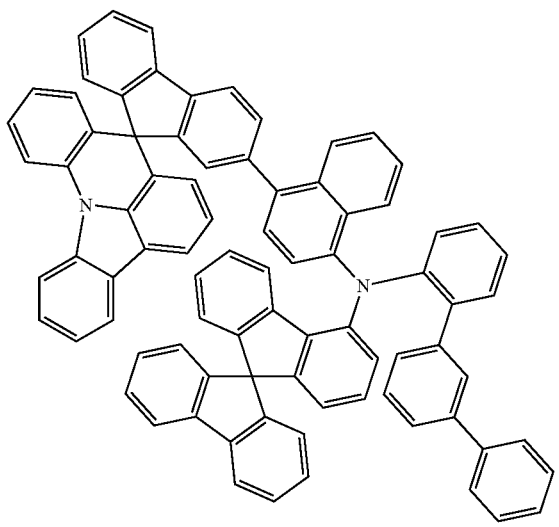

351
-continued
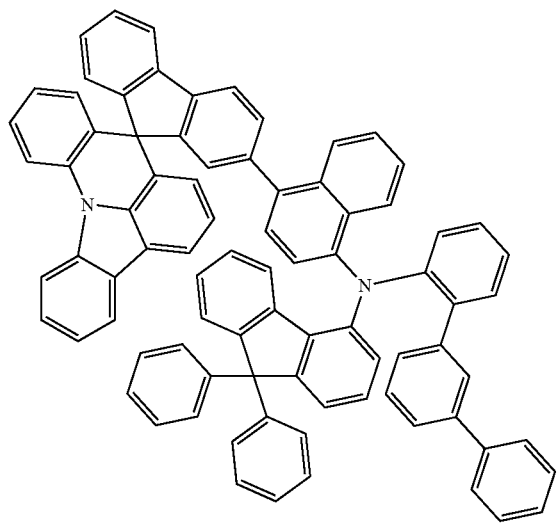
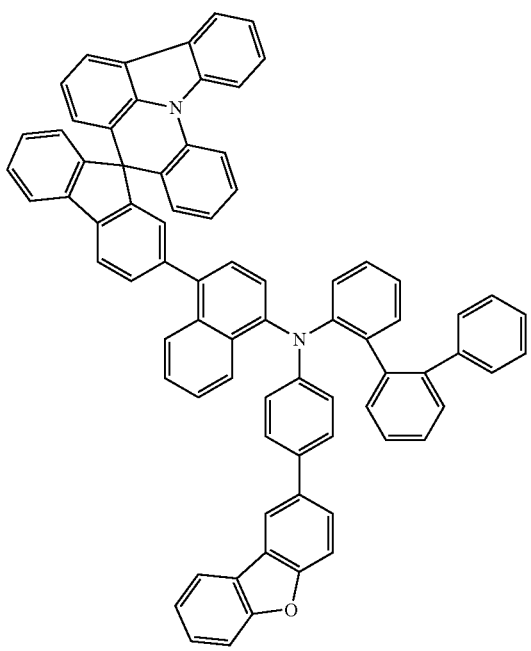
352
-continued
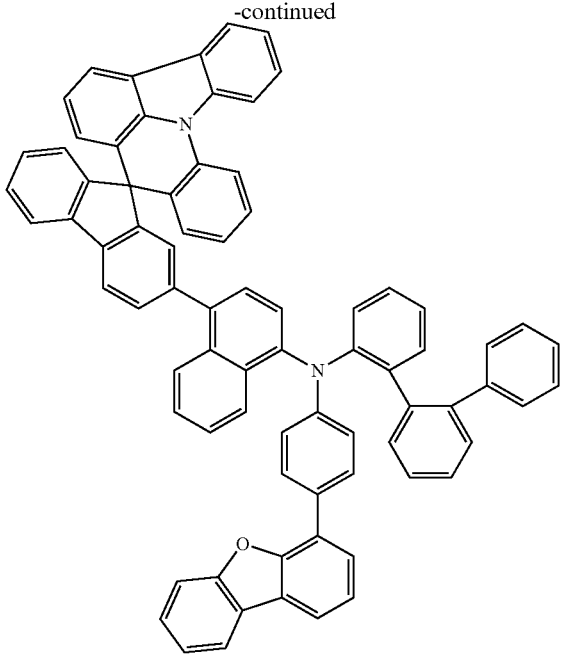
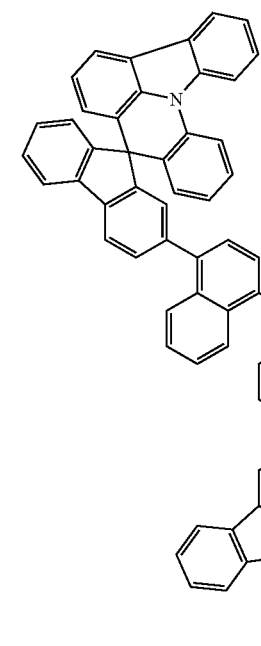

353
-continued
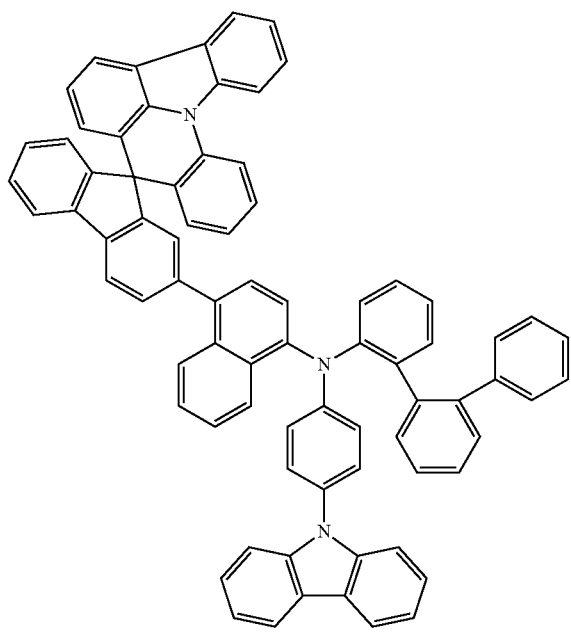
354
-continued
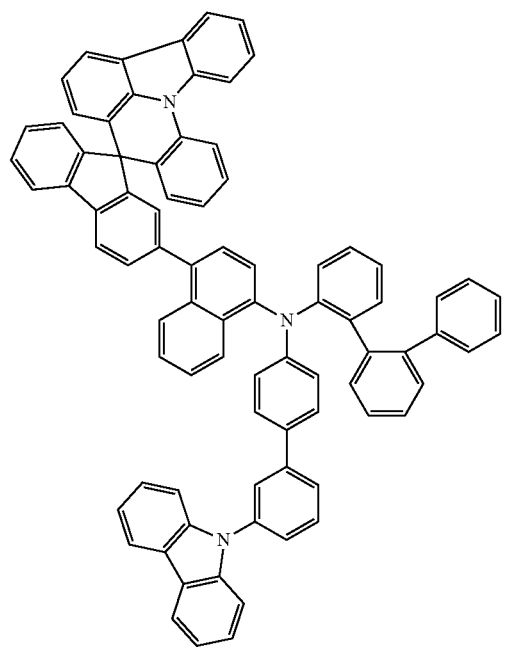
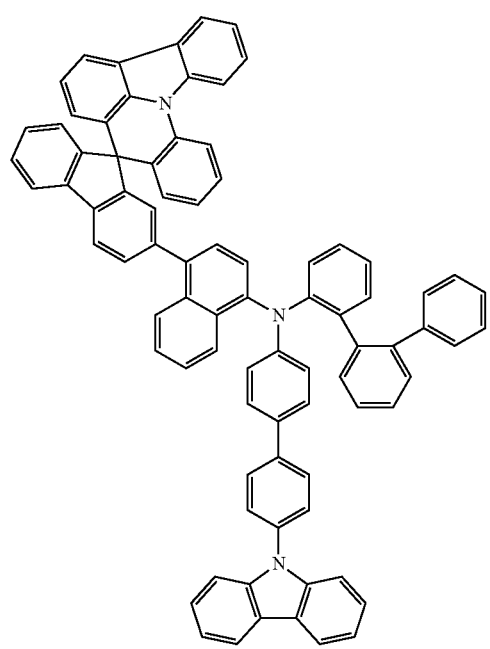
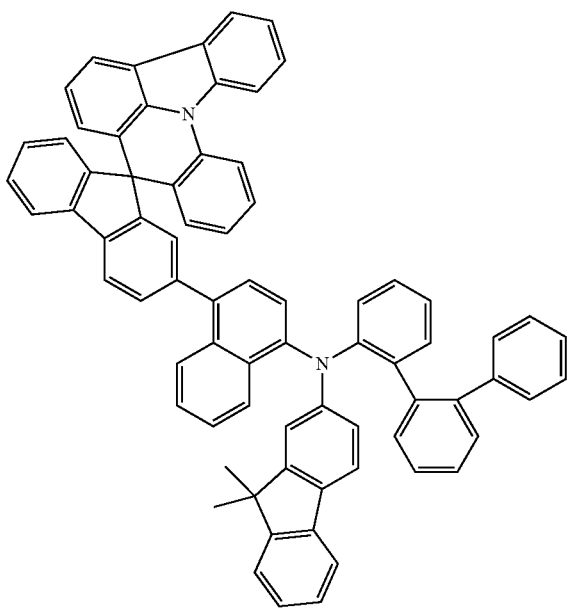

355
-continued
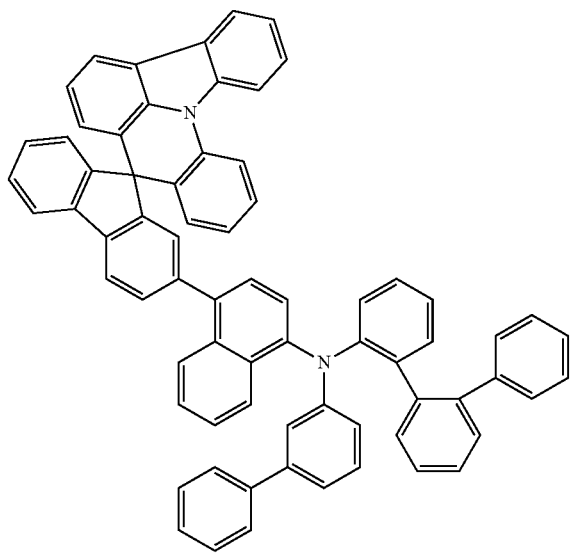
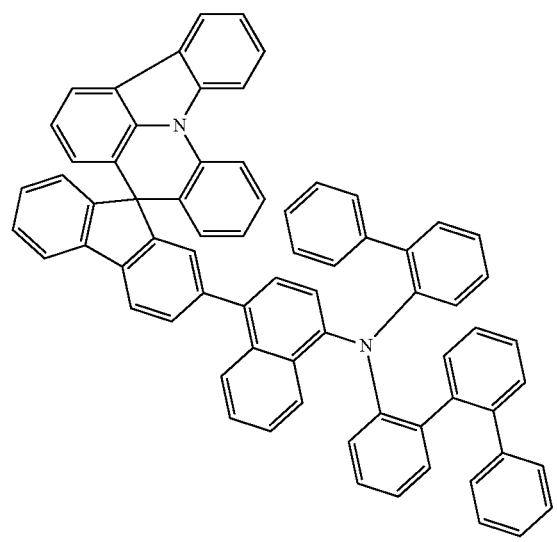
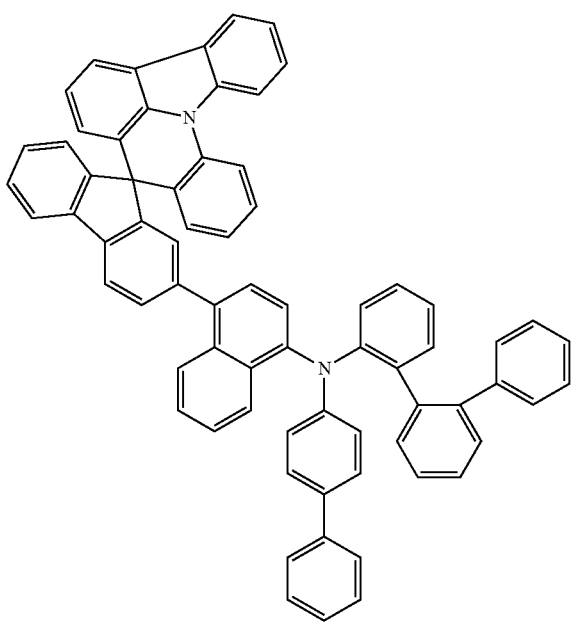
356
-continued
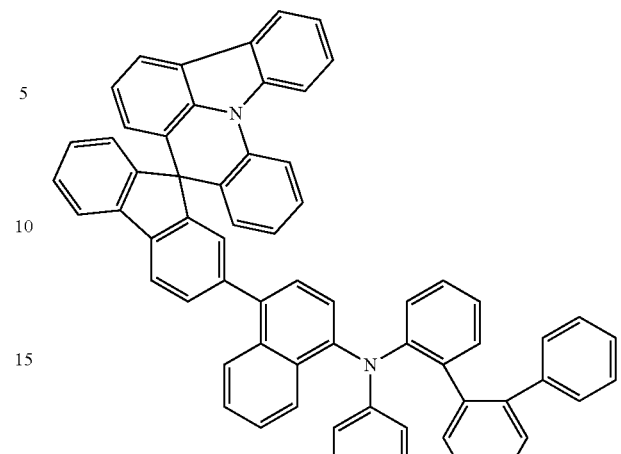
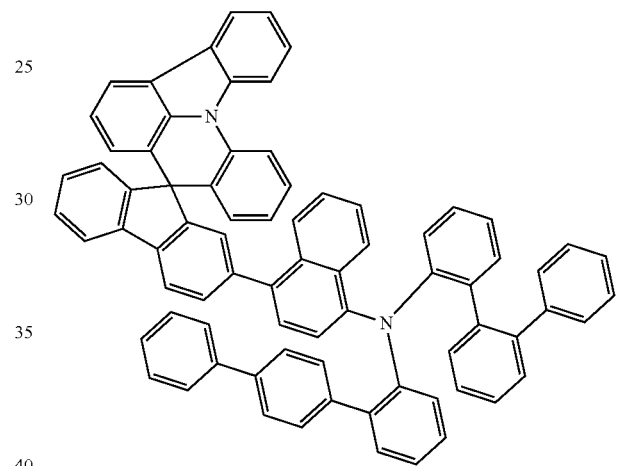
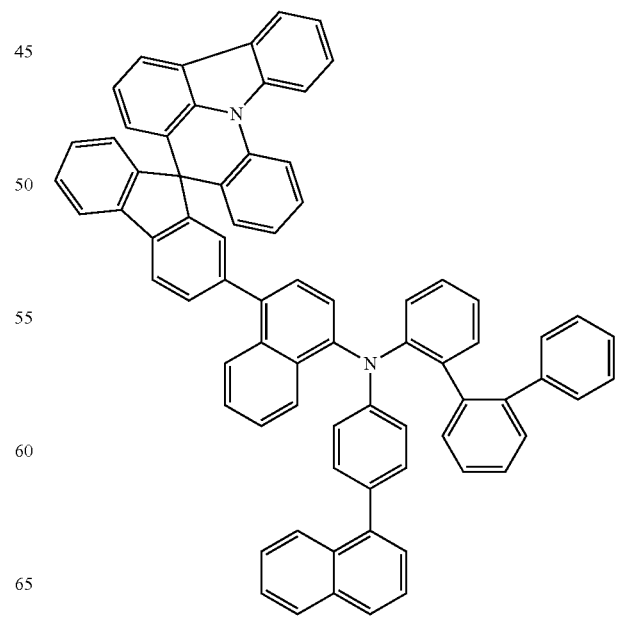

357
-continued
358
-continued
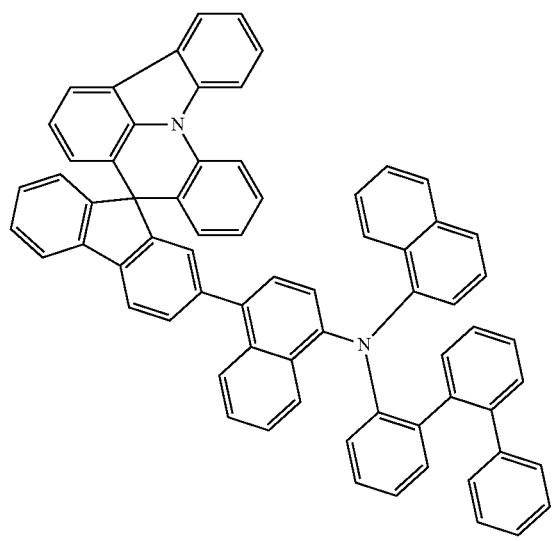
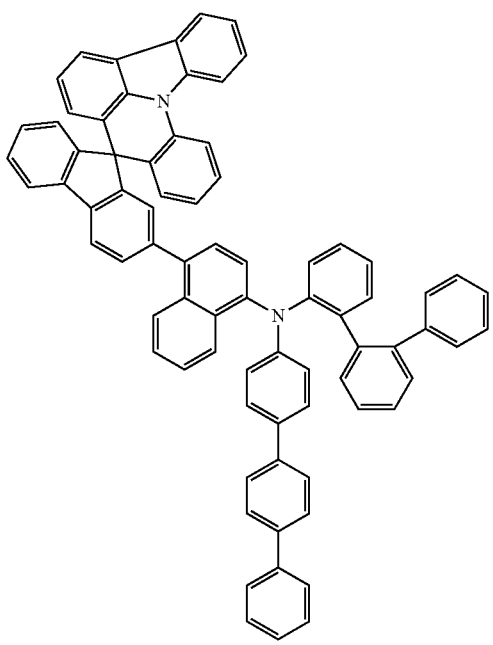
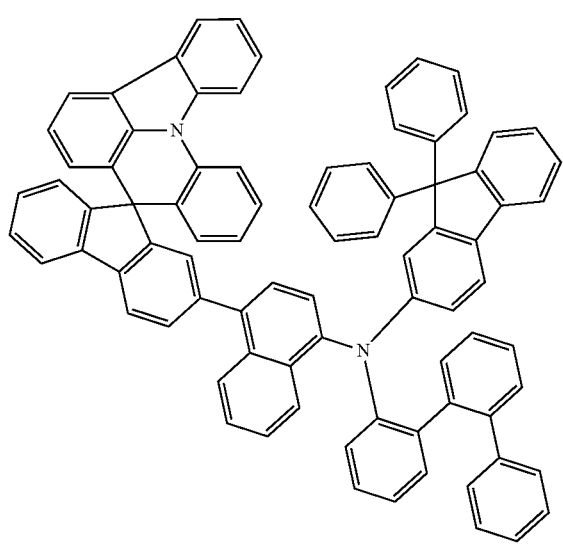
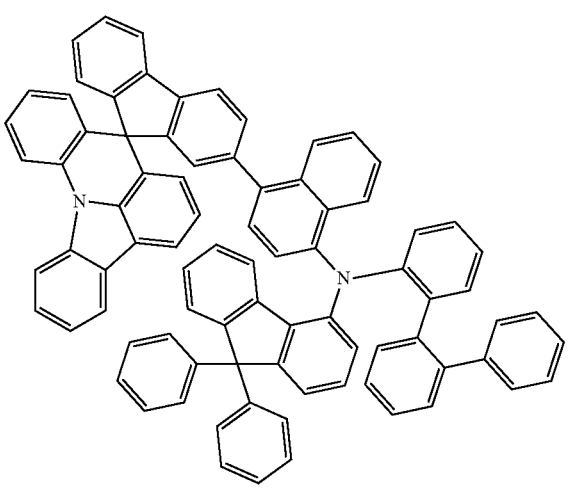

359
-continued
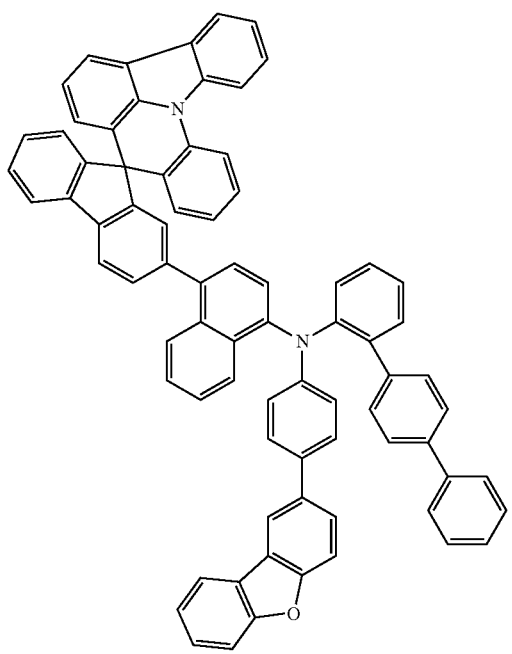
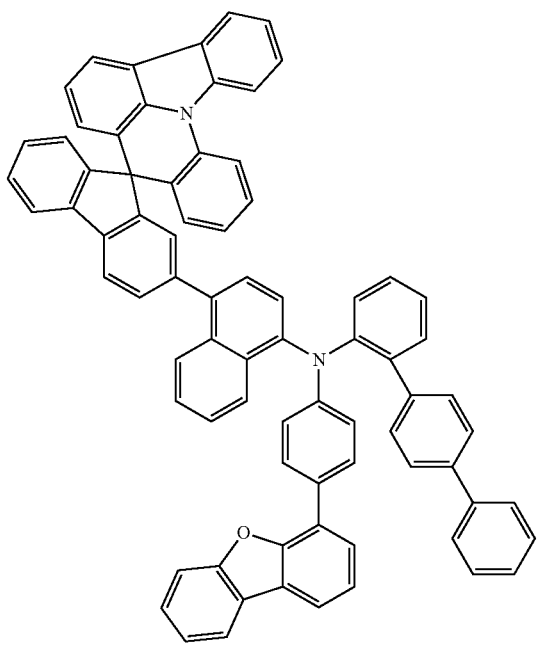
360
-continued
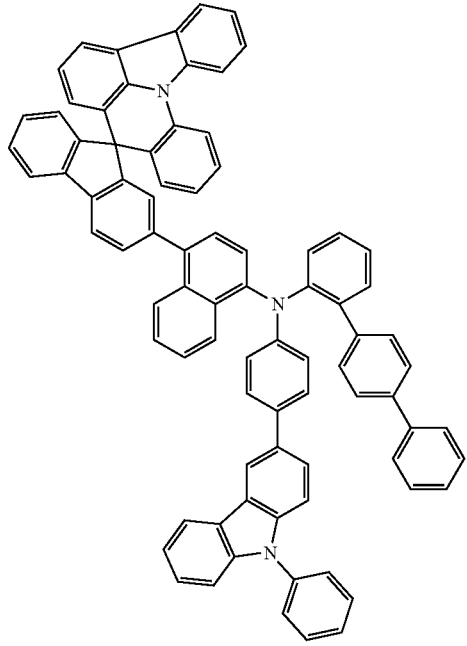
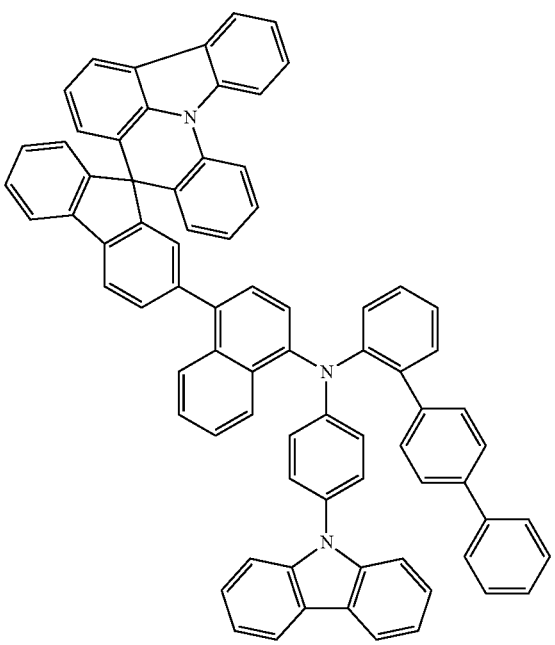

361
-continued
362
-continued
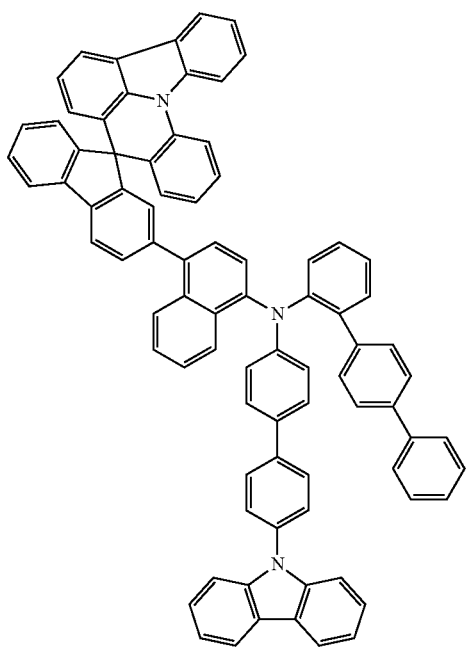
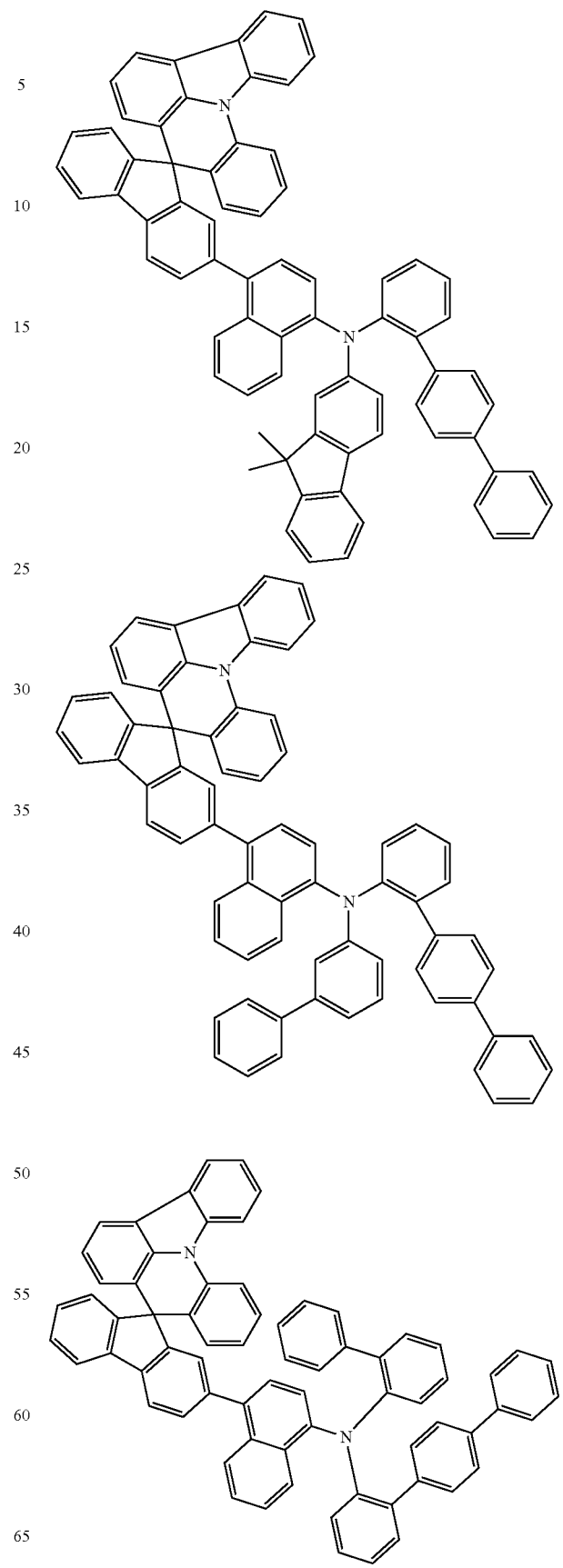

363
-continued
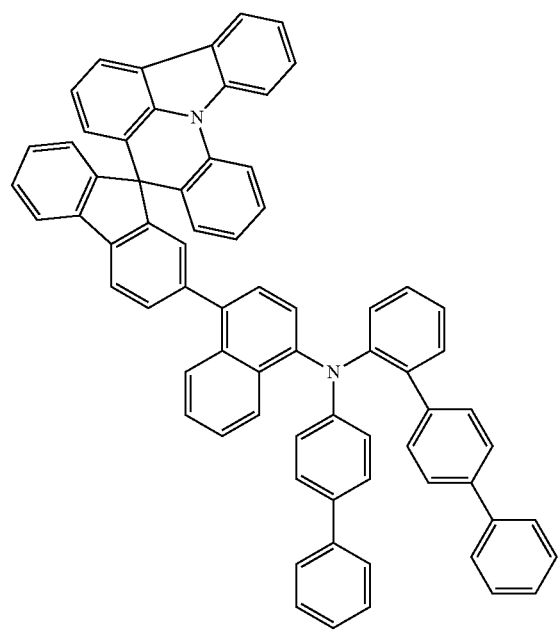
364
-continued
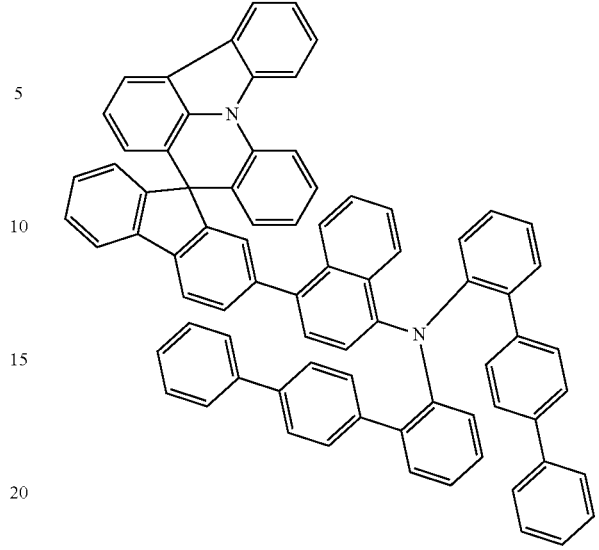
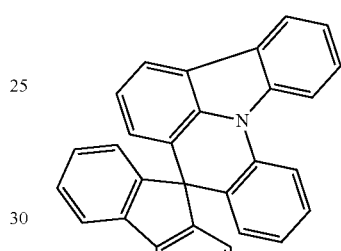
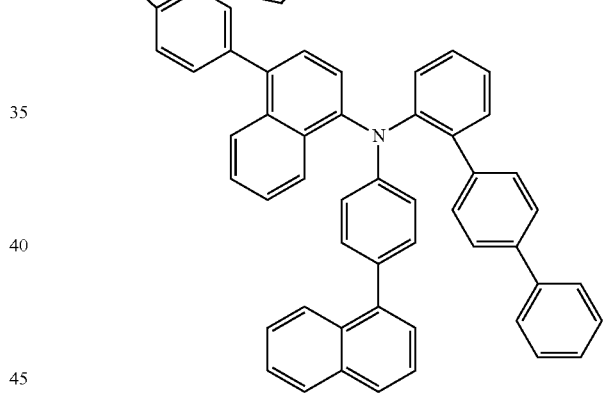
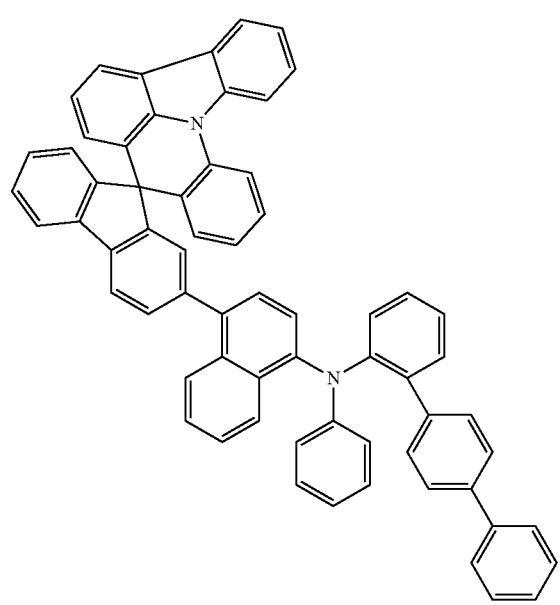
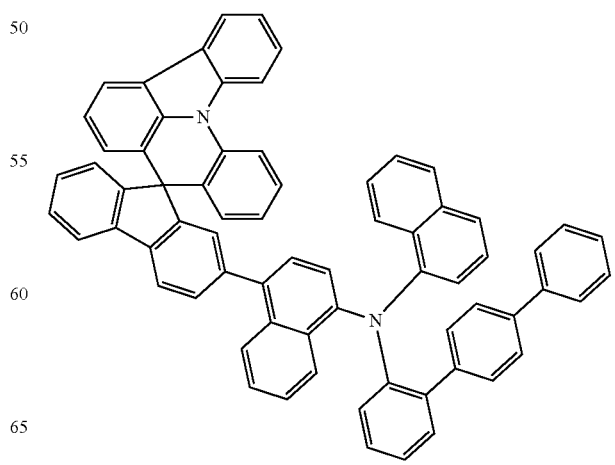

365
-continued
366
-continued
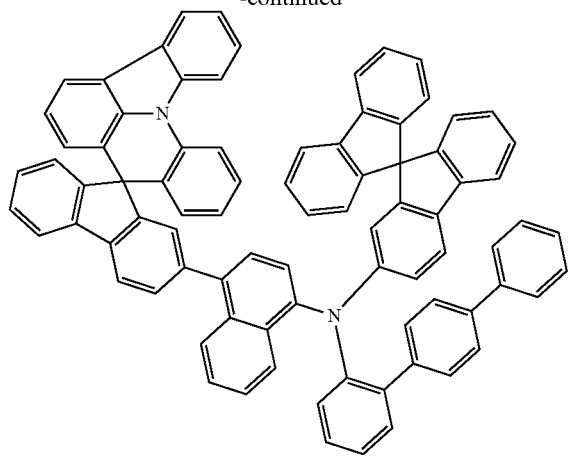
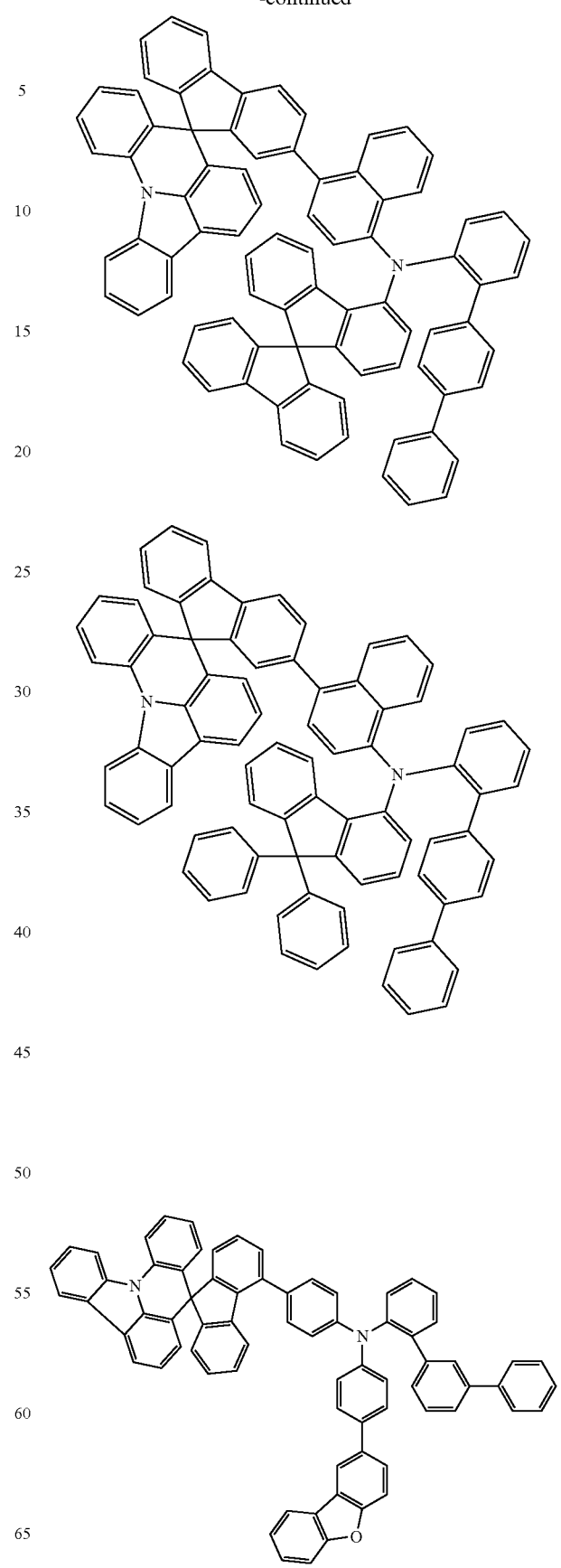

367
-continued
368
-continued
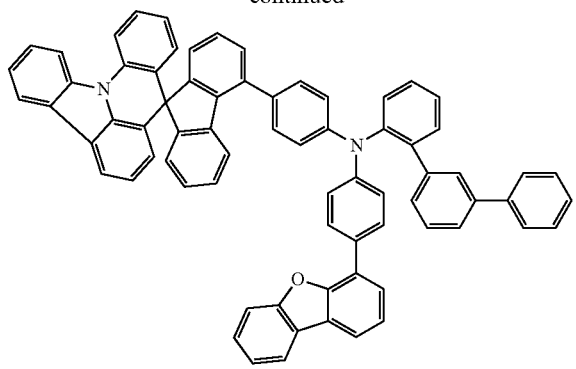
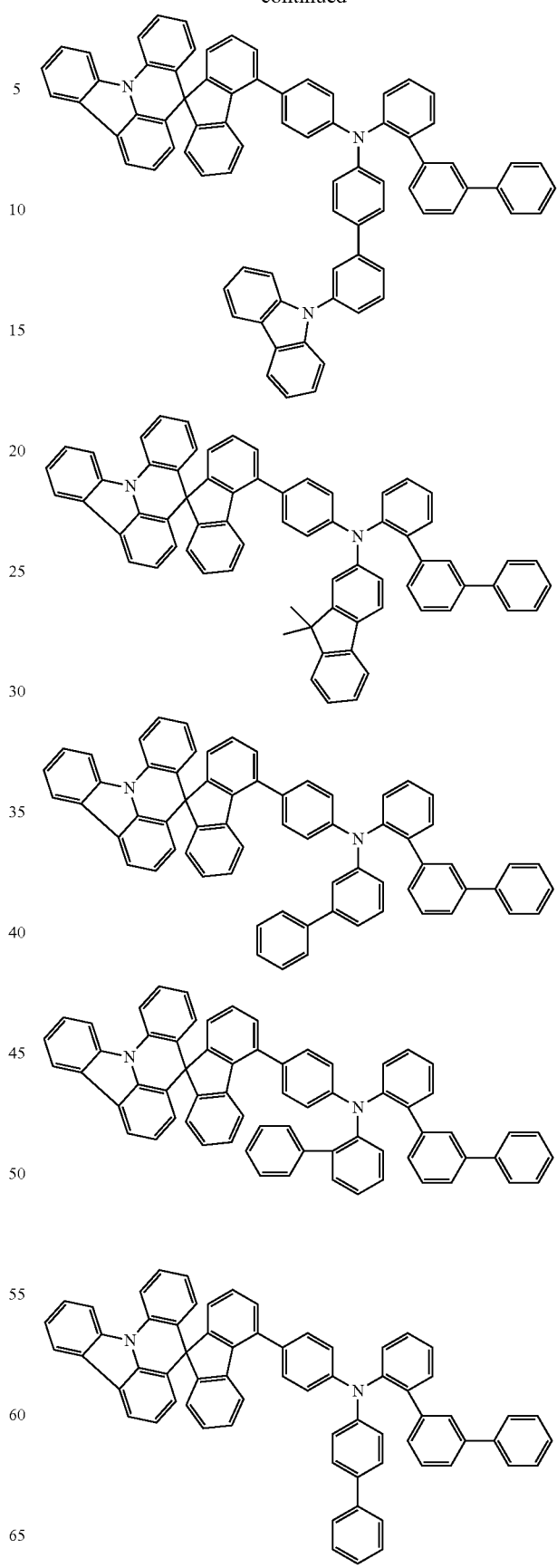

369
-continued
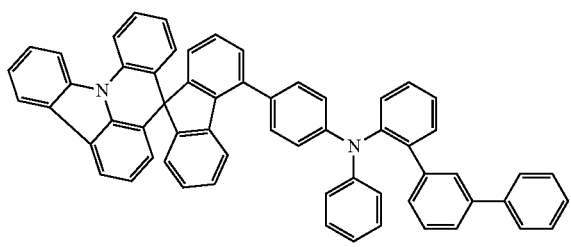
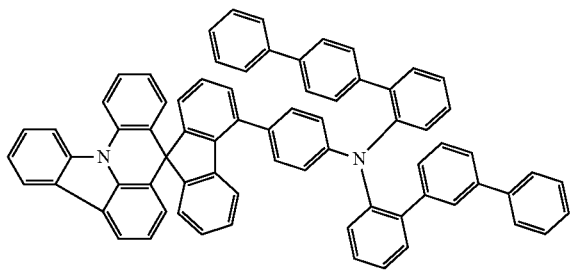
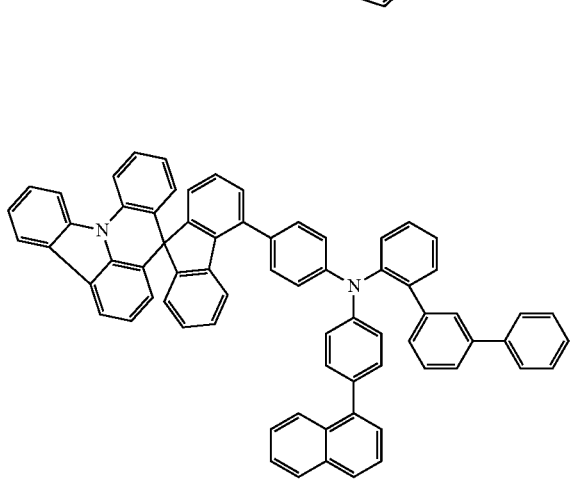
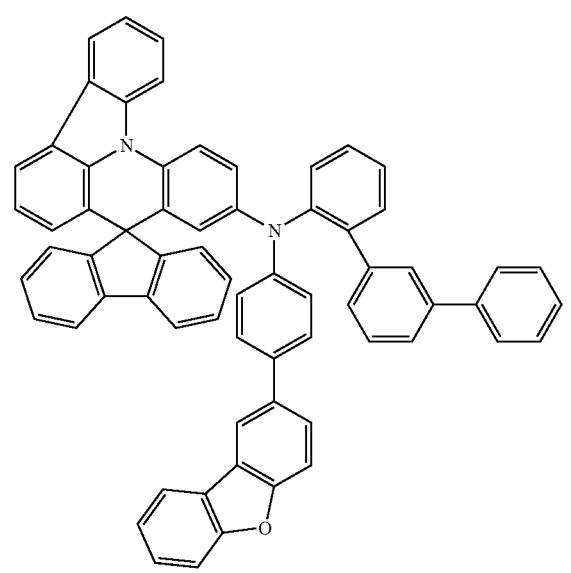
370
-continued
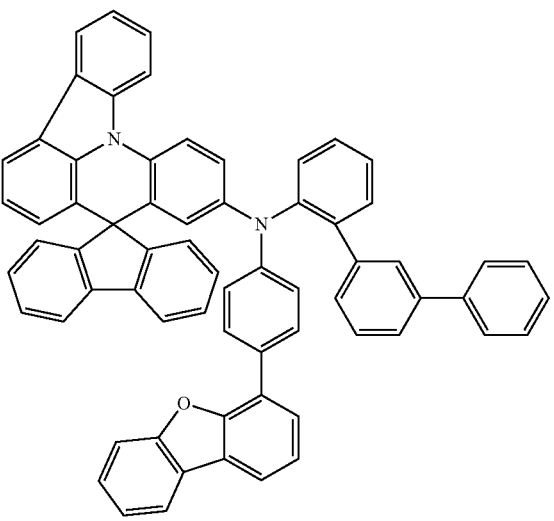
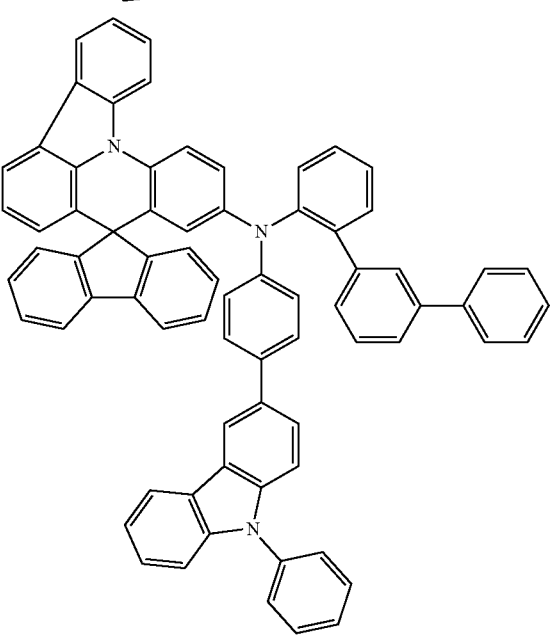

371
-continued
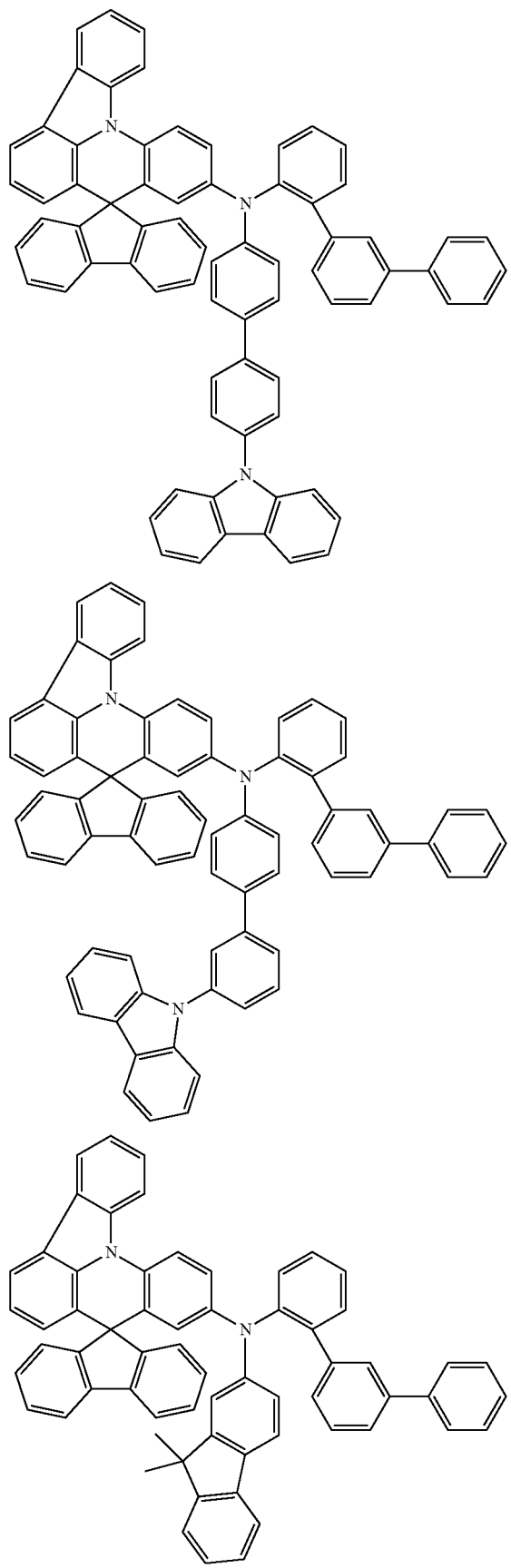
372
-continued
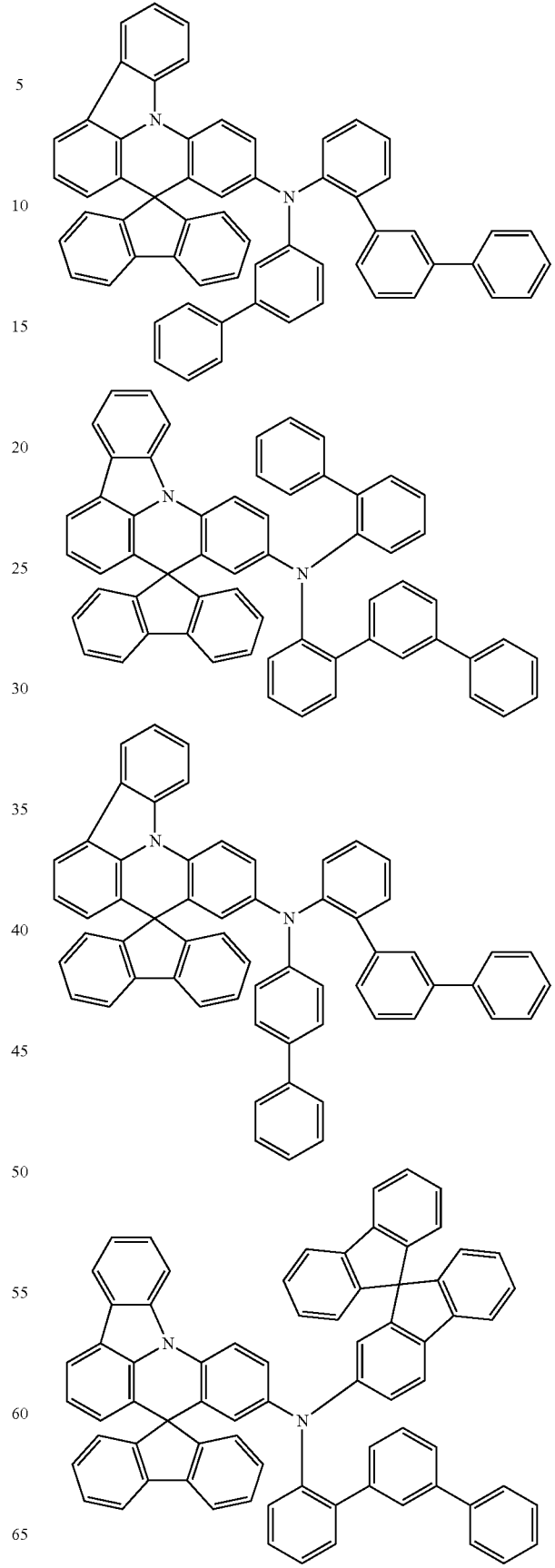

373
-continued
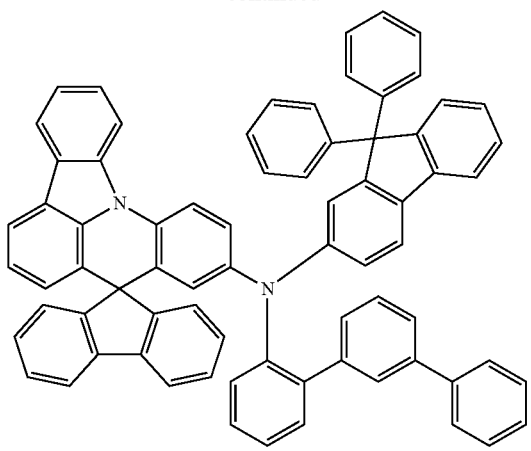
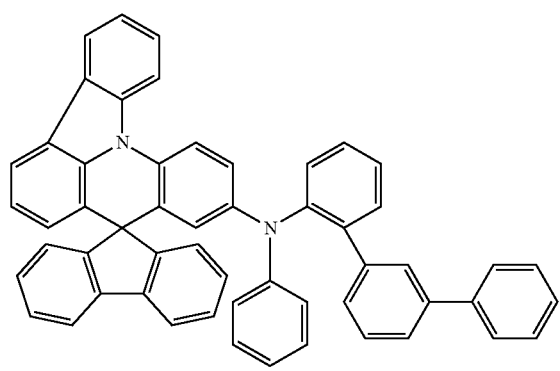
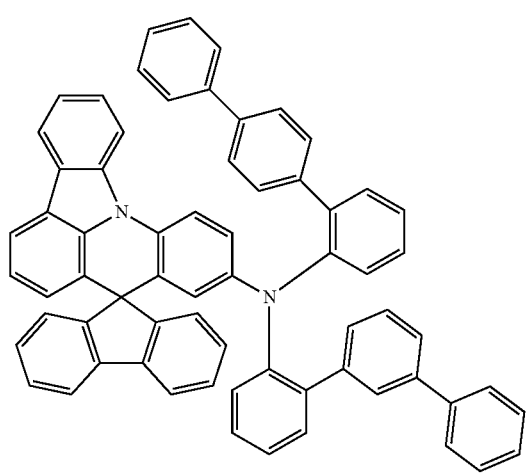
374
-continued
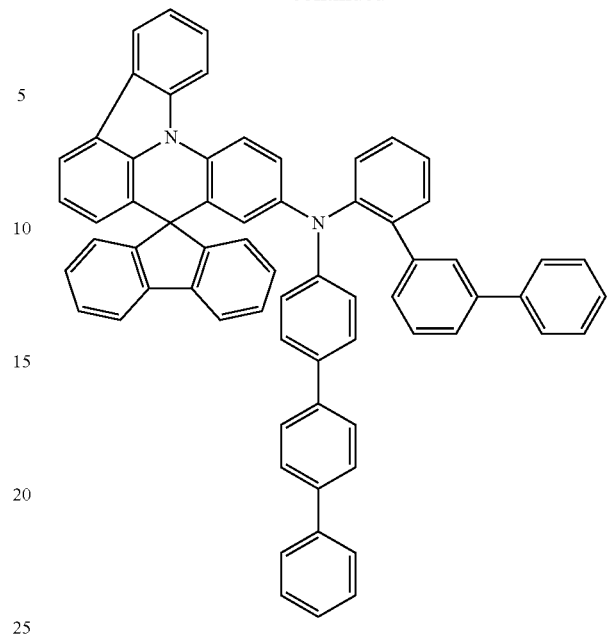
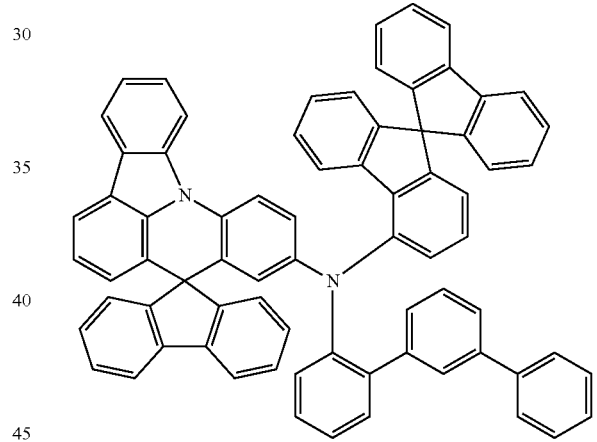
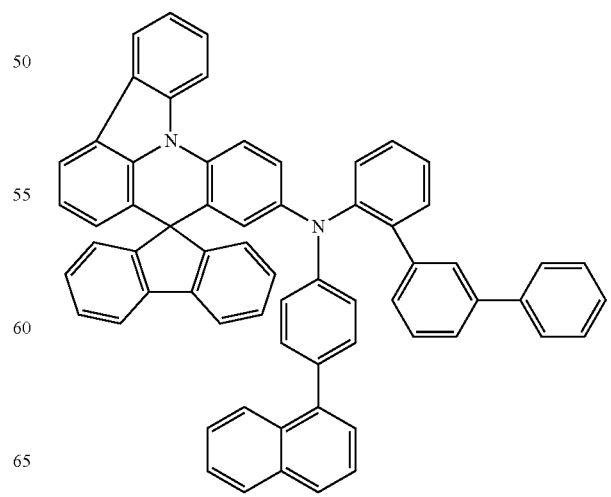

375
-continued
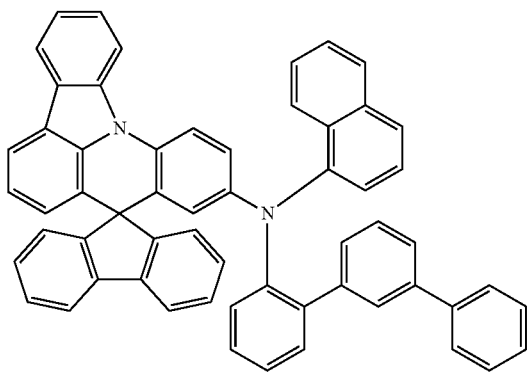
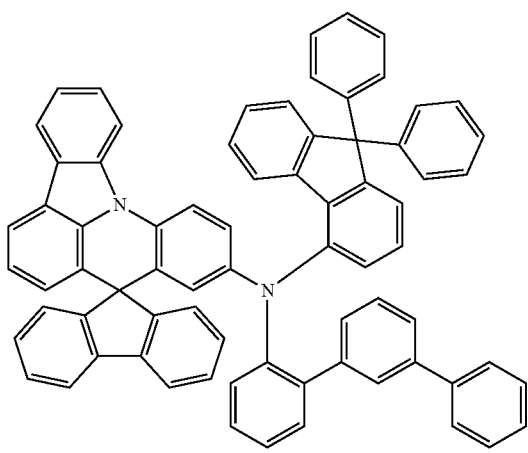
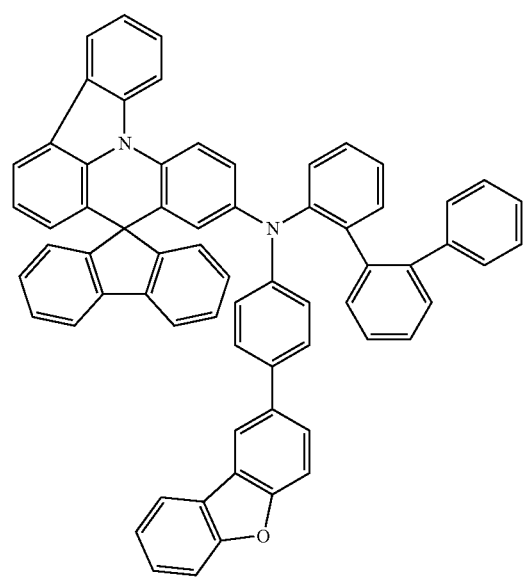
376
-continued
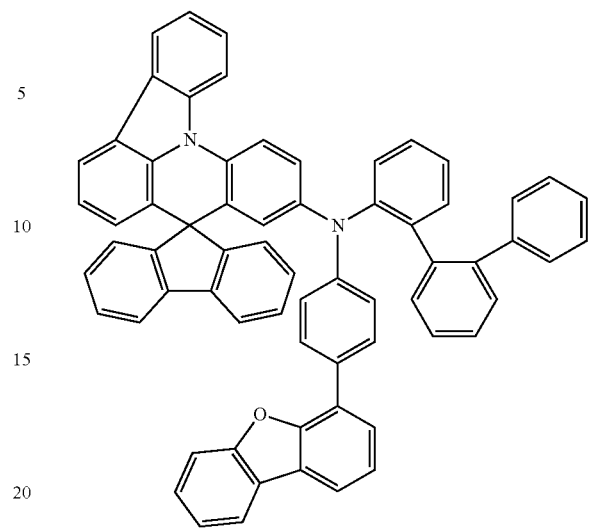
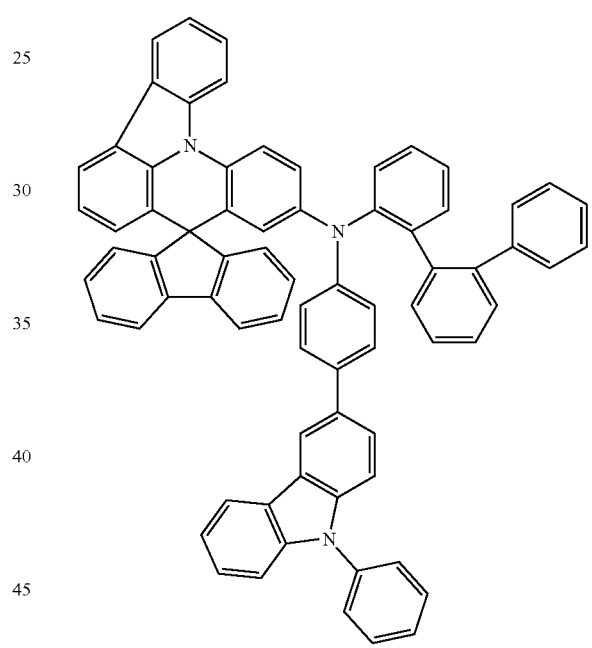
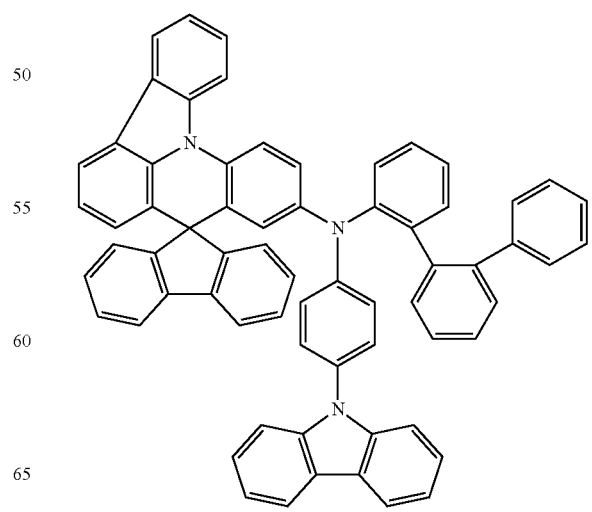

377
-continued
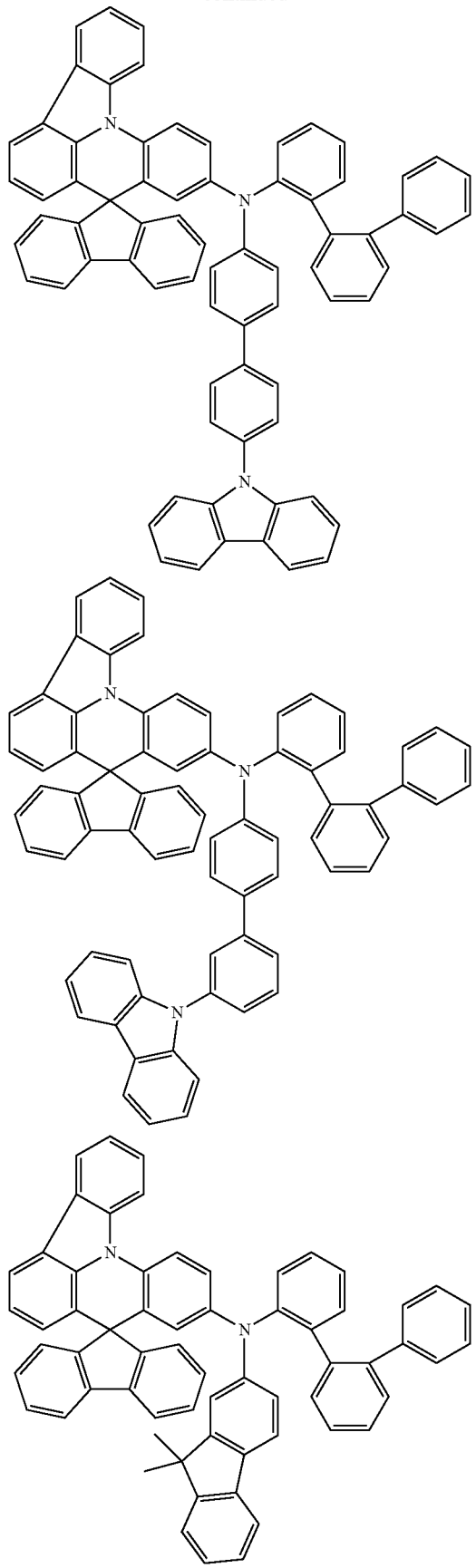
378
-continued
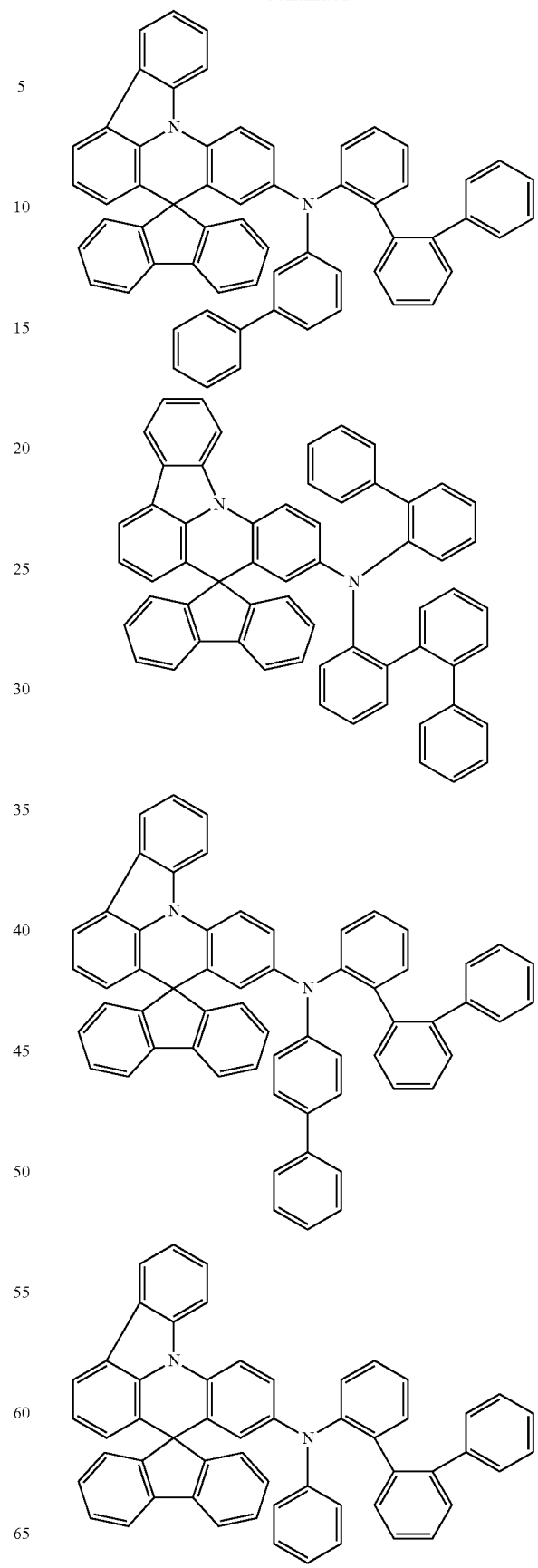

379
-continued
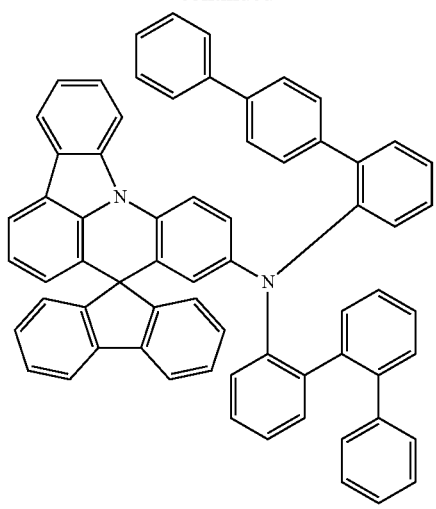
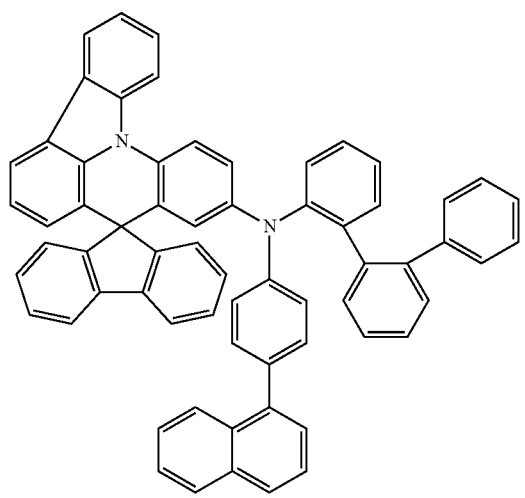
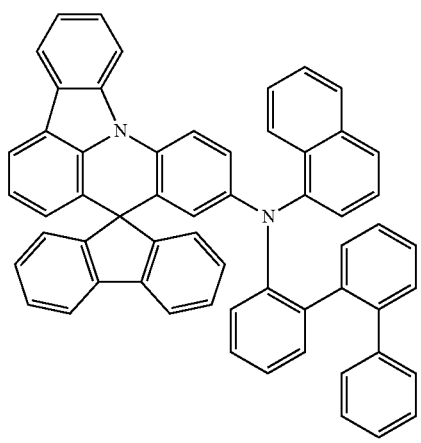
380
-continued
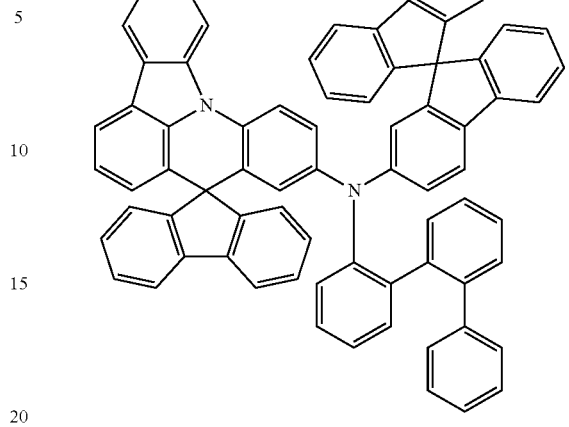
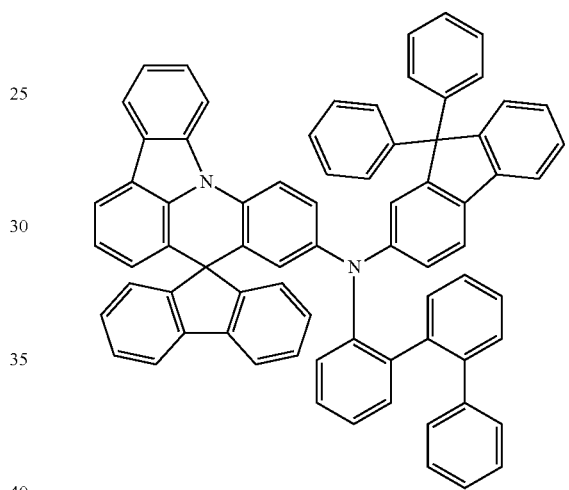
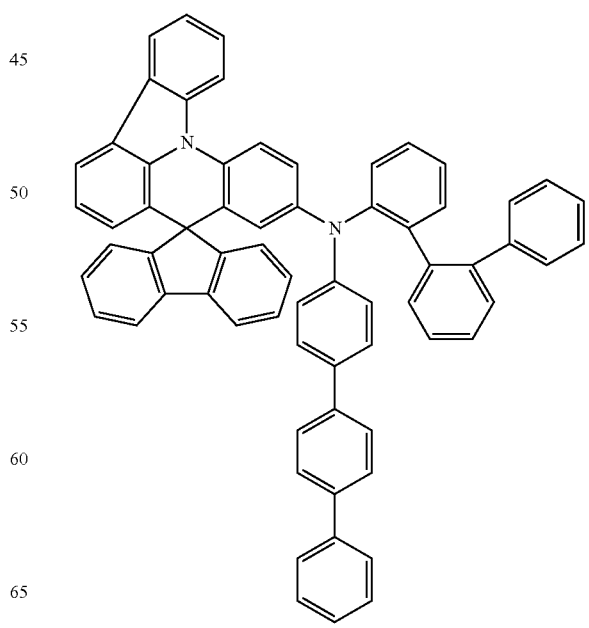

381
-continued
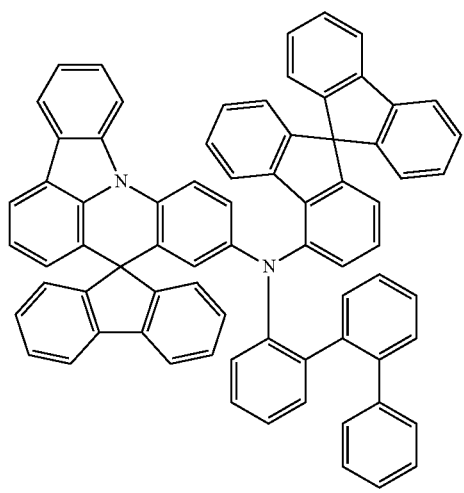
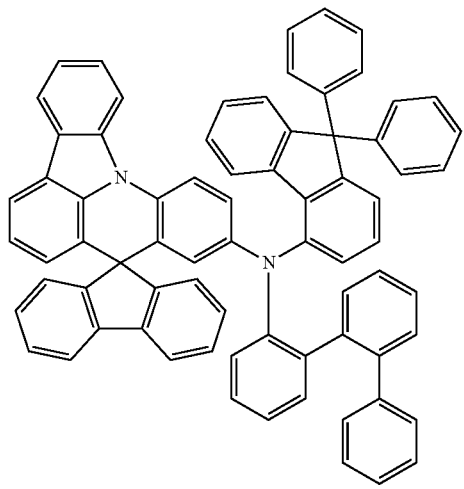
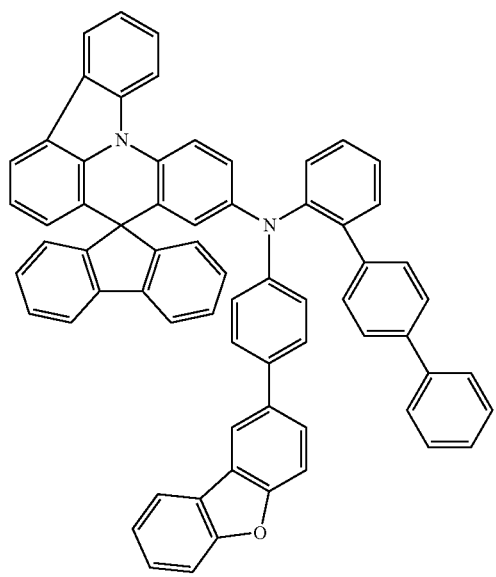
382
-continued
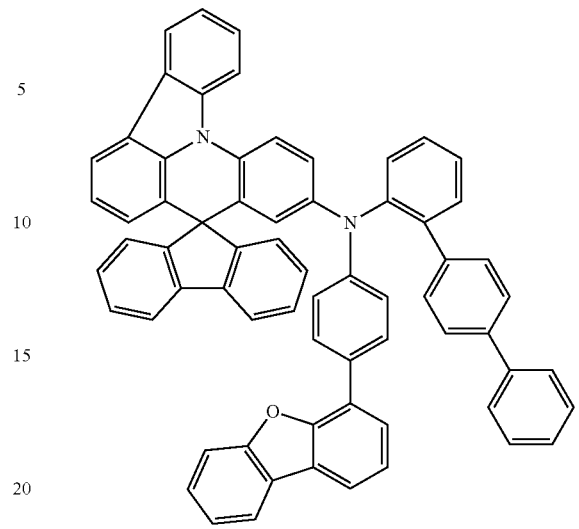
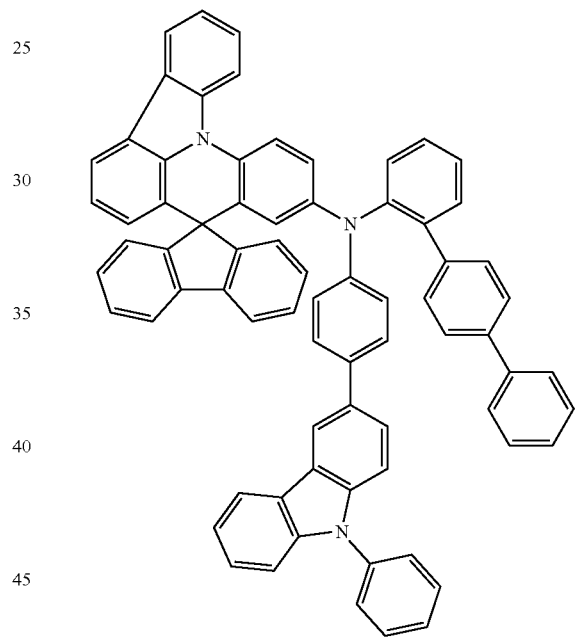
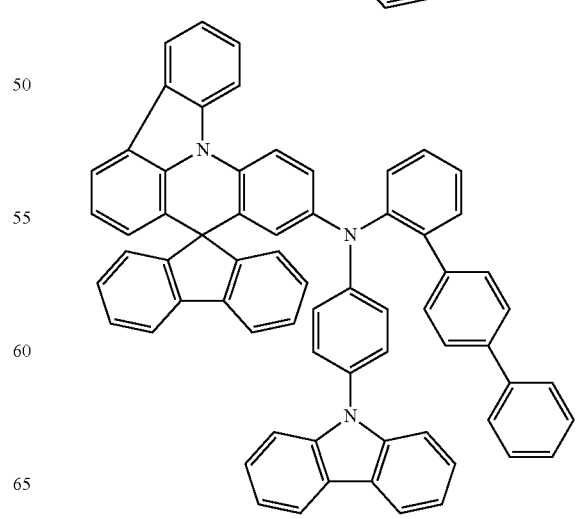

383
-continued
384
-continued
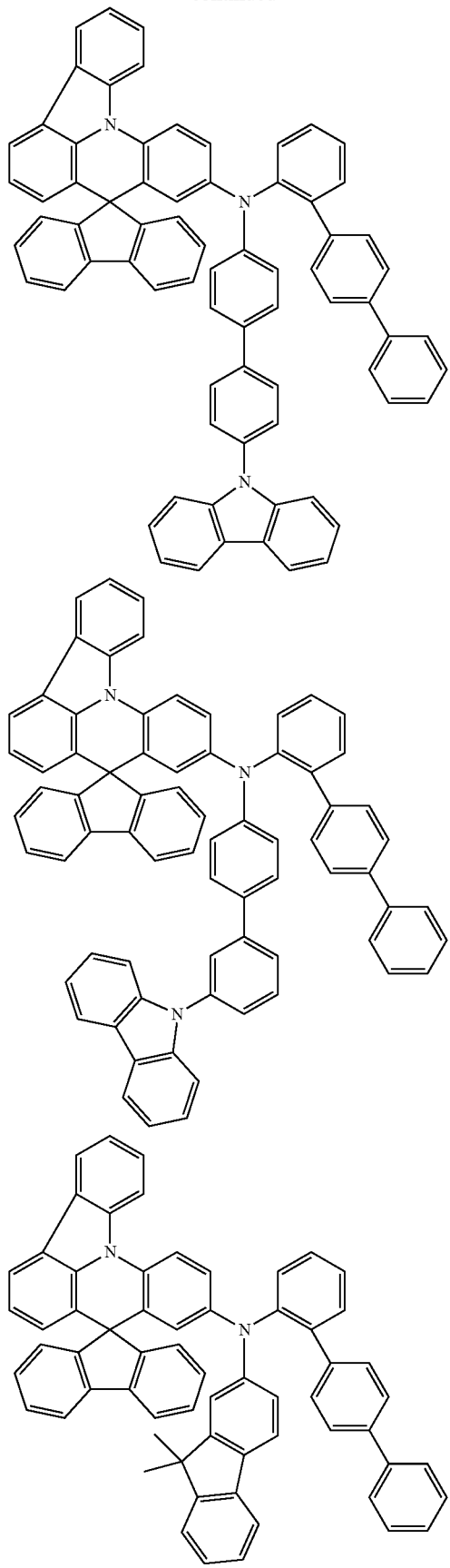
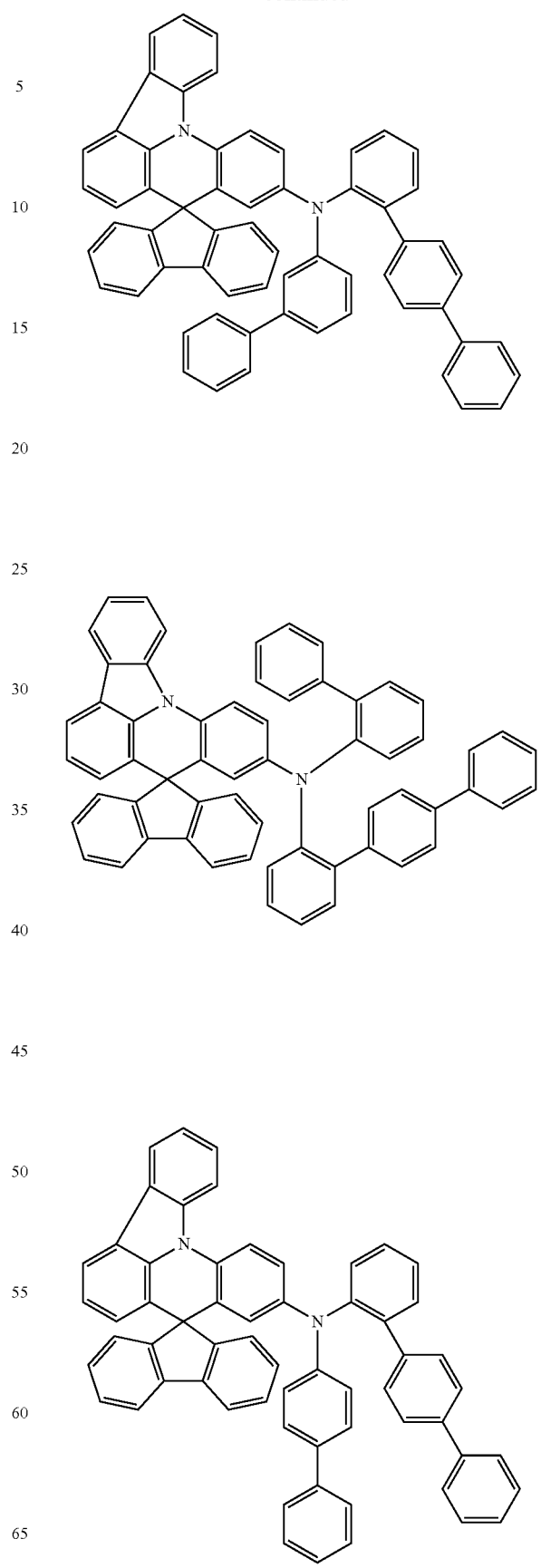

385
-continued
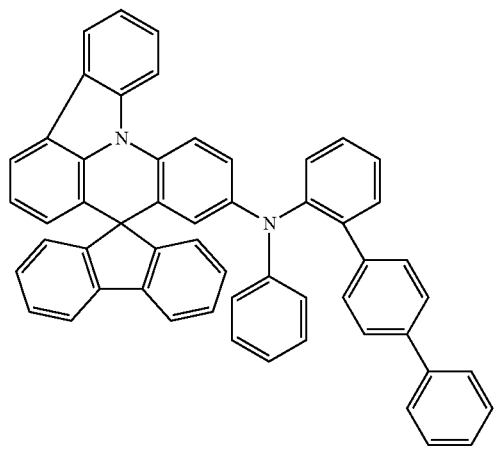
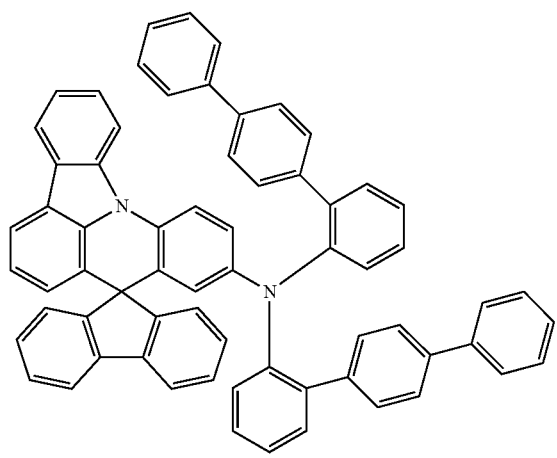
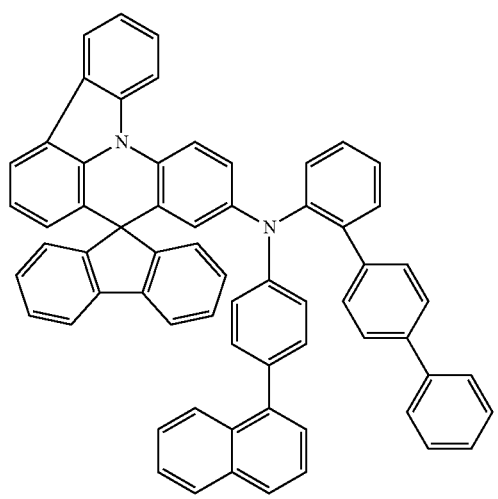
386
-continued
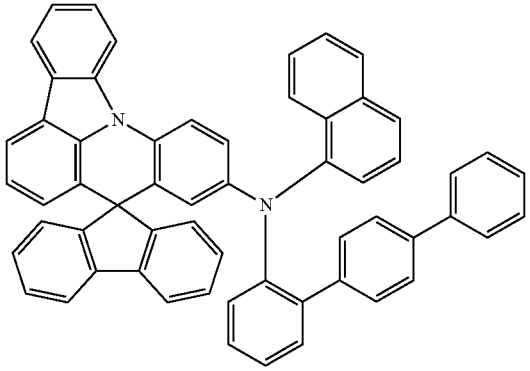
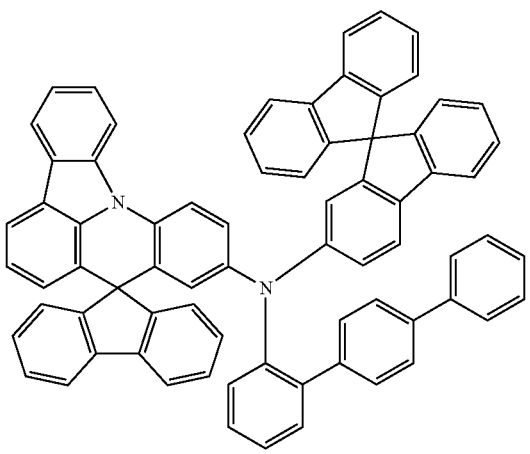
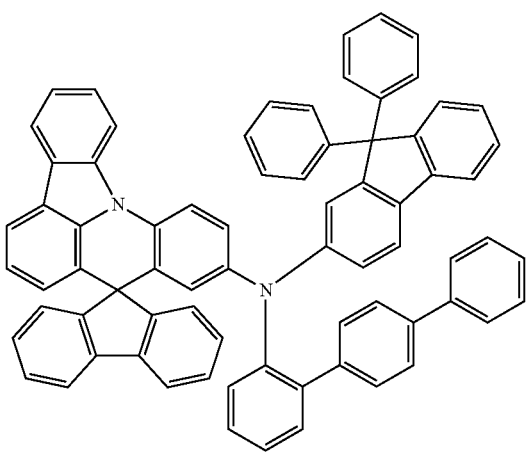

387
-continued
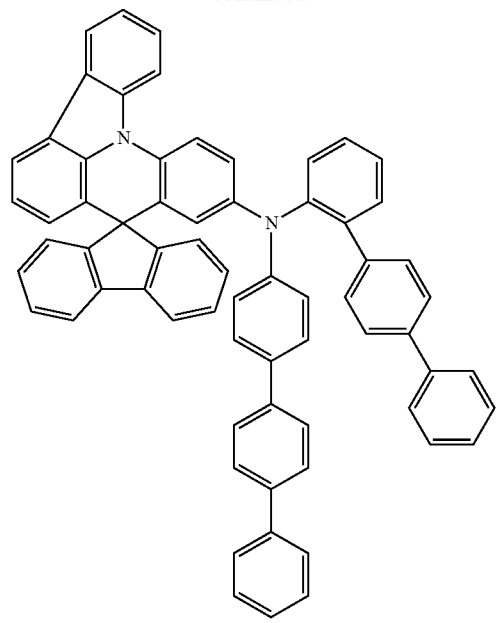
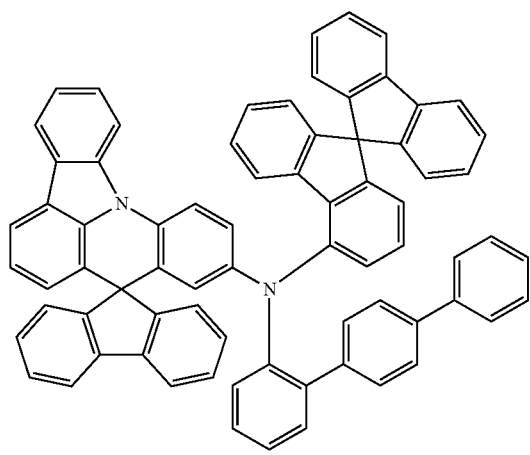
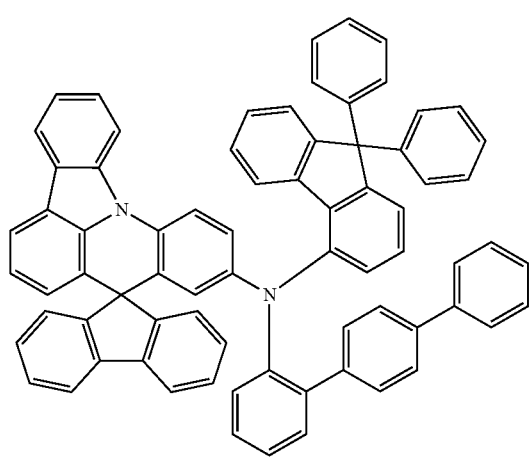
388
-continued
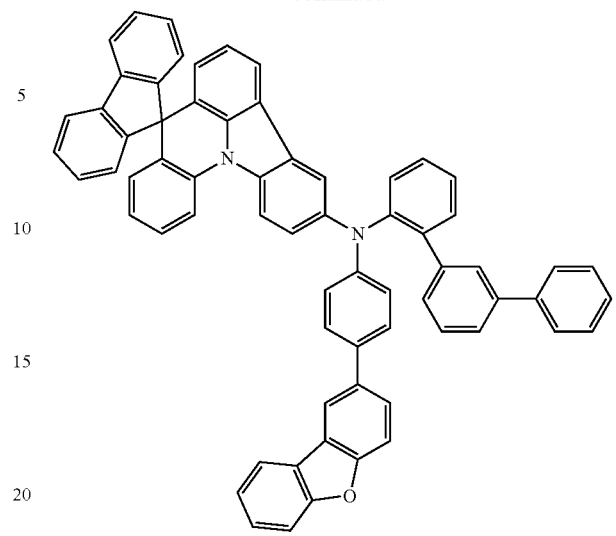
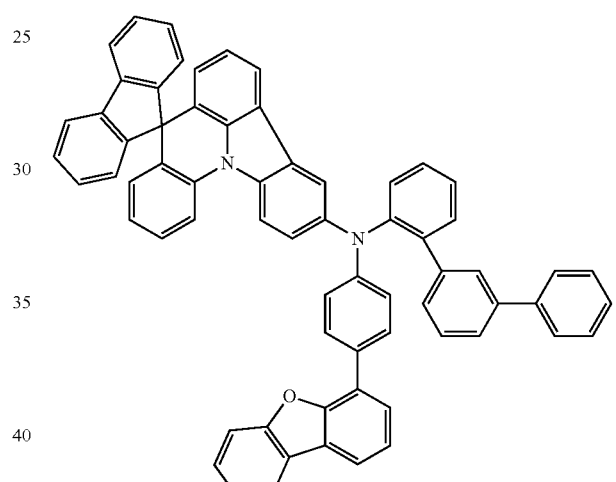
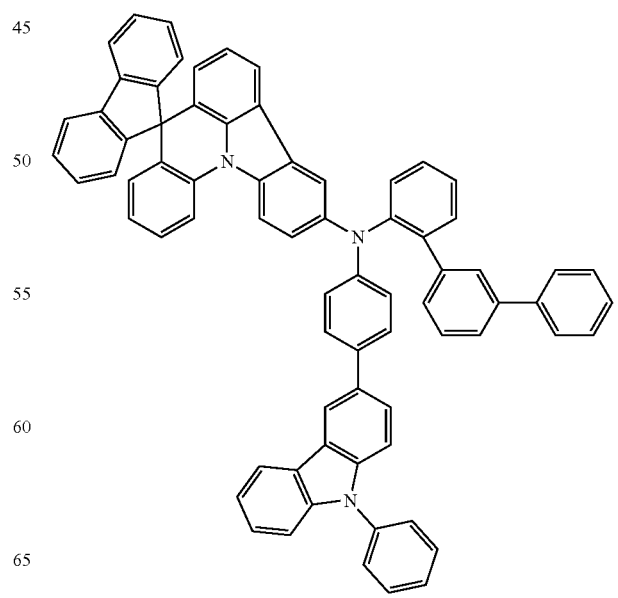

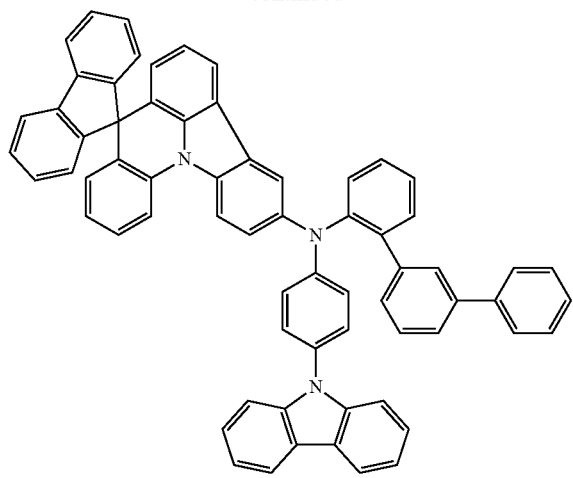
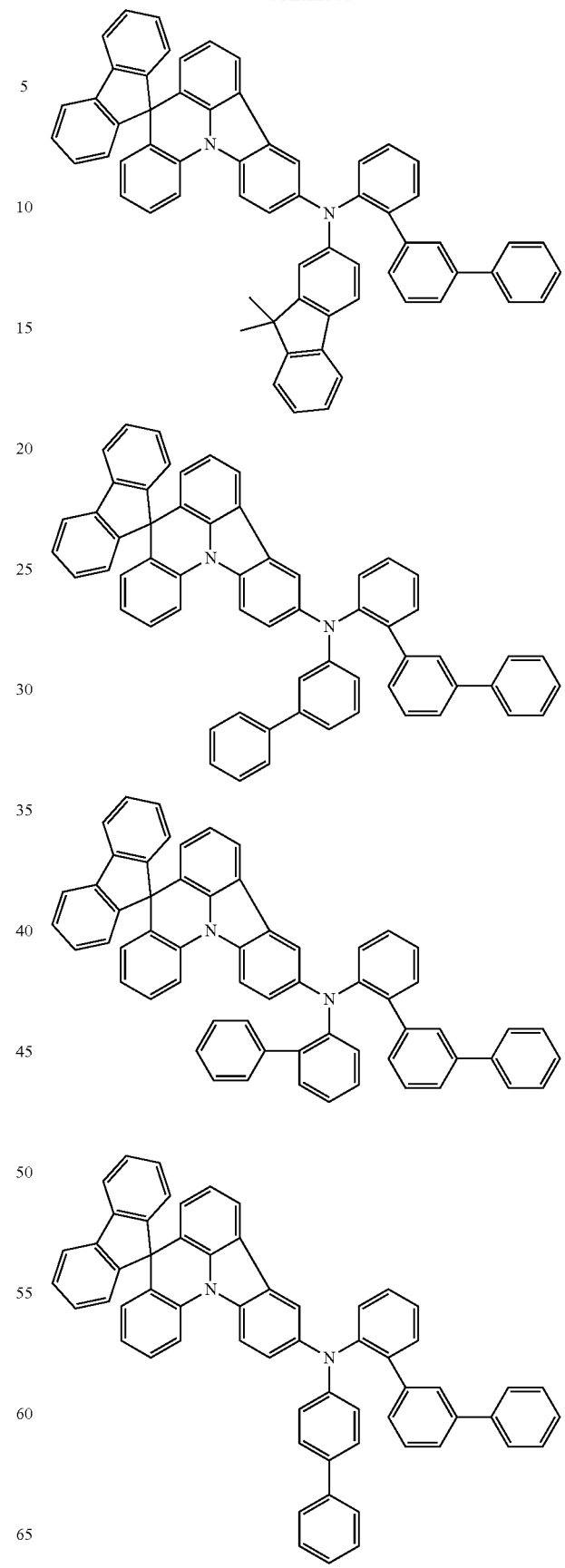

391
-continued
392
-continued
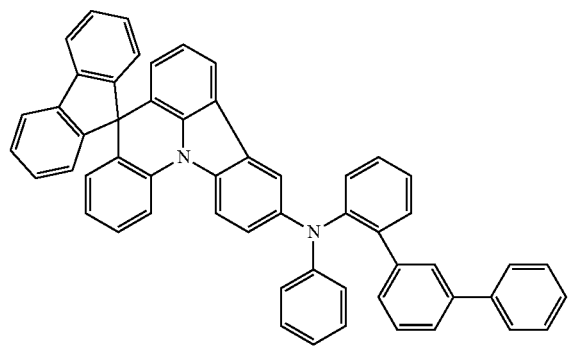
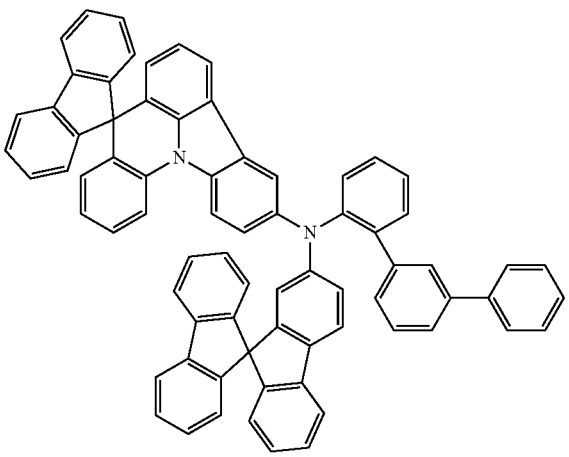
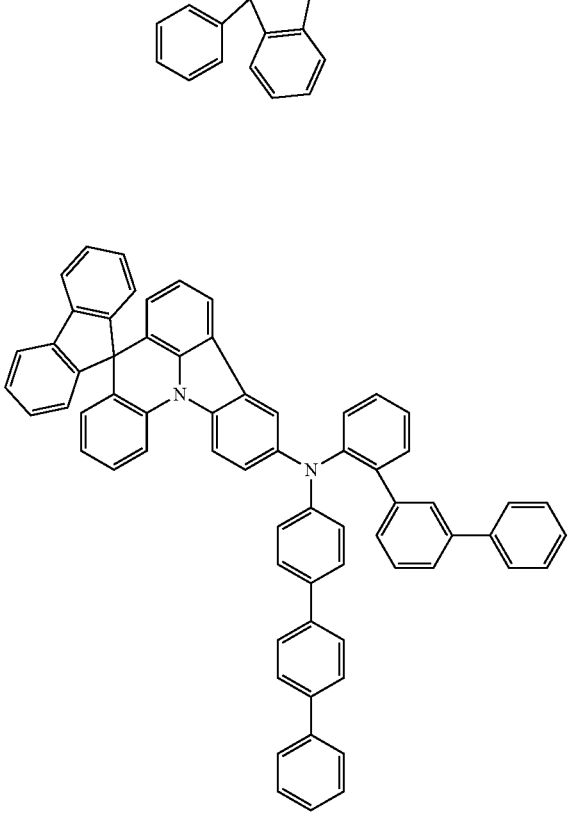

393
-continued
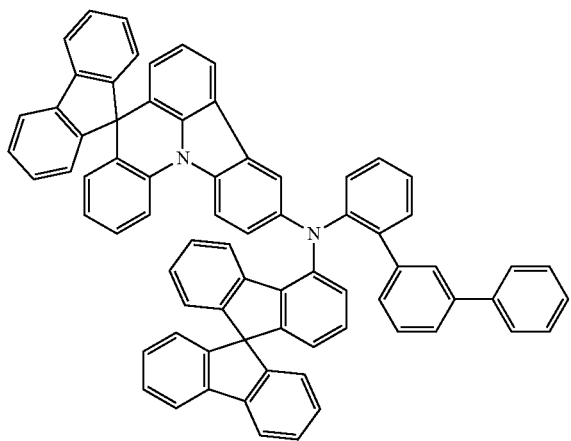
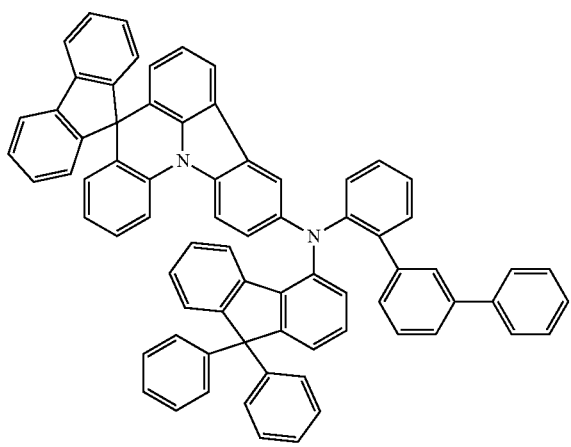
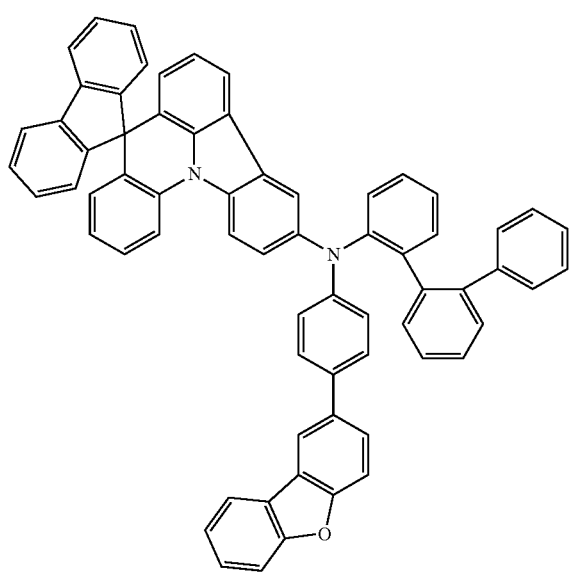
394
-continued
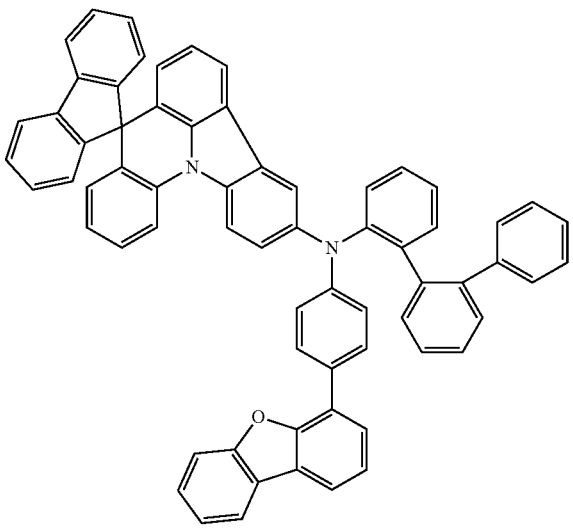
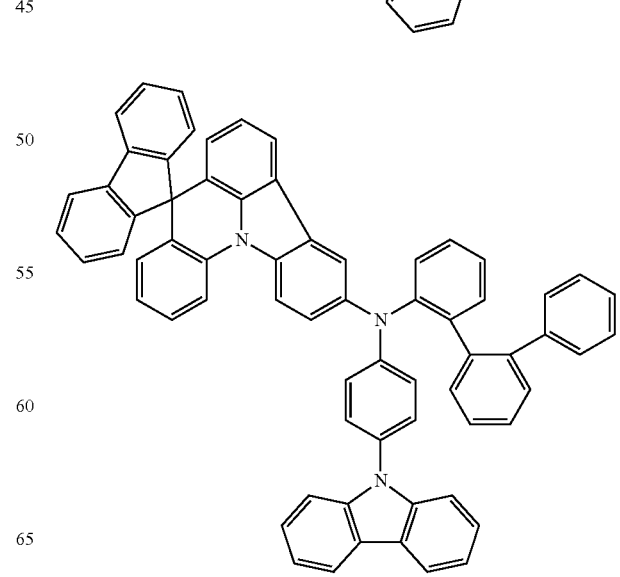

395
-continued
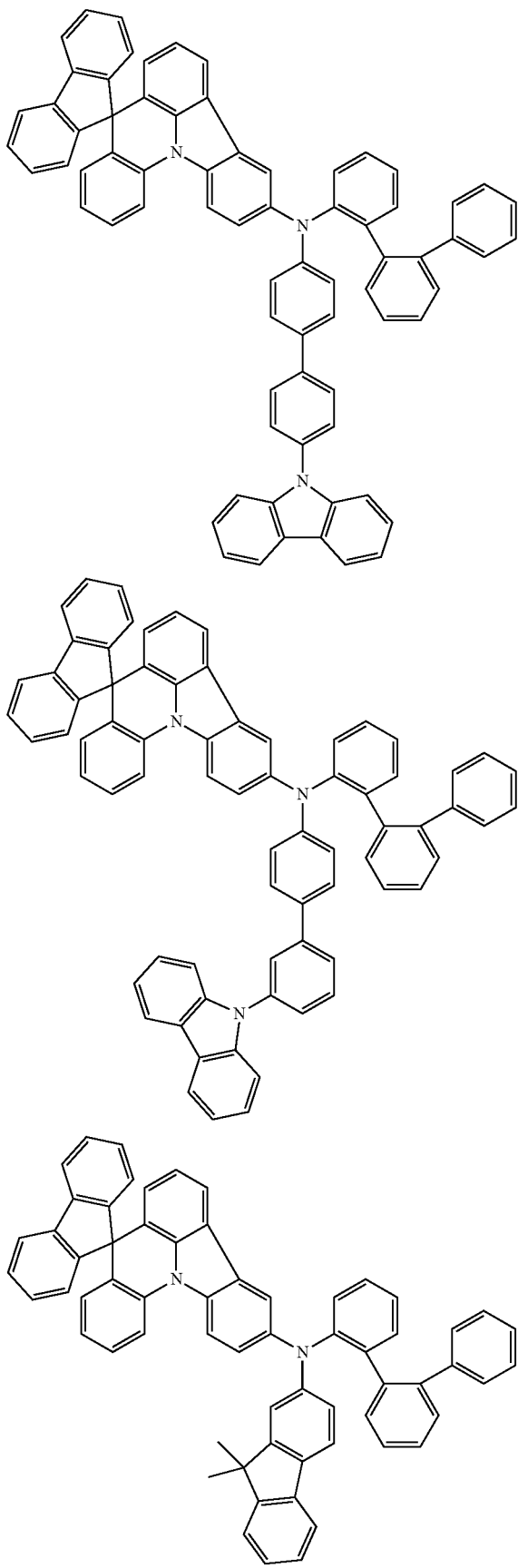
396
-continued
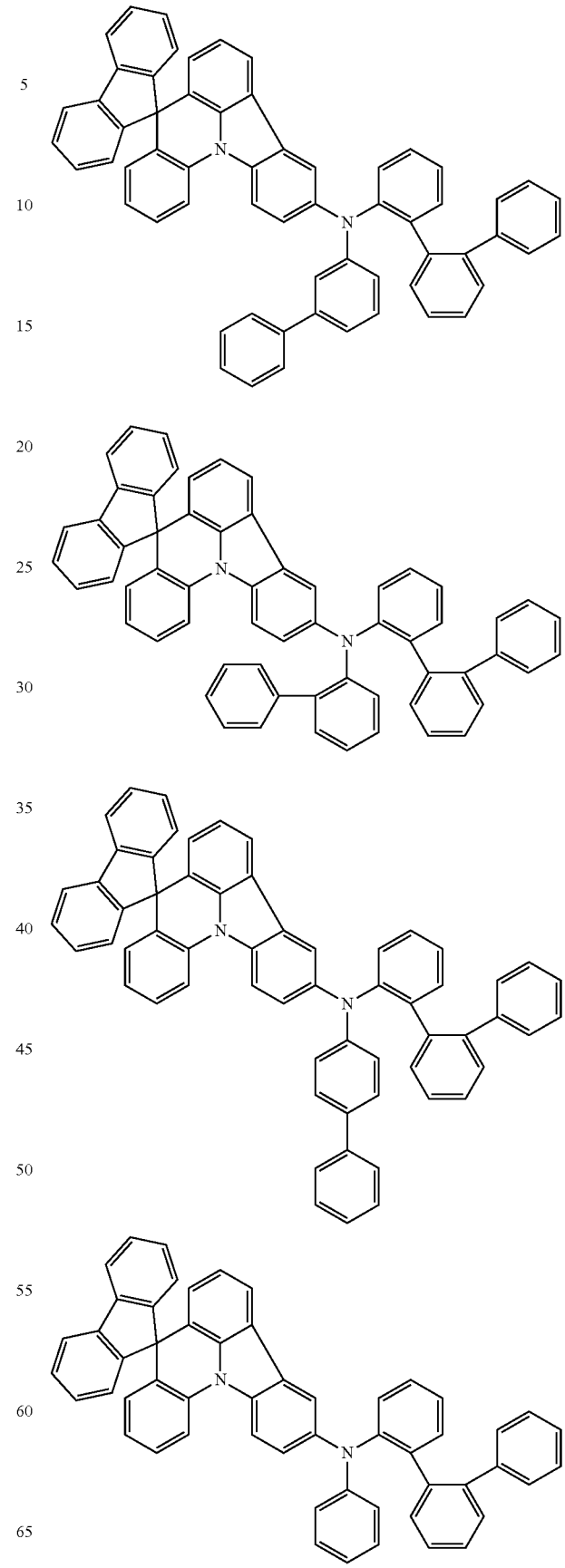

397
-continued
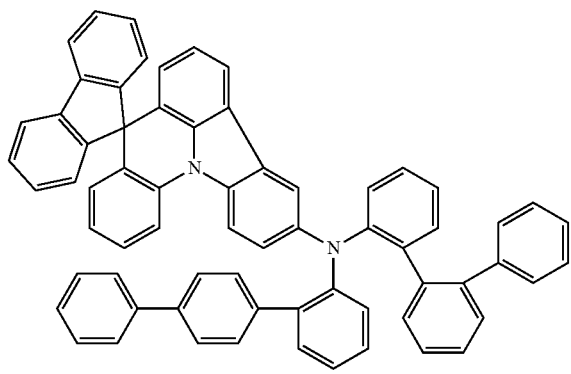
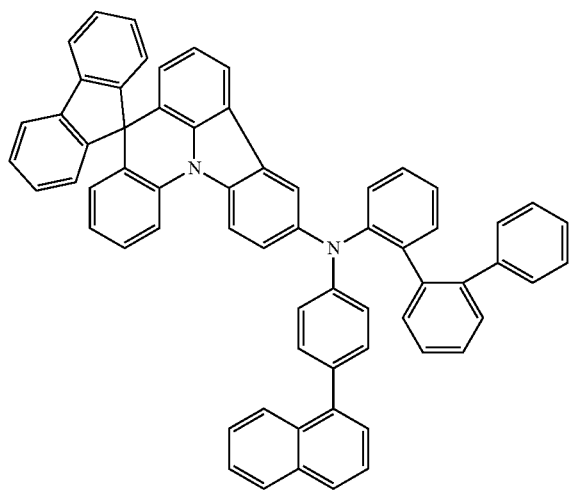
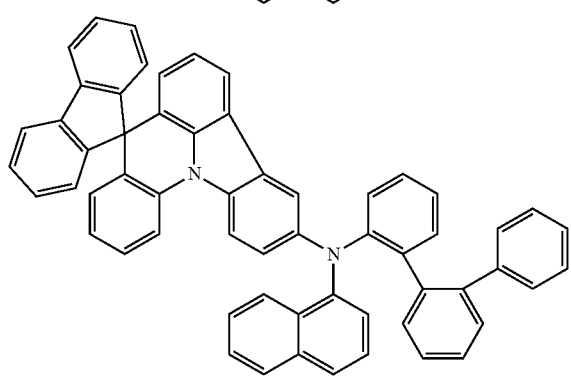
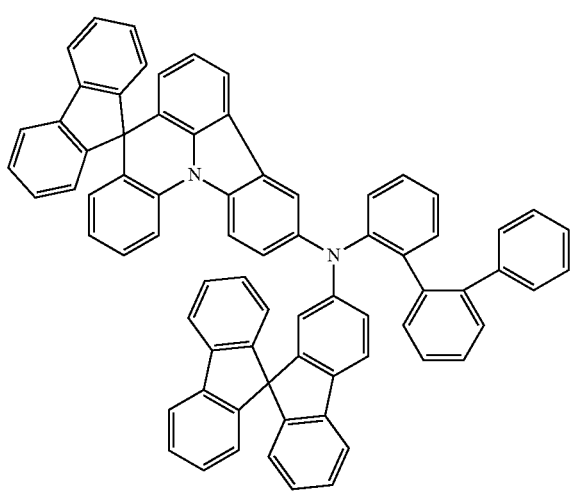
398
-continued
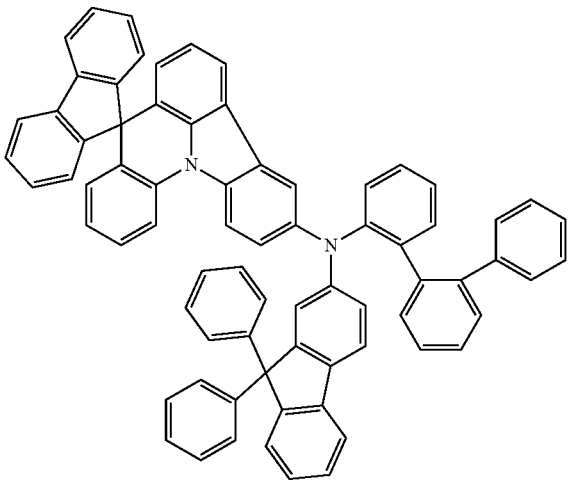
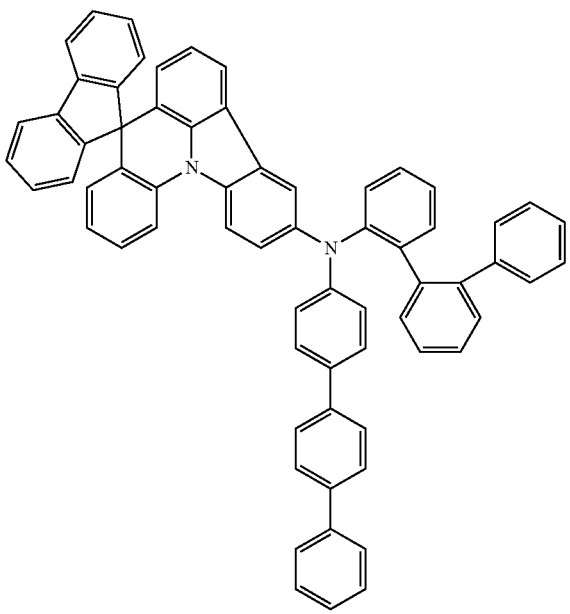
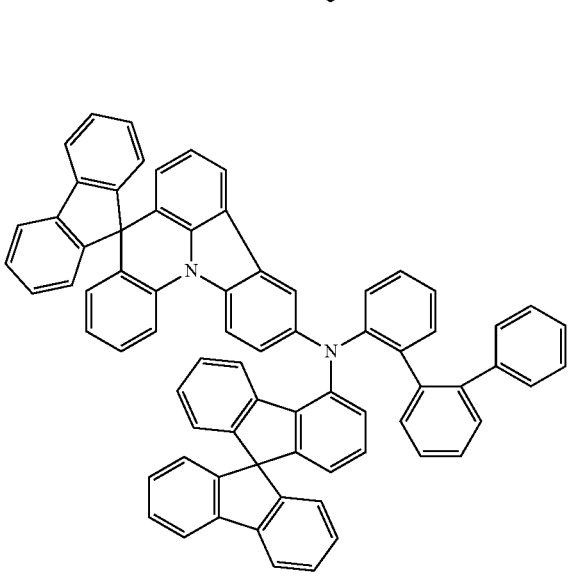

399
-continued
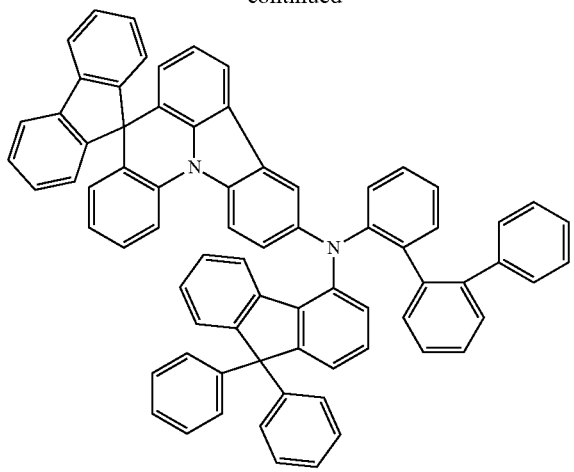
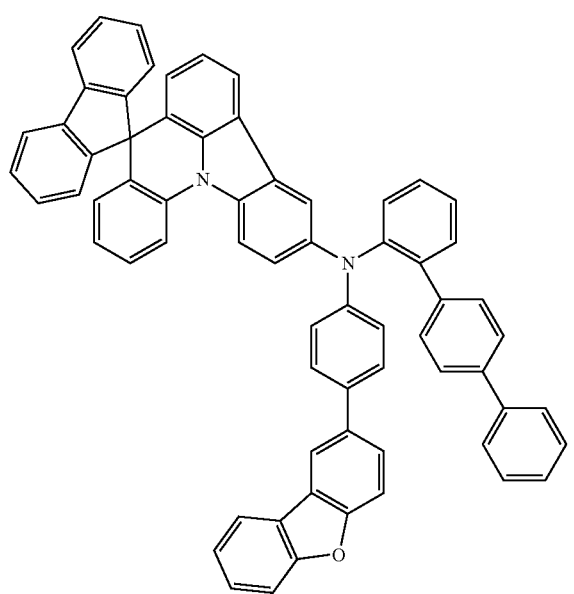
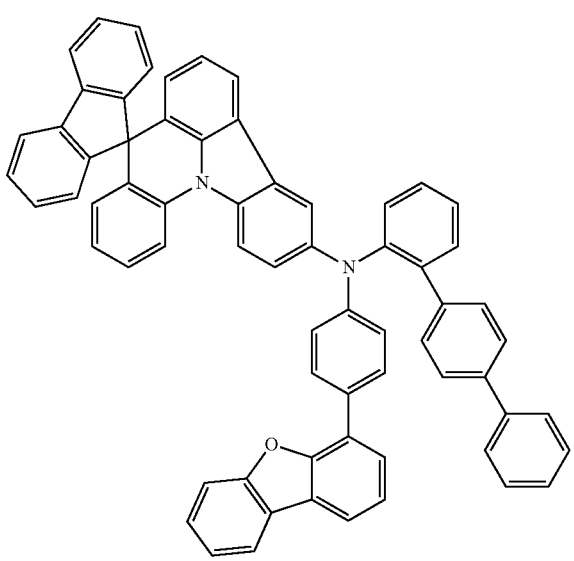
400
-continued
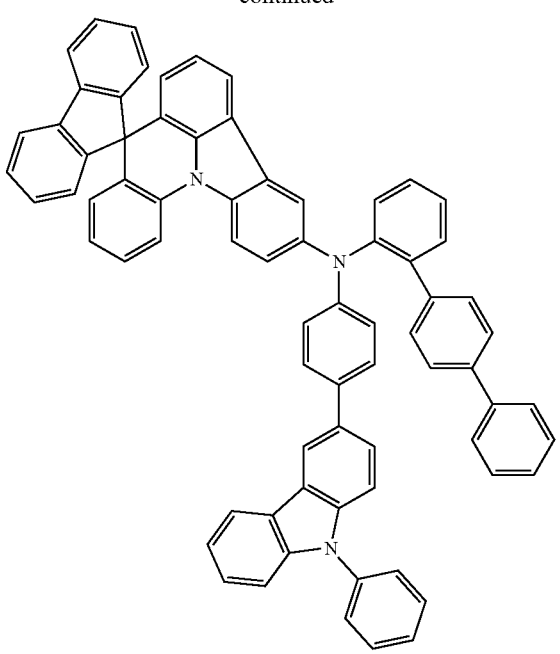
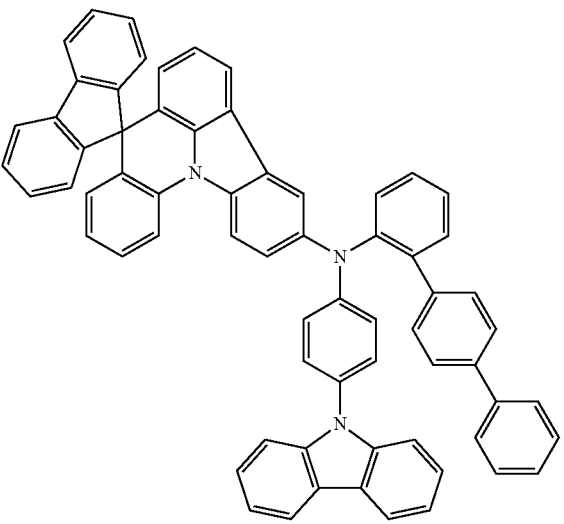

401
-continued
402
-continued
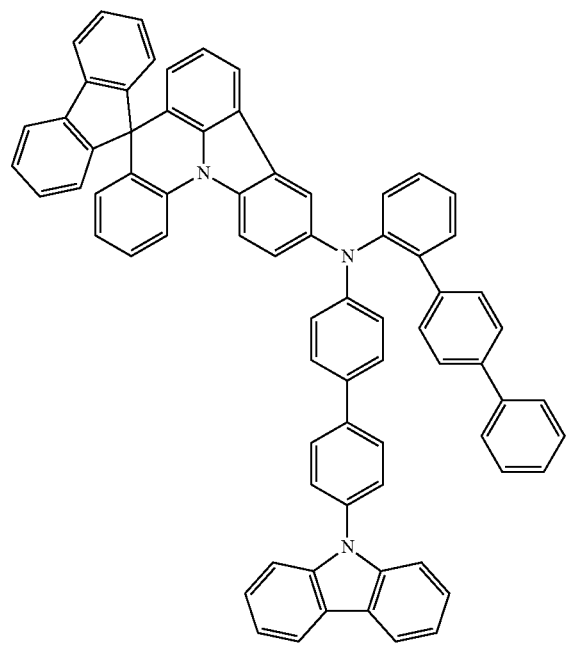
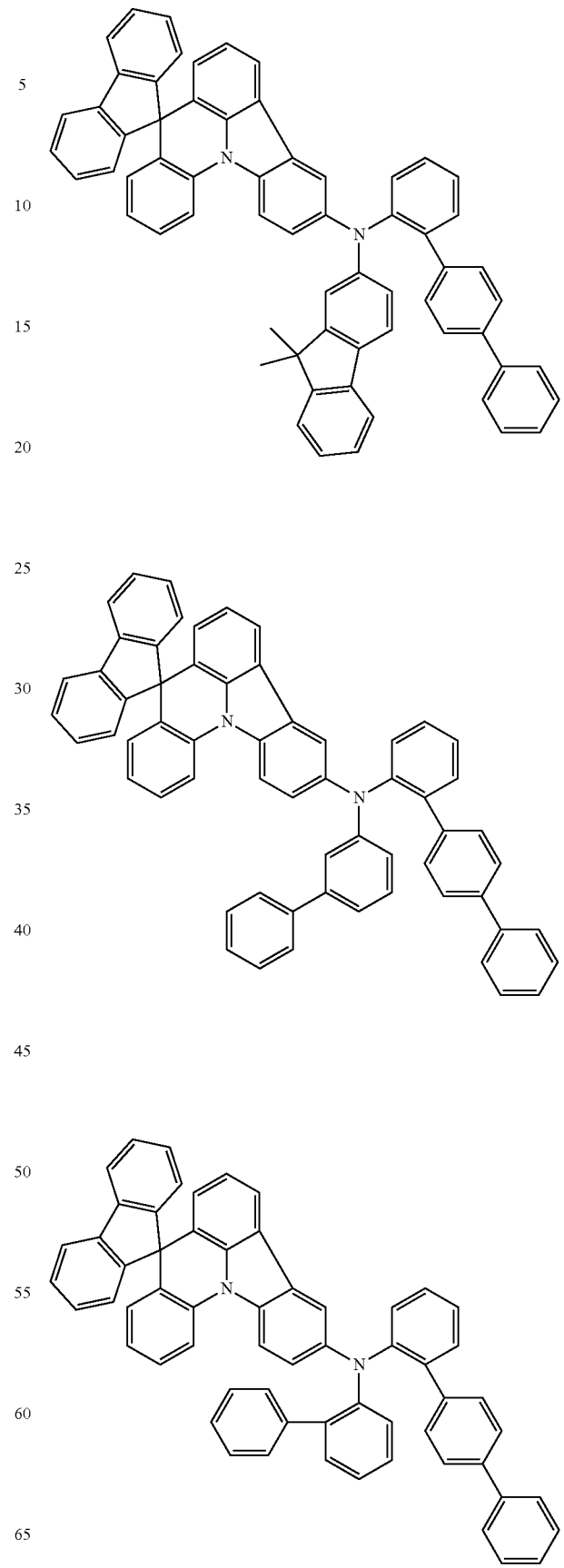

403
-continued
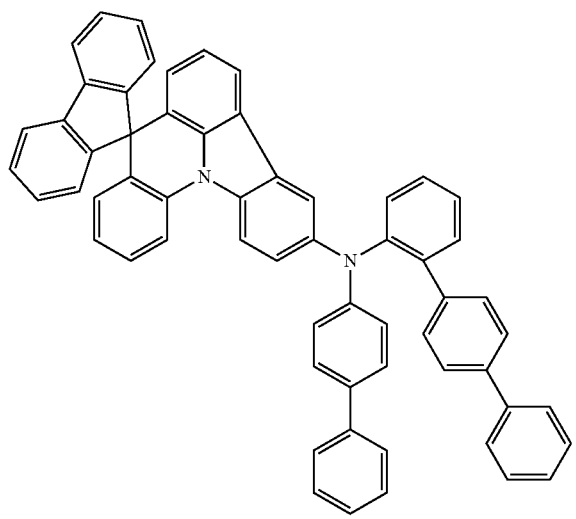
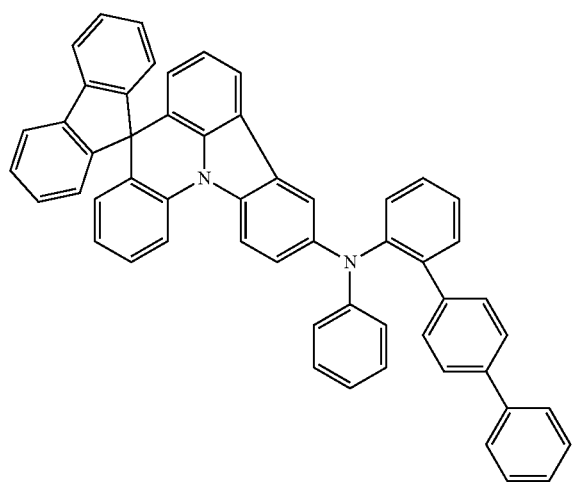
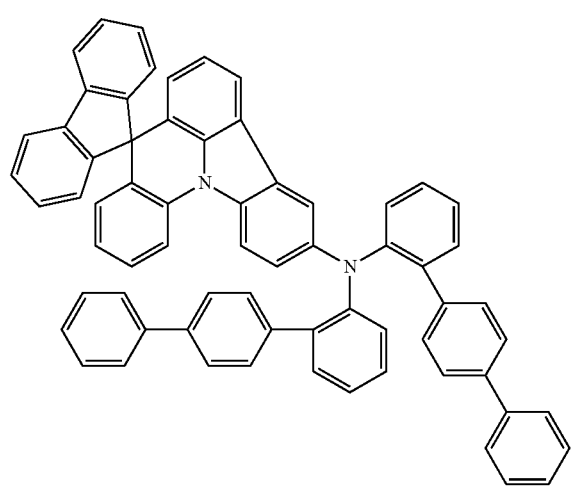
404
-continued
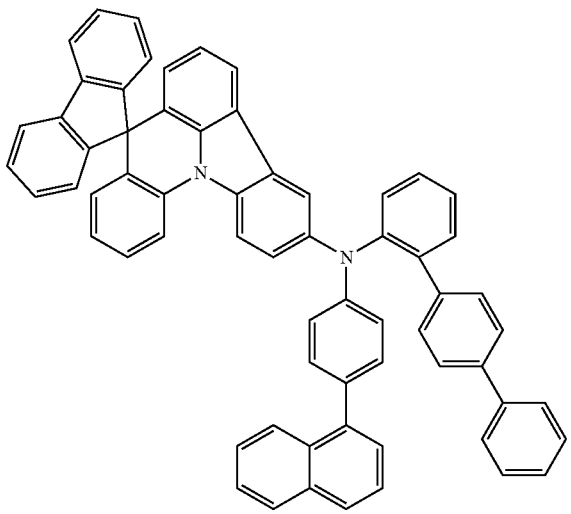
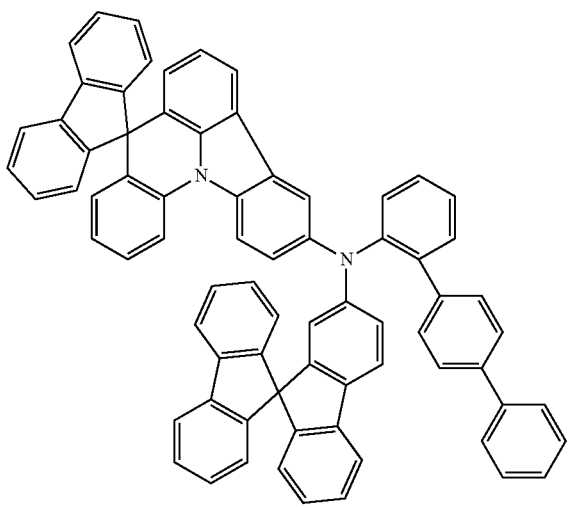

405
-continued
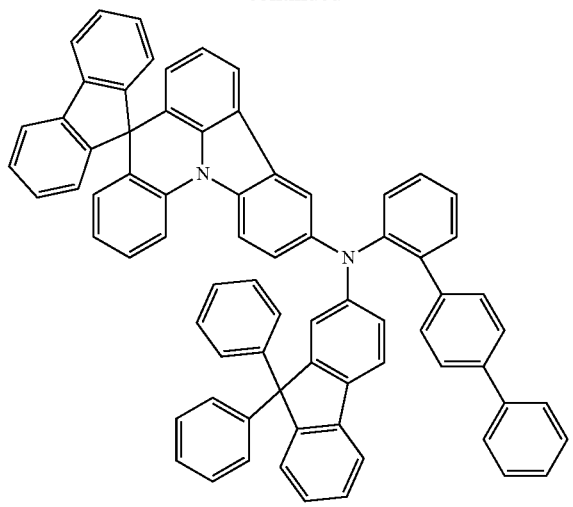
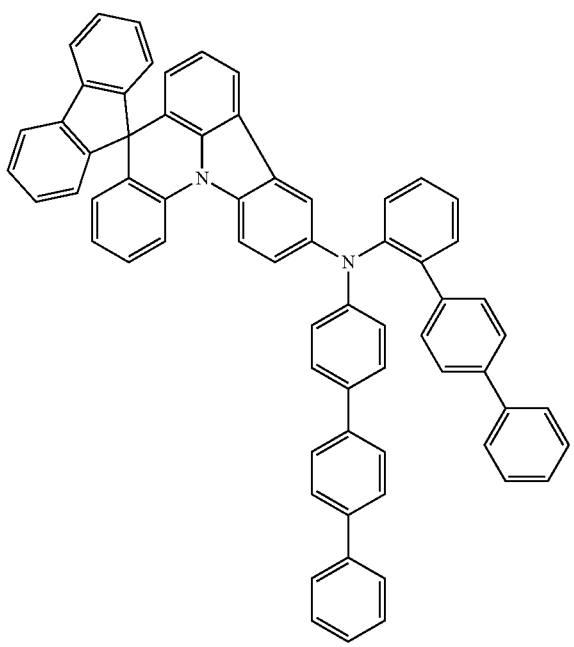
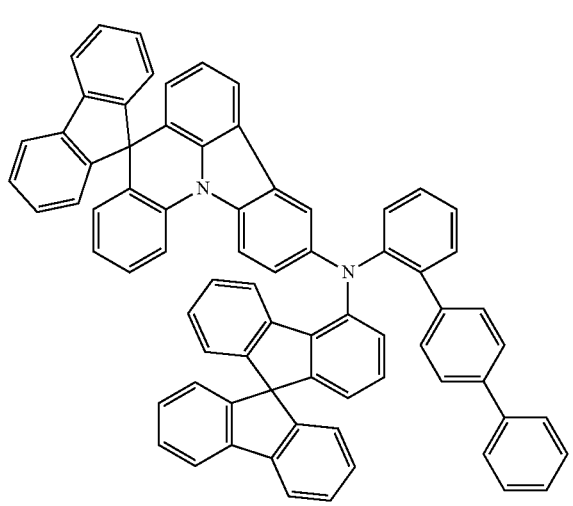
406
-continued
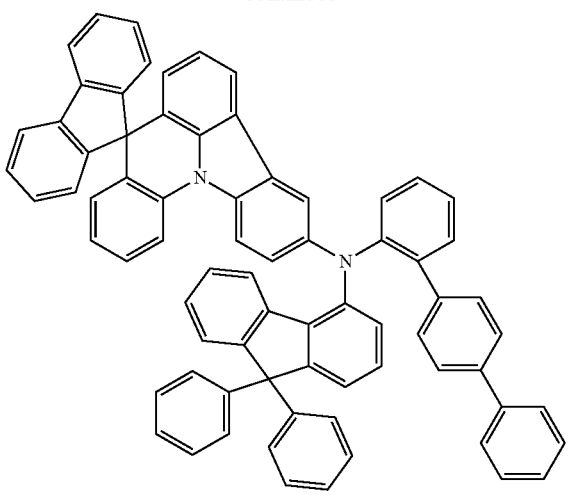
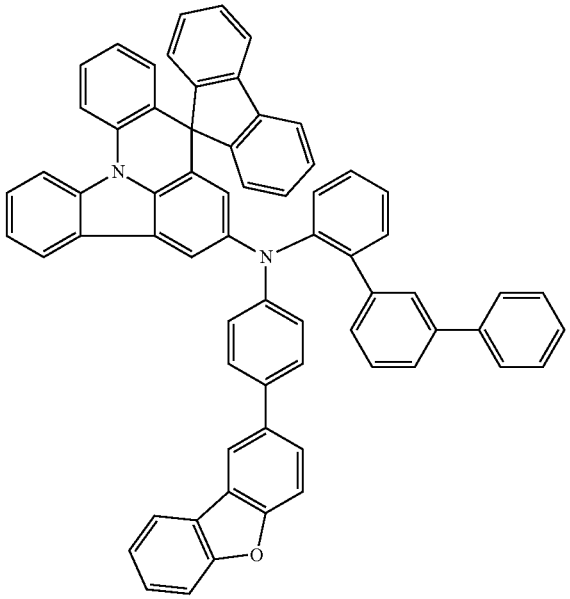
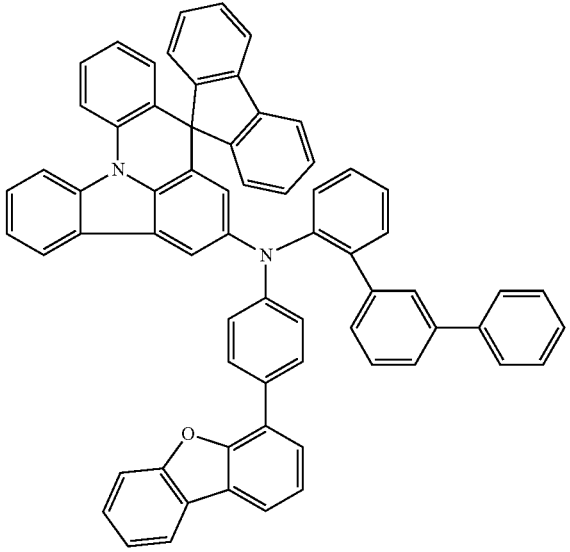

407
-continued
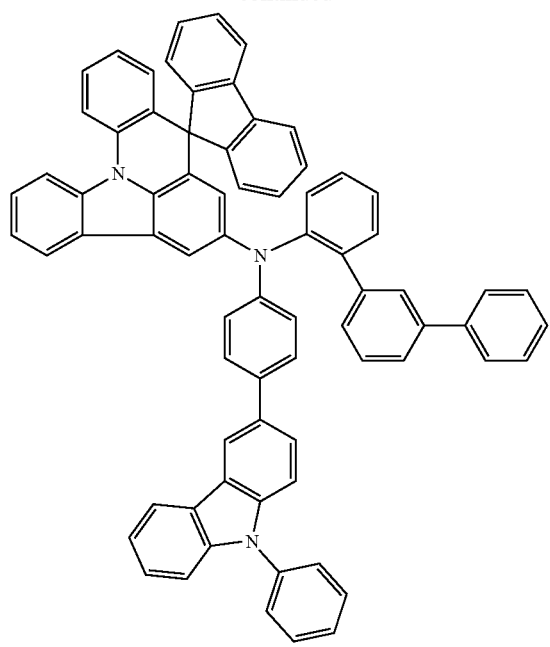
408
-continued
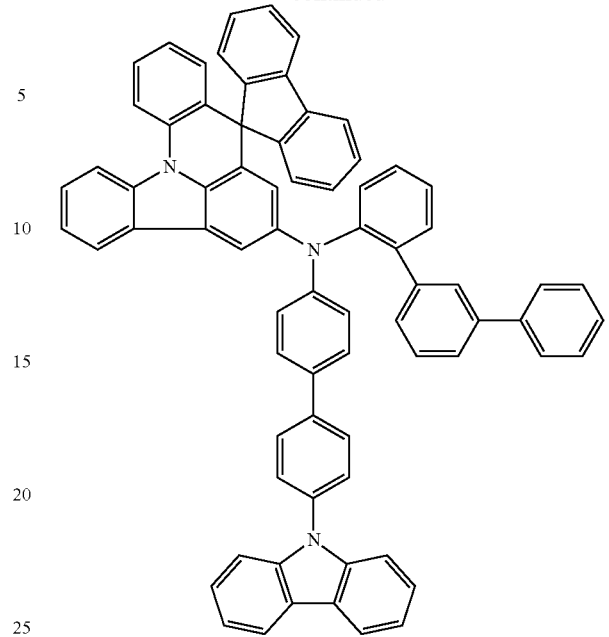
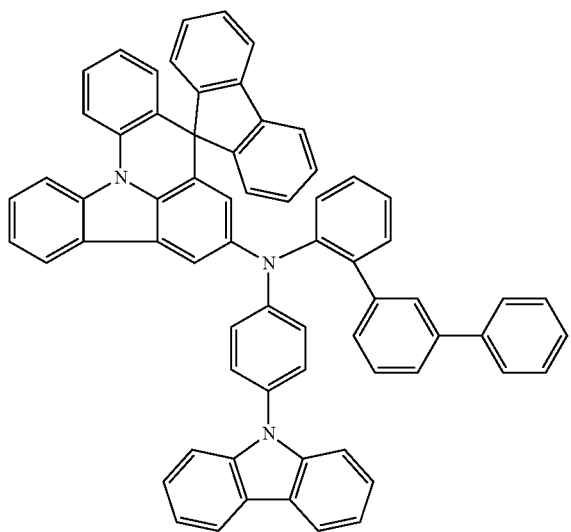
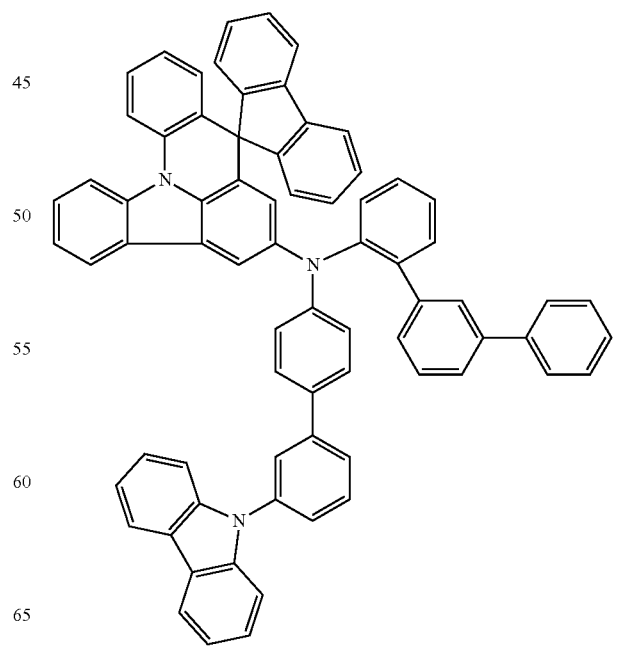

409
-continued
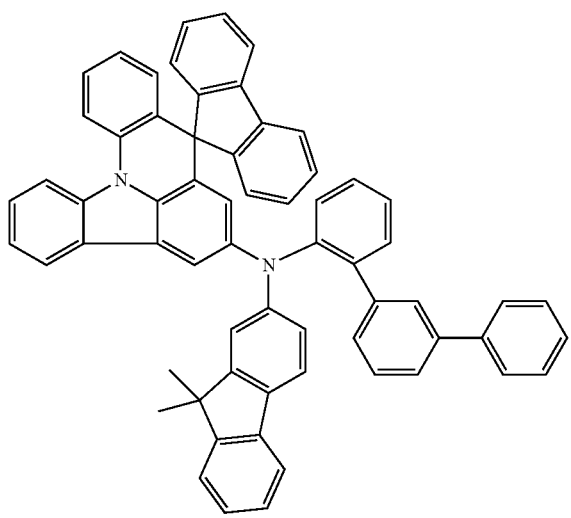
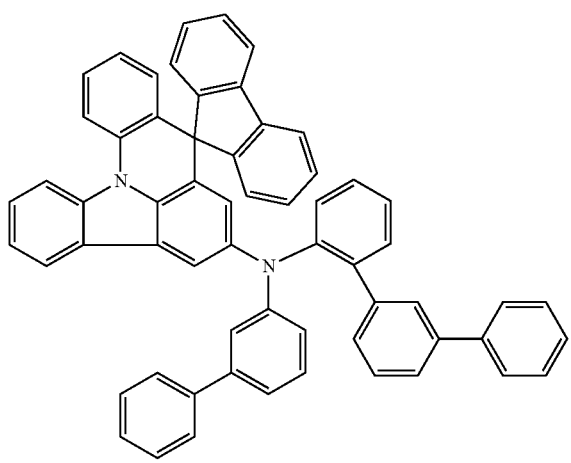
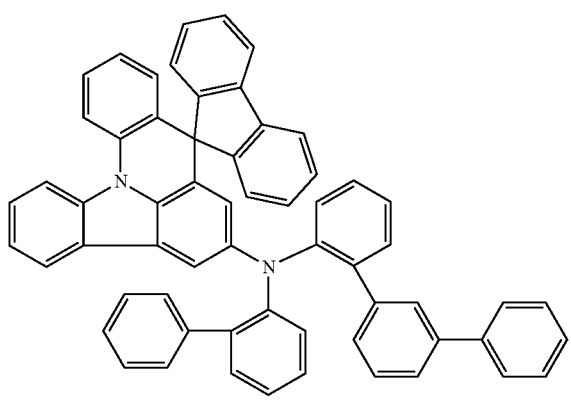
410
-continued
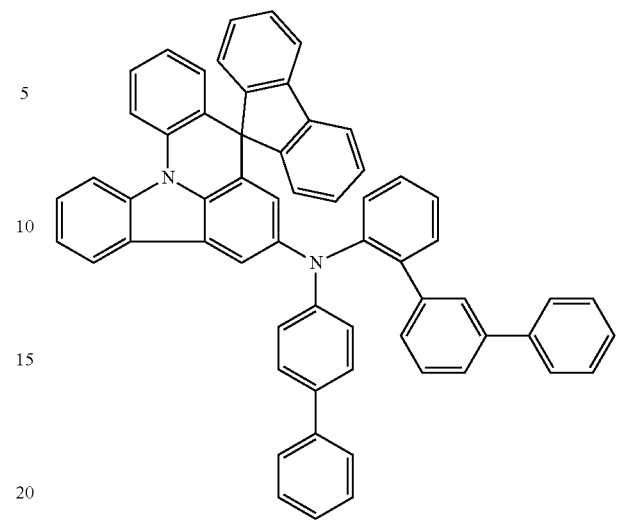

411
-continued
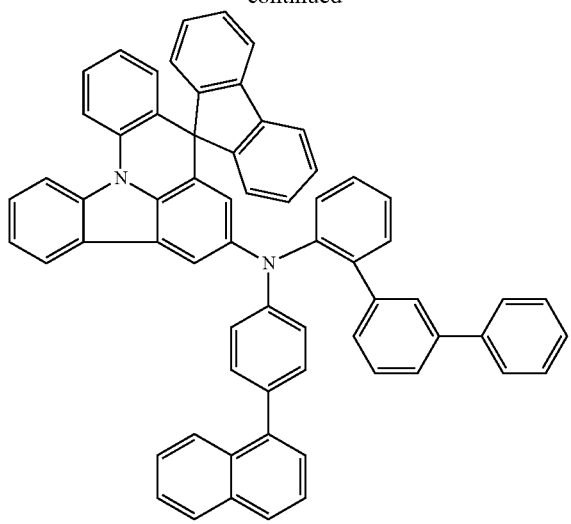
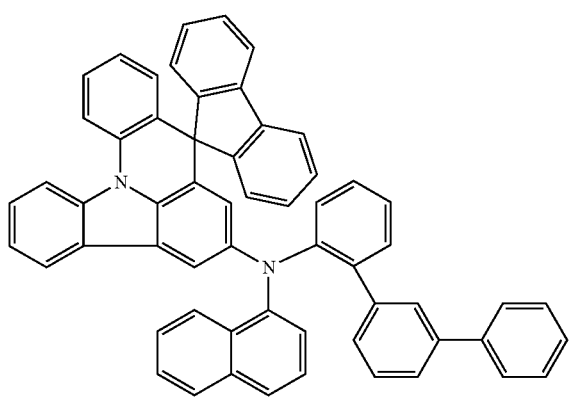
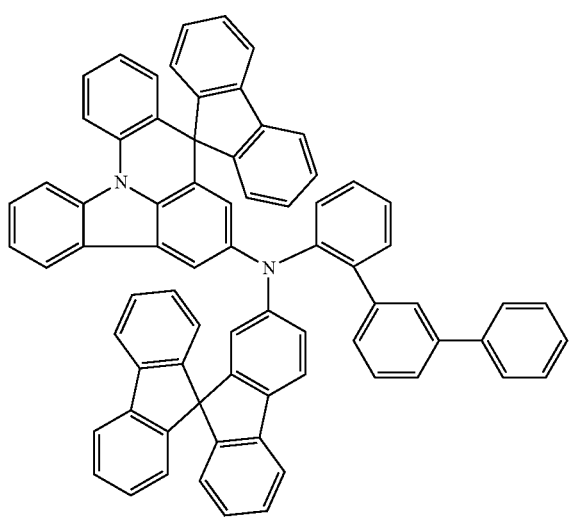
412
-continued
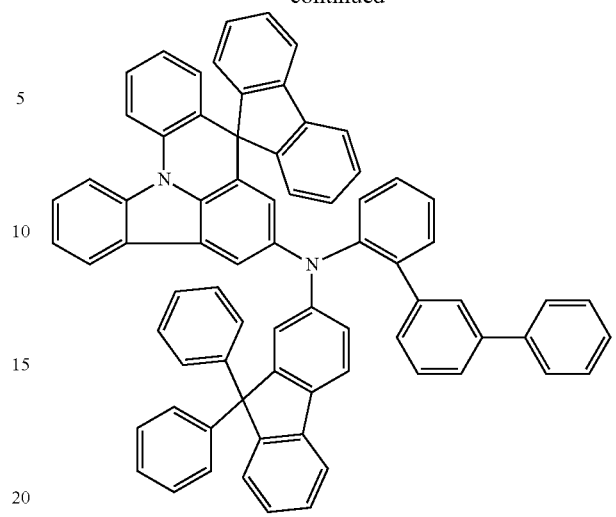
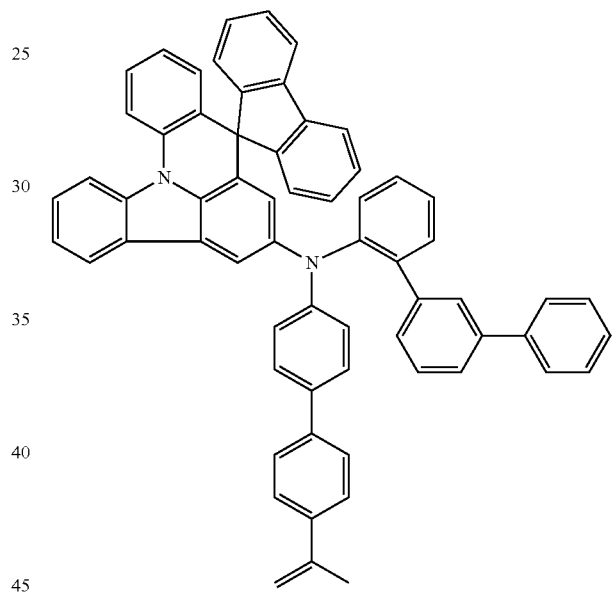
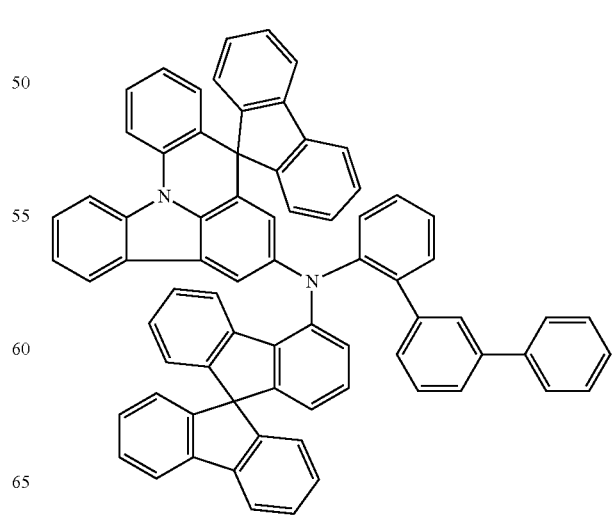

413
-continued
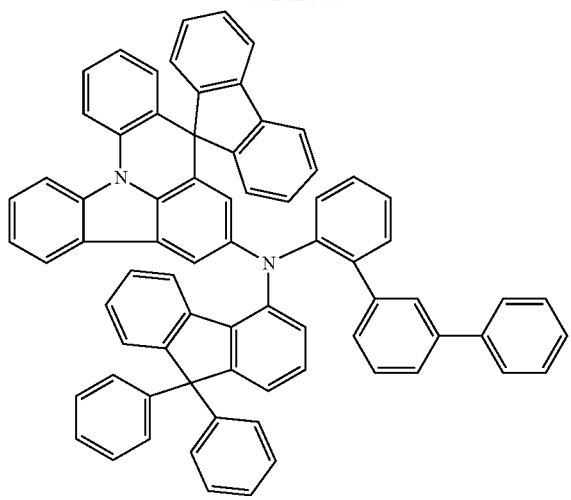
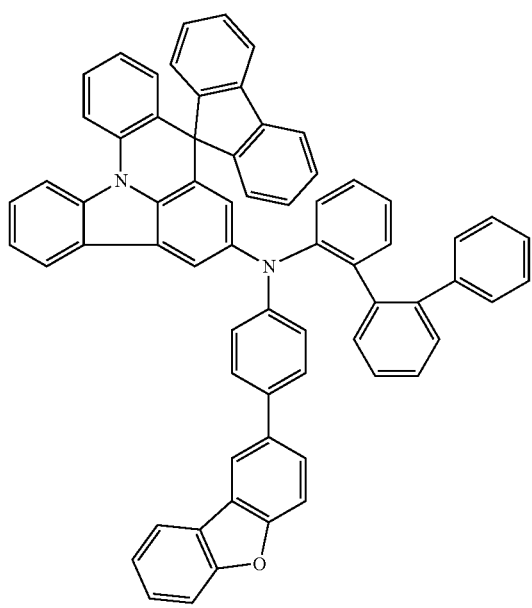
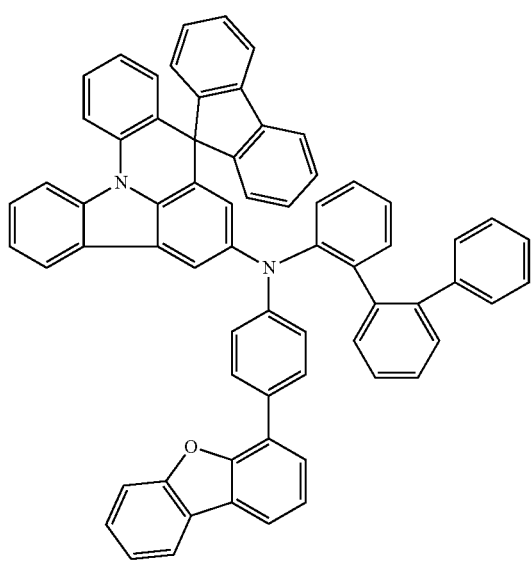
414
-continued
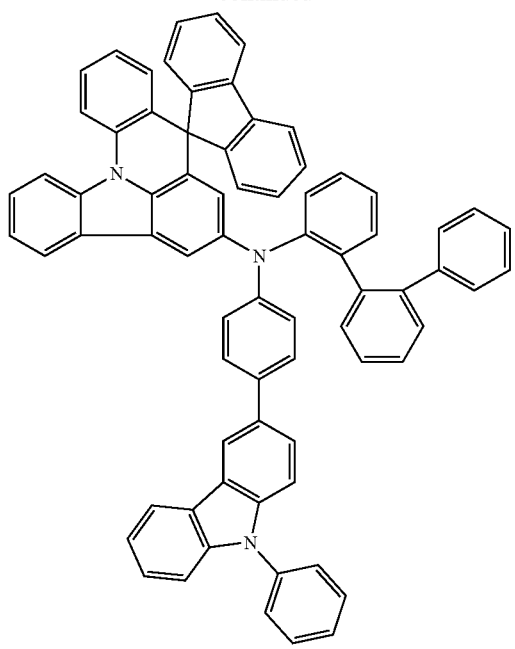
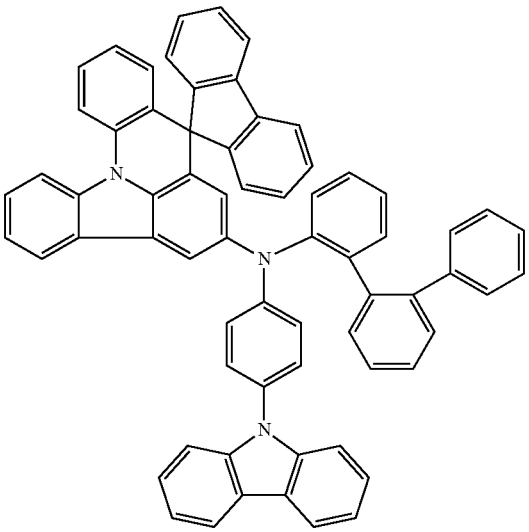

415
-continued
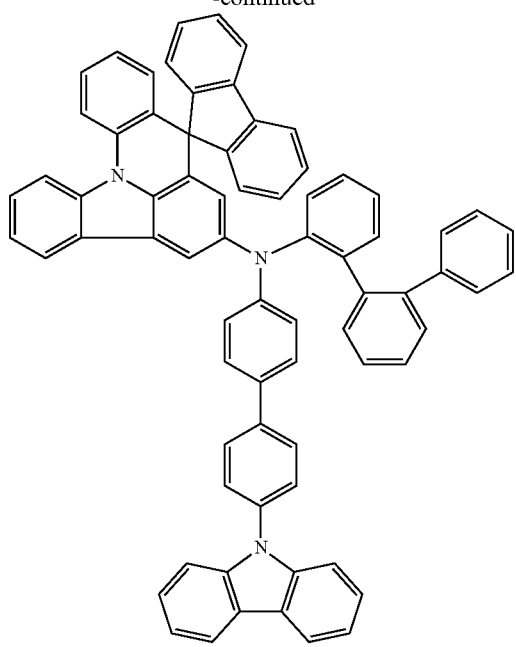
416
-continued
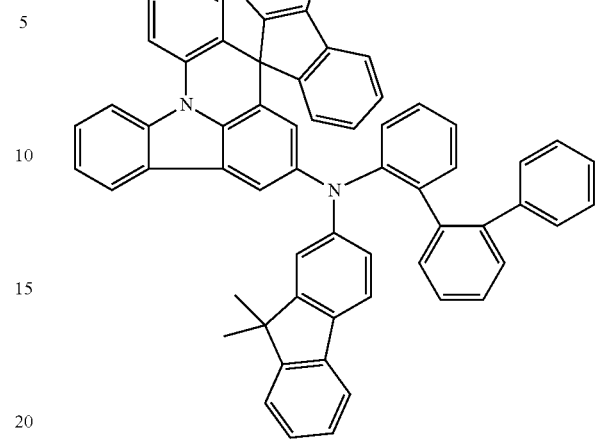
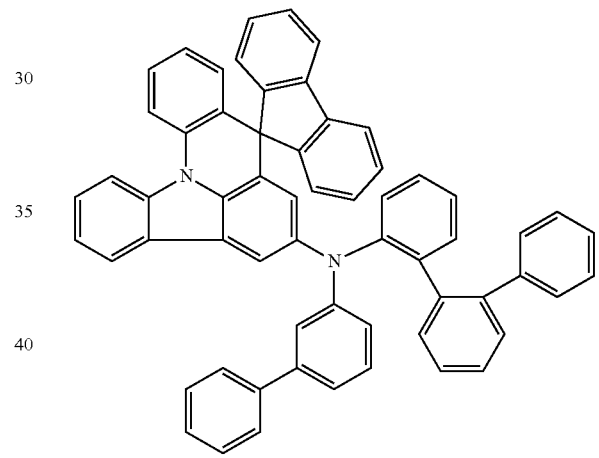
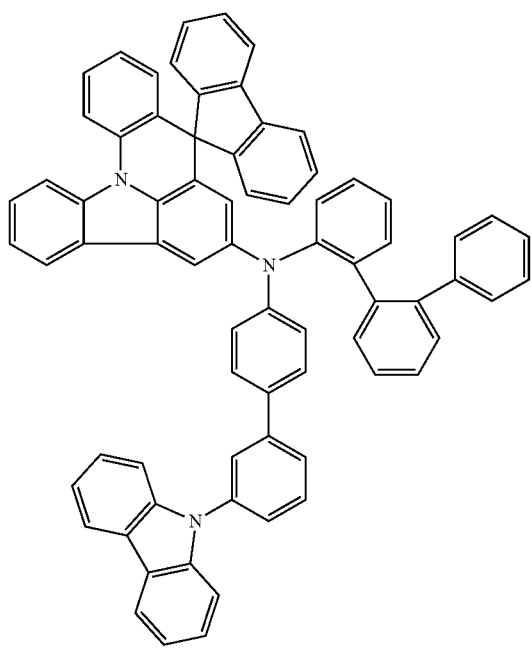

417
-continued
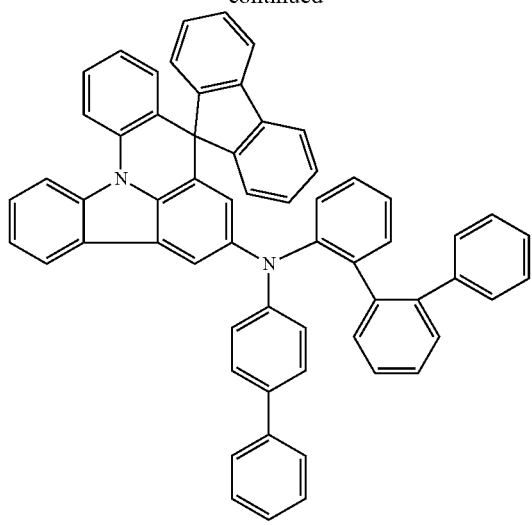
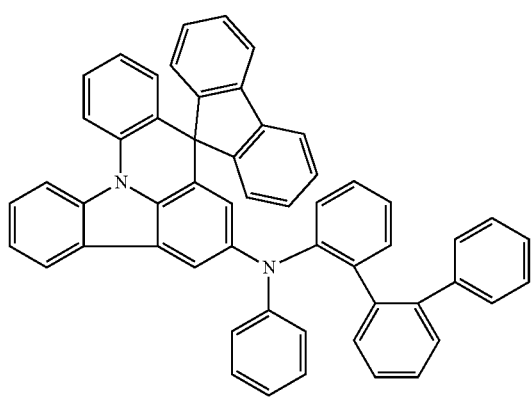
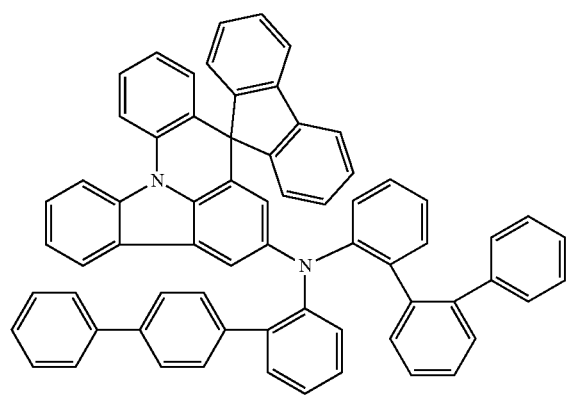
418
-continued
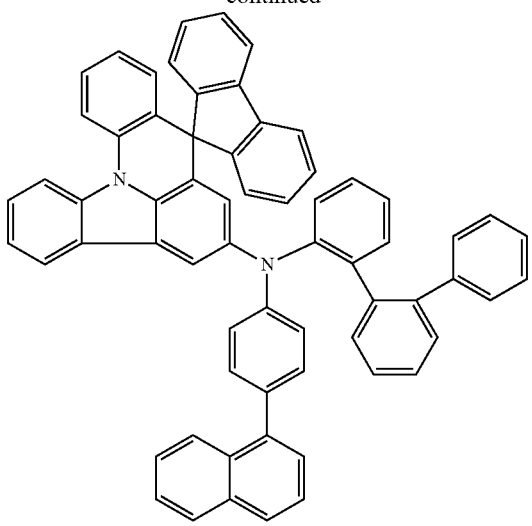
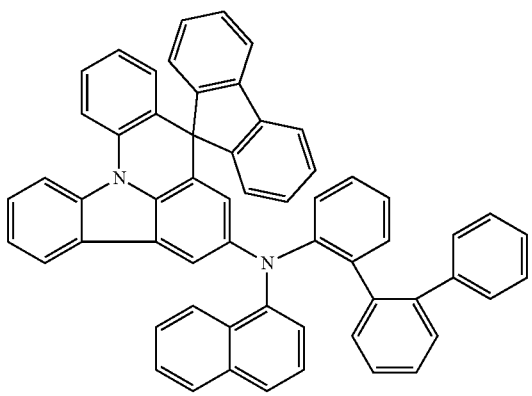
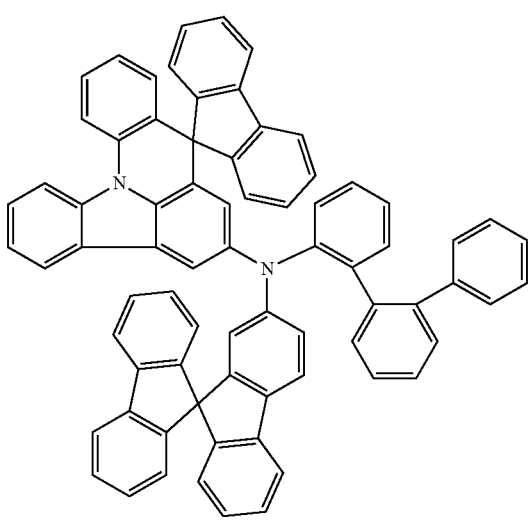

419
-continued
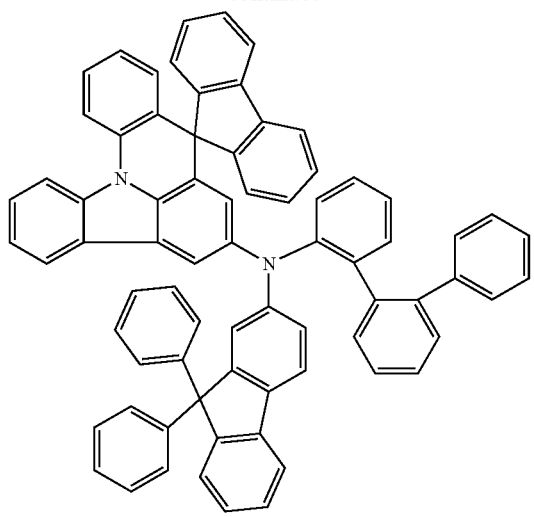
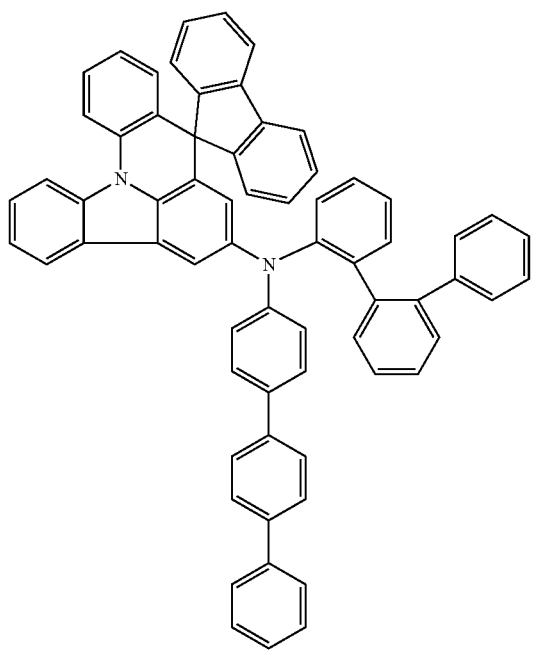
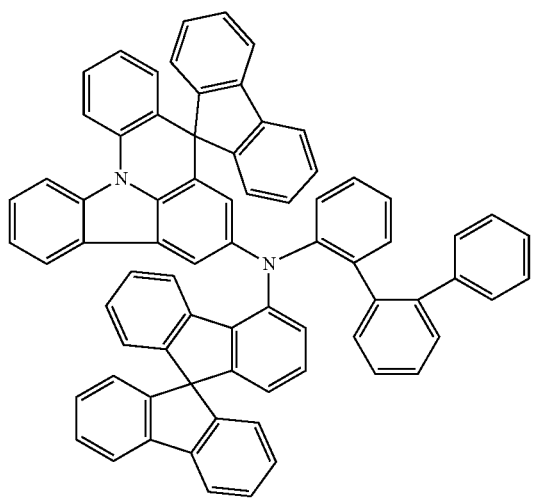
420
-continued
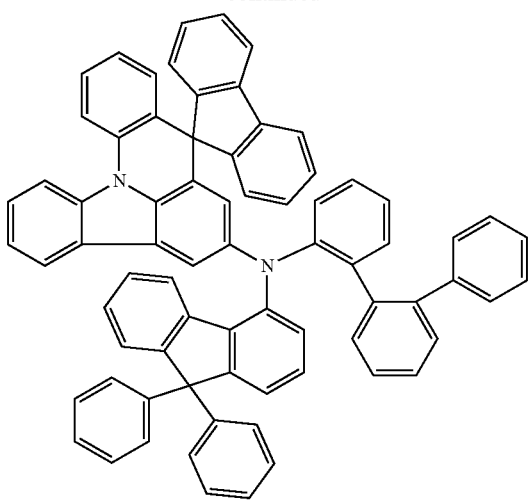
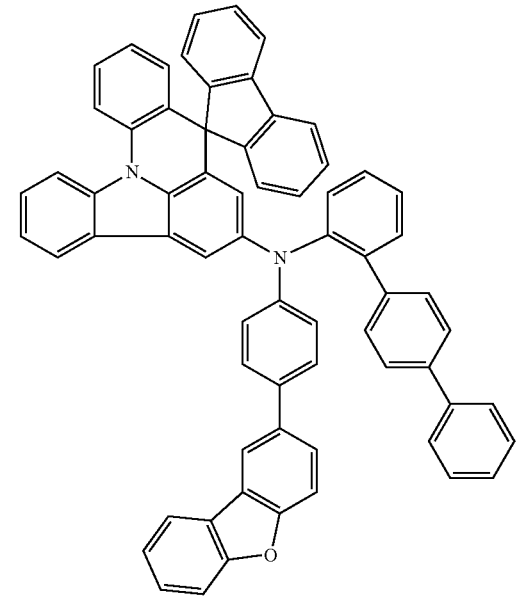
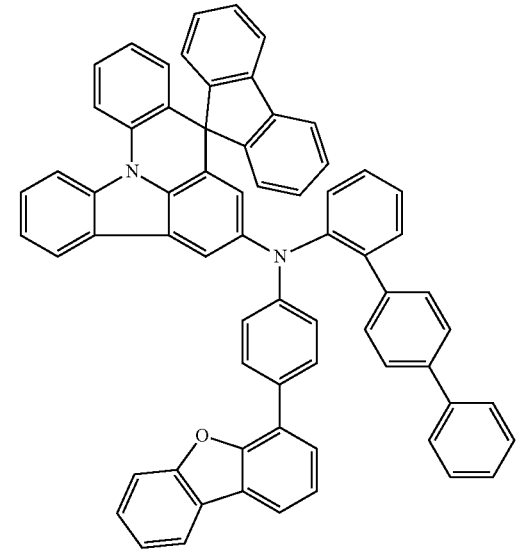

421
-continued
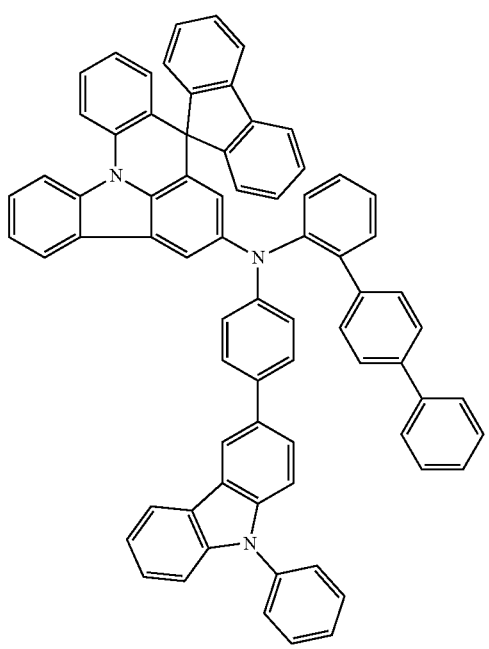
422
-continued
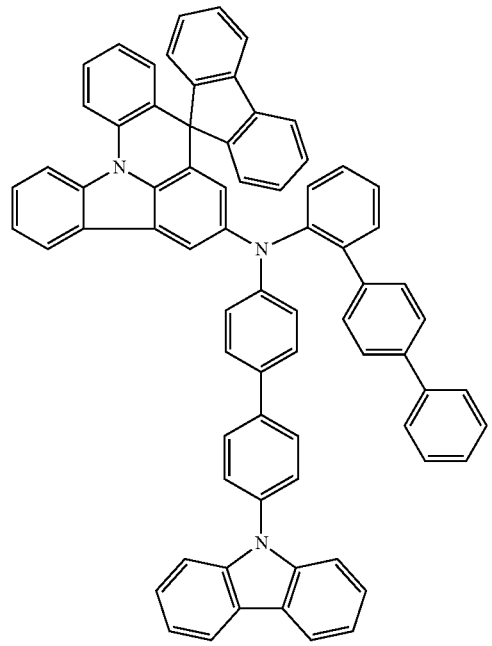
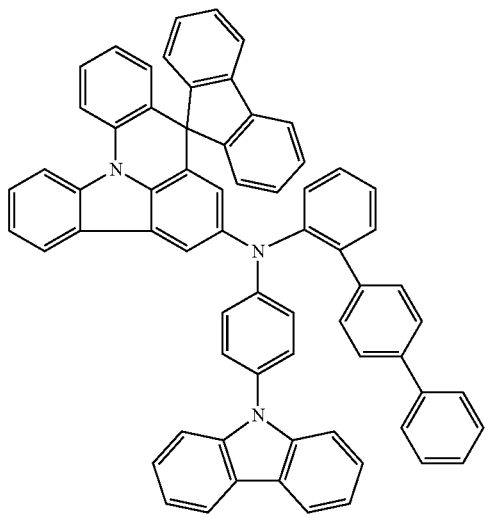
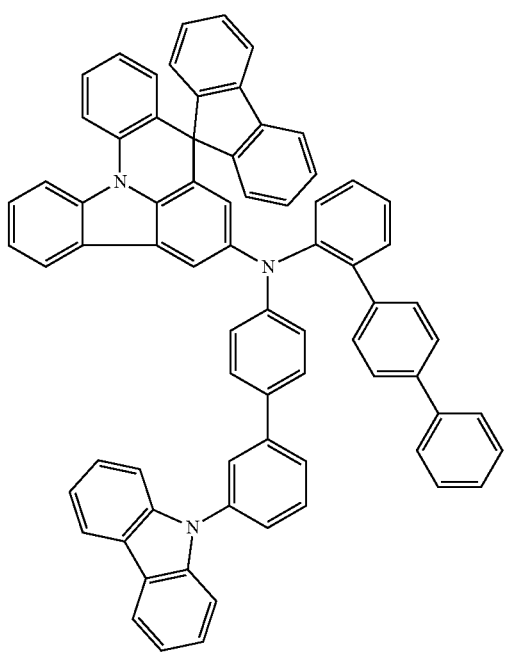

423
-continued
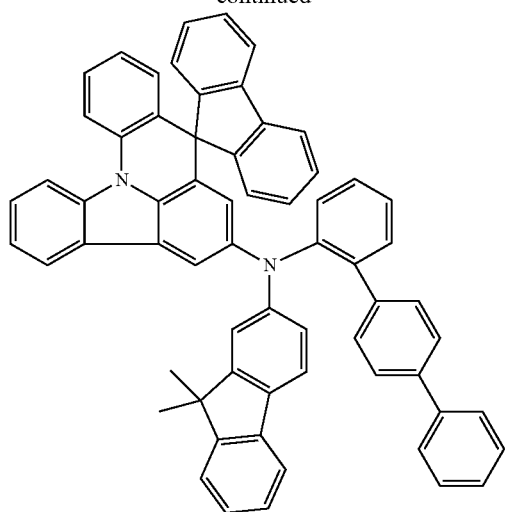
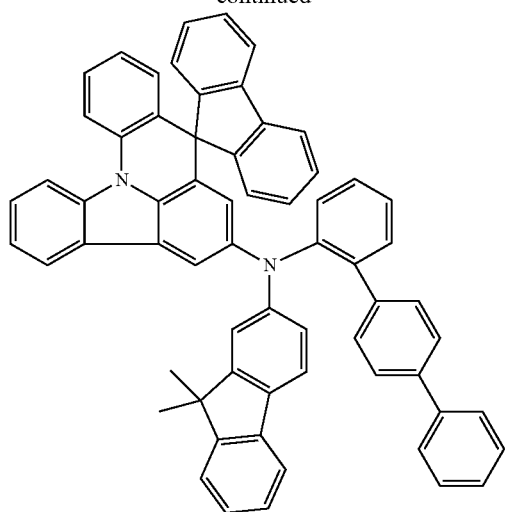
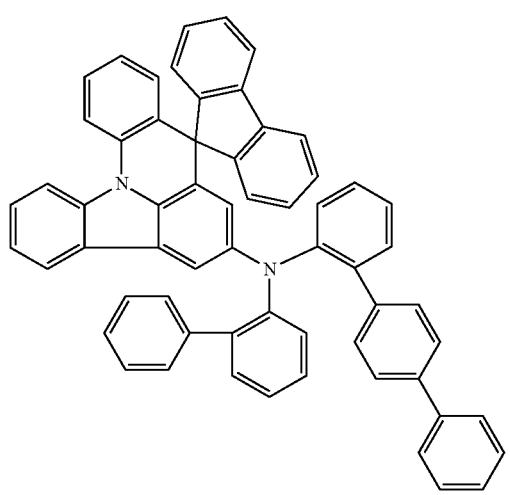
424
-continued
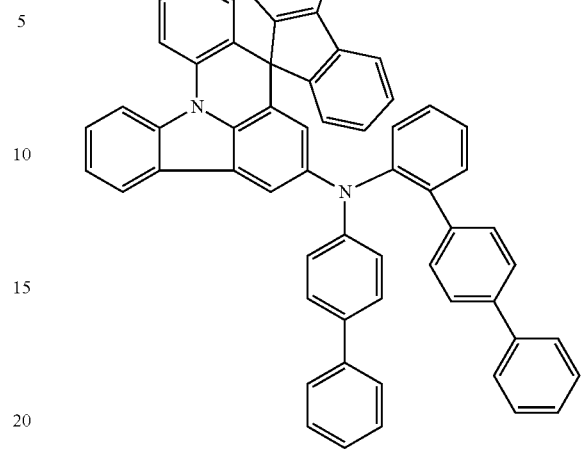
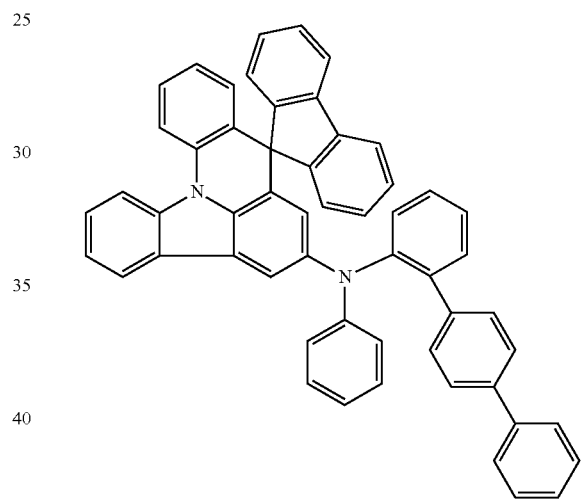
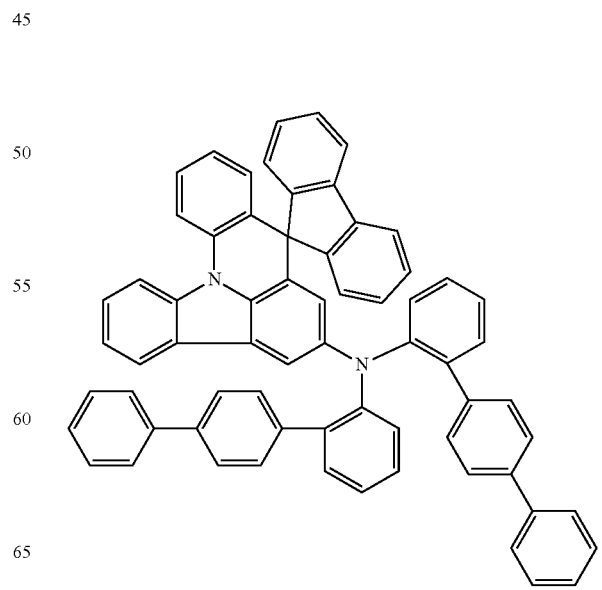

425
-continued
426
-continued
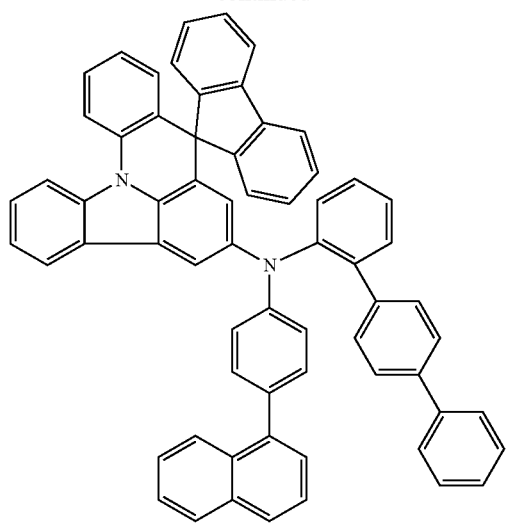
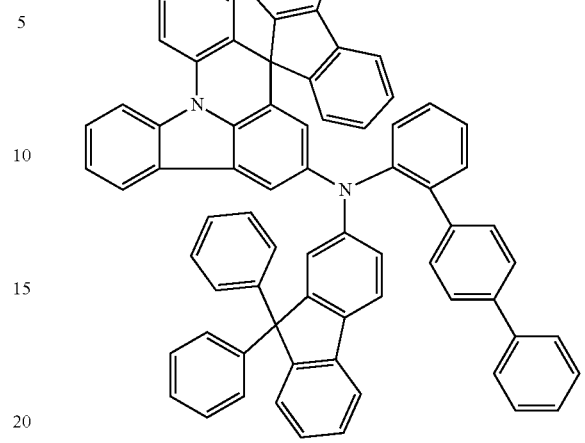
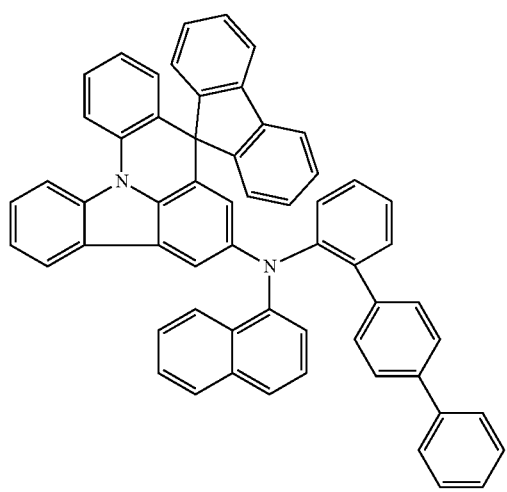
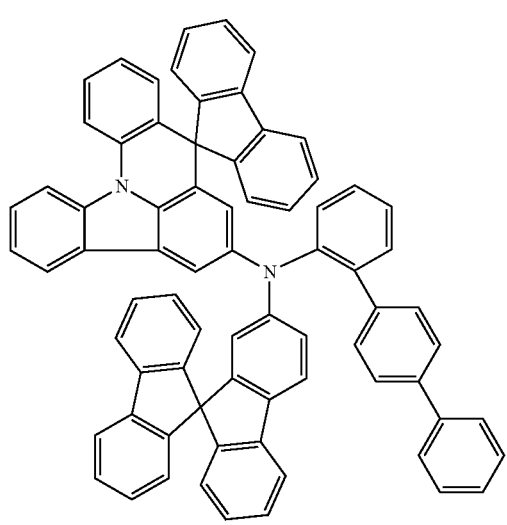

427
-continued
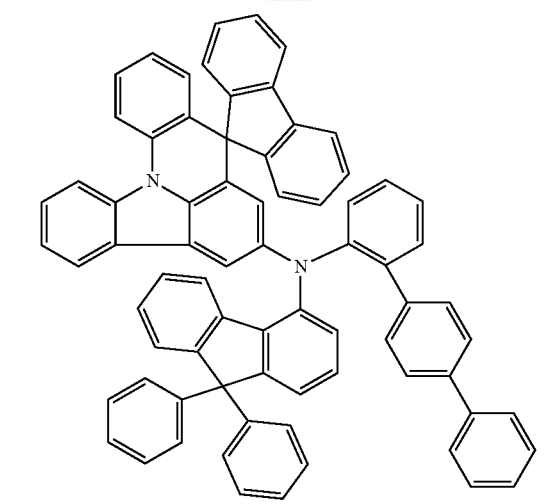
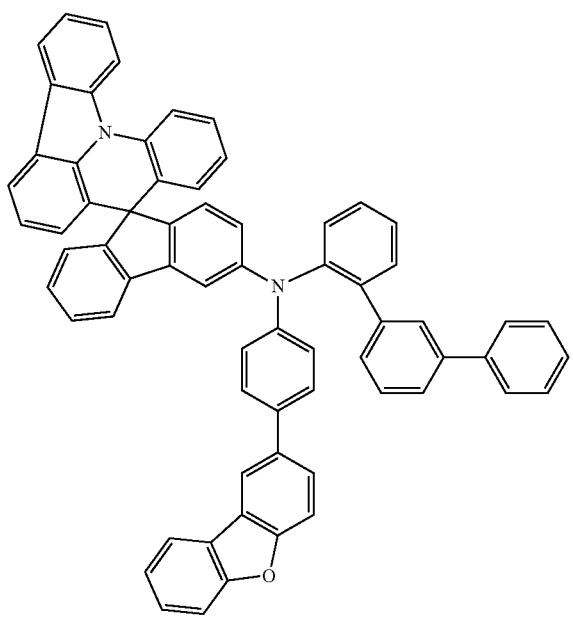
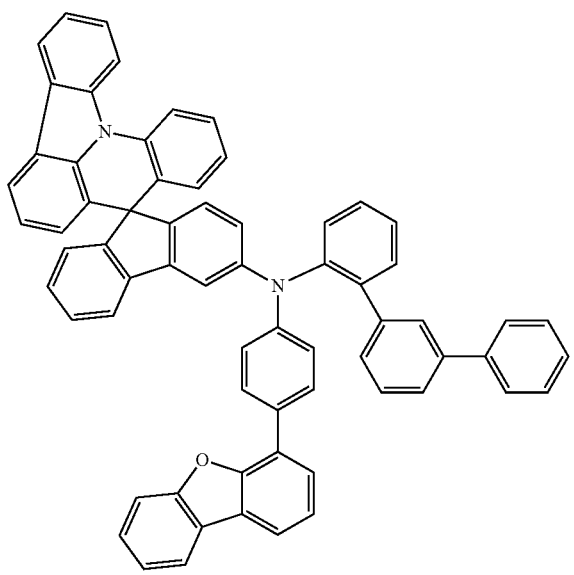
428
-continued
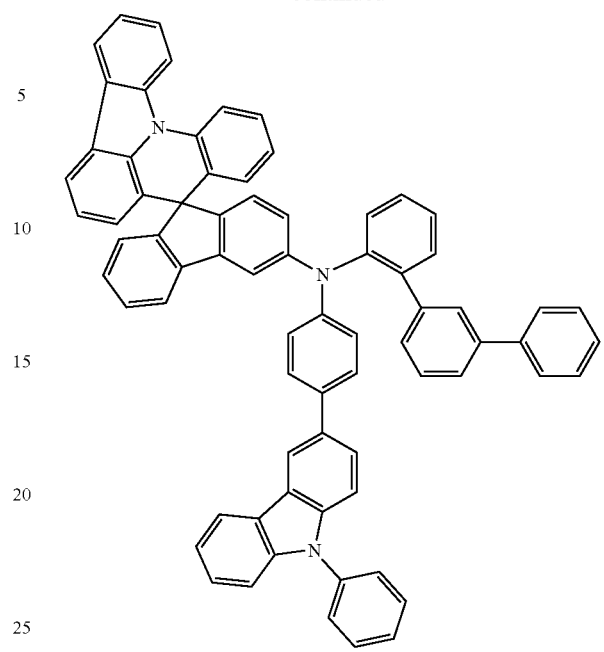
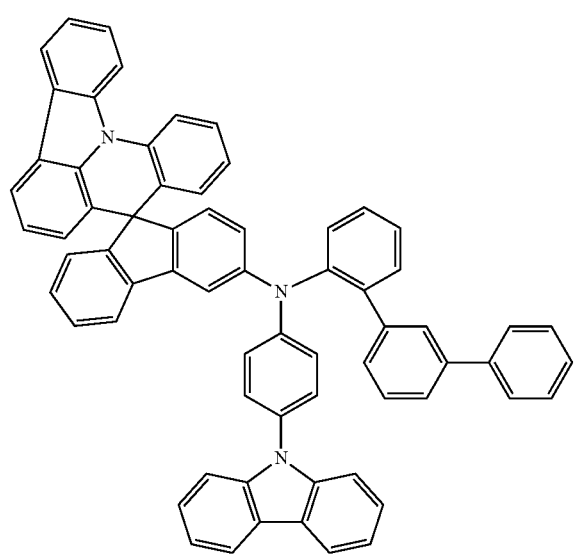

429
-continued
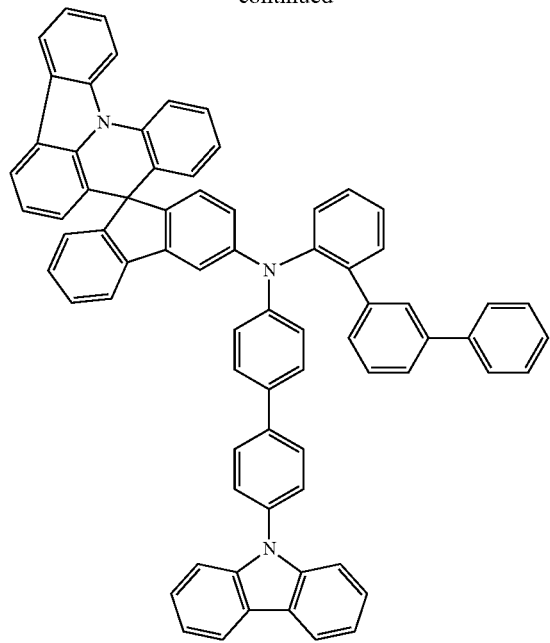
430
-continued
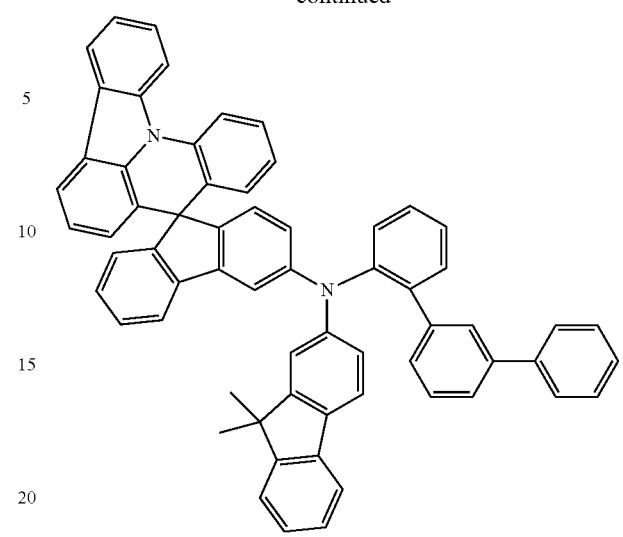
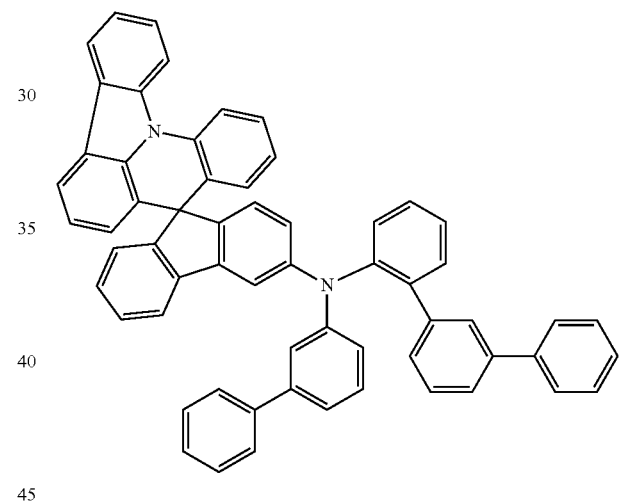
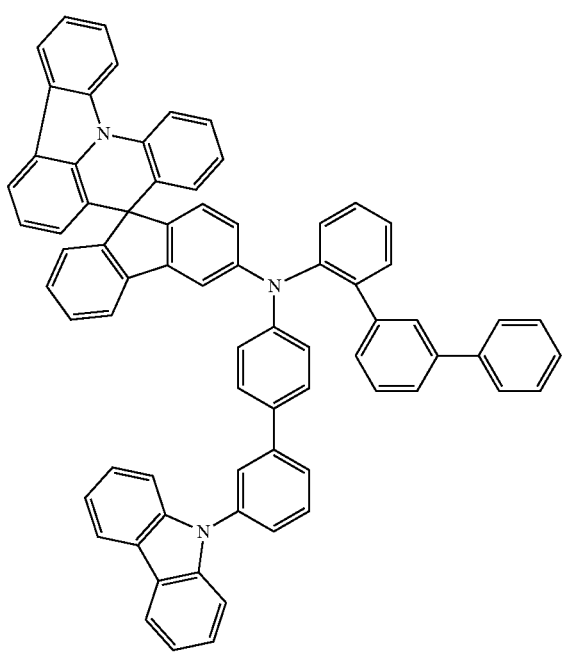
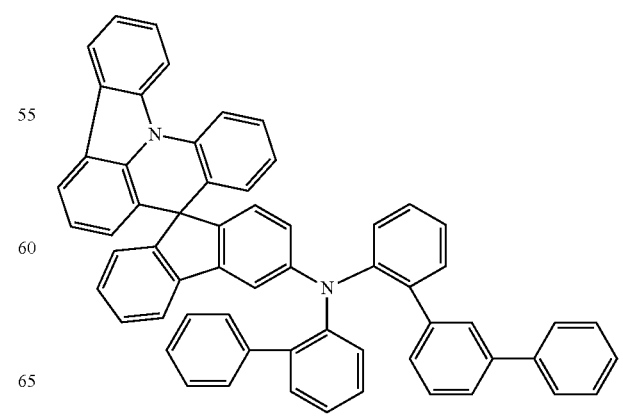

431
-continued
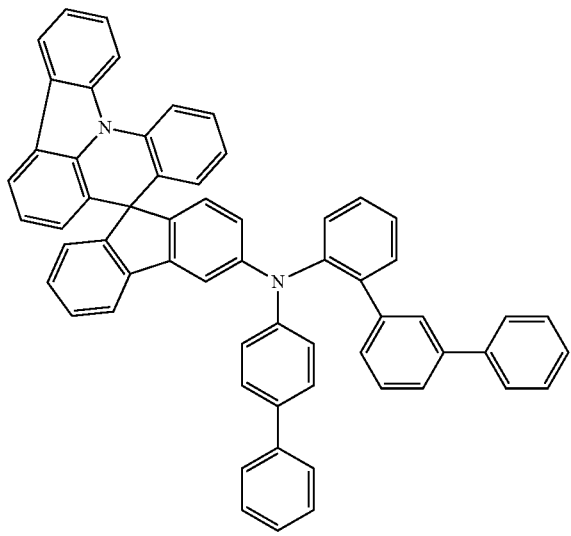
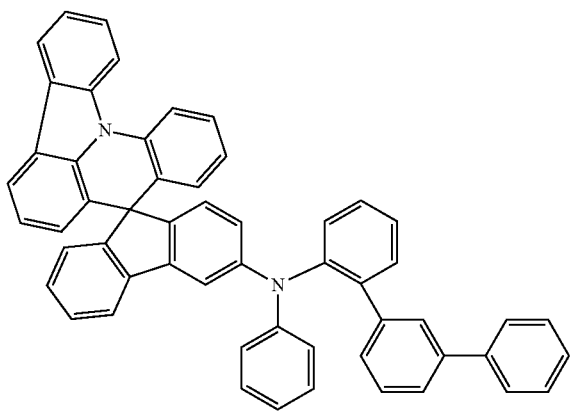
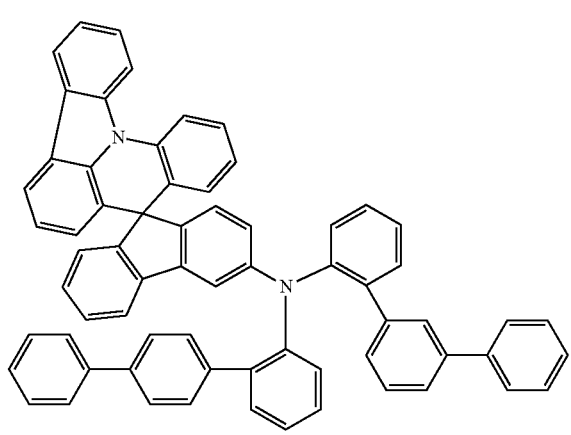
432
-continued
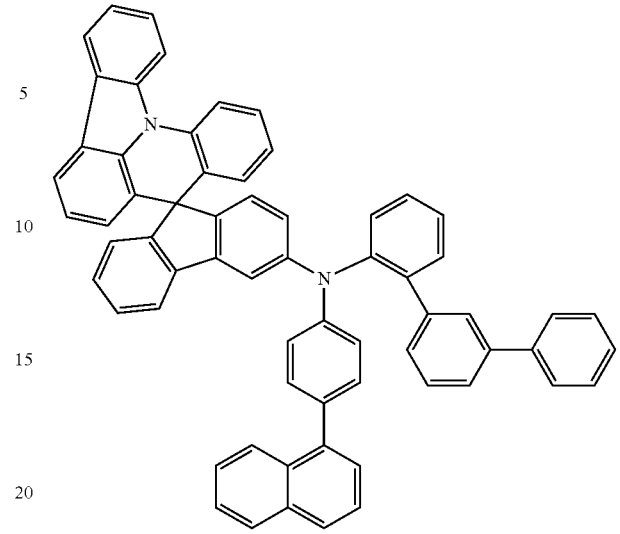
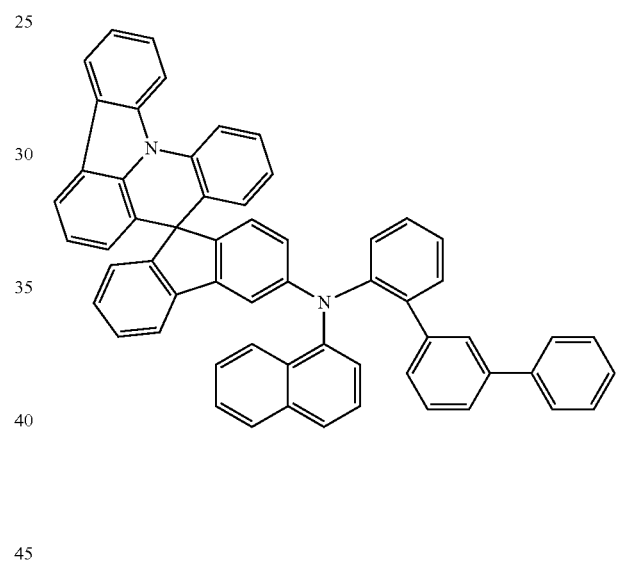
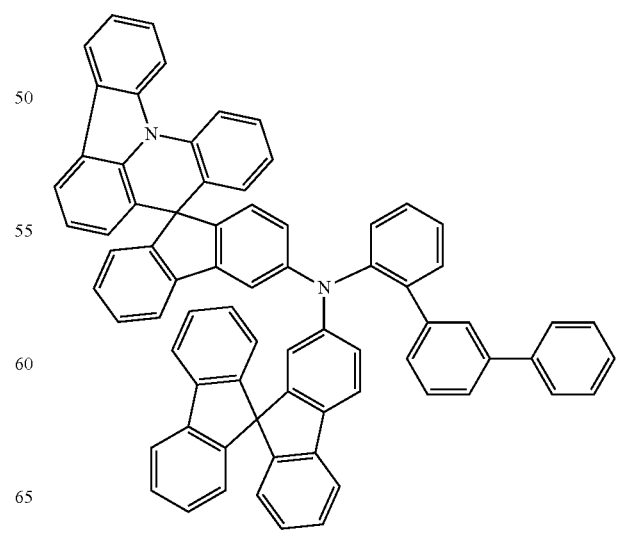

433
-continued
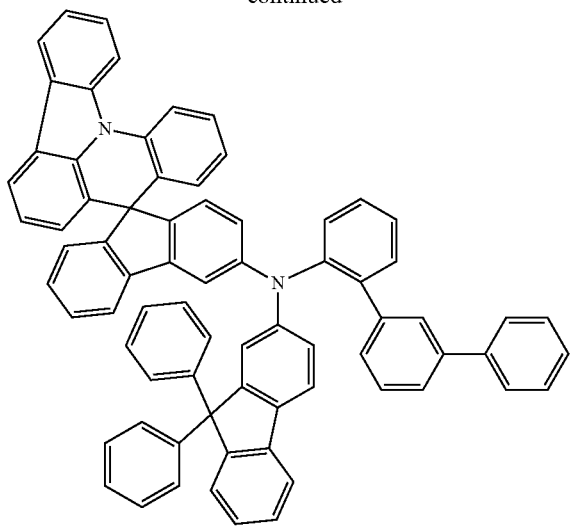
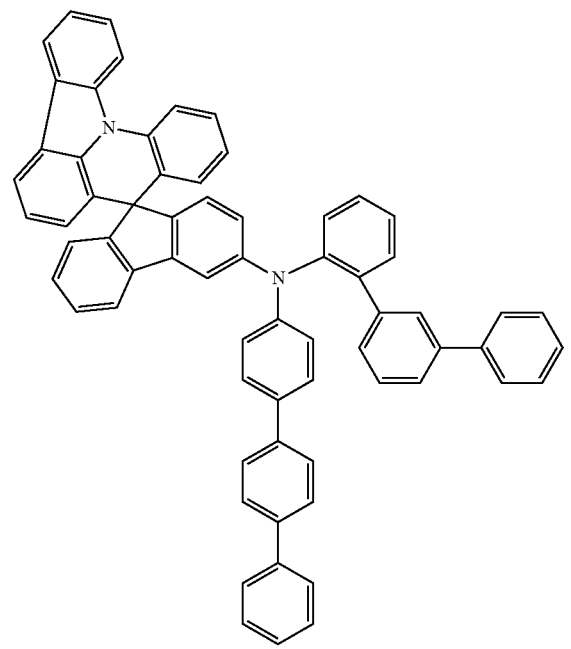
434
-continued
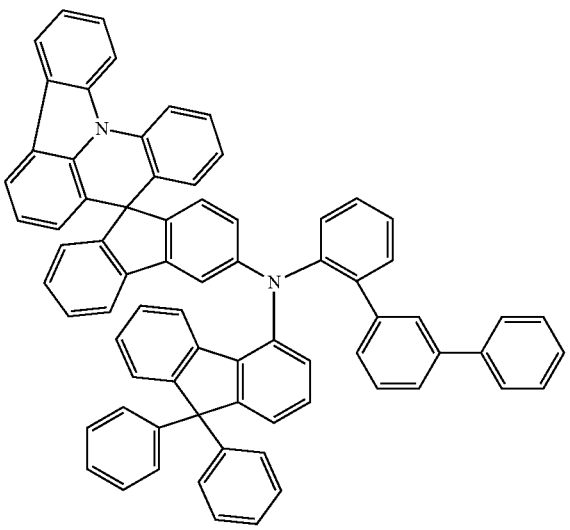
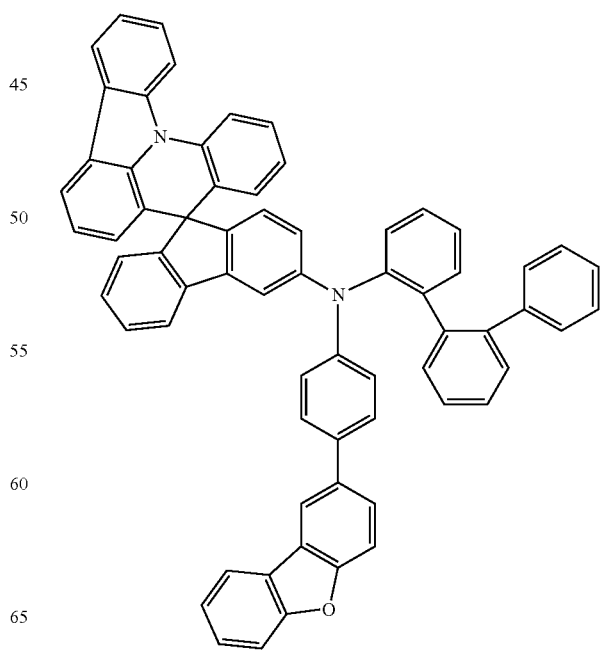

435
-continued
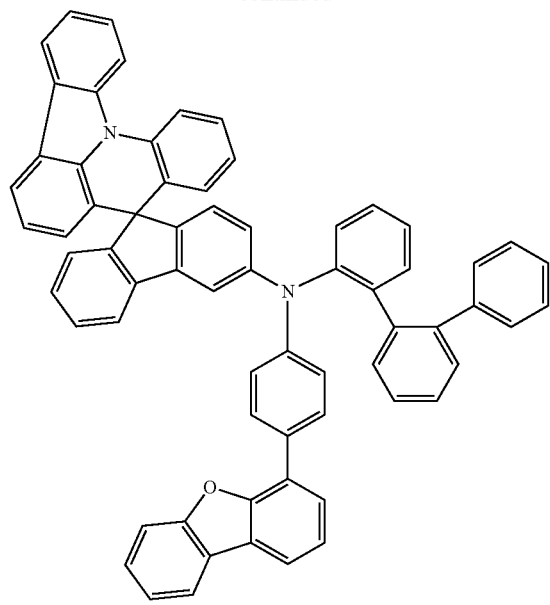
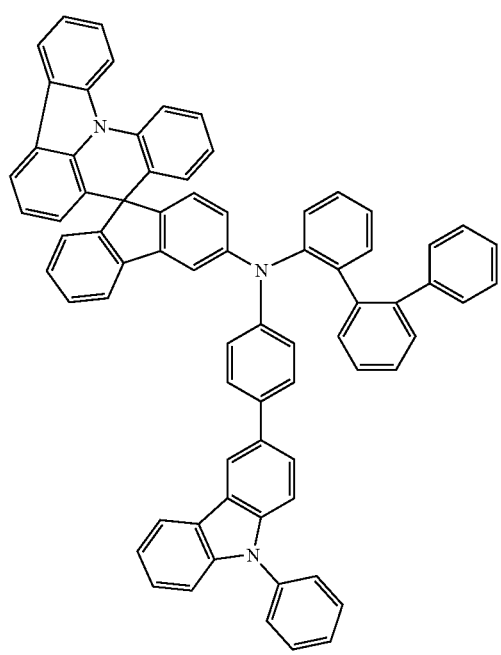
436
-continued
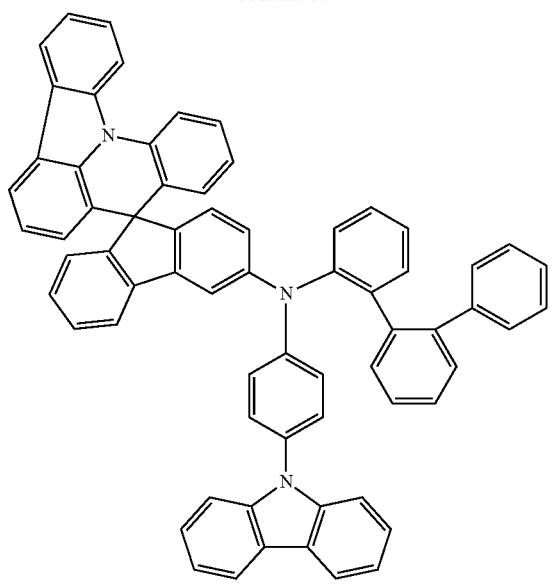
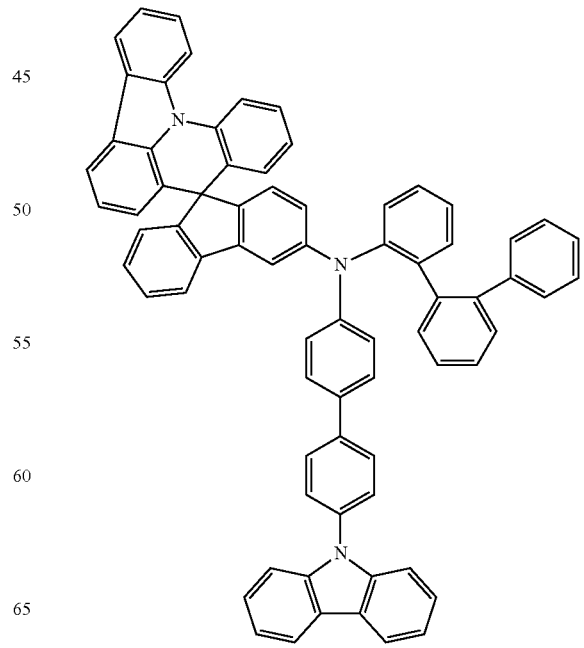

437
-continued
438
-continued
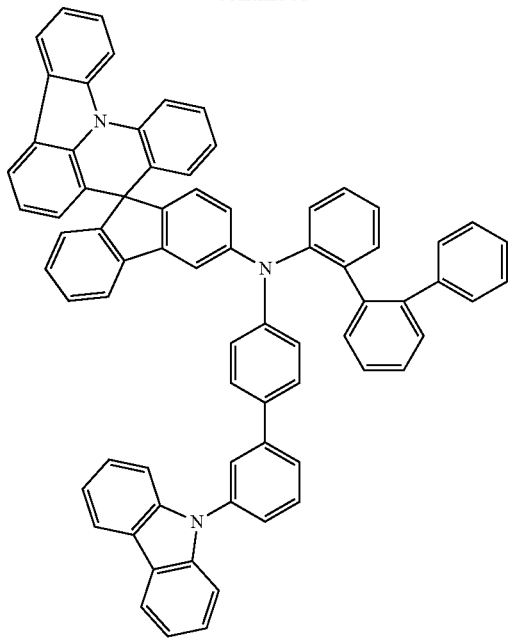
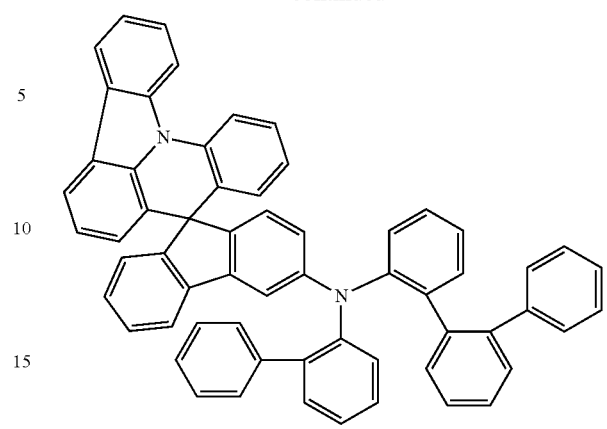
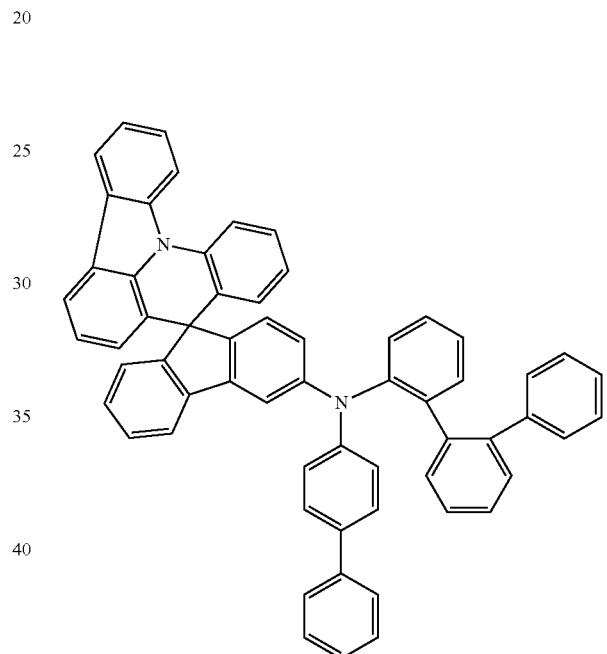
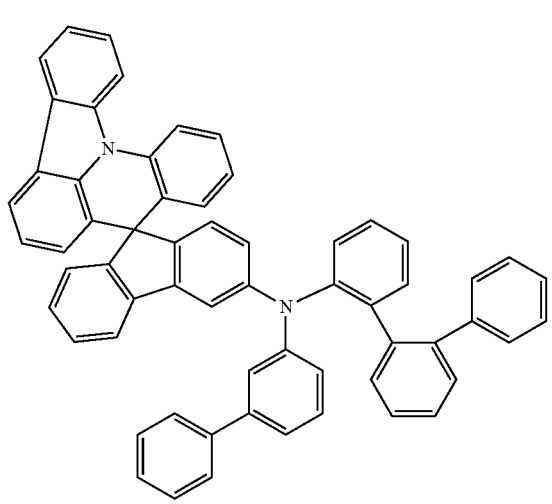
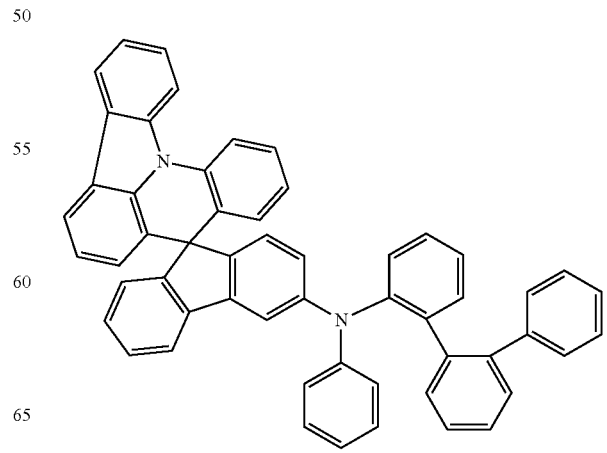

439
-continued
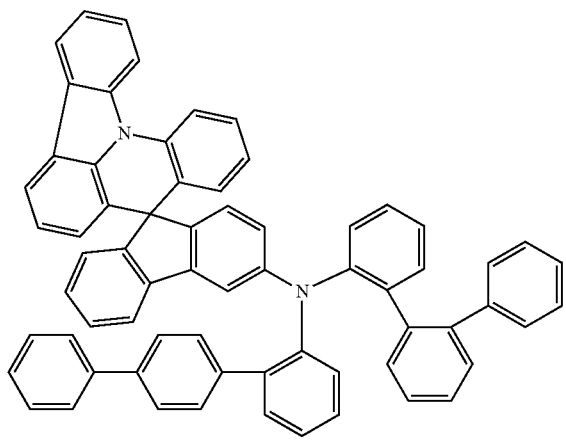
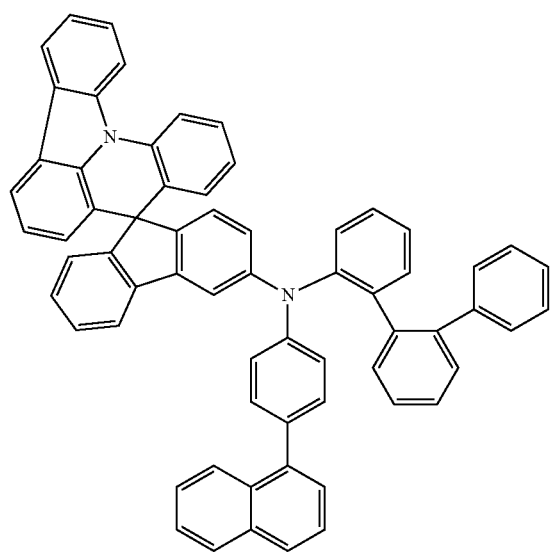
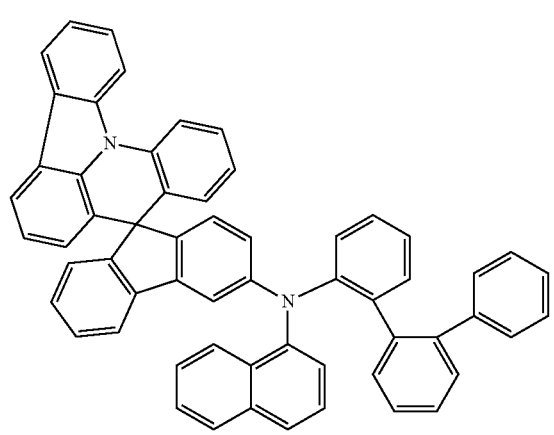
440
-continued
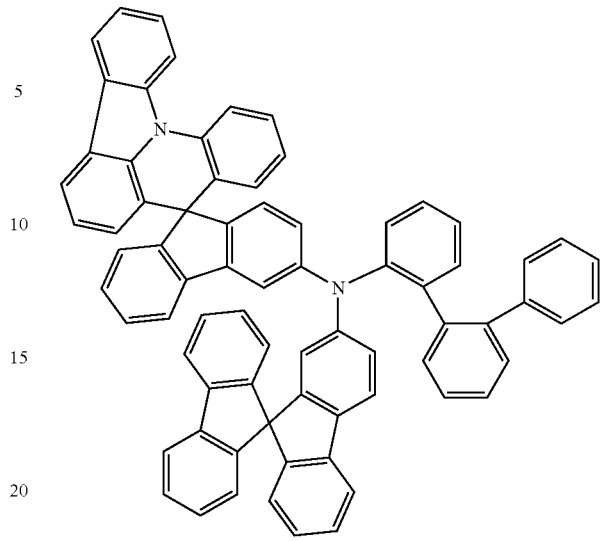
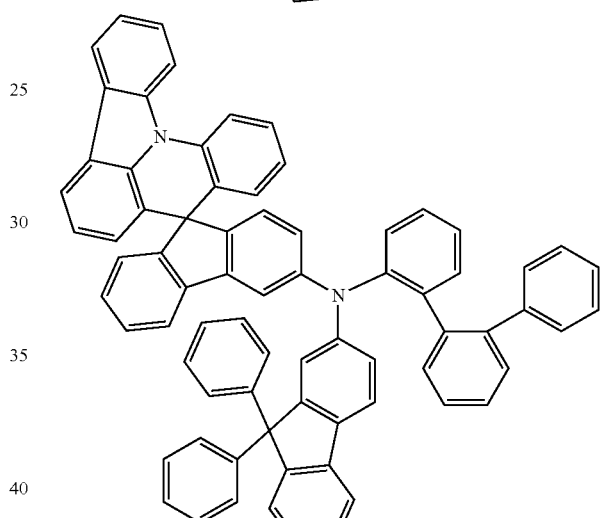

441
-continued
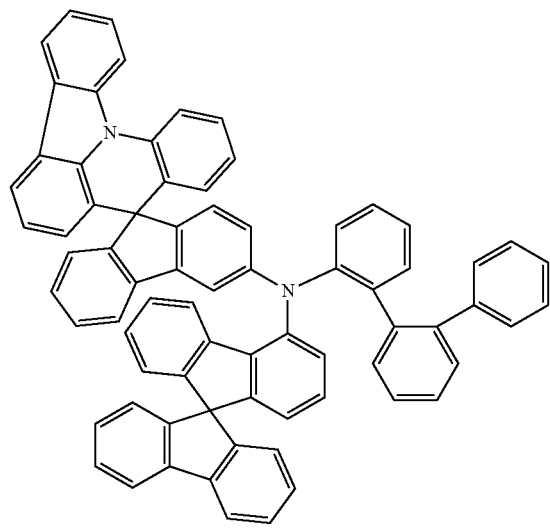
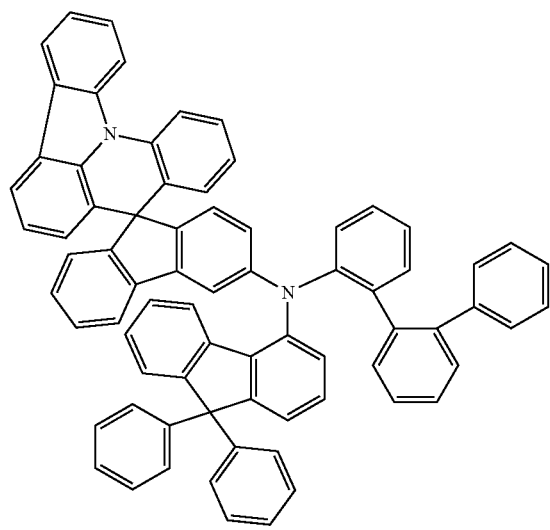
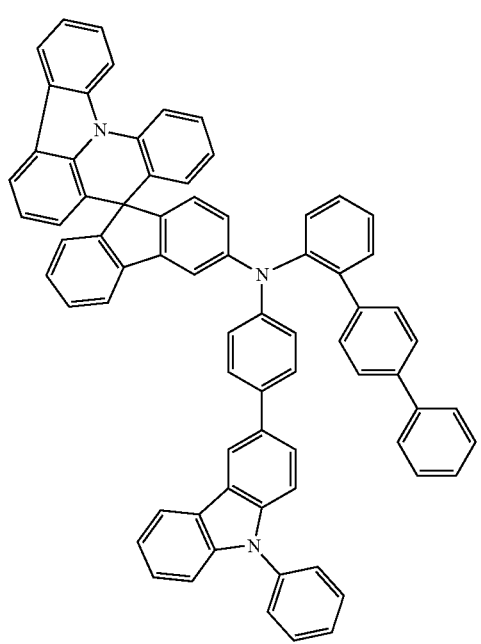
442
-continued
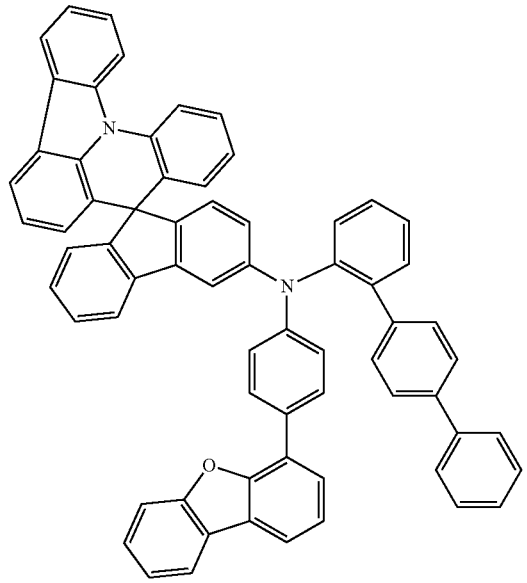

443
-continued
444
-continued
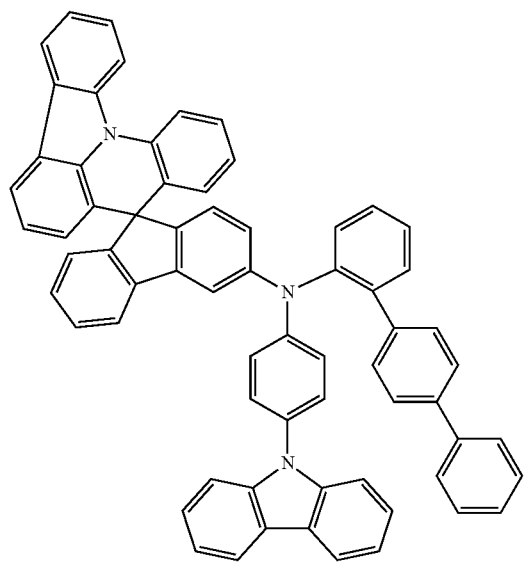
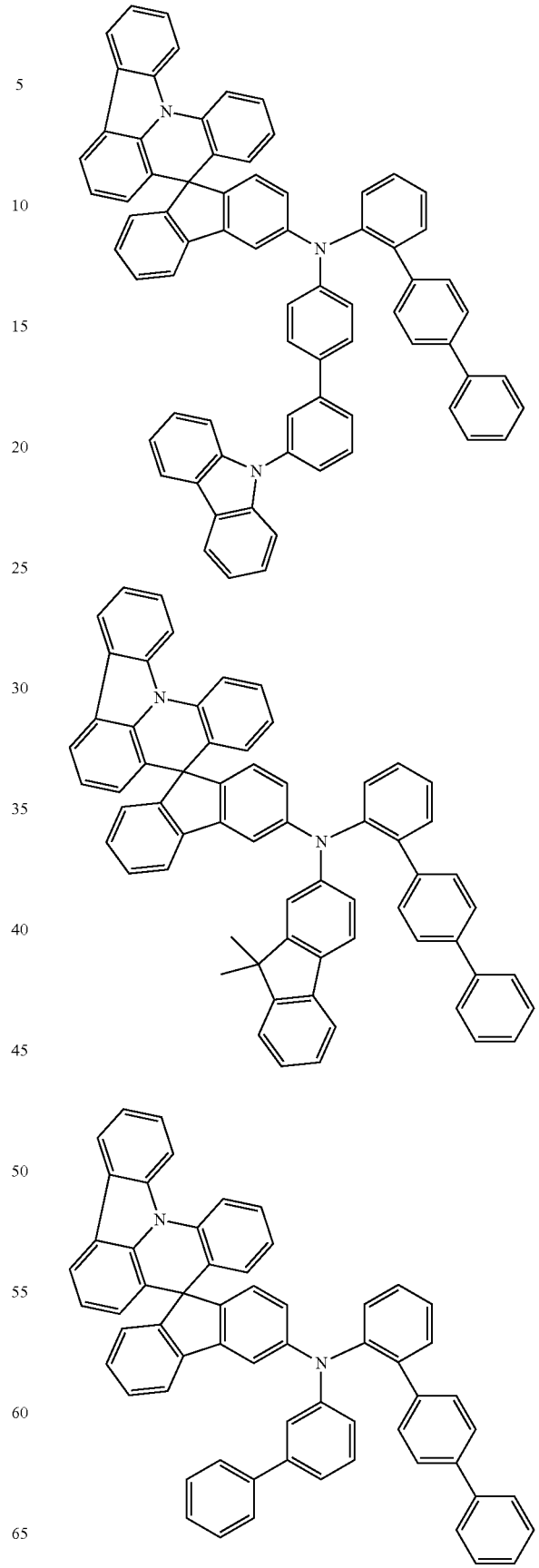

445
-continued
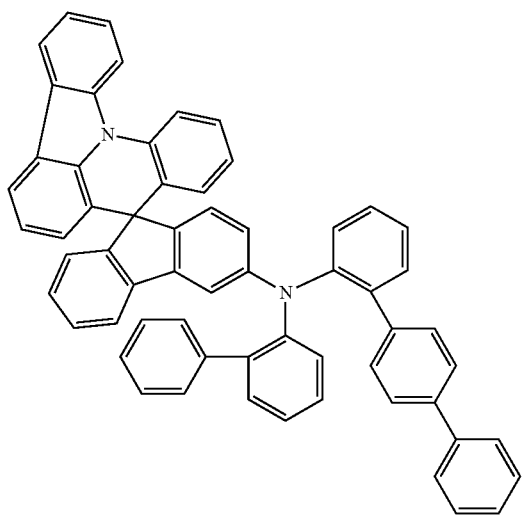
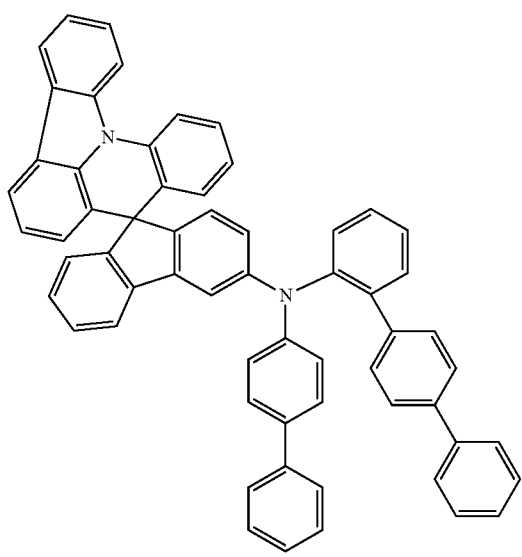
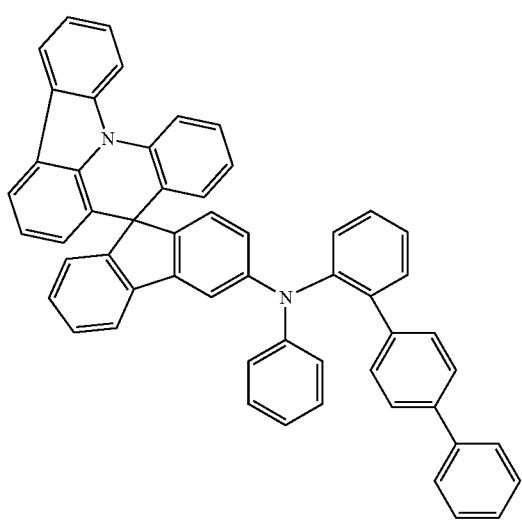
446
-continued
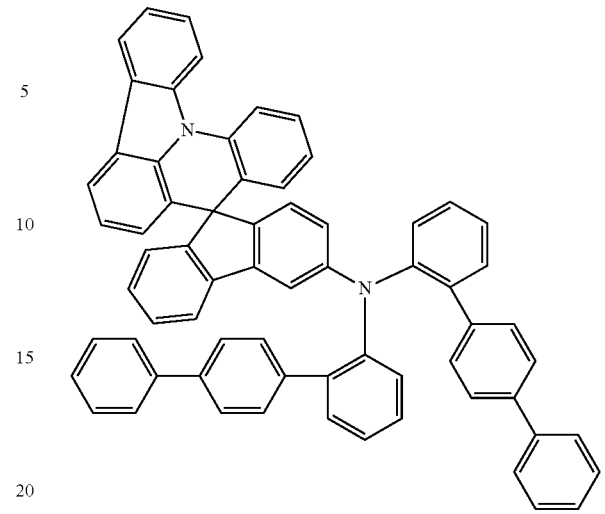
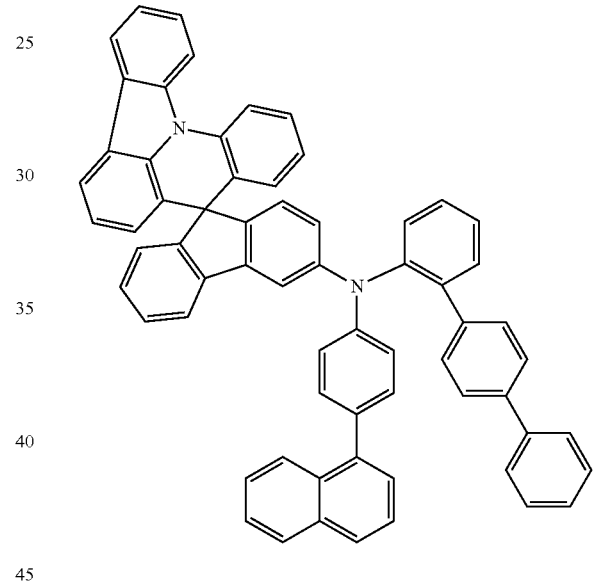
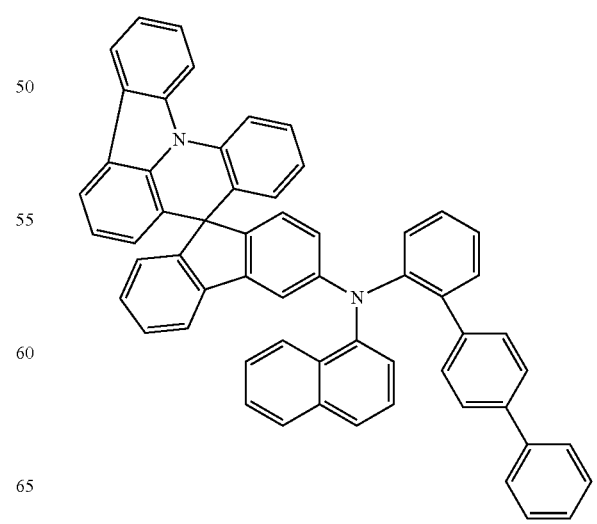

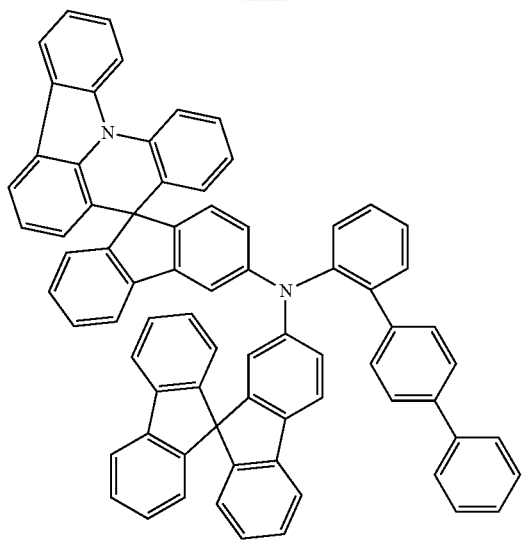
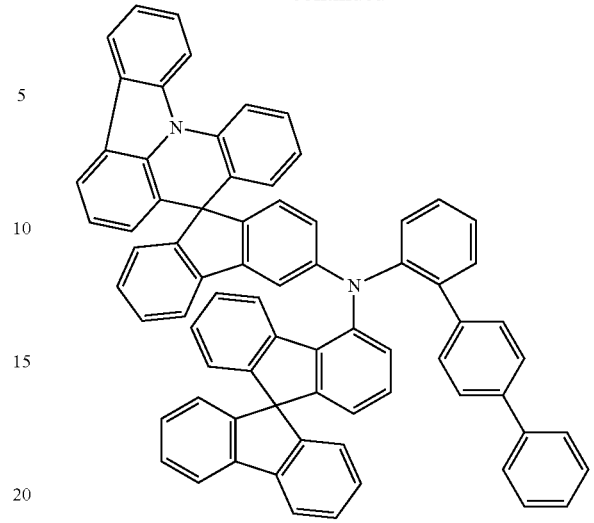
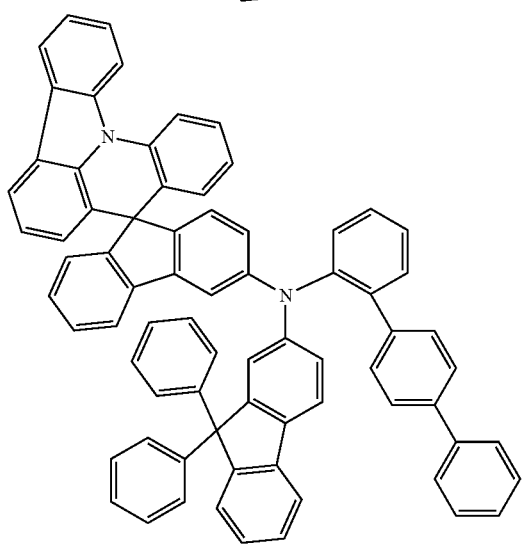
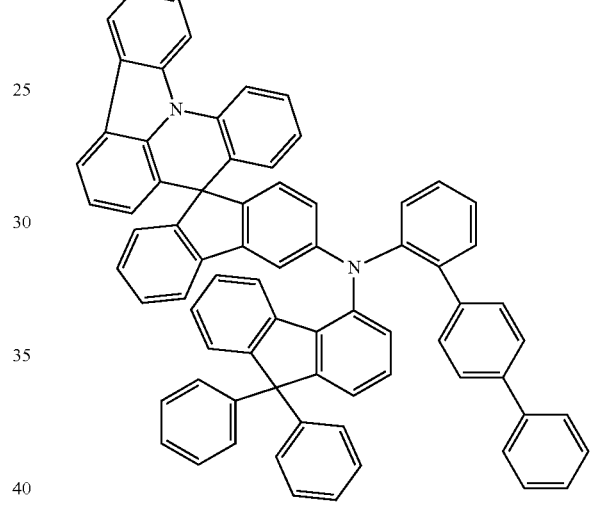
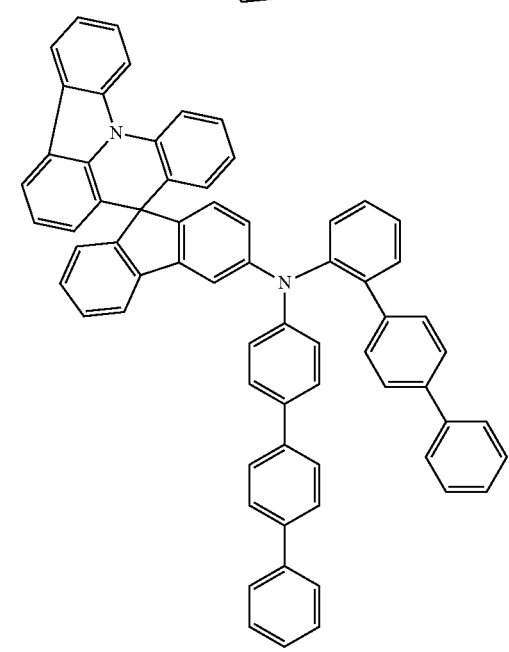

Material for Organic EL Devices

The material for organic EL devices in an aspect of the invention comprises a compound represented by formula (1) ("compound (1)"). The content of the compound (1) in the material for organic EL devices is, for example, 1% by mass or more (inclusive of 100%), preferably 10% by mass or more (inclusive of 100% b), more preferably 50% by mass or more (inclusive of 100%), still more preferably 80% by mass or more (inclusive of 100%), and particularly preferably 90% by mass or more (inclusive of 100%), although not particularly limited thereto.

The material for organic EL devices is useful as a material for producing organic EL devices and usable, for example, as a hole transporting layer material of a phosphorescent emission unit or a fluorescent emission unit, a host material of a light emitting layer, and an electron transporting layer material.

Organic EL Device

The organic EL device in an aspect of the invention will be described below.

The organic EL device comprises an organic layer between a cathode and an anode. The organic layer comprises a light emitting layer and at least one layer of the organic layer comprises the compound (1).

Examples of the organic layer in which the compound (1) is used include a hole transporting layer, a light emitting layer, and an electron transporting layer, although not limited thereto.

The organic EL device of the invention may be any of a fluorescent or phosphorescent single color emitting device, a white-emitting device of fluorescent-phosphorescent hybrid type, a simple-type emitting device having a single emission unit, and a tandem emitting device having two or more emission units, with a fluorescent emitting device being preferred. The "emission unit" referred to herein is the smallest unit for emitting light by the recombination of injected holes and injected electrons, which comprises an organic layer, wherein at least one layer is a light emitting layer.

Representative device structures of the simple-type organic EL device are shown below:

(1) Anode/Emission Unit/Cathode

The emission unit may be a laminated unit comprising two or more layers selected from a phosphorescent light emitting layer and a fluorescent light emitting layer. A space layer may be disposed between the light emitting layers to prevent the diffusion of excitons generated in the phosphorescent light emitting layer into the fluorescent light emitting layer. Representative layered structures of the simple-type emission unit are shown below, with the layers in parentheses being optional:

(a) (Hole injecting layer/) Hole transporting layer/Fluorescent emitting layer (/Electron transporting layer) (/Electron injecting layer);

(b) (Hole injecting layer/) Hole transporting layer/First phosphorescent or fluorescent emitting layer/Second phosphorescent or fluorescent emitting layer (/Electron transporting layer) (/Electron injecting layer);

(c) (Hole injecting layer/) Hole transporting layer/Phosphorescent emitting layer/Space layer/Fluorescent emitting layer (/Electron transporting layer) (/Electron injecting layer);

(d) (Hole injecting layer) Hole transporting layer/First phosphorescent emitting layer/Second phosphorescent emitting layer/Space layer/Fluorescent emitting layer (/Electron transporting layer) (/Electron injecting layer);

(e) (Hole injecting layer/) Hole transporting layer/First phosphorescent emitting layer/Space layer/Second phosphorescent emitting layer/Space layer/Fluorescent emitting layer (/Electron transporting layer) (/Electron injecting layer);

(f) (Hole injecting layer/) Hole transporting layer/Phosphorescent emitting layer/Space layer/First fluorescent emitting layer/Second fluorescent emitting layer (/Electron transporting layer) (/Electron injecting layer);

(g) (Hole injecting layer/) Hole transporting layer/Electron blocking layer/Fluorescent emitting layer (/Electron transporting layer) (/Electron injecting layer);

(h) (Hole injecting layer/) Hole transporting layer/Electron blocking layer/Phosphorescent emitting layer (/Electron transporting layer) (/Electron injecting layer);

(i) (Hole injecting layer/) Hole transporting layer/Exciton blocking layer/Fluorescent emitting layer (/Electron transporting layer) (/Electron injecting layer);

(j) (Hole injecting layer/) Hole transporting layer/Exciton blocking layer/Phosphorescent emitting layer (/Electron transporting layer) (/Electron injecting layer);

(k) (Hole injecting layer) First hole transporting layer/Second hole transporting layer/Fluorescent emitting layer (/Electron transporting layer) (/Electron injecting layer);

(l) (Hole injecting layer/) First hole transporting layer/Second hole transporting layer/Phosphorescent emitting layer (/Electron transporting layer) (/Electron injecting layer);

(m) (Hole injecting layer/) Hole transporting layer/Fluorescent emitting layer/Hole blocking layer (/Electron transporting layer) (/Electron injecting layer); and (n) (Hole injecting layer/) Hole transporting layer/Fluorescent emitting layer/Triplet blocking layer (/Electron transporting layer) (/Electron injecting layer).

The emission color of the fluorescent emitting layer and that of the phosphorescent emitting layer may be different. For example, the layered structure of the laminated emission unit (d) may be (Hole injecting layer/) Hole transporting layer/First phosphorescent emitting layer (red emission)/Second phosphorescent emitting layer (green emission)/Space layer/Fluorescent emitting layer (blue emission)/Electron transporting layer.

An electron blocking layer may be disposed between each light emitting layer and a hole transporting layer or between a light emitting layer and a space layer, if necessary. A hole blocking layer may be disposed between each light emitting layer and an electron transporting layer. With such an electron blocking layer or a hole blocking layer, electrons or holes are confined in a light emitting layer to increase the charge recombination in a light emitting layer, thereby improving the emission efficiency.

Representative device structure of the tandem-type organic EL device is shown below:

(2) Anode/First emission unit/Intermediate layer/Second emission unit/Cathode.

The layered structure of the first emission unit and the second emission unit may be independently selected from, for example, those exemplified above.

Generally, the intermediate layer is also called an intermediate electrode, an intermediate conductive layer, a charge generation layer, an electron withdrawing layer, a connecting layer, or an intermediate insulating layer. The intermediate layer may be formed by known materials which can supply electrons to the first emission unit and holes to the second emission unit.

A schematic structure of an example of the organic EL device is shown in FIG. 1, wherein the organic EL device 1 comprises a substrate 2, an anode 3, a cathode 4, and an emission unit 10 disposed between the anode 3 and the cathode 4. The emission unit 10 comprises at least one light emitting layer 5. A hole injecting layer or a hole transporting layer 6 (anode-side organic thin film layer) may be disposed between the light emitting layer 5 and the anode 3. An electron injecting layer or an electron transporting layer 7 (cathode-side organic thin film layer) may be disposed between the light emitting layer 5 and the cathode 4. An electron blocking layer (not shown) may be formed on the anode 3-side of the light emitting layer 5. A hole blocking layer (not shown) may be formed on the cathode 4-side of the light emitting layer 5. With the electron blocking layer and the hole blocking layer, electrons and holes are confined in the light emitting layer 5 to increase the exciton generation in the light emitting layer 5.

In the present invention, a host is referred to as a fluorescent host when combinedly used with a fluorescent dopant (fluorescent emitting material) and as a phosphorescent host when combinedly used with a phosphorescent dopant. Therefore, the fluorescent host and the phosphorescent host are not distinguished from each other merely by the difference in their molecular structures. Namely, in the present invention, the term "phosphorescent host" means a material for constituting a phosphorescent emitting layer containing a phosphorescent dopant and does not mean a material that cannot be utilized as a material for a fluorescent emitting layer. The same applies to the fluorescent host.

Substrate

The substrate is a support for the emitting device and made of, for example, glass, quartz, and plastics. The substrate may be a flexible substrate, for example, a plastic substrate made of polycarbonate, polyarylate, polyether sulfone, polypropylene, polyester, polyvinyl fluoride, and polyvinyl chloride. An inorganic deposition film is also usable.

Anode

The anode is formed on the substrate preferably from a metal, an alloy, an electrically conductive compound, and a mixture thereof, each having a large work function, for example, 4.5 eV or more. Examples of the material for the anode include indium oxide-tin oxide (ITO: indium tin oxide), indium oxide-tin oxide doped with silicon or silicon oxide, indium oxide-zinc oxide, indium oxide doped with tungsten oxide and zinc oxide, and graphene. In addition, gold (Au), platinum (Pt), nickel (Ni), tungsten (W), chromium (Cr), molybdenum (Mo), iron (Fe), cobalt (Co), copper (Cu), palladium (Pd), titanium (Ti), and a nitride of the above metal (for example, titanium nitride) are also usable.

These materials are made into a film generally by a sputtering method. For example, a film of indium oxide-zinc oxide is formed by sputtering an indium oxide target doped with 1 to 10 wt % of zinc oxide, and a film of indium oxide doped with tungsten oxide and zinc oxide is formed by sputtering an indium oxide target doped with 0.5 to 5 wt % of tungsten oxide and 0.1 to 1 wt % of zinc oxide. In addition, a vacuum vapor deposition method, a coating method, an inkjet method, and a spin coating method are usable.

A hole injecting layer to be optionally formed in contact with the anode is formed from a material which is capable of easily injecting holes independently of the work function of the anode. Therefore, the anode can be formed by a material generally known as an electrode material, for example, a metal, an alloy, an electroconductive compound, a mixture thereof, and a group 1 element and a group 2 element of the periodic table.

A material having a small work function, for example, the group 1 element and the group 2 element of the periodic table, i.e., an alkali metal, such as lithium (Li) and cesium (Cs), an alkaline earth metal, such as magnesium (Mg), calcium (Ca), and strontium (Sr), and an alloy thereof, such as MgAg and AlLi, are also usable. In addition, a rare earth metal, such as europium (Eu) and ytterbium (Yb), and an alloy thereof are also usable. The alkali metal, the alkaline earth metal, and the alloy thereof can be made into the anode by a vacuum vapor deposition or a sputtering method. When a silver paste, etc. is used, a coating method and an inkjet method are usable.

Hole Injecting Layer

The hole injecting layer comprises a highly hole injecting material (hole injecting material). In addition to a hole injecting material, the hole injecting layer may comprise the same material as that contained in the adjacent hole transporting layer. The compound (1) may be used in the hole injecting layer alone or in combination with the hole injecting material mentioned below.

Examples of the hole injecting material include molybdenum oxide, titanium oxide, vanadium oxide, rhenium oxide, ruthenium oxide, chromium oxide, zirconium oxide, hafnium oxide, tantalum oxide, silver oxide, tungsten oxide, and manganese oxide.

The following low molecular aromatic amine compound is also usable as the hole injecting material: 4,4',4''-tris(N, N-diphenylamino)triphenylamine (TDATA), 4,4',4''-tris[N-(3-methylphenyl)-N-phenylamino]triphenylamine (MTDATA), 4,4'-bis[N-(4-diphenylaminophenyl)-N-phenylamino] biphenyl (DPAB), 4,4'-bis(N-{4-[N'-(3-methylphenyl)-N'-phenylamino]phenyl}-N-phenylantino)biphenyl (DNTPD), 1,3,5-tris[N-(4-diphenylaminophenyl)-N-phenylamino]benzene (DPA3B), 3-[N-(9-phenylcarbazole-3-yl)-N-phenylamino]-9-phenylcarbazole (PCzPCA1), 3,6-bis[N-(9-phenylcarbazole-3-yl)-N-phenylamino]-9-phenylcarbazole (PCzPCA2), and 3-[N-(1-naphthyl)-N-(9-phenylcarbazole-3-yl)amino]-9-phenylcarbazole (PCzPCN1). Further, the radialene compound, such as 4-({2,3-bis[cyano-(4-cyano-2, 3,5,6-tetrafluorophenyl)methylene]cyclopropylidene}cyanomethyl)-2,3,5,6-tetrafluorobenzonitrile, is also usable as the hole injecting material. In addition to the radialene compound as the hole injecting material, the hole injecting layer may further comprise the same material as that contained in the adjacent hole transporting layer. The compound (1) may be used in the hole injecting layer in combination with the radialene compound.

A macro molecular compound, such as an oligomer, a dendrimer, a polymer, is also usable. Examples thereof include poly(N-vinylcarbazole) (PVK), poly(4-vinyltriphenylamine) (PVTPA), poly[N-(4-(N'-[4-(4-diphenylamino) phenyl]phenyl-N'-phenylamino}phenyl)methacrylamide] (PTPDMA), and poly[N,N'-bis(4-butylphenyl)-N,N'-bis (phenyl)benzidine](Poly-TPD). An acid-added macro molecular compound, such as poly(3,4-ethylenedioxythiophene)/poly(styrenesulfonic acid) (PEDOT/PSS) and polyaniline/poly(styrenesulfonic acid) (PAni/PSS), is also usable.

In addition, an acceptor material, such as a hexaazatriphenylene (HAT) compound represented by formula (K), is usable as the hole injecting layer material:

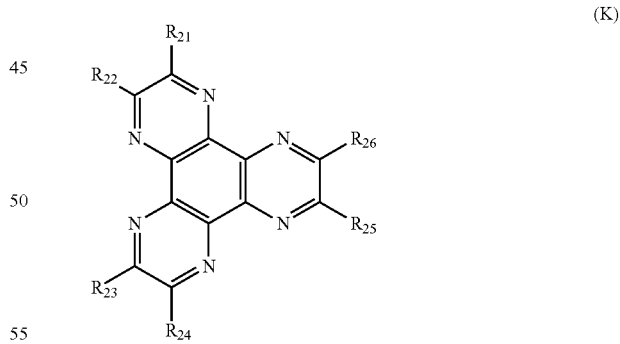

(K)

wherein $R_{21}$ to $R_{26}$ may be the same or different and each of $R_{21}$ to $R_{26}$ is independently a cyano group, —$CONH_2$, a carboxyl group, or —$COOR_{27}$ wherein $R_{27}$ is an alkyl group having 1 to 20 carbon atoms or a cycloalkyl group having 3 to 20 carbon atoms, or $R_{Y1}$ and $R_{22}$, $R_{23}$ and $R_{24}$, or $R_{25}$ and $R_{26}$ may be bonded to each other to form a group represented by —CO—O—CO—.

$R_{27}$ is a methyl group, an ethyl group, a n-propyl group, an isopropyl group, a n-butyl group, an isobutyl group, a t-butyl group, a cyclopentyl group, or a cyclohexyl group.

The compound represented by (2-1) or (2-2) is preferably used as the hole injecting material:

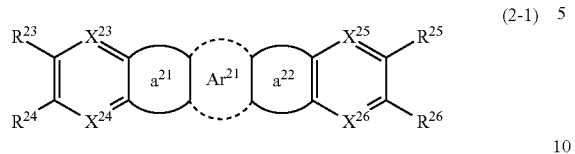
(2-1)

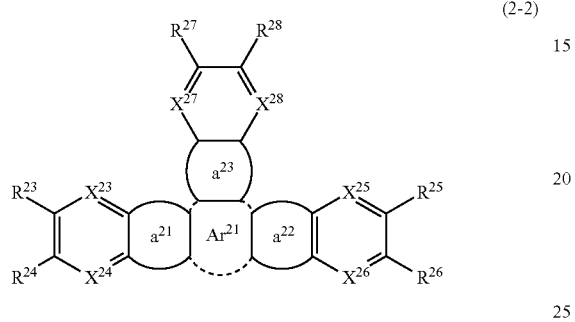
(2-2)

In formulae (2-1) and (2-2), $Ar^{21}$ is a substituted or unsubstituted aromatic hydrocarbon ring having 6 to 30 ring carbon atoms or a substituted or unsubstituted aromatic heterocyclic ring having 5 to 30 ring atoms. The aromatic hydrocarbon ring is preferably a benzene ring. The aromatic heterocyclic ring is preferably a ring having 6 ring atoms, for example, a pyridine ring, a pyrazine ring, and a pyridazine ring.

In formulae (2-1) and (2-2), each of $X^{23}$ to $X^{28}$ is independently C(R) or a nitrogen atom.

Each R is independently a hydrogen atom, a halogen atom, a hydroxyl group, a cyano group, a substituted or unsubstituted alkyl group having 1 to 30 carbon atoms, a substituted or unsubstituted aryl group having 6 to 30 ring carbon atoms, a mono-, di-, or tri-substituted silyl group having a substituent selected from a substituted or unsubstituted alkyl group having 1 to 30 carbon atoms and a substituted or unsubstituted aryl group having 6 to 30 ring carbon atoms, an alkoxy group having a substituted or unsubstituted alkyl group having 1 to 30 carbon atoms, an aryloxy group having a substituted or unsubstituted aryl group having 6 to 30 ring carbon atoms, a mono- or di-substituted amino group having a substituent selected from a substituted or unsubstituted alkyl group having 1 to 30 carbon atoms and a substituted or unsubstituted aryl group having 6 to 30 ring carbon atoms, an alkylthio group having a substituted or unsubstituted alkyl group having 1 to 30 carbon atoms, an arylthio group having a substituted or unsubstituted aryl group having 6 to 30 ring carbon atoms, or a substituted or unsubstituted heteroaryl group having 5 to 30 ring atoms.

The details of the alkyl group, the aryl group, the mono-, di-, or tri-substituted silyl group, the alkoxy group, the aryloxy group, the mono- or di-substituted amino group, the alkylthio group, the arylthio group, and the heteroaryl group are the same as those of the corresponding groups mentioned above with respect to the substituent simply referred to by "substituent" and the optional substituent referred to by "substituted or unsubstituted."

In formulae (2-1) and (2-2), each of $a^{21}$ to $a^{23}$ is a ring structure represented by formula (2b):

(2b)

wherein $X^{20}$ is represented by any of formulae (2b-1) to (2b-12):

(2b-1)

(2b-2)

(2b-3)

(2b-4)

(2b-5)

(2b-6)

(2b-7)

(2b-8)

(2b-9)
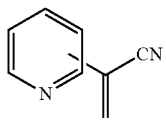
(2b-10)
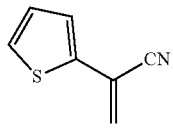
(2b-11)
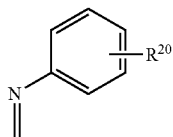
(2b-12)
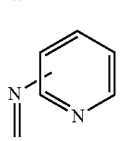
wherein $R^{20}$ is the same as defined with respect to R.
In formulae (2-1) and (2-2), each of $R^{23}$ to $R^{28}$ is independently the same as defined with respect to R.
Examples of the compound represented by formula (2-1) or (2-2) are shown below, although not limited thereto.
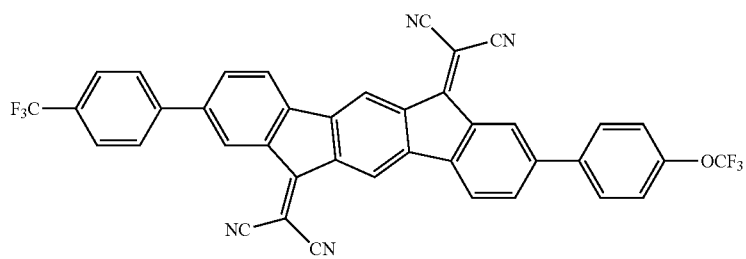
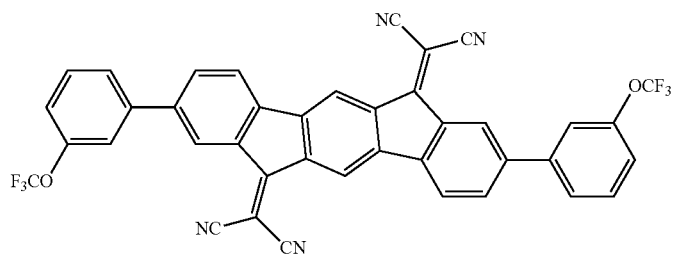
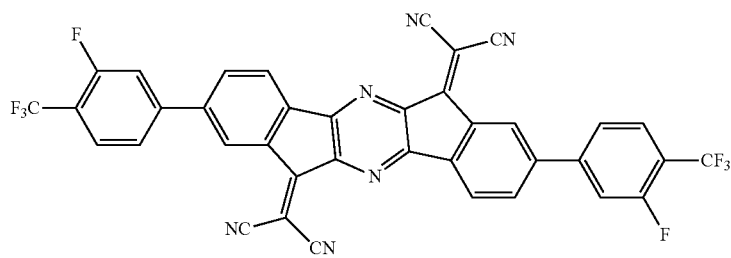
(A-1)
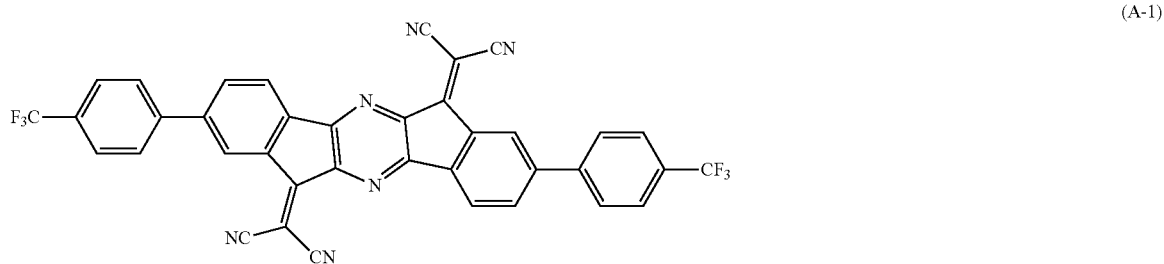

-continued
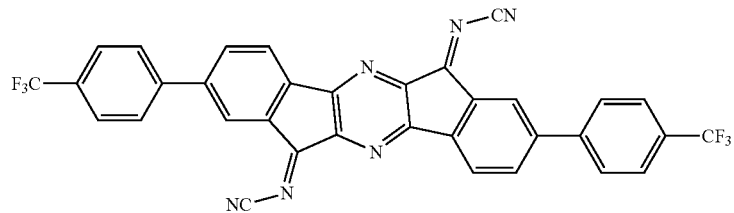
(A-2)
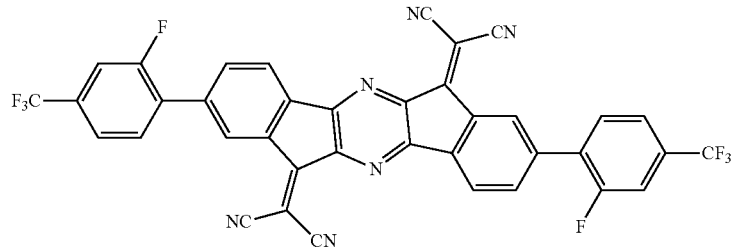
(A-3)
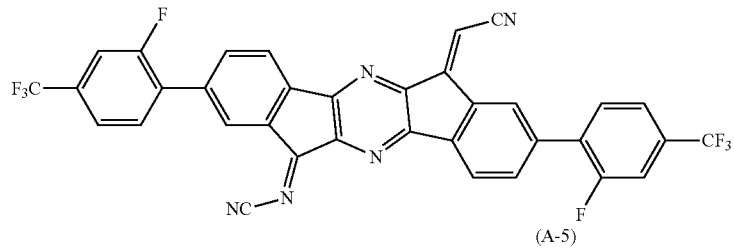
(A-4)
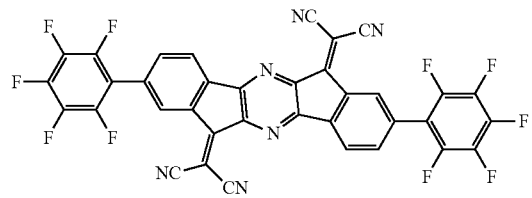
(A-5)
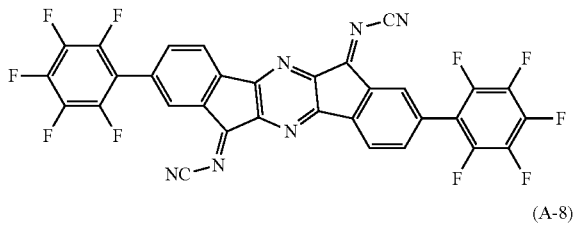
(A-6)
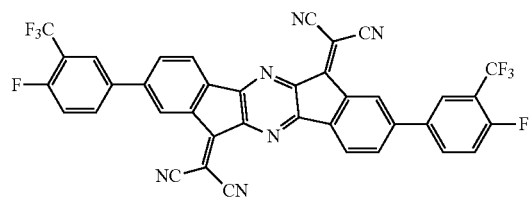
(A-7)
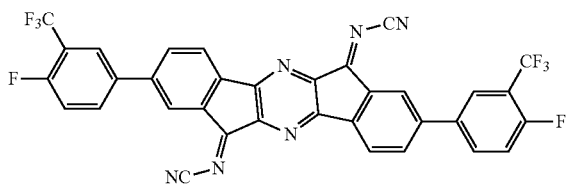
(A-8)
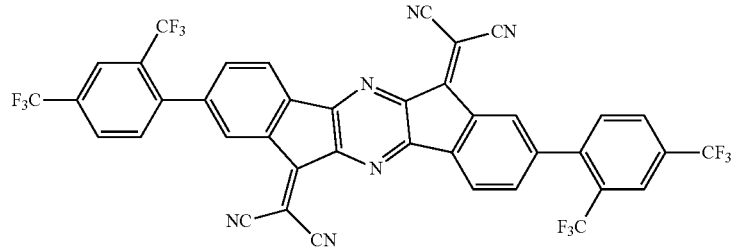
(A-9)
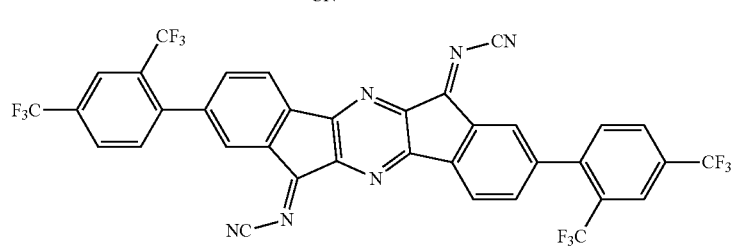
(A-10)

-continued
(A-11)
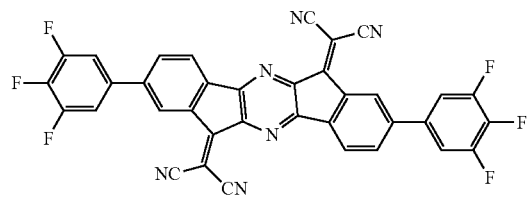
(A-12)
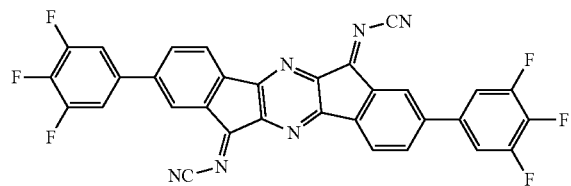
(A-13)
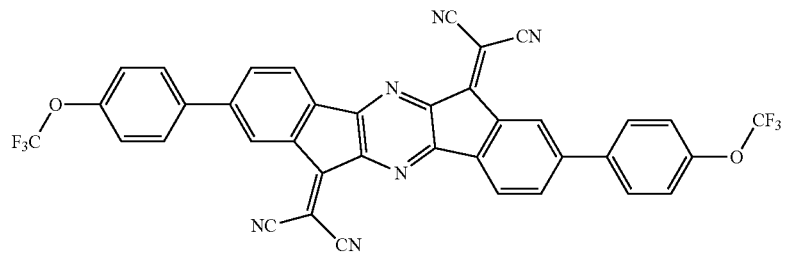
(A-14)
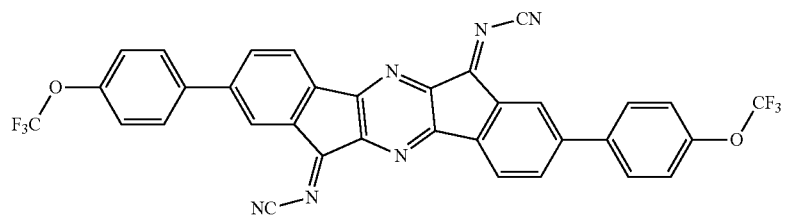
(A-15)
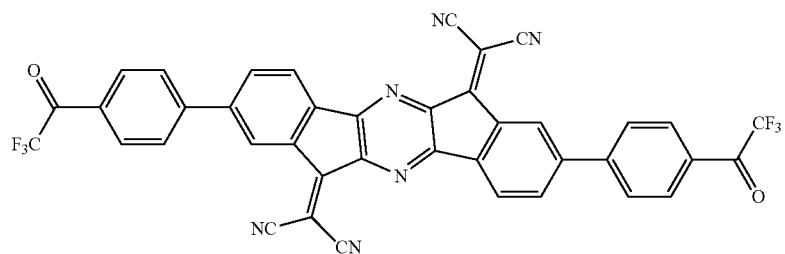
(A-16)
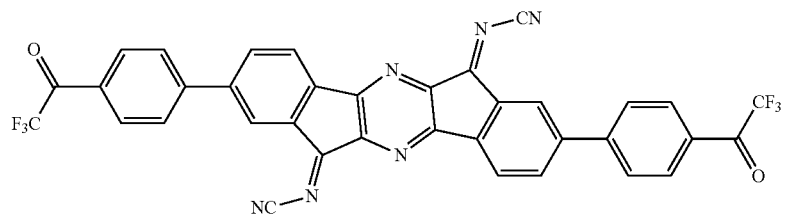
(A-17)
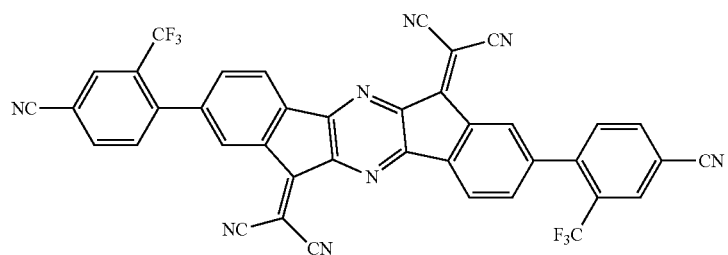

-continued
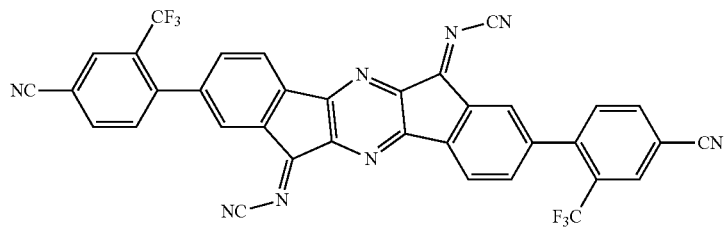
(A-18)
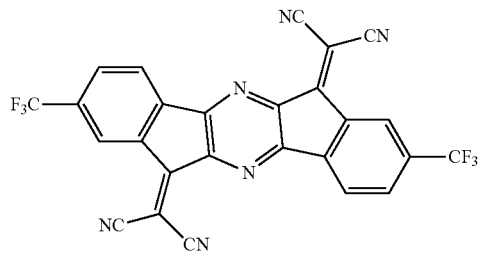
(A-19)
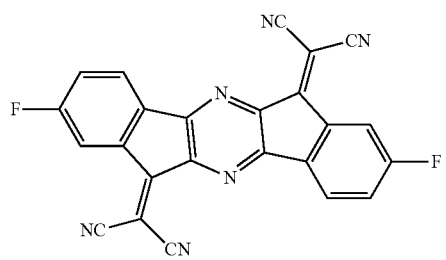
(A-21)
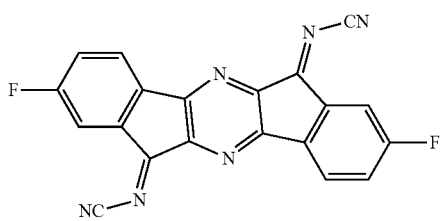
(A-20)
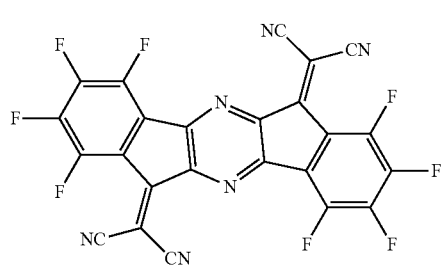
(A-23)
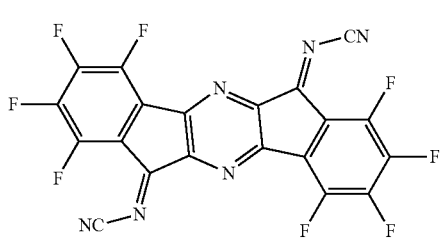
(A-22)
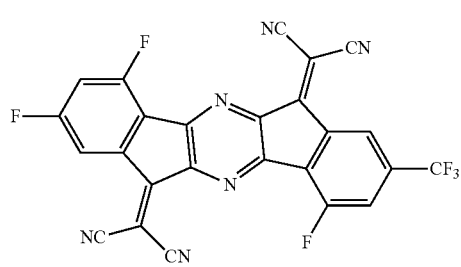
(A-25)
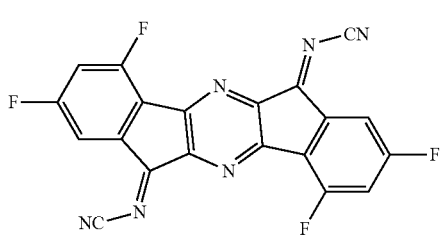
(A-24)
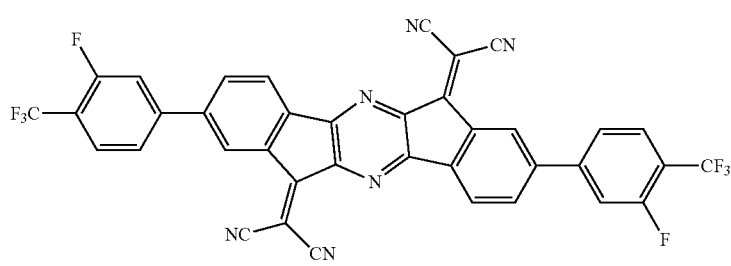
(A-31)

-continued
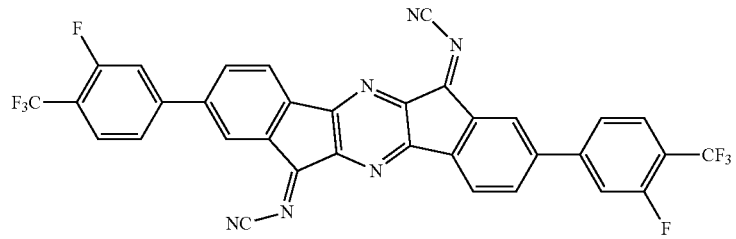
(A-32)
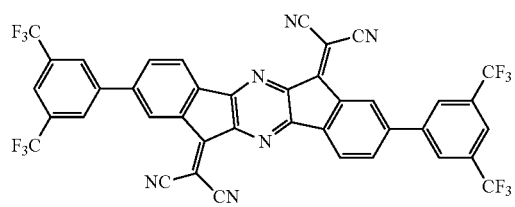
(A-33)
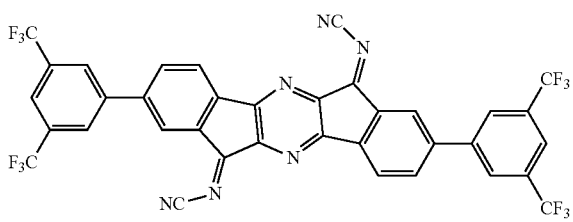
(A-34)
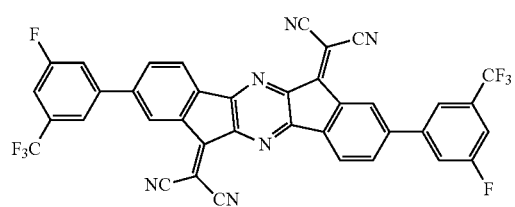
(A-35)
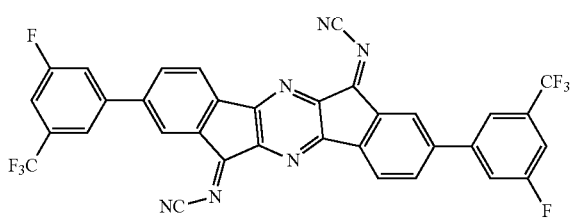
(A-36)
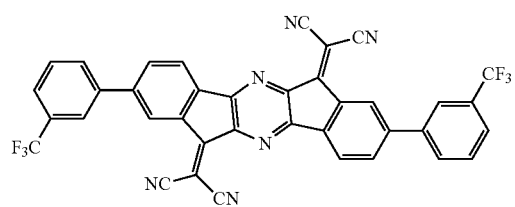
(A-37)
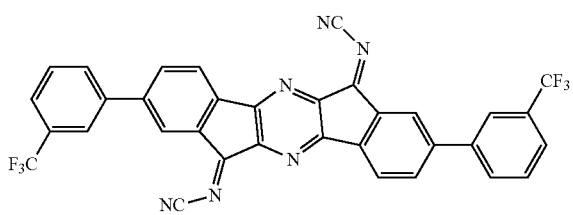
(A-38)
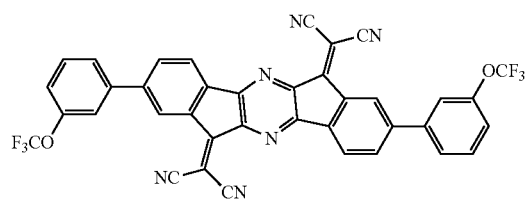
(A-39)
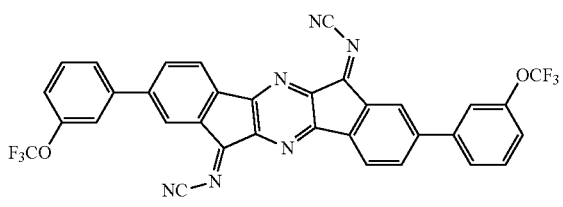
(A-40)
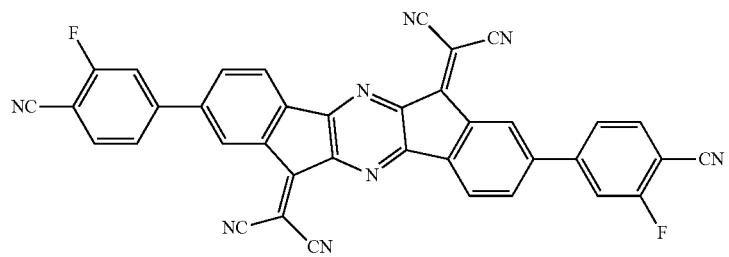
(A-41)

-continued
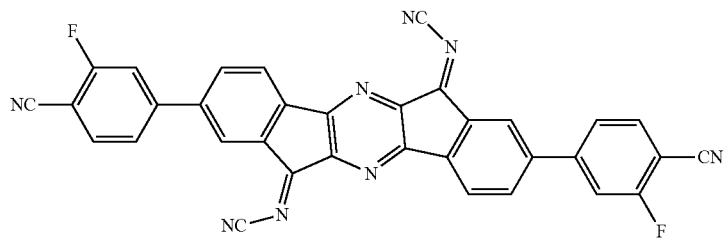
(A-42)
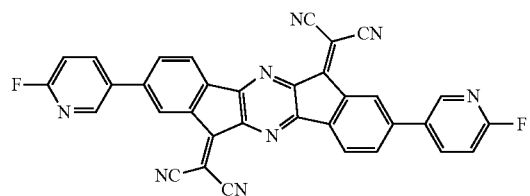
(A-43)
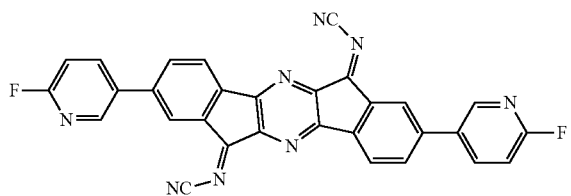
(A-44)
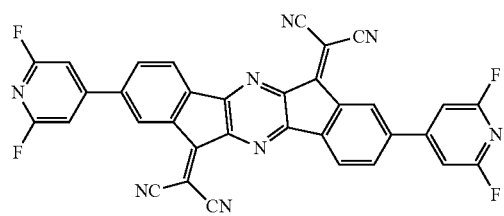
(A-45)
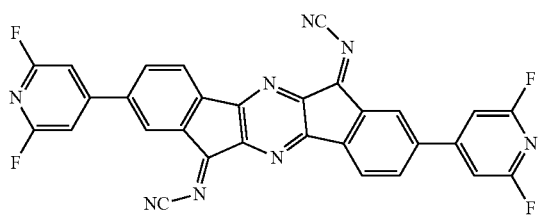
(A-46)
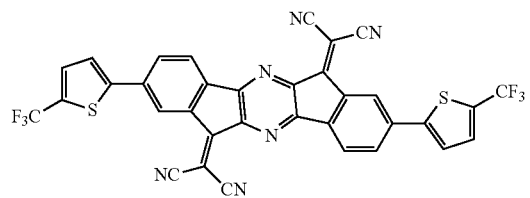
(A-47)
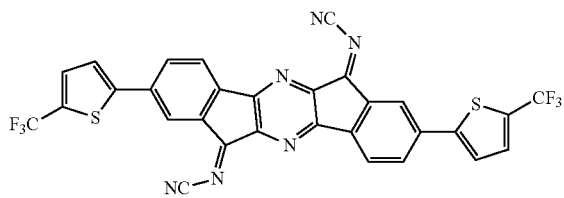
(A-48)
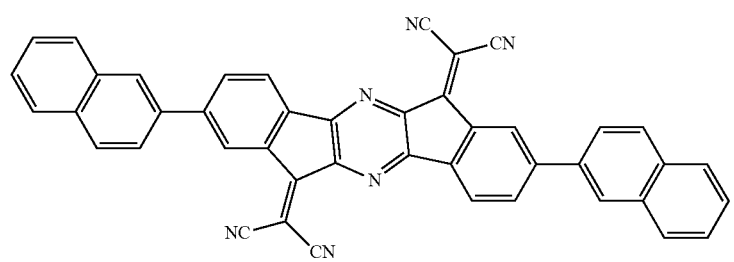
(A-49)
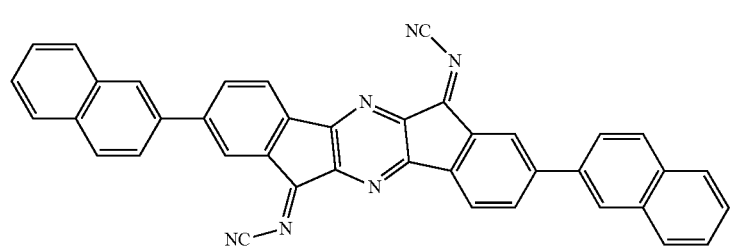
(A-50)

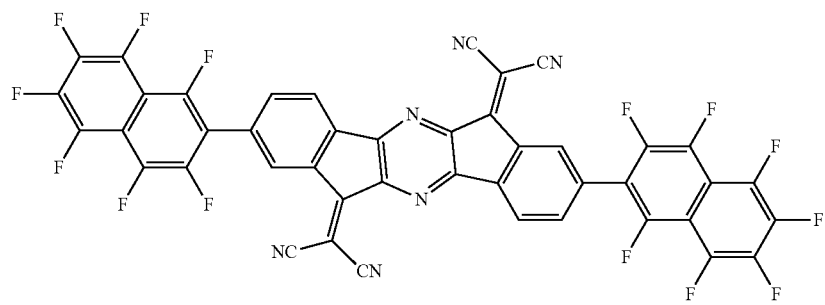
(A-51)
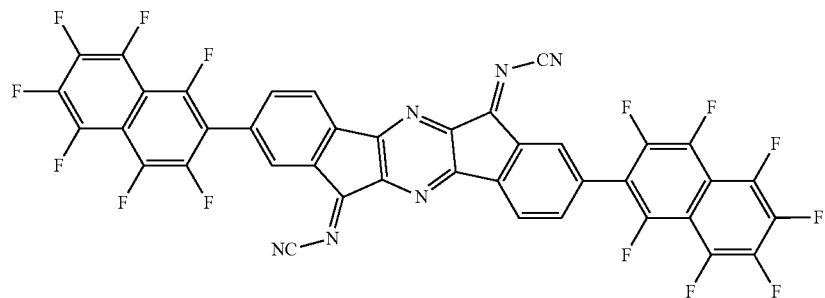
(A-52)
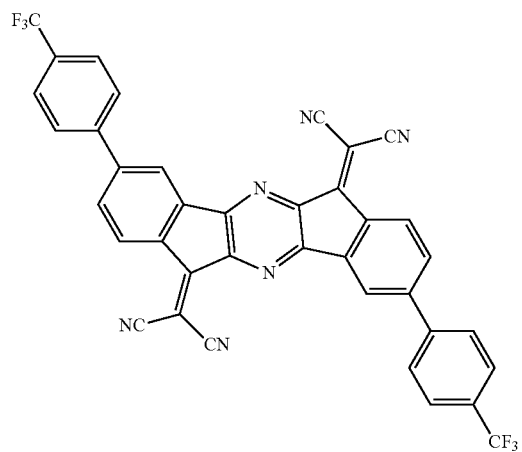
(A-53)
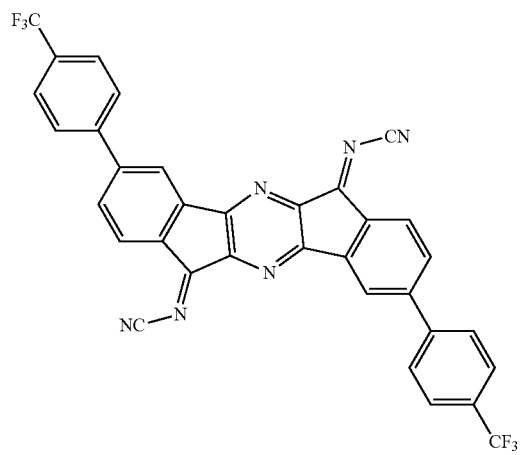
(A-54)
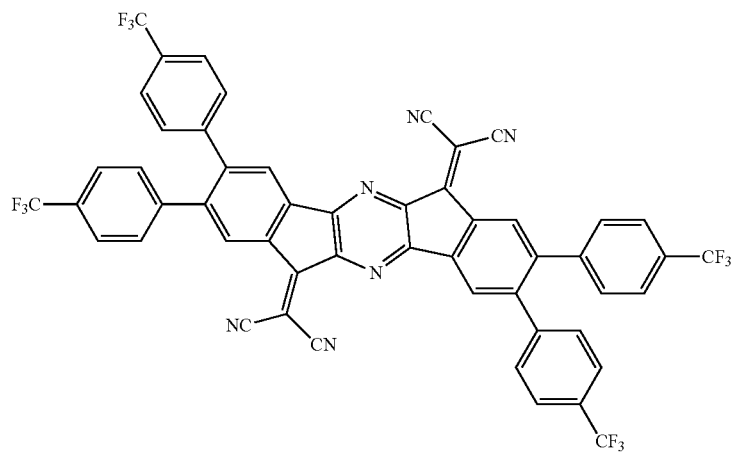
(A-55)

-continued
(A-56)
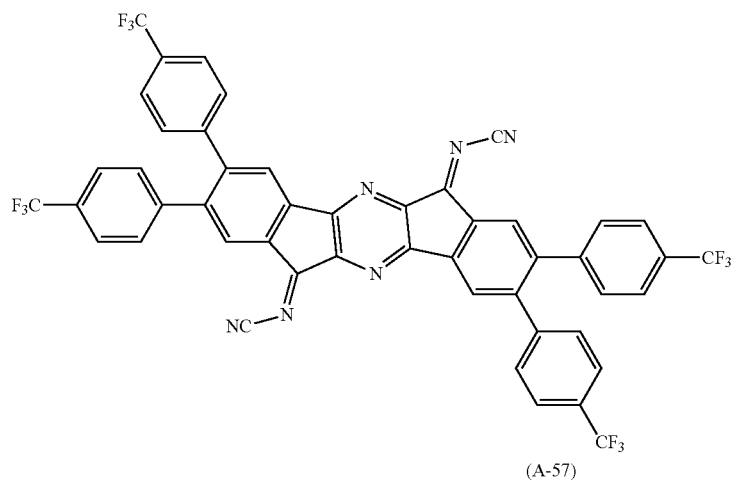
(A-57)
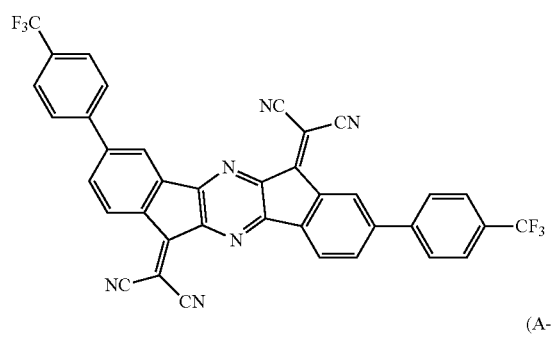
(A-58)
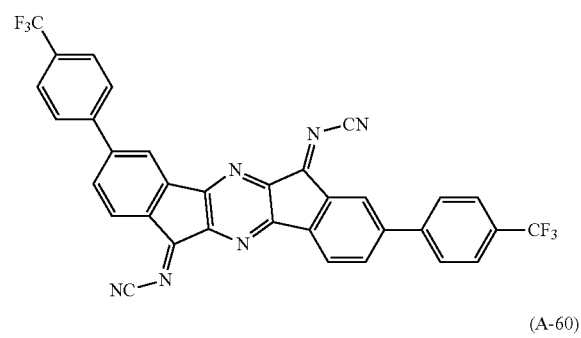
(A-59)
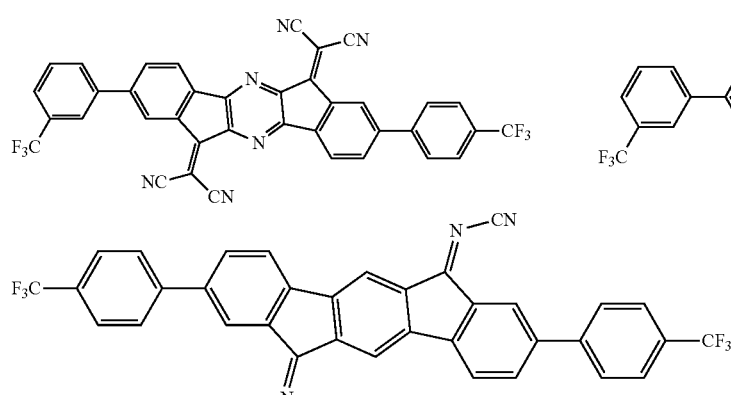
(A-60)
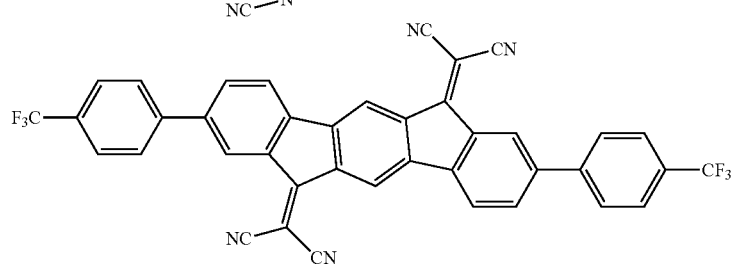
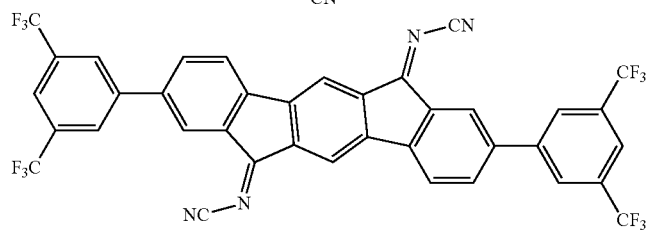

-continued
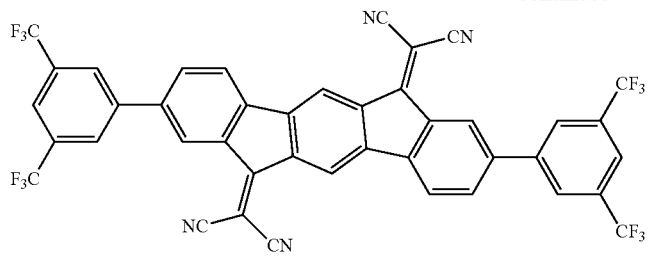
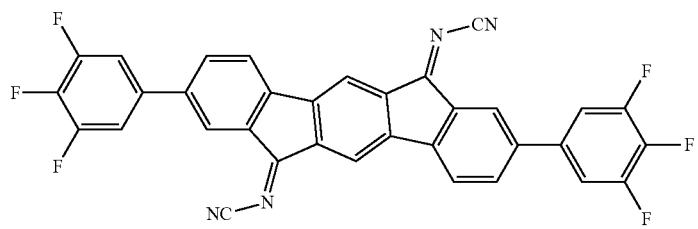
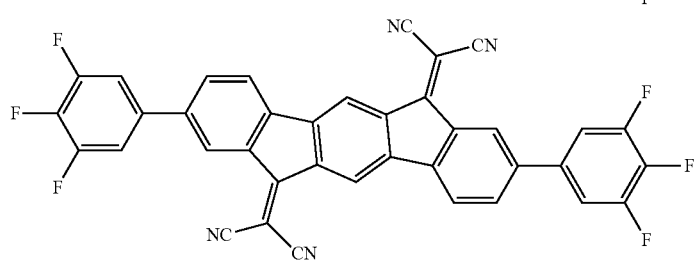
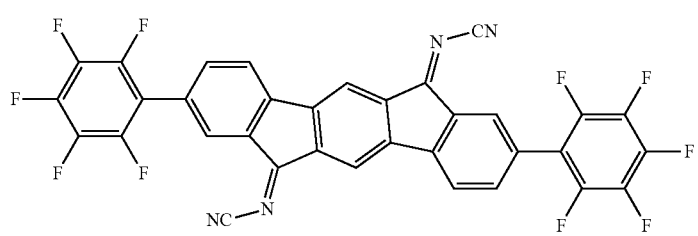
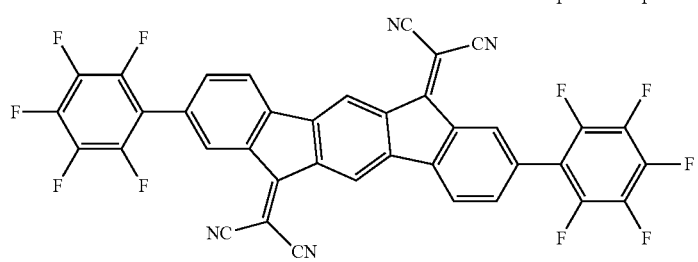
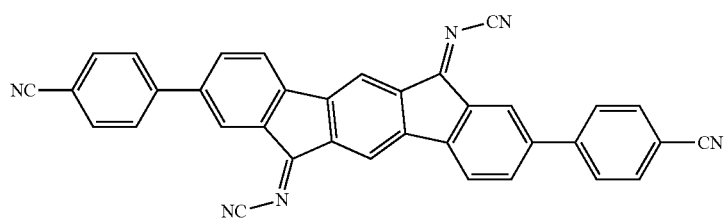
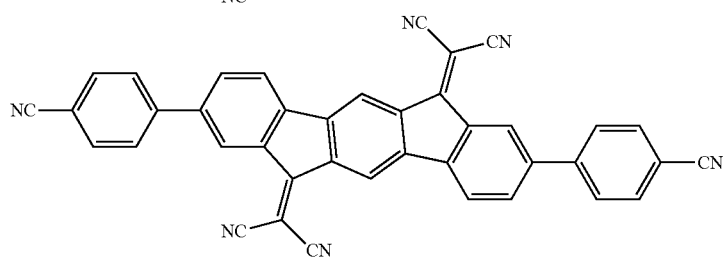

-continued
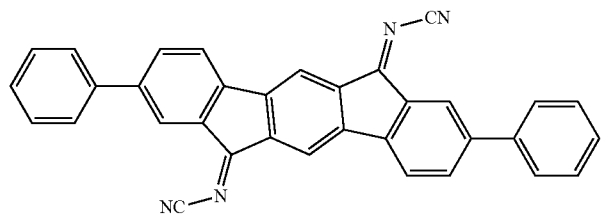
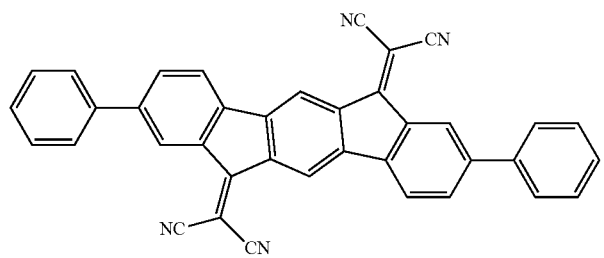
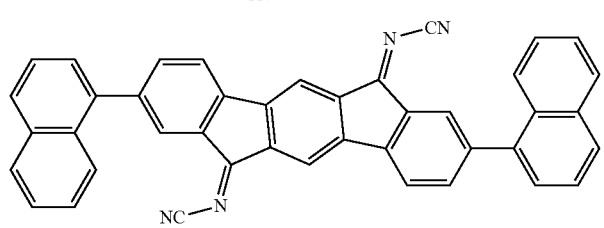
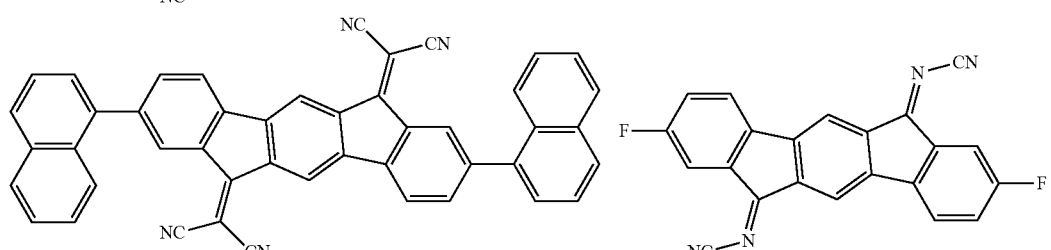
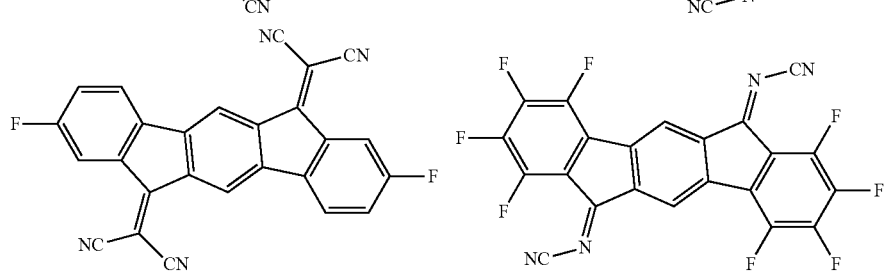
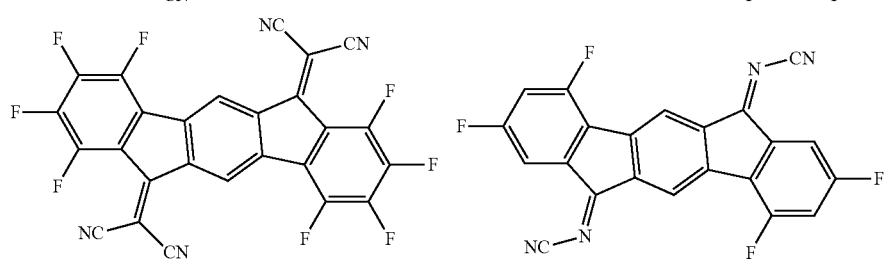
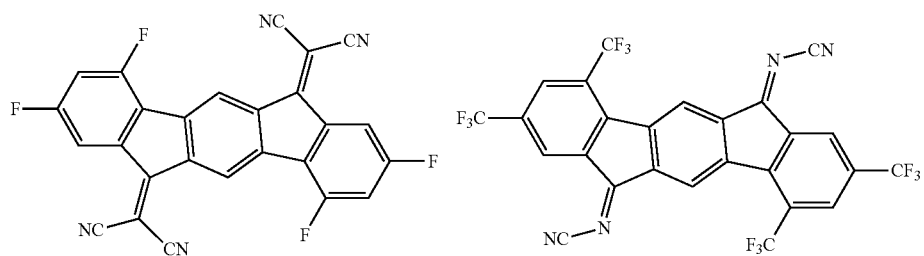

-continued
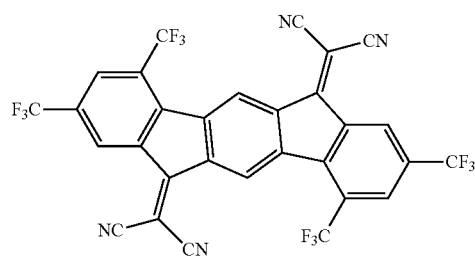
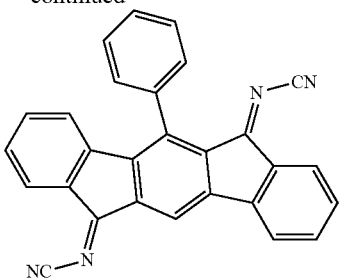
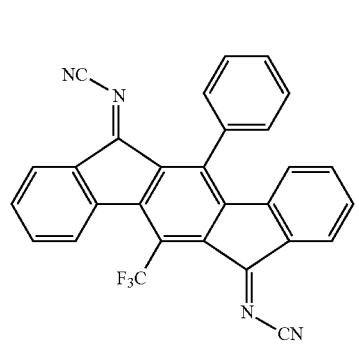
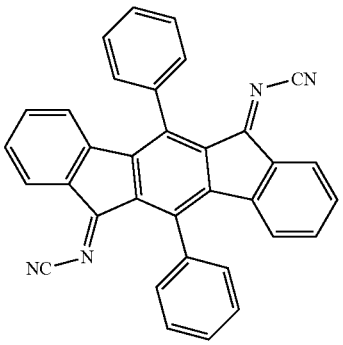
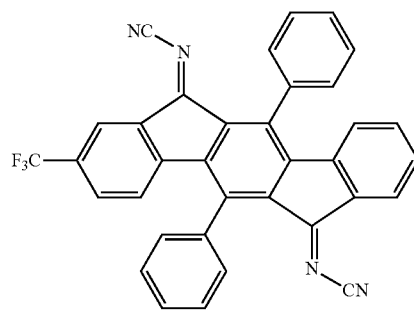
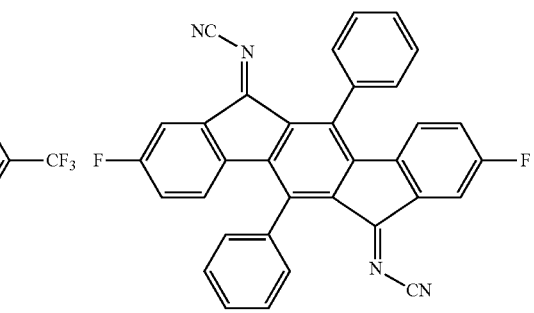
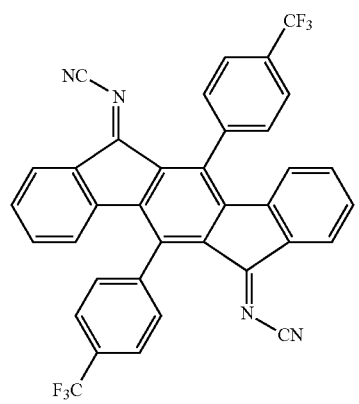
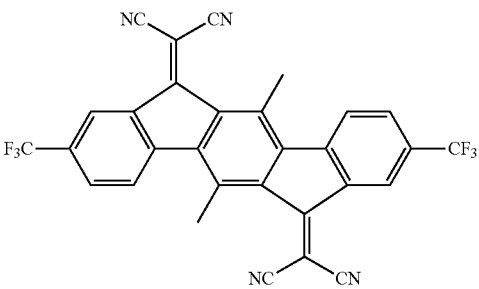
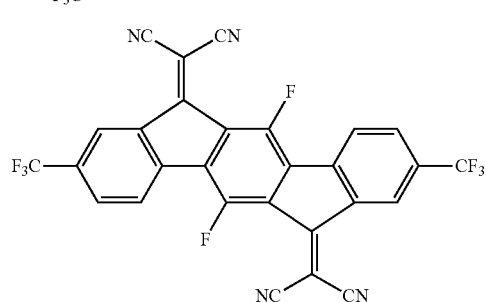
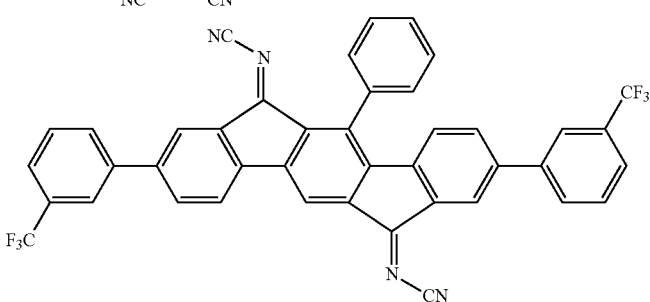

-continued
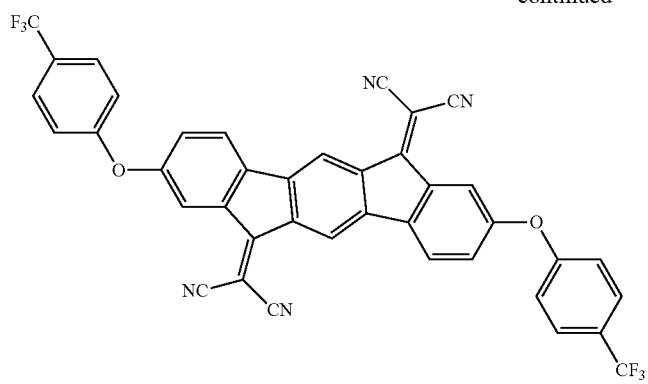
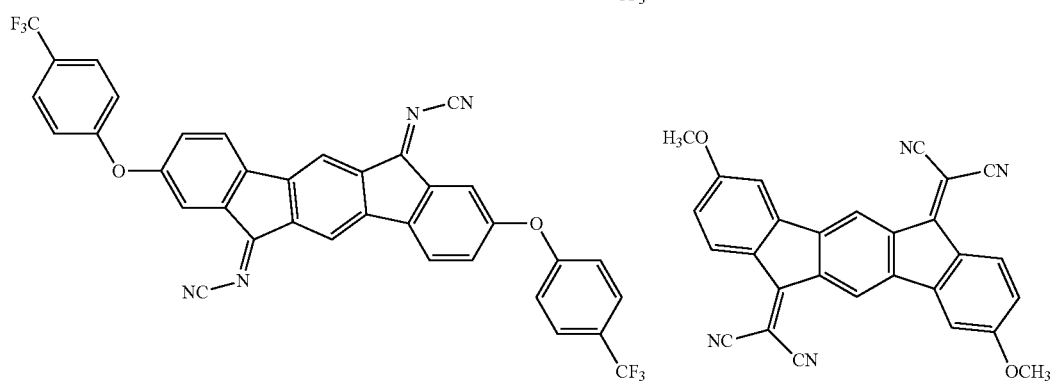
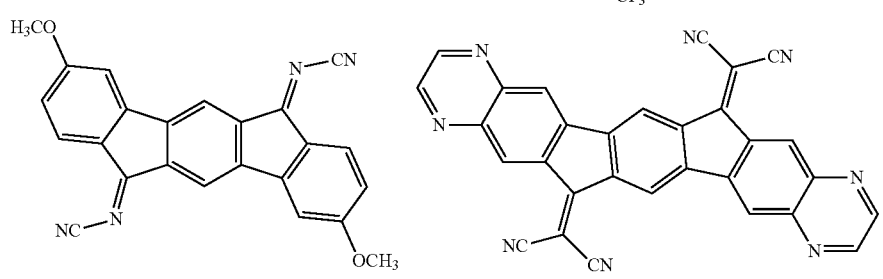
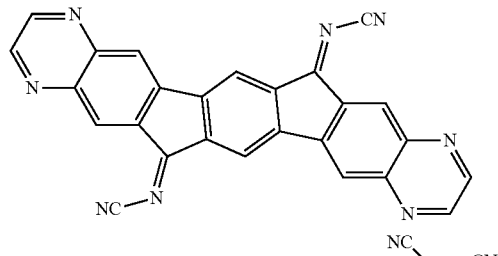
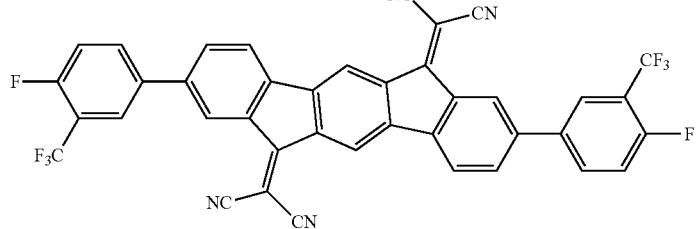
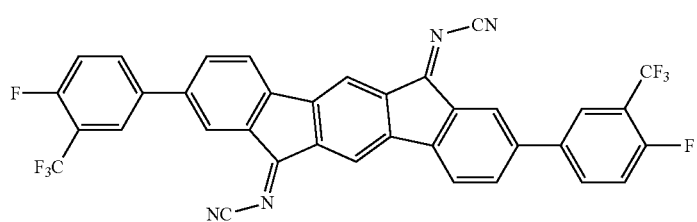

-continued
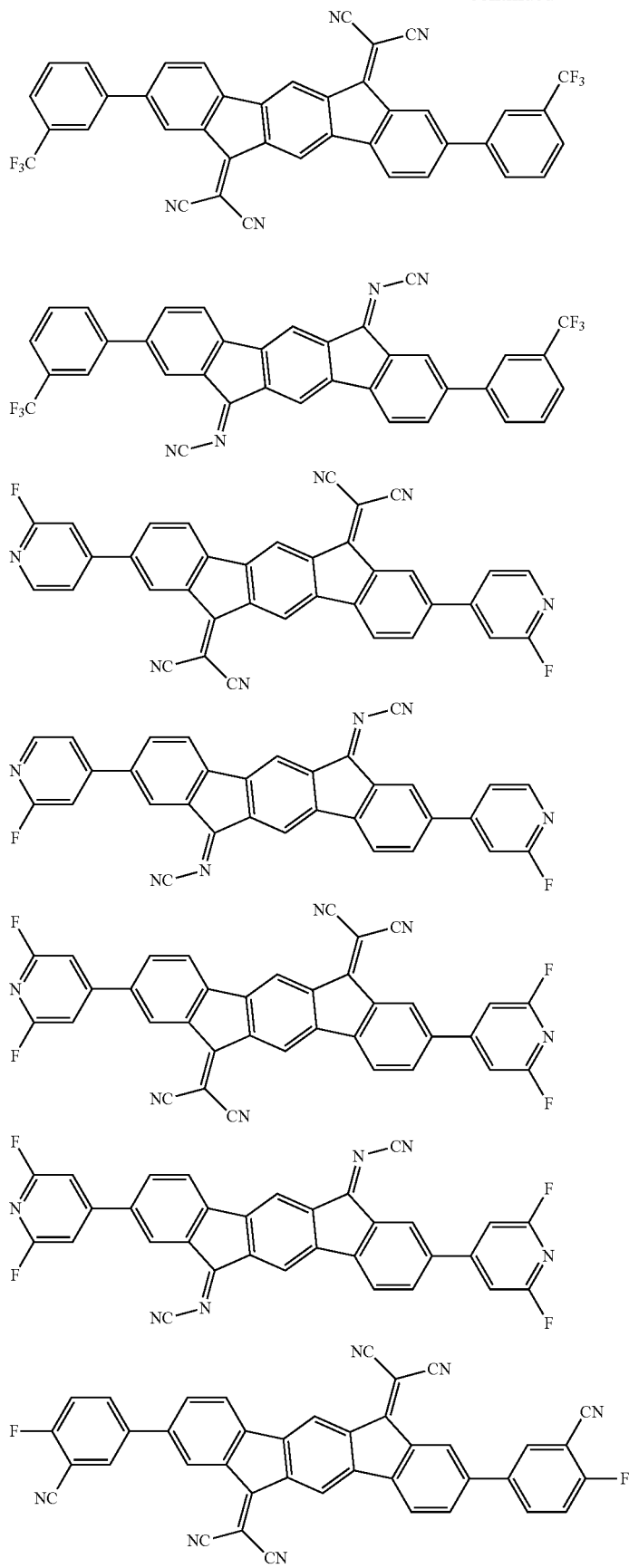

-continued
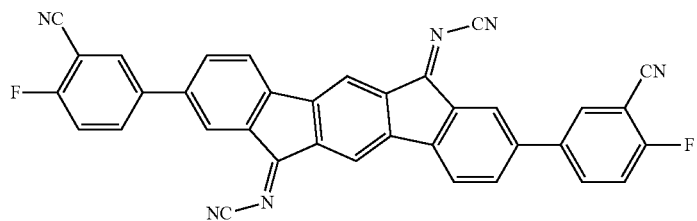
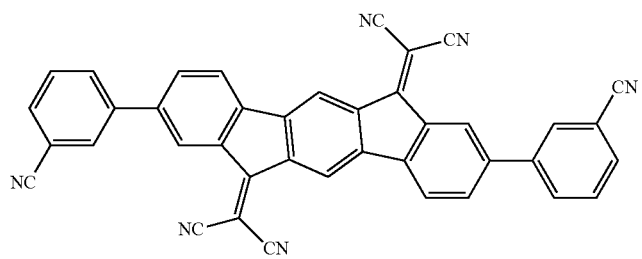
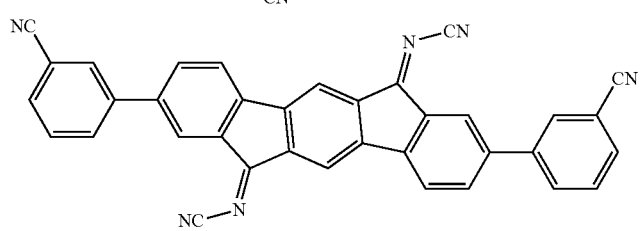
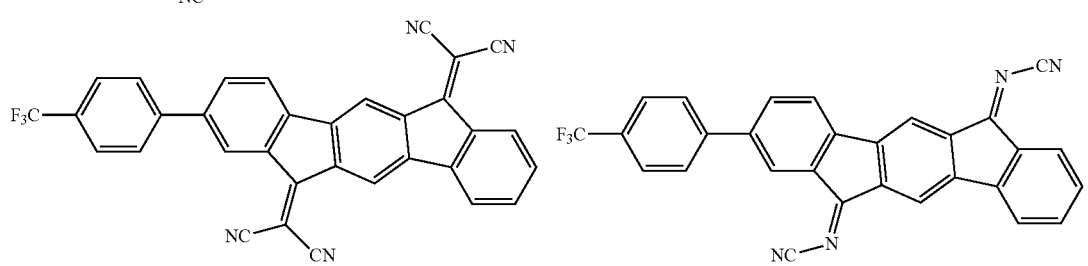
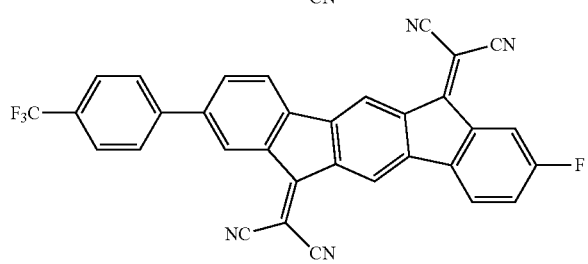
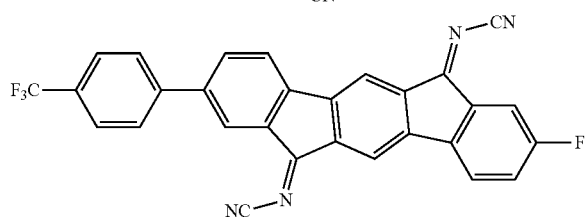
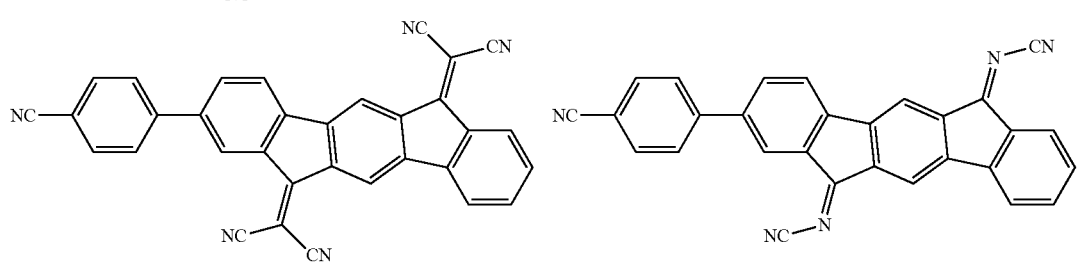

483 484
-continued
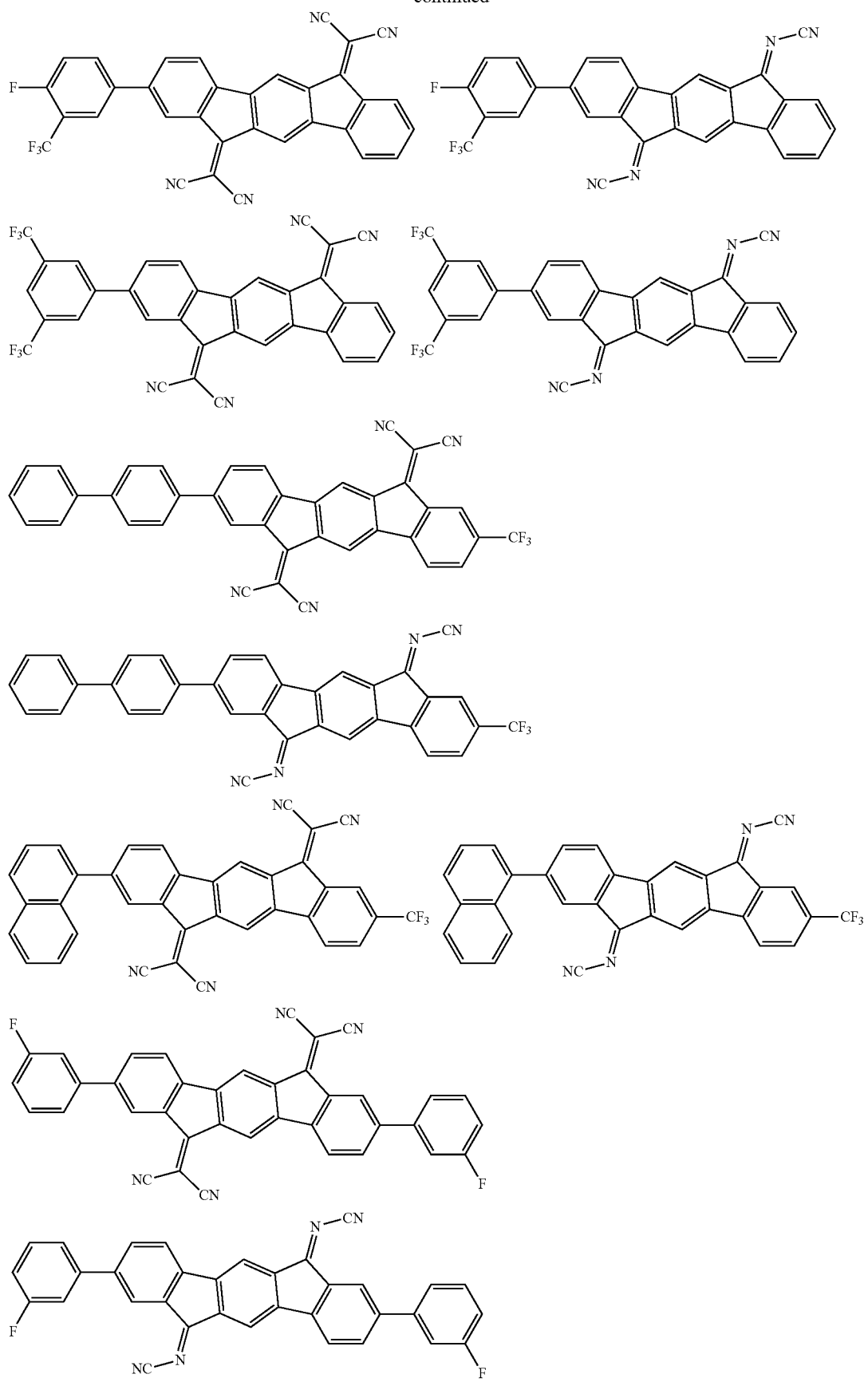

-continued
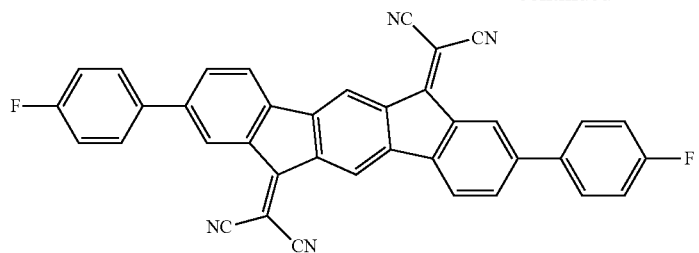
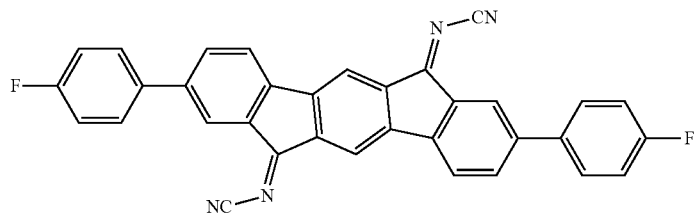
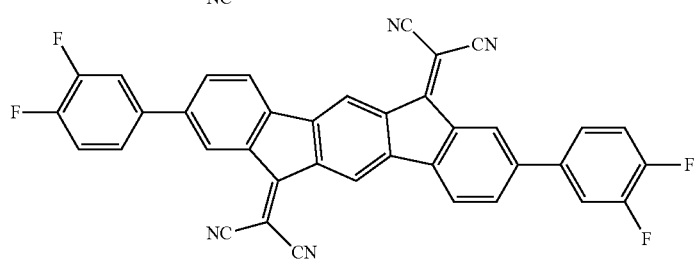
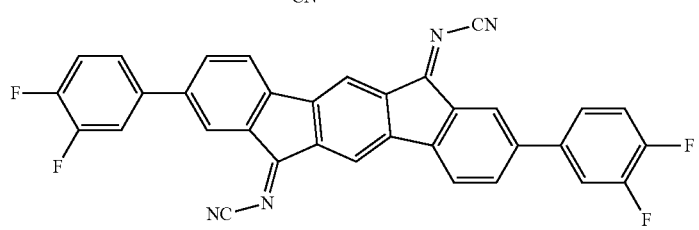
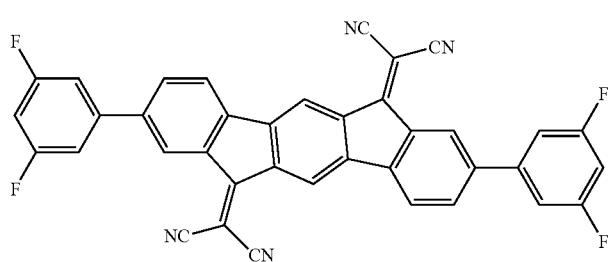
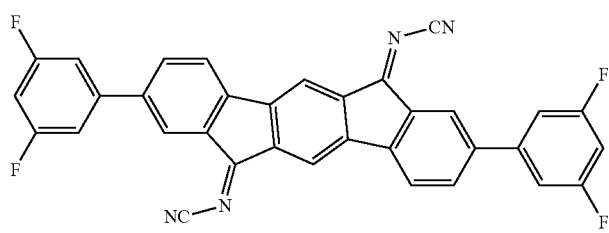
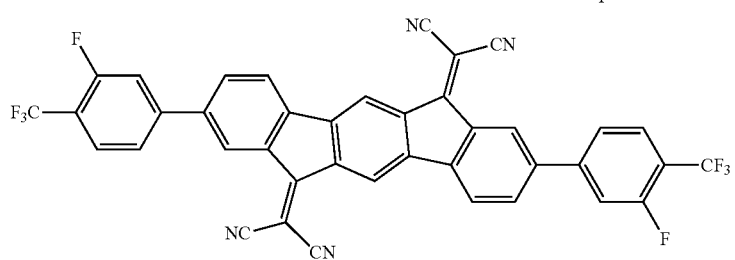

-continued
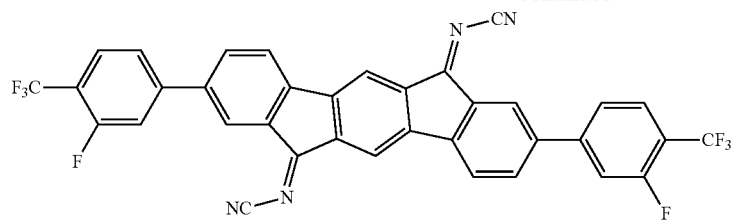
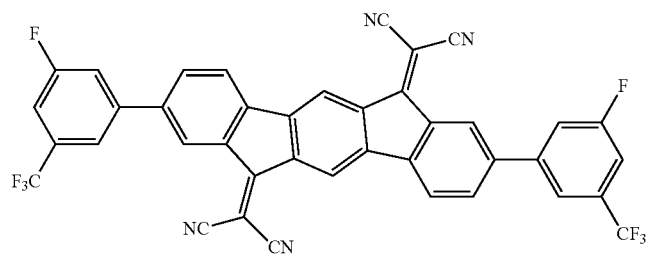
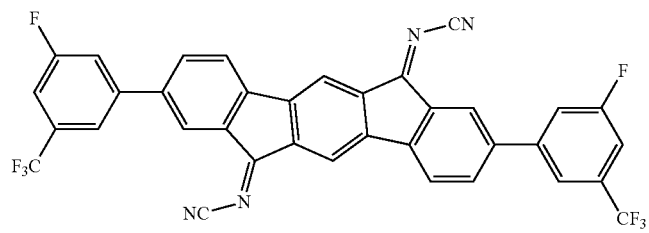
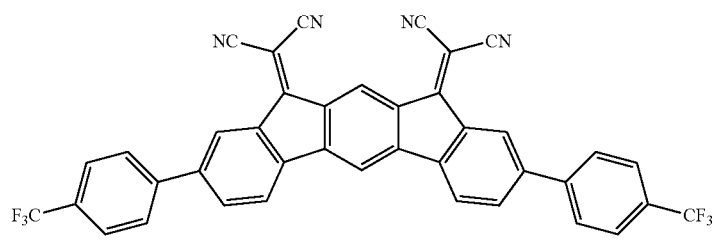
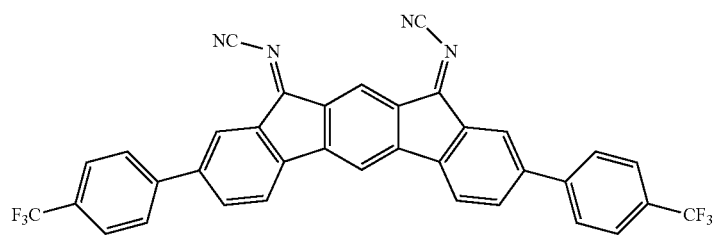
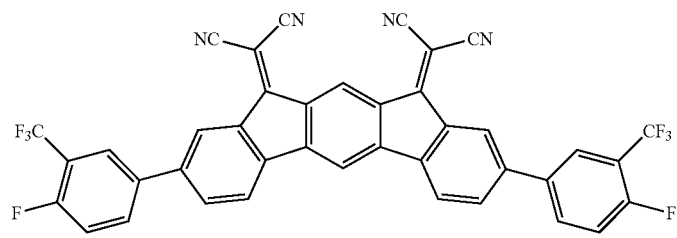
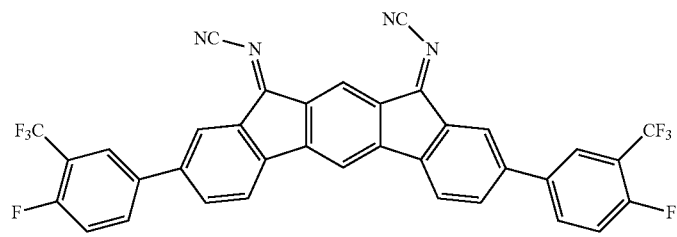

-continued
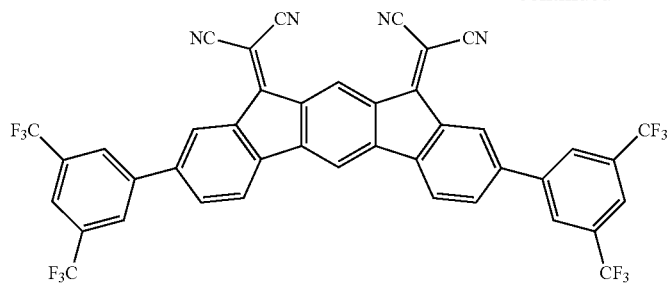
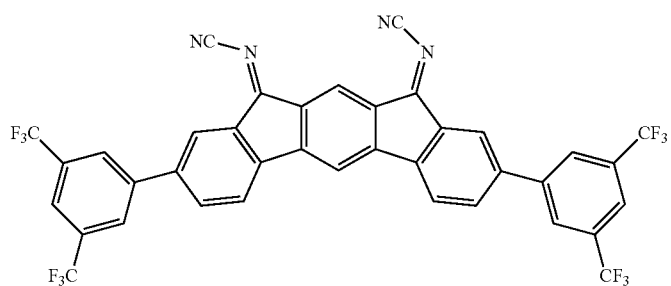
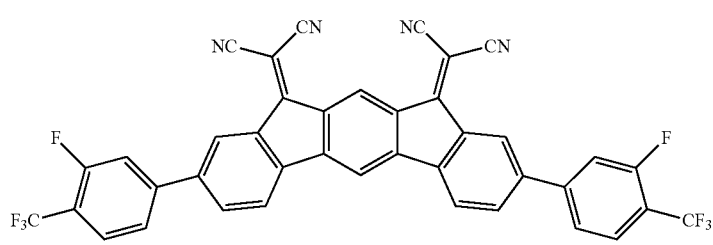
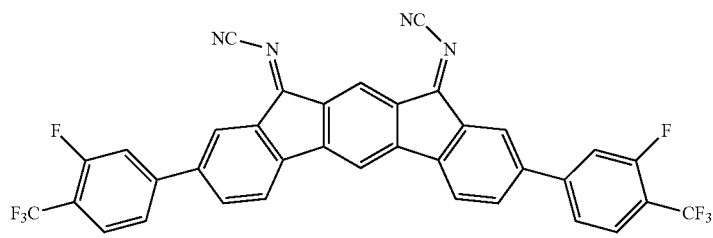
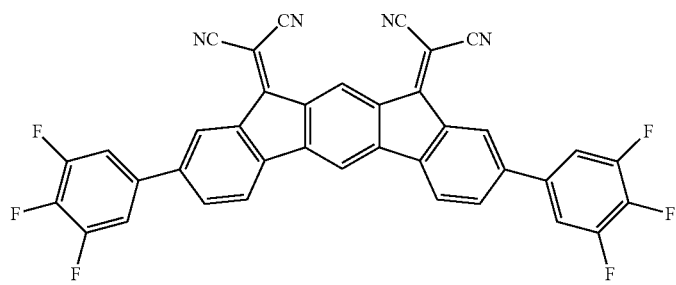
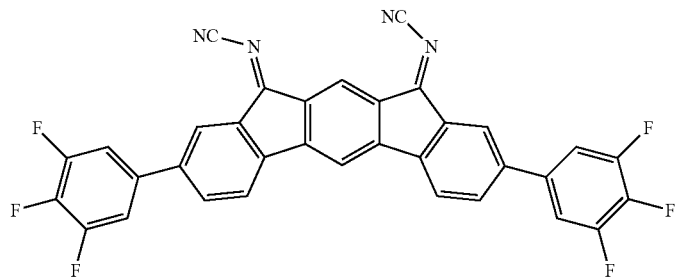

-continued
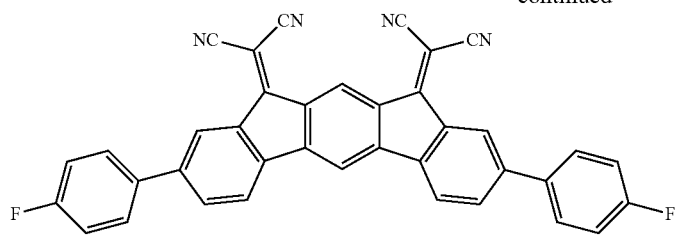
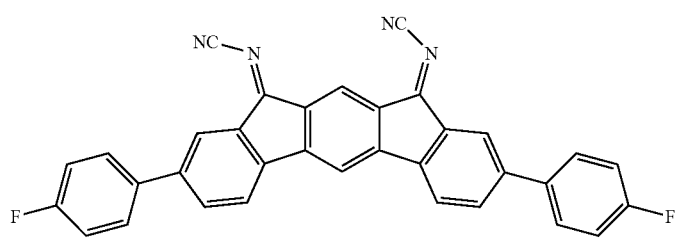
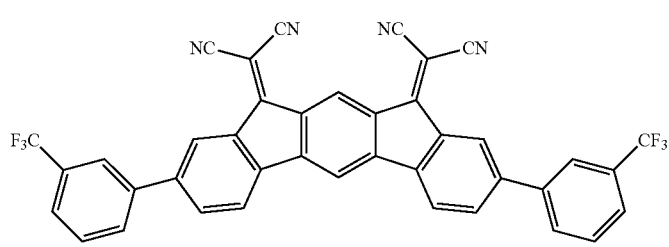
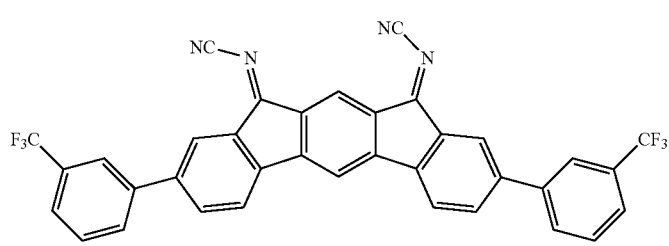
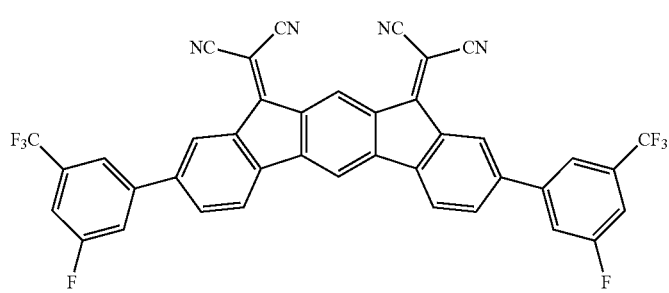
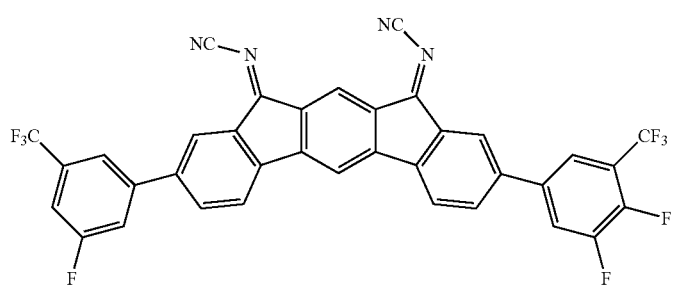

-continued
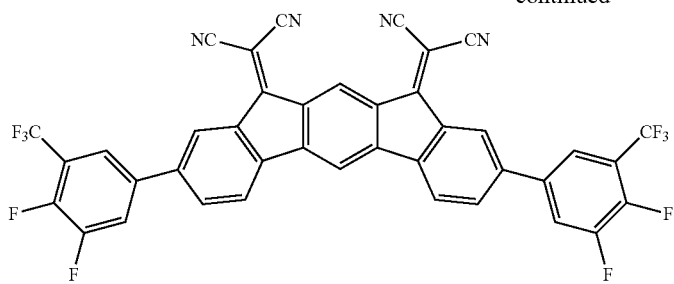
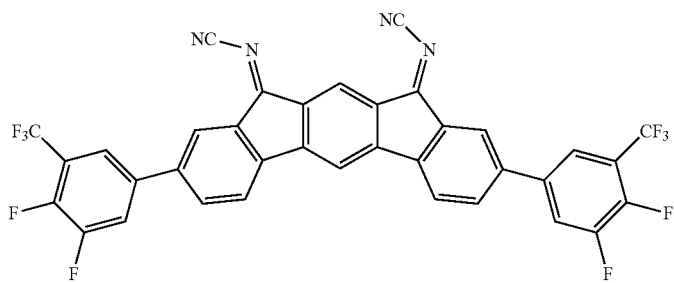
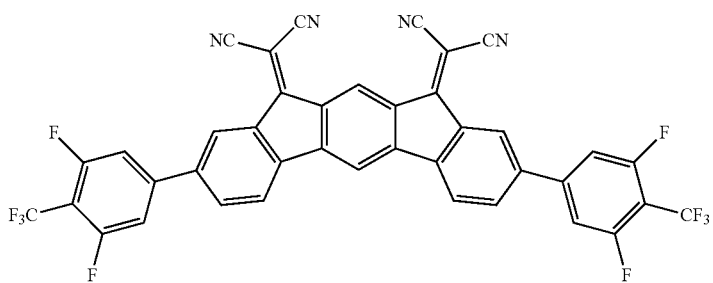
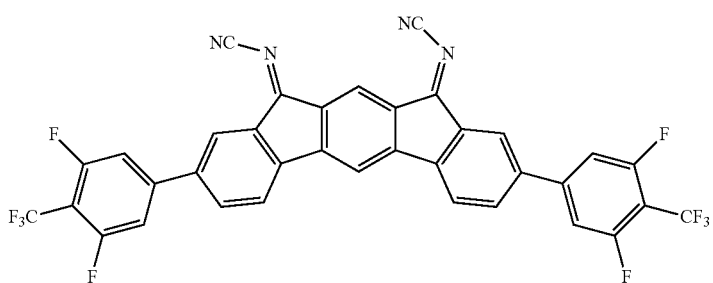
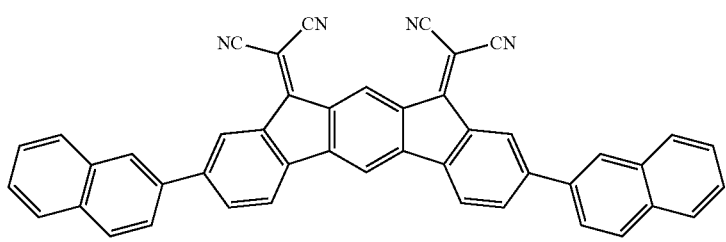
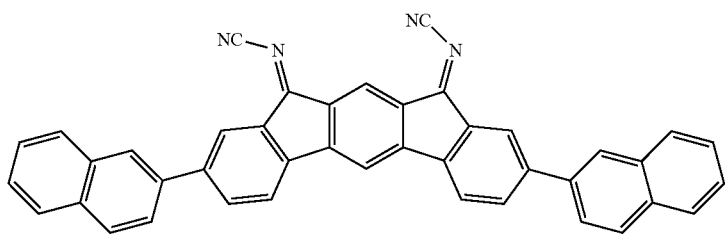

-continued
| 495 | 496 |
|---|---|
| 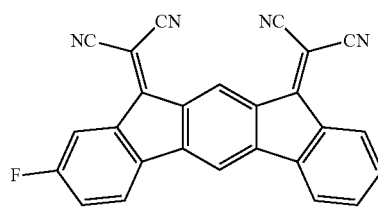 | 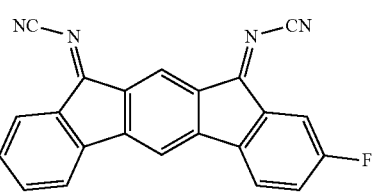 |
| 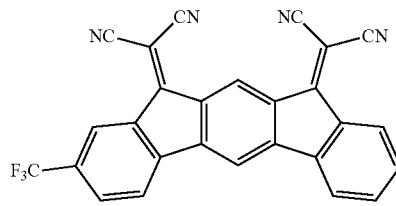 | 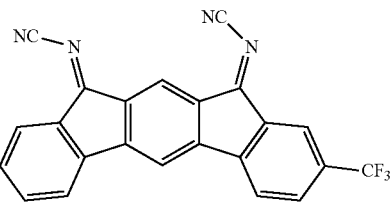 |
| 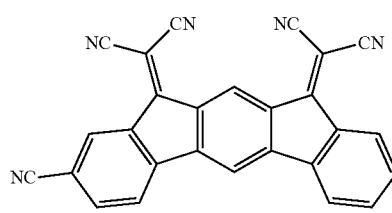 | 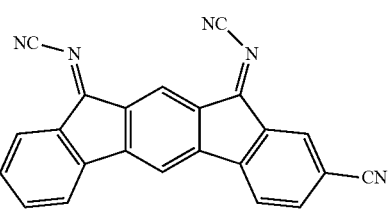 |
| 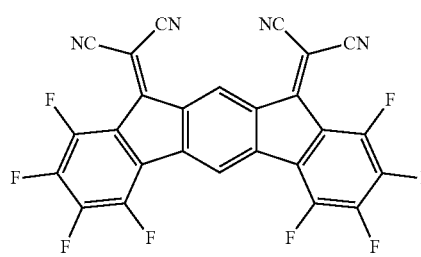 | 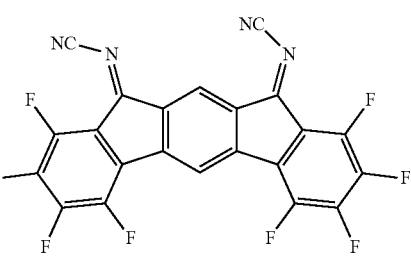 |
| 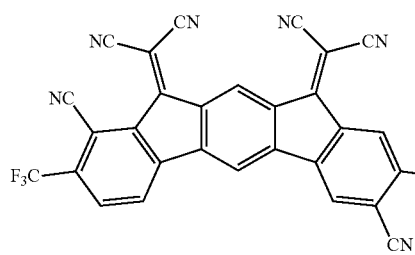 | 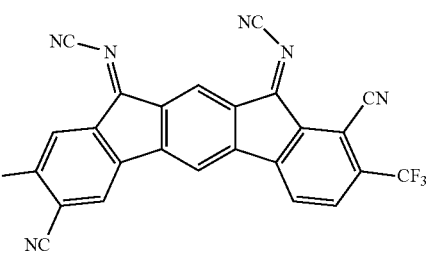 |
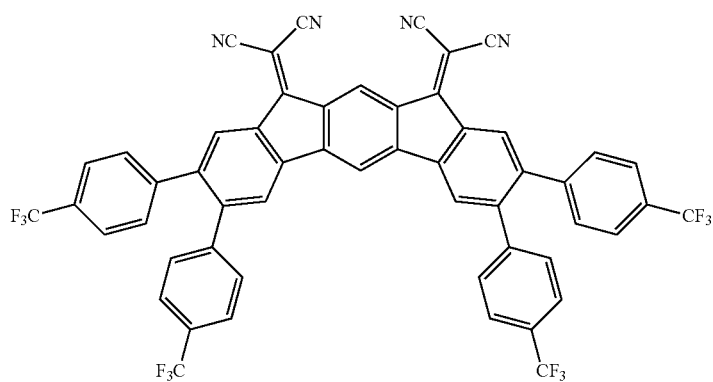

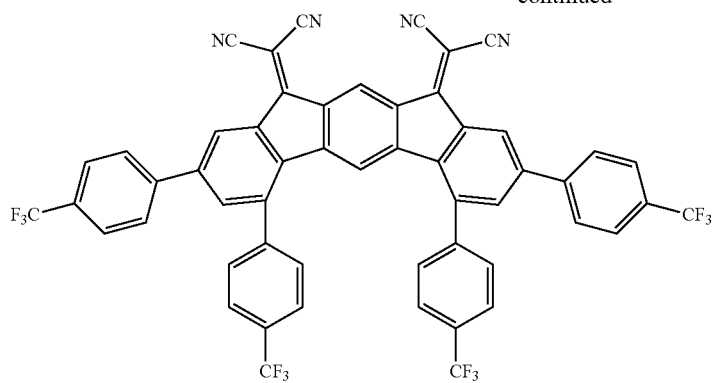
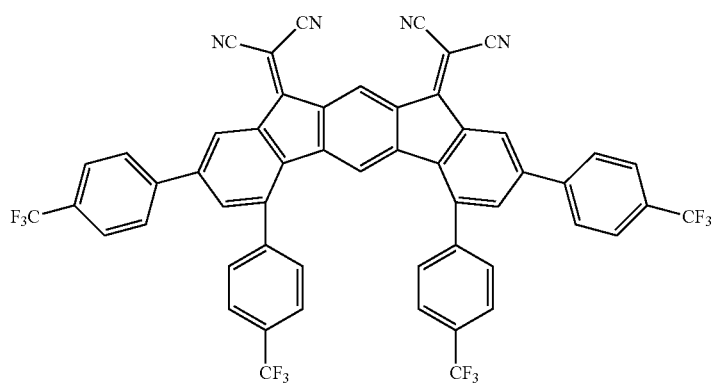
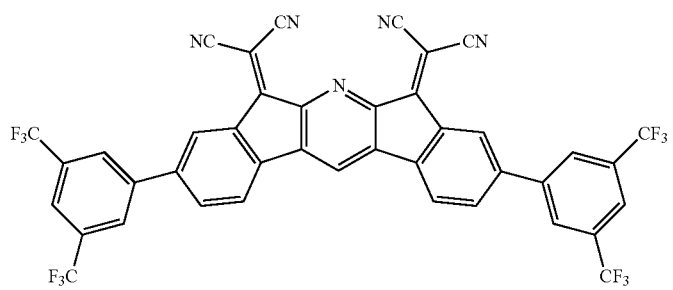
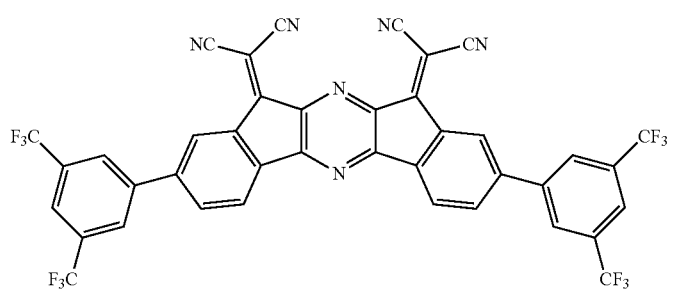
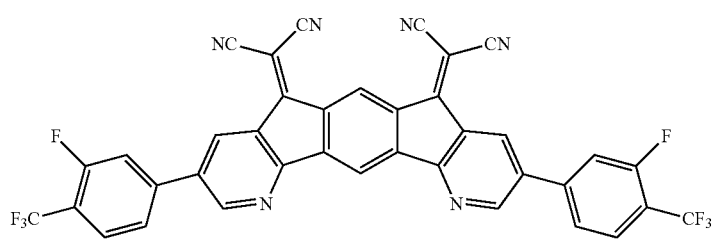

-continued
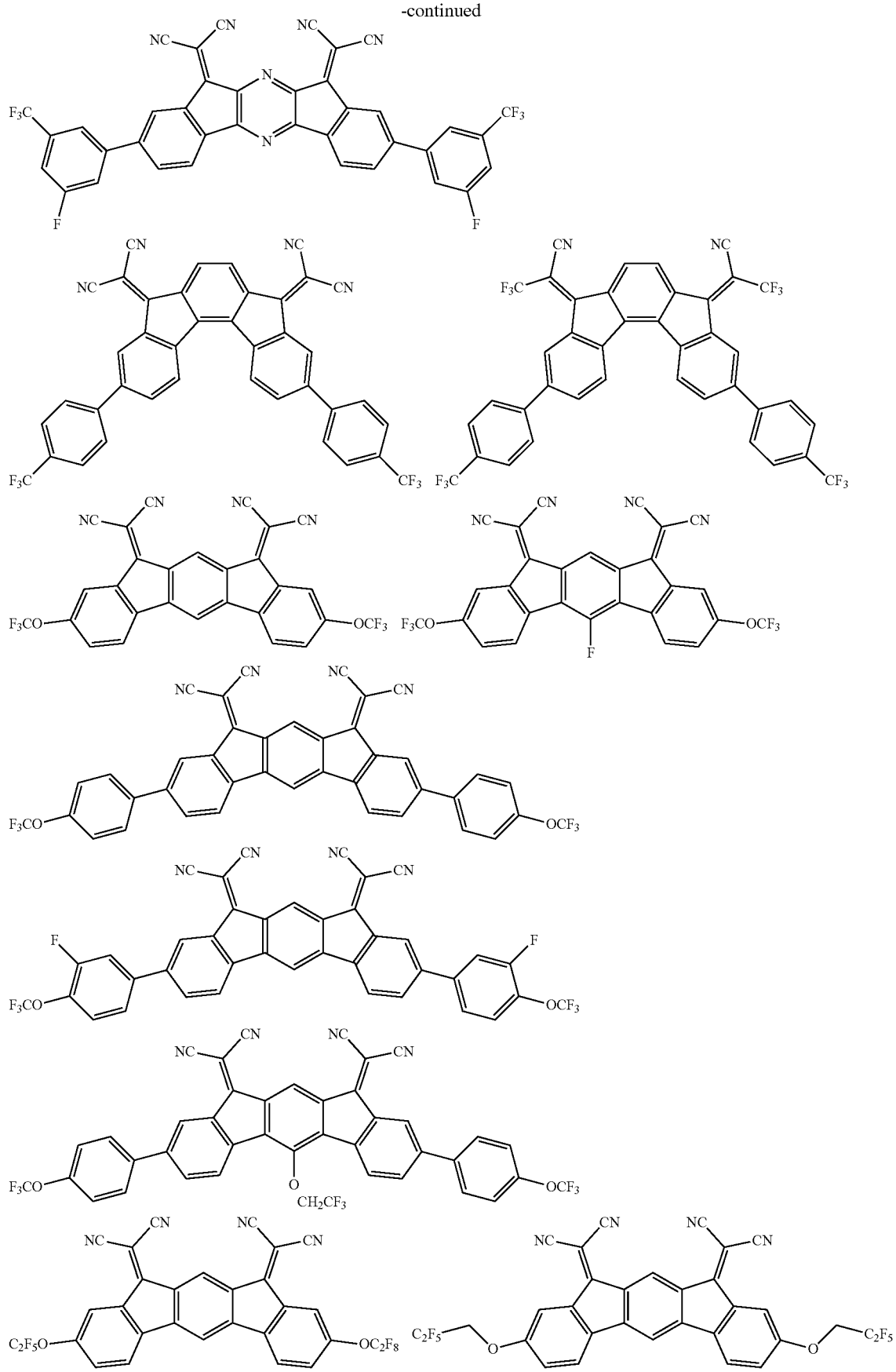

-continued
| 501 | 502 |
|---|---|
| 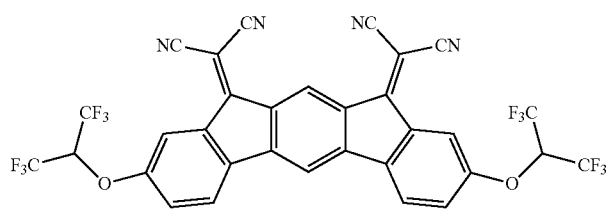 | 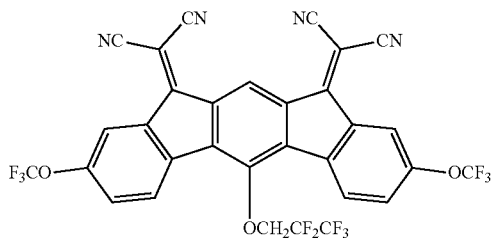 |
| 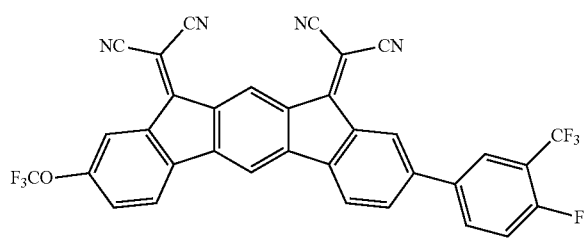 | |
| 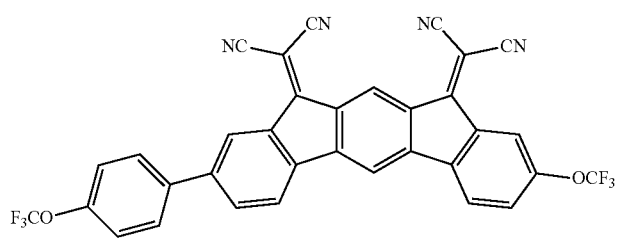 | |
| 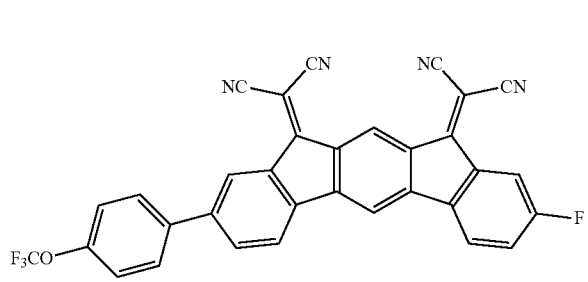 | 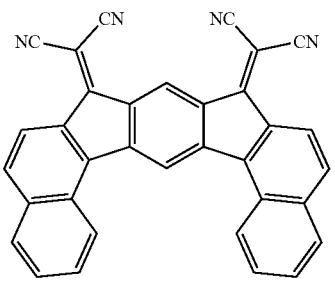 |
| 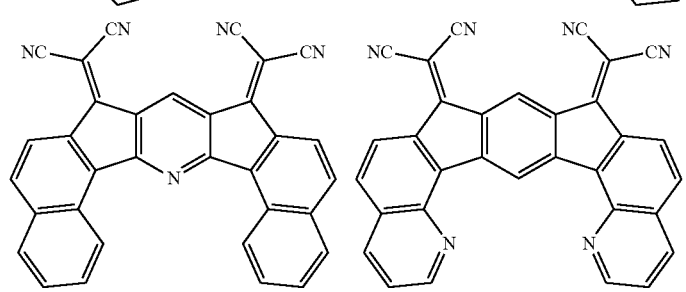 | 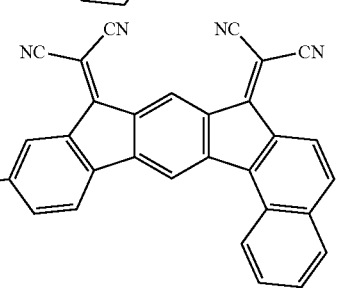 |
| 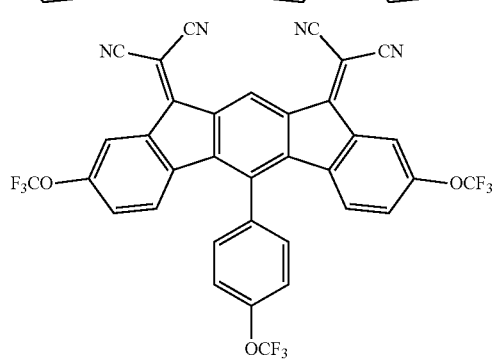 | 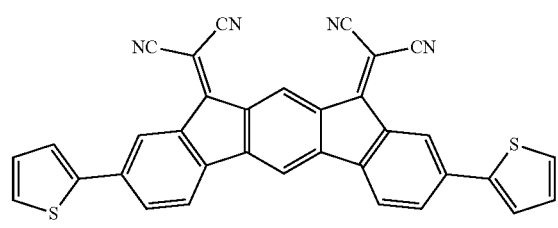 |

503 504
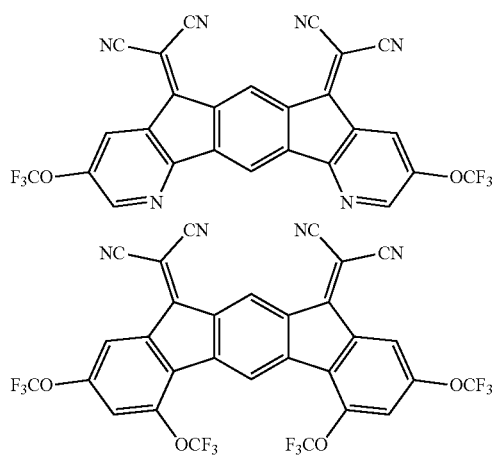
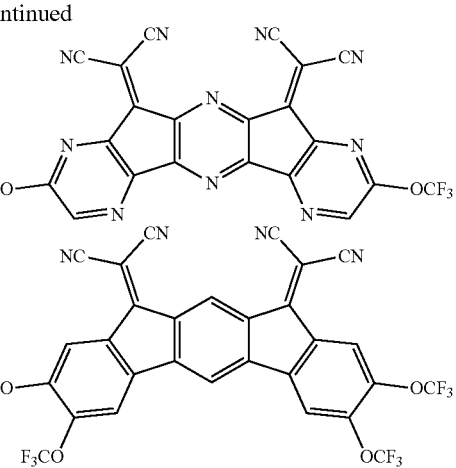
-continued
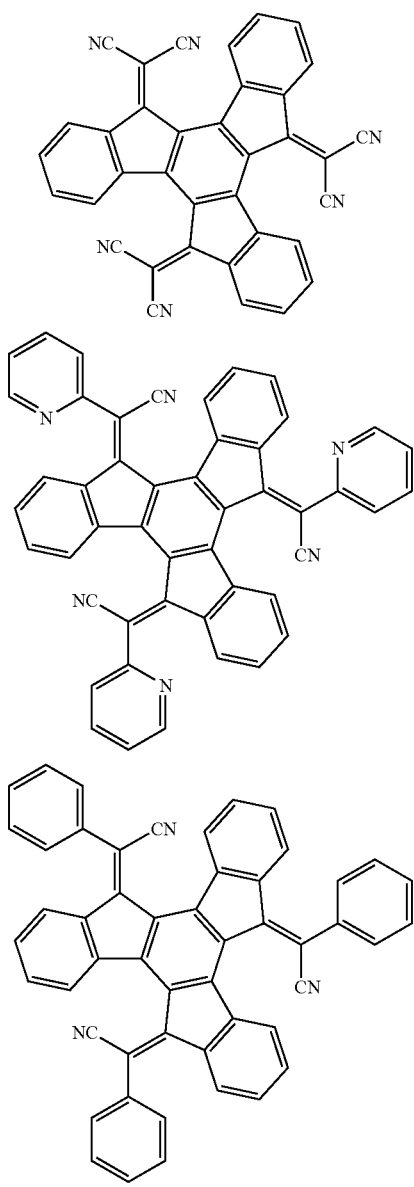
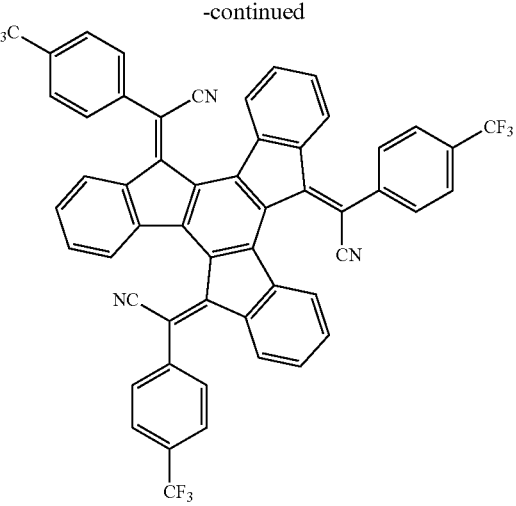
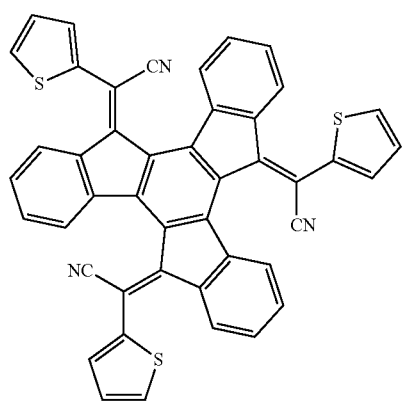

-continued

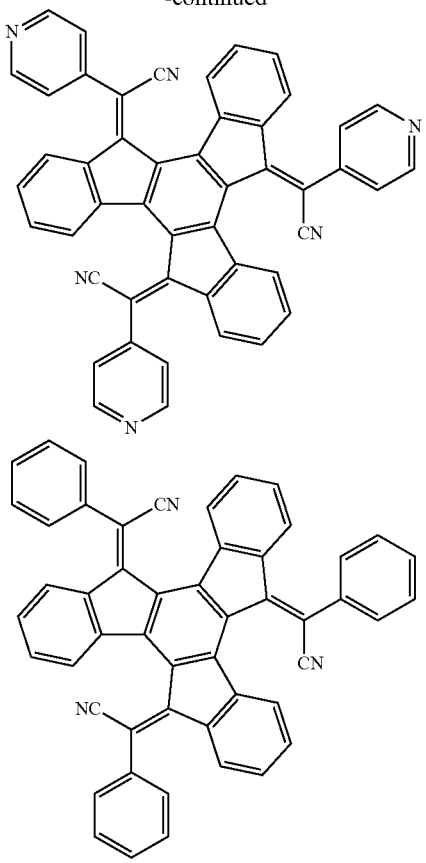

Hole Transporting Layer

The hole transporting layer comprises a highly hole transporting material (hole transporting material). Preferably, the hole transporting layer includes no light emitting material.

The compound (1) of the invention is preferably used in a hole transporting layer.

Examples of the hole transporting material other than the compound (1) of the invention include an aromatic amine compound, a carbazole derivative, and an anthracene derivative. Examples of the aromatic amine compound are 4,4'-bis[N-(1-naphthyl)-N-phenylamino]biphenyl (NPB), N,N'-bis(3-methylphenyl)-N,N'-diphenyl-[1,1'-biphenyl]-4,4'-diamine (TPD), 4-phenyl-4'-(9-phenylfluoren-9-yl)triphenylamine (BAFLP), 4,4'-bis[N-(9,9-dimethylfluoren-2-yl)-N-phenylamino]biphenyl (DFLDPBi), 4,4',4"-tris(N,N-diphenylamino)triphenylamine (TDATA), 4,4',4"-tris[N-(3-methylphenyl)-N-phenylamino]triphenylamine (MTDATA), and 4,4'-bis[N-(spiro-9,9'-bifluoren-2-yl)-N-phenylamino]biphenyl (BSPB). The above compounds have a hole mobility of $10^{-6}$ cm$^2$/Vs or more.

The hole transporting layer may comprise a carbazole derivative, such as 4,4'-di(9-carbazolyl)biphenyl (CBP), 9-[4-(9-carbazolyl)phenyl]-10-phenylanthracene (CzPA), and 9-phenyl-3-[4-(10-phenyl-9-anthryl)phenyl]-9H-carbazole (PCzPA); an anthracene derivative, such as 2-t-butyl-9,10-di(2-naphthyl)anthracene (t-BuDNA), 9,10-di(2-naphthyl)anthracene (DNA), and 9,10-diphenylanthracene (DPAnth); and a macro molecular compound, such as poly(N-vinylcarbazole) (PVK) and poly(4-vinyltriphenylamine) (PVTPA).

A compound other than those mentioned above is also usable if its hole transporting ability is higher than its electron transporting ability. The hole transporting layer may be a single layer or a laminate of two or more layers. For example, the hole transporting layer may be a two-layered structure of a first hole transporting layer (anode side) and a second hole transporting layer (cathode side). In this case, the compound (1) may be used in any of the first hole transporting layer and the second hole transporting layer. Thus, in an embodiment of the invention, the compound (1) is used in the first hole transporting layer; in another embodiment of the invention, the compound (1) is used in the second hole transporting layer; and in still another embodiment of the invention, the compound (1) is used in both the first hole transporting layer and the second hole transporting layer, wherein the compound (1) used in the first hole transporting layer and the compound (1) used in the second hole transporting layer are different from each other in their structures. In addition to the compound (1), the first hole transporting layer may further include a compound other than the compound (1), for example, the compound described above. In addition to the compound (1), the second hole transporting layer may further include a compound other than the compound (1), for example, the compound described above.

Dopant Material of Light Emitting Layer

The light emitting layer comprises a highly light-emitting material (dopant material) and may be formed from a various kind of materials. For example, a fluorescent emitting material and a phosphorescent emitting material are usable as the dopant material. The fluorescent emitting material is a compound which emits light from a singlet excited state, and the phosphorescent emitting material is a compound which emits light from a triplet excited state.

Examples of blue fluorescent emitting material for use in the light emitting layer include a pyrene derivative, a styrylamine derivative, a chrysene derivative, a fluoranthene derivative, a fluorene derivative, a diamine derivative, and a triarylamine derivative, such as N,N'-bis[4-(9H-carbazole-9-yl)phenyl]-N,N'-diphenylstilbene-4,4'-diamine (YGA2S), 4-(9H-carbazole-9-yl)-4'-(10-phenyl-9-anthryl)triphenylamine (YGAPA), and 4-(10-phenyl-9-anthryl)-4'-(9-phenyl-9H-carbazole-3-yl)triphenylamine (PCBAPA).

Examples of green fluorescent emitting material for use in the light emitting layer include an aromatic amine derivative, such as N-(9,10-diphenyl-2-anthryl)-N,9-diphenyl-9H-carbazole-3-amine (2PCAPA), N-[9,10-bis(1,1'-biphenyl-2-yl)-2-anthryl]-N,9-diphenyl-9H-carbazole-3-amine (2PCABPhA), N-(9,10-diphenyl-2-anthryl)-N,N',N'-triphenyl-1,4-phenylenediamine (2DPAPA), N-[9,10-bis(1,1'-biphenyl-2-yl)-2-anthryl]-N,N',N'-triphenyl-1,4-phenylenediamine (2-DPABPhA), N-[9,10-bis(1,1'-biphenyl-2-yl)]-N-[4-(9H-carbazole-9-yl)phenyl]-N-phenylanthracene-2-amine (2YGABPhA), and N,N,9-triphenylanthracene-9-amine (DPhAPhA).

Examples of red fluorescent emitting material for use in the light emitting layer include a tetracene derivative and a diamine derivative, such as N,N,N',N'-tetrakis(4-methylphenyl)tetracene-5,11-diamine (p-mPhTD) and 7,14-diphenyl-N,N,N',N'-tetrakis(4-methylphenyl)acenaphtho[1,2-a]fluoranthene-3,10-diamine (p-mPhAFD).

Examples of blue phosphorescent emitting material for use in the light emitting layer include a metal complex, such as an iridium complex, an osmium complex, and a platinum complex. Examples thereof include bis[2-(4',6'-difluorophenyl)pyridinato-N,C2']iridium(III) tetrakis(1-pyrazolyl)borato (FIr$_6$), bis[2-(4',6'-difluorophenyl)pyridinato-N,C2']

iridium(III) picolinato (FIrpic), bis[2-(3',5'-bistrifluoromethylphenyl)pyridinato-N,C2']iridium(III) picolinato (Ir(CF₃ppy)₂(pic)), and bis[2-(4',6'-difluorophenyl)pyridinato-N,C2']iridium(II) acetylacetonato (FIracac).

Examples of green phosphorescent emitting material for use in the light emitting layer include an iridium complex, such as tris(2-phenylpyridinato-N,C2')iridium(III) (Ir(ppy)₃), bis(2-phenylpyridinato-N,C2')iridium(III) acetylacetonato (Ir(ppy)₂(acac)), bis(1,2-diphenyl-1H-benzimidazolato)iridium(III) acetylacetonato (Ir(pbi)₂(acac)), and bis(benzo[h]quinolinato)iridium(III) acetylacetonato (Ir(bzq)₂(acac)).

Examples of red phosphorescent emitting material for use in the light emitting layer include a metal complex, such as an iridium complex, a platinum complex, a terbium complex, and a europium complex. Examples thereof include an organometallic complex, such as bis[2-(2'-benzo[4,5-α]thienyl)pyridinato-N,C3']iridium(III) acetylacetonato (Ir(btp)₂(acac)), bis(1-phenylisoquinolinato-N,C2')iridium(III) acetylacetonato (Ir(piq)₂(acac)), (acetylacetonato)bis[2,3-bis(4-fluorophenyl)quinoxalinato]iridium(III) (Ir(Fdpq)₂(acac)), and 2,3,7,8,12,13,17,18-octaethyl-21H,23H-porphyrin platinum(II) (PtOEP).

Examples of red phosphorescent emitting material for use in the light emitting layer include a metal complex, such as an iridium complex, a platinum complex, a terbium complex, and a europium complex. Examples thereof include an organometallic complex, such as bis[2-(2'-benzo[4,5-α]thienyl)pyridinato-N,C3']iridium(III) acetylacetonato (Ir(btp)₂(acac)), bis(1-phenylisoquinolinato-N,C2')iridium(III) acetylacetonato (Ir(piq)₂(acac)), (acetylacetonato)bis[2,3-bis(4-fluorophenyl)quinoxalinato]iridium(III) (Ir(Fdpq)₂(acac)), and 2,3,7,8,12,13,17,18-octaethyl-21H,23H-porphyrin platinum(II) (PtOEP).

A rare earth metal complex, such as tris(acetylacetonato)(monophenanthroline)terbium(III) (Tb(acac)₃(Phen)), tris(1,3-diphenyl-1,3-propanedionato)(monophenanthroline)europium(III) (Eu(DBM)₃(Phen)), and tris[1-(2-thenoyl)-3,3,3-trifluoroacetonato](monophenanthroline)europium(III) (Eu(TTA)₃(Phen)), emits light from the rare earth metal ion (electron transition between different multiple states), and therefore, usable as a phosphorescent emitting compound.

Host Material for Light Emitting Layer

The light emitting layer may be formed by dispersing the dopant material mentioned above in another material (host material). The host material may be the compound (1) of the invention or a compound other than the compound (1). The host material preferably has a lowest unoccupied molecular orbital level (LUMO level) higher than that of the dopant material and a highest occupied molecular orbital level (HOMO level) lower than that of the dopant material.

The host material other than the compound (1) may include, for example,
(1) a metal complex, such as an aluminum complex, a beryllium complex, and a zinc complex;
(2) a heterocyclic compound, such as an oxadiazole derivative, a benzimidazole derivative, and a phenanthroline derivative;
(3) a fused aromatic compound, such as a carbazole derivative, an anthracene derivative, a phenanthrene derivative, a pyrene derivative, and a chrysene derivative; and
(4) an aromatic amine compound, such as a triarylamine derivative and a fused aromatic polycyclic amine derivative.

Examples thereof include:
a metal complex, such as tris(8-quinolinolato)aluminum (III) (Alq), tris(4-methyl-8-quinolinolato)aluminum(III) (Almq₃), bis(10-hydroxybenzo[h]quinolinato)beryllium(II) (BeBq₂), bis(2-methyl-8-quinolinolato)(4-phenylphenolato)aluminum(III) (BAlq), bis(8-quinolinolato)zinc(II) (Znq), bis[2-(2-benzoxazolyl)phenolato]zinc(I) (ZnPBO), and bis[2-(2-benzothiazolyl)phenolato]zinc(II) (ZnBTZ);

a heterocyclic compound, such as 2-(4-biphenylyl)-5-(4-tert-butylphenyl)-1,3,4-oxadiazole (PBD), 1,3-bis[5-(p-tert-butylphenyl)-1,3,4-oxadiazole-2-yl]benzene (OXD-7), 3-(4-biphenylyl)-4-phenyl-5-(4-tert-butylphenyl)-1,2,4-triazole (TAZ), 2,2',2"-(1,3,5-benzenetriyl)tris(1-phenyl-1H-benzimidazole) (TPBI), bathophenanthroline (BPhen), and bathocuproin (BCP);

a fused aromatic compound, such as 9-[4-(10-phenyl-9-anthryl)phenyl]-9H-carbazole (CzPA), 3,6-diphenyl-9-[4-(10-phenyl-9-anthryl)phenyl]-9H-carbazole (DPCzPA), 9,10-bis(3,5-diphenylphenyl)anthracene (DPPA), 9,10-di(2-naphthyl)anthracene (DNA), 2-tert-butyl-9,10-di(2-naphthyl)anthracene (t-BuDNA), 9,9'-bianthryl (BANT), 9,9'-(stilbene-3,3'-diyl)diphenanthrene (DPNS), 9,9'-(stilbene-4,4'-diyl)diphenanthrene (DPNS2), 3,3',3"-(benzene-1,3,5-triyl)tripyrene (TPB3), 9,10-diphenylanthracene (DPAnth), and 6,12-dimethoxy-5,11-diphenylchrysene; and an aromatic amine compound, such as N,N-diphenyl-9-[4-(10-phenyl-9-anthryl)phenyl]-9H-carbazole-3-amine (CzA1PA), 4-(10-phenyl-9-anthryl)triphenylamine (DPhPA), N,9-diphenyl-N-[4-(10-phenyl-9-anthryl)phenyl]-9H-carbazole-3-amine (PCAPA), N,9-diphenyl-N-{4-[4-(10-phenyl-9-anthryl)phenyl]phenyl}-9H-carbazole-3-amine (PCAPBA), N-(9,10-diphenyl-2-anthryl)-N,9-diphenyl-9H-carbazole-3-amine (2PCAPA), 4,4'-bis[N-(1-anthryl)-N-phenylamino]biphenyl (NPB or α-NPD), N,N'-bis(3-methylphenyl)-N,N'-diphenyl-[1,1'-biphenyl]-4,4'-diamine (TPD), 4,4'-bis[N-(9,9-dimethylfluorene-2-yl)-N-phenylamino]biphenyl (DFLDPBi), and 4,4'-bis[N-(spiro-9,9'-bifluorene-2-yl)-N-phenylamino]biphenyl (BSPB). The host material may be used in combination of two or more.

Electron Transporting Layer

The electron transporting layer comprises a highly electron-transporting material (electron transporting material). The compound (1) of the invention may be used in the electron transporting layer. Examples of the electron transporting layer material other than the compound (1) include:
(1) a metal complex, such as an aluminum complex, a beryllium complex, and a zinc complex;
(2) a heteroaromatic compound, such as an imidazole derivative, a benzimidazole derivative, an azine derivative, a carbazole derivative, and a phenanthroline derivative; and
(3) a macro molecular compound.

Examples of the metal complex include tris(8-quinolinolato)aluminum (III) (Alq), tris(4-methyl-8-quinolinolato)aluminum (Almq₃), bis(10-hydroxybenzo[h]quinolinato)beryllium (BeBq₂), bis(2-methyl-8-quinolinato)(4-phenylphenolato)aluminum (III) (BAlq), bis(8-quinolinolato)zinc (II) (Znq), bis[2-(2-benzoxazolyl)phenolato]zinc(II) (ZnPBO), and bis[2-(2-benzothiazolyl)phenolato]zinc(II) (ZnBTZ).

Examples of the heteroaromatic compound include 2-(4-biphenylyl)-5-(4-tert-butylphenyl)-1,3,4-oxadiazole (PBD), 1,3-bis[5-(p-tert-butylphenyl)-1,3,4-oxadiazole-2-yl]benzene (OXD-7), 3-(4-tert-butylphenyl)-4-phenyl-5-(4-biphenylyl)-1,2,4-triazole (TAZ), 3-(4-tert-butylphenyl)-4-(4-ethylphenyl)-5-(4-biphenylyl)-1,2,4-triazole (p-EtTAZ), bathophenanthroline (BPhen), bathocuproine (BCP), and 4,4'-bis(5-methylbenzoxazole-2-yl)stilbene (BzOs).

Examples of the macro molecular compound include poly[(9,9-dihexylfluorene-2,7-diyl)-co-(pyridine-3,5-diyl)] (PF-Py), and poly[(9,9-dioctylfluorene-2,7-diyl)-co-(2,2'-bipyridine-6,6'-diyl)](PF-BPy).

The above compounds have an electron mobility of $10^{-6}$ cm$^2$/Vs or more. Materials other than those mentioned above are also usable in the electron transporting layer if their electron transporting ability is higher than their hole transporting ability. The electron transporting layer may be a single layer or a laminate of two or more layers.

Electron Injecting Layer

The electron injecting layer comprises a highly electron-injecting material, for example, an alkali metal, an alkaline earth metal, and a compound of these metals, such as lithium (Li), cesium (Cs), calcium (Ca), lithium fluoride (LiF), cesium fluoride (CsF), calcium fluoride(CaF$_2$), and lithium oxide (LiOx). In addition, an electron transporting material which is doped with an alkali metal, an alkaline earth metal or a compound thereof, for example, Alq doped with magnesium (Mg), is also usable. By using such a material, electrons are efficiently injected from the cathode.

A composite material obtained by mixing an organic compound and an electron donor is also usable in the electron injecting layer. Such a composite material is excellent in the electron injecting ability and the electron transporting ability, because the organic compound receives electrons from the electron donor. The organic compound is preferably a material excellent in transporting the received electrons. Examples thereof are the materials for the electron transporting layer mentioned above, such as the metal complex and the aromatic heterocyclic compound. Any material capable of giving its electron to another organic compound is usable as the electron donor. Preferred examples thereof are an alkali metal, an alkaline earth metal, and a rare earth metal, such as lithium, cesium, magnesium, calcium, erbium, and ytterbium; an alkali metal oxide and an alkaline earth metal oxide, such as, lithium oxide, calcium oxide, and barium oxide; a Lewis base, such as magnesium oxide; and an organic compound, such as tetrathiafulvalene (TTF).

Cathode

The cathode is formed preferably from a metal, an alloy, an electrically conductive compound, or a mixture thereof, each having a small work function, for example, a work function of 3.8 eV or less. Examples of the material for the cathode include a metal of the group 1 or 2 of the periodic table, for example, an alkali metal, such as lithium (Li) and cesium (Cs), an alkaline earth metal, such as magnesium (Mg), an alloy containing these metals (for example, MgAg and AlLi), a rare earth metal, such as europium (Eu) and ytterbium (Yb), and an alloy containing a rare earth metal.

The alkali metal, the alkaline earth metal, and the alloy thereof can be made into the cathode by a vacuum vapor deposition or a sputtering method. When a silver paste, etc. is used, a coating method and an inkjet method are usable.

When the electron injecting layer is formed, the material for the cathode can be selected independently from the work function and various electroconductive materials, such as Al, Ag, ITO, graphene, and indium oxide-tin oxide doped with silicon or silicon oxide, are usable. These electroconductive materials are made into films by a sputtering method, an inkjet method, and a spin coating method.

Insulating Layer

Since electric field is applied to the ultra-thin films of organic EL devices, the pixel defects due to leak and short circuit tends to occur. To prevent the defects, an insulating thin film layer is preferably interposed between the pair of electrodes.

Examples of the material for the insulating layer include aluminum oxide, lithium fluoride, lithium oxide, cesium fluoride, cesium oxide, magnesium oxide, magnesium fluoride, calcium oxide, calcium fluoride, aluminum nitride, titanium oxide, silicon oxide, germanium oxide, silicon nitride, boron nitride, molybdenum oxide, ruthenium oxide, and vanadium oxide. These materials may be used in combination or may be made into laminated layers.

Space Layer

For example, in an organic EL device wherein a fluorescent emitting layer and a phosphorescent emitting layer are laminated, a space layer is disposed between the fluorescent emitting layer and the phosphorescent emitting layer to prevent the diffusion of excitons generated in the phosphorescent emitting layer to the fluorescent emitting layer or to control the carrier balance. The space layer may be disposed between two or more phosphorescent emitting layers.

Since the space layer is disposed between the light emitting layers, a material combining the electron transporting ability and the hole transporting ability is preferably used for forming the space layer. To prevent the diffusion of triplet energy in the adjacent phosphorescent emitting layer, the triplet energy of the material for the space layer is preferably 2.6 eV or more. The materials described with respect to the hole transporting layer are usable as the material for the space layer.

Blocking Layer

In the organic EL device, a blocking layer, such as an electron blocking layer, a hole blocking layer, and a triplet blocking layer, may be provided in the portion adjacent to the light emitting layer. The electron blocking layer is a layer which prevents the diffusion of electrons from the light emitting layer to the hole transporting layer. The hole blocking layer is a layer which prevents the diffusion of holes from the light emitting layer to the electron transporting layer. The triplet blocking layer prevents the diffusion of excitons generated in the light emitting layer to adjacent layers and has a function of confining the excitons in the light emitting layer. The compound (1) of the invention is also suitable as a material for the electron blocking layer and the triplet blocking layer.

Each layer of the organic EL device can be formed by a known method, such as a vapor deposition method and a coating method. For example, each layer can be formed by a known vapor deposition method, such as a vacuum vapor deposition method and a molecular beam evaporation method (MBE method), and a known coating method using a solution of the compound for forming the layer, such as a dipping method, a spin coating method, a casting method, a bar coating method, and a roll coating method.

The thickness of each layer is not particularly limited and preferably 5 nm to 10 µm, more preferably 10 nm to 0.2 µm, because an excessively small thickness may cause defects such as pin holes and an excessively large thickness may require a high driving voltage to reduce the efficiency.

The organic EL device can be used in an electronic device, for example, as display parts, such as organic EL panel module, display devices of television sets, mobile phones, personal computer, etc., and light emitting sources of lighting equipment and vehicle lighting equipment.

EXAMPLES

The invention will be described in more detail with reference to the examples. It should be noted that the scope of the invention is not limited to the following examples.

511

Synthesis of Intermediate a

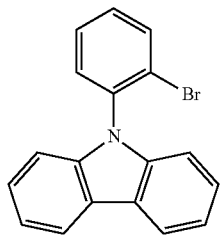

Intermediate a

Under nitrogen atmosphere, a mixture of carbazole (1.7 g), 1-bromo-2-iodobenzene (1.5 ml), potassium carbonate (2.8 g), copper iodide (95 mg), and xylene (25 ml) was refluxed. After cooling to ordinary temperature, the reaction product was extracted with ethyl acetate. The extract was dried over anhydrous magnesium sulfate, and then, the solvent was removed under reduced pressure. The residue was passed through a silica gel column by using a hexane solvent, and then, the solvent was removed under reduced pressure. The obtained residue was vacuum-dried to obtain the intermediate a as a white solid (800 mg, 25% yield).

MS: $[M+H]^+$=323

Synthesis of Intermediate A

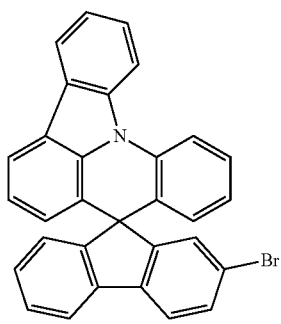

Intermediate A

Into a solution of the intermediate a (4.19) in purified THF (50 ml), a 2.5 M hexane solution of n-butyllithium (4.8 ml) was added dropwise gradually at −78° C. After stirring at the same temperature for 45 min, 2-bromo-9-fluorenone (2.59 g) was added. After stirring at the same temperature for one hour and further stirring at ordinary temperature for 2 h, the reaction was terminated by adding an aqueous solution of ammonium chloride. After extracting the organic substances with ethyl ether, the extract was dried over anhydrous magnesium sulfate, and then the ethyl ether was removed to obtain a yellow solid. After dispersing the obtained solid in ethanol, the dispersion was stirred. The solid collected by filtration was vacuum-dried to obtain 4.5 g of an intermediate, which was then dispersed in 40 ml of acetic acid. After adding 12 drops of concentrated sulfuric acid, the dispersion was refluxed for 3 h and then cooled to ordinary temperature. The precipitated solid was collected by filtration, washed with ethanol, and vacuum-dried to obtain the intermediate A (3.98 g, 82% yield).

MS: $[M+H]^+$=484

512

Synthesis of Intermediate B

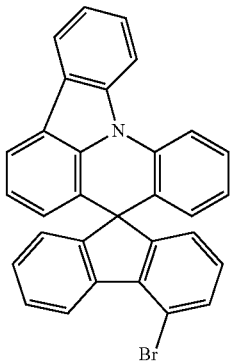

Intermediate B

A solution of the intermediate a (6.96 g) in purified THF (300 ml) was cooled to −78° C. A 2.5 M hexane solution of n-butyllithium (8.64 ml) was gradually added dropwise. After stirring at the same temperature for 30 min, 4-bromo-9-fluorenone (6.08 g) was added. After stirring at the same temperature for 40 min and further stirring at ordinary temperature for 3 h, the reaction was terminated by adding an aqueous solution of ammonium chloride. After extracting the organic substances with ethyl ether, the extract was dried over anhydrous magnesium sulfate, and then the ethyl ether was removed. The obtained solid was dispersed in ethanol and the dispersion was stirred for one day. The solid collected by filtration was vacuum-dried to obtain an intermediate (10.12 g, 97% yield), which was then dispersed in 10 ml of acetic acid. After adding 10 drops of concentrated sulfuric acid, the dispersion was refluxed for 4 h. The precipitated solid was collected by filtration, washed with ethanol, and vacuum-dried to obtain the intermediate B (9.49 g, 97% yield).

MS: $[M+H]^+$=563

Synthesis of Intermediate C

First Step

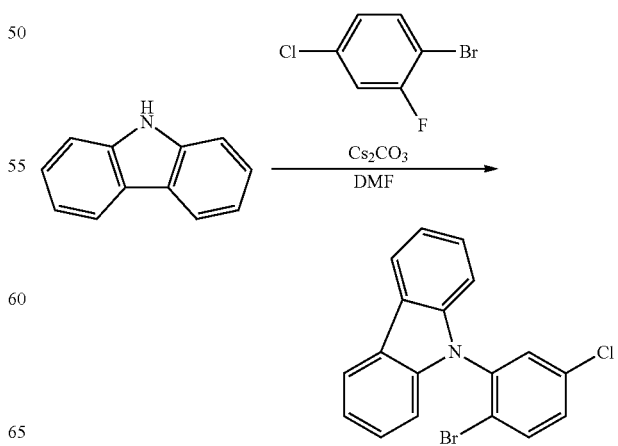

Under argon atmosphere, a mixture of 9H-carbazole (9.3 g), 1-bromo-4-chloro-2-fluorobenzene (23.3 g), cesium carbonate (36.2 g), and DMF (222 mL) was stirred at 150° C. for 7 h. After adding water at room temperature, the resultant mixture was extracted with ethyl acetate. The organic layer was purified by silica gel column chromatography, and then, the solvent was removed to obtain 9-(2-bromo-5-chlorophenyl)carbazole as a white solid (11.4 g, 58% yield).

Second and Third Steps

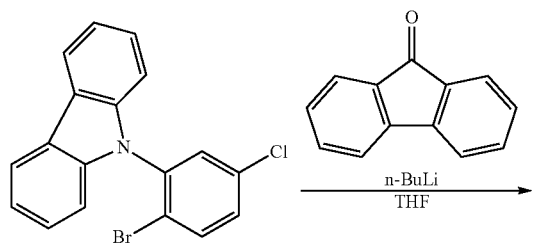

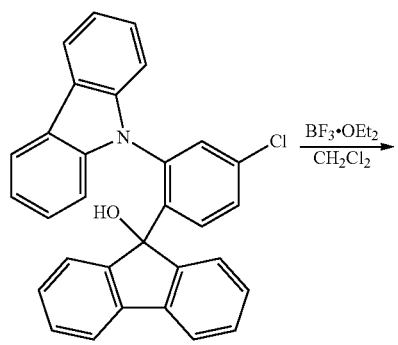

Under argon atmosphere, into a mixture of 9-(2-bromo-5-chlorophenyl)carbazole (11.3 g) and THF (106 mL), a 1.6 M hexane solution of n-butyllithium (25.1 mL) was added dropwise at −78° C. After adding dropwise a solution of fluorenone (6.85 g) in THF (106 mL) at constant temperature, the mixture was stirred for 5 h while raising the temperature gradually. A saturated aqueous solution of ammonium was added dropwise under cooling with ice, and then, the mixture was extracted with ethyl acetate. The obtained organic layer was concentrated to obtain an orange yellow solid, which was used in the next reaction without purification.

In a flask, the obtained orange yellow solid (15.8 g) was dissolved in dichloromethane (463 mL) under heating. After adding boron fluoride ethyl ether complex (3.9 mL) dropwise under cooling with ice, the mixture was stirred at constant temperature for 4 h. The organic layer was extracted and the obtained residue was purified by silica gel column chromatography to obtain a white solid, which was recrystallized from ethyl acetate to obtain the intermediate C (4.9 g, 36% yield (second and third steps)).

Synthesis of Intermediate D

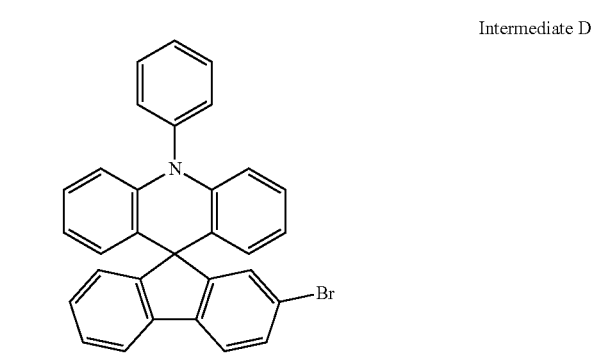 [SMILES: Brc1ccc2c(c1)C1(c3ccccc3-2)c2ccccc2N(c2ccccc2)c2ccccc21]

Intermediate D

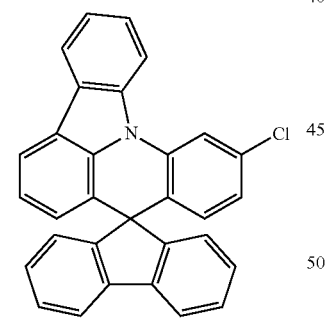

Intermediate C

The intermediate D was synthesized according to the following scheme.

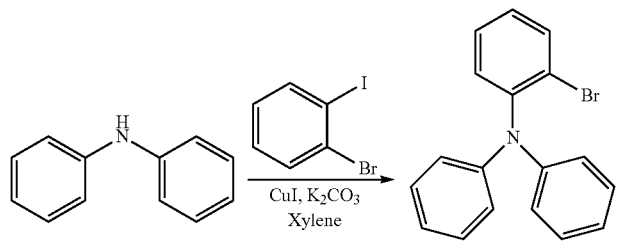

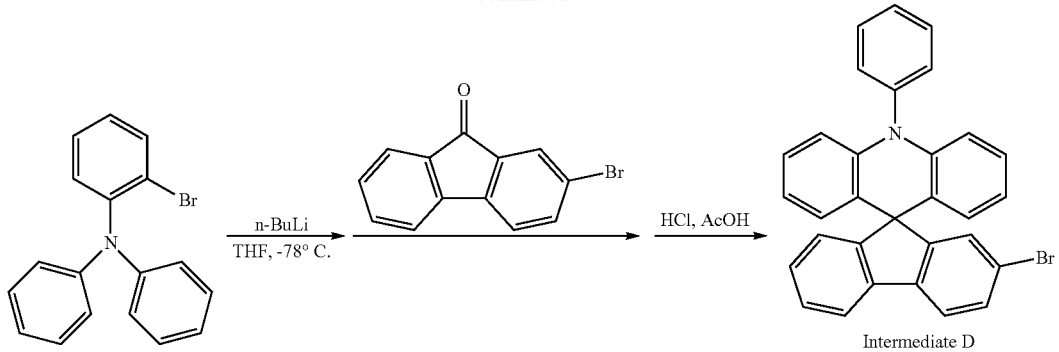

Synthesis of Intermediate E

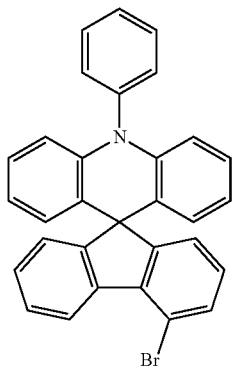

Intermediate E

The intermediate E was synthesized in the same manner as in the synthesis of the intermediate D except for using 4-bromo-9-fluorenone in place of 2-bromo-9-fluorenone.

Synthesis Example 1: Synthesis of Compound 1

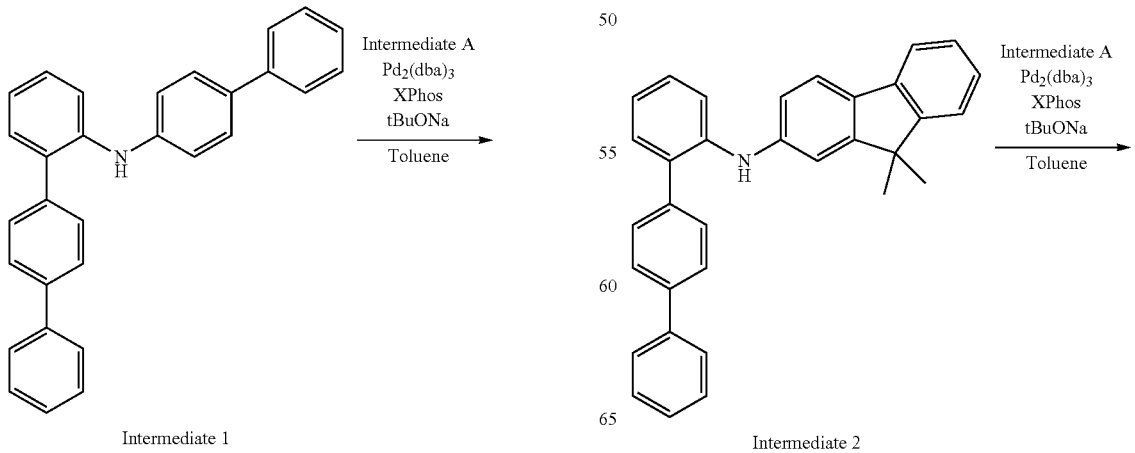

Under argon atmosphere, a mixture of a known intermediate 1 (3.12 g), the intermediate A(3.8 g), tris(dibenzylideneacetone)dipalladium(0) (39 mg), XPhos (78 mg), sodium t-butoxide (2.26 g), and toluene (50 mL) was stirred at 110° C. for 12 h under heating. After leaving the mixture to stand for cooling, the precipitated crystal was removed by filtration, the filtrate was extracted with toluene, and the extract was purified by silica gel column chromatography to obtain the compound 1 as a white solid (4.27 g, 68%). Result of mass spectrometric analysis (Molecular weight of Compound 1)

Calculated: 800
Found: m/e=800

Synthesis Example 2: Synthesis of Compound 2

-continued

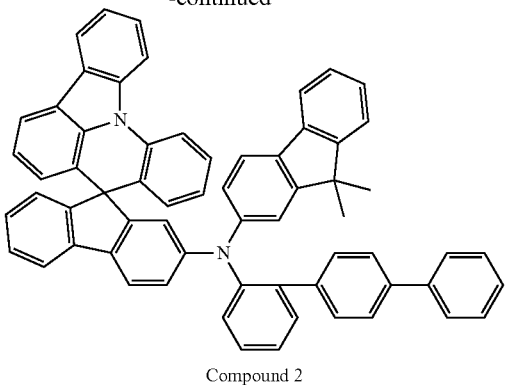

Compound 2

The compound 2 was synthesized in the same manner as in Synthesis Example 1 except for using the intermediate 2 in place of the intermediate 1. Result of mass spectrometric analysis (Molecular weight of Compound 2)

Calculated: 840

Found: m/e=840

Synthesis Example 3: Synthesis of Compound 3

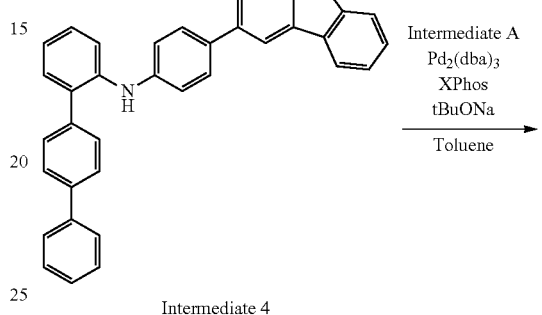

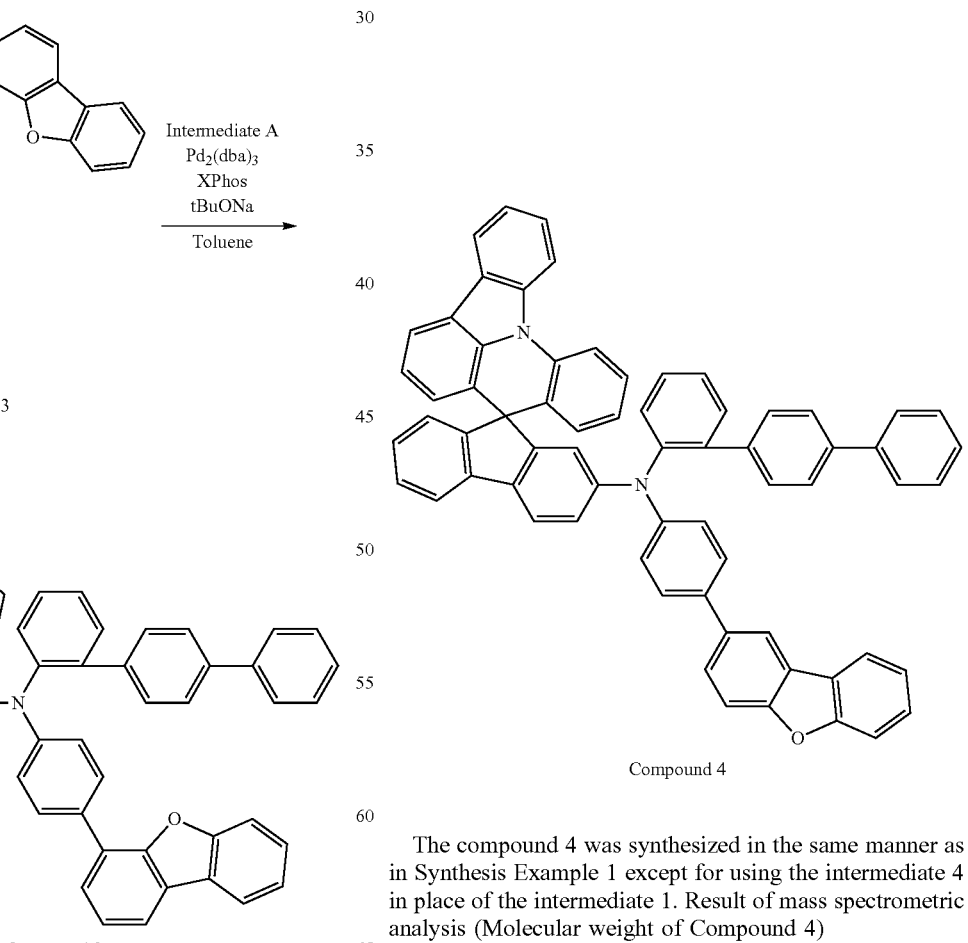

Compound 3

The compound 3 was synthesized in the same manner as in Synthesis Example 1 except for using the intermediate 3 in place of the intermediate 1. Result of mass spectrometric analysis (Molecular weight of Compound 3)

Calculated: 890

Found: m/e=890

Synthesis Example 4: Synthesis of Compound 4

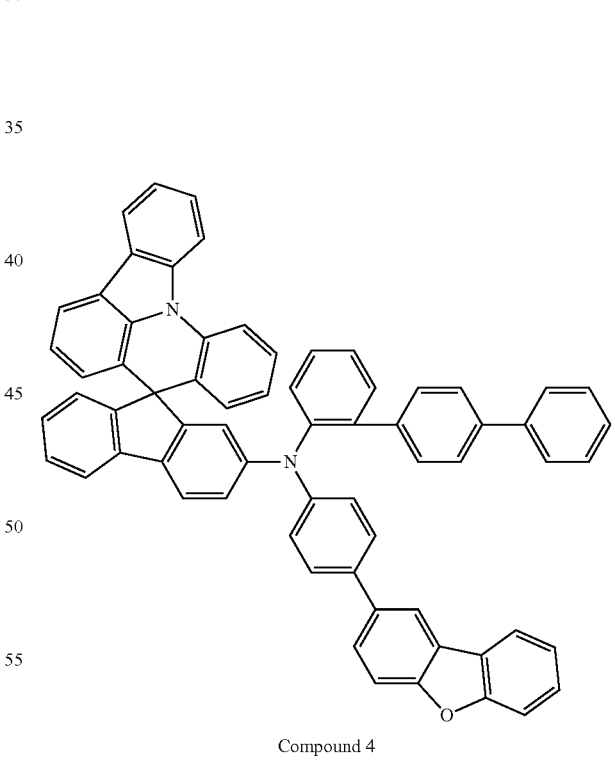

Compound 4

The compound 4 was synthesized in the same manner as in Synthesis Example 1 except for using the intermediate 4 in place of the intermediate 1. Result of mass spectrometric analysis (Molecular weight of Compound 4)

Calculated: 890

Found: m/e=890

Synthesis Example 5: Synthesis of Compound 5

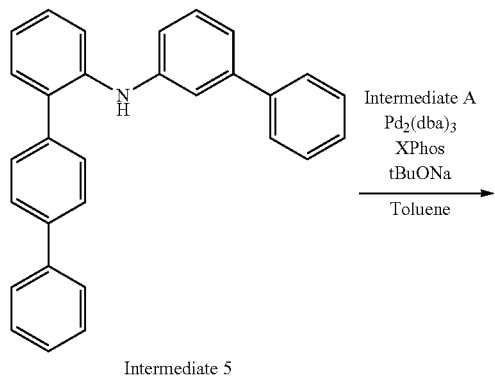

Intermediate 5

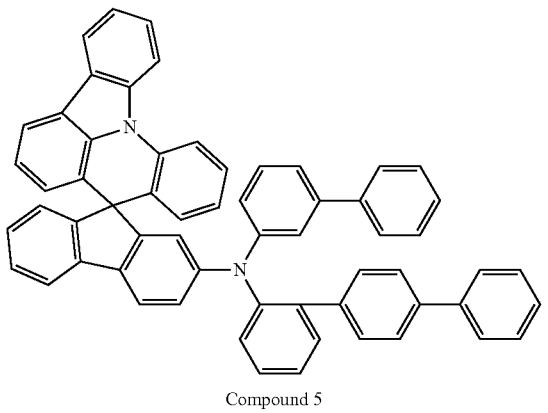

Compound 5

The compound 5 was synthesized in the same manner as in Synthesis Example 1 except for using the intermediate 5 in place of the intermediate 1. Result of mass spectrometric analysis (Molecular weight of Compound 5)

Calculated: 800

Found: m/e=800

Synthesis Example 6: Synthesis of Compound 6

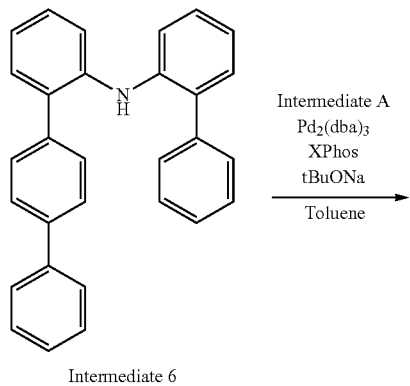

Intermediate 6

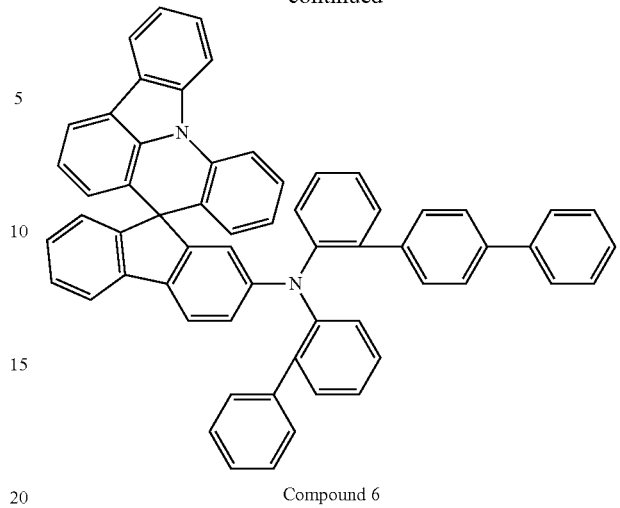

Compound 6

The compound 6 was synthesized in the same manner as in Synthesis Example 1 except for using the intermediate 6 in place of the intermediate 1. Result of mass spectrometric analysis (Molecular weight of Compound 6)

Calculated: 800

Found: m/e=800

Synthesis Example 7: Synthesis of Compound 7

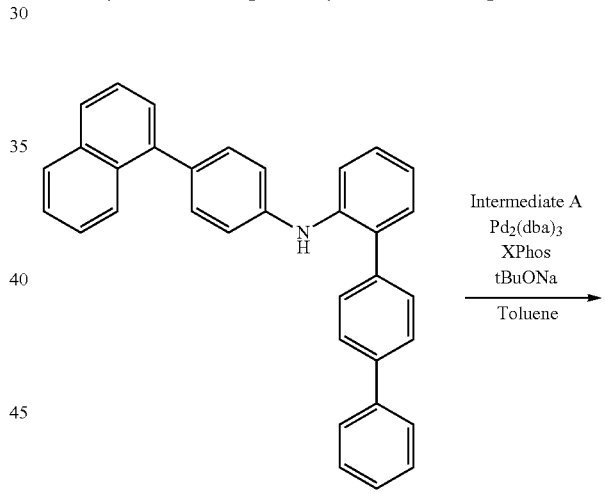

Intermediate 7

Compound 7

The compound 7 was synthesized in the same manner as in Synthesis Example 1 except for using the intermediate 7 in place of the intermediate 1. Result of mass spectrometric analysis (Molecular weight of Compound 7)

Calculated: 850

Found: m/e=850

Synthesis Example 8: Synthesis of Compound 8

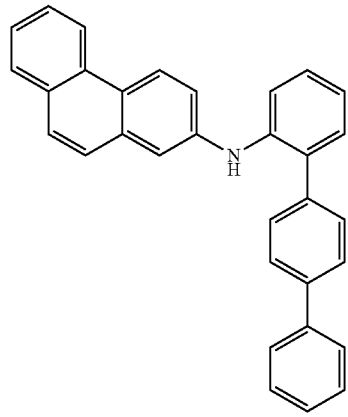

Intermediate 8

Synthesis Example 9: Synthesis of Compound 9

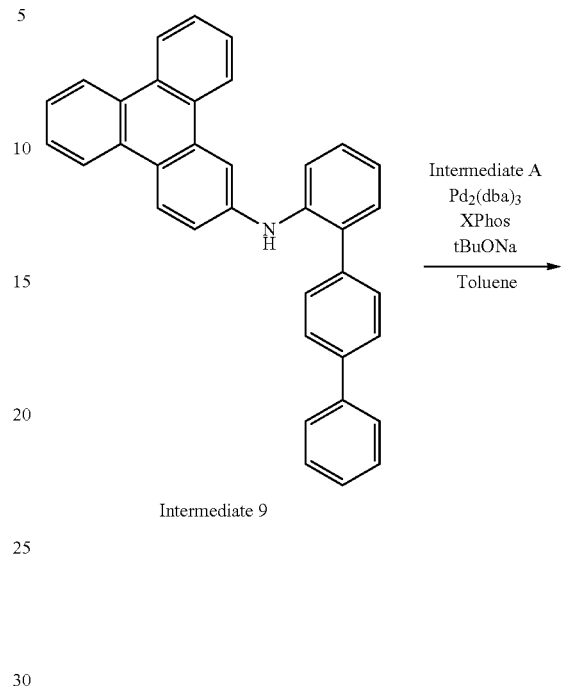

Intermediate 9

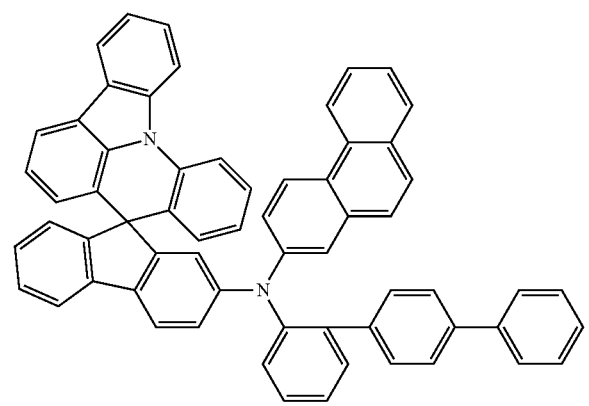

Compound 8

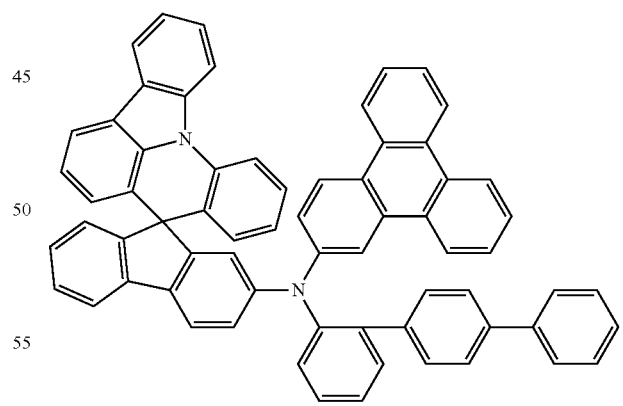

Compound 9

The compound 8 was synthesized in the same manner as in Synthesis Example 1 except for using the intermediate 8 in place of the intermediate 1. Result of mass spectrometric analysis (Molecular weight of Compound 8)

Calculated: 824

Found: m/e=824

The compound 9 was synthesized in the same manner as in Synthesis Example 1 except for using the intermediate 9 in place of the intermediate 1. Result of mass spectrometric analysis (Molecular weight of Compound 9)

Calculated: 874

Found: m/e=874

Synthesis Example 10: Synthesis of Compound 10

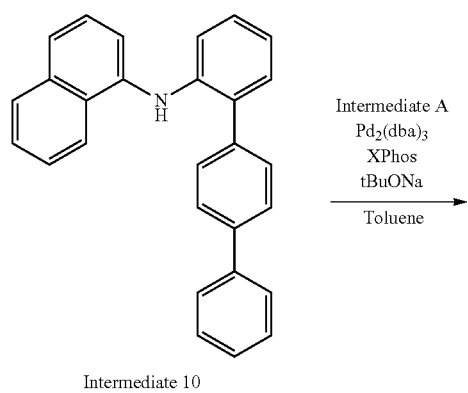

Intermediate 10

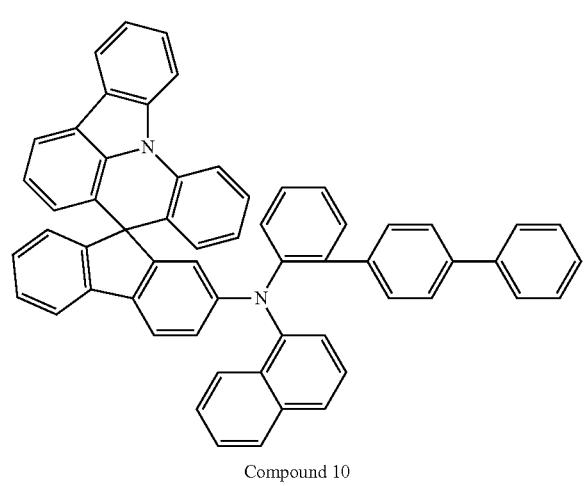

Compound 10

The compound 10 was synthesized in the same manner as in Synthesis Example 1 except for using the intermediate 10 in place of the intermediate 1. Result of mass spectrometric analysis (Molecular weight of Compound 10)

Calculated: 774

Found: m/e=774

Synthesis Example 11: Synthesis of Compound 11

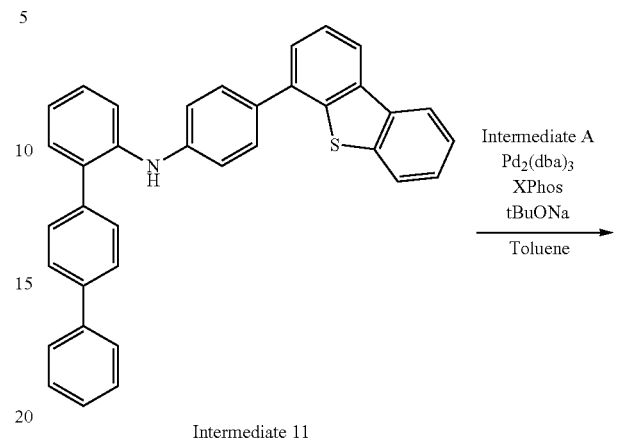

Intermediate 11

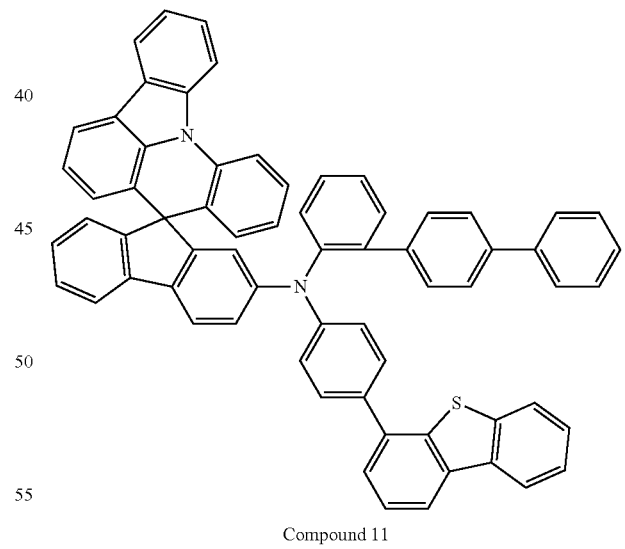

Compound 11

The compound 11 was synthesized in the same manner as in Synthesis Example 1 except for using the intermediate 11 in place of the intermediate 1. Result of mass spectrometric analysis (Molecular weight of Compound 11)

Calculated: 906

Found: m/e=906

Synthesis Example 12: Synthesis of Compound 12

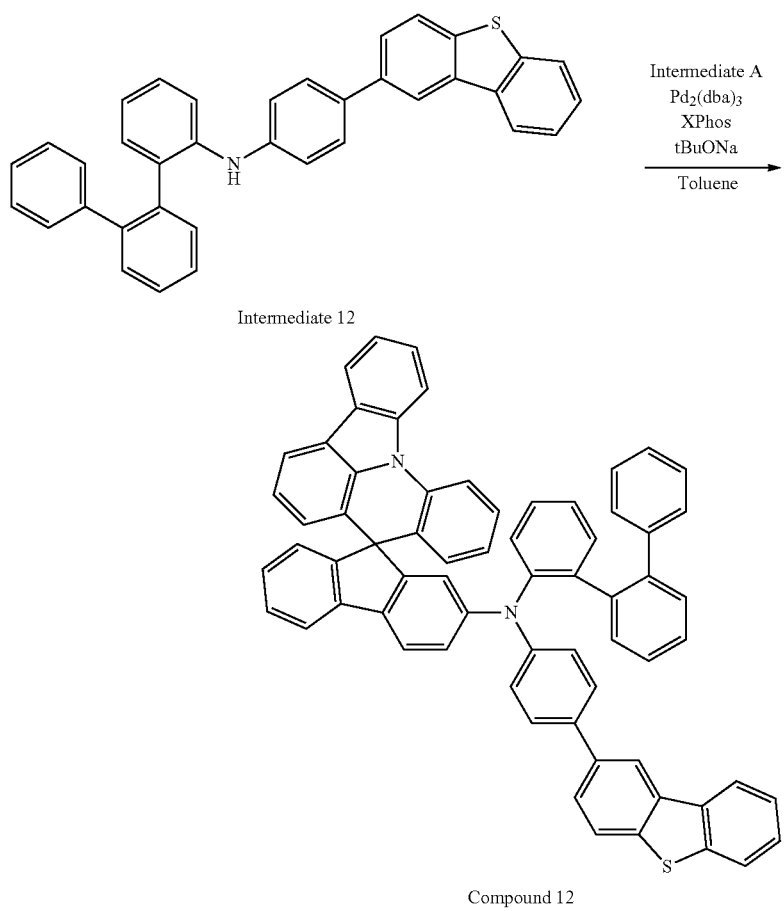

Intermediate 12

Compound 12

The compound 12 was synthesized in the same manner as in Synthesis Example 1 except for using the intermediate 12 in place of the intermediate 1. Result of mass spectrometric analysis (Molecular weight of Compound 12)

Calculated: 906

Found: m/e=906

Synthesis Example 13: Synthesis of Compound 13

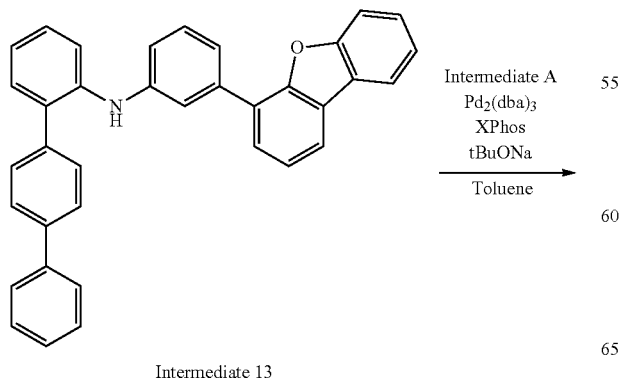

Intermediate 13

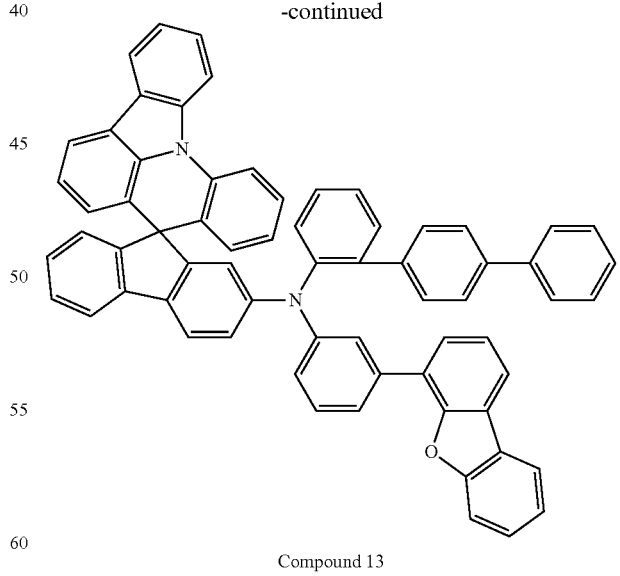

Compound 13

The compound 13 was synthesized in the same manner as in Synthesis Example 1 except for using the intermediate 13 in place of the intermediate 1. Result of mass spectrometric analysis (Molecular weight of Compound 13)

Calculated: 890

Found: m/e=890

Synthesis Example 14: Synthesis of Compound 14

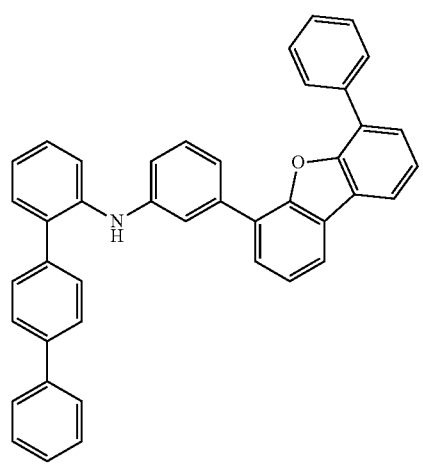

Intermediate 14

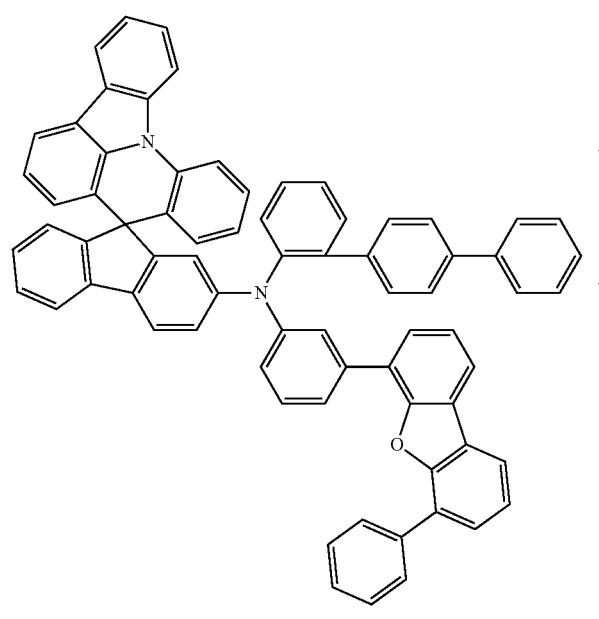

Compound 14

The compound 14 was synthesized in the same manner as in Synthesis Example 1 except for using the intermediate 14 in place of the intermediate 1. Result of mass spectrometric analysis (Molecular weight of Compound 14)

Calculated: 966

Found: m/e=966

Synthesis Example 15: Synthesis of Compound 15

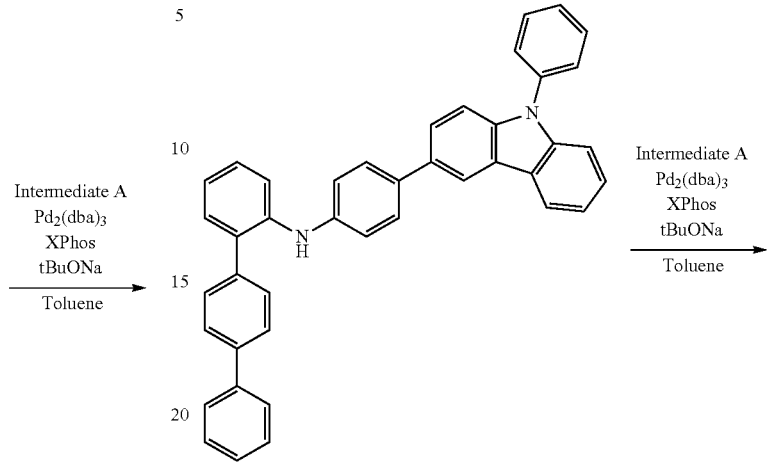

Intermediate 15

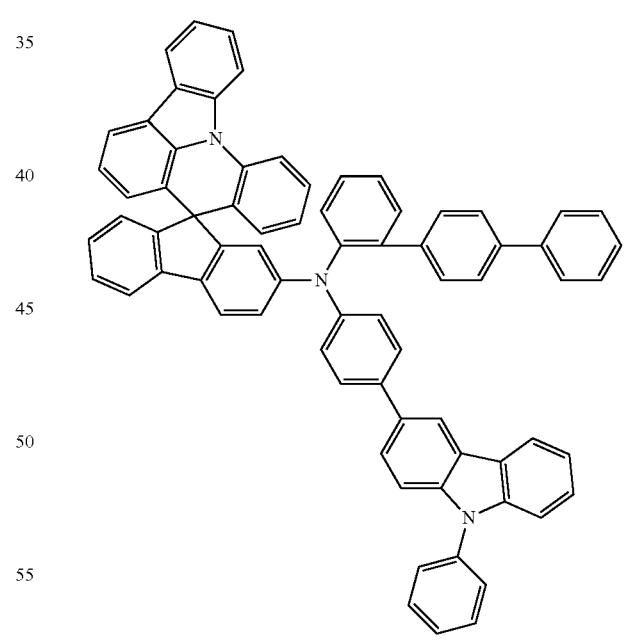

Compound 15

The compound 15 was synthesized in the same manner as in Synthesis Example 1 except for using the intermediate 15 in place of the intermediate 1. Result of mass spectrometric analysis (Molecular weight of Compound 15)

Calculated: 965

Found: m/e=965

Synthesis Example 16: Synthesis of Compound 16

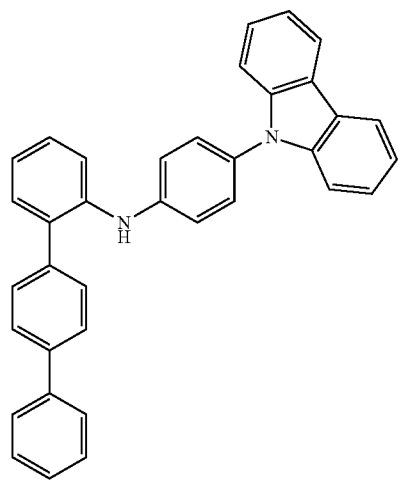

Intermediate 16

Intermediate A, Pd₂(dba)₃, XPhos, tBuONa, Toluene

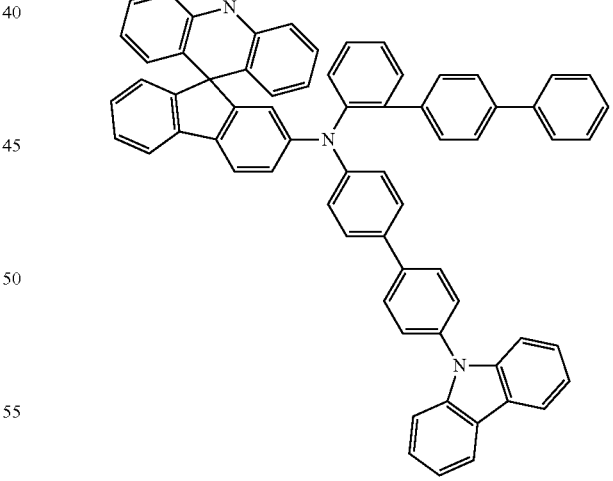

Compound 16

The compound 16 was synthesized in the same manner as in Synthesis Example 1 except for using the intermediate 16 in place of the intermediate 1. Result of mass spectrometric analysis (Molecular weight of Compound 16)

Calculated: 889

Found: m/e=889

Synthesis Example 17: Synthesis of Compound 17

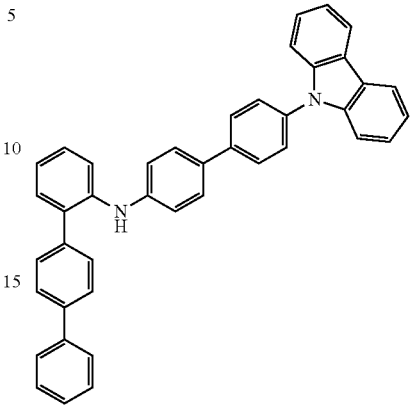

Intermediate 17

Intermediate A, Pd₂(dba)₃, XPhos, tBuONa, Toluene

Compound 17

The compound 17 was synthesized in the same manner as in Synthesis Example 1 except for using the intermediate 17 in place of the intermediate 1. Result of mass spectrometric analysis (Molecular weight of Compound 17)

Calculated: 965

Found: m/e=965

Synthesis Example 18: Synthesis of Compound 18

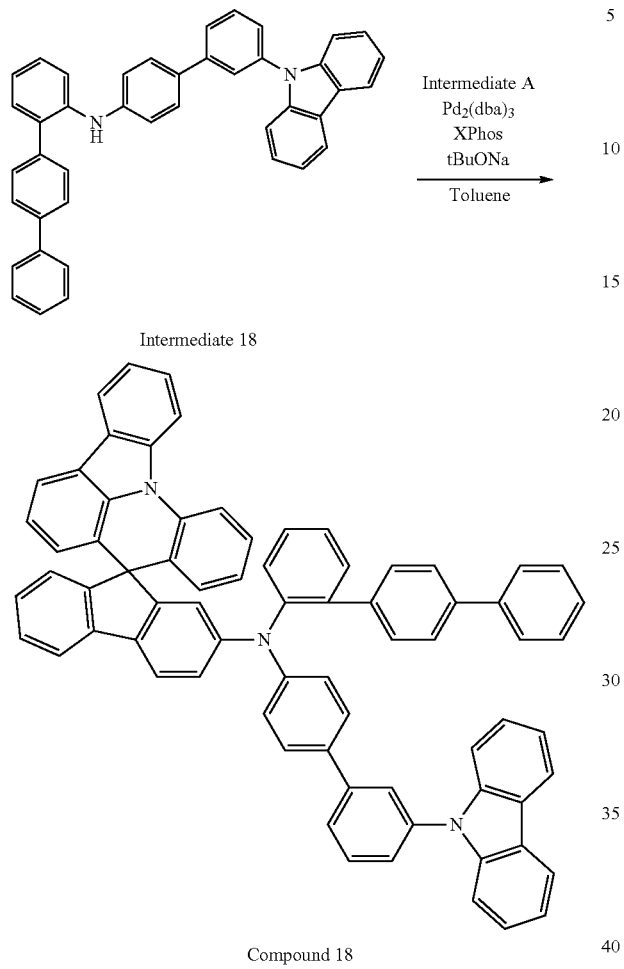

Intermediate 18

Compound 18

The compound 18 was synthesized in the same manner as in Synthesis Example 1 except for using the intermediate 18 in place of the intermediate 1. Result of mass spectrometric analysis (Molecular weight of Compound 18)

Calculated: 965
Found: m/e=965

Synthesis Example 19: Synthesis of Compound 19

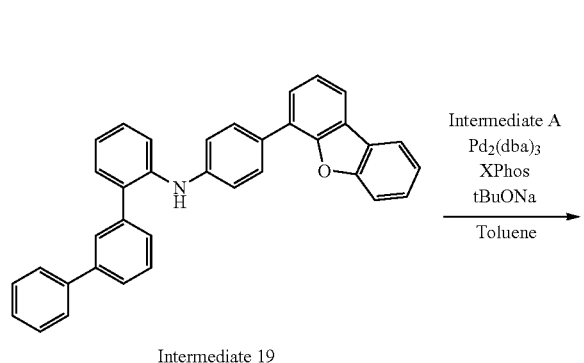

Intermediate 19

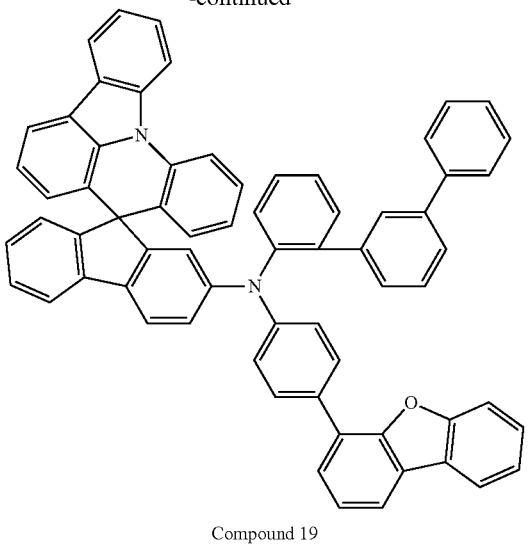

Compound 19

The compound 19 was synthesized in the same manner as in Synthesis Example 1 except for using the intermediate 19 in place of the intermediate 1. Result of mass spectrometric analysis (Molecular weight of Compound 19)

Calculated: 890
Found: W/e=890

Synthesis Example 20: Synthesis of Compound 20

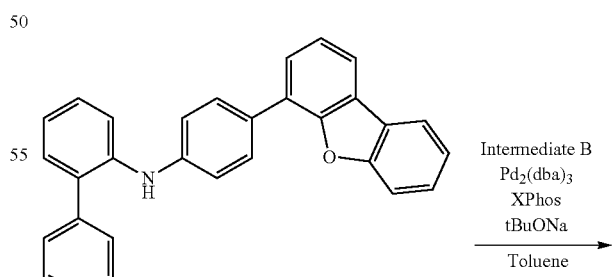

Intermediate 3

-continued

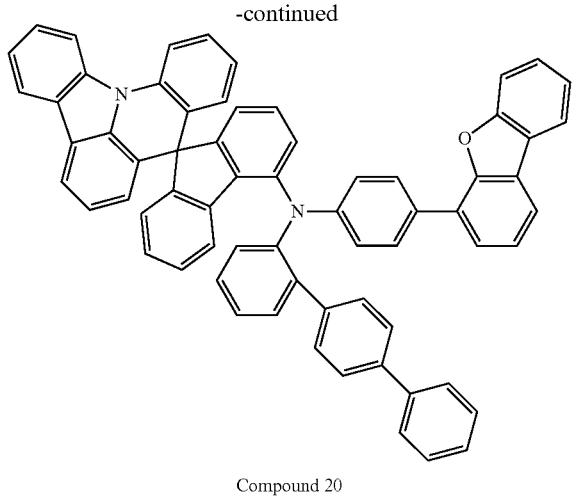

Compound 20

The compound 20 was synthesized in the same manner as in Synthesis Example 3 except for using the intermediate B in place of the intermediate A. Result of mass spectrometric analysis (Molecular weight of Compound 20)
Calculated: 890
Found: m/e=890

Synthesis Example 21: Synthesis of Compound 21

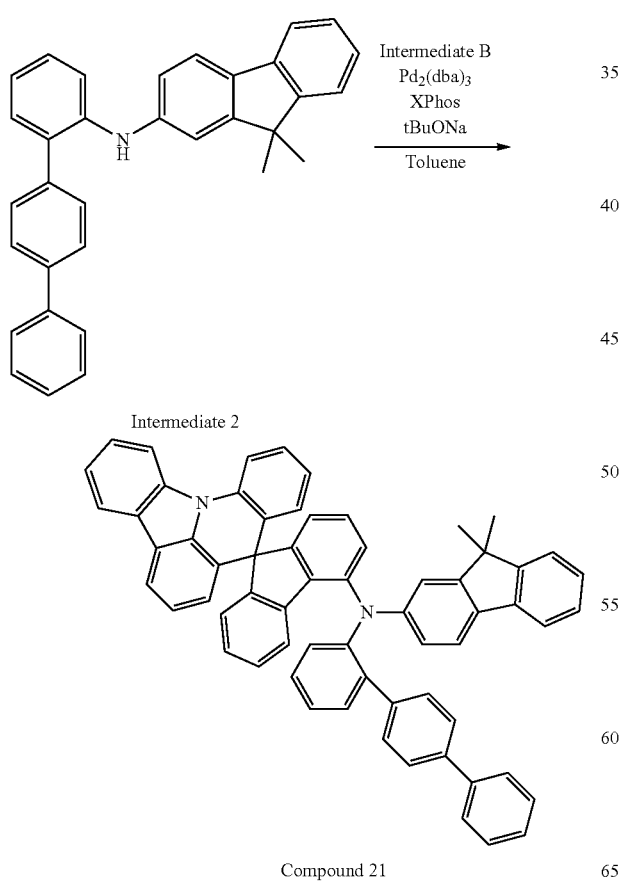

Compound 21

The compound 21 was synthesized in the same manner as in Synthesis Example 2 except for using the intermediate B in place of the intermediate A. Result of mass spectrometric analysis (Molecular weight of Compound 21)
Calculated: 840
Found: m/e=840

Synthesis Example 22: Synthesis of Compound 22

Compound 22

The compound 22 was synthesized in the same manner as in Synthesis Example 15 except for using the intermediate B in place of the intermediate A. Result of mass spectrometric analysis (Molecular weight of Compound 22)
Calculated: 965
Found: m/e=965

Synthesis Example 23: Synthesis of Compound 23

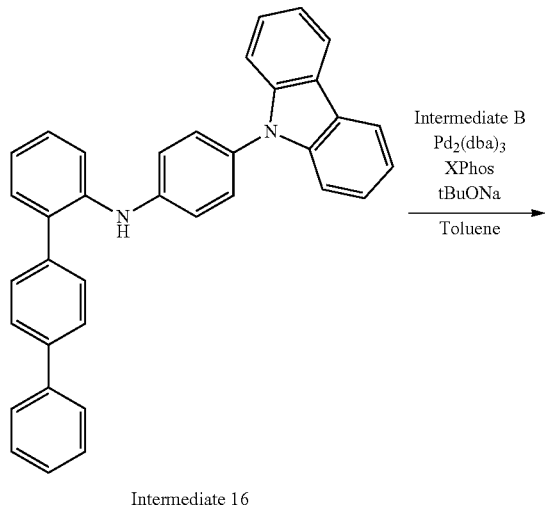

Intermediate 16

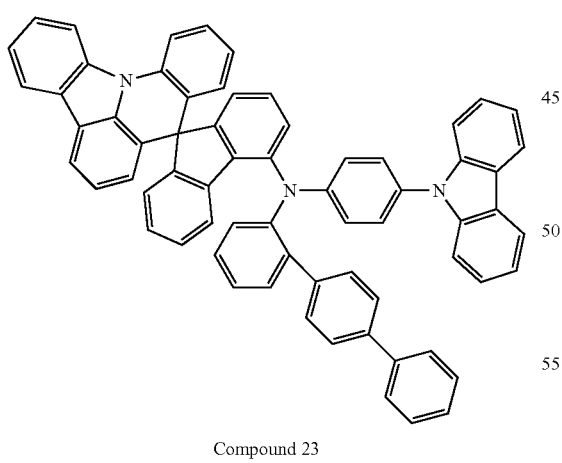

Compound 23

The compound 23 was synthesized in the same manner as in Synthesis Example 16 except for using the intermediate B in place of the intermediate A. Result of mass spectrometric analysis (Molecular weight of Compound 23)

Calculated: 889
Found: m/e=889

Synthesis Example 24: Synthesis of Compound 24

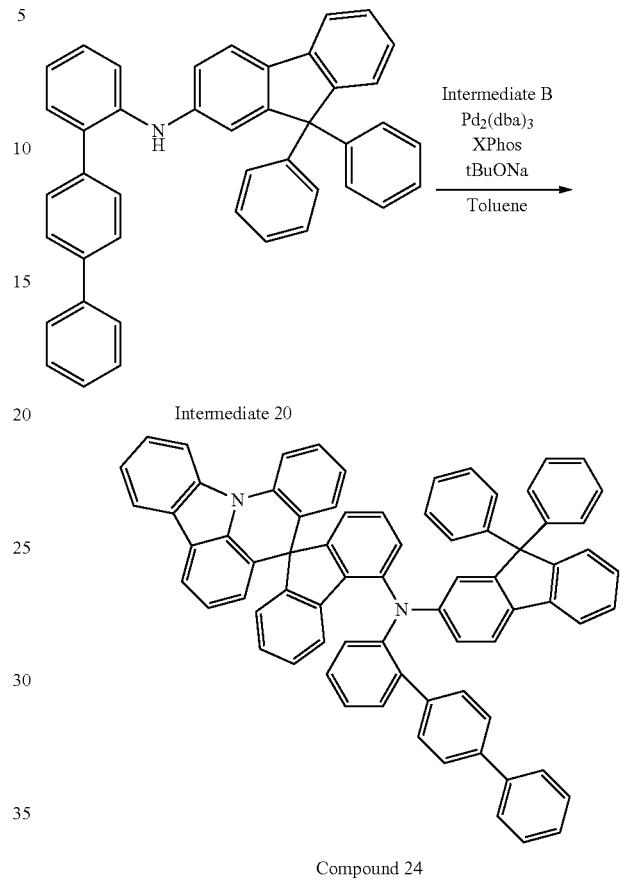

Intermediate 20

Compound 24

The compound 24 was synthesized in the same manner as in Synthesis Example 1 except for using the intermediate B in place of the intermediate A and using the intermediate 20 in place of the intermediate 1. Result of mass spectrometric analysis (Molecular weight of Compound 24)

Calculated: 964
Found: m/e=964

Synthesis Example 25: Synthesis of Compound 25

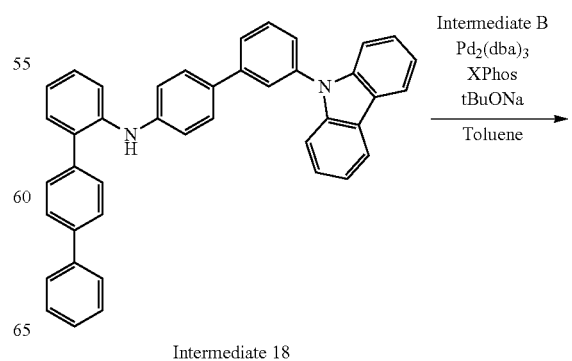

Intermediate 18

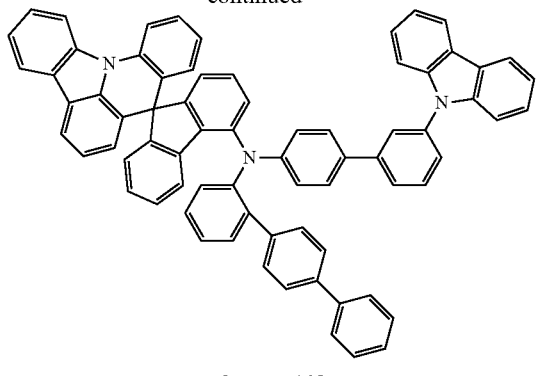

Compound 25

The compound 25 was synthesized in the same manner as in Synthesis Example 18 except for using the intermediate B in place of the intermediate A. Result of mass spectrometric analysis (Molecular weight of Compound 25)
Calculated: 965
Found: m/e=965

Synthesis Example 26: Synthesis of Compound 26

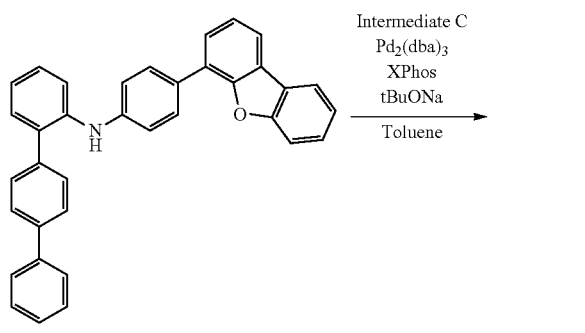

Intermediate 3

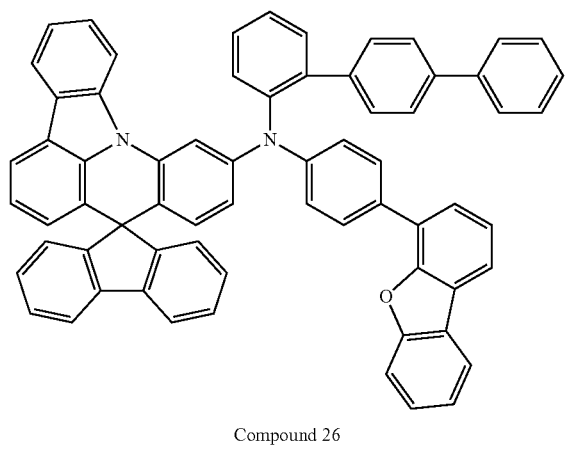

Compound 26

The compound 26 was synthesized in the same manner as in Synthesis Example 3 except for using the intermediate C in place of the intermediate A. Result of mass spectrometric analysis (Molecular weight of Compound 26)
Calculated: 890
Found: m/e=890

Synthesis Example 27: Synthesis of Compound 27

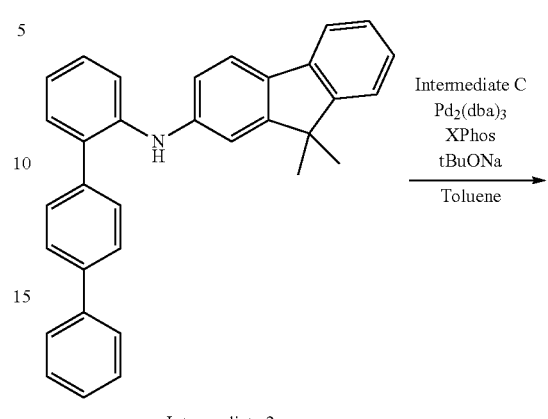

Intermediate 2

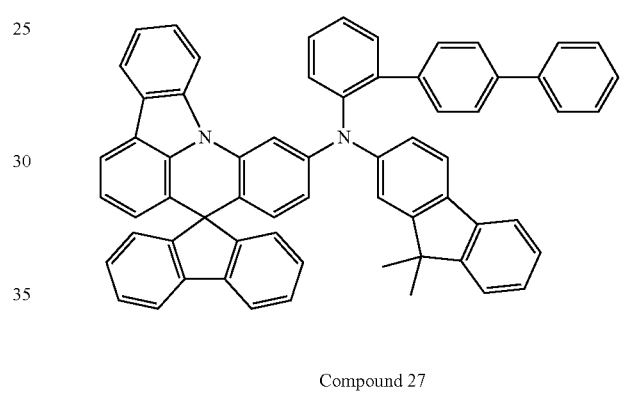

Compound 27

The compound 27 was synthesized in the same manner as in Synthesis Example 2 except for using the intermediate C in place of the intermediate A. Result of mass spectrometric analysis (Molecular weight of Compound 27)
Calculated: 840
Found: m/e=840

Synthesis Example 28: Synthesis of Compound 28

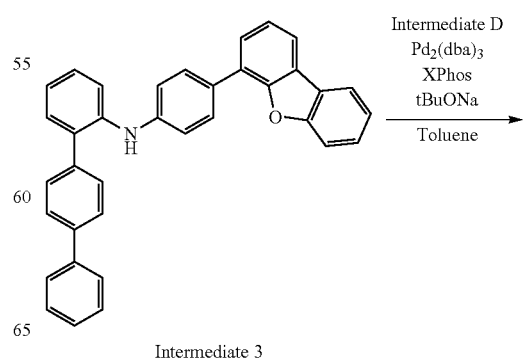

Intermediate 3

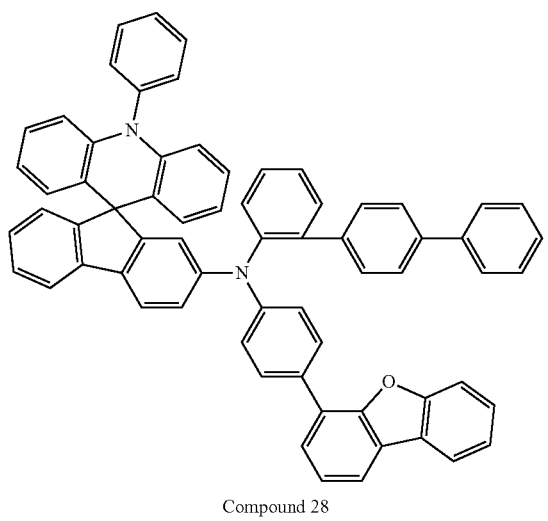

Compound 28

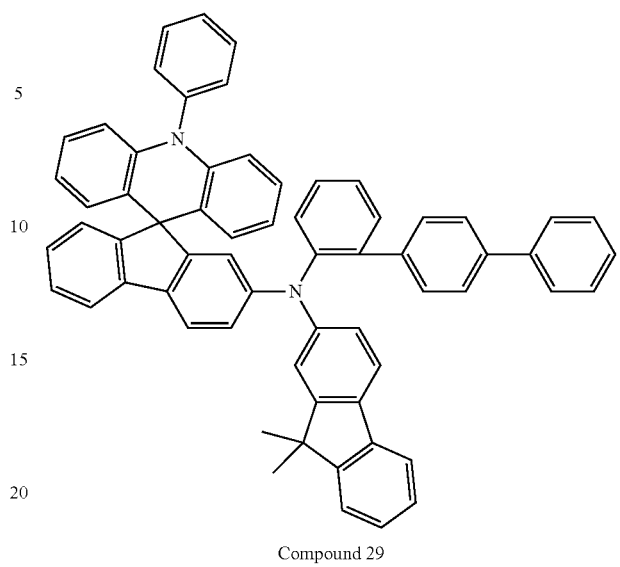

Compound 29

The compound 28 was synthesized in the same manner as in Synthesis Example 3 except for using the intermediate D in place of the intermediate A. Result of mass spectrometric analysis (Molecular weight of Compound 28)

Calculated: 892

Found: m/e=892

Synthesis Example 29: Synthesis of Compound 29

The compound 29 was synthesized in the same manner as in Synthesis Example 2 except for using the intermediate D in place of the intermediate A. Result of mass spectrometric analysis (Molecular weight of Compound 29)

Calculated: 842

Found: m/e=842

Synthesis Example 30: Synthesis of Compound 30

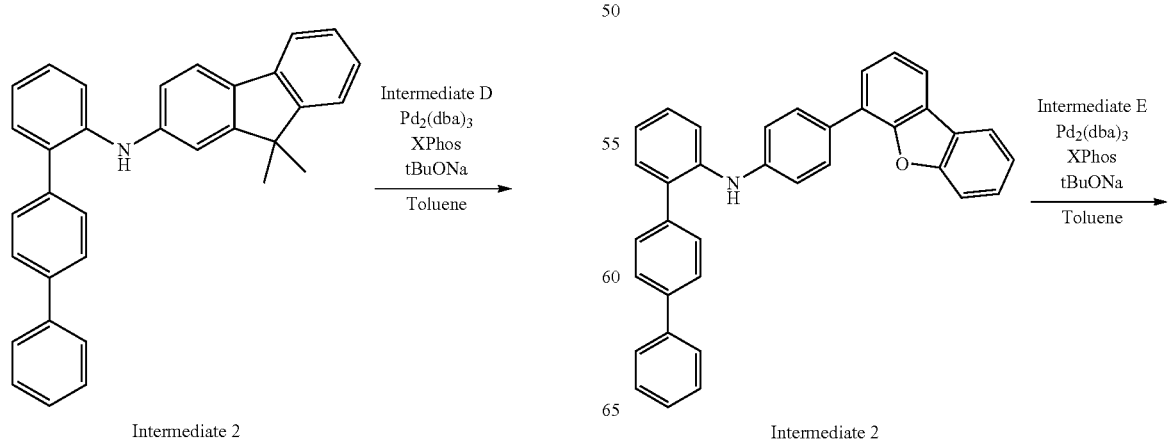

541
-continued

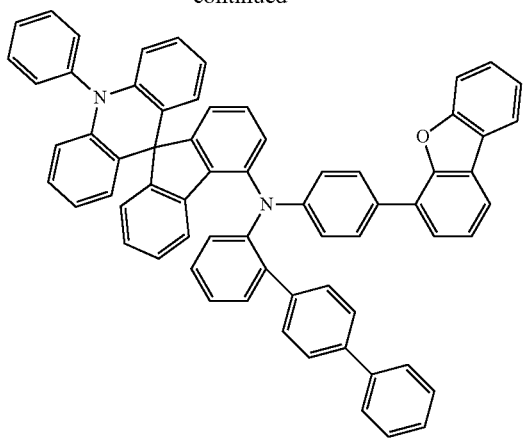

Compound 30

The compound 30 was synthesized in the same manner as in Synthesis Example 3 except for using the intermediate E in place of the intermediate A. Result of mass spectrometric analysis (Molecular weight of Compound 30)

Calculated: 892

Found: m/e=892

Synthesis Example 31: Synthesis of Compound 31

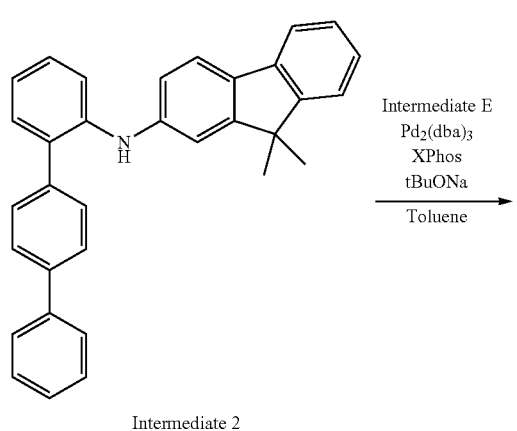

Intermediate 2

542
-continued

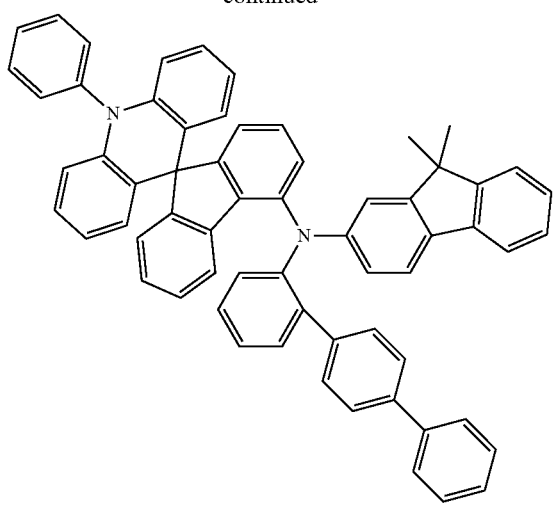

Compound 31

The compound 31 was synthesized in the same manner as in Synthesis Example 2 except for using the intermediate E in place of the intermediate A. Result of mass spectrometric analysis (Molecular weight of Compound 31)

Calculated: 842

Found: m/e=842

Synthesis of Intermediate F

The intermediate F was synthesized by using the intermediate C obtained above.

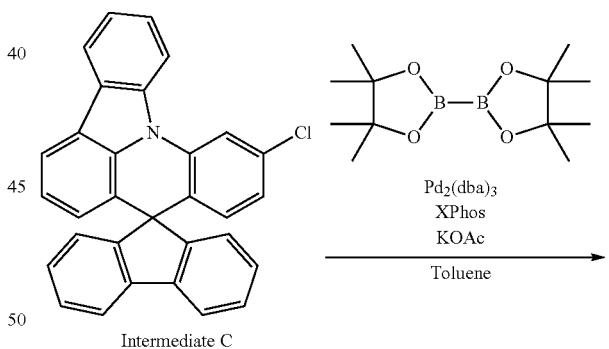

Intermediate C

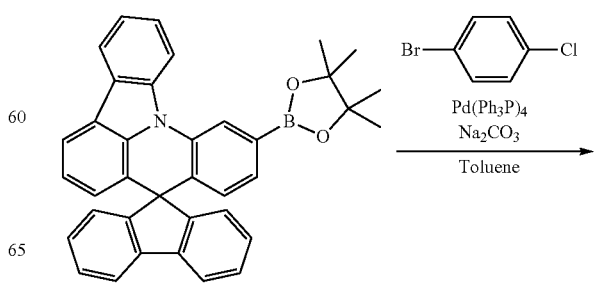

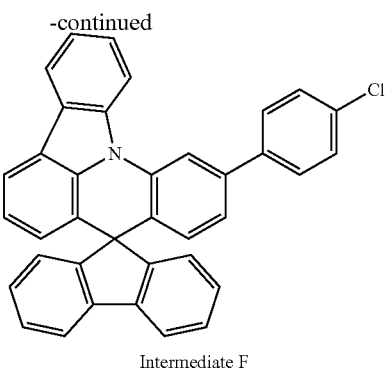

Intermediate F

Under argon atmosphere, a mixture of the intermediate C (7.9 g), bis(pinacolato)diboron (4.25 g), tris(dibenzylideneacetone)dipalladium(0) (824 mg). XPhos (858 mg), potassium acetate (3.53 g), and toluene (200 mL) was stirred at 110° C. for 12 h under heating. After leaving the mixture to stand for cooling, the mixture was extracted with toluene and the extract was purified by silica gel column chromatography to obtain a pinacol ester (7.5 g, 78% yield). Result of mass spectrometric analysis (Molecular weight of pinacol ester)

Calculated: 531

Found: m/e=531

Under argon atmosphere, a mixture of the obtained pinacol ester (5.0 g), 1-bromo-4-chlorobenzene (1.8 g), tetrakis(triphenylphosphine)palladium(0) (1.09 g), and a 2 M aqueous solution of sodium carbonate (60 ml) in toluene (100 ml) was stirred at 120° C. for 6 h under heating. After leaving the mixture to stand for cooling, the mixture was extracted with toluene and the extract was purified by silica gel column chromatography to obtain the intermediate F (4.2 g, 87% yield).

Result of mass spectrometric analysis (Molecular weight of Intermediate F)

Calculated: 515

Found: m/e=515

Synthesis Example 32: Synthesis of Compound 32

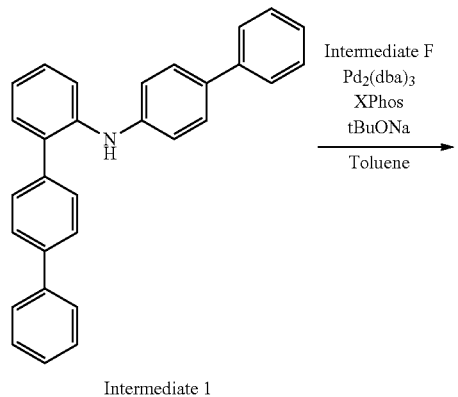

Intermediate 1

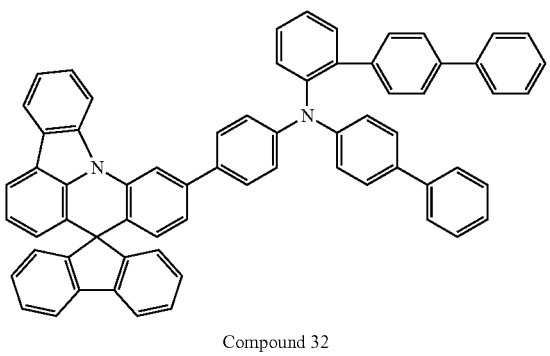

Compound 32

The compound 32 was synthesized in the same manner as in Synthesis Example 1 except for using the intermediate F in place of the intermediate A. Result of mass spectrometric analysis (Molecular weight of Compound 32)

Calculated: 876

Found: m/e=876

Synthesis Example 33: Synthesis of Compound 33

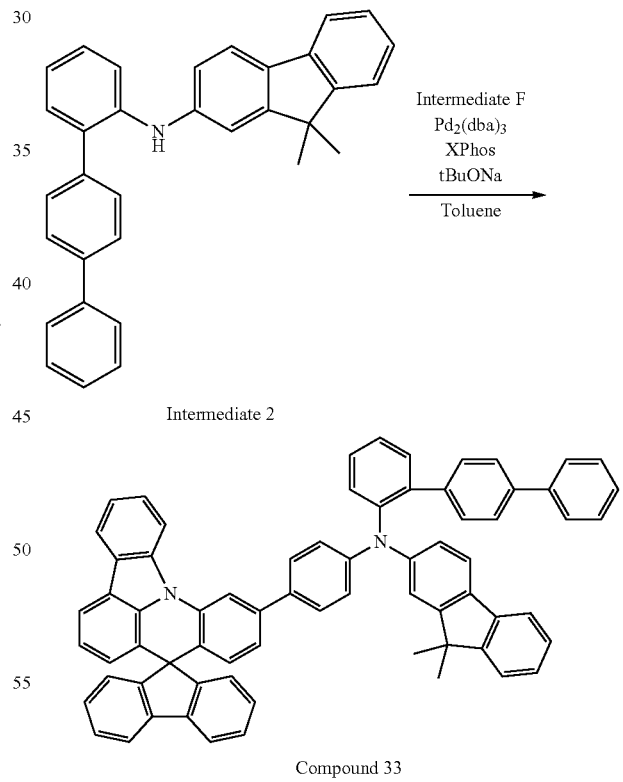

Intermediate 2

Compound 33

The compound 33 was synthesized in the same manner as in Synthesis Example 2 except for using the intermediate F in place of the intermediate A. Result of mass spectrometric analysis (Molecular weight of Compound 33)

Calculated: 916

Found: m/e=916

Synthesis Example 34: Synthesis of Compound 34

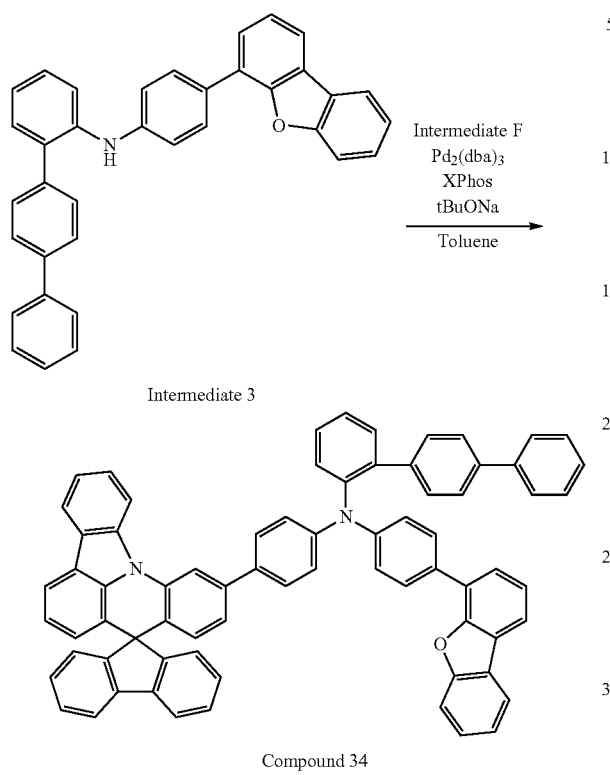

Intermediate 3

Compound 34

The compound 34 was synthesized in the same manner as in Synthesis Example 3 except for using the intermediate F in place of the intermediate A. Result of mass spectrometric analysis (Molecular weight of Compound 34)
Calculated: 966
Found: m/e=966

Example 1

A glass substrate of 25 mm×75 mm×1.1 mm thick having ITO transparent electrode (product of Geomatec Company) was ultrasonically cleaned in isopropyl alcohol for 5 min and then UV/ozone cleaned for 30 min. The thickness of ITO was 130 nm.

The cleaned glass substrate having the transparent electrode line was mounted to a substrate holder of a vacuum vapor deposition apparatus. First, the compound HI was vapor-deposited so as to cover the transparent electrode line to form a hole injecting layer with a thickness of 5 nm.

On the hole injecting layer, the compound 1 was vapor-deposited to form a first hole transporting layer with a thickness of 80 nm.

On the first hole transporting layer, the compound HT2 was vapor-deposited to form a second hole transporting layer with a thickness of 10 nm.

On the second hole transporting layer, the compound BH (host material) and the compound BD (dopant material) were vapor co-deposited to form a light emitting layer with a thickness of 25 nm. The concentration of the compound BD in the light emitting layer was 4% by mass.

Successively after forming the light emitting layer, the compound ET1 was vapor-deposited to form a first electron transporting layer with a thickness of 10 nm, and then, the compound ET2 was vapor-deposited to form a second electron transporting layer with a thickness of 15 nm.

On the second electron transporting layer, LiF was vapor-deposited to form an electron injecting layer with a thickness of 1 nm.

On the electron injecting layer, metallic Al was vapor-deposited to form a metallic cathode with a thickness of 80 nm, thereby producing an organic EL device.

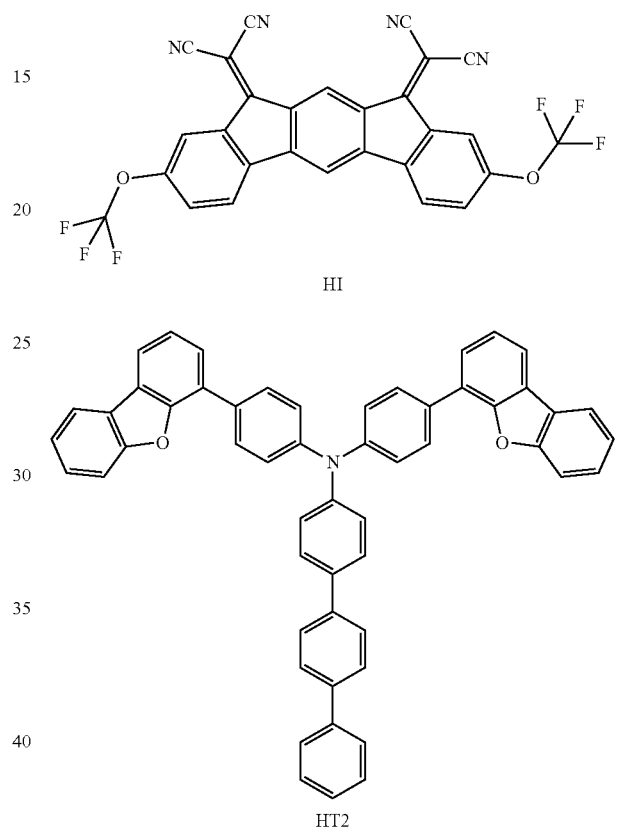

HI

HT2

BH

BD

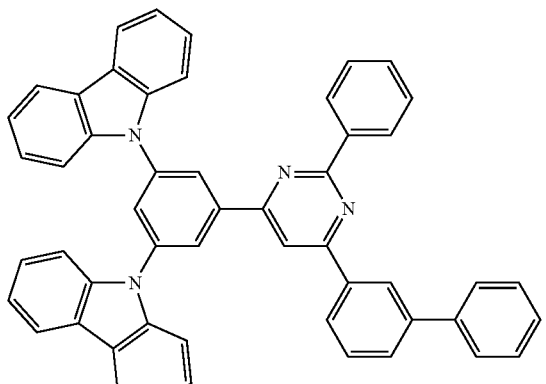

ET1

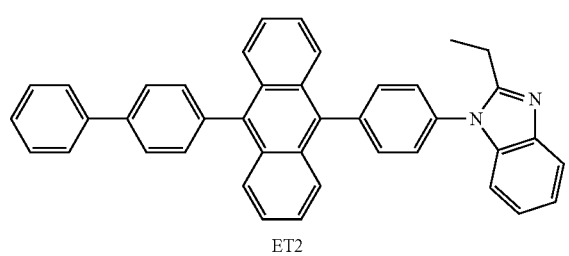

ET2

Compound 1

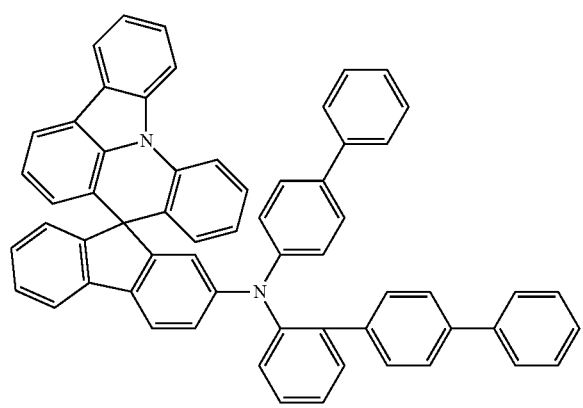

Comparative Examples 1 and 2

Each EL device was produced in the same manner as in Example 1 except for forming the first hole transporting layer by using the comparative compound 1 or the comparative compound 2 in place of the compound 1.

Comparative compound 1

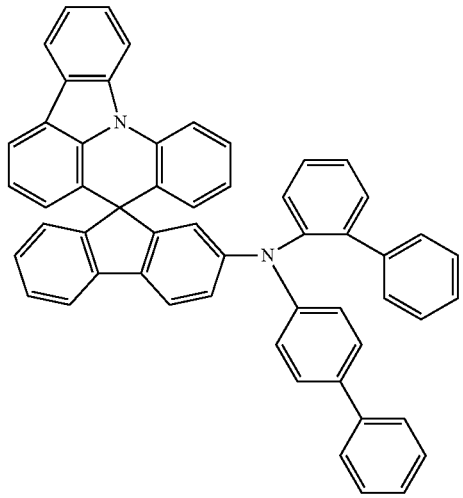

Comparative compound 2

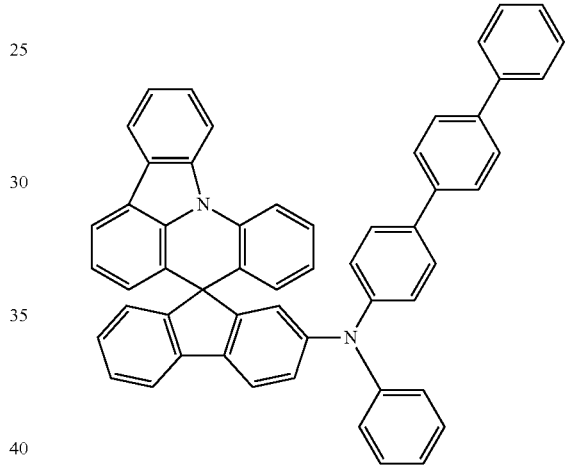

Example 2

A glass substrate of 25 mm×75 mm×1.1 mm thick having ITO transparent electrode (product of Geomatec Company) was ultrasonically cleaned in isopropyl alcohol for 5 min and then ULV/ozone cleaned for 30 min. The thickness of ITO was 130 nm.

The cleaned glass substrate having the transparent electrode line was mounted to a substrate holder of a vacuum vapor deposition apparatus. First, the compound HI was vapor-deposited so as to cover the transparent electrode line to form a hole injecting layer with a thickness of 5 nm.

On the hole injecting layer, the compound HT1 was vapor-deposited to form a first hole transporting layer with a thickness of 80 nm.

On the first hole transporting layer, the compound 1 was vapor-deposited to form a second hole transporting layer with a thickness of 10 nm.

On the second hole transporting layer, the compound BH (host material) and the compound BD (dopant material) were vapor co-deposited to form a light emitting layer with a thickness of 25 nm. The concentration of the compound BD in the light emitting layer was 4% by mass.

Successively after forming the light emitting layer, the compound ET1 was vapor-deposited to form a first electron transporting layer with a thickness of 10 nm, and then, the compound ET2 was vapor-deposited to form a second electron transporting layer with a thickness of 15 nm.

On the second electron transporting layer, LiF was vapor-deposited to form an electron injecting layer with a thickness of 1 nm.

On the electron injecting layer, metallic Al was vapor-deposited to form a metallic cathode with a thickness of 80 nm, thereby producing an organic EL device.

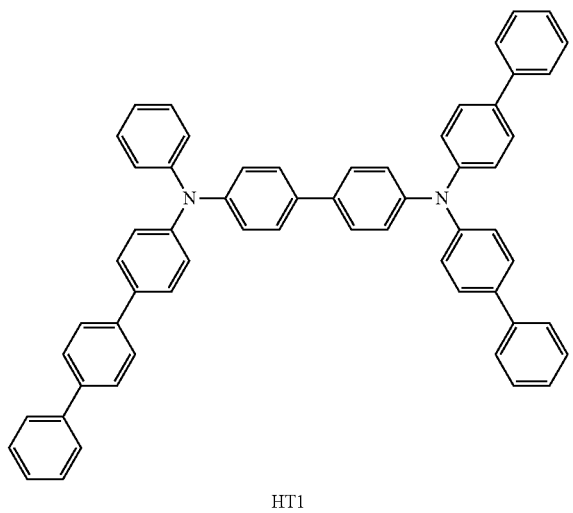 [SMILES: c1ccc(-c2ccc(-c3ccc(N(c4ccccc4)c4ccc(-c5ccc(N(c6ccc(-c7ccccc7)cc6)c6ccc(-c7ccccc7)cc6)cc5)cc4)cc3)cc2)cc1 ; "HT1"]

HT1

Comparative Examples 3 and 4

Each EL device was produced in the same manner as in Example 2 except for forming the second hole transporting layer by using the comparative compound 1 or 2 in place of the compound 1.

Evaluation of EL Device Performance

Each organic EL device thus produced was operated at a constant direct current to measure the driving voltage at a current density of 10 mA/cm² and a luminance and emission spectrum using a luminance meter. Using the obtained results, the external quantum efficiency (EQE (%)) was determined.

The results are shown in Table 1. Table 1 shows that the organic EL device of Example 1 which comprises the compound represented by formula (1) in the first hole transporting layer has an improved emission efficiency, as compared with the organic EL devices of Comparative Examples 1 and 2. Similarly, the organic EL device of Example 2 which comprises the compound represented by formula (1) in the second hole transporting layer has an improved emission efficiency, as compared with the organic EL devices of Comparative Examples 3 and 4.

TABLE 1

| | First hole transporting layer | Second hole transporting layer | EQE (%) |
|---|---|---|---|
| Example 1 | Compound 1 | HT2 | 7.8 |
| Comparative example 1 | Comparative compound 1 | HT2 | 5.8 |
| Comparative example 2 | Comparative compound 2 | HT2 | 6.0 |
| Example 2 | HT1 | Compound 1 | 8.1 |

TABLE 1-continued

| | First hole transporting layer | Second hole transporting layer | EQE (%) |
|---|---|---|---|
| Comparative example 3 | HT1 | Comparative compound 1 | 7.0 |
| Comparative example 4 | HT1 | Comparative compound 2 | 6.5 |

REFERENCE SIGNS LIST

1: Organic EL device
2: Substrate
3: Anode
4: Cathode
5: Light emitting layer
6: Anode-side organic layer (hole transporting layer)
7: Cathode-side organic layer (electron transporting layer)
10: Emission unit

The invention claimed is:
1. A compound represented by formula (1):

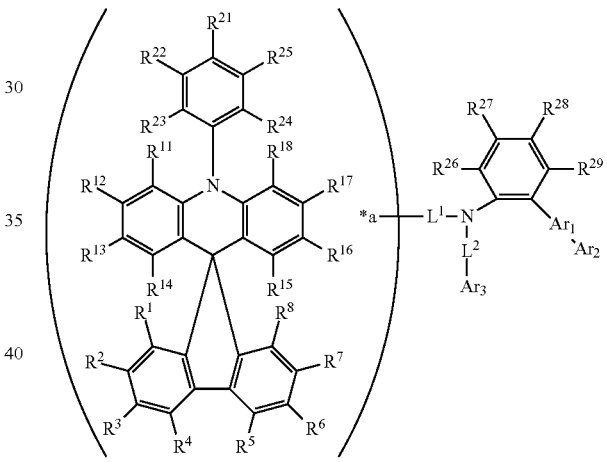

(1)

wherein:
one selected from $R^1$ to $R^8$, $R^{11}$ to $R^{18}$, and $R^{21}$ to $R^{25}$ is a single bond bonded to *a;
each of $R^1$ to $R^8$, $R^{11}$ to $R^{18}$, and $R^{21}$ to $R^{25}$ which is not the single bond bonded to *a is independently a hydrogen atom or a substituent;
provided that $R^{11}$ and $R^{23}$ each being not the single bond bonded to *a, or $R^{18}$ and $R^{24}$ each being not the single bond bonded to *a may be bonded to each other to form a single bond;
each of $R^{26}$ to $R^{29}$ is a hydrogen atom or a substituent;
adjacent two selected from $R^{26}$ to $R^{29}$ may be bonded to each other to form a ring structure;
each of $L^1$ and $L^2$ is independently a single bond or a substituted or unsubstituted arylene group having 6 to 30 ring carbon atoms;
$Ar_1$ is a substituted or unsubstituted arylene group having 6 to 30 ring carbon atoms; and
each of $Ar_2$ and $Ar_3$ is independently a substituted or unsubstituted aryl group having 6 to 30 ring carbon atoms or a substituted or unsubstituted heteroaryl group having 5 to 30 ring atoms.

2. The compound according to claim 1, wherein the compound is represented by formula (2):

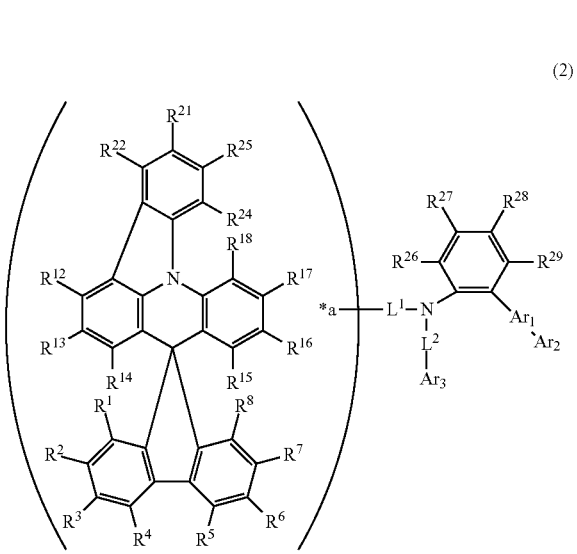

(2)

wherein each of $R^{18}$ and $R^{24}$ is independently a hydrogen atom or a substituent and the other symbols are as defined above.

3. The compound according to claim 1, wherein the compound is represented by formula (3):

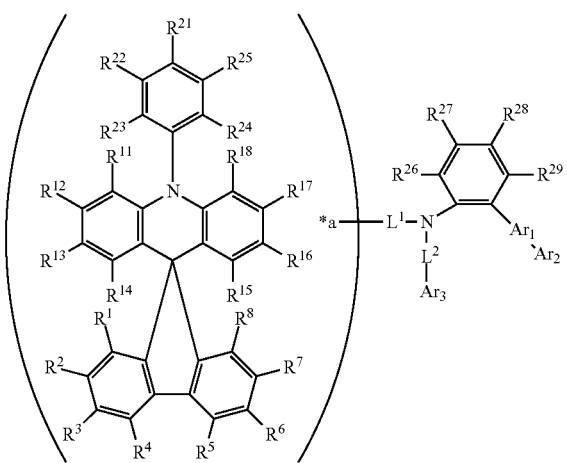

(3)

wherein each of $R^{11}$, $R^{23}$, $R^{18}$, and $R^{24}$ is a hydrogen atom or a substituent, $R^{11}$ and $R^{23}$ do not form a single bond, $R^{18}$ and $R^{24}$ do not form a single bond, and the other symbols are as defined above.

4. The compound according to claim 1, wherein $R^2$, $R^4$, $R^5$, or $R^7$ is a single bond bonded to *a.

5. The compound according to claim 1, wherein the compound is represented by formula (2A):

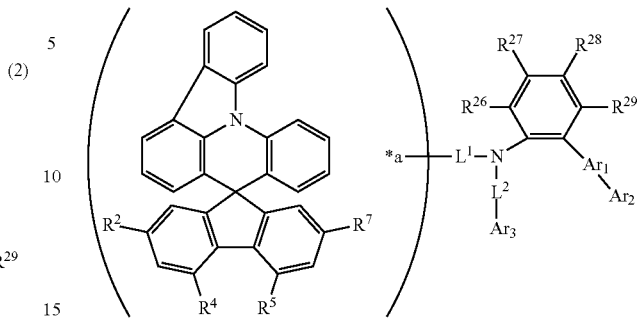

(2A)

wherein one selected from $R^2$, $R^4$, $R^5$, and $R^7$ is a single bond bonded to *a, the others of $R^2$, $R^4$, $R^5$, and $R^7$ are each hydrogen atom, and the other symbols are as defined above.

6. The compound according to claim 1, wherein the compound is represented by formula (3A):

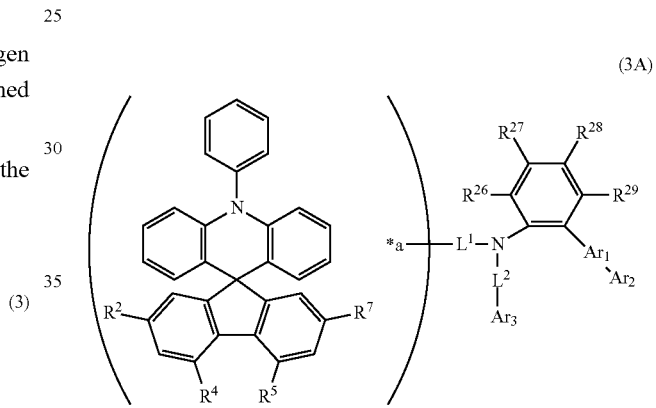

(3A)

wherein one selected from $R^2$, $R^4$, $R^5$, and $R^7$ is a single bond bonded to *a, the others of $R^2$, $R^4$, $R^5$, and $R^7$ are each hydrogen atom, and the other symbols are as defined above.

7. The compound according to claim 1, wherein $Ar_1$ is a substituted or unsubstituted arylene group having 6 to 30 ring carbon atoms and the arylene group is a phenylene group, a biphenylene group, a terphenylene group, a biphenylenylene group, a naphthylene group, an acenaphthylene group, an anthrylene group, a benzanthrylene group, an aceanthrylene group, a phenanthrylene group, a benzophenanthrylene group, a phenalenylene group, a pentacenylene group, a picenylene group, a pentaphenylene group, a pyrenylene group, a chrysenylene group, a benzochrysenylene group, a s-indacenylene group, an as-indacenylene group, a fluoranthenylene group, a perylenylene group, a triphenylenylene group, a fluorenylene group, or a 9,9'-spirobifluorenylene group.

8. The compound according to claim 1, wherein the compound is represented by formula (2B):

(2B)

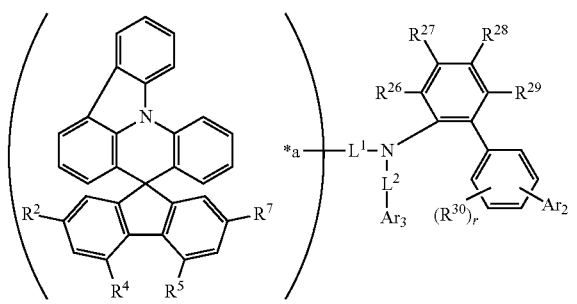

wherein:
  one selected from $R^2$, $R^4$, $R^5$, and $R^7$ is a single bond bonded to *a and the others of $R^2$, $R^4$, $R^5$, and $R^7$ are each hydrogen atom;
  each $R^{30}$ is independently a hydrogen atom, a substituted or unsubstituted alkyl group having 1 to 30 carbon atoms, a substituted or unsubstituted cycloalkyl group having 3 to 30 ring carbon atoms, a substituted or unsubstituted aryl group having 6 to 30 ring carbon atoms, a substituted or unsubstituted heteroaryl group having 5 to 30 ring atoms, an alkoxy group having a substituted or unsubstituted alkyl group having 1 to 30 carbon atoms, a substituted or unsubstituted haloalkyl group having 1 to 30 carbon atoms, a haloalkoxy group having a substituted or unsubstituted haloalkyl group having 1 to 30 carbon atoms, a halogen atom, a cyano group, or a nitro group;
  r is an integer of 0 to 4; and
  the other symbols are as defined above.

9. The compound according to claim 1, wherein the compound is represented by formula (3B):

(3B)

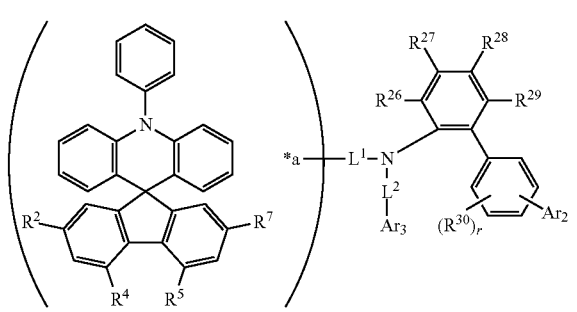

wherein:
  one selected from $R^2$, $R^4$, $R^5$, and $R^7$ is a single bond bonded to *a and the others of $R^2$, $R^4$, $R^5$, and $R^7$ are each hydrogen atom;
  each $R^{30}$ is independently a hydrogen atom, a substituted or unsubstituted alkyl group having 1 to 30 carbon atoms, a substituted or unsubstituted cycloalkyl group having 3 to 30 ring carbon atoms, a substituted or unsubstituted aryl group having 6 to 30 ring carbon atoms, a substituted or unsubstituted heteroaryl group having 5 to 30 ring atoms, an alkoxy group having a substituted or unsubstituted alkyl group having 1 to 30 carbon atoms, a substituted or unsubstituted haloalkyl group having 1 to 30 carbon atoms, a haloalkoxy group having a substituted or unsubstituted haloalkyl group having 1 to 30 carbon atoms, a halogen atom, a cyano group, or a nitro group;
  r is an integer of 0 to 4; and
  the other symbols are as defined above.

10. The compound according to claim 1, wherein $Ar_2$ is a substituted or unsubstituted aryl group having 6 to 30 ring carbon atoms and the aryl group is a phenyl group, a biphenylyl group, a terphenylyl group, a biphenylenyl group, a naphthyl group, an acenaphthylenyl group, an anthryl group, a benzanthryl group, an aceanthryl group, a phenanthryl group, a benzophenanthryl group, a phenalenyl group, a fluorenyl group, a pentacenyl group, a picenyl group, a pentaphenyl group, a pyrenyl group, a chrysenyl group, a benzochrysenyl group, a s-indacenyl group, an as-indacenyl group, a fluoranthenyl group, a perylenyl group, a triphenylenyl group, a fluorenyl group, or a 9,9'-spirobifluorenyl group.

11. The compound according to claim 10, wherein $Ar_2$ is a substituted or unsubstituted phenyl group, a substituted or unsubstituted biphenylyl group, a substituted or unsubstituted terphenylyl group, a substituted or unsubstituted naphthyl group, a substituted or unsubstituted phenanthryl group, or a substituted or unsubstituted triphenylenyl group.

12. The compound according to claim 1, wherein each of $L^1$ and $L^2$ is independently a phenylene group, a biphenylene group, a terphenylene group, or a naphthylene group.

13. The compound according to claim 1, wherein $L^1$ is a single bond.

14. The compound according to claim 1, wherein $Ar_3$ is a substituted or unsubstituted aryl group having 6 to 30 ring carbon atoms.

15. The compound according to claim 1, wherein $Ar_3$ is a substituted or unsubstituted heteroaryl group having 5 to 30 ring atoms.

16. The compound according to claim 1, wherein $L^2$ is a substituted or unsubstituted arylene group having 6 to 30 ring carbon atoms.

17. The compound according to claim 1, wherein each of the substituent, and an optional substituent which is referred to by "substituted or unsubstituted" are at least one selected from the group consisting of an alkyl group having 1 to 30 carbon atoms; a cycloalkyl group having 3 to 30 ring carbon atoms; an aryl group having 6 to 30 ring carbon atoms; an aralkyl group having 7 to 31 carbon atoms which includes an aryl group having 6 to 30 ring carbon atoms: an alkoxy group having an alkyl group having 1 to 30 carbon atoms; an aryloxy group having an aryl group having 6 to 30 ring carbon atoms; a mono-, di- or tri-substituted silyl group having a substituent selected from an alkyl group having 1 to 30 carbon atoms and an aryl group having 6 to 30 ring carbon atoms; a haloalkyl group having 1 to 30 carbon atoms; a haloalkoxy group having a haloalkyl group having 1 to 30 carbon atoms; a halogen atom; a cyano group; and a nitro group.

18. The compound according to claim 8, wherein:
  each $R^{30}$ is independently a hydrogen atom, a substituted or unsubstituted alkyl group having 1 to 30 carbon atoms, a substituted or unsubstituted aryl group having 6 to 30 ring carbon atoms, or a substituted or unsubstituted heteroaryl group having 5 to 30 ring atoms and
  r is an integer of 0 to 1.

19. A material for organic electroluminescence devices comprising the compound according to claim 1.

20. An organic electroluminescence device comprising a cathode, an anode and an organic layer between the cathode and the anode, wherein the organic layer comprises a light emitting layer and at least one layer of the organic layer comprises the compound according to claim 1.

21. The organic electroluminescence device according to claim 20, wherein the organic layer comprises a hole transporting region between the anode and the light emitting layer and the hole transporting region comprises the compound.

22. The organic electroluminescence device according to claim 21, wherein the hole transporting region comprises a first hole transporting layer and a second hole transporting layer from the anode toward the light emitting layer in this order, and one of the first hole transporting layer and the second hole transporting layer comprises the compound.

23. The organic electroluminescence device according to claim 22, wherein the first hole transporting layer comprises the compound.

24. The organic electroluminescence device according to claim 22, wherein the second hole transporting layer comprises the compound.

25. The organic electroluminescence device according to claim 20, wherein the light emitting layer comprises a dopant material, and the dopant material is a fluorescent emitting material or a phosphorescent emitting material.

26. An electronic device comprising the organic electroluminescence device according to claim 20.

* * * * *